(12) United States Patent  (10) Patent No.: US 8,796,271 B2
Hirose et al.  (45) Date of Patent: Aug. 5, 2014

(54) HETEROARYLS AND USES THEREOF

(75) Inventors: Masaaki Hirose, Kanagawa (JP);
Zhigen Hu, Newton Center, MA (US);
Yongbo Hu, Winchester, MA (US);
Hong Myung Lee, Cambridge, MA (US);
Zhan Shi, Concord, MA (US);
Stepan Vyskocil, Arlington, MA (US);
Tianlin Xu, Shrewsbury, MA (US)

(73) Assignee: Millennium Pharmaceuticals, Inc., Cambridge, MA (US)

(*) Notice: Subject to any disclaimer, the term of this patent is extended or adjusted under 35 U.S.C. 154(b) by 0 days.

(21) Appl. No.: 13/207,696

(22) Filed: Aug. 11, 2011

(65) Prior Publication Data
US 2012/0178723 A1 Jul. 12, 2012

Related U.S. Application Data

(60) Provisional application No. 61/372,594, filed on Aug. 11, 2010, provisional application No. 61/438,375, filed on Feb. 1, 2011.

(51) Int. Cl.
A61K 31/4439 (2006.01)
A61K 31/437 (2006.01)
A61K 31/4375 (2006.01)
A61K 31/495 (2006.01)
A61K 31/4155 (2006.01)
A61K 31/4725 (2006.01)
C07D 409/14 (2006.01)
C07D 409/04 (2006.01)
C07D 417/14 (2006.01)
C07D 413/14 (2006.01)

(52) U.S. Cl.
CPC ......... A61K 31/4725 (2013.01); A61K 31/4155 (2013.01); A61K 31/495 (2013.01); A61K 31/4375 (2013.01); A61K 31/437 (2013.01); A61K 31/4439 (2013.01); C07D 409/14 (2013.01); C07D 409/04 (2013.01); C07D 417/14 (2013.01); C07D 413/14 (2013.01)
USPC ...... 514/252.01; 514/301; 514/302; 514/307; 514/337; 514/340; 514/277; 514/342; 544/297; 544/333; 548/247; 546/280.4; 546/272.4

(58) Field of Classification Search
CPC .. C07D 409/14; C07D 417/14; C07D 413/14; C07D 409/04; A61K 31/4439; A61K 31/437; A61K 31/4375; A61K 31/495; A61K 31/4155; A61K 31/4725
USPC ............ 514/342, 252.01, 301, 302, 307, 337, 514/340, 277; 546/280.4, 272.4; 544/297; 544/333; 548/247
See application file for complete search history.

(56) References Cited

U.S. PATENT DOCUMENTS

| 3,257,203 | A | 6/1966 | Sus et al. |
| 3,821,384 | A | 6/1974 | Ariyan et al. |
| 3,852,293 | A | 12/1974 | Ariyan et al. |
| 4,371,607 | A | 2/1983 | Donges |
| 5,134,142 | A | 7/1992 | Matsuo et al. |
| 6,015,826 | A | 1/2000 | Pechacek et al. |
| 6,608,087 | B1 | 8/2003 | Charifson et al. |
| 6,984,652 | B2 | 1/2006 | Yager et al. |

(Continued)

FOREIGN PATENT DOCUMENTS

| DE | 275870 A1 | 2/1990 |
| EP | 0853083 A1 | 7/1998 |

(Continued)

OTHER PUBLICATIONS

4-Oxazolecarboxylic acid, 5-[(ethoxymethylene)amino]-2-(4-pyridinyl)-, ethyl ester-(CA Index Name), CAS Registry No. 885901-22-4, entered May 29, 2006.
Adib, M. et al., Facile One-Pot Three-Component Synthesis of Functionalized Pyridylfuran-2-amines, Helvetica Chimica Acta, 89(2):299-303 (2006).
Boppana, K. et al., Knowledge based identification of MAO-B selective inhibitors using pharmacophore and structure based virtual screening models, European Journal of Medicinal Chemistry, 44:3584-3590 (2009).

(Continued)

Primary Examiner — Rebecca Anderson
(74) Attorney, Agent, or Firm — Choate, Hall & Stewart LLP; Andrea L. C. Reid

(57) ABSTRACT

This invention provides compounds of formula IA-a or IB-a and subsets thereof:

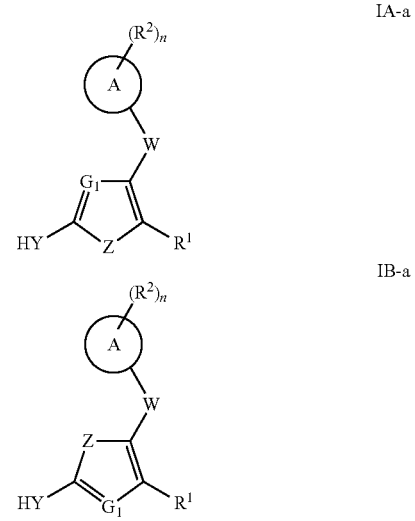

wherein Z, HY, $R^1$, $R^2$, $G_1$, W, n, and A and subsets thereof are as described in the specification. The compounds are inhibitors of PI3K and are thus useful for treating proliferative, inflammatory, or cardiovascular disorders.

48 Claims, No Drawings

(56) References Cited

U.S. PATENT DOCUMENTS

| | | |
|---|---|---|
| 7,074,801 B1 | 7/2006 | Yoshida et al. |
| 7,405,235 B2 | 7/2008 | Levy et al. |
| 7,504,513 B2 | 3/2009 | Boylan et al. |
| 7,741,348 B2 | 6/2010 | Nan et al. |
| 8,440,664 B2 | 5/2013 | Cardin et al. |
| 8,586,582 B2 | 11/2013 | Liang et al. |
| 2002/0022729 A1 | 2/2002 | Kawai et al. |
| 2003/0096816 A1 | 5/2003 | Cao et al. |
| 2004/0116425 A1 | 6/2004 | Li et al. |
| 2004/0198773 A1 | 10/2004 | Hart et al. |
| 2004/0248896 A1 | 12/2004 | Dean et al. |
| 2005/0004122 A1 | 1/2005 | Brown et al. |
| 2005/0054697 A1 | 3/2005 | Yager et al. |
| 2005/0124678 A1 | 6/2005 | Levy et al. |
| 2006/0041006 A1 | 2/2006 | Ibrahim et al. |
| 2006/0074119 A1 | 4/2006 | Andrews et al. |
| 2006/0199804 A1 | 9/2006 | Hummersone et al. |
| 2007/0203210 A1 | 8/2007 | Boylan et al. |
| 2008/0021217 A1 | 1/2008 | Borchardt et al. |
| 2008/0045570 A1 | 2/2008 | Brenchley et al. |
| 2008/0132546 A1 | 6/2008 | Basarab et al. |
| 2008/0255120 A1 | 10/2008 | Lin et al. |
| 2008/0293716 A1 | 11/2008 | Drewry et al. |
| 2008/0306060 A1 | 12/2008 | Alexander et al. |
| 2009/0012031 A1 | 1/2009 | Chinnaiyan et al. |
| 2009/0030016 A1 | 1/2009 | Gandhi et al. |
| 2009/0036435 A1 | 2/2009 | Curry et al. |
| 2009/0247567 A1 | 10/2009 | Do et al. |
| 2009/0325925 A1 | 12/2009 | Renou et al. |
| 2010/0075951 A1 | 3/2010 | Cardin et al. |
| 2010/0256172 A1 | 10/2010 | Shi et al. |
| 2010/0267759 A1 | 10/2010 | Seefeld et al. |
| 2011/0003806 A1 | 1/2011 | Hirose et al. |
| 2011/0003807 A1 | 1/2011 | Banno et al. |
| 2011/0021531 A1 | 1/2011 | Chobanian et al. |
| 2012/0142732 A1 | 6/2012 | Cullis et al. |
| 2012/0172345 A1 | 7/2012 | Freeze et al. |
| 2012/0178723 A1 | 7/2012 | Hirose et al. |
| 2012/0214794 A1 | 8/2012 | Freeze et al. |
| 2013/0165464 A1 | 6/2013 | Chau et al. |
| 2013/0165472 A1 | 6/2013 | Chau et al. |
| 2013/0165483 A1 | 6/2013 | Chau et al. |
| 2013/0217689 A1 | 8/2013 | Cardin et al. |
| 2013/0267563 A1 | 10/2013 | Hirose et al. |

FOREIGN PATENT DOCUMENTS

| | | |
|---|---|---|
| GB | 874634 A | 8/1961 |
| JP | 10087490 | 4/1998 |
| JP | 2007-197324 A | 8/2007 |
| WO | WO-97/12615 A1 | 4/1997 |
| WO | WO-98/08845 A1 | 3/1998 |
| WO | WO-98/47894 A1 | 10/1998 |
| WO | WO-00/02871 A1 | 1/2000 |
| WO | WO-00/35912 A1 | 6/2000 |
| WO | WO-00/63204 A2 | 10/2000 |
| WO | WO-02/088107 A1 | 11/2002 |
| WO | WO-03/015776 A1 | 2/2003 |
| WO | WO-03/027085 A2 | 4/2003 |
| WO | WO-03/027107 A1 | 4/2003 |
| WO | WO-03/040096 A2 | 5/2003 |
| WO | WO-2004/016592 A1 | 2/2004 |
| WO | WO-2004/016741 A2 | 2/2004 |
| WO | WO-2004/096797 A1 | 11/2004 |
| WO | WO-2006/046031 A1 | 5/2006 |
| WO | WO-2006/068933 A2 | 6/2006 |
| WO | WO-2006/078287 A2 | 7/2006 |
| WO | WO-2006/097030 A1 | 9/2006 |
| WO | WO-2006/102194 A1 | 9/2006 |
| WO | WO-2006/114313 A1 | 11/2006 |
| WO | WO-2007/002559 A1 | 1/2007 |
| WO | WO-2007/043400 A1 | 4/2007 |
| WO | WO-2007/087488 A2 | 8/2007 |
| WO | WO-2007/096315 A1 | 8/2007 |
| WO | WO-2007/110344 A1 | 10/2007 |
| WO | WO-2007/129044 A1 | 11/2007 |
| WO | WO-2007/129161 A2 | 11/2007 |
| WO | WO-2007/138110 A2 | 12/2007 |
| WO | WO-2008/014238 A2 | 1/2008 |
| WO | WO-2008/021235 A2 | 2/2008 |
| WO | WO-2008/023159 A1 | 2/2008 |
| WO | WO-2008/024980 A2 | 2/2008 |
| WO | WO-2008/036541 A1 | 3/2008 |
| WO | WO-2008/083070 A1 | 7/2008 |
| WO | WO-2008/090382 A1 | 7/2008 |
| WO | WO-2008/097835 A2 | 8/2008 |
| WO | WO-2008/098105 A1 | 8/2008 |
| WO | WO-2008/134679 A1 | 11/2008 |
| WO | WO-2008/139161 A1 | 11/2008 |
| WO | WO-2008/157273 A1 | 12/2008 |
| WO | WO-2009/040730 A2 | 4/2009 |
| WO | WO-2009/042607 A1 | 4/2009 |
| WO | WO-2009/049028 A1 | 4/2009 |
| WO | WO-2009/094224 A1 | 7/2009 |
| WO | WO-2009/106885 A1 | 9/2009 |
| WO | WO-2009/122148 A1 | 10/2009 |
| WO | WO-2009/154741 A1 | 12/2009 |
| WO | WO-2009/158374 A2 | 12/2009 |
| WO | WO-2010/001126 A1 | 1/2010 |
| WO | WO 2010/005841 * | 1/2010 |
| WO | WO-2010/017079 A1 | 2/2010 |
| WO | WO-2010/055304 A2 | 5/2010 |
| WO | WO-2010/080873 A1 | 7/2010 |
| WO | WO 2010/090716 * | 8/2010 |
| WO | WO-2010/090716 A1 | 8/2010 |
| WO | WO-2010/132598 A1 | 11/2010 |
| WO | WO-2011/043371 A1 | 4/2011 |

OTHER PUBLICATIONS

Chattopadhyay, S. K. et al., Efficient Construction of the Carbon Skeleton of the Novel Polyoxazole-Based Cyclopeptide IB-01211 via a Biomimetic Macrocyclisation, SYNLETT, 4:555-558 (2010).

Fletcher, A. N. et al., Laser Dye Stability, Part 12. The Pyridinium Salts, Applied Physics, B43:155-160 (1987).

Hernandez, D. et al., Synthesis and Antitumor Activity of Mechercharmycin A Analogues, Journal of Medicinal Chemistry, 51: 5722-5730 (2008).

Hernandez, D. et al., Synthesis of Natural Product Derivatives Containing 2,4-Concatenated Oxazoles, European Journal of Organic Chemistry, (19): 3389-3396 (2008).

International Search Report for PCT/US09/00513, 3 pages (Jun. 10, 2009).

International Search Report for PCT/US09/03607, 4 pages (Sep. 23, 2009).

International Search Report for PCT/US10/00234, 3 pages (Jun. 1, 2010).

International Search Report for PCT/US11/47245, 2 pages (Dec. 22, 2011).

International Search Report for PCT/US11/47407, 2 pages (Dec. 22, 2011).

International Search Report for PCT/US11/56135 4 pages (May 31, 2012).

Liang, J. et al., Crystal Structure of PI3K SH3 Domain at 2.0 A Resolution, Journal of Molecular Biology, 257:632-643 (1996).

Menear, K. A. et al., Identification and optimisation of novel and selective small molecular weight kinase inhibitors of mTOR, Bioorganic & Medicinal Chemistry Letters, 19:5898-5901 (2009).

Revesz, L. et al., SAR of 2,6-Diamino-3,5-difluoropyridinyl Substituted Heterocycles as Novel p38 MAP Kinase Inhibitors, Bioorganic & Medicinal Chemistry Letters, 12(16):2109-2112 (2002).

Thompson, M. J. et al., Development of a Diversity-Oriented Approach to Oxazole-5-amide Libraries, Journal of Organic Chemistry, 74(10):3856-3865 (2009).

Wang, Q. et al., Copper-Mediated Amidation of Heterocyclic and Aromatic C—H Bonds, Organic Letters, 11(22): 5178-5180 (2009).

Written Opinion for PCT/US09/00513, 5 pages (Jun. 10, 2009).

Written Opinion for PCT/US09/03607, 5 pages (Sep. 23, 2009).

Written Opinion for PCT/US10/00234, 6 pages (Jun. 1, 2010).

Written Opinion for PCT/US11/47245, 5 pages (Dec. 22, 2011).

Written Opinion for PCT/US11/47407, 7 pages (Jun. 10, 2009).

(56) References Cited

OTHER PUBLICATIONS

Written Opinion for PCT/US11/56135, 13 pages (May 31, 2012).
Zhang, F. et al., Decarboxylative C—H Cross-Coupling of Azoles, Angew. Chem. Int. Ed., 49(15): 2768-2771 (2010).
2-Thiophenecarboxylic acid, 3-(4-chlorophenyl)-4-cyano-5-(4-morpholinyl)-(CA Index Name), CAS Registry No. 883097-33-4, entered May 5, 2006.
2-Thiophenecarboxylic acid, 3-(4-chlorophenyl)-4-cyano-5-(4-morpholinyl)-, methyl ester (CA Index Name), CAS Registry No. 882283-38-7, entered Apr. 30, 2006.
Abdelrazek et al., Heterocyclic Synthesis with Nitriles: Synthesis of Some Novel Thiophene and Thieno[2,3-d]Pyrimidine Derivatives, Phosphorus, Sulfur, Silicons, 71:93-97 (1992).
Al-Azawe et al., Synthesis of 2, 5-Disubstituted Thiazoles and Their Reactions with Grignard Reagents, Journal of the Iraqi Chemical Society, 13(1): 1-13 (1988).
Batista et al., Synthesis and characterization of new thienylpyrrolyl-benzothiazoles as efficient and thermally stable nonlinear optical chromophores, Tetrahedron, 63(20):4258-4265 (2007).
Batista et al., Synthesis and Second-Order Nonlinear Optical Properties of New Chromophores Containing Benzimidazole, Thiophene, and Pyrrole Heterocycles, Tetrahedron, 63(39): 9842-9849 (2007).
Berndt, A. et al., The p110σ crystal structure uncovers mechanisms for selectivity and potency of novel PI3K inhibitors, Nature Chemical Biology, 6(2):117-124 (2010).
Choi, W. et al., Synthesis and Antiproliferative Activities of 1-Substituted-3-(3-chloro-5-methoxy phenyl)-4-pyridinylpyrazole Derivatives Against Melanoma Cell Line, Bulletin of the Korean Chemical Society, 30(9):2027-2031 (2009).
Cudworth et al., Structure-Activity Relationship Development of Dihaloaryl Triazole Compounds as Insecticides and Acaricides. 1. Phenyl Thiophen-2-yl Triazoles, Journal of Agricultural and Food Chemistry, 55(18): 7517-7526 (2007).
Database CHEMCATS, Chemical Abstracts Service, Columbus, Ohio, US, XP002545555, order No. T5337328, 2008.
Datta et al., A Novel Route to Methyl 3-3(3,4-Disubstituted 5-alkylthio/amino-2-thienyl) propenoates, Synthesis, 7:556-567 (1988).
Emmitte et al., Discovery of Thiophene Inhibitors of Polo-like Kinase, Bioorganic & Medicinal Chemistry Letters, 19(3): 1018-1021 (2009).
Fridman et al., Spectroscopy, Photophysical and Photochemical Properties of Bisimidazole, Derivatives, Journal of Photochemistry and Photobiology, A: Chemistry, 188(1): 25-33 (2007).
Green et al., Parallel Synthesis of 2-aryl-4-aminobenzimidazoles and their Evaluation as Gonadotropin Releasing Hormone Antagonists, Journal of Combinatorial Chemistry, 11(1): 117-125 (2009).
Heyde et al., A Simple Route to N,N-Dialkyl Derivatives of 2-Amino-5-thiophenecarboxylates, Eur. J. Org. Chem.: 3273-3278 (2000).
Hirai et al., Heterocyclic Cation Systems. 14. Sythesis of Thieno[3,2-e][1,4]diazepine, Thiazolo[4,5-e][1,4]diazepine, and s-Triazolo[3,4-c]thiazolo[4,5-e][1,4]diazepine Derivatives, Journal of Organic Chemistry, 45:253-260 (1980).
Hirai et al., Novel Synthesis of Thiophene Derivatives from 1,3-Oxathil-2-ylideneimmonium Salt, Chemical & Pharmaceutical Bulletin, 19(10):2194-2197 (1971).
Laszlo et al., Pyrroles and Other Heterocycles as Inhibitors of P38 Kinase, Bioorganic and Medical Chemistry Letters, 8: 2689-2694 (1998).
Lethu et al., Discovery of a New Class of Protein Farnesyltransferase Inhibitors in the Arylthiophene Series, J. Med. Chem., 52: 6205-6208 (2009).
Liu et al., Highly Selective and Potent Thiophenes as P13K Inhibitors with Oral Antitumor Activity, Med. Chem. Lett., 2:809-813 (2011).
Lucchesini, A Simple Way to Sequentially Connected Polycycles Containing Terminal Pyrrole Rings: Synthesis of Possible Prcursors of Materials for Nonlinear Optics, Tetrahedron, 48(45): 9951-9966 (1992).

Mamedov et al., Synthesis and Some Properties of the Methyl Ester and N,N-diethylamide of 2-Azido-5-Phyenyl-4-Thiazolecarboxylic Acic, Chemistry of Heterocyclic Compounds, 29(5): 607-611 (1993).
Matschke et al., Quinomethides Versus Unsymmetric Hybrids: Two Variations of Non-Radicaloid SEM-States in Four-Electron Redox Systems of bis-4H-imidazoles, Structural Chemistry, 19(3):399-405 (2008).
Moorthy et al., In Silico-Based Structural Analysis of Arylthiophene Derivatives for Ftase Inhibitory Activity, hERG, and Other Toxic Effects, Journal of Biomolecular Screening, 16(9):1037-1046 (2011).
Morpholine, 4-(5-(4,5-diphenyl-1H-imidazol-2-yl)-2-thienyl]-, Ryan Scientific Screening Library, Publication date: Jan. 25, 2008, CAS Registry No. 851954-74-0.
Nagasaki et al., CASREACT 139:52925 (2003).
Nagasaki et al., Useful Synthesis of Various Thiazole and Polythiazolyl Derivatives from Thiocarboxamide and -Bromacyl Compound, Heterocycles, 60(2): 321-335 (2003).
Pinto et al., The Synthesis of 5-alkoxy and 5-amino Substituted Thiophenes, Tetrahedron Letters, 41(10): 1597-1600 (2000).
Raap, Some Synthesis with Dimethyl Monothionemalonate, Canadian Journal of Chemistry, 46:13, 2255-2261 (1968).
Rehwald et al., New Synthesis of 2,4-Diaminothiophenes—Use of (1,3-oxathiol-2-ylidene)Malononitrile, Heterocycles, 45(3): 493-500 (1997).
Sheridan, The Most Common Chemical Replacements in Drug-Like Compounds, J. Chem. Inf. Comput. Sci., 42:103-108 (2002).
Welker et al., Recent Syntheses of PI3K/Akt/mTOR signaling pathway inhibitors, Bioorganic & Medicinal Chemistry, 21(14): 4063-4091 (2013).
Zhou et al., Selenium-Containing Heterocycles from Isoselenocyanates: Synthesis of 1,3-Selenazoles from N-Phenylimidoyl Isoselenocyanates, Helvetica Chimica Acta, 83: 1576-1598 (2000).
Benzamide, N-[2-(5-amino-1-phenyl-1H-pyrazol-4-yl)-4-phenyl-5-thiazolyl]-4-methyl-(CA Index Name), CAS Registry No. 1017527-68-2, entered Apr. 27, 2008.
5-Thiazolecarboxamide, N-[2'-(aminosulfonyl)[1,1'-biphenyl]-2-yl]-4-(4-methoxyphenyl)-2-(1H-pyrrol-1-yl)-(CA Index Name), CAS Registry No. 1027033-64-2, entered Jun. 10, 2008.
1,2,4-Oxadiazole-3-ethanamine, 5-[5-(1H-imidazol-2-y1)-2-thienyl]-N,N-dimethyl-(CA Index Name), CAS Registry No. 1066888-52-5, entered Oct. 27, 2008.
1,2,4-Oxadiazole, 5-[5-(1H-imidazol-2-yl)-2-thienyl]-3-(methoxymethyl)-(CA Index Name), CAS Registry No. 1069660-66-7, entered Nov. 2, 2008.
2,7-Naphthyridine, 1,2,3,4-tetrahydro-5-[5-[-(1H-imidazol-2-yl)-2-thienyl]-1,2,4-oxadiazol-3-yl]-6-methyl-(CA Index Name), CAS Registry No. 1069717-72-1, entered Nov. 2, 2008.
Pyrazolo[1,5-a]pyrimidin-7(4H)-one,3-ethyl-5-[5-(1H-imidazol-2-yl)-2-thienyl]-(CA Index Name), CAS Registry No. 1087437-07-7, entered Dec. 21, 2008.
3H-1,2,4-Triazole-3-thione, 2,4-dihydro-4-methyl-5-[4-methyl-2-(5-methyl-3-isoxazolyl)-5-thiazolyl]-(CA Index Name), CAS Registry No. 264616-86-6, entered May 12, 2000.
Acetamide, N-(3,5-dichlorophenyl)-2-[[4-methyl-5-[4-methyl-2-(5-methyl-3-isoxazolyl)-5-thiazolyl]-4H-1,2,4-triazol-3-yl]thio]-(CA Index Name), CAS Registry No. 264626-19-9, entered May 12, 2000.
Acetamide, N-(4-chlorophenyl)-2-[[4-methyl-5-[4-methyl-2-(5-methyl-3-isoxazolyl)-5-thiazolyl]-4H-1,2,4-triazol-3-yl]thio]-(CA Index Name), CAS Registry No. 264626-21-3, entered May 12, 2000.
Carbamic acid,4,4'-diphenyl[2,2'-bithiazole]-5,5'-diyl)bis-, dimethyl ester (9CI)(CA Index Name), CAS Registry No. 505060-78-6, entered Apr. 25, 2003.
Benzamide, N,N'-(4,4'-di-2-thienyl[2,2'-bithiazole]-5,5'-diyl)bis-(CA Index Name) CAS Registry No. 691381-57-4, entered Jun. 10, 2004.
Carbamic acid, N,N'-(4,4'-di-2-thienyl[2,2'-bithiazole]-5,5'-diyl)bis-, C,C'-dimethyl ester (CA Index Name) CAS Registry No. 691381-58-5, entered Jun. 10, 2004.

(56) References Cited

OTHER PUBLICATIONS

Benzamide, N,N'-[4,4'-bis(4-fluorophenyl)[2,2'-bithiazole]-5,5'-diyl]bis[4-methyl-(CA Index Name) CAS Registry No. 691381-60-9, entered Jun. 10, 2004.

Imidazo[1,2-a]pyridine, 6-[3-[5-(2H-tetrazol-5-yl)-2-thienyl]-1H-pyrazol-4-yl]-3-(2-thiazolyl)-(CA Index Name) CAS Registry No. 732241-18-8, entered Aug. 25, 2004).

Benzamide, N-(4'-amino-2',3'-dihydro-3',4-diphenyl-2'-thioxo[2,5'-bithiazol]-5-yl)-(CA Index Name)CAS Registry No. 879910-33-5, entered Apr. 10, 2006.

2-Thiazolamine, 4-[5-(2H-tetrazol-5-yl)-2-thienyl]-(CA Index Name), CAS Registry No. 937625-84-8, entered Jun. 17, 2007.

1H-Pyrazole-1-carboxylic acid, 5-[2,2'-bithiophen]-5-yl-, ethyl ester (CA Index Name), CAS Registry No. 957595-63-0, entered Dec. 12, 2007.

4-Thiazolecarboxamide, 2-(4-acetyl-5-methyl-1H-1,2,3-triazol-1-yl)-N,N-diethyl-5-phenyl-(CA Index Name), CAS Registry No. 709639-21-4, entered Jul. 14, 2004.

Database CAS Registry (Columbus, Ohio), RN 893689-50-4 (Entered Jul. 17, 2006).

Database CAS Registry (Columbus, Ohio), RN 893692-42-7 (Entered Jul. 17, 2006).

Database CAS Registry (Columbus, Ohio), RN 893704-20-6 (Entered Jul. 17, 2006).

Database CAS Registry (Columbus, Ohio), RN 893705-40-3 (Entered Jul. 17, 2006).

Database CAs Registry (Columbus, Ohio), RN 898517-78-7 (Entered Aug. 3, 2006).

\* cited by examiner

HETEROARYLS AND USES THEREOF

The present application claims the benefit of U.S. Provisional Application Ser. No. 61/372,594, filed Aug. 11, 2010 (pending), and U.S. Provisional Application Ser. No. 61/438,375, filed Feb. 1, 2011 (pending) which are hereby incorporated by reference in their entirety.

BACKGROUND OF THE INVENTION

Phosphatidylinositol 3-kinase (PI3K) is a family of lipid kinases that phosphorylate phosphatidylinositol at the 3' position of the inositol ring. PI3K is comprised of several classes of genes, including Class IA, IB, II and III and some of these classes contain several isoforms (reviewed in Engelman et al., Nature Review Genetics 7:606-619 (2006)). Adding to the complexity of this family is the fact that PI3Ks function as heterodimers, comprising a catalytic domain and a regulatory domain. The PI3K family is structurally related to a larger group of lipid and serine/threonine protein kinases known as the phosphatidylinositol 3-kinase like kinases (PIKKs), which also includes DNA-PK, ATM, ATR, mTOR, TRRAP and SMG1.

PI3K is activated downstream of various mitogenic signals mediated through receptor tyrosine kinases, and subsequently stimulates a variety of biological outcomes; including increased cell survival, cell cycle progression, cell growth, cell metabolism, cell migration and angiogenesis (reviewed in Cantley, Science 296:1655-57 (2002); Hennessy et al., Nature Reviews Drug Discovery 4:988-1004 (2005); Engelman et al., Nature Review Genetics 7:606-619 (2006)). Thus, PI3K hyper-activation is associated with a number of hyper-proliferative, inflammatory, or cardiovascular disorders; including cancer, inflammation, and cardiovascular disease.

There are a number of genetic aberrations that lead to constitutive PI3K signaling; including activating mutations in PI3K itself (Hennessy et al., Nature Reviews Drug Discovery 4:988-1004 (2005); reviewed in Bader et al., Nature Reviews Cancer 5:921-9 (2005)); RAS (reviewed in Downward Nature Reviews Cancer 3:11-22 (2003)) and upstream receptor tyrosine kinases (reviewed in Zwick et al., Trends in Molecular Medicine 8:17-23 (2002)) as well as inactivating mutations in the tumor suppressor PTEN (reviewed in Cully et al., Nature Reviews Cancer 6:184-92 (2006)). Mutations in each of these gene classes have proven to be oncogenic and are commonly found in a variety of cancers.

The molecules defined within this invention inhibit the activity of PI3K, and therefore may be useful for the treatment of proliferative, inflammatory, or cardiovascular disorders. Cases where PI3K pathway mutations have been linked to proliferative disorders where the molecules defined within this invention may have a therapeutic benefit include benign and malignant tumors and cancers from diverse lineage, including but not limited to those derived from colon (Samuels et al., Science 304:554 (2004); reviewed in Karakas et al., British Journal of Cancer 94: 455-59 (2006)), liver (reviewed in Karakas et al., British Journal of Cancer 94: 455-59 (2006)), intestine (reviewed in Hennessy et al., Nature Reviews Drug Discovery 4:988-1004 (2005)), stomach (Samuels et al., Science 304:554 (2004); reviewed in Karakas et al., British Journal of Cancer 94: 455-59 (2006)), esophagus (Phillips et al., International Journal of Cancer 118:2644-6 (2006)); pancreas (reviewed in Downward Nature Reviews Cancer 3:11-22 (2003)); skin (reviewed in Hennessy et al., Nature Reviews Drug Discovery 4:988-1004 (2005)), prostate (reviewed in Hennessy et al., Nature Reviews Drug Discovery 4:988-1004 (2005)), lung (Samuels et al., Science 304:554 (2004); reviewed in Karakas et al., British Journal of Cancer 94: 455-59 (2006)), breast (Samuels et al., Science 304:554 (2004); Isakoff et al., Can Res 65:10992-1000 (2005); reviewed in Karakas et al., British Journal of Cancer 94: 455-59 (2006)), endometrium (Oda et al., Can Res 65:10669-73 (2005); reviewed in Hennessy et al., Nature Reviews Drug Discovery 4:988-1004 (2005)), cervix (reviewed in Hennessy et al., Nature Reviews Drug Discovery 4:988-1004 (2005)); ovary (Shayesteh et al., Nature Genetics 21:99-102 (1999); reviewed in Karakas et al., British Journal of Cancer 94: 455-59 (2006)), testes (Moul et al., Genes Chromosomes Cancer 5:109-18 (1992); DiVizio et al., Oncogene 24:1882-94 (2005)), hematological cells (reviewed in Karakas et al., British Journal of Cancer 94: 455-59 (2006); Hennessy et al., Nature Reviews Drug Discovery 4:988-1004 (2005)), pancreas (reviewed in Downward Nature Reviews Cancer 3:11-22 (2003)), thyroid (reviewed in Downward Nature Reviews Cancer 3:11-22 (2003); reviewed in Hennessy et al., Nature Reviews Drug Discovery 4:988-1004 (2005)); brain (Samuels et al., Science 304:554 (2004); reviewed in Karakas et al., British Journal of Cancer 94: 455-59 (2006)), bladder (Lopez-Knowles et al., Cancer Research 66:7401-7404 (2006); Hennessy et al., Nature Reviews Drug Discovery 4:988-1004 (2005)); kidney (reviewed in Downward Nature Reviews Cancer 3:11-22 (2003)) and Head and Neck (reviewed in Engelman et al., Nature Reviews Genetics 7:606-619 (2006)).

Other classes of disorders with aberrant PI3K pathway signaling where the molecules defined within this invention may have a therapeutic benefit include inflammatory and cardiovascular diseases, including but not limited to allergies/anaphylaxis (reviewed in Rommel et al., Nature Reviews Immunology 7:191-201 (2007)), acute and chronic inflammation (reviewed in Ruckle et al., Nature Reviews Drug Discovery 5:903-12 (2006); reviewed in Rommel et al., Nature Reviews Immunology 7:191-201 (2007)), rheumatoid arthritis (reviewed in Rommel et al., Nature Reviews Immunology 7:191-201 (2007)); autoimmunity disorders (reviewed in Ruckle et al., Nature Reviews Drug Discovery 5:903-12 (2006)), thrombosis (Jackson et al., Nature Medicine 11:507-14 (2005); reviewed in Ruckle et al., Nature Reviews Drug Discovery 5:903-12 (2006)), hypertension (reviewed in Ruckle et al., Nature Reviews Drug Discovery 5:903-12 (2006)), cardiac hypertrophy (reviewed in Proud et al., Cardiovascular Research 63:403-13 (2004)), and heart failure (reviewed in Mocanu et al., British Journal of Pharmacology 150:833-8 (2007)).

Vacuolar Protein Sorting 34 (VPS34) is the sole Class III PI3K family member. VPS34 functions in the formation and trafficking of multiple intracellular vesicles, including vacuoles, endosomes, multivessicular bodies, lysosomes and autophagosomes (reviewed in Backer Biochem J 2008; Yan and Backer Biochem J 2007). VPS34 carries out these activities by phosphorylating PtdIns forming PtdIns3P, resulting in the recruitment and localization of a variety of FYVE and PX domain containing effector proteins that facilitate vesicular formation, elongation and movement. At a cellular level, inhibition of VPS34 results in defects in protein sorting and autophagy. Broadly defined, autophagy is a regulated process whereby cells catabolize subcellular components targeted for degradation by enclosing them in double-membrane vesicles which then fuse with lysosomes. Autophagy has been best characterized as occurring during times of nutrient deprivation, but also plays a role in normal cellular and tissue homeostasis and functions, including the development of multiple tissue types, the immune response, clearance of neuronal aggregates and tumor suppression. In addition to functioning in vesicle formation and movement, VPS34 may also participate in several signal transduction pathways (reviewed in Backer Biochem J 2008). Given that VPS34 plays an important role in many critical cellular processes including autophagy, inhibitors of VPS34 may have therapeutic application in a number of diseases, including but not limited to cancer, muscular disorders, neurodegeneration, inflammatory disease, infectious disease and other age related illnesses (reviewed in Shintani and Klionshy Science 2004; Kondo et al Nat Rev Cancer 2005; Delgato et al Immunol Rev 2009).

Clearly, it would be beneficial to provide novel PI3K inhibitors that possess good therapeutic properties, especially for the treatment of proliferative, inflammatory, or cardiovascular disorders.

1. General Description of Compounds of the Invention

This invention provides compounds that are inhibitors of PI3K, and accordingly are useful for the treatment of proliferative, inflammatory, or cardiovascular disorders. In one embodiment, the compounds of this invention are represented by formula IA-a or IB-a:

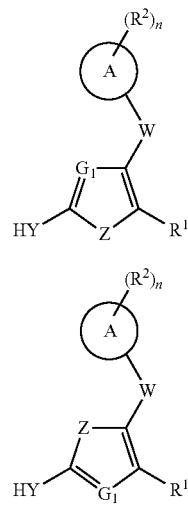

or a pharmaceutically acceptable salt thereof, wherein:
Z is S or Se;
$R^1$ is CY, —C(O)N($R^3$)$_2$, —C(O)O$R^3$, —C(O)(NH)OH, —C(=NH)NHOH, —C(O)N$R^3$N($R^3$)$_2$, —C(=N—NH$_2$)NH$_2$, —C(=N)N($R^3$)$_2$, wherein:
CY is

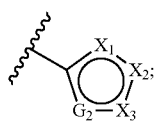

wherein:
$G_2$ is —N=, =N—, or —N($R^{3'}$)—, wherein:
each occurrence of $R^3$ and $R^{3'}$ is independently hydrogen or an optionally substituted $C_{1-6}$ aliphatic, wherein:
$X_1$, $X_2$, and $X_3$, are each independently N, N$R^{3'}$, O, S, or C$R^4$, provided that only one of $X_1$, $X_2$, or $X_3$ may be O, S, or N$R^{3'}$;

each occurrence of $R^4$ is independently hydrogen, —CN, halogen, —$Z_3$—$R^6$, or an optionally substituted group selected from $C_{1-6}$ aliphatic, or 3-10-membered cycloaliphatic, wherein:
$Z_3$ is selected from an optionally substituted $C_{1-3}$ alkylene chain, —O—, —N($R^{4a}$)—, —S—, —S(O)—, —S(O)$_2$—, —C(O)—, —CO$_2$—, —C(O)N$R^{4a}$—, —N($R^{4a}$)C(O)—, —N($R^{4a}$)CO$_2$—, —S(O)$_2$N$R^{4a}$—, —N($R^{4a}$)S(O)$_2$—, —OC(O)N($R^{4a}$)—, —N($R^{4a}$)C(O)N$R^{4a}$—, —N($R^{4a}$)S(O)$_2$N($R^{4a}$)—, or —OC(O)—;
$R^{4a}$ is hydrogen or an optionally substituted $C_{1-4}$ aliphatic, and
$R^6$ is hydrogen or an optionally substituted group selected from $C_{1-6}$ aliphatic,
3-10-membered cycloaliphatic, 4-10-membered heterocyclyl having 1-5 heteroatoms independently selected from nitrogen, oxygen, or sulfur, 6-10-membered aryl, or 5-10-membered heteroaryl having 1-5 heteroatoms independently selected from nitrogen, oxygen, or sulfur;
or wherein two adjacent occurrences of $R^3$ or $R^4$, taken together with the atom to which they are bound, form an optionally substituted fused group selected from 5-6-membered aryl, or 5-6-membered heteroaryl having 1-5 heteroatoms independently selected from nitrogen, oxygen, or sulfur;
Ring A is a group selected from 3-10-membered cycloaliphatic, 4-10-membered heterocyclyl having 1-5 heteroatoms independently selected from nitrogen, oxygen, or sulfur, 6-10-membered aryl, or 5-10-membered heteroaryl having 1-5 heteroatoms independently selected from nitrogen, oxygen, or sulfur;
each occurrence of $R^2$ is independently —$R^{12a}$, -$T_2$-$R^{12d}$, or —$V_2$-$T_2$-$R^{12d}$, and:
each occurrence of $R^{12a}$ is independently halogen, —CN, —NO$_2$, —$R^{12c}$, —N($R^{12b}$)$_2$, OR$^{12b}$, —SR$^{12c}$, —S(O)$_2$R$^{12c}$, —C(O)R$^{12b}$, —C(O)OR$^{12b}$, —C(O)N($R^{12b}$)$_2$, —S(O)$_2$N($R^{12b}$)$_2$, —OC(O)N($R^{12b}$)$_2$, N($R^{12e}$)C(O)R$^{12b}$, —N($R^{12e}$)SO$_2$R$^{12c}$, —N($R^{12e}$)C(O)OR$^{12b}$, —N($R^{12e}$)C(O)N($R^{12b}$)$_2$, or —N($R^{12e}$)SO$_2$N($R^{12b}$)$_2$, or two occurrences of $R^{12b}$, taken together with a nitrogen atom to which they are bound, form an optionally substituted 4-7-membered heterocyclyl ring having 0-1 additional heteroatoms selected from nitrogen, oxygen, or sulfur;
each occurrence of $R^{12b}$ is independently hydrogen or an optionally substituted group selected from $C_1$-$C_6$ aliphatic, 3-10-membered cycloaliphatic, 4-10-membered heterocyclyl having 1-5 heteroatoms independently selected from nitrogen, oxygen, or sulfur, 6-10-membered aryl, or 5-10-membered heteroaryl having 1-5 heteroatoms independently selected from nitrogen, oxygen, or sulfur;
each occurrence of $R^{12c}$ is independently an optionally substituted group selected from $C_1$-$C_6$ aliphatic, 3-10-membered cycloaliphatic, 4-10-membered heterocyclyl having 1-5 heteroatoms independently selected from nitrogen, oxygen, or sulfur, 6-10-membered aryl, or 5-10-membered heteroaryl having 1-5 heteroatoms independently selected from nitrogen, oxygen, or sulfur;
each occurrence of $R^{12d}$ is independently hydrogen or an optionally substituted from 3-10-membered cycloaliphatic, 4-10-membered heterocyclyl having 1-5 heteroatoms independently selected from nitrogen, oxygen, or sulfur, 6-10-membered aryl, or 5-10- membered heteroaryl having 1-5 heteroatoms independently selected from nitrogen, oxygen, or sulfur;
each occurrence of $R^{12e}$ is independently hydrogen or an optionally substituted $C_{1-6}$ aliphatic group;
each occurrence of $V_2$ is independently —N($R^{12e}$)—, —O—, —S—, —S(O)—, —S(O)$_2$—, —C(O)—, —C(O)O—, —C(O)N($R^{12e}$)—, —S(O)$_2$N($R^{12e}$)—, —OC(O)N($R^{12e}$)—, —N($R^{12e}$)C(O)—, —N($R^{12e}$)SO$_2$—, —N($R^{12e}$)C(O)O—, —N($R^{12e}$)C(O)N($R^{12e}$)—, —N($R^{12e}$)SO$_2$N($R^{12e}$)—, —OC(O)—, or —C(O)N($R^{12e}$)—O—; and
$T_2$ is an optionally substituted $C_1$-$C_6$ alkylene chain wherein the alkylene chain optionally is interrupted by —N($R^{13}$)—, —O—, —S—, —S(O)—, —S(O)$_2$—, —C(O)—, —C(O)O—, —C(O)N($R^{13}$)—, —S(O)$_2$N($R^{13}$)—, —OC(O)N($R^{13}$)—, —N($R^{13}$)C(O)—, —N($R^{13}$)SO$_2$—, —N($R^{13}$)C(O)O—, —N($R^{13}$)C(O)N($R^{13}$)—, —N($R^{13}$)S(O)$_2$N($R^{13}$)—, —OC(O)—, or —C(O)N($R^{13}$)—O— or wherein $T_2$ or a portion thereof optionally forms part of an optionally substituted 3-7 membered cycloaliphatic or heterocyclyl ring, wherein $R^{13}$ is hydrogen or an optionally substituted $C_{1-4}$ aliphatic group;
n is 0 to 4;
W is selected from —C($R^7$)$_2$—, —C(=C($R^7$)$_2$)—, —C($R^7$)$_2$O—, —C($R^7$)$_2$N$R^{7a}$—, —O—, —N($R^{7b}$)—, —S—, —S(O)—, —S(O)$_2$—, —C(O)—, —C(O)N$R^{7a}$—, or —N($R^{7a}$)C(O)—, wherein:
  each occurrence of $R^7$ is independently hydrogen, or an optionally substituted group selected from $C_{1-6}$ aliphatic, 6-10-membered aryl, 5-10-membered heteroaryl having 1-5 heteroatoms independently selected from nitrogen, oxygen, or sulfur, —N($R^{7b}$)$_2$, —O$R^{7a}$, —S$R^{7a}$, halo, or —CN;
  each occurrence of $R^{7a}$ is independently hydrogen or optionally substituted $C_{1-6}$ aliphatic or optionally substituted $C_{3-6}$ cycloaliphatic;
  each occurrence of $R^{7b}$ is independently hydrogen, optionally substituted $C_{1-6}$ aliphatic, optionally substituted $C_{3-6}$ cycloaliphatic, —C(O)$R^{7a}$, —C(O)O$R^{7a}$, S(O)$R^{7a}$, or —S(O)$_2R^{7a}$; or
  wherein any two occurrences of $R^7$, $R^{7a}$, or $R^{7b}$ taken together with the atom to which they are bound, form an optionally substituted group selected from a 3-6-membered cycloaliphatic ring, 6-10-membered aryl, 3-6-membered heterocyclyl having 1-5 heteroatoms independently selected from nitrogen, oxygen, or sulfur, or 5-10-membered heteroaryl having 1-5 heteroatoms independently selected from nitrogen, oxygen, or sulfur;
  or wherein any two occurrences of $R^{7a}$ and $R^2$, or $R^{7b}$ and $R^2$ taken together with the nitrogen atom to which they are bound, form an optionally substituted group selected from 3-6-membered heterocyclyl having 1-5 heteroatoms independently selected from nitrogen, oxygen, or sulfur, or 5-10-membered heteroaryl having 1-5 heteroatoms independently selected from nitrogen, oxygen, or sulfur;
$G_1$ is N or —C$R^8$, wherein $R^8$ is H, —CN, halogen, —$Z_2$—$R^9$, $C_{1-6}$ aliphatic, or 3-10-membered cycloaliphatic, wherein:
  $Z_2$ is selected from an optionally substituted $C_{1-3}$ alkylene chain, —O—, —N($R^{8a}$)—, —S—, —S(O)—, S(O)$_2$—, —C(O)—, —CO$_2$—, —C(O)N$R^{8a}$, —N($R^{8a}$)C(O)—, —N($R^{8a}$)CO$_2$—, —S(O)$_2$N$R^{8a}$—, —N($R^{8a}$)S(O)$_2$—, —OC(O)N($R^{8a}$)—, —N($R^{8a}$)C(O)N$R^{8a}$—, —N($R^{8a}$)S(O)$_2$N($R^{8a}$)—, or —OC(O)—;
  $R^{8a}$ is hydrogen or an optionally substituted $C_{1-4}$ aliphatic, and $R^9$ is hydrogen or an optionally substituted group selected from $C_{1-6}$ aliphatic, 3-10-membered cycloaliphatic, 4-10-membered heterocyclyl having 1-5 heteroatoms independently selected from nitrogen, oxygen, or sulfur, 6-10-membered aryl, or 5-10-membered heteroaryl having 1-5 heteroatoms independently selected from nitrogen, oxygen, or sulfur; and
HY is an optionally substituted group selected from:

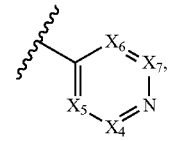
A

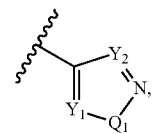
B

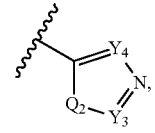
C

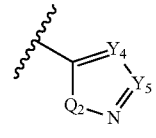
D

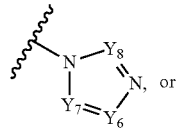
E

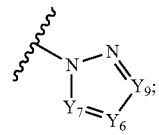
F wherein each occurrence of $X_4$, $X_5$, $X_6$, and $X_7$ is independently —$CR^{10}$ or N, provided no more than two occurrences of $X_4$, $X_5$, $X_6$, and $X_7$ are N;
each occurrence of $Q_1$ and $Q_2$ is independently S, O or —$NR^5$;
each occurrence of $Y_1$, $Y_2$, $Y_3$, $Y_4$, $Y_5$, $Y_6$, $Y_7$, $Y_8$, and $Y_9$ is independently —$CR^{10}$ or N, provided no more than two occurrences of $Y_6$, $Y_7$, $Y_8$, and $Y_9$ are N;
  or wherein two adjacent occurrences of $X_4$ and $X_5$, $X_6$ and $X_7$, $Y_1$ and $Q_1$, $Y_3$ and $Q_2$, or $Y_4$ and $Y_5$ taken together with the atom to which they are bound, form an optionally substituted fused group selected from 5-6-membered aryl, or 5-6-membered heteroaryl having 1-5 heteroatoms independently selected from nitrogen, oxygen, or sulfur;
wherein $R^{10}$ is —$R^{10b}$, —$V_1$—$R^{10c}$, -$T_1$-$R^{10b}$, —$V_1$-$T_1$-$R^{10b}$ wherein:
  $V_1$ is —$NR^{11}$—, —$NR^{11}$—C(O)—, —$NR^{11}$—C(S)—, —$NR^{11}$—C($NR^{11}$)—, —$NR^{11}$C(O)O$R^{10a}$—, —$NR^{11}$C(O)N$R^{11}$—, —$NR^{11}$C(O)S$R^{10a}$—, —$NR^{11}$C (S)OR$^{10a}$—, —NR$^{11}$C(S)NR$^{11}$—, —NR$^{11}$C(S)SR$^{10a}$—, —NR$^{11}$C(NR$^{11}$)OR$^{10a}$—, —NR$^{11}$C(NR$^{11}$)NR$^{11}$—, —NR$^{11}$S(O)$_2$—, —NR$^{11}$S(O)$_2$NR$^{11}$—, —C(O)—, —CO$_2$—, —C(O)NR$^{11}$—, —C(O)NR$^{11}$O—, —SO$_2$—, or —SO$_2$NR$^{11}$—;

each occurrence of R$^{10a}$ is independently hydrogen or an optionally substituted group selected from C$_{1-6}$ aliphatic, 3-10-membered cycloaliphatic, 4-10-membered heterocyclyl having 1-5 heteroatoms independently selected from nitrogen, oxygen, or sulfur, 6-10-membered aryl, or 5-10-membered heteroaryl having 1-5 heteroatoms independently selected from nitrogen, oxygen, or sulfur;

T$_1$ is an optionally substituted C$_1$-C$_6$alkylene chain wherein the alkylene chain optionally is interrupted by —N(R$^{11}$)—, —O—, —S—, —S(O)—, —S(O)$_2$—, —C(O)—, —C(O)O—, —C(O)N(R$^{11}$)—, —S(O)$_2$N(R$^{11}$)—, —OC(O)N(R$^{11}$)—, —N(R$^{11}$)C(O)—, —N(R$^{11}$)SO$_2$—, —N(R$^{11a}$)C(O)O—, —NR$^{10a}$C(O)N(R$^{10a}$)—, —N(R$^{10a}$)S(O)$_2$N(R$^{10a}$)—, —OC(O)—, or —C(O)N(R$^{11}$)—O— or wherein T$_1$ forms part of an optionally substituted 3-7 membered cycloaliphatic or heterocyclyl ring;

each occurrence of R$^{10b}$ is independently hydrogen, halogen, —CN, —NO$_2$, —N(R$^{11}$)$_2$, —OR$^{10a}$, —SR$^{10a}$, —S(O)$_2$R$^{10a}$, —C(O)R$^{10a}$, —C(O)OR$^{10a}$, —C(O)N(R$^{11}$)$_2$, —S(O)$_2$N(R$^{11}$)$_2$, —OC(O)N(R$^{11}$)$_2$, —N(R$^{11}$)C(O)R$^{10a}$, —N(R$^{11}$)SO$_2$R$^{10a}$, —N(R$^{11}$)C(O)OR$^{10a}$, —N(R$^{11}$)C(O)N(R$^{11}$)$_2$, or —N(R$^{11}$)SO$_2$N(R$^{11}$)$_2$, or an optionally substituted group selected from C$_{1-6}$ aliphatic, 3-10-membered cycloaliphatic, 4-10-membered heterocyclyl having 1-5 heteroatoms independently selected from nitrogen, oxygen, or sulfur, 6-10-membered aryl, or 5-10-membered heteroaryl having 1-5 heteroatoms independently selected from nitrogen, oxygen, or sulfur;

each occurrence of R$^{10c}$ is independently hydrogen or an optionally substituted group selected from C$_{1-6}$ aliphatic, 3-10-membered cycloaliphatic, 4-10-membered heterocyclyl having 1-5 heteroatoms independently selected from nitrogen, oxygen, or sulfur, 6-10-membered aryl, or 5-10-membered heteroaryl having 1-5 heteroatoms independently selected from nitrogen, oxygen, or sulfur, or R$^{10a}$ and R$^{10c}$ taken together with a nitrogen atom to which they are bound form an optionally substituted 4-7-membered heterocyclyl ring having 0-1 additional heteroatoms independently selected from nitrogen, oxygen, or sulfur;

each occurrence of R$^{11}$ is independently hydrogen, —C(O)R$^{11a}$, —CO$_2$R$^{11a}$, —C(O)N(R$^{11a}$)$_2$, —C(O)N(R$^{11a}$)—OR$^{11a}$, —SO$_2$R$^{11a}$, —SO$_2$N(R$^{11a}$)$_2$, or an optionally substituted group selected from C$_{1-6}$ aliphatic, 3-10-membered cycloaliphatic, 4-10-membered heterocyclyl having 1-5 heteroatoms independently selected from nitrogen, oxygen, or sulfur, 6-10-membered aryl, or 5-10-membered heteroaryl having 1-5 heteroatoms independently selected from nitrogen, oxygen, or sulfur;

wherein each occurrence of R$^{11a}$ is independently hydrogen or an optionally substituted group selected from C$_{1-6}$aliphatic, 3-10-membered cycloaliphatic, 4-10-membered heterocyclyl having 1-5 heteroatoms independently selected from nitrogen, oxygen, or sulfur, 6-10-membered aryl, or 5-10-membered heteroaryl having 1-5 heteroatoms independently selected from nitrogen, oxygen, or sulfur;

each occurrence of R$^5$ is independently hydrogen, —C(O)R$^{5a}$, —CO$_2$R$^{5a}$, —C(O)N(R$^{5b}$)$_2$, —SO$_2$R$^{5a}$, —SO$_2$N(R$^{5b}$)$_2$, or an optionally substituted group selected from C$_{1-6}$ aliphatic, 3-10-membered cycloaliphatic, 4-10-membered heterocyclyl having 1-5 heteroatoms independently selected from nitrogen, oxygen, or sulfur, 6-10-membered aryl, or 5-10-membered heteroaryl having 1-5 heteratoms independently selected from nitrogen, oxygen, or sulfur;

wherein each occurrence of R$^{5a}$ is independently hydrogen or an optionally substituted group selected from C$_{1-6}$ aliphatic, 3-10-membered cycloaliphatic, 4-10-membered heterocyclyl having 1-5 heteroatoms independently selected from nitrogen, oxygen, or sulfur, 6-10-membered aryl, or 5-10-membered heteroaryl having 1-5 heteroatoms independently selected from nitrogen, oxygen, or sulfur;

wherein each occurrence of R$^{5b}$ is independently hydrogen or an optionally substituted group selected from C$_{1-6}$ aliphatic, 3-10-membered cycloaliphatic, 4-10-membered heterocyclyl having 1-5 heteroatoms independently selected from nitrogen, oxygen, or sulfur, 6-10-membered aryl, or 5-10-membered heteroaryl having 1-5 heteratoms independently selected from nitrogen, oxygen, or sulfur; or two occurrences of R$^{5b}$ taken together with the nitrogen atom to which they are bound, form an optionally substituted group selected from 3-6-membered heterocyclyl having 1-5 heteroatoms independently selected from nitrogen, oxygen, or sulfur, or 5-10-membered heteroaryl having 1-5 heteroatoms independently selected from nitrogen, oxygen, or sulfur, provided that:

a) for compounds of formula IB-a compounds are other than:

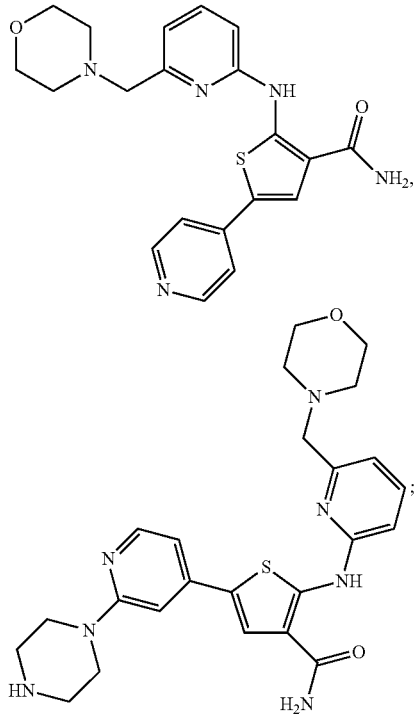

and when G$^1$ is CR$^8$, R$^1$ is CONH$_2$, and W is NH, then HY is other than

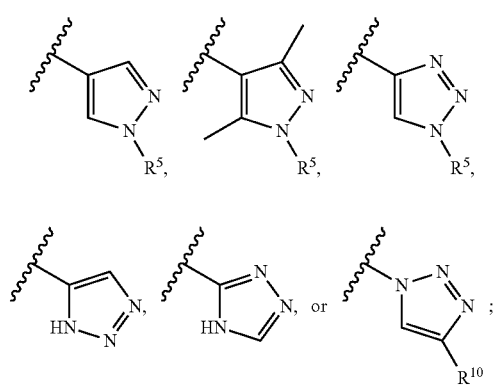
and
b) the compound is other than:
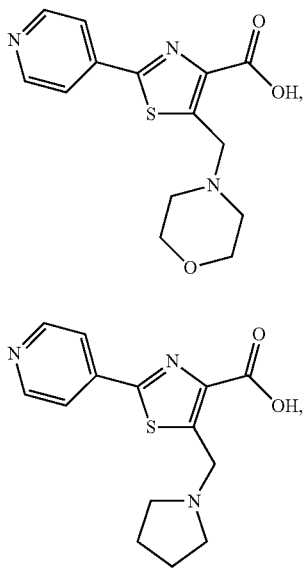
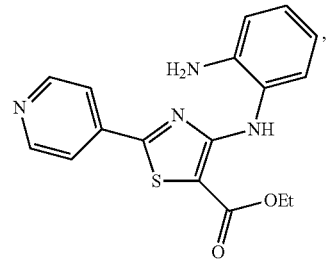
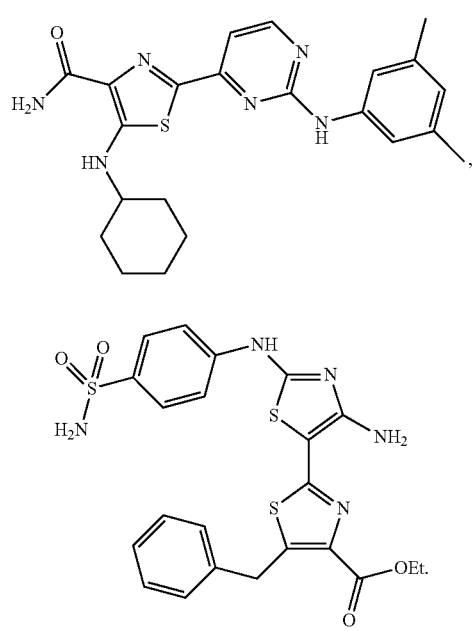
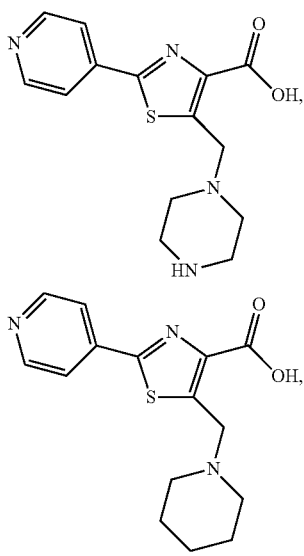
In another embodiment, the compounds of this invention are represented by formula IA or IB:
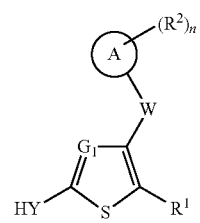
IA
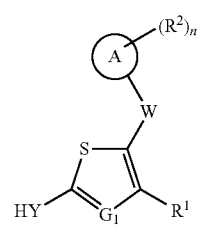
IB
or a pharmaceutically acceptable salt thereof, wherein:
$R^1$ is CY, —C(O)N($R^3$)$_2$, —C(O)O$R^3$, —C(O)(NH)OH, —C(=NH)NHOH, —C(O)N$R^3$N($R^3$)$_2$, —C(=N—NH$_2$)NH$_2$, —C(=N)N($R^3$)$_2$, wherein:

CY is an optionally substituted group selected from:

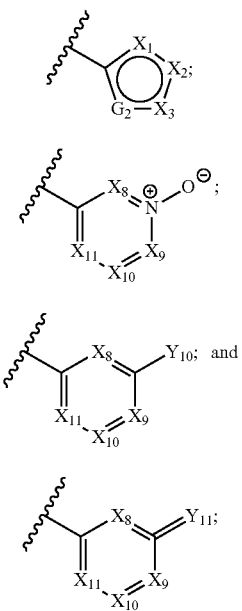

wherein:
G$_2$ is —N=, =N—, or —N(R$^{3'}$)—, wherein:
each occurrence of R$^3$ and R$^{3'}$ is independently hydrogen or an optionally substituted C$_{1-6}$ aliphatic, wherein:
X$_1$, X$_2$, and X$_3$, are each independently N, NR$^{3'}$, O, S, or CR$^4$, provided that only one of X$_1$, X$_2$, or X$_3$ may be O, S, or NR$^{3'}$;
X$_8$, X$_9$, X$_{10}$, and X$_{11}$ are each independently N, or CR$^4$, provided no more than two occurrences of X$_8$, X$_9$, X$_{10}$, and X$_{11}$ are N;
each occurrence of R$^4$ is independently hydrogen, —CN, halogen, —Z$_3$—R$^6$, or an optionally substituted group selected from C$_{1-6}$ aliphatic, or 3-10-membered cycloaliphatic, wherein:
Z$_3$ is selected from an optionally substituted C$_{1-3}$ alkylene chain, —O—, —N(R$^{4a}$)—, —S—, —S(O)—, —S(O)$_2$—, —C(O)—, —CO$_2$—, —C(O)NR$^{4a}$—, —N(R$^{4a}$)C(O)—, —N(R$^{4a}$)CO$_2$—, —S(O)$_2$NR$^{4a}$—, —N(R$^{4a}$)S(O)$_2$—, —OC(O)N(R$^{4a}$)—, —N(R$^{4a}$)C(O)NR$^{4a}$—, —N(R$^{4a}$)S(O)$_2$N(R$^{4a}$)—, or —OC(O)—;
R$^{4a}$ is hydrogen or an optionally substituted C$_{1-4}$ aliphatic, and
R$^6$ is hydrogen or an optionally substituted group selected from C$_{1-6}$ aliphatic, 3-10-membered cycloaliphatic, 4-10-membered heterocyclyl having 1-5 heteroatoms independently selected from nitrogen, oxygen, or sulfur, 6-10-membered aryl, or 5-10-membered heteroaryl having 1-5 heteroatoms independently selected from nitrogen, oxygen, or sulfur;
or wherein two adjacent occurrences of R$^{3'}$ or R$^4$, taken together with the atom to which they are bound, form an optionally substituted fused group selected from 5-6-membered aryl, or 5-6-membered heteroaryl having 1-5 heteroatoms independently selected from nitrogen, oxygen, or sulfur;
Y$_{10}$ is —OR$^{4'}$ or —N(R$^{4'}$)$_2$;
Y$_{11}$ is O or N—R$^{4'}$;
each occurrence of R$^{4'}$ is independently hydrogen or an optionally substituted C$_{1-6}$ aliphatic;
Ring A is a group selected from 3-10-membered cycloaliphatic, 4-10-membered heterocyclyl having 1-5 heteroatoms independently selected from nitrogen, oxygen, or sulfur, 6-10-membered aryl, or 5-10-membered heteroaryl having 1-5 heteroatoms independently selected from nitrogen, oxygen, or sulfur;
each occurrence of R$^2$ is independently —R$^{12a}$, or -T$_2$-R$^{12d}$, —V$_2$-T$_2$-R$^{12d}$, and:
each occurrence of R$^{12a}$ is independently halogen, —CN, —NO$_2$, —R$^{12c}$, —N(R$^{12b}$)$_2$, OR$^{12b}$, —SR$^{12c}$, —S(O)$_2$R$^{12c}$, —C(O)R$^{12b}$, —C(O)OR$^{12b}$, —C(O)N(R$^{12b}$)$_2$, —S(O)$_2$N(R$^{12b}$)$_2$, —OC(O)N(R$^{12b}$)$_2$, —N(R$^{12e}$)C(O)R$^{12b}$, —N(R$^{12e}$)SO$_2$R$^{12c}$, —N(R$^{12e}$)C(O)OR$^{12b}$, —N(R$^{12e}$)C(O)N(R$^{12b}$)$_2$, or —N(R$^{12e}$)SO$_2$N(R$^{12b}$)$_2$, or two occurrences of R$^{12b}$, taken together with a nitrogen atom to which they are bound, form an optionally substituted 4-7-membered heterocyclyl ring having 0-1 additional heteroatoms selected from nitrogen, oxygen, or sulfur;
each occurrence of R$^{12b}$ is independently hydrogen or an optionally substituted group selected from C$_1$-C$_6$ aliphatic, 3-10-membered cycloaliphatic, 4-10-membered heterocyclyl having 1-5 heteroatoms independently selected from nitrogen, oxygen, or sulfur, 6-10-membered aryl, or 5-10-membered heteroaryl having 1-5 heteroatoms independently selected from nitrogen, oxygen, or sulfur;
each occurrence of R$^{12c}$ is independently an optionally substituted group selected from C$_1$-C$_6$ aliphatic, 3-10-membered cycloaliphatic, 4-10-membered heterocyclyl having 1-5 heteroatoms independently selected from nitrogen, oxygen, or sulfur, 6-10-membered aryl, or 5-10-membered heteroaryl having 1-5 heteroatoms independently selected from nitrogen, oxygen, or sulfur;
each occurrence of R$^{12d}$ is independently hydrogen or an optionally substituted from 3-10-membered cycloaliphatic, 4-10-membered heterocyclyl having 1-5 heteroatoms independently selected from nitrogen, oxygen, or sulfur, 6-10-membered aryl, or 5-10-membered heteroaryl having 1-5 heteroatoms independently selected from nitrogen, oxygen, or sulfur;
each occurrence of R$^{12e}$ is independently hydrogen or an optionally substituted C$_{1-6}$ aliphatic group;
each occurrence of V$_2$ is independently —N(R$^{12e}$)—, —O—, —S—, —S(O)—, —S(O)$_2$—, —C(O)—, —C(O)O—, —C(O)N(R$^{12e}$)—, —S(O)$_2$N(R$^{12e}$)—, —OC(O)N(R$^{12e}$)—, —N(R$^{12e}$)C(O)—, —N(R$^{12e}$)SO$_2$—, —N(R$^{12e}$)C(O)O—, —N(R$^{12e}$)C(O)N(R$^{12a}$)—, —N(R$^{12e}$)SO$_2$N(R$^{12e}$)—, —OC(O)—, or —C(O)N(R$^{12a}$)—O—; and
T$_2$ is an optionally substituted C$_1$-C$_6$alkylene chain wherein the alkylene chain optionally is interrupted by —N(R$^{13}$)—, —O—, —S—, —S(O)—, —S(O)$_2$—, —C(O)—, —C(O)O—, —C(O)N(R$^{13}$)—, —S(O)$_2$N(R$^{13}$)—, —OC(O)N(R$^{13}$)—, —N(R$^{13}$)C(O)—, —N(R$^{13}$)SO$_2$—, —N(R$^{13}$)C(O)O—, —N(R$^{13}$)C(O)N(R$^{13}$)—, —N(R$^{13}$)S(O)$_2$N(R$^{13}$)—, —OC(O)—, or —C(O)N(R$^{13}$)—O— or wherein T$_2$ or a portion thereof optionally forms part of an optionally substituted 3-7 membered cycloaliphatic or heterocyclyl ring, wherein R$^{13}$ is hydrogen or an optionally substituted C$_{1-4}$aliphatic group;
n is 0 to 4;

W is selected from —C(R$^7$)$_2$—, —C(=C(R$^7$)$_2$)—, —C(R$^7$)$_2$O—, —C(R$^7$)$_2$NR$^{7a}$—, —O—, —N(R$^{7b}$)—, —S—, —S(O)—, —S(O)$_2$—, —C(O)—, —C(O)NR$^{7a}$—, or —N(R$^{7a}$)C(O)—, wherein:

each occurrence of R$^7$ is independently hydrogen, or an optionally substituted group selected from C$_{1-6}$ aliphatic, 6-10-membered aryl, 5-10-membered heteroaryl having 1-5 heteroatoms independently selected from nitrogen, oxygen, or sulfur, —N(R$^{7b}$)$_2$, —OR$^{7a}$, —SR$^{7a}$, halo, or —CN;

each occurrence of R$^{7a}$ is independently hydrogen or optionally substituted C$_{1-6}$ aliphatic or optionally substituted C$_{3-6}$ cycloaliphatic;

each occurrence of R$^{7b}$ is independently hydrogen, optionally substituted C$_{1-6}$ aliphatic, optionally substituted C$_{3-6}$ cycloaliphatic, —C(O)R$^{7a}$, —C(O)OR$^{7a}$, S(O)R$^{7a}$, or —S(O)$_2$R$^{7a}$; or wherein any two occurrences of R$^7$, R$^{7a}$, or R$^{7b}$ taken together with the atom to which they are bound, form an optionally substituted group selected from a 3-6-membered cycloaliphatic ring, 6-10-membered aryl, 3-6-membered heterocyclyl having 1-5 heteroatoms independently selected from nitrogen, oxygen, or sulfur, or 5-10-membered heteroaryl having 1-5 heteroatoms independently selected from nitrogen, oxygen, or sulfur;

or wherein any two occurrences of R$^{7a}$ and R$^2$, or R$^{7b}$ and R$^2$ taken together with the nitrogen atom to which they are bound, form an optionally substituted group selected from 3-6-membered heterocyclyl having 1-5 heteroatoms independently selected from nitrogen, oxygen, or sulfur, or 5-10-membered heteroaryl having 1-5 heteroatoms independently selected from nitrogen, oxygen, or sulfur;

G$_1$ is N or —CR$^8$, wherein R$^8$ is H, —CN, halogen, —Z$_2$—R$^9$, C$_{1-6}$ aliphatic, or 3-10-membered cycloaliphatic, wherein:

Z$_2$ is selected from an optionally substituted C$_{1-3}$ alkylene chain, —O—, —N(R$^{8a}$)—, —S—, —S(O)—, S(O)$_2$—, —C(O)—, —CO$_2$—, —C(O)NR$^{8a}$—, —N(R$^{8a}$)C(O)—, —N(R$^{8a}$)CO$_2$—, —S(O)$_2$NR$^{8a}$—, —N(R$^{8a}$)S(O)$_2$—, —OC(O)N(R$^{8a}$)—, —N(R$^{8a}$)C(O)NR$^{8a}$—, —N(R$^{8a}$)S(O)$_2$N(R$^{8a}$)—, or —OC(O)—;

R$^{8a}$ is hydrogen or an optionally substituted C$_{1-4}$ aliphatic, and

R$^9$ is hydrogen or an optionally substituted group selected from C$_{1-6}$ aliphatic, 3-10-membered cycloaliphatic, 4-10-membered heterocyclyl having 1-5 heteroatoms independently selected from nitrogen, oxygen, or sulfur, 6-10-membered aryl, or 5-10-membered heteroaryl having 1-5 heteroatoms independently selected from nitrogen, oxygen, or sulfur; and HY is an optionally substituted group selected from:

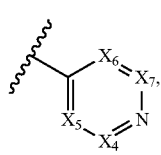

A

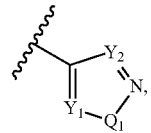

B

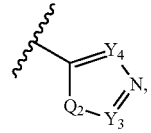

C

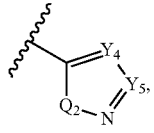

D

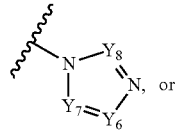

E, or

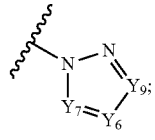

F wherein each occurrence of X$_4$, X$_5$, X$_6$, and X$_7$ is independently —CR$^{10}$ or N, provided no more than two occurrences of X$_4$, X$_5$, X$_6$, and X$_7$ are N;

each occurrence of Q$_1$ and Q$_2$ is independently S, O or —NR$^5$;

each occurrence of Y$_1$, Y$_2$, Y$_3$, Y$_4$, Y$_5$, Y$_6$, Y$_7$, Y$_8$, and Y$_9$ is independently —CR$^{10}$ or N, provided no more than two occurrences of Y$_6$, Y$_7$, Y$_8$, and Y$_9$ are N;

or wherein two adjacent occurrences of X$_4$ and X$_5$, X$_6$ and X$_7$, Y$_1$ and Q$_1$, Y$_3$ and Q$_2$, or Y$_4$ and Y$_5$ taken together with the atom to which they are bound, form an optionally substituted fused group selected from 5-6-membered aryl, or 5-6-membered heteroaryl having 1-5 heteroatoms independently selected from nitrogen, oxygen, or sulfur;

wherein R$^{10}$ is —R$^{10b}$, —V$_1$—R$^{10c}$, -T$_1$-R$^{10b}$, or —V$_1$-T$_1$-R$^{10b}$ wherein:

V$_1$ is —NR$^{11}$—, —NR$^{11}$—C(O)—, —NR$^{11}$—C(S)—, —NR$^{11}$—C(NR$^{11}$)—, —NR$^{11}$C(O)OR$^{10a}$—, —NR$^{11}$C(O)NR$^{11}$—, —NR$^{11}$C(O)SR$^{10a}$—, —NR$^{11}$C(S)OR$^{10a}$—, —NR$^{11}$C(S)NR$^{11}$—, —NR$^{11}$C(S)SR$^{10a}$—, —NR$^{11}$C(NR$^{11}$)OR$^{10a}$—, —NR$^{11}$C(NR$^{11}$)NR$^{11}$—, —NR$^{11}$S(O)$_2$—, —NR$^{11}$S(O)$_2$NR$^{11}$—, —C(O)—, —CO$_2$—, —C(O)NR$^{11}$—, —C(O)NR$^{11}$O—, —SO$_2$—, or —SO$_2$NR$^{11}$—;

each occurrence of R$^{10a}$ is independently hydrogen or an optionally substituted group selected from C$_{1-6}$ aliphatic, 3-10-membered cycloaliphatic, 4-10-membered heterocyclyl having 1-5 heteroatoms independently selected from nitrogen, oxygen, or sulfur, 6-10-membered aryl, or 5-10-membered heteroaryl having 1-5 heteroatoms independently selected from nitrogen, oxygen, or sulfur;

T$_1$ is an optionally substituted C$_1$-C$_6$ alkylene chain wherein the alkylene chain optionally is interrupted by —N(R$^{11}$)—, —O—, —S—, —S(O)—, —S(O)$_2$—, —C(O)—, —C(O)O—, —C(O)N(R$^{11}$)—, —S(O)$_2$N(R$^{11}$)—, —OC(O)N(R$^{11}$)—, —N(R$^{11}$)C(O)—, —N(R$^{11}$)SO$_2$—, —N(R$^{11a}$)C(O)O—, —NR$^{10a}$C(O)N(R$^{10a}$)—, —N(R$^{10a}$)S(O)$_2$N(R$^{10a}$)—, —OC(O)—, or —C(O)N(R$^{11}$)—O— or wherein T$_1$ forms part of an optionally substituted 3-7 membered cycloaliphatic or heterocyclyl ring;

each occurrence of R$^{10b}$ is independently hydrogen, halogen, —CN, —NO$_2$, —N(R$^{11}$)$_2$, —OR$^{10a}$, —SR$^{10a}$, —S(O)$_2$R$^{10a}$, —C(O)R$^{10a}$, —C(O)OR$^{10a}$, —C(O)N(R$^{11}$)$_2$, —S(O)$_2$N(R$^{11}$)$_2$, —OC(O)N(R$^{11}$)$_2$, —N(R$^{11}$)C(O)R$^{10a}$, —N(R$^{11}$)SO$_2$R$^{10a}$, —N(R$^{11}$)C(O)OR$^{10a}$, —N(R$^{11}$)C(O)N(R$^{11}$)$_2$, or —N(R$^{11}$)SO$_2$N(R$^{11}$)$_2$, or an optionally substituted group selected from C$_{1-6}$ aliphatic, 3-10-membered cycloaliphatic, 4-10-membered heterocyclyl having 1-5 heteroatoms independently selected from nitrogen, oxygen, or sulfur, 6-10-membered aryl, or 5-10-membered heteroaryl having 1-5 heteroatoms independently selected from nitrogen, oxygen, or sulfur;

each occurrence of R$^{10c}$ is independently hydrogen or an optionally substituted group selected from C$_{1-6}$ aliphatic, 3-10-membered cycloaliphatic, 4-10-membered heterocyclyl having 1-5 heteroatoms independently selected from nitrogen, oxygen, or sulfur, 6-10-membered aryl, or 5-10-membered heteroaryl having 1-5 heteroatoms independently selected from nitrogen, oxygen, or sulfur, or R$^{10a}$ and R$^{10c}$ taken together with a nitrogen atom to which they are bound form an optionally substituted 4-7-membered heterocyclyl ring having 0-1 additional heteroatoms independently selected from nitrogen, oxygen, or sulfur;

each occurrence of R$^{11}$ is independently hydrogen, —C(O)R$^{11a}$, —CO$_2$R$^{11a}$, —C(O)N(R$^{11a}$)$_2$, —C(O)N(R$^{11a}$)—OR$^{11a}$, —SO$_2$R$^{11a}$, —SO$_2$N(R$^{11a}$)$_2$, or an optionally substituted group selected from C$_{1-6}$ aliphatic, 3-10-membered cycloaliphatic, 4-10-membered heterocyclyl having 1-5 heteroatoms independently selected from nitrogen, oxygen, or sulfur, 6-10-membered aryl, or 5-10-membered heteroaryl having 1-5 heteroatoms independently selected from nitrogen, oxygen, or sulfur;

wherein each occurrence of R$^{11a}$ is independently hydrogen or an optionally substituted group selected from C$_{1-6}$aliphatic, 3-10-membered cycloaliphatic, 4-10-membered heterocyclyl having 1-5 heteroatoms independently selected from nitrogen, oxygen, or sulfur, 6-10-membered aryl, or 5-10-membered heteroaryl having 1-5 heteroatoms independently selected from nitrogen, oxygen, or sulfur;

each occurrence of R$^5$ is independently hydrogen, —C(O)R$^{5a}$, —CO$_2$R$^{5a}$, —C(O)N(R$^{5b}$)$_2$, —SO$_2$R$^{5a}$, —SO$_2$N(R$^{5b}$)$_2$, or an optionally substituted group selected from C$_{1-6}$ aliphatic, 3-10-membered cycloaliphatic, 4-10-membered heterocyclyl having 1-5 heteroatoms independently selected from nitrogen, oxygen, or sulfur, 6-10-membered aryl, or 5-10-membered heteroaryl having 1-5 heteratoms independently selected from nitrogen, oxygen, or sulfur;

wherein each occurrence of R$^{5a}$ is independently hydrogen or an optionally substituted group selected from C$_{1-6}$ aliphatic, 3-10-membered cycloaliphatic, 4-10-membered heterocyclyl having 1-5 heteroatoms independently selected from nitrogen, oxygen, or sulfur, 6-10-membered aryl, or 5-10-membered heteroaryl having 1-5 heteroatoms independently selected from nitrogen, oxygen, or sulfur;

wherein each occurrence of R$^{5b}$ is independently hydrogen or an optionally substituted group selected from C$_{1-6}$ aliphatic, 3-10-membered cycloaliphatic, 4-10-membered heterocyclyl having 1-5 heteroatoms independently selected from nitrogen, oxygen, or sulfur, 6-10-membered aryl, or 5-10-membered heteroaryl having 1-5 heteratoms independently selected from nitrogen, oxygen, or sulfur; or two occurrences of R$^{5b}$ taken together with the nitrogen atom to which they are bound, form an optionally substituted group selected from 3-6-membered heterocyclyl having 1-5 heteroatoms independently selected from nitrogen, oxygen, or sulfur, or 5-10-membered heteroaryl having 1-5 heteroatoms independently selected from nitrogen, oxygen, or sulfur;

provided that:
a) for compounds of formula IB compounds are other than:

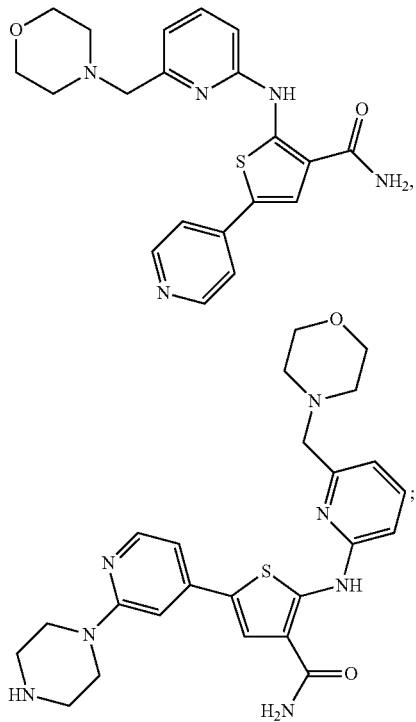

and
when G$^1$ is CR$^8$, R$^1$ is CONH$_2$, and W is NH, then HY is other than

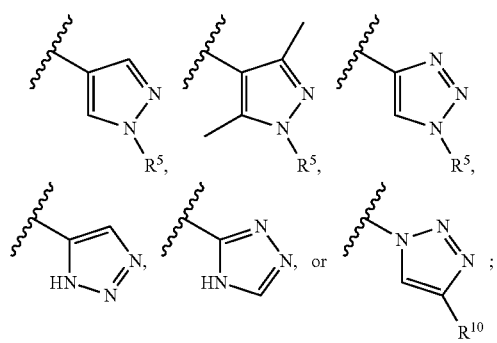

and b) the compound is other than:

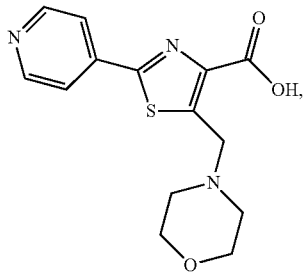

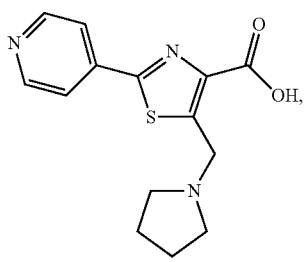

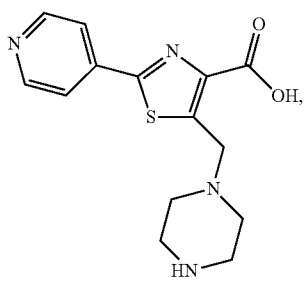

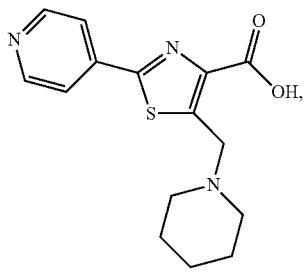

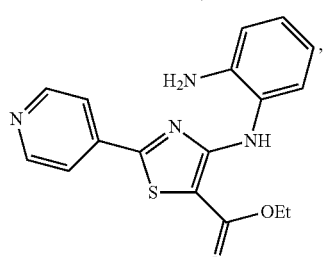

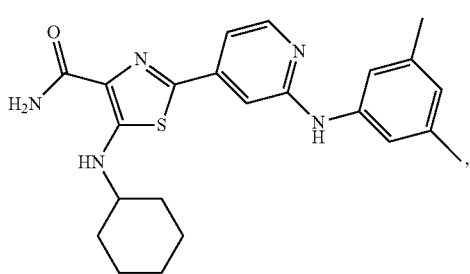

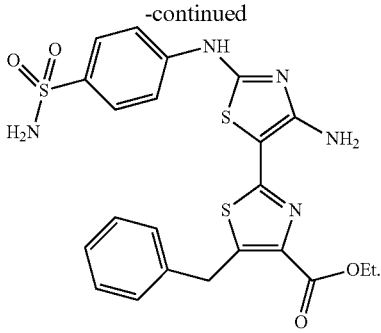

In another aspect, the compounds of this invention are represented by formula IA or IB:

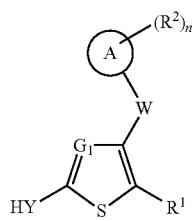

IA

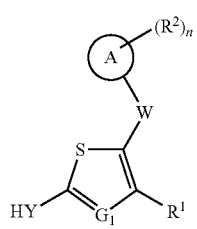

IB or a pharmaceutically acceptable salt thereof, wherein:
$R^1$ is CY, —C(O)N($R^3$)$_2$, —C(O)O$R^3$, —C(O)(NH)OH, —C(=NH)NHOH, —C(O)N$R^3$N($R^3$)$_2$, —C(=N—NH$_2$)NH$_2$, —C(=N)N($R^3$)$_2$, wherein:
CY is

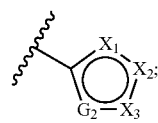

wherein:
$G_2$ is —N=, =N—, or —N($R^{3'}$)—, wherein:
each occurrence of $R^3$ and $R^{3'}$ is independently hydrogen or an optionally substituted $C_{1-6}$ aliphatic, wherein:
$X_1$, $X_2$, and $X_3$, are each independently N, N$R^{3'}$, O, S, or C$R^4$, provided that only one of $X_3$, $X_2$, or $X_3$ may be O, S, or N$R^{3'}$;
each occurrence of $R^4$ is independently hydrogen, —CN, halogen, —$Z_3$—$R^6$, or an optionally substituted group selected from $C_{1-6}$ aliphatic, or 3-10-membered cycloaliphatic, wherein:
$Z_3$ is selected from an optionally substituted $C_{1-3}$ alkylene chain, —O—, —N($R^{4a}$)—, —S—, —S(O)—, —S(O)$_2$—, —C(O)—, —C(O)$_2$—, —C(O)N$R^{4a}$—, —N($R^{4a}$)C(O)—, —N($R^{4a}$)CO$_2$—, —S(O)$_2$N$R^{4a}$—, —N($R^{4a}$)S(O)$_2$—, —OC(O)N($R^{4a}$)—, —N($R^{4a}$)C(O)N$R^{4a}$—, —N($R^{4a}$)S(O)$_2$N($R^{4a}$)—, or —OC(O)—;

$R^{4a}$ is hydrogen or an optionally substituted $C_{1-4}$ aliphatic, and $R^6$ is hydrogen or an optionally substituted group selected from $C_{1-6}$ aliphatic, 3-10-membered cycloaliphatic, 4-10-membered heterocyclyl having 1-5 heteroatoms independently selected from nitrogen, oxygen, or sulfur, 6-10-membered aryl, or 5-10-membered heteroaryl having 1-5 heteroatoms independently selected from nitrogen, oxygen, or sulfur;

or wherein two adjacent occurrences of $R^{3'}$ or $R^4$, taken together with the atom to which they are bound, form an optionally substituted fused group selected from 5-6-membered aryl, or 5-6-membered heteroaryl having 1-5 heteroatoms independently selected from nitrogen, oxygen, or sulfur;

Ring A is a group selected from 3-10-membered cycloaliphatic, 4-10-membered heterocyclyl having 1-5 heteroatoms independently selected from nitrogen, oxygen, or sulfur, 6-10-membered aryl, or 5-10-membered heteroaryl having 1-5 heteroatoms independently selected from nitrogen, oxygen, or sulfur;

each occurrence of $R^2$ is independently —$R^{12a}$, -$T_2$-$R^{12d}$, or —$V_2$-$T_2$-$R^{12d}$, and:

each occurrence of $R^{12a}$ is independently halogen, —CN, —NO$_2$, —$R^{12c}$, —N($R^{12b}$)$_2$, —O$R^{12b}$, —S$R^{12c}$, —S(O)$_2R^{12c}$, —C(O)$R^{12b}$, —C(O)O$R^{12b}$, —C(O)N($R^{12b}$)$_2$, —S(O)$_2$N($R^{12b}$)$_2$, —OC(O)N($R^{12b}$)$_2$, —N($R^{12e}$)C(O)$R^{12b}$, —N($R^{12e}$)SO$_2R^{12c}$, —N($R^{12e}$)C(O)O$R^{12b}$, —N($R^{12e}$)C(O)N($R^{12b}$)$_2$, or —N($R^{12e}$)SO$_2$N($R^{12b}$)$_2$, or two occurrences of $R^{12b}$, taken together with a nitrogen atom to which they are bound, form an optionally substituted 4-7-membered heterocyclyl ring having 0-1 additional heteroatoms selected from nitrogen, oxygen, or sulfur;

each occurrence of $R^{12b}$ is independently hydrogen or an optionally substituted group selected from $C_1$-$C_6$ aliphatic, 3-10-membered cycloaliphatic, 4-10-membered heterocyclyl having 1-5 heteroatoms independently selected from nitrogen, oxygen, or sulfur, 6-10-membered aryl, or 5-10-membered heteroaryl having 1-5 heteroatoms independently selected from nitrogen, oxygen, or sulfur;

each occurrence of $R^{12c}$ is independently an optionally substituted group selected from $C_1$-$C_6$ aliphatic, 3-10-membered cycloaliphatic, 4-10-membered heterocyclyl having 1-5 heteroatoms independently selected from nitrogen, oxygen, or sulfur, 6-10-membered aryl, or 5-10-membered heteroaryl having 1-5 heteroatoms independently selected from nitrogen, oxygen, or sulfur;

each occurrence of $R^{12d}$ is independently hydrogen or an optionally substituted from 3-10-membered cycloaliphatic, 4-10-membered heterocyclyl having 1-5 heteroatoms independently selected from nitrogen, oxygen, or sulfur, 6-10-membered aryl, or 5-10-membered heteroaryl having 1-5 heteroatoms independently selected from nitrogen, oxygen, or sulfur;

each occurrence of $R^{12e}$ is independently hydrogen or an optionally substituted $C_{1-6}$ aliphatic group;

each occurrence of $V_2$ is independently —N($R^{12e}$)—, —O—, —S—, —S(O)—, —S(O)$_2$—, —C(O)—, —C(O)O—, —C(O)N($R^{12e}$)—, —S(O)$_2$N($R^{12e}$)—, —OC(O)N($R^{12e}$)—, —N($R^{12e}$)C(O)—, —N($R^{12e}$)SO$_2$—, —N($R^{12e}$)C(O)O—, —N($R^{12e}$)C(O)N($R^{12e}$)—, —N($R^{12e}$)SO$_2$N($R^{12e}$), —OC(O)—, or —C(O)N($R^{12e}$)—O—; and $T_2$ is an optionally substituted $C_1$-$C_6$alkylene chain wherein the alkylene chain optionally is interrupted by —N($R^{13}$)—, —O—, —S—, —S(O)—, —S(O)$_2$—, —C(O)—, —C(O)O—, —C(O)N($R^{13}$)—, —S(O)$_2$N ($R^{13}$)—, —OC(O)N($R^{13}$)—, —N($R^{13}$)C(O)—, —N($R^{13}$) SO$_2$—, —N($R^{13}$)C(O)O—, —N($R^{13}$)C(O)N($R^{13}$)—, —N($R^{13}$)S(O)$_2$N($R^{13}$)—, —OC(O)—, or —C(O)N($R^{13}$)—O— or wherein $T_2$ or a portion thereof optionally forms part of an optionally substituted 3-7 membered cycloaliphatic or heterocyclyl ring, wherein $R^{13}$ is hydrogen or an optionally substituted $C_{1-4}$aliphatic group;

n is 0 to 4;

W is selected from —C($R^7$)$_2$—, —C(=C($R^7$)$_2$)—, —C($R^7$)$_2$O—, —C($R^7$)$_2$N$R^{7a}$—, —O—, —N($R^{7b}$)—, —S—, —S(O)—, —S(O)$_2$—, —C(O)—, —C(O)N$R^{7a}$—, or —N($R^{7a}$)C(O)—, wherein:

each occurrence of $R^7$ is independently hydrogen, or an optionally substituted group selected from $C_{1-6}$ aliphatic, 6-10-membered aryl, 5-10-membered heteroaryl having 1-5 heteroatoms independently selected from nitrogen, oxygen, or sulfur, —N($R^{7b}$)$_2$, —O$R^{7a}$, —S$R^{7a}$, halo, or —CN;

each occurrence of $R^{7a}$ is independently hydrogen or optionally substituted $C_{1-6}$ aliphatic or optionally substituted $C_{3-6}$ cycloaliphatic;

each occurrence of $R^{7b}$ is independently hydrogen, optionally substituted $C_{1-6}$ aliphatic, optionally substituted $C_{3-6}$ cycloaliphatic, —C(O)$R^{7a}$, —C(O)O$R^{7a}$, S(O)$R^{7a}$, or —S(O)$_2R^{7a}$; or wherein any two occurrences of $R^7$, $R^{7a}$, or $R^{7b}$ taken together with the atom to which they are bound, form an optionally substituted group selected from a 3-6-membered cycloaliphatic ring, 6-10-membered aryl, 3-6-membered heterocyclyl having 1-5 heteroatoms independently selected from nitrogen, oxygen, or sulfur, or 5-10-membered heteroaryl having 1-5 heteroatoms independently selected from nitrogen, oxygen, or sulfur;

or wherein any two occurrences of $R^{7a}$ and $R^2$, or $R^{7b}$ and $R^2$ taken together with the nitrogen atom to which they are bound, form an optionally substituted group selected from 3-6-membered heterocyclyl having 1-5 heteroatoms independently selected from nitrogen, oxygen, or sulfur, or 5-10-membered heteroaryl having 1-5 heteroatoms independently selected from nitrogen, oxygen, or sulfur;

$G_1$ is N or —C$R^8$, wherein $R^8$ is H, —CN, halogen, —$Z_2$—$R^9$, $C_{1-6}$ aliphatic, or 3-10-membered cycloaliphatic, wherein:

$Z_2$ is selected from an optionally substituted $C_{1-3}$ alkylene chain, —O—, —N($R^{8a}$)—, —S—, —S(O)—, S(O)$_2$—, —C(O)—, —CO$_2$—, —C(O)N$R^{8a}$—, —N($R^{8a}$)C (O)—, —N($R^{8a}$)CO$_2$—, —S(O)$_2$N$R^{8a}$—, —N($R^{8a}$)S (O)$_2$—, —OC(O)N($R^{8a}$)—, —N($R^{8a}$)C(O)N$R^{8a}$—, —N($R^{8a}$)S (O)$_2$N($R^{8a}$)—, or —OC(O)—;

$R^{8a}$ is hydrogen or an optionally substituted $C_{1-4}$ aliphatic, and $R^9$ is hydrogen or an optionally substituted group selected from $C_{1-6}$ aliphatic, 3-10-membered cycloaliphatic, 4-10-membered heterocyclyl having 1-5 heteroatoms independently selected from nitrogen, oxygen, or sulfur, 6-10-membered aryl, or 5-10-membered heteroaryl having 1-5 heteroatoms independently selected from nitrogen, oxygen, or sulfur; and HY is an optionally substituted group selected from:

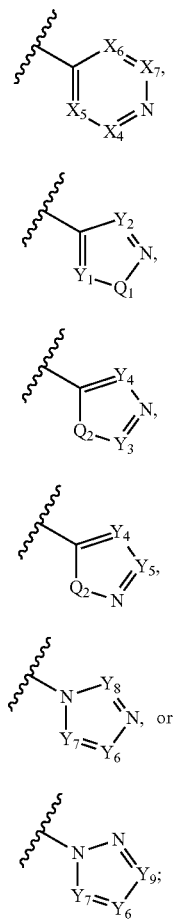

A

B

C

D

E

F wherein each occurrence of $X_4$, $X_5$, $X_6$, and $X_7$ is independently —$CR^{10}$ or N, provided no more than two occurrences of $X_4$, $X_5$, $X_6$, and $X_7$ are N;

each occurrence of $Q_1$ and $Q_2$ is independently S, O or —$NR^5$;

each occurrence of $Y_1$, $Y_2$, $Y_3$, $Y_4$, $Y_5$, $Y_6$, $Y_7$, $Y_8$, and $Y_9$ is independently —$CR^{10}$ or N, provided no more than two occurrences of $Y_6$, $Y_7$, $Y_8$, and $Y_9$ are N;

or wherein two adjacent occurrences of $X_4$ and $X_5$, $X_6$ and $X_7$, $Y_1$ and $Q_1$, $Y_3$ and $Q_2$, or $Y_4$ and $Y_5$ taken together with the atom to which they are bound, form an optionally substituted fused group selected from 5-6-membered aryl, or 5-6-membered heteroaryl having 1-5 heteroatoms independently selected from nitrogen, oxygen, or sulfur;

wherein $R^{10}$ is —$R^{10b}$, -$T_1$-$R^{10b}$, or —$V_1$-$T_1$-$R^{10b}$ wherein:
$V_1$ is —$NR^{11}$—, —$NR^{11}$—C(O)—, —$NR^{11}$—C(S)—, —$NR^{11}$—C($NR^{11}$)—, —$NR^{11}$C(O)$OR^{10a}$—, —$NR^{11}$C(O)$NR^{11}$—, —$NR^{11}$C(O)$SR^{10a}$—, —$NR^{11}$C(S)$OR^{10a}$—, —$NR^{11}$C(S)$NR^{11}$—, —$NR^{11}$C(S)$SR^{10a}$—, —$NR^{11}$C($NR^{11}$)$OR^{10a}$—, —$NR^{11}$C($NR^{11}$)$NR^{11}$—, —$NR^{11}$S(O)$_2$—, —$NR^{11}$S(O)$_2NR^{11}$—, —C(O)—, —$CO_2$—, —C(O)$NR^{11}$—, —C(O)$NR^{11}$O—, —$SO_2$—, or —$SO_2NR^{11}$—;

each occurrence of $R^{10a}$ is independently hydrogen or an optionally substituted group selected from $C_{1-6}$ aliphatic, 3-10-membered cycloaliphatic, 4-10-membered heterocyclyl having 1-5 heteroatoms independently selected from nitrogen, oxygen, or sulfur, 6-10-membered aryl, or 5-10-membered heteroaryl having 1-5 heteroatoms independently selected from nitrogen, oxygen, or sulfur;

$T_1$ is an optionally substituted $C_1$-$C_6$alkylene chain wherein the alkylene chain optionally is interrupted by —N($R^{11}$)—, —O—, —S—, —S(O)—, —S(O)$_2$—, —C(O)—, —C(O)O—, —C(O)N($R^{11}$)—, —S(O)$_2$N($R^{11}$)—, —OC(O)N($R^{11}$)—, —N($R^{11}$)C(O)—, —N($R^{11}$)$SO_2$—, —N($R^{11a}$)C(O)O—, —$NR^{10a}$C(O)N($R^{10a}$)—, —N($R^{10a}$)S(O)$_2$N($R^{10a}$)—, —OC(O)—, or —C(O)N($R^{11}$)—O— or wherein $T_1$ forms part of an optionally substituted 3-7 membered cycloaliphatic or heterocyclyl ring;

each occurrence of $R^{10b}$ is independently hydrogen, halogen, —CN, —$NO_2$, —N($R^{11}$)$_2$, —$OR^{10a}$, —$SR^{10a}$, —S(O)$_2R^{10a}$, —C(O)$R^{10a}$, —C(O)$OR^{10a}$, —C(O)N($R^{11}$)$_2$, —S(O)$_2$N($R^{11}$)$_2$, —OC(O)N($R^{11}$)$_2$, —N($R^{11}$)C(O)$R^{10a}$, —N($R^{11}$)$SO_2R^{10a}$, —N($R^{11}$)C(O)$OR^{10a}$, —N($R^{11}$)C(O)N($R^{11}$)$_2$, or —N($R^{11}$)$SO_2$N($R^{11}$)$_2$, or an optionally substituted group selected from $C_{1-6}$ aliphatic, 3-10-membered cycloaliphatic, 4-10-membered heterocyclyl having 1-5 heteroatoms independently selected from nitrogen, oxygen, or sulfur, 6-10-membered aryl, or 5-10-membered heteroaryl having 1-5 heteroatoms independently selected from nitrogen, oxygen, or sulfur;

each occurrence of $R^{10c}$ is independently hydrogen or an optionally substituted group selected from $C_{1-6}$ aliphatic, 3-10-membered cycloaliphatic, 4-10-membered heterocyclyl having 1-5 heteroatoms independently selected from nitrogen, oxygen, or sulfur, 6-10-membered aryl, or 5-10-membered heteroaryl having 1-5 heteroatoms independently selected from nitrogen, oxygen, or sulfur, or $R^{10a}$ and $R^{10c}$ taken together with a nitrogen atom to which they are bound form an optionally substituted 4-7-membered heterocyclyl ring having 0-1 additional heteroatoms independently selected from nitrogen, oxygen, or sulfur;

each occurrence of $R^{11}$ is independently hydrogen, —C(O)$R^{11a}$, —$CO_2R^{11a}$, —C(O)N($R^{11a}$)$_2$, —C(O)N($R^{11a}$)—$OR^{11a}$, —$SO_2R^{11a}$, —$SO_2$N($R^{11a}$)$_2$, or an optionally substituted group selected from $C_{1-6}$ aliphatic, 3-10-membered cycloaliphatic, 4-10-membered heterocyclyl having 1-5 heteroatoms independently selected from nitrogen, oxygen, or sulfur, 6-10-membered aryl, or 5-10-membered heteroaryl having 1-5 heteroatoms independently selected from nitrogen, oxygen, or sulfur;

wherein each occurrence of $R^{11a}$ is independently hydrogen or an optionally substituted group selected from $C_{1-6}$aliphatic, 3-10-membered cycloaliphatic, 4-10-membered heterocyclyl having 1-5 heteroatoms independently selected from nitrogen, oxygen, or sulfur, 6-10-membered aryl, or 5-10-membered heteroaryl having 1-5 heteroatoms independently selected from nitrogen, oxygen, or sulfur;

each occurrence of $R^5$ is independently hydrogen, —C(O)$R^{5a}$, —$CO_2R^{5a}$, —C(O)N($R^{5b}$)$_2$, —$SO_2R^{5a}$, —$SO_2$N($R^{5b}$)$_2$, or an optionally substituted group selected from $C_{1-6}$ aliphatic, 3-10-membered cycloaliphatic, 4-10-membered heterocyclyl having 1-5 heteroatoms independently selected from nitrogen, oxygen, or sulfur, 6-10-membered aryl, or 5-10-membered heteroaryl having 1-5 heteratoms independently selected from nitrogen, oxygen, or sulfur;

wherein each occurrence of $R^{5a}$ is independently hydrogen or an optionally substituted group selected from $C_{1-6}$ aliphatic, 3-10-membered cycloaliphatic, 4-10-membered heterocyclyl having 1-5 heteroatoms independently selected from nitrogen, oxygen, or sulfur, 6-10-membered aryl, or 5-10-membered heteroaryl having 1-5 heteroatoms independently selected from nitrogen, oxygen, or sulfur;

wherein each occurrence of $R^{5b}$ is independently hydrogen or an optionally substituted group selected from $C_{1-6}$ aliphatic, 3-10-membered cycloaliphatic, 4-10-membered heterocyclyl having 1-5 heteroatoms independently selected from nitrogen, oxygen, or sulfur, 6-10-membered aryl, or 5-10-membered heteroaryl having 1-5 heteroatoms independently selected from nitrogen, oxygen, or sulfur; or two occurrences of $R^{5b}$ taken together with the nitrogen atom to which they are bound, form an optionally substituted group selected from 3-6-membered heterocyclyl having 1-5 heteroatoms independently selected from nitrogen, oxygen, or sulfur, or 5-10-membered heteroaryl having 1-5 heteroatoms independently selected from nitrogen, oxygen, or sulfur;

provided that:

a) for compounds of formula IB compounds are other than:

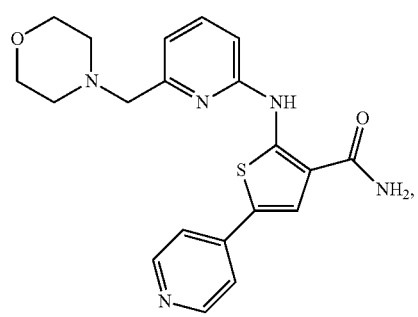

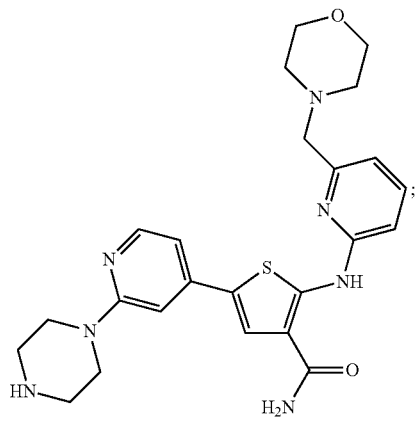

and when $G^1$ is $CR^8$, $R^1$ is $CONH_2$, and W is NH, then HY is other than

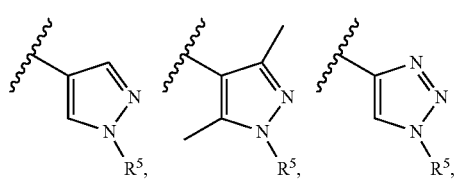

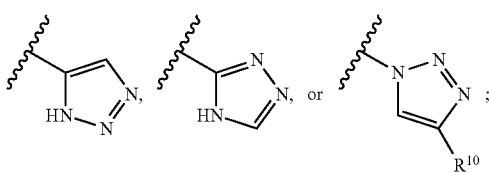

and b) the compound is other than:

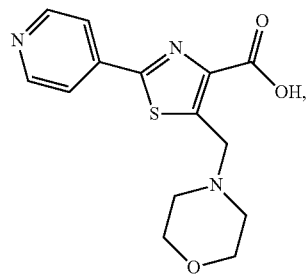

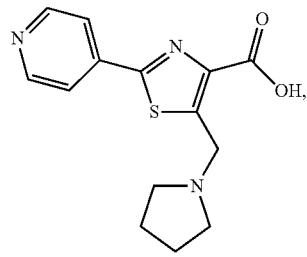

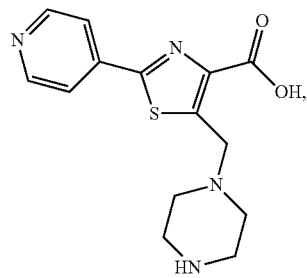

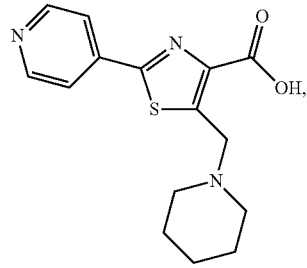

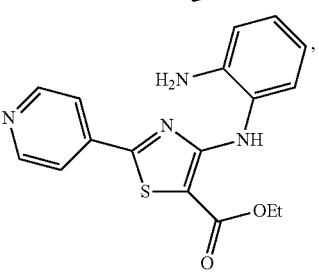

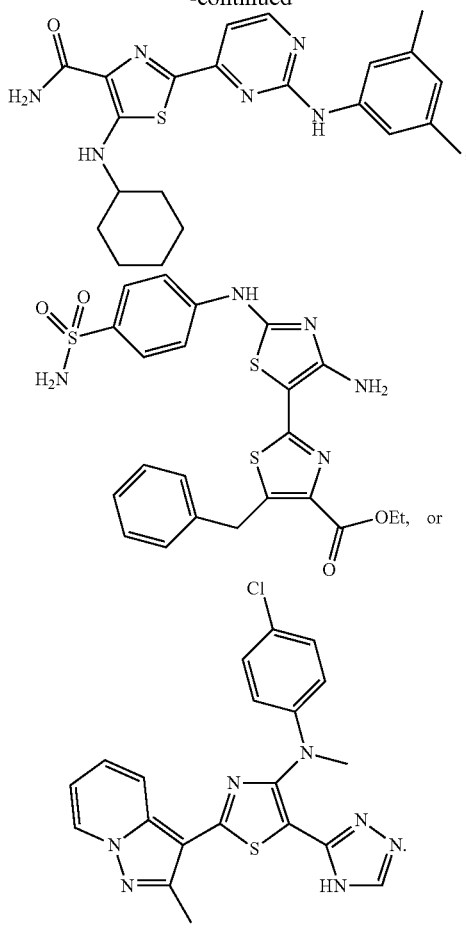

In another aspect, the compounds of this invention are represented by formula IA or IB:

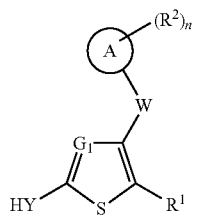

IA

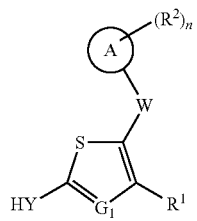

IB or a pharmaceutically acceptable salt thereof, wherein:

$R^1$ is —C(O)N($R^3$)$_2$, —C(O)O$R^3$, —C(O)(NH)OH, —C(=NH)NHOH, —C(O)N$R^3$N($R^3$)$_2$, —C(=N—NH)NH$_2$, —C(=N)N($R^3$)$_2$;

each occurrence of $R^3$ is independently hydrogen or an optionally substituted $C_{1-6}$ aliphatic;

Ring A is a group selected from 3-10-membered cycloaliphatic, 4-10-membered heterocyclyl having 1-5 heteroatoms independently selected from nitrogen, oxygen, or sulfur, 6-10-membered aryl, or 5-10-membered heteroaryl having 1-5 heteroatoms independently selected from nitrogen, oxygen, or sulfur;

each occurrence of $R^2$ is independently —$R^{12a}$, -$T_2$-$R^{12d}$, or —$V_2$-$T_2$-$R^{12d}$, and:

each occurrence of $R^{12a}$ is independently halogen, —CN, —NO$_2$, —N($R^{12b}$)$_2$, —O$R^{12b}$, —S$R^{12c}$, —S(O)$_2$$R^{12c}$, —C(O)$R^{12b}$, —C(O)O$R^{12b}$, —C(O)N($R^{12b}$)$_2$, —S(O)$_2$N($R^{12b}$)$_2$, —OC(O)N($R^{12b}$)$_2$, —N($R^{12e}$)C(O)$R^{12b}$, —N($R^{12e}$)SO$_2$$R^{12c}$, —N($R^{12e}$)C(O)O$R^{12b}$, —N($R^{12e}$)C(O)N($R^{12b}$)$_2$, or —N($R^{12a}$)SO$_2$N($R^{12b}$)$_2$, or two occurrences of $R^{12b}$, taken together with a nitrogen atom to which they are bound, form an optionally substituted 4-7-membered heterocyclyl ring having 0-1 additional heteroatoms selected from nitrogen, oxygen, or sulfur;

each occurrence of $R^{12b}$ is independently hydrogen or an optionally substituted group selected from $C_1$-$C_6$ aliphatic, 3-10-membered cycloaliphatic, 4-10-membered heterocyclyl having 1-5 heteroatoms independently selected from nitrogen, oxygen, or sulfur, 6-10-membered aryl, or 5-10-membered heteroaryl having 1-5 heteroatoms independently selected from nitrogen, oxygen, or sulfur;

each occurrence of $R^{12c}$ is independently an optionally substituted group selected from $C_1$-$C_6$ aliphatic, 3-10-membered cycloaliphatic, 4-10-membered heterocyclyl having 1-5 heteroatoms independently selected from nitrogen, oxygen, or sulfur, 6-10-membered aryl, or 5-10-membered heteroaryl having 1-5 heteroatoms independently selected from nitrogen, oxygen, or sulfur;

each occurrence of $R^{12d}$ is independently hydrogen or an optionally substituted from 3-10-membered cycloaliphatic, 4-10-membered heterocyclyl having 1-5 heteroatoms independently selected from nitrogen, oxygen, or sulfur, 6-10-membered aryl, or 5-10-membered heteroaryl having 1-5 heteroatoms independently selected from nitrogen, oxygen, or sulfur;

each occurrence of $R^{12e}$ is independently hydrogen or an optionally substituted $C_{1-6}$ aliphatic group;

each occurrence of $V_2$ is independently —N($R^{12e}$)—, —O—, —S—, —S(O)—, —S(O)$_2$—, —C(O)—, —C(O)O—, —C(O)N($R^{12e}$) S(O)$_2$N($R^{12e}$)—, —OC(O)N($R^{12e}$)—, —N($R^{12e}$)C(O)—, —N($R^{12e}$)SO$_2$—, —N($R^{12e}$)C(O)O—, —N($R^{12e}$)C(O)N($R^{12e}$)—, —N($R^{12e}$)SO$_2$N($R^{12e}$)—, —OC(O)—, or —C(O)N($R^{12e}$)—O—; and $T_2$ is an optionally substituted $C_1$-$C_6$ alkylene chain wherein the alkylene chain optionally is interrupted by —N($R^{13}$)—, —O—, —S—, —S(O)—, —S(O)$_2$—, —C(O)—, —C(O)O—, —C(O)N($R^{13}$)—, —S(O)$_2$N($R^{13}$)—, —OC(O)N($R^{13}$)—, —N($R^{13}$)C(O)—, —N($R^{13}$)SO$_2$—, —N($R^{13}$)C(O)O—, —N($R^{13}$)C(O)N($R^{13}$)—, —N($R^{13}$)S(O)$_2$N($R^{13}$)—, —OC(O)—, or —C(O)N($R^{13}$)—O— or wherein $T_2$ or a portion thereof optionally forms part of an optionally substituted 3-7 membered cycloaliphatic or heterocyclyl ring, wherein $R^{13}$ is hydrogen or an optionally substituted $C_{1-4}$ aliphatic group;

n is 0 to 4;

W is selected from —C($R^7$)$_2$—, —C(=C($R^7$)$_2$)—, —C($R^7$)$_2$O—, —C($R^7$)$_2$N$R^{7a}$—, —O—, —N($R^{7b}$)—, —S—, —S(O)—, —S(O)$_2$—, —C(O)—, —C(O)N$R^{7a}$—, or —N($R^{7a}$)C(O)—, wherein:

each occurrence of $R^7$ is independently hydrogen, or an optionally substituted group selected from $C_{1-6}$ aliphatic, 6-10-membered aryl, 5-10-membered heteroaryl having 1-5 heteroatoms independently selected from nitrogen, oxygen, or sulfur, —N($R^{7b}$)$_2$, —O$R^{7a}$, —S$R^{7a}$, halo, or —CN;

each occurrence of $R^{7a}$ is independently hydrogen or optionally substituted $C_{1-6}$ aliphatic or optionally substituted $C_{3-6}$ cycloaliphatic;

each occurrence of $R^{7b}$ is independently hydrogen, optionally substituted $C_{1-6}$ aliphatic, optionally substituted $C_{3-6}$ cycloaliphatic, —C(O)$R^{7a}$, —C(O)O$R^{7a}$, S(O)$R^{7a}$, or —S(O)$_2R^{7a}$; or wherein any two occurrences of $R^7$, $R^{7a}$, or $R^{7b}$ taken together with the atom to which they are bound, form an optionally substituted group selected from a 3-6-membered cycloaliphatic ring, 6-10-membered aryl, 3-6-membered heterocyclyl having 1-5 heteroatoms independently selected from nitrogen, oxygen, or sulfur, or 5-10-membered heteroaryl having 1-5 heteroatoms independently selected from nitrogen, oxygen, or sulfur;

or wherein any two occurrences of $R^{7a}$ and $R^2$, or $R^{7b}$ and $R^2$ taken together with the nitrogen atom to which they are bound, form an optionally substituted group selected from 3-6-membered heterocyclyl having 1-5 heteroatoms independently selected from nitrogen, oxygen, or sulfur, or 5-10-membered heteroaryl having 1-5 heteroatoms independently selected from nitrogen, oxygen, or sulfur;

$G_1$ is N; and

HY is

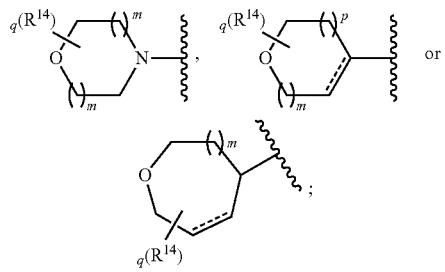

wherein each occurrence of $R^{14}$ is independently —$R^{14a}$ or -$T_r$-$R^{14d}$, wherein:

each occurrence of $R^{14a}$, as valency and stability permit, is independently fluorine, =O, =S, —CN, —NO$_2$, —$R^{14c}$, —N($R^{14b}$)$_2$, —O$R^{14b}$, —S$R^{14c}$, —S(O)$_2R^{14c}$, —C(O)$R^{14b}$, —C(O)O$R^{14b}$, —C(O)N($R^{14b}$)$_2$, —S(O)$_2$N($R^{14b}$)$_2$, —OC(O)N($R^{14b}$)$_2$, —N($R^{14e}$)C(O)$R^{14b}$, —N($R^{14e}$)SO$_2R^{14c}$, —N($R^{14e}$)C(O)O$R^{14b}$, —N($R^{14e}$)C(O)N($R^{14b}$)$_2$, or —N($R^{14e}$)SO$_2$N($R^{14b}$)$_2$), or two occurrences of $R^{14b}$, taken together with a nitrogen atom to which they are bound, form an optionally substituted 4-7-membered heterocyclyl ring having 0-1 additional heteroatoms selected from nitrogen, oxygen, or sulfur;

each occurrence of $R^{14b}$ is independently hydrogen or an optionally substituted group selected from $C_1$-$C_6$ aliphatic, 3-10-membered cycloaliphatic, 4-10-membered heterocyclyl having 1-5 heteroatoms independently selected from nitrogen, oxygen, or sulfur, 6-10-membered aryl, or 5-10-membered heteroaryl having 1-5 heteroatoms independently selected from nitrogen, oxygen, or sulfur;

each occurrence of $R^{14c}$ is independently an optionally substituted group selected from $C_1$-$C_6$aliphatic, 3-10-membered cycloaliphatic, 4-10-membered heterocyclyl having 1-5 heteroatoms independently selected from nitrogen, oxygen, or sulfur, 6-10-membered aryl, or 5-10-membered heteroaryl having 1-5 heteroatoms independently selected from nitrogen, oxygen, or sulfur;

each occurrence of $R^{14d}$ is independently hydrogen or an optionally substituted from 3-10-membered cycloaliphatic, 4-10-membered heterocyclyl having 1-5 heteroatoms independently selected from nitrogen, oxygen, or sulfur, 6-10-membered aryl, or 5-10-membered heteroaryl having 1-5 heteroatoms independently selected from nitrogen, oxygen, or sulfur;

each occurrence of $R^{14e}$ is independently hydrogen or an optionally substituted $C_{1-6}$ aliphatic group; and $T_1$ is an optionally substituted $C_1$-$C_6$alkylene chain wherein the alkylene chain optionally is interrupted by —N($R^{14a}$)—, —O—, —S—, —S(O)—, —S(O)$_2$—, —C(O)—, —C(O)O—, —C(O)N($R^{14a}$)—, —S(O)$_2$N($R^{14a}$)—, —OC(O)N($R^{14a}$)—, —N($R^{14a}$)C(O)—, —N($R^{14a}$)SO$_2$—, —N($R^{14a}$)C(O)O—, —N$R^{14a}$C(O)N($R^{14a}$)—, —N($R^{14a}$)S(O)$_2$N($R^{14a}$)—, —OC(O)—, or —C(O)N($R^{14a}$)—O— or wherein $T_1$ or a portion thereof optionally forms part of an optionally substituted 3-7 membered cycloaliphatic or heterocyclyl ring;

n is 0-6;

m is 1 or 2;

p is 0, 1, or 2;

provided that the compound is other than:

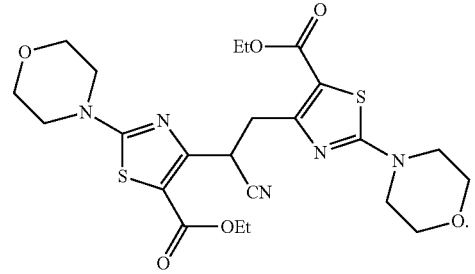 [SMILES: CCOC(=O)c1sc(N2CCOCC2)nc1CC(C#N)c1nc(N2CCOCC2)sc1C(=O)OCC]

In some embodiments for compounds described directly above, HY is

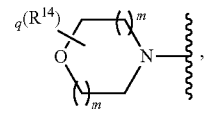

wherein both occurrences of m are 1.

In other embodiments for compounds described directly above, HY is

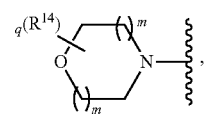

wherein both occurrences of m are 1, and $R^1$ is COOH.

In yet another aspect, the compounds of this invention are represented by formula IA or IB:

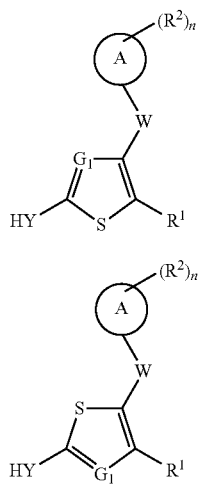

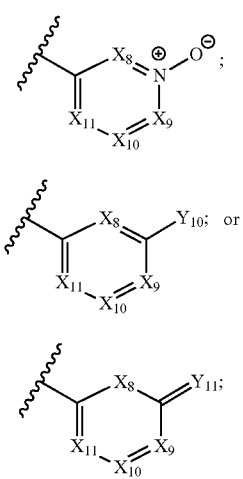

or a pharmaceutically acceptable salt thereof, wherein:
$R^1$ is CY, wherein:
CY is an optionally substituted group selected from:

R

S

T wherein:
each occurrence of $R^3$ is independently hydrogen or an optionally substituted $C_{1-6}$ aliphatic, wherein:
$X_8$, $X_9$, $X_{10}$, and $X_{11}$ are each independently N, or $CR^4$, provided no more than two occurrences of $X_8$, $X_9$, $X_{10}$, and $X_{11}$ are N;
each occurrence of $R^4$ is independently hydrogen, —CN, halogen, —$Z_3$—$R^6$, or an optionally substituted group selected from $C_{1-6}$ aliphatic, or 3-10-membered cycloaliphatic, wherein:
$Z_3$ is selected from an optionally substituted $C_{1-3}$ alkylene chain, —O—, —N($R^{4a}$)—, —S—, —S(O)—, —S(O)$_2$—, —C(O)—, —CO$_2$—, —C(O)NR$^{4a}$—, —N($R^{4a}$)C(O)—, —N($R^{4a}$)CO$_2$—, —S(O)$_2$N$R^{4a}$—, —N($R^{4a}$)S(O)$_2$—, —OC(O)N($R^{4a}$)—, —N($R^{4a}$)C(O)NR$^{4a}$—, —N($R^{4a}$)S(O)$_2$N($R^{4a}$)—, or —OC(O)—;
$R^{4a}$ is hydrogen or an optionally substituted $C_{1-4}$ aliphatic, and
$R^6$ is hydrogen or an optionally substituted group selected from $C_{1-6}$ aliphatic, 3-10-membered cycloaliphatic, 4-10-membered heterocyclyl having 1-5 heteroatoms independently selected from nitrogen, oxygen, or sulfur, 6-10-membered aryl, or 5-10-membered heteroaryl having 1-5 heteroatoms independently selected from nitrogen, oxygen, or sulfur;
$Y_{10}$ is —$OR^{4'}$ or —$N(R^{4'})_2$;
$Y_{11}$ is O or N—$R^{4'}$;
each occurrence of $R^{4'}$ is independently hydrogen or an optionally substituted $C_{1-6}$ aliphatic;
Ring A is a group selected from 3-10-membered cycloaliphatic, 4-10-membered heterocyclyl having 1-5 heteroatoms independently selected from nitrogen, oxygen, or sulfur, 6-10-membered aryl, or 5-10-membered heteroaryl having 1-5 heteroatoms independently selected from nitrogen, oxygen, or sulfur;
each occurrence of $R^2$ is independently —$R^{12a}$, -$T_2$-$R^{12d}$, or —$V_2$-$T_2$-$R^{12d}$, and:
each occurrence of $R^{12a}$ is independently halogen, —CN, —NO$_2$, —$R^{12c}$, N($R^{12b}$)$_2$, —$OR^{12b}$, —$SR^{12c}$, —S(O)$_2$$R^{12c}$, —C(O)$R^{12b}$, —C(O)$OR^{12b}$, —C(O)N($R^{12b}$)$_2$, —S(O)$_2$N($R^{12b}$)$_2$, —OC(O)N($R^{12b}$)$_2$, —N($R^{12e}$)C(O)$R^{12b}$, —N($R^{12e}$)SO$_2$$R^{12c}$, —N($R^{12e}$)C(O)$OR^{12b}$, —N($R^{12e}$)C(O)N($R^{12b}$)$_2$, or —N($R^{12e}$)SO$_2$N($R^{12b}$)$_2$, or two occurrences of $R^{12b}$, taken together with a nitrogen atom to which they are bound, form an optionally substituted 4-7-membered heterocyclyl ring having 0-1 additional heteroatoms selected from nitrogen, oxygen, or sulfur;
each occurrence of $R^{12b}$ is independently hydrogen or an optionally substituted group selected from $C_1$-$C_6$ aliphatic, 3-10-membered cycloaliphatic, 4-10-membered heterocyclyl having 1-5 heteroatoms independently selected from nitrogen, oxygen, or sulfur, 6-10-membered aryl, or 5-10-membered heteroaryl having 1-5 heteroatoms independently selected from nitrogen, oxygen, or sulfur;
each occurrence of $R^{12c}$ is independently an optionally substituted group selected from $C_1$-$C_6$ aliphatic, 3-10-membered cycloaliphatic, 4-10-membered heterocyclyl having 1-5 heteroatoms independently selected from nitrogen, oxygen, or sulfur, 6-10-membered aryl, or 5-10-membered heteroaryl having 1-5 heteroatoms independently selected from nitrogen, oxygen, or sulfur;
each occurrence of $R^{12d}$ is independently hydrogen or an optionally substituted from 3-10-membered cycloaliphatic, 4-10-membered heterocyclyl having 1-5 heteroatoms independently selected from nitrogen, oxygen, or sulfur, 6-10-membered aryl, or 5-10-membered heteroaryl having 1-5 heteroatoms independently selected from nitrogen, oxygen, or sulfur;
each occurrence of $R^{12e}$ is independently hydrogen or an optionally substituted $C_{1-6}$ aliphatic group;
each occurrence of $V_2$ is independently —N($R^{12e}$)—, —O—, —S—, —S(O)—, —S(O)$_2$—, —C(O)—, —C(O)O—, —C(O)N($R^{12e}$)—, —S(O)$_2$N($R^{12e}$)—, —OC(O)N($R^{12e}$)—, —N($R^{12e}$)C(O)—, —N($R^{12e}$)SO$_2$—, —N($R^{12e}$)C(O)O—, —N($R^{12e}$)C(O)N($R^{12e}$)—, —N($R^{12e}$)SO$_2$N($R^{12e}$)—, —OC(O)—, or —C(O)N($R^{12e}$)—O—; and
$T_2$ is an optionally substituted $C_h$$C_6$ alkylene chain wherein the alkylene chain optionally is interrupted by —N($R^{13}$)—, —O—, —S—, —S(O)—, —S(O)$_2$—, —C(O)—, —C(O)O—, —C(O)N($R^{13}$)—, —S(O)$_2$N($R^{13}$)—, —OC(O)N($R^{13}$)—, —N($R^{13}$)C(O)—, —N($R^{13}$)SO$_2$—, —N($R^{13}$)C(O)O—, —N($R^{13}$)C(O)N($R^{13}$)—, —N($R^{13}$)S(O)$_2$N($R^{13}$)—, —OC(O)—, or —C(O)N($R^{13}$)—O— or wherein $T_2$ or a portion thereof optionally forms part of an optionally substituted 3-7 membered cycloaliphatic or heterocyclyl ring, wherein $R^{13}$ is hydrogen or an optionally substituted $C_{1-4}$aliphatic group;

n is 0 to 4;

W is selected from —C($R^7$)$_2$—, —C(=C($R^7$)$_2$)—, —C($R^7$)$_2$O—, —C($R^7$)$_2$N$R^{7a}$—, —O—, —N($R^{7b}$)—, —S—, —S(O)—, —S(O)$_2$—, —C(O)—, —C(O)N$R^{7a}$—, or —N($R^{7a}$)C(O)—, wherein:

each occurrence of $R^7$ is independently hydrogen, or an optionally substituted group selected from $C_{1-6}$ aliphatic, 6-10-membered aryl, 5-10-membered heteroaryl having 1-5 heteroatoms independently selected from nitrogen, oxygen, or sulfur, —N($R^{7b}$)$_2$, —O$R^{7a}$, —S$R^{7a}$, halo, or —CN;

each occurrence of $R^{7a}$ is independently hydrogen or optionally substituted $C_{1-6}$ aliphatic or optionally substituted $C_{3-6}$ cycloaliphatic;

each occurrence of $R^{7b}$ is independently hydrogen, optionally substituted $C_{1-6}$ aliphatic, optionally substituted $C_{3-6}$ cycloaliphatic, —C(O)$R^{7a}$, —C(O)O$R^{7a}$, S(O)$R^{7a}$, or —S(O)$_2$$R^{7a}$; or wherein any two occurrences of $R^7$, $R^{7a}$, or $R^{7b}$ taken together with the atom to which they are bound, form an optionally substituted group selected from a 3-6-membered cycloaliphatic ring, 6-10-membered aryl, 3-6-membered heterocyclyl having 1-5 heteroatoms independently selected from nitrogen, oxygen, or sulfur, or 5-10-membered heteroaryl having 1-5 heteroatoms independently selected from nitrogen, oxygen, or sulfur;

or wherein any two occurrences of $R^{7a}$ and $R^2$, or $R^{7b}$ and $R^2$ taken together with the nitrogen atom to which they are bound, form an optionally substituted group selected from 3-6-membered heterocyclyl having 1-5 heteroatoms independently selected from nitrogen, oxygen, or sulfur, or 5-10-membered heteroaryl having 1-5 heteroatoms independently selected from nitrogen, oxygen, or sulfur;

$G_1$ is N or —C$R^8$, wherein $R^8$ is H, —CN, halogen, —$Z_2$—$R^9$, $C_{1-6}$ aliphatic, or 3-10-membered cycloaliphatic, wherein:

$Z_2$ is selected from an optionally substituted $C_{1-3}$ alkylene chain, —O—, —N($R^{8a}$)—, —S—, —S(O)—, S(O)$_2$—, —C(O)—, —CO$_2$—, —C(O)N$R^{8a}$—, —N$R^{8a}$C(O)—, —N($R^{8a}$)CO$_2$—, —S(O)$_2$N$R^{8a}$—, —N($R^{8a}$)S(O)$_2$—, —OC(O)N($R^{8a}$)—, —N($R^{8a}$)C(O)N$R^{8a}$—, —N($R^{8a}$)S(O)$_2$N($R^{8a}$)—, or —OC(O)—;

$R^{8a}$ is hydrogen or an optionally substituted $C_{1-4}$ aliphatic, and $R^9$ is hydrogen or an optionally substituted group selected from $C_{1-6}$ aliphatic, 3-10-membered cycloaliphatic, 4-10-membered heterocyclyl having 1-5 heteroatoms independently selected from nitrogen, oxygen, or sulfur, 6-10-membered aryl, or 5-10-membered heteroaryl having 1-5 heteroatoms independently selected from nitrogen, oxygen, or sulfur; and HY is

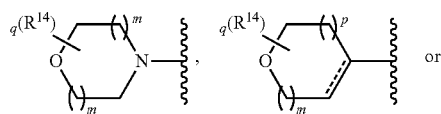

-continued

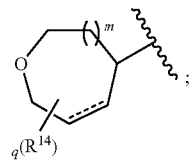

wherein each occurrence of $R^{14}$ is independently —$R^{14a}$ or -$T_1$-$R^{14d}$, wherein:

each occurrence of $R^{14a}$, as valency and stability permit, is independently fluorine, =O, =S, —CN, —NO$_2$, —$R^{14c}$, —N($R^{14b}$)$_2$, —O$R^{14b}$, —S$R^{14c}$, —S(O)$_2$$R^{14c}$, —C(O)$R^{14b}$, —C(O)O$R^{14b}$, —C(O)N($R^{14b}$)$_2$, —S(O)$_2$N($R^{14b}$)$_2$, —OC(O)N($R^{14b}$)$_2$, —N($R^{14e}$)C(O)$R^{14b}$, —N($R^{14e}$)SO$_2$$R^{14c}$, —N($R^{14e}$)C(O)O$R^{14b}$, —N($R^{14e}$)C(O)N($R^{14b}$)$_2$, or —N($R^{14e}$)SO$_2$N($R^{14b}$)$_2$, or two occurrences of $R^{14b}$, taken together with a nitrogen atom to which they are bound, form an optionally substituted 4-7-membered heterocyclyl ring having 0-1 additional heteroatoms selected from nitrogen, oxygen, or sulfur;

each occurrence of $R^{14b}$ is independently hydrogen or an optionally substituted group selected from $C_1$-$C_6$ aliphatic, 3-10-membered cycloaliphatic, 4-10-membered heterocyclyl having 1-5 heteroatoms independently selected from nitrogen, oxygen, or sulfur, 6-10-membered aryl, or 5-10-membered heteroaryl having 1-5 heteroatoms independently selected from nitrogen, oxygen, or sulfur;

each occurrence of $R^{14c}$ is independently an optionally substituted group selected from $C_1$-$C_6$aliphatic, 3-10-membered cycloaliphatic, 4-10-membered heterocyclyl having 1-5 heteroatoms independently selected from nitrogen, oxygen, or sulfur, 6-10-membered aryl, or 5-10-membered heteroaryl having 1-5 heteroatoms independently selected from nitrogen, oxygen, or sulfur;

each occurrence of $R^{14d}$ is independently hydrogen or an optionally substituted from 3-10-membered cycloaliphatic, 4-10-membered heterocyclyl having 1-5 heteroatoms independently selected from nitrogen, oxygen, or sulfur, 6-10-membered aryl, or 5-10-membered heteroaryl having 1-5 heteroatoms independently selected from nitrogen, oxygen, or sulfur;

each occurrence of $R^{14e}$ is independently hydrogen or an optionally substituted $C_{1-6}$ aliphatic group; and $T_1$ is an optionally substituted $C_1$-$C_6$ alkylene chain wherein the alkylene chain optionally is interrupted by —N($R^{14a}$)—, —O—, —S—, —S(O)—, —S(O)$_2$—, —C(O)—, —C(O)O—, —C(O)N($R^{14a}$)—, —S(O)$_2$N ($R^{14a}$)—, —OC(O)N($R^{14a}$)—, —N($R^{14a}$)C(O)—, —N($R^{14a}$)SO$_2$—, —N($R^{14a}$)C(O)O—, —N$R^{14a}$C(O) N($R^{14a}$)—, —N($R^{14a}$)S(O)$_2$N($R^{14a}$)—, —OC(O)—, or —C(O)N($R^{14a}$)—O— or wherein $T_1$ or a portion thereof optionally forms part of an optionally substituted 3-7 membered cycloaliphatic or heterocyclyl ring;

n is 0-6;

m is 1 or 2; and p is 0, 1, or 2.

In still another embodiment of the invention, compounds of this invention are represented by formula IA-i-a or IB-i-a:

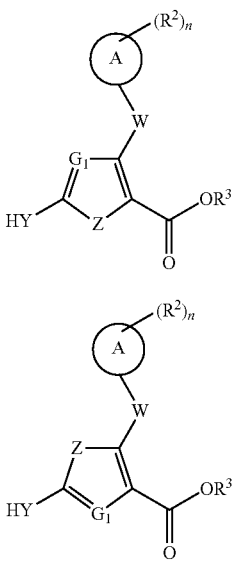

IA-i-a

IB-i-a or a pharmaceutically acceptable salt thereof, wherein:

Z is S or Se;

$R^3$ is hydrogen or an optionally substituted $C_{1-6}$ aliphatic;

Ring A is a group selected from 3-10-membered cycloaliphatic, 4-10-membered heterocyclyl having 1-5 heteroatoms independently selected from nitrogen, oxygen, or sulfur, 6-10-membered aryl, or 5-10-membered heteroaryl having 1-5 heteroatoms independently selected from nitrogen, oxygen, or sulfur;

each occurrence of $R^2$ is independently —$R^{12a}$, -$T_2$-$R^{12d}$, or —$V_2$-$T_2R^{12d}$, or:

two adjacent $R^2$ groups are taken together with their intervening atoms to form an optionally substituted 4-7 membered saturated, partially unsaturated, or aryl ring having 0-4 heteroatoms selected from nitrogen, oxygen, or sulfur;

each occurrence of $R^{12a}$ is independently halogen, —CN, —$NO_2$, —$R^{12c}$, —$N(R^{12b})_2$, —$OR^{12b}$, —$SR^{12c}$, —$S(O)_2R^{12c}$, —$C(O)R^{12b}$, —$C(O)OR^{12b}$, —$C(O)N(R^{12b})_2$, —$S(O)_2N(R^{12b})_2$, —$OC(O)N(R^{12b})_2$, —$N(R^{12e})C(O)R^{12b}$, —$N(R^{12e})SO_2R^{12c}$, —$N(R^{12e})C(O)OR^{12b}$, —$N(R^{12e})C(O)N(R^{12b})_2$, or —$N(R^{12e})SO_2N(R^{12b})_2$;

each occurrence of $R^{12b}$ is independently hydrogen or an optionally substituted group selected from $C_{1-6}$ aliphatic, 3-10-membered cycloaliphatic, 4-10-membered heterocyclyl having 1-5 heteroatoms independently selected from nitrogen, oxygen, or sulfur, 6-10-membered aryl, or 5-10-membered heteroaryl having 1-5 heteroatoms independently selected from nitrogen, oxygen, or sulfur, or two occurrences of $R^{12b}$, taken together with a nitrogen atom to which they are bound, form an optionally substituted 4-7-membered heterocyclyl ring having 0-1 additional heteroatoms selected from nitrogen, oxygen, or sulfur;

each occurrence of $R^{12c}$ is independently an optionally substituted group selected from $C_{1-6}$ aliphatic, 3-10-membered cycloaliphatic, 4-10-membered heterocyclyl having 1-5 heteroatoms independently selected from nitrogen, oxygen, or sulfur, 6-10-membered aryl, or 5-10-membered heteroaryl having 1-5 heteroatoms independently selected from nitrogen, oxygen, or sulfur;

each occurrence of $R^{12d}$ is independently hydrogen, —$N(R^{7b})_2$, or an optionally substituted group selected from 3-10-membered cycloaliphatic, 4-10-membered heterocyclyl having 1-5 heteroatoms independently selected from nitrogen, oxygen, or sulfur, 6-10-membered aryl, or 5-10-membered heteroaryl having 1-5 heteroatoms independently selected from nitrogen, oxygen, or sulfur;

each occurrence of $R^{12e}$ is independently hydrogen or an optionally substituted $C_{1-6}$ aliphatic group;

each occurrence of $V_2$ is independently —$N(R^{12e})$—, —O—, —S—, —S(O)—, —$S(O)_2$—, —C(O)—, —C(O)O—, —$C(O)N(R^{12e})$—, —$S(O)_2N(R^{12e})$—, —$OC(O)N(R^{12e})$—, —$N(R^{12e})C(O)$—, —$N(R^{12e})SO_2$—, —$N(R^{12e})C(O)O$—, —$N(R^{12e})C(O)N(R^{12e})$—, —$N(R^{12e})SO_2N(R^{12e})$—, —OC(O)—, or —$C(O)N(R^{12e})$—O—; and $T_2$ is an optionally substituted $C_{1-6}$ alkylene chain wherein the alkylene chain optionally is interrupted by —$N(R^{13})$—, —O—, —S—, —S(O)—, —$S(O)_2$—, —C(O)—, —C(O)O—, —$C(O)N(R^{13})$—, —$S(O)_2N(R^{13})$—, —$OC(O)N(R^{13})$—, —$N(R^{13})C(O)$—, —$N(R^{13})SO_2$—, —$N(R^{13})C(O)O$—, —$N(R^{13})C(O)N(R^{13})$—, —$N(R^{13})S(O)_2N(R^{13})$—, —OC(O)—, or —$C(O)N(R^{13})$—O— or wherein $T_2$ or a portion thereof optionally forms part of an optionally substituted 3-7 membered cycloaliphatic or heterocyclyl ring, wherein $R^{13}$ is hydrogen or an optionally substituted $C_{1-4}$ aliphatic group;

W is selected from a covalent bond, —$C(R^7)_2$—, —C(=$C(R^7)_2$)—, —$C(R^7)_2O$—, —$C(R^7)_2NR^{7a}$—, —O—, —$N(R^{7b})$—, —S—, —S(O)—, —$S(O)_2$—, —C(O)—, —$C(O)NR^{7a}$—, or —$N(R^{7a})C(O)$—, wherein:

each occurrence of $R^7$ is independently hydrogen, or an optionally substituted group selected from $C_{1-6}$ aliphatic, 6-10-membered aryl, 5-10-membered heteroaryl having 1-5 heteroatoms independently selected from nitrogen, oxygen, or sulfur, —$N(R^{7b})_2$, —$OR^{7c}$, —$SR^{7a}$, or F;

each occurrence of $R^{7a}$ is independently hydrogen or optionally substituted $C_{1-6}$ aliphatic;

each occurrence of $R^{7b}$ is independently hydrogen, optionally substituted $C_{1-6}$ aliphatic, —$C(O)R^{7a}$, —$C(O)OR^{7a}$, $S(O)R^{7a}$, or —$S(O)_2R^{7a}$; or each occurrence of $R^{7c}$ is independently an optionally substituted $C_{1-6}$ aliphatic or an optionally substituted 3-7 membered cycloalphatic; or wherein any two occurrences of $R^7$, $R^{7a}$, $R^{7b}$, or $R^{7c}$, taken together with atom to which they are bound, form an optionally substituted group selected from a 3-6-membered cycloaliphatic ring, 6-10-membered aryl, 3-6-membered heterocyclyl having 1-5 heteroatoms independently selected from nitrogen, oxygen, or sulfur, or 5-10-membered heteroaryl having 1-5 heteroatoms independently selected from nitrogen, oxygen, or sulfur;

or wherein any two occurrences of $R^{7a}$ and $R^2$, or $R^{7b}$ and $R^2$ taken together with the nitrogen atom to which they are bound, form an optionally substituted group selected from 3-6-membered heterocyclyl having 1-5 heteroatoms independently selected from nitrogen, oxygen, or sulfur, or 5-10-membered heteroaryl having 1-5 heteroatoms independently selected from nitrogen, oxygen, or sulfur;

$G_1$ is N or —$CR^8$, wherein $R^8$ is H, —CN, halogen, —$Z_2$—$R^9$, $C_{1-6}$ aliphatic, or 3-10-membered cycloaliphatic, wherein:

$Z_2$ is selected from an optionally substituted $C_{1-3}$ alkylene chain, —O—, —$N(R^{8a})$—, —S—, —S(O)—, $S(O)_2$—, —C(O)—, —CO$_2$—, —C(O)NR$^{8a}$—, —N(R$^{8a}$)C(O)—, —N(R$^{8a}$)CO$_2$—, —S(O)$_2$NR$^{8a}$—, —N(R$^{8a}$)S(O)$_2$—, —OC(O)N(R$^{8a}$)—, —N(R$^{8a}$)C(O)NR$^{8a}$—, —N(R$^{8a}$)S(O)$_2$N(R$^{8a}$)—, or —OC(O)—;

R$^{8a}$ is hydrogen or an optionally substituted C$_{1-4}$ aliphatic, and

R$^9$ is hydrogen or an optionally substituted group selected from C$_{1-6}$ aliphatic, 3-10-membered cycloaliphatic, 4-10-membered heterocyclyl having 1-5 heteroatoms independently selected from nitrogen, oxygen, or sulfur, 6-10-membered aryl, or 5-10-membered heteroaryl having 1-5 heteroatoms independently selected from nitrogen, oxygen, or sulfur; and HY is

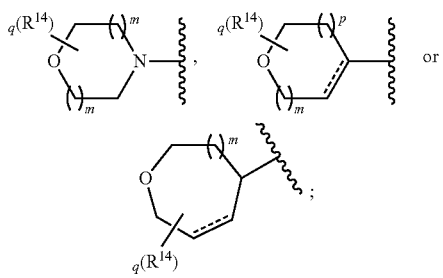

----- represents a single bond or a double bond;

wherein each occurrence of R$^{14}$ is independently —R$^{14a}$ or -T$_1$-R$^{14d}$, wherein:

each occurrence of R$^{14a}$, as valency and stability permit, is independently fluorine, =O, =S, —CN, —NO$_2$, —R$^{14c}$, —N(R$^{14b}$)$_2$, —SR$^{14c}$, —S(O)$_2$R$^{14c}$, —C(O)R$^{14b}$, —C(O)OR$^{14b}$, —C(O)N(R$^{14b}$)$_2$, —S(O)$_2$N(R$^{14b}$)$_2$, —OC(O)N(R$^{14b}$)$_2$, —N(R$^{14e}$)C(O)R$^{14b}$, —N(R$^{14e}$)SO$_2$R$^{14c}$, —N(R$^{14e}$)C(O)OR$^{14b}$, —N(R$^{14e}$)C(O)N(R$^{14b}$)$_2$, or —N(R$^{14e}$)SO$_2$N(R$^{14b}$)$_2$, or two occurrences of R$^{14b}$, taken together with a nitrogen atom to which they are bound, form an optionally substituted 4-7-membered heterocyclyl ring having 0-1 additional heteroatoms selected from nitrogen, oxygen, or sulfur;

each occurrence of R$^{14b}$ is independently hydrogen or an optionally substituted group selected from C$_{1-6}$ aliphatic, 3-10-membered cycloaliphatic, 4-10-membered heterocyclyl having 1-5 heteroatoms independently selected from nitrogen, oxygen, or sulfur, 6-10-membered aryl, or 5-10-membered heteroaryl having 1-5 heteroatoms independently selected from nitrogen, oxygen, or sulfur;

each occurrence of R$^{14c}$ is independently an optionally substituted group selected from C$_{1-6}$ aliphatic, 3-10-membered cycloaliphatic, 4-10-membered heterocyclyl having 1-5 heteroatoms independently selected from nitrogen, oxygen, or sulfur, 6-10-membered aryl, or 5-10-membered heteroaryl having 1-5 heteroatoms independently selected from nitrogen, oxygen, or sulfur;

each occurrence of R$^{14d}$ is independently hydrogen or an optionally substituted from 3-10-membered cycloaliphatic, 4-10-membered heterocyclyl having 1-5 heteroatoms independently selected from nitrogen, oxygen, or sulfur, 6-10-membered aryl, or 5-10-membered heteroaryl having 1-5 heteroatoms independently selected from nitrogen, oxygen, or sulfur;

each occurrence of R$^{14e}$ is independently hydrogen or an optionally substituted C$_{1-6}$ aliphatic group; and T$_1$ is an optionally substituted C$_{1-6}$ alkylene chain wherein the alkylene chain optionally is interrupted by —N(R$^{14a}$)—, —O—, —S—, —S(O)—, —S(O)$_2$—, —C(O)—, —C(O)O—, —C(O)N(R$^{14a}$)—, —S(O)$_2$N(R$^{14a}$)—, —OC(O)N(R$^{14a}$)—, —N(R$^{14a}$)C(O)—, —N(R$^{14a}$)SO$_2$—, —N(R$^{14a}$)C(O)O—, —NR$^{14a}$C(O)N(R$^{14a}$)—, —N(R$^{14a}$)S(O)$_2$N(R$^{14a}$)—, —OC(O)—, or —C(O)N(R$^{14a}$)—O— or wherein T$_1$ or a portion thereof optionally forms part of an optionally substituted 3-7 membered cycloaliphatic or heterocyclyl ring;

n is 0-6;

q is 0-4;

m is 1 or 2; and p is 0, 1, or 2;

provided that:

a) when G$_1$ is C—CN, HY is unsubstituted morpholine, R$^1$ is —C(O)OH, —C(O)OMe, or —C(O)OEt, and W is a covalent bond, then Ring A is other than unsubstituted phenyl, 2-chlorophenyl, 4-chlorophenyl, 2-fluorophenyl, 4-fluorophenyl, 2,4-dichlorophenyl, 3,4-dichlorophenyl, 4-methylphenyl, 3-methoxyphenyl, 4-methoxyphenyl, 3,4-dimethoxyphenyl, 3-(trifluoromethyl)phenyl, 4-(trifluoromethyl)phenyl, or 3-(acetylamino)phenyl;

b) when G$_1$ is N, HY is unsubstituted morpholine, R$^1$ is —C(O)OH, —C(O)OMe, or —C(O)OEt, and W is a covalent bond, then Ring A is other than unsubstituted phenyl or 2-chlorophenyl; and c) the compound is other than:

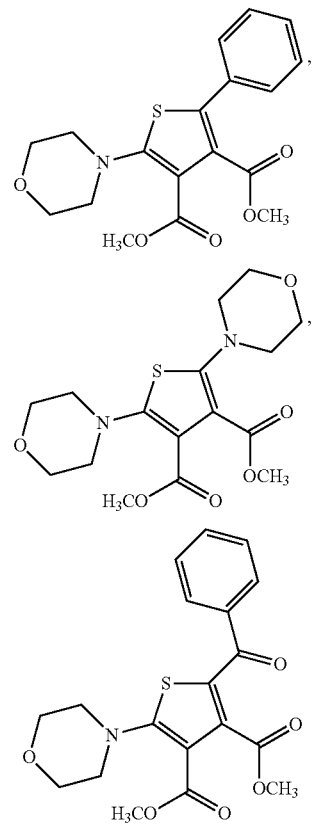

-continued

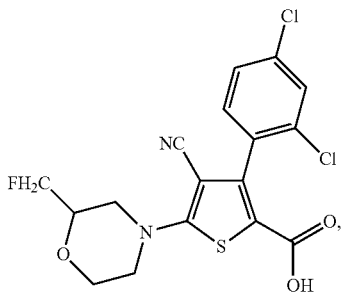

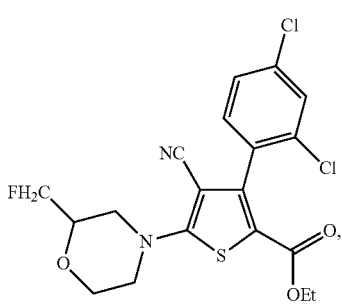

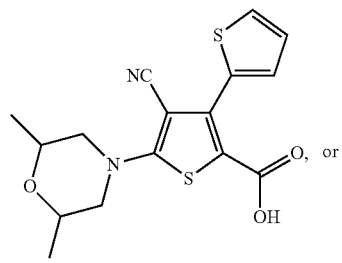

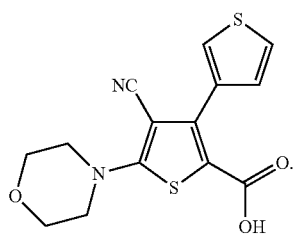 [SMILES: N#Cc1c(N2CCOCC2)sc(C(=O)O)c1-c1ccsc1]

In yet another embodiment of the invention, compounds of this invention are represented by formula IA-i or IB-i:

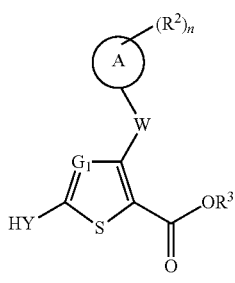

IA-i

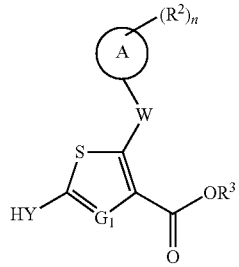

IB-i or a pharmaceutically acceptable salt thereof, wherein:
$R^3$ is hydrogen or an optionally substituted $C_{1-6}$ aliphatic;
Ring A is a group selected from 3-10-membered cycloaliphatic, 4-10-membered heterocyclyl having 1-5 heteroatoms independently selected from nitrogen, oxygen, or sulfur, 6-10-membered aryl, or 5-10-membered heteroaryl having 1-5 heteroatoms independently selected from nitrogen, oxygen, or sulfur;
each occurrence of $R^2$ is independently —$R^{12a}$, -$T_2$-$R^{12d}$, —$V_2$-$T_2$-$R^{12d}$, or:
two adjacent $R^2$ groups are taken together with their intervening atoms to form an optionally substituted 4-7 membered saturated, partially unsaturated, or aryl ring having 0-4 heteroatoms selected from nitrogen, oxygen, or sulfur;
each occurrence of $R^{12c}$ is independently halogen, —CN, —$NO_2$, —$R^{12c}$, N($R^{12b}$)$_2$, —O$R^{12b}$, —S$R^{12c}$, —S(O)$_2$$R^{12c}$, —C(O)$R^{12b}$, —C(O)O$R^{12b}$, —C(O)N($R^{12b}$)$_2$, —S(O)$_2$N($R^{12b}$)$_2$, —OC(O)N($R^{12b}$)$_2$, —N($R^{12e}$)C(O)$R^{12b}$, —N($R^{12e}$)SO$_2$$R^{12c}$, —N($R^{12e}$)C(O)O$R^{12b}$, —N($R^{12e}$)C(O)N($R^{12b}$)$_2$, or —N($R^{12e}$)SO$_2$N($R^{12b}$)$_2$;
each occurrence of $R^{12b}$ is independently hydrogen or an optionally substituted group selected from $C_{1-6}$ aliphatic, 3-10-membered cycloaliphatic, 4-10-membered heterocyclyl having 1-5 heteroatoms independently selected from nitrogen, oxygen, or sulfur, 6-10-membered aryl, or 5-10-membered heteroaryl having 1-5 heteroatoms independently selected from nitrogen, oxygen, or sulfur, or two occurrences of $R^{12b}$, taken together with a nitrogen atom to which they are bound, form an optionally substituted 4-7-membered heterocyclyl ring having 0-1 additional heteroatoms selected from nitrogen, oxygen, or sulfur;
each occurrence of $R^{12c}$ is independently an optionally substituted group selected from $C_{1-6}$ aliphatic, 3-10-membered cycloaliphatic, 4-10-membered heterocyclyl having 1-5 heteroatoms independently selected from nitrogen, oxygen, or sulfur, 6-10-membered aryl, or 5-10-membered heteroaryl having 1-5 heteroatoms independently selected from nitrogen, oxygen, or sulfur;
each occurrence of $R^{12d}$ is independently hydrogen, —N($R^{7b}$)$_2$, or an optionally substituted group selected from 3-10-membered cycloaliphatic, 4-10-membered heterocyclyl having 1-5 heteroatoms independently selected from nitrogen, oxygen, or sulfur, 6-10-membered aryl, or 5-10-membered heteroaryl having 1-5 heteroatoms independently selected from nitrogen, oxygen, or sulfur;
each occurrence of $R^{12e}$ is independently hydrogen or an optionally substituted $C_{1-6}$ aliphatic group;
each occurrence of $V_2$ is independently —N($R^{12e}$)—, —O—, —S—, —S(O)—, —S(O)$_2$—, —C(O)—, —C(O)O—, —C(O)N($R^{12e}$)—, —S(O)$_2$N($R^{12e}$)—, —OC(O)N(R$^{12e}$)—, —N(R$^{12e}$)C(O)—, —N(R$^{12e}$)SO$_2$—, —N(R$^{12e}$)C(O)O—, —N(R$^{12e}$)C(O)N(R$^{12e}$), N(R$^{12e}$)SO$_2$N(R$^{12e}$)—, —OC(O)—, or —C(O)N(R$^{12e}$)—O—; and T$_2$ is an optionally substituted C$_{1-6}$ alkylene chain wherein the alkylene chain optionally is interrupted by —N(R$^{13}$)—, —O—, —S—, —S(O)—, —S(O)$_2$—, —C(O)—, —C(O)O—, —C(O)N(R$^{13}$)—, —S(O)$_2$N(R$^{13}$)—, —OC(O)N(R$^{13}$)—, —N(R$^{13}$)C(O)—, —N(R$^{13}$)SO$_2$—, —N(R$^{13}$)C(O)O—, —N(R$^{13}$)C(O)N(R$^{13}$)—, —N(R$^{13}$)S(O)$_2$N(R$^{13}$)—, —OC(O)—, or —C(O)N(R$^{13}$)—O— or wherein T$_2$ or a portion thereof optionally forms part of an optionally substituted 3-7 membered cycloaliphatic or heterocyclyl ring, wherein R$^{13}$ is hydrogen or an optionally substituted C$_{1-4}$aliphatic group;

W is selected from a covalent bond, —C(R$^7$)$_2$—, —C(=C(R$^7$)$_2$)—, —C(R$^7$)$_2$O—, —C(R$^7$)$_2$NR$^{7a}$—, —O—, —N(R$^{7b}$)—, —S—, —S(O)—, —S(O)$_2$—, —C(O)—, —C(O)NR$^{7a}$—, or —N(R$^{7a}$)C(O)—, wherein:

each occurrence of R$^7$ is independently hydrogen, or an optionally substituted group selected from C$_{1-6}$ aliphatic, 6-10-membered aryl, 5-10-membered heteroaryl having 1-5 heteroatoms independently selected from nitrogen, oxygen, or sulfur, —N(R$^{7b}$)$_2$, —OR$^{7c}$, —SR$^{7a}$, or F;

each occurrence of R$^{7a}$ is independently hydrogen or optionally substituted C$_{1-6}$ aliphatic or optionally substituted C$_{3-6}$ cycloaliphatic;

each occurrence of R$^{7b}$ is independently hydrogen, optionally substituted C$_{1-6}$ aliphatic, optionally substituted C$_{3-6}$ cycloaliphatic, —C(O)R$^{7a}$, —C(O)OR$^{7a}$, S(O)R$^{7a}$, or —S(O)$_2$R$^{7a}$; or each occurrence of R$^7$ is independently an optionally substituted C$_{1-6}$aliphatic or an optionally substituted 3-7 membered cycloalphatic; or wherein any two occurrences of R$^7$, R$^{7a}$, R$^{7b}$, or R$^{7e}$, taken together with atom to which they are bound, form an optionally substituted group selected from a 3-6-membered cycloaliphatic ring, 6-10-membered aryl, 3-6-membered heterocyclyl having 1-5 heteroatoms independently selected from nitrogen, oxygen, or sulfur, or 5-10-membered heteroaryl having 1-5 heteroatoms independently selected from nitrogen, oxygen, or sulfur;

or wherein any two occurrences of R$^{7a}$ and R$^2$, or R$^{7b}$ and R$^2$ taken together with the nitrogen atom to which they are bound, form an optionally substituted group selected from 3-6-membered heterocyclyl having 1-5 heteroatoms independently selected from nitrogen, oxygen, or sulfur, or 5-10-membered heteroaryl having 1-5 heteroatoms independently selected from nitrogen, oxygen, or sulfur;

G$_1$ is N or —CR$^8$, wherein R$^8$ is H, —CN, halogen, —Z$_2$—R$^9$, C$_{1-6}$ aliphatic, or 3-10-membered cycloaliphatic, wherein:

Z$_2$ is selected from an optionally substituted C$_{1-3}$ alkylene chain, —O—, —N(R$^{8a}$)—, —S—, —S(O)—, S(O)$_2$—, —C(O)—, —CO$_2$—, —C(O)NR$^{8a}$, —N(R$^{8a}$)C(O)—, —N(R$^{8a}$)CO$_2$—, —S(O)$_2$NR$^{8a}$—, —N(R$^{8a}$)S(O)$_2$—, —OC(O)N(R$^{8a}$)—, —N(R$^{8a}$)C(O)NR$^{8a}$—, —N(R$^{8a}$)S(O)$_2$N(R$^{8a}$)—, or —OC(O)—;

R$^{8a}$ is hydrogen or an optionally substituted C$_{1-4}$ aliphatic, and

R$^9$ is hydrogen or an optionally substituted group selected from C$_{1-6}$ aliphatic, 3-10-membered cycloaliphatic, 4-10-membered heterocyclyl having 1-5 heteroatoms independently selected from nitrogen, oxygen, or sulfur, 6-10-membered aryl, or 5-10-membered heteroaryl having 1-5 heteroatoms independently selected from nitrogen, oxygen, or sulfur; and HY is

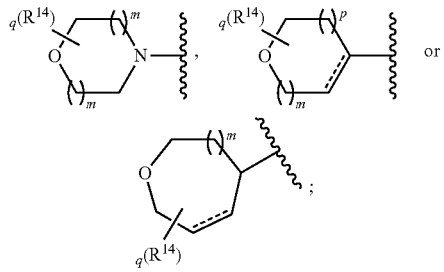

----- represents a single bond or a double bond;

wherein each occurrence of R$^{14}$ is independently —R$^{14a}$ or -T$_1$-R$^{14d}$, wherein:

each occurrence of R$^{14a}$, as valency and stability permit, is independently fluorine, =O, =S, —CN, —NO$_2$, —R$^{12e}$, —N(R$^{14b}$)$_2$, —OR$^{14b}$, —SR$^{14c}$, —S(O)$_2$R$^{14c}$, —C(O)R$^{14b}$, —C(O)OR$^{14b}$, —C(O)N(R$^{14b}$)$_2$, —S(O)$_2$N(R$^{14b}$)$_2$, —OC(O)N(R$^{14b}$)$_2$, —N(R$^{14e}$)C(O)R$^{14b}$, —N(R$^{14e}$)SO$_2$R$^{14a}$, —N(R$^{14e}$)C(O)OR$^{14b}$, —N(R$^{14e}$)C(O)N(R$^{14b}$)$_2$, or —N(R$^{14e}$)SO$_2$N(R$^{14b}$)$_2$, or two occurrences of R$^{14b}$, taken together with a nitrogen atom to which they are bound, form an optionally substituted 4-7-membered heterocyclyl ring having 0-1 additional heteroatoms selected from nitrogen, oxygen, or sulfur;

each occurrence of R$^{14b}$ is independently hydrogen or an optionally substituted group selected from C$_{1-6}$ aliphatic, 3-10-membered cycloaliphatic, 4-10-membered heterocyclyl having 1-5 heteroatoms independently selected from nitrogen, oxygen, or sulfur, 6-10-membered aryl, or 5-10-membered heteroaryl having 1-5 heteroatoms independently selected from nitrogen, oxygen, or sulfur;

each occurrence of R$^{14c}$ is independently an optionally substituted group selected from C$_{1-6}$ aliphatic, 3-10-membered cycloaliphatic, 4-10-membered heterocyclyl having 1-5 heteroatoms independently selected from nitrogen, oxygen, or sulfur, 6-10-membered aryl, or 5-10-membered heteroaryl having 1-5 heteroatoms independently selected from nitrogen, oxygen, or sulfur;

each occurrence of R$^{14d}$ is independently hydrogen or an optionally substituted from 3-10-membered cycloaliphatic, 4-10-membered heterocyclyl having 1-5 heteroatoms independently selected from nitrogen, oxygen, or sulfur, 6-10-membered aryl, or 5-10-membered heteroaryl having 1-5 heteroatoms independently selected from nitrogen, oxygen, or sulfur;

each occurrence of R$^{14e}$ is independently hydrogen or an optionally substituted C$_{1-6}$ aliphatic group; and T$_1$ is an optionally substituted C$_{1-6}$ alkylene chain wherein the alkylene chain optionally is interrupted by —N(R$^{14a}$)—, —O—, —S—, —S(O)—, —S(O)$_2$—, —C(O)—, —C(O)O—, —C(O)N(R$^{14a}$)—, —S(O)$_2$N(R$^{14a}$)—, —OC(O)N(R$^{14a}$)—, —N(R$^{14a}$)C(O)—, —N(R$^{14a}$)SO$_2$—, —N(R$^{14a}$)C(O)O—, —NR$^{14a}$C(O)N(R$^{14a}$)—, —N(R$^{14a}$)S(O)$_2$N(R$^{14a}$)—, —OC(O)—, or —C(O)N(R$^{14a}$)—O— or wherein T$_1$ or a portion thereof optionally forms part of an optionally substituted 3-7 membered cycloaliphatic or heterocyclyl ring;

n is 0-6;

q is 0-4;

m is 1 or 2; and p is 0, 1, or 2;

provided that:

a) when $G_1$ is C—CN, HY is unsubstituted morpholine, $R^1$ is —C(O)OH, —C(O)OMe, or —C(O)OEt, and W is a covalent bond, then Ring A is other than unsubstituted phenyl, 2-chlorophenyl, 4-chlorophenyl, 2-fluorophenyl, 4-fluorophenyl, 2,4-dichlorophenyl, 3,4-dichlorophenyl, 4-methylphenyl, 3-methoxyphenyl, 4-methoxyphenyl, 3,4-dimethoxyphenyl, 3-(trifluoromethyl)phenyl, 4-(trifluoromethyl)phenyl, or 3-(acetylamino)phenyl;

b) when $G_1$ is N, HY is unsubstituted morpholine, $R^1$ is —C(O)OH, —C(O)OMe, or —C(O)OEt, and W is a covalent bond, then Ring A is other than unsubstituted phenyl or 2-chlorophenyl; and c) the compound is other than:

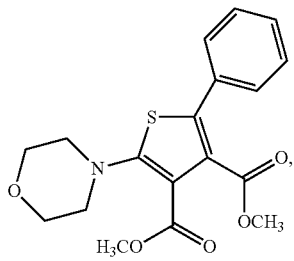

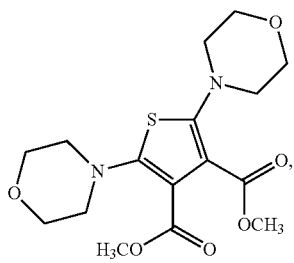

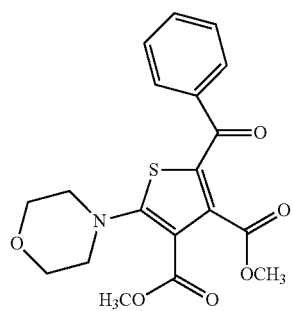

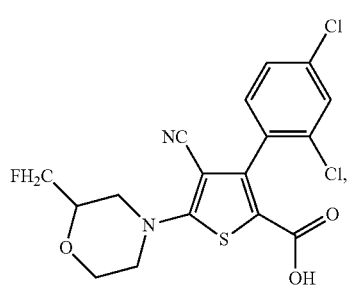

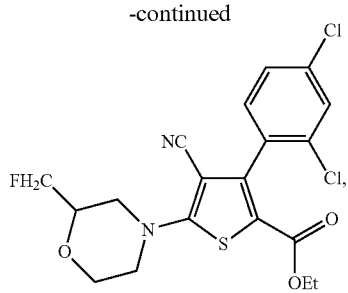

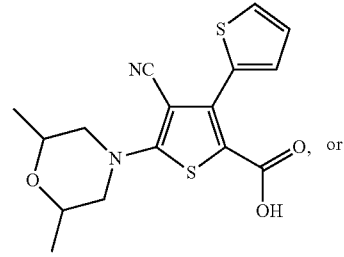

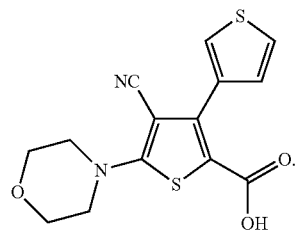

In some embodiments for compounds described directly above, $G_1$ is N.

In some embodiments for compounds described directly above, $G_1$ is $C(R^8)$, wherein $R^8$ is —CN or $C_{2-4}$ alkynyl.

In some embodiments for compounds described directly above, HY is

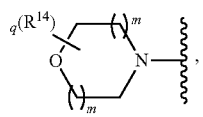

wherein both occurrences of m are 1.

In some embodiments for compounds described directly above, $R^3$ is H.

DETAILED DESCRIPTION OF THE INVENTION

2. Compounds and Definitions

Compounds of this invention include those described generally above, and are further illustrated by the classes, subclasses, and species disclosed herein. It will be appreciated that preferred subsets described for each variable herein can be used for any of the structural subsets as well. As used herein, the following definitions shall apply unless otherwise indicated.

As described herein, compounds of the invention may be optionally substituted with one or more substituents, such as are illustrated generally above, or as exemplified by particular classes, subclasses, and species of the invention. It will be appreciated that the phrase "optionally substituted" is used interchangeably with the phrase "substituted or unsubstituted." In general, the term "substituted", whether preceded by the term "optionally" or not, means that a hydrogen radical of the designated moiety is replaced with the radical of a specified substituent, provided that the substitution results in a stable or chemically feasible compound. The term "substitutable", when used in reference to a designated atom, means that attached to the atom is a hydrogen radical, which hydrogen atom can be replaced with the radical of a suitable substituent. Unless otherwise indicated, an "optionally substituted" group may have a substituent at each substitutable position of the group, and when more than one position in any given structure may be substituted with more than one substituent selected from a specified group, the substituent may be either the same or different at every position. Combinations of substituents envisioned by this invention are preferably those that result in the formation of stable or chemically feasible compounds.

A stable compound or chemically feasible compound is one in which the chemical structure is not substantially altered when kept at a temperature from about −80° C. to about +40°, in the absence of moisture or other chemically reactive conditions, for at least a week, or a compound which maintains its integrity long enough to be useful for therapeutic or prophylactic administration to a patient.

The phrase "one or more substituents", as used herein, refers to a number of substituents that equals from one to the maximum number of substituents possible based on the number of available bonding sites, provided that the above conditions of stability and chemical feasibility are met.

As used herein, the term "independently selected" means that the same or different values may be selected for multiple instances of a given variable in a single compound.

As used herein, "a 3-7-membered saturated, partially unsaturated, or aromatic monocyclic ring having 0-3 heteroatoms independently selected from nitrogen, oxygen, or sulfur, or an 8-10-membered partially unsaturated, or aromatic bicyclic ring system having 0-5 heteroatoms independently selected from nitrogen, oxygen, or sulfur" includes cycloaliphatic, heterocyclic, aryl and heteroaryl rings.

As used herein, the term "aromatic" includes aryl and heteroaryl groups as described generally below and herein.

The term "aliphatic" or "aliphatic group", as used herein, means an optionally substituted straight-chain or branched $C_{1-12}$ hydrocarbon, or a cyclic $C_{1-12}$ hydrocarbon which is completely saturated or which contains one or more units of unsaturation, but which is not aromatic (also referred to herein as "carbocycle", "cycloaliphatic", "cycloalkyl", or "cycloalkenyl"). For example, suitable aliphatic groups include optionally substituted linear, branched or cyclic alkyl, alkenyl, alkynyl groups and hybrids thereof, such as (cycloalkyl)alkyl, (cycloalkenyl)alkyl, or (cycloalkyl)alkenyl. Unless otherwise specified, in various embodiments, aliphatic groups have 1-12, 1-10, 1-8, 1-6, 1-4, 1-3, or 1-2 carbon atoms.

The term "alkyl", used alone or as part of a larger moiety, refers to an optionally substituted straight or branched chain hydrocarbon group having 1-12, 1-10, 1-8, 1-6, 1-4, 1-3, or 1-2 carbon atoms.

The term "alkenyl", used alone or as part of a larger moiety, refers to an optionally substituted straight or branched chain hydrocarbon group having at least one double bond and having 2-12, 2-10, 2-8, 2-6, 2-4, or 2-3 carbon atoms.

The term "alkynyl", used alone or as part of a larger moiety, refers to an optionally substituted straight or branched chain hydrocarbon group having at least one triple bond and having 2-12, 2-10, 2-8, 2-6, 2-4, or 2-3 carbon atoms.

The terms "cycloaliphatic", "carbocycle", "carbocyclyl", "carbocyclo", or "carbocyclic", used alone or as part of a larger moiety, refer to an optionally substituted saturated or partially unsaturated cyclic aliphatic ring system having from 3 to about 14 ring carbon atoms. In some embodiments, the cycloaliphatic group is an optionally substituted monocyclic hydrocarbon having 3-8 or 3-6 ring carbon atoms. Cycloaliphatic groups include, without limitation, optionally substituted cyclopropyl, cyclobutyl, cyclopentyl, cyclopentenyl, cyclohexyl, cyclohexenyl, cycloheptyl, cycloheptenyl, cyclooctyl, cyclooctenyl, or cyclooctadienyl. The terms "cycloaliphatic", "carbocycle", "carbocyclyl", "carbocyclo", or "carbocyclic" also include optionally substituted bridged or fused bicyclic rings having 6-12, 6-10, or 6-8 ring carbon atoms, wherein any individual ring in the bicyclic system has 3-8 ring carbon atoms.

The term "cycloalkyl" refers to an optionally substituted saturated ring system of about 3 to about 10 ring carbon atoms. Exemplary monocyclic cycloalkyl rings include cyclopropyl, cyclobutyl, cyclopentyl, cyclohexyl, and cycloheptyl.

The term "cycloalkenyl" refers to an optionally substituted non-aromatic monocyclic or multicyclic ring system containing at least one carbon-carbon double bond and having about 3 to about 10 carbon atoms. Exemplary monocyclic cycloalkenyl rings include cyclopentyl, cyclohexenyl, and cycloheptenyl.

The terms "haloaliphatic", "haloalkyl", "haloalkenyl" and "haloalkoxy" refer to an aliphatic, alkyl, alkenyl or alkoxy group, as the case may be, which is substituted with one or more halogen atoms. As used herein, the term "halogen" or "halo" means F, Cl, Br, or I. The term "fluoroaliphatic" refers to a haloaliphatic wherein the halogen is fluoro, including perfluorinated aliphatic groups. Examples of fluoroaliphatic groups include, without limitation, fluoromethyl, difluoromethyl, trifluoromethyl, 2-fluoroethyl, 2,2,2-trifluoroethyl, 1,1,2-trifluoroethyl, 1,2,2-trifluoroethyl, and pentafluoroethyl.

The term "heteroatom" refers to one or more of oxygen, sulfur, nitrogen, phosphorus, or silicon (including, any oxidized form of nitrogen, sulfur, phosphorus, or silicon; the quaternized form of any basic nitrogen or; a substitutable nitrogen of a heterocyclic ring, for example N (as in 3,4-dihydro-2H-pyrrolyl), NH (as in pyrrolidinyl) or $NR^+$ (as in N-substituted pyrrolidinyl)).

The terms "aryl" and "ar-", used alone or as part of a larger moiety, e.g., "aralkyl", "aralkoxy", or "aryloxyalkyl", refer to an optionally substituted $C_{6-14}$ aromatic hydrocarbon moiety comprising one to three aromatic rings. Preferably, the aryl group is a $C_{6-10}$ aryl group. Aryl groups include, without limitation, optionally substituted phenyl, naphthyl, or anthracenyl. The terms "aryl" and "ar-", as used herein, also include groups in which an aryl ring is fused to one or more cycloaliphatic rings to form an optionally substituted cyclic structure such as a tetrahydronaphthyl, indenyl, or indanyl ring. The term "aryl" may be used interchangeably with the terms "aryl group", "aryl ring", and "aromatic ring".

An "aralkyl" or "arylalkyl" group comprises an aryl group covalently attached to an alkyl group, either of which independently is optionally substituted. Preferably, the aralkyl group is $C_{6-10}$ aryl$C_{1-6}$alkyl, including, without limitation, benzyl, phenethyl, and naphthylmethyl.

The terms "heteroaryl" and "heteroar-", used alone or as part of a larger moiety, e.g., "heteroaralkyl", or "heteroaralkoxy", refer to groups having 5 to 14 ring atoms, preferably 5, 6, 9, or 10 ring atoms; having 6, 10, or 14π electrons shared in a cyclic array; and having, in addition to carbon atoms, from one to five heteroatoms. A heteroaryl group may be mono-, bi-, tri-, or polycyclic, preferably mono-, bi-, or tricyclic, more preferably mono- or bicyclic.

The term "heteroatom" refers to nitrogen, oxygen, or sulfur, and includes any oxidized form of nitrogen or sulfur, and any quaternized form of a basic nitrogen. For example, a nitrogen atom of a heteroaryl may be a basic nitrogen atom and may also be optionally oxidized to the corresponding N-oxide. When a heteroaryl is substituted by a hydroxy group, it also includes its corresponding tautomer. The terms "heteroaryl" and "heteroar-", as used herein, also include groups in which a heteroaromatic ring is fused to one or more aryl, cycloaliphatic, or heterocycloaliphatic rings. Nonlimiting examples of heteroaryl groups include thienyl, furanyl, pyrrolyl, imidazolyl, pyrazolyl, triazolyl, tetrazolyl, oxazolyl, isoxazolyl, oxadiazolyl, thiazolyl, isothiazolyl, thiadiazolyl, pyridyl, pyridazinyl, pyrimidinyl, pyrazinyl, indolizinyl, purinyl, naphthyridinyl, pteridinyl, indolyl, isoindolyl, benzothienyl, benzofuranyl, dibenzofuranyl, indazolyl, benzimidazolyl, benzthiazolyl, quinolyl, isoquinolyl, cinnolinyl, phthalazinyl, quinazolinyl, quinoxalinyl, 4H-quinolizinyl, carbazolyl, acridinyl, phenazinyl, phenothiazinyl, phenoxazinyl, tetrahydroquinolinyl, tetrahydroisoquinolinyl, and pyrido[2,3-b]-1,4-oxazin-3(4H)-one. The term "heteroaryl" may be used interchangeably with the terms "heteroaryl ring", "heteroaryl group", or "heteroaromatic", any of which terms include rings that are optionally substituted. The term "heteroaralkyl" refers to an alkyl group substituted by a heteroaryl, wherein the alkyl and heteroaryl portions independently are optionally substituted.

As used herein, the terms "heterocycle", "heterocyclyl", "heterocyclic radical", and "heterocyclic ring" are used interchangeably and refer to a stable 3- to 8-membered monocyclic or 7-10-membered bicyclic heterocyclic moiety that is either saturated or partially unsaturated, and having, in addition to carbon atoms, one or more, preferably one to four, heteroatoms, as defined above. When used in reference to a ring atom of a heterocycle, the term "nitrogen" includes a substituted nitrogen. As an example, in a saturated or partially unsaturated ring having 0-3 heteroatoms selected from oxygen, sulfur or nitrogen, the nitrogen may be N (as in 3,4-dihydro-2H-pyrrolyl), NH (as in pyrrolidinyl), or NR$^+$ (as in N-substituted pyrrolidinyl).

A heterocyclic ring can be attached to its pendant group at any heteroatom or carbon atom that results in a stable structure and any of the ring atoms can be optionally substituted. Examples of such saturated or partially unsaturated heterocyclic radicals include, without limitation, tetrahydrofuranyl, tetrahydrothienyl, piperidinyl, decahydroquinolinyl, oxazolidinyl, piperazinyl, dioxanyl, dioxolanyl, diazepinyl, oxazepinyl, thiazepinyl, morpholinyl, and thiamorpholinyl. A heterocyclyl group may be mono-, bi-, tri-, or polycyclic, preferably mono-, bi-, or tricyclic, more preferably mono- or bicyclic. The term "heterocyclylalkyl" refers to an alkyl group substituted by a heterocyclyl, wherein the alkyl and heterocyclyl portions independently are optionally substituted. Additionally, a heterocyclic ring also includes groups in which the heterocyclic ring is fused to one or more aryl rings.

As used herein, the term "partially unsaturated" refers to a ring moiety that includes at least one double or triple bond between ring atoms. The term "partially unsaturated" is intended to encompass rings having multiple sites of unsaturation, but is not intended to include aromatic (e.g., aryl or heteroaryl) moieties, as herein defined.

The term "alkylene" refers to a bivalent alkyl group. An "alkylene chain" is a polymethylene group, i.e., —(CH$_2$)$_n$—, wherein n is a positive integer, preferably from 1 to 6, from 1 to 4, from 1 to 3, from 1 to 2, or from 2 to 3. An optionally substituted alkylene chain is a polymethylene group in which one or more methylene hydrogen atoms is optionally replaced with a substituent. Suitable substituents include those described below for a substituted aliphatic group and also include those described in the specification herein. It will be appreciated that two substituents of the alkylene group may be taken together to form a ring system. In certain embodiments, two substituents can be taken together to form a 3-7-membered ring. The substituents can be on the same or different atoms.

An alkylene chain also can be optionally interrupted by a functional group. An alkylene chain is "interrupted" by a functional group when an internal methylene unit is interrupted by the functional group. Examples of suitable "interrupting functional groups" are described in the specification and claims herein.

For purposes of clarity, all bivalent groups described herein, including, e.g., the alkylene chain linkers described above, are intended to be read from left to right, with a corresponding left-to-right reading of the formula or structure in which the variable appears.

An aryl (including aralkyl, aralkoxy, aryloxyalkyl and the like) or heteroaryl (including heteroaralkyl and heteroarylalkoxy and the like) group may contain one or more substituents and thus may be "optionally substituted". In addition to the substituents defined above and herein, suitable substituents on the unsaturated carbon atom of an aryl or heteroaryl group also include and are generally selected from -halo, —NO$_2$, —CN, —R$^+$, —C(R$^+$)=C(R$^+$)$_2$, —C≡C—R$^+$, —OR$^+$, —SR$^o$, —S(O)R$^o$, —SO$_2$R$^o$, —SO$_3$R$^+$, —SO$_2$N(R$^+$)$_2$, —N(R$^+$)$_2$, —NR$^+$C(O)R$^+$, —NR$^+$C(S)R$^+$, —NR$^+$C(O)N(R$^+$)$_2$, —NR$^+$C(S)N(R$^+$)$_2$, —N(R$^+$)C(=NR$^+$)—N(R$^+$)$_2$, —N(R$^+$)C(=NR$^+$)—R$^o$, —NR$^+$CO$_2$R$^+$, —NR$^+$SO$_2$R$^o$, —NR$^+$SO$_2$N(R$^+$)$_2$, —O—C(O)R$^+$, —O—CO$_2$R$^+$, —OC(O)N(R$^+$)$_2$, —C(O)R$^+$, —C(S)R$^o$, —CO$_2$R$^+$, —C(O)—C(O)R$^+$, —C(O)N(R$^+$)$_2$, —C(S)N(R$^+$)$_2$, —C(O)N(R$^+$)—OR$^+$, —C(O)N(R$^+$)C(=NR$^+$)—N(R$^+$)$_2$, —N(R$^+$)C(=NR$^+$)—N(R$^+$)—C(O)R$^+$, —C(=NR$^+$)—N(R$^+$)$_2$, —C(=NR$^+$)—OR$^+$, —N(R$^+$)—N(R$^+$)$_2$, —C(=NR$^+$)—N(R$^+$)—OR$^+$, —C(R$^o$)=N—OR$^+$, —P(O)(R$^+$)$_2$, —P(O)(OR$^+$)$_2$, —O—P(O)—OR$^+$, and —P(O)(NR$^+$)—N(R$^+$)$_2$, wherein R$^+$, independently, is hydrogen or an optionally substituted aliphatic, aryl, heteroaryl, cycloaliphatic, or heterocyclyl group, or two independent occurrences of R$^+$ are taken together with their intervening atom(s) to form an optionally substituted 5-7-membered aryl, heteroaryl, cycloaliphatic, or heterocyclyl ring. Each R$^o$ is an optionally substituted aliphatic, aryl, heteroaryl, cycloaliphatic, or heterocyclyl group.

An aliphatic or heteroaliphatic group, or a non-aromatic carbycyclic or heterocyclic ring may contain one or more substituents and thus may be "optionally substituted". Unless otherwise defined above and herein, suitable substituents on the saturated carbon of an aliphatic or heteroaliphatic group, or of a non-aromatic carbocyclic or heterocyclic ring are selected from those listed above for the unsaturated carbon of an aryl or heteroaryl group and additionally include the following: =O, =S, =C(R*)$_2$, =N—N(R*)$_2$, =N—OR*, =N—NHC(O)R*, =N—NHCO$_2$R$^o$, =N—NHSO$_2$R$^o$ or =N—R* where R$^o$ is defined above, and each R* is independently selected from hydrogen or an optionally substituted C$_{1-6}$ aliphatic group.

In addition to the substituents defined above and herein, optional substituents on the nitrogen of a non-aromatic heterocyclic ring also include and are generally selected from —R$^+$, —N(R$^+$)$_2$, —C(O)R$^+$, —C(O)OR$^+$, —C(O)C(O)R$^+$, —C(O)CH$_2$C(O)R$^+$, —S(O)$_2$R$^+$, —S(O)$_2$N(R$^+$)$_2$, —C(S)N(R$^+$)$_2$, —C(=NH)—N(R$^+$)$_2$, or —N(R$^+$)S(O)$_2$R$^+$; wherein each R$^+$ is defined above. A ring nitrogen atom of a heteroaryl or non-aromatic heterocyclic ring also may be oxidized to form the corresponding N-hydroxy or N-oxide compound. A nonlimiting example of such a heteroaryl having an oxidized ring nitrogen atom is N-oxidopyridyl.

As detailed above, in some embodiments, two independent occurrences of $R^+$ (or any other variable similarly defined in the specification and claims herein), are taken together with their intervening atom(s) to form a monocyclic or bicyclic ring selected from 3-13-membered cycloaliphatic, 3-12-membered heterocyclyl having 1-5 heteroatoms independently selected from nitrogen, oxygen, or sulfur, 6-10-membered aryl, or 5-10-membered heteroaryl having 1-5 heteroatoms independently selected from nitrogen, oxygen, or sulfur.

Exemplary rings that are formed when two independent occurrences of $R^+$ (or any other variable similarly defined in the specification and claims herein), are taken together with their intervening atom(s) include, but are not limited to the following: a) two independent occurrences of $R^+$ (or any other variable similarly defined in the specification or claims herein) that are bound to the same atom and are taken together with that atom to form a ring, for example, $N(R^+)_2$, where both occurrences of $R^+$ are taken together with the nitrogen atom to form a piperidin-1-yl, piperazin-1-yl, or morpholin-4-yl group; and b) two independent occurrences of $R^+$ (or any other variable similarly defined in the specification or claims herein) that are bound to different atoms and are taken together with both of those atoms to form a ring, for example where a phenyl group is substituted with two occurrences of

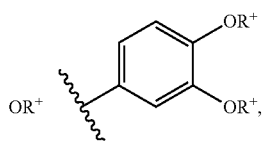

these two occurrences of $R^+$ are taken together with the oxygen atoms to which they are bound to form a fused 6-membered oxygen containing ring:

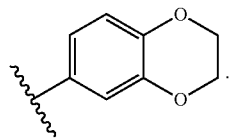 [SMILES: *c1ccc2c(c1)OCCO2]

It will be appreciated that a variety of other rings (e.g., Spiro and bridged rings) can be formed when two independent occurrences of $R^+$ (or any other variable similarly defined in the specification and claims herein) are taken together with their intervening atom(s) and that the examples detailed above are not intended to be limiting.

Exemplary rings that are formed when two independent occurrences of $R^{3'}$ or $R^4$ are taken together with their intervening atom(s) include, but are not limited to the following: indolizinyl, imidazopyridyl, indolyl, isoindolyl, indazolyl, benzimidazolyl, benzthiazolyl, benzoxazolyl, 4H-furo[3,2-b]pyrrolyl, pyrazolopyrimidinyl, purinyl, and pyrrolizinyl.

Exemplary rings that are formed when two independent occurrences of $R^7$, $R^{7a}$, or $R^{7b}$ are taken together with their intervening atom(s) include, but are not limited to the following: cyclopropyl, cyclobutyl, cyclopentyl, cyclohexyl, cycloheptyl, cyclooctyl, cyclopentenyl, cyclohexenyl, cycloheptenyl, cyclooctenyl, tetrahydropyranyl, tetrahydropyranyl, tetrahydrothienyl, pyrrolidinyl, pyrrolidonyl, piperidinyl, pyrrolinyl, oxazolidinyl, piperazinyl, dioxanyl, furanyl, thienyl, pyrrolyl, oxazolyl, thiazolyl, imidazolyl, pyranyl, pyridyl, pyrimidinyl, pyrazinyl, triazinyl, morpholinyl, and thiomorpholinyl.

Exemplary rings that are formed when two independent occurrences of $R^{7a}$ and $R^2$, or $R^{7b}$ and $R^2$ are taken together with their intervening atom(s) include, but are not limited to the following: isoindolyl, indazolyl, benzothienyl, dihydrobenzothienyl, isobenzofuranyl, benzoisoxazolyl, dihydroisobenzofuranyl, pyrazolopyrimidinyl, pyrazolopyridinyl, isoquinolyl, tetrahydroisoquinolinyl, phthalazinyl, isochromanyl, isothiochromanyl, isoindolinyl, and benzoisothiazolyl.

Exemplary rings that are formed when two independent occurrences of $X_4$ and $X_5$, or $X_6$ and $X_7$; are taken together with their intervening atom(s) include, but are not limited to the following: pyrazolopyrimidinyl, purinyl, quinolyl, tetrahydroquinolinyl, quinazolinyl, naphthyridinyl, pyridopyrimidinyl, pyrazolopyridinyl, pyrrolopyridinyl, pyrrolopyrimidinyl, imidazopyridinyl, 1H-pyrrolo[2,3-b]pyridinyl-2(3H)-one, 3,4-dihydro-1,8-naphthyridinyl-2(1H)-one, 1,8-naphthyridinyl-2(1H)-one, 1H-pyridyl[2,3-d][1,3]oxazin-2(4H)-one, 1H-imidazo[4,5-b]pyridyl-2(3H)-one, oxazolo[4,5-b]pyridyl-2(3H)-one, 1,2-dihydropyridyl[2,3-b]pyrazin-3(4H)-one, 2H-pyridyl[3,2-b][1,4]oxazin-3(4H)-one, 3,4-dihydropyridyl[2,3-d]pyrimidin-2(1H)-one, imidazopyridinyl, and tetrahydroquinazolinyl.

Exemplary rings that are formed when two independent occurrences of $Y_1$ and $Q_1$, $Y_3$ and $Q_2$, or $Y_4$ and $Y_5$ are taken together with their intervening atom(s) include, but are not limited to the following: indolyl, indazolyl, 4H-furo[3,2-b]pyrrolyl, 4H-thieno[3,2-b]pyrrolyl, 5H-furo[2,3-b]pyrrolyl, 5H-thieno[2,3-b]pyrrolyl, pyrrolo[3,4-b]pyrrolyl, pyrrolo[3,2-b]pyrrolyl, pyrrolo[2,3-b]pyrrolyl, dihydropyrrolo[3,2-b]pyrrolyl, dihydropyrrolo[2,3-b]pyrrolyl, 5H-pyrrolo[3,2-d]oxazole, 5H-pyrrolo[3,2-d]thiazole, pyrrolopyrimidinyl, pyrrolopyridinyl, pyrazolopyrimidinyl and pyrazolopyridinyl.

Unless otherwise stated, structures depicted herein are also meant to include all isomeric (e.g., enantiomeric, diastereomeric, and geometric (or conformational)) forms of the structure; for example, the R and S configurations for each asymmetric center, (Z) and (E) double bond isomers, and (Z) and (E) conformational isomers. Therefore, single stereochemical isomers as well as enantiomeric, diastereomeric, and geometric (or conformational) mixtures of the present compounds are within the scope of the invention. Unless otherwise stated, all tautomeric forms of the compounds of the invention are within the scope of the invention. Additionally, unless otherwise stated, structures depicted herein are also meant to include compounds that differ only in the presence of one or more isotopically enriched atoms. For example, compounds having the present structures where there is a replacement of hydrogen by deuterium or tritium, or a replacement of a carbon by a $^{13}$C- or $^{14}$C-enriched carbon are within the scope of this invention. Such compounds are useful, as a nonlimiting example, as analytical tools or probes in biological assays.

It is to be understood that, when a disclosed compound has at least one chiral center, the present invention encompasses one enantiomer of inhibitor free from the corresponding optical isomer, racemic mixture of the inhibitor and mixtures enriched in one enantiomer relative to its corresponding optical isomer. When a mixture is enriched in one enantiomer relative to its optical isomers, the mixture contains, for example, an enantiomeric excess of at least 50%, 75%, 90%, 95% 99% or 99.5%.

The enantiomers of the present invention may be resolved by methods known to those skilled in the art, for example by formation of diastereoisomeric salts which may be separated, for example, by crystallization; formation of diastereoisomeric derivatives or complexes which may be separated, for example, by crystallization, gas-liquid or liquid chromatography; selective reaction of one enantiomer with an enantiomer-specific reagent, for example enzymatic esterification; or gas-liquid or liquid chromatography in a chiral environment, for example on a chiral support for example silica with a bound chiral ligand or in the presence of a chiral solvent. Where the desired enantiomer is converted into another chemical entity by one of the separation procedures described above, a further step is required to liberate the desired enantiomeric form. Alternatively, specific enantiomers may be synthesized by asymmetric synthesis using optically active reagents, substrates, catalysts or solvents, or by converting one enantiomer into the other by asymmetric transformation.

When a disclosed compound has at least two chiral centers, the present invention encompasses a diastereomer free of other diastereomers, a pair of diastereomers free from other diasteromeric pairs, mixtures of diasteromers, mixtures of diasteromeric pairs, mixtures of diasteromers in which one diastereomer is enriched relative to the other diastereomer(s) and mixtures of diasteromeric pairs in which one diastereomeric pair is enriched relative to the other diastereomeric pair(s). When a mixture is enriched in one diastereomer or diastereomeric pair(s) relative to the other diastereomers or diastereomeric pair(s), the mixture is enriched with the depicted or referenced diastereomer or diastereomeric pair(s) relative to other diastereomers or diastereomeric pair(s) for the compound, for example, by a molar excess of at least 50%, 75%, 90%, 95%, 99% or 99.5%.

The diastereoisomeric pairs may be separated by methods known to those skilled in the art, for example chromatography or crystallization and the individual enantiomers within each pair may be separated as described above. Specific procedures for chromatographically separating diastereomeric pairs of precursors used in the preparation of compounds disclosed herein are provided the examples herein.

3. Description of Exemplary Compounds

In certain embodiments, for compounds of general formula IA, IA-a, IB or IB-a, CY is:

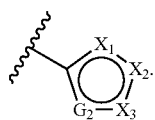

In certain embodiments, for compounds of general formula IA, IA-a, IB or IB-a, $X_1$ is N, $G_2$ is —N($R^{3'}$)—, and $X_2$ and $X_3$ are CH. In certain other embodiments, $X_1$ and $X_2$ are N, $G_2$ is —N($R^{3'}$)—, and $X_3$ is CH. In certain other embodiments, $X_3$ is N, $G_2$ is —N($R^{3'}$)—, and $X_1$ and $X_2$ are CH. In certain other embodiments, $X_1$ is N, $X_2$ is CH, $X_3$ is —N($R^{3'}$)— and $G_2$ is =N—.

In certain embodiments, for compounds of general formula IA, IA-a, IB or IB-a, HY is selected from:

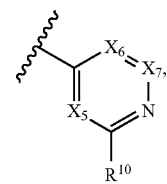

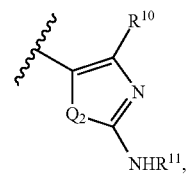

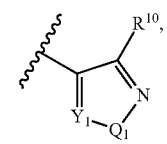

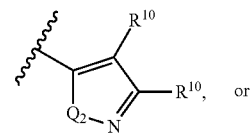

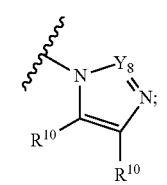

wherein each occurrence of $X_5$, $X_6$, and $X_7$ is independently —$CR^{10}$ or N, provided no more than two occurrences of $X_5$, $X_6$, and $X_7$ are N;

each occurrence of $Q_1$ and $Q_2$ is independently S, O or —$NR^5$;

each occurrence of $Y_1$ and $Y_7$ is independently —$CR^{10}$ or N;

or wherein two adjacent occurrences of $X_6$ and $X_7$, or $Y_1$ and $Q_1$, taken together with the atom to which they are bound, form an optionally substituted fused group selected from 5-6-membered aryl, or 5-6-membered heteroaryl having 1-5 heteroatoms independently selected from nitrogen, oxygen, or sulfur.

In certain embodiments, for compounds of general formula IA, IA-a, IB or IB-a, HY is selected from:

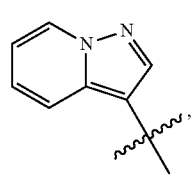

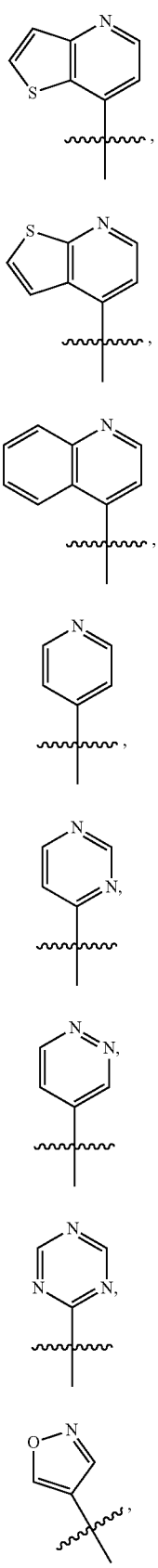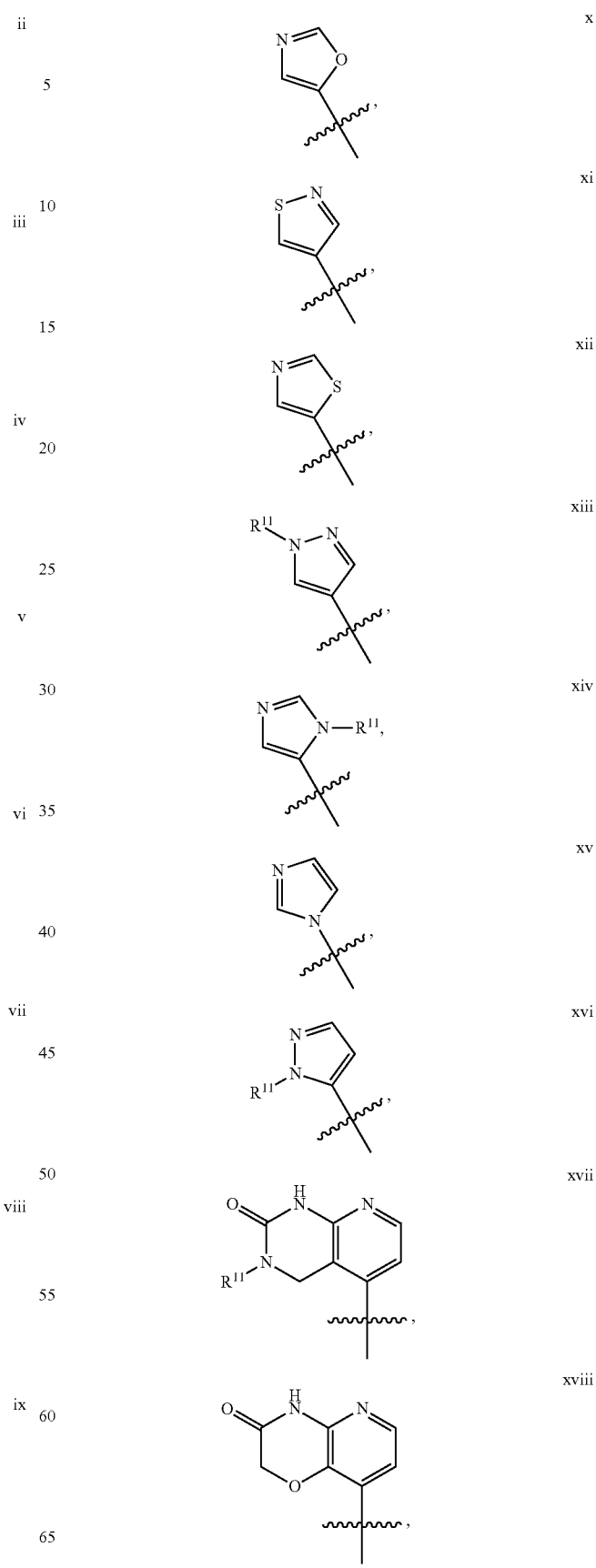

-continued
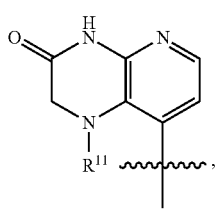
xix
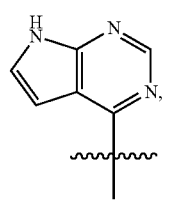
xx
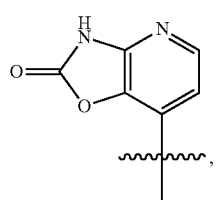
xxi
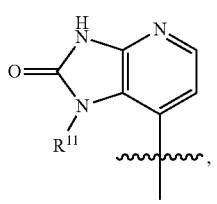
xxii
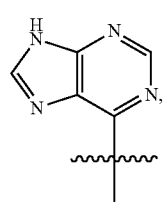
xxiii
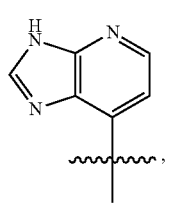
xxiv
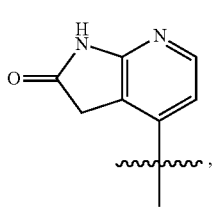
xxv
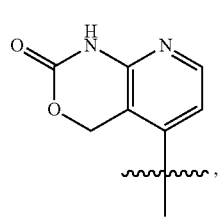
xxvi
-continued
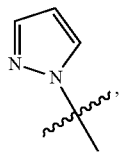
xxvii
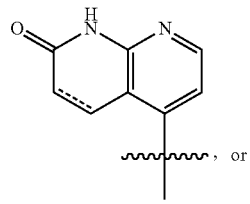
xxviii
, or
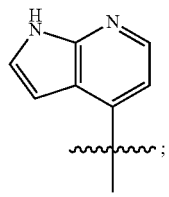
xxix
;
wherein each HY group is optionally additionally substituted with one or more occurrences of $R^{10}$, and ----- in xviii represents a single bond or a double bond.
In certain embodiments, for compounds of general formula IA, IA-a, IB or IB-a, HY is selected from:
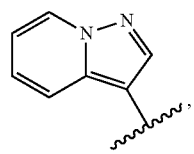
i
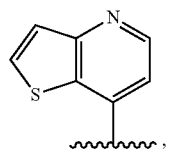
ii
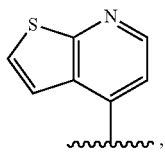
iii
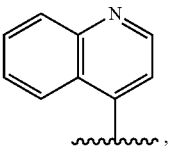
iv
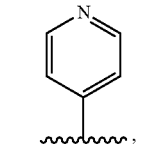
v 55
-continued vi
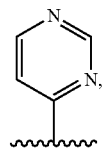

vii
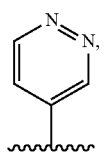

ix
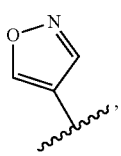

xxviii
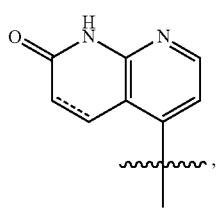

xxix
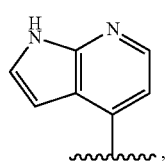

xxx
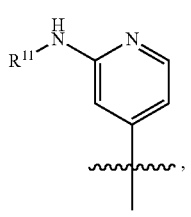

xxxi
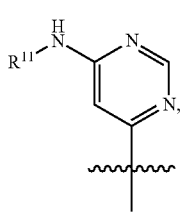

xxxii
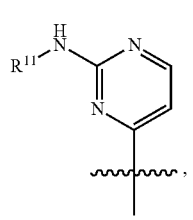

56
-continued xxxiii
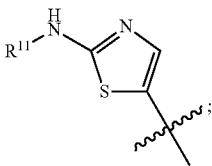

wherein each HY group is optionally additionally substituted with one or more occurrences of $R^{10}$, and ===== in xviii represents a single bond or a double bond.

In yet other embodiments, for compounds of general formula IA, IA-a, IB or IB-a, $G_1$ is $C(R^8)$. In other embodiments, $G_1$ is CH.

In still other embodiments, $G_1$ is N.

In certain embodiments, for compounds of general formula IA, IA-a, IB or IB-a, W is —$C(R^7)_2$—, wherein one occurrence of $R^7$ is hydrogen and the other occurrence of $R^7$ is hydrogen, optionally substituted $C_{1-6}$ aliphatic, —$N(R^{7b})_2$, —$OR^{7a}$, —$SR^{7a}$, halo, or —CN; and wherein each occurrence of $R^{7a}$ is independently hydrogen or optionally substituted $C_{1-6}$ aliphatic; and each occurrence of $R^{7b}$ is independently hydrogen, optionally substituted $C_{1-6}$ aliphatic, —$C(O)R^{7a}$, or —$S(O)_2R^{7a}$; or wherein two occurrences of $R^{7b}$, taken together with the nitrogen atom to which they are bound, form an optionally substituted 3-6-membered heterocyclic ring.

In certain embodiments, for compounds of general formula IA, IA-a, IB or IB-a, W is —C(H)(N($R^{7b}$)$_2$)—, —$CH_2$—, —C(H)($OR^{7a}$)—, —$NR^{7b}$—, or —N($R^{7a}$)C(O)—, wherein each occurrence of $R^{7a}$ is independently hydrogen or optionally substituted $C_{1-6}$ aliphatic; and each occurrence of $R^{7b}$ is independently hydrogen or optionally substituted $C_{1-6}$ aliphatic.

In certain embodiments, for compounds of general formula IA, IA-a, IB or IB-a, Ring A is 6-10-membered aryl or 5-10-membered heteroaryl having 1-5 heteroatoms independently selected from nitrogen, oxygen, or sulfur; and n is 0 to 3.

In other embodiments, ring A is a group selected from:

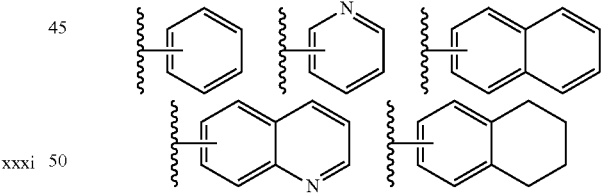

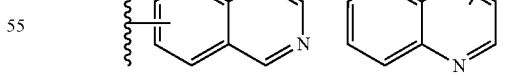

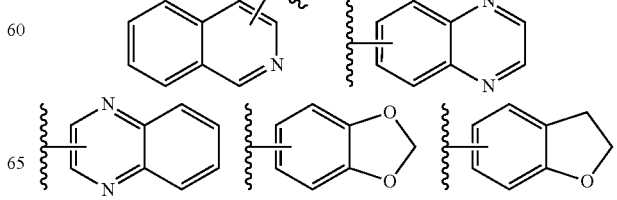

wherein ring A is optionally further substituted by n occurrences of $R^2$, and wherein $R^{2a}$ is hydrogen or an optionally substituted group selected from $C_{1-6}$aliphatic, 3-10-membered cycloaliphatic, 4-10-membered heterocyclyl having 1-5 heteroatoms independently selected from nitrogen, oxygen, or sulfur, 6-10-membered aryl, or 5-10-membered heteroaryl having 1-5 heteroatoms independently selected from nitrogen, oxygen, or sulfur.

In certain other embodiments, for compounds of general formula IA, IA-a, IB or IB-a, Ring A is a group selected from:

wherein ring A is optionally further substituted by n occurrences of $R^2$, and wherein $R^{2a}$ is hydrogen or an optionally substituted group selected from $C_{1-6}$aliphatic, 3-10-membered cycloaliphatic, 4-10-membered heterocyclyl having 1-5 heteroatoms independently selected from nitrogen, oxygen, or sulfur, 6-10-membered aryl, or 5-10-membered heteroaryl having 1-5 heteroatoms independently selected from nitrogen, oxygen, or sulfur.

In still other embodiments, ring A is a naphthyl group; each occurrence of $R^2$ is independently halogen, $C_{1-3}$ alkyl, —CN, $C_{1-3}$ haloalkyl, —$OC_{1-3}$ alkyl, —$OC_{1-3}$ haloalkyl, —NHC(O) $C_{1-3}$ alkyl, —NHC(O)NHC$_{1-3}$ alkyl, —NHS(O)$_2$C$_{1-3}$ alkyl, or —C(O)H; and n is 0 to 3.

In still other embodiments, ring A is a naphthyl group, $R^2$ is halogen and n is 1 to 2. In yet other embodiments, ring A is a naphthyl group and n is 0. In yet other embodiments, Ring A is a phenyl group, $R^2$ is halogen and n is 1 to 2.

In certain embodiments, for compounds of general formula IA, IA-a, IB or IB-a, Ring A is a phenyl group; each occurrence of $R^2$ is independently halogen, $C_{1-3}$ alkyl, —CN, $C_{1-3}$ haloalkyl, —$OC_{1-3}$ alkyl, —$OC_{1-3}$haloalkyl, —NHC(O)$C_{1-3}$ alkyl, —NHC(O)NHC$_{1-3}$alkyl, —NHS(O)$_2$C$_{1-3}$ alkyl, or —C(O)H; and n is 0 to 3.

In still other embodiments, Ring A is a phenyl group, $R^2$ is halogen and n is 1 to 2.

In still other embodiments, a compound having the structure of formula II is provided:

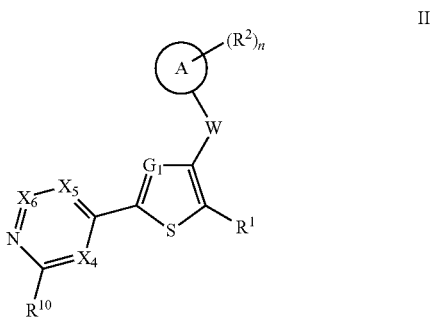

II wherein:

$X_4$, $X_5$ and $X_6$ are each independently —$CR^{10}$ or N, provided no more than two occurrences of $X_4$, $X_5$ and $X_6$ are N;

or two adjacent groups selected from $R^{10}$, $X_4$, $X_5$, and $X_6$, taken together, form an optionally substituted group selected from 3-10-membered cycloaliphatic, 4-10-membered heterocyclyl having 1-5 heteroatoms independently selected from nitrogen, oxygen, or sulfur, 6-10-membered aryl, or 5-10-membered heteroaryl having 1-5 heteroatoms independently selected from nitrogen, oxygen, or sulfur.

In some embodiments, for compounds of formula II, one of $X^4$, $X^5$, or $X^6$ is N.

In still other embodiments, for compounds of formula II, all of $X^4$, $X^5$, or $X^6$ are $CR^{10}$.

In other embodiments, for compounds of formula II, each occurrence of $R^{10}$ is independently selected from —CN, —$OR^{10a}$, —$N(R^{11})_2$, halogen, $C_{1-4}$alkyl, —$N(R^{11})COR^{10a}$, or wherein two occurrences of $R^{10}$, taken together with the atoms to which they are bound form an optionally substituted group selected from a fused 5- or 6-membered cycloaliphatic, 4-10-membered heterocyclyl, 6-10-membered aryl or 5-10-membered heteroaryl ring, wherein the heterocyclyl and heteroaryl rings have 1-3 heteroatoms independently selected from nitrogen, oxygen, or sulfur.

In some other embodiments, for compounds of formula II, CY is

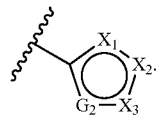

In some other embodiments, for compounds of formula II, $X_1$ is N, $G_2$ is —N($R^{3'}$)—, and $X_2$ and $X_3$ are CH.

In some other embodiments, for compounds of formula II, $X_1$ and $X_2$ are N, $G_2$ is —N($R^{3'}$)—, and $X_3$ is CH.

In some other embodiments, for compounds of formula II, $X_3$ is N, $G_2$ is —N($R^{3'}$)—, and $X_1$ and $X_2$ are CH.

In some other embodiments, for compounds of formula II, $X_1$ is N, $X_2$ is CH, $X_3$ is —N($R^{3'}$)— and $G_2$ is =N—.

In some other embodiments, for compounds of formula II, Ring A is an optionally substituted 6-10-membered aryl or 5-10-membered heteroaryl having 1-5 heteroatoms independently selected from nitrogen, oxygen, or sulfur; and n is 0 to 3.

In other embodiments, for compounds of formula II, ring A is a group selected from:

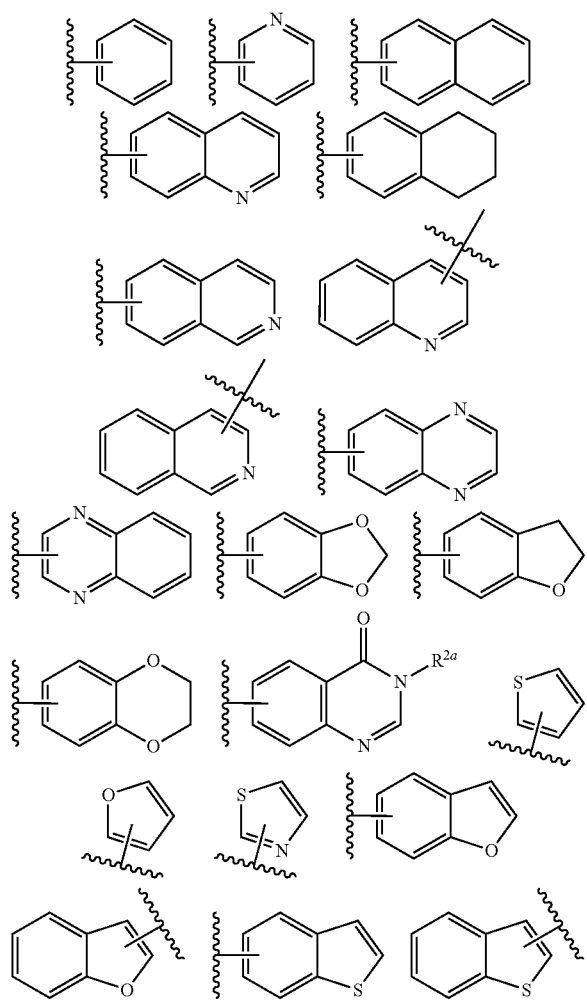

wherein ring A is optionally further substituted by n occurrences of $R^2$, and wherein $R^{2a}$ is hydrogen or an optionally substituted group selected from $C_{1-6}$aliphatic, 3-10-membered cycloaliphatic, 4-10-membered heterocyclyl having 1-5 heteroatoms independently selected from nitrogen, oxygen, or sulfur, 6-10-membered aryl, or 5-10-membered heteroaryl having 1-5 heteroatoms independently selected from nitrogen, oxygen, or sulfur.

In certain other embodiments, for compounds of general formula II, Ring A is a group selected from:

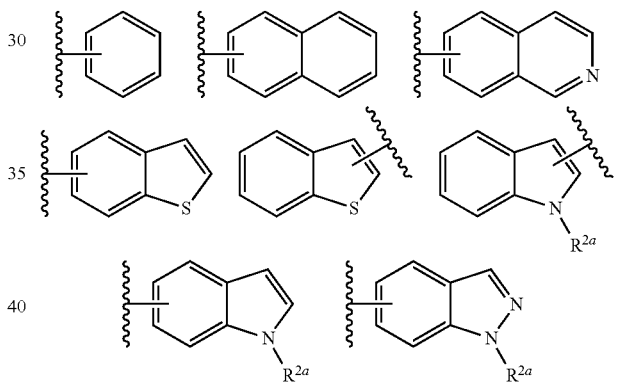

wherein ring A is optionally further substituted by n occurrences of $R^2$, and wherein $R^{2a}$ is hydrogen or an optionally substituted group selected from $C_{1-6}$aliphatic, 3-10-membered cycloaliphatic, 4-10-membered heterocyclyl having 1-5 heteroatoms independently selected from nitrogen, oxygen, or sulfur, 6-10-membered aryl, or 5-10-membered heteroaryl having 1-5 heteroatoms independently selected from nitrogen, oxygen, or sulfur.

In still other embodiments, ring A is a naphthyl group; each occurrence of $R^2$ is independently halogen, $C_{1-3}$ alkyl, —CN, $C_{1-3}$ haloalkyl, —O$C_{1-3}$ alkyl, —O$C_{1-3}$ haloalkyl, —NHC(O) $C_{1-3}$ alkyl, —NHC(O)NH$C_{1-3}$ alkyl, —NHS(O)$_2$C$_{1-3}$ alkyl, or —C(O)H; and n is 0 to 3.

In still other embodiments, ring A is a naphthyl group, $R^2$ is halogen and n is 1 to 2. In yet other embodiments, ring A is a naphthyl group and n is 0. In yet other embodiments, Ring A is a phenyl group, $R^2$ is halogen and n is 1 to 2.

In some other embodiments, for compounds of formula II, Ring A is a phenyl group optionally substituted with 1-3 independent occurrences of halogen, $C_{1-3}$ alkyl, —CN, —O$C_{1-3}$ alkyl, —O$C_{1-3}$ haloalkyl, —NHC(O)$C_{1-3}$ alkyl, —NHC(O)NH$C_{1-3}$ alkyl, NHS(O)$_2$$C_{1-3}$ alkyl, or —C(O)H; and n is 0 to 3.

In still other embodiments, Ring A is a phenyl group, $R^2$ is halogen and n is 1 to 2.

In some other embodiments, for compounds of formula II, W is —$C(R^7)_2$—, wherein one occurrence of $R^7$ is hydrogen and the other occurrence of $R^7$ is selected from hydrogen, optionally substituted $C_{1-4}$ aliphatic, —$N(R^{7b})_2$, —$OR^{7a}$, —$SR^{7a}$, halo, or —CN; and wherein each occurrence of $R^{7a}$ is independently hydrogen or optionally substituted $C_{1-6}$ aliphatic;

each occurrence of $R^{7b}$ is independently hydrogen, optionally substituted $C_{1-6}$ aliphatic, —$C(O)R^{7a}$, or —$S(O)_2R^{7a}$; or wherein any two occurrences of $R^7$, $R^{7a}$, or $R^{7b}$ taken together with the atom to which they are bound, form an optionally substituted group selected from a 3-6-membered cycloaliphatic ring, 6-10-membered aryl, 3-6-membered heterocyclyl having 1-5 heteroatoms independently selected from nitrogen, oxygen, or sulfur, or 5-10-membered heteroaryl having 1-5 heteroatoms independently selected from nitrogen, oxygen, or sulfur; or any two occurrences of $R^{7a}$ and $R^2$, or $R^{7b}$ and $R^2$ taken together with the nitrogen atom to which they are bound, form an optionally substituted group selected from 3-6-membered heterocyclyl having 1-5 heteroatoms independently selected from nitrogen, oxygen, or sulfur, or 5-10-membered heteroaryl having 1-5 heteroatoms independently selected from nitrogen, oxygen, or sulfur.

In some other embodiments, for compounds of formula II, W is —$C(H)(N(R^{7b})_2)$—, —$CH_2$—, —$C(H)(OR^{7a})$—, —$NR^{7b}$—, or —$N(R^{7a})C(O)$—, wherein each occurrence of $R^{7a}$ is independently hydrogen or optionally substituted $C_{1-6}$ aliphatic; and each occurrence of $R^{7b}$ is independently hydrogen or optionally substituted $C_{1-6}$ aliphatic.

In still other embodiments, a compound having the structure of formula III is provided:

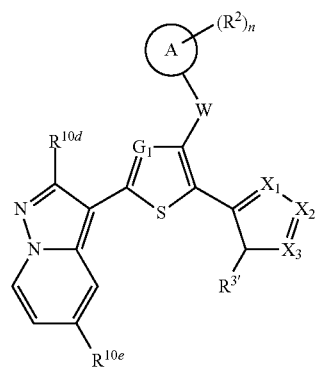

III wherein $R^{10d}$ is hydrogen or optionally substituted $C_{1-4}$alkyl, and $R^{10e}$ is $R^{10}$.

In some other embodiments, for compounds of formula III, $R^{10e}$ is -$T_1$-$R^{10b}$, or hydrogen.

In still other embodiments, for compounds of formula III, $R^{10e}$ is hydrogen, —$CH_2N(R^{11})_2$, or —$CH_2N(R^{11})C(=NR^{11})N(R^{11})_2$, wherein $R^{11}$ is —$C(O)R^{11a}$, an optionally substituted group selected from $C_{1-6}$ aliphatic, 3-10-membered cycloaliphatic, 4-10-membered heterocyclyl having 1-5 heteroatoms independently selected from nitrogen, oxygen or sulfur, 6-10-membered aryl, or 5-10-membered heteroaryl having 1-5 heteroatoms independently selected from nitrogen, oxygen, or sulfur.

In some other embodiments, for compounds of formula III, $R^{11}$ is an optionally substituted $C_{1-6}$ aliphatic group, the $C_{1-6}$ aliphatic group is further defined as —$(CH_2)_xR^{11b}$ or —$(CH_2)_xN(R^{11b})_2$, —$(CH_2)_xN(R^{11b})C(O)R^{11b}$, or —$(CH_2)_xN(R^{11b})C(O)OR^{11b}$, wherein $R^{11b}$ is hydrogen or an optionally substituted group selected from $C_{1-6}$ aliphatic, 3-10-membered cycloaliphatic, 4-10-membered heterocyclyl having 1-5 heteroatoms independently selected from nitrogen, oxygen, or sulfur, 6-10-membered aryl, or 5-10-membered heteroaryl having 1-5 heteroatoms independently selected from nitrogen, oxygen, or sulfur; and x is 1 to 3.

In some other embodiments, for compounds of formula III, $X_1$ is N, and $X_2$ and $X_3$ are CH.

In some other embodiments, for compounds of formula III, $X_1$ and $X_2$ are N, and $X_3$ is CH.

In some other embodiments, for compounds of formula III, $X_3$ is N, and $X_1$ and $X_2$ are CH.

In some other embodiments, for compounds of formula III, Ring A is an optionally substituted 6-10-membered aryl or 5-10-membered heteroaryl having 1-5 heteroatoms independently selected from nitrogen, oxygen, or sulfur; and n is 0 to 3.

In other embodiments, ring A is a group selected from:

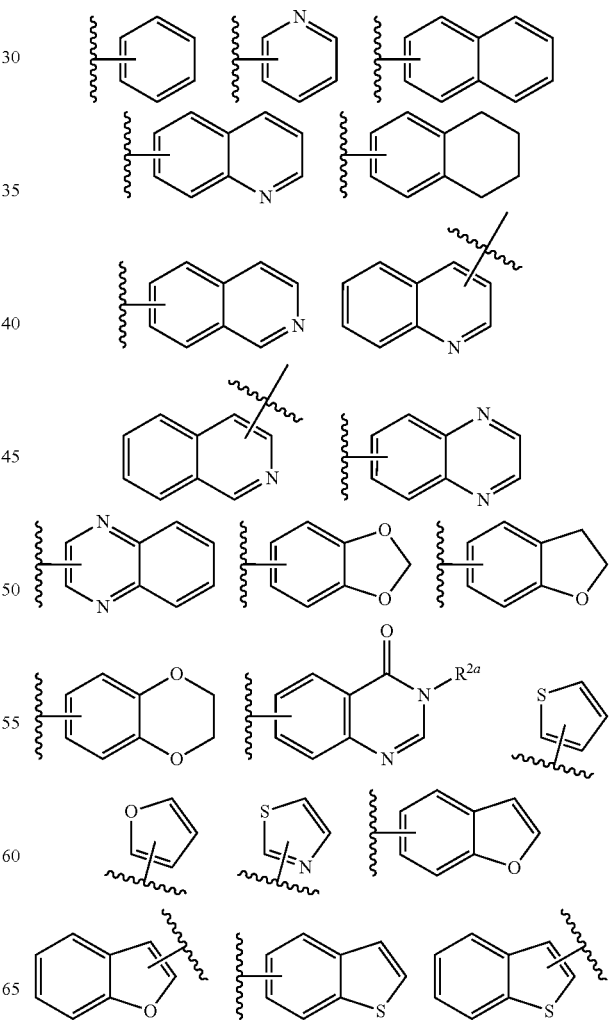

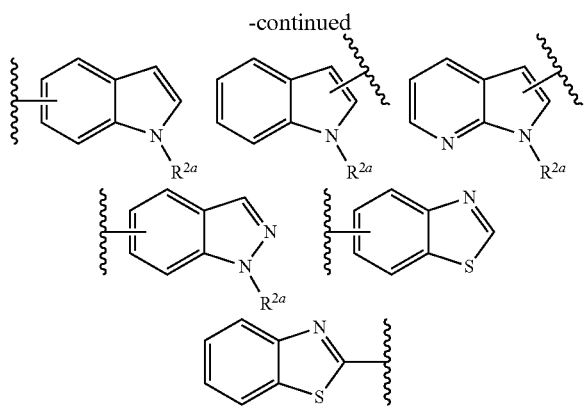

wherein ring A is optionally further substituted by n occurrences of $R^2$, and wherein $R^{2a}$ is hydrogen or an optionally substituted group selected from $C_{1-6}$aliphatic, 3-10-membered cycloaliphatic, 4-10-membered heterocyclyl having 1-5 heteroatoms independently selected from nitrogen, oxygen, or sulfur, 6-10-membered aryl, or 5-10-membered heteroaryl having 1-5 heteroatoms independently selected from nitrogen, oxygen, or sulfur.

In certain other embodiments, for compounds of general formula III, Ring A is a group selected from:

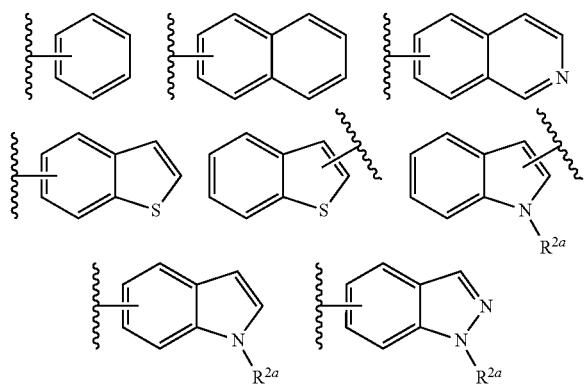

wherein ring A is optionally further substituted by n occurrences of $R^2$, and wherein $R^{2a}$ is hydrogen or an optionally substituted group selected from $C_{1-6}$aliphatic, 3-10-membered cycloaliphatic, 4-10-membered heterocyclyl having 1-5 heteroatoms independently selected from nitrogen, oxygen, or sulfur, 6-10-membered aryl, or 5-10-membered heteroaryl having 1-5 heteroatoms independently selected from nitrogen, oxygen, or sulfur.

In still other embodiments, ring A is a naphthyl group; each occurrence of $R^2$ is independently halogen, $C_{1-3}$ alkyl, —CN, $C_{1-3}$ haloalkyl, —$OC_{1-3}$ alkyl, —$OC_{1-3}$ haloalkyl, —NHC(O) $C_{1-3}$ alkyl, —NHC(O)NHC$_{1-3}$ alkyl, —NHS(O)$_2C_{1-3}$ alkyl, or —C(O)H; and n is 0 to 3.

In still other embodiments, ring A is a naphthyl group, $R^2$ is halogen and n is 1 to 2. In yet other embodiments, ring A is a naphthyl group and n is 0. In yet other embodiments, Ring A is a phenyl group, $R^2$ is halogen and n is 1 to 2.

In some other embodiments, for compounds of formula III, Ring A is a phenyl group optionally substituted with 1-3 independent occurrences of halogen, $C_{1-3}$ alkyl, —CN, $C_{1-3}$haloalkyl, —$OC_{1-3}$ alkyl, —$OC_{1-3}$ haloalkyl, —NHC(O) $C_{1-3}$ alkyl, —NHC(O)NHC$_{1-3}$ alkyl, —NHS(O)$_2C_{1-3}$ alkyl, or —C(O)H; and n is 0 to 3.

In some other embodiments, Ring A is a phenyl group, $R^2$ is halogen and n is 1 to 2.

In some other embodiments, for compounds of formula III, W is —C($R^7$)$_2$—, wherein one occurrence of $R^7$ is hydrogen and the other occurrence of $R^7$ is selected from hydrogen, optionally substituted $C_{1-4}$ aliphatic, —N($R^{7b}$)$_2$, —$OR^{7a}$, —$SR^{7a}$, halo, or —CN; and wherein each occurrence of $R^{7a}$ is independently hydrogen or optionally substituted $C_{1-6}$ aliphatic;

each occurrence of $R^{7b}$ is independently hydrogen, optionally substituted $C_{1-6}$ aliphatic, —C(O)$R^{7a}$, or —S(O)$_2R^{7a}$; or wherein any two occurrences of $R^7$, $R^{7a}$, or $R^{7b}$ taken together with the atom to which they are bound, form an optionally substituted group selected from a 3-6-membered cycloaliphatic ring, 6-10-membered aryl, 3-6-membered heterocyclyl having 1-5 heteroatoms independently selected from nitrogen, oxygen, or sulfur, or 5-10-membered heteroaryl having 1-5 heteroatoms independently selected from nitrogen, oxygen, or sulfur; or any two occurrences of $R^{7a}$ and $R^2$, or $R^{7b}$ and $R^2$ taken together with the nitrogen atom to which they are bound, form an optionally substituted group selected from 3-6-membered heterocyclyl having 1-5 heteroatoms independently selected from nitrogen, oxygen, or sulfur, or 5-10-membered heteroaryl having 1-5 heteroatoms independently selected from nitrogen, oxygen, or sulfur.

In some other embodiments, for compounds of formula III, W is —C(H)(N($R^{7b}$)$_2$)—, —CH$_2$—, —C(H)(OR$^{7a}$)—, —NR$^{7b}$—, or —N(R$^{7a}$)C(O)—, wherein each occurrence of $R^{7a}$ is independently hydrogen or optionally substituted $C_{1-6}$ aliphatic; and each occurrence of $R^{7b}$ is independently hydrogen or optionally substituted $C_{1-6}$ aliphatic.

In certain embodiments, for compounds of general formula IA-a, IB-a, IA, IB, II or III, CY is:

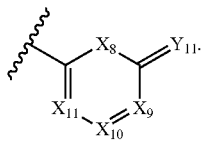

In certain embodiments, for compounds of general formula IA-a, IB-a, IA, IB, II or III, $X_8$ and $X_{11}$ are N, $X_9$ and $X_{10}$ are $CR^4$, and $Y_{11}$ is O.

In certain embodiments, for compounds of general formula IA-a, IB-a, IA, IB, II or III, HY is selected from:

wherein each HY group is optionally additionally substituted with one or more occurrences of $R^{14}$.

In yet other embodiments, for compounds of general formula IA-a, IB-a, IA, IB, II or III, $G_1$ is N.

In still other embodiments, for compounds of general formula IA-a, IB-a, IA, IB, II or III, $R^1$ is —C(O)OH.

In certain other embodiments, for compounds of general formula IA-i-a, IB-i-a, IA-i, or IB-i, $R^3$ is H. In certain other embodiments, $R^3$ is $C_{1-6}$ aliphatic. In certain embodiments, $R^3$ is $C_{1-4}$ alkyl. In certain embodiments, $R^3$ is methyl or ethyl.

In certain embodiments, for compounds of general formula IA-i-a, IB-i-a, IA-i, or IB-i, $G_1$ is N. In certain other embodiments, $G_1$ is $C(R^8)$. In certain embodiments, $G_1$ is $C(R^8)$ and $R^8$ is —CN, halogen, or $C_{1-6}$ aliphatic. In certain embodiments, $R^8$ is $C_{1-4}$ alkyl, $C_{2-4}$ alkenyl, or $C_{2-4}$ alkynyl. In certain embodiments, $R^8$ is —CN or $C_{2-4}$ alkynyl.

In certain embodiments, for compounds of general formula IA-i-a, IB-i-a, IA-i, or IB-i, HY is selected from:

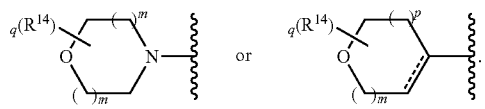

In certain embodiments, HY is

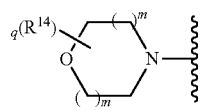

wherein each occurrence of m is 1 and q is 0 or 1. In certain embodiments, q is 0.

In certain embodiments, HY is

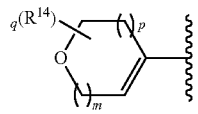

wherein m and p are 1 and q is 0 or 1. In certain embodiments, q is 0.

In certain embodiments, for compounds of general formula IA-i-a, IB-i-a, IA-i, or IB-i, W is —$C(R^7)_2$—, wherein one occurrence of $R^7$ is hydrogen and the other occurrence of $R^7$ is hydrogen, optionally substituted $C_{1-6}$ aliphatic, —$N(R^{7b})_2$, or F; and each occurrence of $R^{7b}$ is independently hydrogen, optionally substituted $C_{1-6}$ aliphatic, —$C(O)R^{7a}$, or —$S(O)_2R^{7a}$; or wherein two occurrences of $R^{7b}$, taken together with the nitrogen atom to which they are bound, form an optionally substituted 3-6-membered heterocyclic ring; and wherein each occurrence of $R^{7a}$ is independently hydrogen or optionally substituted $C_{1-6}$ aliphatic.

In certain embodiments, for compounds of general formula IA-i-a, IB-i-a, IA-i, or IB-i, W is —$C(H)(N(R^{7b})_2)$— or —$CH_2$—, wherein each occurrence of $R^{7b}$ is independently hydrogen or optionally substituted $C_{1-6}$ aliphatic.

In certain embodiments, for compounds of general formula IA-i-a, IB-i-a, IA-i, or IB-i, W is a covalent bond.

In certain embodiments, for compounds of general formula IA-i-a, IB-i-a, IA-i, or IB-i, Ring A is 6-10-membered aryl or 5-10-membered heteroaryl having 1-5 heteroatoms independently selected from nitrogen, oxygen, or sulfur; and n is 0 to 3.

In other embodiments, for compounds of general formula IA-i-a, IB-i-a, IA-i, or IB-i, ring A is a group selected from:

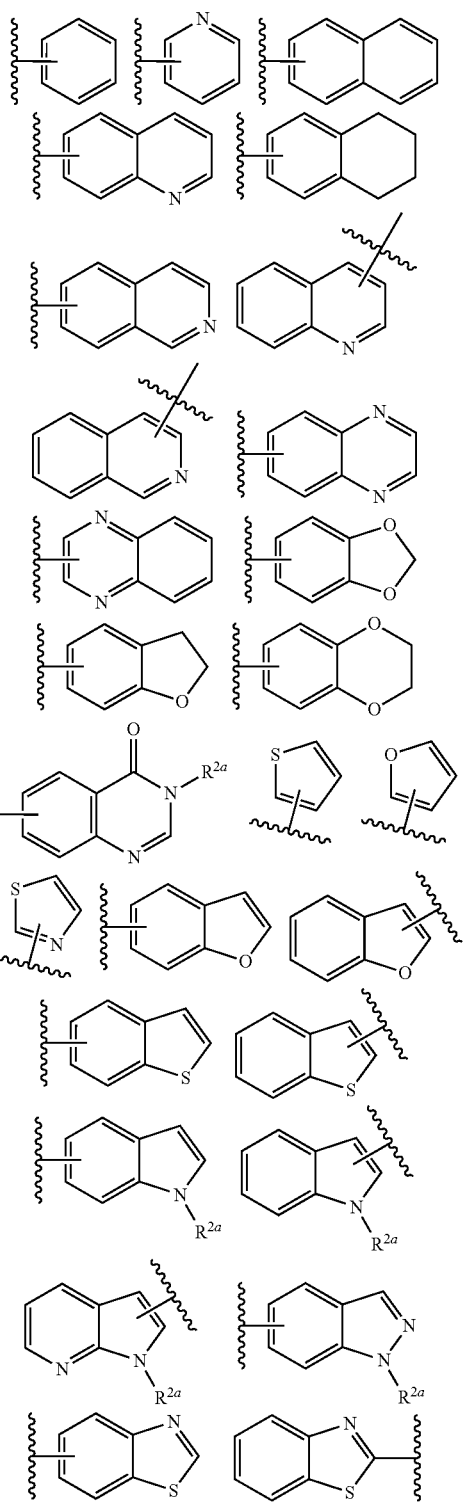

wherein ring A is optionally further substituted by n occurrences of $R^2$, and wherein $R^{2a}$ is hydrogen or an optionally substituted group selected from $C_{1-6}$ aliphatic, 3-10-membered cycloaliphatic, 4-10-membered heterocyclyl having 1-5 heteroatoms independently selected from nitrogen, oxygen, or sulfur, 6-10-membered aryl, or 5-10-membered heteroaryl having 1-5 heteroatoms independently selected from nitrogen, oxygen, or sulfur.

In certain other embodiments, for compounds of general formula IA-i-a, IB-i-a, IA-i, or IB-i, Ring A is a group selected from:

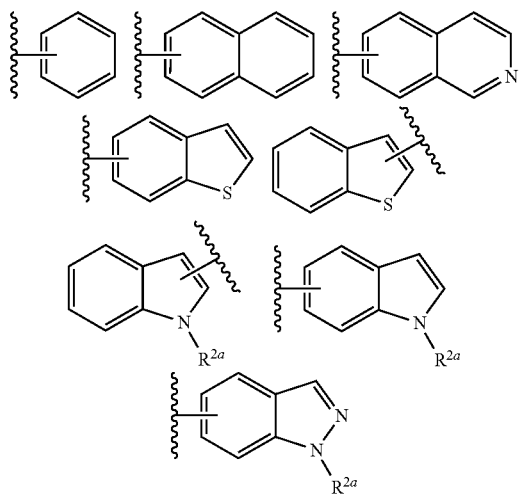

wherein ring A is optionally further substituted by n occurrences of $R^2$, and wherein $R^{2a}$ is hydrogen or an optionally substituted group selected from $C_{1-6}$aliphatic, 3-10-membered cycloaliphatic, 4-10-membered heterocyclyl having 1-5 heteroatoms independently selected from nitrogen, oxygen, or sulfur, 6-10-membered aryl, or 5-10-membered heteroaryl having 1-5 heteroatoms independently selected from nitrogen, oxygen, or sulfur.

In still other embodiments, ring A is a naphthyl group; each occurrence of $R^2$ is independently halogen, $C_{1-3}$ alkyl, —CN, $C_{1-3}$ haloalkyl, —$OC_{1-3}$ alkyl, —$OC_{1-3}$ haloalkyl, —NHC(O)$C_{1-3}$ alkyl, —NHC(O)NHC$_{1-3}$alkyl, —NHS(O)$_2C_{1-3}$ alkyl, or —C(O)H; and n is 0 to 3.

In yet other embodiments, ring A is a phenyl group; each occurrence of $R^2$ is independently halogen, $C_{1-3}$ alkyl, —CN, $C_{1-3}$ haloalkyl, —$OC_{1-3}$ alkyl, —$OC_{1-3}$ haloalkyl, —NHC(O)$C_{1-3}$ alkyl, —NHC(O)NHC$_{1-3}$alkyl, —NHS(O)$_2C_{1-3}$ alkyl, or —C(O)H; and n is 0 to 3.

In still other embodiments, ring A is a naphthyl group, $R^2$ is halogen and n is 1 to 2. In yet other embodiments, ring A is a naphthyl group and n is 0. In yet other embodiments, Ring A is a phenyl group, $R^2$ is halogen and n is 1 to 2.

In certain embodiments, for compounds of general formula IA-i-a, IB-i-a, IA-i, or IB-i, Ring A is 6-10-membered aryl or 5-10-membered heteroaryl having 1-5 heteroatoms independently selected from nitrogen, oxygen, or sulfur; n is 0 to 3, and W is —C(H)(N($R^{7b}$)$_2$)— or —CH$_2$—, wherein each occurrence of $R^{7b}$ is independently hydrogen or optionally substituted $C_{1-6}$ aliphatic. In certain embodiments, Ring A is 6-10-membered aryl or 5-10-membered heteroaryl having 1-5 heteroatoms independently selected from nitrogen, oxygen, or sulfur; n is 0 to 3, and W is —CH$_2$—.

In certain embodiments, for compounds of general formula IA-i-a, IB-i-a, IA-i, or IB-i, Ring A is a phenyl group; each occurrence of $R^2$ is independently halogen, $C_{1-3}$ alkyl, —CN, $C_{1-3}$ haloalkyl, —$OC_{1-3}$ alkyl, —$OC_{1-3}$ haloalkyl, —NHC(O)$C_{1-3}$ alkyl, —NHC(O)NHC$_{1-3}$ alkyl, —NHS(O)$_2C_{1-3}$ alkyl, or —C(O)H; and n is 0 to 3.

In certain embodiments, for compounds of general formula IA-i-a, IB-i-a, IA-i, or IB-i, Ring A is a phenyl group; each occurrence of $R^2$ is independently halogen, $C_{1-3}$ alkyl, $C_{1-3}$ haloalkyl, —$OC_{1-3}$ alkyl, —$OC_{1-3}$ haloalkyl, —NHC(O)$C_{1-3}$ alkyl, or -T$_2$-$R^{12d}$, T$_2$ is an optionally substituted $C_{1-6}$ alkylene chain, $R^{12d}$ is —N($R^{7b}$)$_2$, and each occurrence of $R^{7b}$ is independently hydrogen or optionally substituted $C_{1-6}$ aliphatic, or any two occurrences of $R^{7b}$ taken together with the atom to which they are bound, form an optionally substituted group selected from a 3-6-membered cycloaliphatic ring, 6-10-membered aryl, 3-6-membered heterocyclyl having 1-5 heteroatoms independently selected from nitrogen, oxygen, or sulfur, or 5-10-membered heteroaryl having 1-5 heteroatoms independently selected from nitrogen, oxygen, or sulfur; and n is 0 to 3.

In certain embodiments, for compounds of general formula IA-i-a, IB-i-a, IA-i, or IB-i, Ring A is a phenyl group; each occurrence of $R^2$ is independently halogen, —CN, —$OC_{1-3}$ alkyl, or —$OC_{1-3}$ haloalkyl; and n is 0 to 3. In certain embodiments, Ring A is a phenyl group; each occurrence of $R^2$ is independently halogen, —CN, —OCH$_3$, or —OCF$_3$; and n is 0 to 3.

In still other embodiments, Ring A is a phenyl group, $R^2$ is halogen and n is 1 to 2.

In still other embodiments, Ring A is a phenyl group, $R^2$ is halogen or —(CH$_2$)N($R^{7b}$)$_2$ and each occurrence of $R^{7b}$ is independently hydrogen or optionally substituted $C_{1-6}$ aliphatic, or any two occurrences of $R^{7b}$ taken together with the atom to which they are bound, form an optionally substituted group selected from a 3-6-membered cycloaliphatic ring, 6-10-membered aryl, 3-6-membered heterocyclyl having 1-5 heteroatoms independently selected from nitrogen, oxygen, or sulfur, or 5-10-membered heteroaryl having 1-5 heteroatoms independently selected from nitrogen, oxygen, or sulfur; and n is 2.

In certain embodiments, Ring A is a phenyl group, n is 1, and $R^2$ is in the para position. In certain other embodiments, Ring A is a phenyl group, n is 2, and the two $R^2$ groups are in the para and meta positions. In certain other embodiments, Ring A is a phenyl group, n is 2, and the two $R^2$ groups are in the ortho and meta positions, and para with respect to each other.

In certain embodiments, Ring A is 2-chloro-5(dimethylaminomethyl)phenyl. In certain other embodiments, Ring A is 2-chloro-5(pyrrolidin-1-ylmethyl)phenyl.

In certain embodiments, for compounds of general formula IA-i-a, IB-i-a, IA-i, or IB-i, Ring A is a 2-naphthyl group. In certain other embodiments, Ring A is

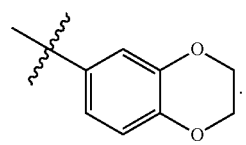

In certain embodiments, for compounds of general formula IA-i-a, IB-i-a, IA-i, or IB-i, Ring A is a 3-10-membered cycloaliphatic or 4-10-membered heterocyclyl having 1-5 heteroatoms independently selected from nitrogen, oxygen, or sulfur. In some embodiments, Ring A is an N-linked 3-, 4-, 5-, 6-, or 7-membered heterocyclyl ring. In some embodiments, Ring A is substituted with one or more $C_{1-3}$ alkyl groups.

In still other embodiments, a compound having the structure of formula II-i is provided:

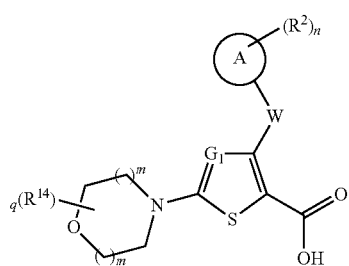

wherein Ring A, $G_1$, W, $R^2$, n, m, q, and $R^{14}$ are as defined for the compounds described generally above and in subsets herein.

In certain embodiments, for compounds of general formula II-i:
a) when $G_1$ is C—CN, HY is unsubstituted morpholine, and W is a covalent bond, then Ring A is other than unsubstituted phenyl, 2-chlorophenyl, 4-chlorophenyl, 2-fluorophenyl, 4-fluorophenyl, 2,4-dichlorophenyl, 3,4-dichlorophenyl, 4-methylphenyl, 3-methoxyphenyl, 4-methoxyphenyl, 3,4-dimethoxyphenyl, 3-(trifluoromethyl)phenyl, 4-(trifluoromethyl)phenyl, or 3-(acetylamino)phenyl;
b) when $G_1$ is N, HY is unsubstituted morpholine, and W is a covalent bond, then Ring A is other than unsubstituted phenyl or 2-chlorophenyl; and
c) the compound is other than:

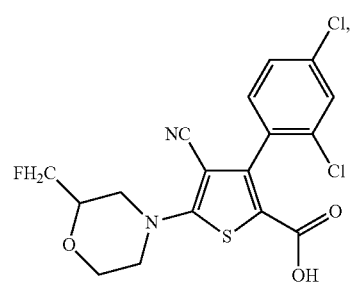

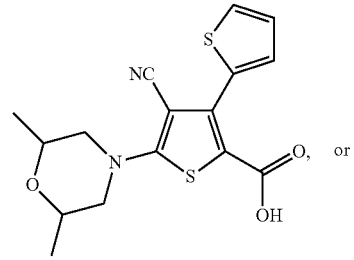

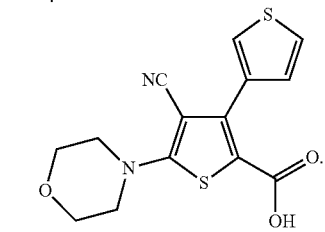

In certain embodiments, for compounds of general formula II-i, W is —C($R^7$)$_2$—, wherein one occurrence of $R^7$ is hydrogen and the other occurrence of $R^7$ is hydrogen, optionally substituted $C_{1-6}$ aliphatic, —N($R^{7b}$)$_2$, or F; and wherein each occurrence of $R^{7b}$ is independently hydrogen, optionally substituted $C_{1-6}$ aliphatic, C(O)$R^{7a}$, or —S(O)$_2R^{7a}$; or wherein two occurrences of $R^{7b}$, taken together with the nitrogen atom to which they are bound, form an optionally substituted 3-6-membered heterocyclic ring; and each occurrence of $R^{7a}$ is independently hydrogen or optionally substituted $C_{1-6}$ aliphatic.

In certain embodiments, for compounds of general formula II-i, W is —C(H)(N($R^{7b}$)$_2$)— or —CH$_2$—, wherein each occurrence of $R^{7b}$ is independently hydrogen or optionally substituted $C_{1-6}$ aliphatic.

In certain embodiments, for compounds of general formula II-i, W is a covalent bond.

In certain embodiments, for compounds of general formula II-i, Ring A is 6-10-membered aryl or 5-10-membered heteroaryl having 1-5 heteroatoms independently selected from nitrogen, oxygen, or sulfur; and n is 0 to 3.

In other embodiments, ring A is a group selected from:

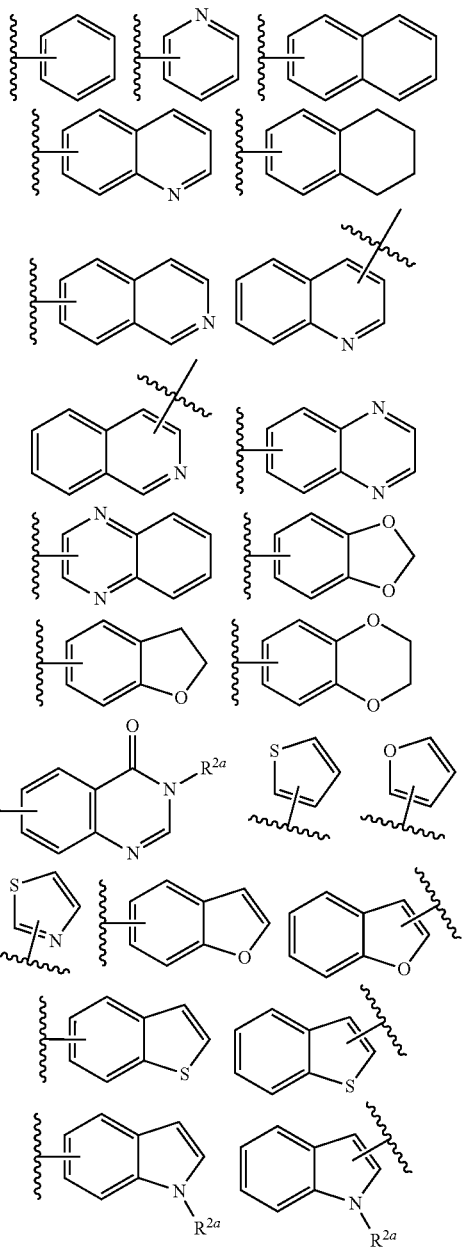

-continued

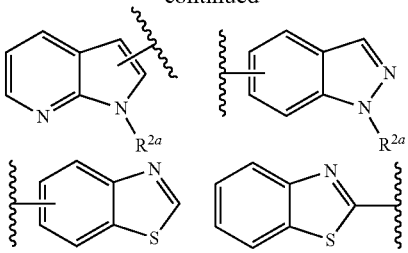

wherein ring A is optionally further substituted by n occurrences of $R^2$, and wherein $R^{2a}$ is hydrogen or an optionally substituted group selected from $C_{1-6}$aliphatic, 3-10-membered cycloaliphatic, 4-10-membered heterocyclyl having 1-5 heteroatoms independently selected from nitrogen, oxygen, or sulfur, 6-10-membered aryl, or 5-10-membered heteroaryl having 1-5 heteroatoms independently selected from nitrogen, oxygen, or sulfur.

In certain other embodiments, for compounds of general formula II-i, Ring A is a group selected from:

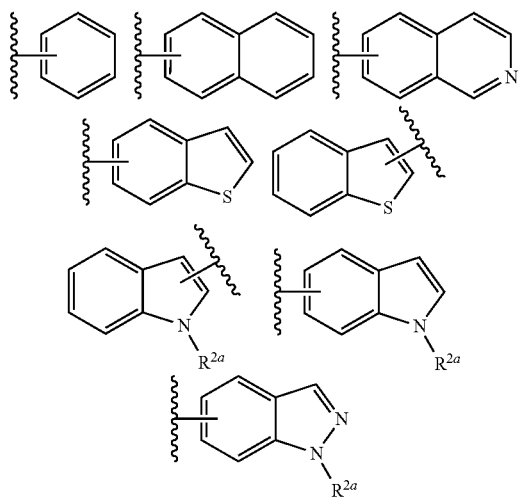

wherein ring A is optionally further substituted by n occurrences of $R^2$, and wherein $R^{2a}$ is hydrogen or an optionally substituted group selected from $C_{1-6}$aliphatic, 3-10-membered cycloaliphatic, 4-10-membered heterocyclyl having 1-5 heteroatoms independently selected from nitrogen, oxygen, or sulfur, 6-10-membered aryl, or 5-10-membered heteroaryl having 1-5 heteroatoms independently selected from nitrogen, oxygen, or sulfur.

In still other embodiments, ring A is a naphthyl group; each occurrence of $R^2$ is independently halogen, $C_{1-3}$ alkyl, —CN, $C_{1-3}$ haloalkyl, —$OC_{1-3}$ alkyl, —$OC_{1-3}$ haloalkyl, —NHC(O) $C_{1-3}$ alkyl, —NHC(O)NH$C_{1-3}$ alkyl, —NHS(O)$_2C_{1-3}$ alkyl, or —C(O)H; and n is 0 to 3.

In still other embodiments, ring A is a naphthyl group, $R^2$ is halogen and n is 1 to 2. In yet other embodiments, ring A is a naphthyl group and n is 0. In yet other embodiments, Ring A is a phenyl group, $R^2$ is halogen and n is 1 to 2.

In certain embodiments, for compounds of general formula II-i, Ring A is 6-10-membered aryl or 5-10-membered heteroaryl having 1-5 heteroatoms independently selected from nitrogen, oxygen, or sulfur; n is 0 to 3, and W is —C(H)(N($R^{7b}$)$_2$)— or —CH$_2$—, wherein each occurrence of $R^{7b}$ is independently hydrogen or optionally substituted $C_{1-6}$ aliphatic. In certain embodiments, Ring A is 6-10-membered aryl or 5-10-membered heteroaryl having 1-5 heteroatoms independently selected from nitrogen, oxygen, or sulfur; n is 0 to 3, and W is —CH$_2$—.

In certain embodiments, for compounds of general formula II-i, Ring A is a phenyl group; each occurrence of $R^2$ is independently halogen, $C_{1-3}$ alkyl, —CN, $C_{1-3}$ haloalkyl, —$OC_{1-3}$ alkyl, —$OC_{1-3}$ haloalkyl, —NHC(O)$C_{1-3}$ alkyl, —NHC(O)NH$C_{1-3}$ alkyl, —NHS(O)$_2$ $C_{1-3}$ alkyl, or —C(O)H; and n is 0 to 3.

In certain embodiments, for compounds of general formula II-i, Ring A is a phenyl group; each occurrence of $R^2$ is independently halogen, $C_{1-3}$ alkyl, $C_{1-3}$ haloalkyl, —$OC_{1-3}$ alkyl, —$OC_{1-3}$ haloalkyl, —NHC(O)$C_{1-3}$ alkyl, or -$T_2$-$R^{12d}$, $T_2$ is an optionally substituted $C_{1-6}$ alkylene chain, $R^{12d}$ is —N($R^{7b}$)$_2$, and each occurrence of $R^{7b}$ is independently hydrogen or optionally substituted $C_{1-6}$ aliphatic, or any two occurrences of $R^{7b}$ taken together with the atom to which they are bound, form an optionally substituted group selected from a 3-6-membered cycloaliphatic ring, 6-10-membered aryl, 3-6-membered heterocyclyl having 1-5 heteroatoms independently selected from nitrogen, oxygen, or sulfur, or 5-10-membered heteroaryl having 1-5 heteroatoms independently selected from nitrogen, oxygen, or sulfur; and n is 0 to 3.

In certain embodiments, for compounds of general formula II-i, Ring A is a phenyl group; each occurrence of $R^2$ is independently halogen, —CN, —$OC_{1-3}$ alkyl, or —$OC_{1-3}$ haloalkyl; and n is 0 to 3. In certain embodiments, Ring A is a phenyl group; each occurrence of $R^2$ is independently halogen, —CN, —OCH$_3$, or —OCF$_3$; and n is 0 to 3.

In still other embodiments, Ring A is a phenyl group, $R^2$ is halogen and n is 1 to 2.

In still other embodiments, Ring A is a phenyl group, $R^2$ is halogen or —(CH$_2$)N($R^{7b}$)$_2$ and each occurrence of $R^{7b}$ is independently hydrogen or optionally substituted $C_{1-6}$ aliphatic, or any two occurrences of $R^{7b}$ taken together with the atom to which they are bound, form an optionally substituted group selected from a 3-6-membered cycloaliphatic ring, 6-10-membered aryl, 3-6-membered heterocyclyl having 1-5 heteroatoms independently selected from nitrogen, oxygen, or sulfur, or 5-10-membered heteroaryl having 1-5 heteroatoms independently selected from nitrogen, oxygen, or sulfur; and n is 2.

In certain embodiments, Ring A is a phenyl group, n is 1, and $R^2$ is in the para position. In certain other embodiments, Ring A is a phenyl group, n is 2, and the two $R^2$ groups are in the para and meta positions. In certain other embodiments, Ring A is a phenyl group, n is 2, and the two $R^2$ groups are in the ortho and meta positions, and para with respect to each other.

In certain embodiments, Ring A is 2-chloro-5(dimethylaminomethyl)phenyl. In certain other embodiments, Ring A is 2-chloro-5(pyrrolidin-1-ylmethyl)phenyl.

In certain embodiments, for compounds of general formula II-i, Ring A is a 2-naphthyl group. In certain other embodiments, Ring A is

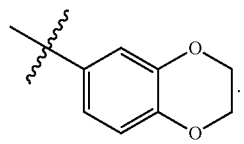

In certain embodiments, for compounds of general formula II-i, Ring A is a 3-10-membered cycloaliphatic or 4-10-membered heterocyclyl having 1-5 heteroatoms independently selected from nitrogen, oxygen, or sulfur. In some embodiments, Ring A is an N-linked 3-, 4-, 5-, 6-, or 7-membered heterocyclyl ring. In some embodiments, Ring A is substituted with one or more $C_{1-3}$ alkyl groups.

In certain embodiments, for compounds of general formula II-i, each occurrence of m is 1 and q is 0.

In still other embodiments, a compound having the structure of formula II-i is provided:

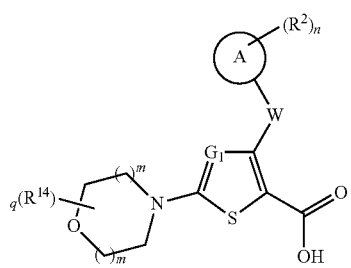

II-i wherein $G_1$ is N or —$CR^8$, and $R^8$ is —CN; ring A is a naphthyl group; each occurrence of $R^2$ is independently halogen, $C_{1-3}$ alkyl, —CN, $C_{1-3}$ haloalkyl, —$OC_{1-3}$ alkyl, —$OC_{1-3}$ haloalkyl, —NHC(O)$C_{1-3}$ alkyl, —NHC(O)NHC$_{1-3}$ alkyl, —NHS(O)$_2$C$_{1-3}$ alkyl, or —C(O)H; and n is 0 to 3; and W is —$C(R^7)_2$—, or >=O, wherein one occurrence of $R^7$ is hydrogen and the other occurrence of $R^7$ is hydrogen, optionally substituted $C_{1-6}$ aliphatic, —$OR^{7a}$, —$N(R^{7b})_2$, or F; and wherein each occurrence of $R^{7b}$ is independently hydrogen, optionally substituted $C_{1-6}$ aliphatic, —$C(O)R^{7a}$, or —$S(O)_2R^{7a}$; or wherein two occurrences of $R^{7b}$, taken together with the nitrogen atom to which they are bound, form an optionally substituted 3-6-membered heterocyclic ring; and each occurrence of $R^{7a}$ is independently hydrogen or optionally substituted $C_{1-6}$ aliphatic.

In still other embodiments, a compound having the structure of formula III-i is provided:

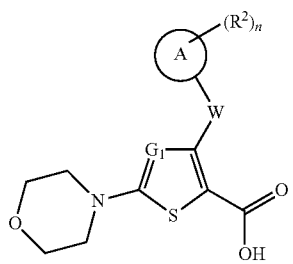

III wherein $G_1$ is N or —$CR^8$, and $R^8$ is —CN; and wherein Ring A, n and $R^2$ are as defined for the compounds described generally and in subsets herein.

In certain embodiments, for compounds of general formula III-i, Ring A is 6-10-membered aryl or 5-10-membered heteroaryl having 1-5 heteroatoms independently selected from nitrogen, oxygen, or sulfur; and n is 0 to 3.

In other embodiments, ring A is a group selected from:

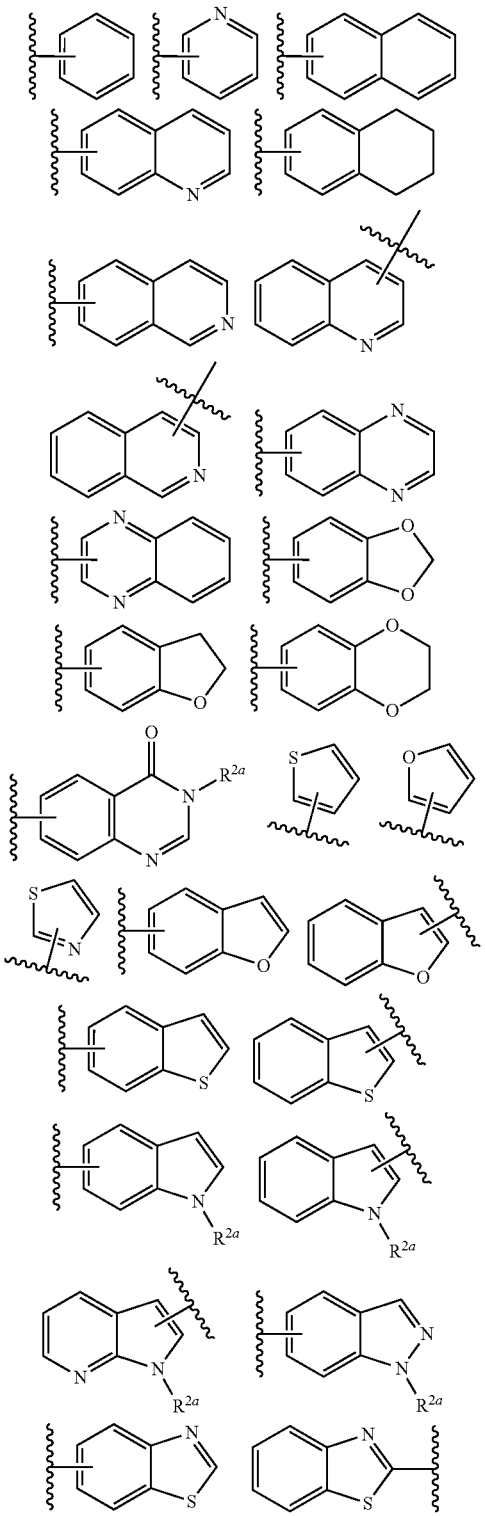

wherein ring A is optionally further substituted by n occurrences of $R^2$, and wherein $R^{2a}$ is hydrogen or an optionally substituted group selected from $C_{1-6}$aliphatic, 3-10-membered cycloaliphatic, 4-10-membered heterocyclyl having 1-5 heteroatoms independently selected from nitrogen, oxygen, or sulfur, 6-10-membered aryl, or 5-10-membered heteroaryl having 1-5 heteroatoms independently selected from nitrogen, oxygen, or sulfur.

In certain other embodiments, for compounds of general formula III-i, Ring A is a group selected from:

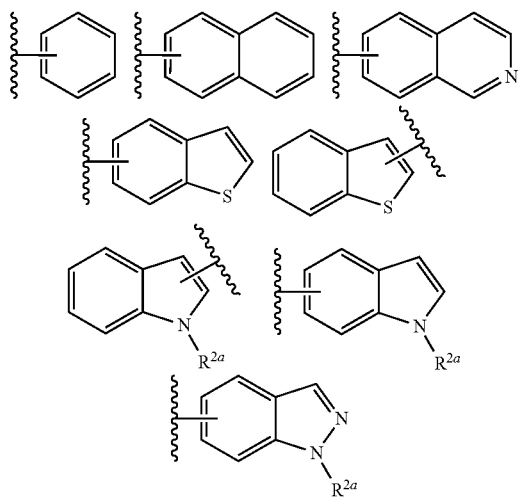

wherein ring A is optionally further substituted by n occurrences of $R^2$, and wherein $R^{2a}$ is hydrogen or an optionally substituted group selected from $C_{1-6}$aliphatic, 3-10-membered cycloaliphatic, 4-10-membered heterocyclyl having 1-5 heteroatoms independently selected from nitrogen, oxygen, or sulfur, 6-10-membered aryl, or 5-10-membered heteroaryl having 1-5 heteroatoms independently selected from nitrogen, oxygen, or sulfur.

In still other embodiments, ring A is a naphthyl group; each occurrence of $R^2$ is independently halogen, $C_{1-3}$ alkyl, —CN, $C_{1-3}$ haloalkyl, —$OC_{1-3}$ alkyl, —$OC_{1-3}$ haloalkyl, —NHC(O)$C_{1-3}$ alkyl, —NHC(O)NHC$_{1-3}$ alkyl, —NHS(O)$_2$C$_{1-3}$ alkyl, or —C(O)H; and n is 0 to 3.

In still other embodiments, ring A is a naphthyl group, $R^2$ is halogen and n is 1 to 2. In yet other embodiments, ring A is a naphthyl group and n is 0. In yet other embodiments, Ring A is a phenyl group, $R^2$ is halogen and n is 1 to 2.

In certain embodiments, for compounds of general formula III-i, Ring A is a phenyl group; each occurrence of $R^2$ is independently halogen, $C_{1-3}$ alkyl, —CN, $C_{1-3}$ haloalkyl, —$OC_{1-3}$ alkyl, —$OC_{1-3}$ haloalkyl, —NHC(O)C$_{1-3}$ alkyl, —NHC(O)NHC$_{1-3}$ alkyl, —NHS(O)$_2$C$_{1-3}$ alkyl, or —C(O)H; and n is 0 to 3.

In certain embodiments, for compounds of general formula III-i, Ring A is a phenyl group; each occurrence of $R^2$ is independently halogen, $C_{1-3}$ alkyl, $C_{1-3}$ haloalkyl, —$OC_{1-3}$ alkyl, —$OC_{1-3}$ haloalkyl, —NHC(O)C$_{1-3}$ alkyl, or -$T_2$-$R^{12d}$, $T_2$ is an optionally substituted $C_{1-6}$ alkylene chain, $R^{12d}$ is —N($R^{7b}$)$_2$, and each occurrence of $R^{7b}$ is independently hydrogen or optionally substituted $C_{1-6}$ aliphatic, or any two occurrences of $R^{7b}$ taken together with the atom to which they are bound, form an optionally substituted group selected from a 3-6-membered cycloaliphatic ring, 6-10-membered aryl, 3-6-membered heterocyclyl having 1-5 heteroatoms independently selected from nitrogen, oxygen, or sulfur; or 5-10-membered heteroaryl having 1-5 heteroatoms independently selected from nitrogen, oxygen, or sulfur; and n is 0 to 3.

In certain embodiments, for compounds of general formula III-i, Ring A is a phenyl group; each occurrence of $R^2$ is independently halogen, —CN, —OC$_{1-3}$ alkyl, or —OC$_{1-3}$ haloalkyl; and n is 0 to 3. In certain embodiments, Ring A is a phenyl group; each occurrence of $R^2$ is independently halogen, —CN, —OCH$_3$, or —OCF$_3$; and n is 0 to 3.

In still other embodiments, Ring A is a phenyl group, $R^2$ is halogen and n is 1 to 2.

In still other embodiments, Ring A is a phenyl group, $R^2$ is halogen or —(CH$_2$)N($R^{7b}$)$_2$ and each occurrence of $R^{7b}$ is independently hydrogen or optionally substituted $C_{1-6}$ aliphatic, or any two occurrences of $R^{7b}$ taken together with the atom to which they are bound, form an optionally substituted group selected from a 3-6-membered cycloaliphatic ring, 6-10-membered aryl, 3-6-membered heterocyclyl having 1-5 heteroatoms independently selected from nitrogen, oxygen, or sulfur, or 5-10-membered heteroaryl having 1-5 heteroatoms independently selected from nitrogen, oxygen, or sulfur; and n is 2.

In certain embodiments, Ring A is a phenyl group, n is 1, and $R^2$ is in the para position. In certain other embodiments, Ring A is a phenyl group, n is 2, and the two $R^2$ groups are in the para and meta positions. In certain other embodiments, Ring A is a phenyl group, n is 2, and the two $R^2$ groups are in the ortho and meta positions, and para with respect to each other.

In certain embodiments, Ring A is 2-chloro-5(dimethylaminomethyl)phenyl. In certain other embodiments, Ring A is 2-chloro-5(pyrrolidin-1-ylmethyl)phenyl.

In certain embodiments, for compounds of general formula III-i, Ring A is a 2-naphthyl group. In certain other embodiments, Ring A is

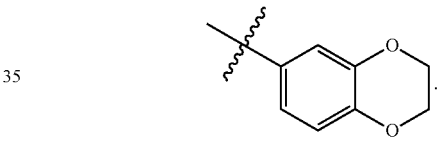

In certain embodiments, for compounds of general formula III-i, Ring A is a 3-10-membered cycloaliphatic or 4-10-membered heterocyclyl having 1-5 heteroatoms independently selected from nitrogen, oxygen, or sulfur. In some embodiments, Ring A is an N-linked 3-, 4-, 5-, 6-, or 7-membered heterocyclyl ring. In some embodiments, Ring A is substituted with one or more $C_{1-3}$ alkyl groups.

In yet other embodiments, a compound having the structure of formula IV-i is provided:

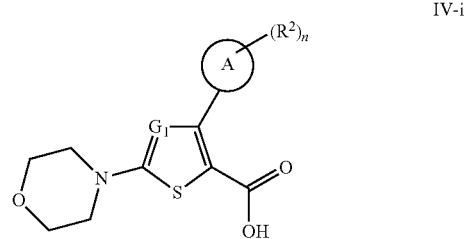

IV-i wherein Ring A, $G_1$, n and $R^2$ are as defined for compounds described generally above in subsets herein.

In certain embodiments, for compounds of general formula IV-i:
a) when $G_1$ is C—CN, then Ring A is other than unsubstituted phenyl, 2-chlorophenyl, 4-chlorophenyl, 2-fluorophenyl, 4-fluorophenyl, 2,4-dichlorophenyl, 3,4-dichlorophenyl, 4-methylphenyl, 3-methoxyphenyl, 4-methoxyphenyl, 3,4-dimethoxyphenyl, 3-(trifluoromethyl)phenyl, 4-(trifluoromethyl)phenyl, or 3-(acetylamino)phenyl;

b) when $G_1$ is N, then Ring A is other than unsubstituted phenyl or 2-chlorophenyl; and c) the compound is other than:

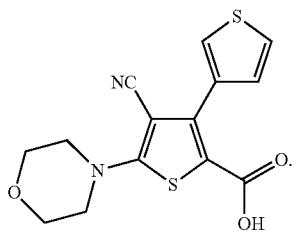 [SMILES: N#Cc1c(N2CCOCC2)sc(C(=O)O)c1-c1ccsc1]

In certain embodiments, for compounds of general formula IV-i, Ring A is 6-10-membered aryl or 5-10-membered heteroaryl having 1-5 heteroatoms independently selected from nitrogen, oxygen, or sulfur; and n is 0 to 3.

In other embodiments, ring A is a group selected from:

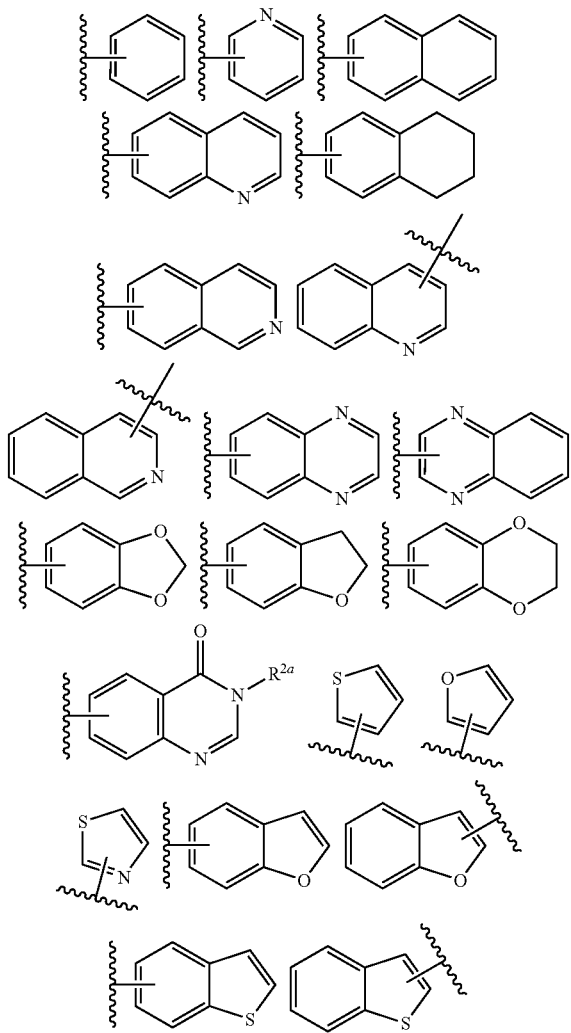

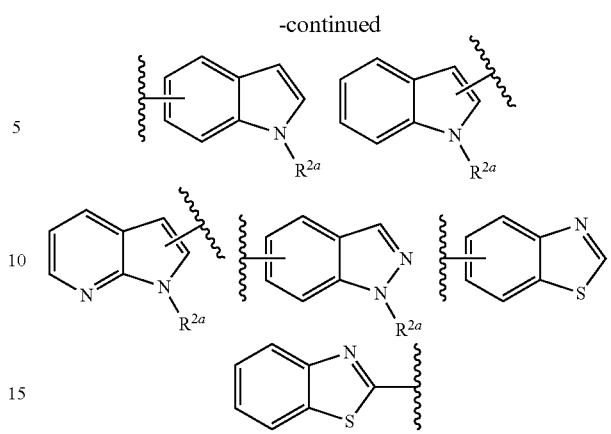

wherein ring A is optionally further substituted by n occurrences of $R^2$, and wherein $R^{2a}$ is hydrogen or an optionally substituted group selected from $C_{1-6}$ aliphatic, 3-10-membered cycloaliphatic, 4-10-membered heterocyclyl having 1-5 heteroatoms independently selected from nitrogen, oxygen, or sulfur, 6-10-membered aryl, or 5-10-membered heteroaryl having 1-5 heteroatoms independently selected from nitrogen, oxygen, or sulfur.

In certain other embodiments, for compounds of general formula VI-i, Ring A is a group selected from:

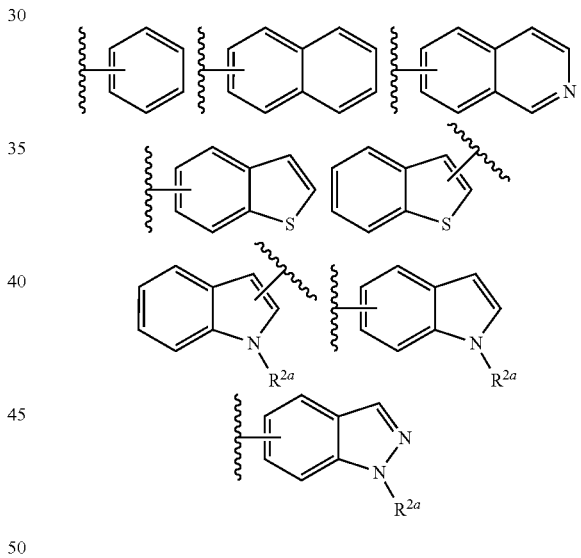

wherein ring A is optionally further substituted by n occurrences of $R^2$, and wherein $R^a$ is hydrogen or an optionally substituted group selected from $C_{1-6}$ aliphatic, 3-10-membered cycloaliphatic, 4-10-membered heterocyclyl having 1-5 heteroatoms independently selected from nitrogen, oxygen, or sulfur, 6-10-membered aryl, or 5-10-membered heteroaryl having 1-5 heteroatoms independently selected from nitrogen, oxygen, or sulfur.

In still other embodiments, ring A is a naphthyl group; each occurrence of $R^2$ is independently halogen, $C_{1-3}$ alkyl, —CN, $C_{1-3}$ haloalkyl, —$OC_{1-3}$ alkyl, —$OC_{1-3}$ haloalkyl, —NHC(O)$C_{1-3}$ alkyl, —NHC(O)NHC$_{1-3}$alkyl, —NHS(O)$_2$C$_{1-3}$ alkyl, or —C(O)H; and n is 0 to 3.

In still other embodiments, ring A is a naphthyl group, $R^2$ is halogen and n is 1 to 2. In yet other embodiments, ring A is a naphthyl group and n is 0. In yet other embodiments, Ring A is a phenyl group, $R^2$ is halogen and n is 1 to 2.

In certain embodiments, for compounds of general formula IV-i, Ring A is a phenyl group; each occurrence of $R^2$ is independently halogen, $C_{1-3}$ alkyl, —CN, $C_{1-3}$ haloalkyl, —$OC_{1-3}$ alkyl, —$OC_{1-3}$ haloalkyl, —NHC(O)$C_{1-3}$ alkyl, —NHC(O)NH$C_{1-3}$ alkyl, —NHS(O)$_2C_{1-3}$ alkyl, or —C(O)H; and n is 0 to 3.

In certain embodiments, for compounds of general formula IV-i, Ring A is a phenyl group; each occurrence of $R^2$ is independently halogen, $C_{1-3}$ alkyl, $C_{1-3}$ haloalkyl, —$OC_{1-3}$ alkyl, —$OC_{1-3}$ haloalkyl, —NHC(O)$C_{1-3}$ alkyl, or -$T_2$-$R^{12d}$, $T_2$ is an optionally substituted $C_{1-6}$ alkylene chain, $R^{12d}$ is —N($R^{7b}$)$_2$, and each occurrence of $R^{7b}$ is independently hydrogen or optionally substituted $C_{1-6}$ aliphatic, or any two occurrences of $R^{7b}$ taken together with the atom to which they are bound, form an optionally substituted group selected from a 3-6-membered cycloaliphatic ring, 6-10-membered aryl, 3-6-membered heterocyclyl having 1-5 heteroatoms independently selected from nitrogen, oxygen, or sulfur, or 5-10-membered heteroaryl having 1-5 heteroatoms independently selected from nitrogen, oxygen, or sulfur; and n is 0 to 3.

In certain embodiments, for compounds of general formula IV-i, Ring A is a phenyl group; each occurrence of $R^2$ is independently halogen, —CN, —$OC_{1-3}$ alkyl, or —$OC_{1-3}$ haloalkyl; and n is 0 to 3. In certain embodiments, Ring A is a phenyl group; each occurrence of $R^2$ is independently halogen, —CN, —$OCH_3$, or —$OCF_3$; and n is 0 to 3.

In still other embodiments, Ring A is a phenyl group, $R^2$ is halogen and n is 1 to 2.

In still other embodiments, Ring A is a phenyl group, $R^2$ is halogen or —(CH$_2$)N($R^{7b}$)$_2$ and each occurrence of $R^{7b}$ is independently hydrogen or optionally substituted $C_{1-6}$ aliphatic, or any two occurrences of $R^{7b}$ taken together with the atom to which they are bound, form an optionally substituted group selected from a 3-6-membered cycloaliphatic ring, 6-10-membered aryl, 3-6-membered heterocyclyl having 1-5 heteroatoms independently selected from nitrogen, oxygen, or sulfur, or 5-10-membered heteroaryl having 1-5 heteroatoms independently selected from nitrogen, oxygen, or sulfur; and n is 2.

In certain embodiments, Ring A is a phenyl group, n is 1, and $R^2$ is in the para position. In certain other embodiments, Ring A is a phenyl group, n is 2, and the two $R^2$ groups are in the para and meta positions. In certain other embodiments, Ring A is a phenyl group, n is 2, and the two $R^2$ groups are in the ortho and meta positions, and para with respect to each other.

In certain embodiments, Ring A is 2-chloro-5-(dimethylaminomethyl)phenyl. In certain other embodiments, Ring A is 2-chloro-5-(pyrrolidin-1-ylmethyl)phenyl.

In certain embodiments, for compounds of general formula IV-i, Ring A is a 2-naphthyl group. In certain other embodiments, Ring A is

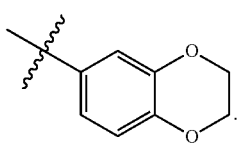

In certain embodiments, for compounds of general formula IV-i, Ring A is a 3-10-membered cycloaliphatic or 4-10-membered heterocyclyl having 1-5 heteroatoms independently selected from nitrogen, oxygen, or sulfur. In some embodiments, Ring A is an N-linked 3-, 4-, 5-, 6-, or 7-membered heterocyclyl ring. In some embodiments, Ring A is substituted with one or more $C_{1-3}$ alkyl groups.

In certain embodiments, for compounds of general formula IA-i or IB-i, HY is selected from:

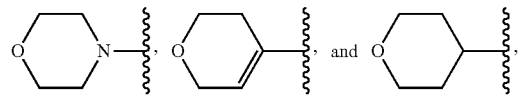

wherein each HY group is optionally additionally substituted with one or more occurrences of $R^{14}$.

In yet other embodiments, for compounds of general formula IA-i or IB-i, $G_1$ is N.

4. Uses, Formulation and Administration

As discussed above, the present invention provides compounds that are useful as inhibitors of PI3K enzymes, and thus the present compounds are useful for treating proliferative, inflammatory, or cardiovascular disorders such as tumor and/or cancerous cell growth mediated by PI3K. In particular, the compounds are useful in the treatment of cancers in a subject, including, but not limited to, lung and bronchus, prostate, breast, pancreas, colon and rectum, thyroid, liver and intrahepatic bile duct, hepatocellular, gastric, glioma/glioblastoma, endometrial, melanoma, kidney, and renal pelvis, urinary bladder, uterine corpus, uterine cervix, ovary, multiple myeloma, esophagus, acute myelogenous leukemia, chronic myelogenous leukemia, lymphocytic leukemia, myeloid leukemia, brain, oral cavity, and pharynx, small intestine, non-Hodgkin lymphoma, and villous colon adenoma.

In some embodiments, compounds of the invention are suitable for the treatment of breast cancer, bladder cancer, colon cancer, glioma, glioblastoma, lung cancer, hepatocellular cancer, gastric cancer, melanoma, thyroid cancer, endometrial cancer, renal cancer, cervical cancer, pancreatic cancer, esophageal cancer, prostate cancer, brain cancer, or ovarian cancer.

In other embodiments, compounds of the invention are suitable for the treatment of inflammatory and cardiovascular disorders including, but not limited to, allergies/anaphylaxis, acute and chronic inflammation, rheumatoid arthritis; autoimmunity disorders, thrombosis, hypertension, cardiac hypertrophy, and heart failure.

Accordingly, in another aspect of the present invention, pharmaceutical compositions are provided, wherein these compositions comprise any of the compounds as described herein, and optionally comprise a pharmaceutically acceptable carrier, adjuvant or vehicle. In certain embodiments, these compositions optionally further comprise one or more additional therapeutic agents.

It will also be appreciated that certain of the compounds of present invention can exist in free form for treatment, or where appropriate, as a pharmaceutically acceptable derivative thereof. According to the present invention, a pharmaceutically acceptable derivative includes, but is not limited to, pharmaceutically acceptable prodrugs, salts, esters, salts of such esters, or any other adduct or derivative which upon administration to a patient in need is capable of providing, directly or indirectly, a compound as otherwise described herein, or a metabolite or residue thereof.

As used herein, the term "pharmaceutically acceptable salt" refers to those salts which are, within the scope of sound medical judgment, suitable for use in contact with the tissues of humans and lower animals without undue toxicity, irritation, allergic response and the like, and are commensurate with a reasonable benefit/risk ratio. A "pharmaceutically acceptable salt" means any non-toxic salt or salt of an ester of a compound of this invention that, upon administration to a recipient, is capable of providing, either directly or indirectly, a compound of this invention or an inhibitorily active metabolite or residue thereof. As used herein, the term "inhibitorily active metabolite or residue thereof" means that a metabolite or residue thereof is also an inhibitor of PI3K.

Pharmaceutically acceptable salts are well known in the art. For example, S. M. Berge et al., describe pharmaceutically acceptable salts in detail in J. Pharmaceutical Sciences, 1977, 66, 1-19, incorporated herein by reference. Pharmaceutically acceptable salts of the compounds of this invention include those derived from suitable inorganic and organic acids and bases. Examples of pharmaceutically acceptable, nontoxic acid addition salts are salts of an amino group formed with inorganic acids such as hydrochloric acid, hydrobromic acid, phosphoric acid, sulfuric acid and perchloric acid or with organic acids such as acetic acid, oxalic acid, maleic acid, tartaric acid, citric acid, succinic acid or malonic acid or by using other methods used in the art such as ion exchange. Other pharmaceutically acceptable salts include adipate, alginate, ascorbate, aspartate, benzenesulfonate, benzoate, bisulfate, borate, butyrate, camphorate, camphorsulfonate, citrate, cyclopentanepropionate, digluconate, dodecylsulfate, ethanesulfonate, formate, fumarate, glucoheptonate, glycerophosphate, gluconate, hemisulfate, heptanoate, hexanoate, hydroiodide, 2-hydroxy-ethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, picrate, pivalate, propionate, stearate, succinate, sulfate, tartrate, thiocyanate, p-toluenesulfonate, undecanoate, valerate salts, and the like. Salts derived from appropriate bases include alkali metal, alkaline earth metal, ammonium and $N^+(C_{1-4}alkyl)_4$ salts. This invention also envisions the quaternization of any basic nitrogen-containing groups of the compounds disclosed herein. Water or oil-soluble or dispersable products may be obtained by such quaternization. Representative alkali or alkaline earth metal salts include sodium, lithium, potassium, calcium, magnesium, and the like. Further pharmaceutically acceptable salts include, when appropriate, nontoxic ammonium, quaternary ammonium, and amine cations formed using counterions such as halide, hydroxide, carboxylate, sulfate, phosphate, nitrate, lower alkyl sulfonate and aryl sulfonate.

As described above, the pharmaceutically acceptable compositions of the present invention additionally comprise a pharmaceutically acceptable carrier, adjuvant, or vehicle, which, as used herein, includes any and all solvents, diluents, or other liquid vehicle, dispersion or suspension aids, surface active agents, isotonic agents, thickening or emulsifying agents, preservatives, solid binders, lubricants and the like, as suited to the particular dosage form desired. Remington's Pharmaceutical Sciences, Sixteenth Edition, E. W. Martin (Mack Publishing Co., Easton, Pa., 1980) discloses various carriers used in formulating pharmaceutically acceptable compositions and known techniques for the preparation thereof. Except insofar as any conventional carrier medium is incompatible with the compounds of the invention, such as by producing any undesirable biological effect or otherwise interacting in a deleterious manner with any other component(s) of the pharmaceutically acceptable composition, its use is contemplated to be within the scope of this invention. Some examples of materials which can serve as pharmaceutically acceptable carriers include, but are not limited to, ion exchangers, alumina, aluminum stearate, lecithin, serum proteins, such as human serum albumin, buffer substances such as phosphates, glycine, sorbic acid, or potassium sorbate, partial glyceride mixtures of saturated vegetable fatty acids, water, salts or electrolytes, such as protamine sulfate, disodium hydrogen phosphate, potassium hydrogen phosphate, sodium chloride, zinc salts, colloidal silica, magnesium trisilicate, polyvinyl pyrrolidone, polyacrylates, waxes, polyethylene-polyoxypropylene-block polymers, wool fat, sugars such as lactose, glucose and sucrose; starches such as corn starch and potato starch; cellulose and its derivatives such as sodium carboxymethyl cellulose, ethyl cellulose and cellulose acetate; powdered tragacanth; malt; gelatin; talc; excipients such as cocoa butter and suppository waxes; oils such as peanut oil, cottonseed oil; safflower oil; sesame oil; olive oil; corn oil and soybean oil; glycols; such a propylene glycol or polyethylene glycol; esters such as ethyl oleate and ethyl laurate; agar; buffering agents such as magnesium hydroxide and aluminum hydroxide; alginic acid; pyrogen-free water; isotonic saline; Ringer's solution; ethyl alcohol, and phosphate buffer solutions, as well as other non-toxic compatible lubricants such as sodium lauryl sulfate and magnesium stearate, as well as coloring agents, releasing agents, coating agents, sweetening, flavoring and perfuming agents, preservatives and antioxidants can also be present in the composition, according to the judgment of the formulator.

In yet another aspect, a method for treating a proliferative, inflammatory, or cardiovascular disorder is provided comprising administering an effective amount of a compound, or a pharmaceutical composition to a subject in need thereof. In certain embodiments of the present invention an "effective amount" of the compound or pharmaceutical composition is that amount effective for treating a proliferative, inflammatory, or cardiovascular disorder, or is that amount effective for treating cancer. In other embodiments, an "effective amount" of a compound is an amount which inhibits binding of PI3K and thereby blocks the resulting signaling cascades that lead to the abnormal activity of growth factors, receptor tyrosine kinases, protein serine/threonine kinases, G protein coupled receptors and phospholipid kinases and phosphatases.

The compounds and compositions, according to the Method of the present invention, may be administered using any amount and any route of administration effective for treating the disease. The exact amount required will vary from subject to subject, depending on the species, age, and general condition of the subject, the severity of the infection, the particular agent, its mode of administration, and the like. The compounds of the invention are preferably formulated in dosage unit form for ease of administration and uniformity of dosage. The expression "dosage unit form" as used herein refers to a physically discrete unit of agent appropriate for the patient to be treated. It will be understood, however, that the total daily usage of the compounds and compositions of the present invention will be decided by the attending physician within the scope of sound medical judgment. The specific effective dose level for any particular patient or organism will depend upon a variety of factors including the disease being treated and the severity of the disease; the activity of the specific compound employed; the specific composition employed; the age, body weight, general health, sex and diet of the patient; the time of administration, route of administration, and rate of excretion of the specific compound employed; the duration of the treatment; drugs used in combination or coincidental with the specific compound employed, and like factors well known in the medical arts.

The term "patient", as used herein, means an animal, preferably a mammal, and most preferably a human.

The pharmaceutically acceptable compositions of this invention can be administered to humans and other animals orally, rectally, parenterally, intracisternally, intravaginally, intraperitoneally, topically (as by powders, ointments, or drops), bucally, as an oral or nasal spray, or the like, depending on the severity of the infection being treated. In certain embodiments, the compounds of the invention may be administered orally or parenterally at dosage levels of about 0.01 mg/kg to about 50 mg/kg and preferably from about 1 mg/kg to about 25 mg/kg, of subject body weight per day, one or more times a day, to obtain the desired therapeutic effect.

Liquid dosage forms for oral administration include, but are not limited to, pharmaceutically acceptable emulsions, microemulsions, solutions, suspensions, syrups and elixirs. In addition to the active compounds, the liquid dosage forms may contain inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethylformamide, oils (in particular, cottonseed, groundnut, corn, germ, olive, castor, and sesame oils), glycerol, tetrahydrofurfuryl alcohol, polyethylene glycols and fatty acid esters of sorbitan, and mixtures thereof. Besides inert diluents, the oral compositions can also include adjuvants such as wetting agents, emulsifying and suspending agents, sweetening, flavoring, and perfuming agents.

Injectable preparations, for example, sterile injectable aqueous or oleaginous suspensions may be formulated according to the known art using suitable dispersing or wetting agents and suspending agents. The sterile injectable preparation may also be a sterile injectable solution, suspension or emulsion in a nontoxic parenterally acceptable diluent or solvent, for example, as a solution in 1,3-butanediol. Among the acceptable vehicles and solvents that may be employed are water, Ringer's solution, U.S.P. and isotonic sodium chloride solution. In addition, sterile, fixed oils are conventionally employed as a solvent or suspending medium. For this purpose any bland fixed oil can be employed including synthetic mono- or diglycerides. In addition, fatty acids such as oleic acid are used in the preparation of injectables.

The injectable formulations can be sterilized, for example, by filtration through a bacterial-retaining filter, or by incorporating sterilizing agents in the form of sterile solid compositions which can be dissolved or dispersed in sterile water or other sterile injectable medium prior to use.

In order to prolong the effect of a compound of the present invention, it is often desirable to slow the absorption of the compound from subcutaneous or intramuscular injection. This may be accomplished by the use of a liquid suspension of crystalline or amorphous material with poor water solubility. The rate of absorption of the compound then depends upon its rate of dissolution that, in turn, may depend upon crystal size and crystalline form. Alternatively, delayed absorption of a parenterally administered compound form is accomplished by dissolving or suspending the compound in an oil vehicle. Injectable depot forms are made by forming microencapsule matrices of the compound in biodegradable polymers such as polylactide-polyglycolide. Depending upon the ratio of compound to polymer and the nature of the particular polymer employed, the rate of compound release can be controlled. Examples of other biodegradable polymers include poly (orthoesters) and poly(anhydrides). Depot injectable formulations are also prepared by entrapping the compound in liposomes or microemulsions that are compatible with body tissues.

Compositions for rectal or vaginal administration are preferably suppositories which can be prepared by mixing the compounds of this invention with suitable non-irritating excipients or carriers such as cocoa butter, polyethylene glycol or a suppository wax which are solid at ambient temperature but liquid at body temperature and therefore melt in the rectum or vaginal cavity and release the active compound.

Solid dosage forms for oral administration include capsules, tablets, pills, powders, and granules. In such solid dosage forms, the active compound is mixed with at least one inert, pharmaceutically acceptable excipient or carrier such as sodium citrate or dicalcium phosphate and/or a) fillers or extenders such as starches, lactose, sucrose, glucose, mannitol, and silicic acid, b) binders such as, for example, carboxymethylcellulose, alginates, gelatin, polyvinylpyrrolidinone, sucrose, and acacia, c) humectants such as glycerol, d) disintegrating agents such as agar—agar, calcium carbonate, potato or tapioca starch, alginic acid, certain silicates, and sodium carbonate, e) solution retarding agents such as paraffin, f) absorption accelerators such as quaternary ammonium compounds, g) wetting agents such as, for example, cetyl alcohol and glycerol monostearate, h) absorbents such as kaolin and bentonite clay, and i) lubricants such as talc, calcium stearate, magnesium stearate, solid polyethylene glycols, sodium lauryl sulfate, and mixtures thereof. In the case of capsules, tablets and pills, the dosage form may also comprise buffering agents.

Solid compositions of a similar type may also be employed as fillers in soft and hard-filled gelatin capsules using such excipients as lactose or milk sugar as well as high molecular weight polyethylene glycols and the like. The solid dosage forms of tablets, dragees, capsules, pills, and granules can be prepared with coatings and shells such as enteric coatings and other coatings well known in the pharmaceutical formulating art. They may optionally contain opacifying agents and can also be of a composition that they release the active ingredient (s) only, or preferentially, in a certain part of the intestinal tract, optionally, in a delayed manner. Examples of embedding compositions that can be used include polymeric substances and waxes. Solid compositions of a similar type may also be employed as fillers in soft and hard-filled gelatin capsules using such excipients as lactose or milk sugar as well as high molecular weight polethylene glycols and the like.

The active compounds can also be in micro-encapsulated form with one or more excipients as noted above. The solid dosage forms of tablets, dragees, capsules, pills, and granules can be prepared with coatings and shells such as enteric coatings, release controlling coatings and other coatings well known in the pharmaceutical formulating art. In such solid dosage forms the active compound may be admixed with at least one inert diluent such as sucrose, lactose or starch. Such dosage forms may also comprise, as is normal practice, additional substances other than inert diluents, e.g., tableting lubricants and other tableting aids such a magnesium stearate and microcrystalline cellulose. In the case of capsules, tablets and pills, the dosage forms may also comprise buffering agents. They may optionally contain opacifying agents and can also be of a composition that they release the active ingredient(s) only, or preferentially, in a certain part of the intestinal tract, optionally, in a delayed manner. Examples of embedding compositions that can be used include polymeric substances and waxes.

Dosage forms for topical or transdermal administration of a compound of this invention include ointments, pastes, creams, lotions, gels, powders, solutions, sprays, inhalants or patches. The active component is admixed under sterile conditions with a pharmaceutically acceptable carrier and any needed preservatives or buffers as may be required. Ophthalmic formulation, ear drops, and eye drops are also contemplated as being within the scope of this invention. Additionally, the present invention contemplates the use of transdermal patches, which have the added advantage of providing controlled delivery of a compound to the body. Such dosage forms can be made by dissolving or dispensing the compound in the proper medium. Absorption enhancers can also be used to increase the flux of the compound across the skin. The rate can be controlled by either providing a rate controlling membrane or by dispersing the compound in a polymer matrix or gel.

While one or more of the inventive compounds may be used in an application of monotherapy to treat a disorder, disease or symptom, they also may be used in combination therapy, in which the use of an inventive compound or composition (therapeutic agent) is combined with the use of one or more other therapeutic agents for treating the same and/or other types of disorders, symptoms and diseases. Combination therapy includes administration of the therapeutic agents concurrently or sequentially. Alternatively, the therapeutic agents can be combined into one composition which is administered to the patient.

In one embodiment, the compounds of this invention are used in combination with other therapeutic agents, such as other inhibitors of PI3K or other inhibitors such as mTor. In some embodiments, a compound of the invention is administered in conjunction with a therapeutic agent selected from the group consisting of cytotoxic agents, radiotherapy, and immunotherapy. It is understood that other combinations may be undertaken while remaining within the scope of the invention.

Another aspect of the invention relates to inhibiting PI3K, activity in a biological sample or a patient, which method comprises administering to the patient, or contacting said biological sample with a compound of formula I or a composition comprising said compound. The term "biological sample", as used herein, generally includes in vivo, in vitro, and ex vivo materials, and also includes, without limitation, cell cultures or extracts thereof; biopsied material obtained from a mammal or extracts thereof; and blood, saliva, urine, feces, semen, tears, or other body fluids or extracts thereof.

Still another aspect of this invention is to provide a kit comprising separate containers in a single package, wherein the inventive pharmaceutical compounds, compositions and/or salts thereof are used in combination with pharmaceutically acceptable carriers to treat disorders, symptoms and diseases where PI3K kinase plays a role.

EXPERIMENTAL PROCEDURES

I-A. Preparation of Certain Exemplary Compounds

Compounds 1 through 92 (Shown in Table 1 below) were prepared using the general methods and specific examples described directly below.

1. General Synthetic Methods and Intermediates:

The compounds of the present invention can be prepared by methods known to one of ordinary skill in the art and/or by reference to the schemes shown below and the synthetic examples that follow. Exemplary synthetic routes are set forth in Schemes 1-52 below, and in the Examples.

In methods defined below X represents halogen (Br, I or Cl), P is HY itself or a substituent convertible to HY by applying a generally known method, $R^A$ represents Ring A, $W^R$ is W—$R^A$ itself, or a substituent convertible to W—$R^A$ by applying a generally known method, $W^L$ is $R^A$ itself, or a part of W linker connected to $R^A$ and Q is $R^1$ itself or a substituent convertible to $R^1$ by applying a generally known method.

Examples of the solvent for the below-mentioned reactions include, but are not limited to halogenated hydrocarbons such as dichloromethane, chloroform, carbon tetrachloride, 1,2-dichloroethane and the like, aromatic hydrocarbons such as benzene, toluene, xylene and the like, alcohols such as methanol, ethanol, isopropanol, tert-butanol, phenol and the like, ethers such as diethyl ether, tetrahydrofuran, dioxane, DME and the like, acetone, acetonitrile, ethyl acetate, N,N-dimethylformamide, N,N-dimethylacetamide, 1-methyl-2-pyrrolidone, dimethyl sulfoxide, hexamethylphosphoramide, water or a mixed solvent thereof and the like.

One of ordinary skill in the art will recognise that numerous variations in reaction conditions including variations in solvent, reagents, catalysts, reaction temperatures and times are possible for each of the reactions described. Variation of order of synthetic steps and alternative synthetic routes are also possible.

In many cases, synthesis can be started from commercially available thiophene/thiazole analogs to prepare target compounds. In some cases, specially functionalized thiophene/thiazole analogs can be prepared by the procedures described in Schemes 1-4.

Scheme 1: General method for the synthesis of 2-aminothiophenes

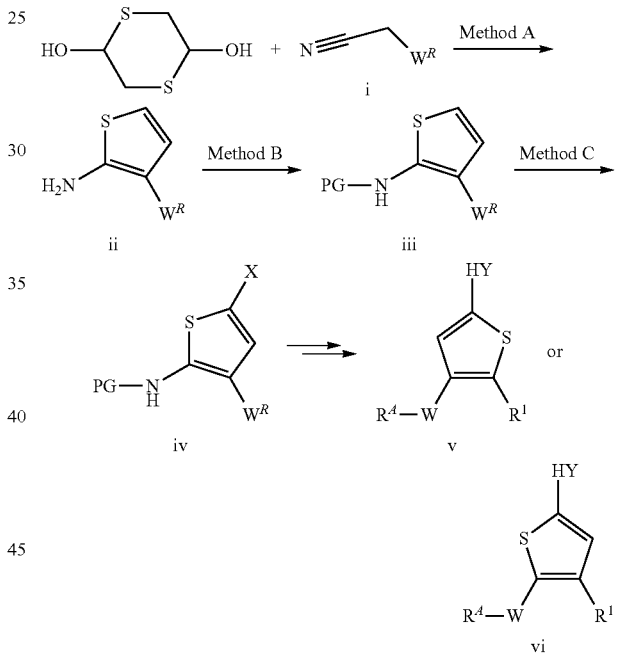

Scheme 1 shows a procedure to prepare compounds of formula v. Condensation of nitriles i with 2,5-dihydroxy-1,4-dithiane can be accomplished using reported procedure (C. E. Stephens et al. Bioorg. Med. Chem., 2001, 9, 1123-1132, Method A). Aminothiophenes ii may then be protected with an appropriate protecting group, for example Boc using standard conditions, such as Boc anhydride, DMAP, dioxane (Method B). Halogenation of protected thiophenes iii may be achieved using a suitable reagent, for example NBS in DCM to afford halides of formula iv (Method C), that can be converted into compounds of formula v by a combination of generally known functional group conversion reactions described below.

Alternatively, reverse type of thiophene analogs vi can also be prepared using functional group transformations described below.

Scheme 2: General method for the synthesis of 4-hydroxyl thiophenes

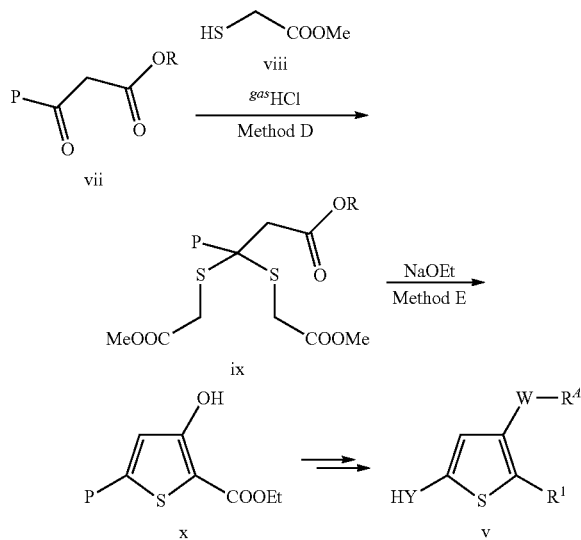

Suitably functionalized 4-hydroxyl thiophenes can be prepared according to the published procedure such as M. D. Mullican, et al., J. Med. Chem., 1991, 34, 2186-2194.

For example, scheme 2 describes a general procedure for preparing 4-hydroxythiophenes of formula x. Beta-ketoesters vii may be treated with thiols, such as methyl thioglycolate viii in the presence of suitable acid, such as HCl in ethanol (Method D), to afford dithio-ketal ix, which may then be treated with an appropriate base, like sodium ethoxide in a suitable solvent, for example, ethanol, to give 4-hydroxythiophenes of formula x (Method E). These 4-hydroxythiophenes can be converted to target compounds v according to the procedures described below.

Scheme 3: General method for synthesis of substituted thiazoles

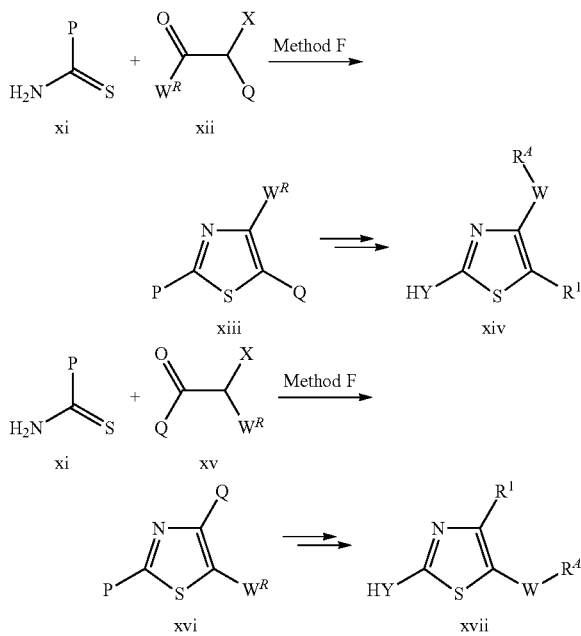

Scheme 3 shows a general route for the synthesis of compounds of formula xiii and xvi. Thioamides xi or thioureas (When P=NHR) may be treated with alpha-halogenated carbonyl compounds xii in a suitable solvent, such as isopropanol at elevated temperature to give thiazoles xiii. (Method F). When P=NH$_2$, 2-aminothiazoles xiii that are obtained can be then subjected to Sandmeyer reaction to afford 2-halothiazoles xxxi (P=X), which can be used for further functional transformations described below. A conversion reaction from xiii to compounds xiv can be performed, for example, by a combination of generally known functional group conversion reactions shown below.

If an alpha-halogenated carbonyl compound is suitably selected, i.e. xv, reverse type thiazole analogs xvi and xvii can be also prepared using well known organic functional group transformation reactions described below.

Scheme 4: General method for the preparation of 4-hydroxythiazoles

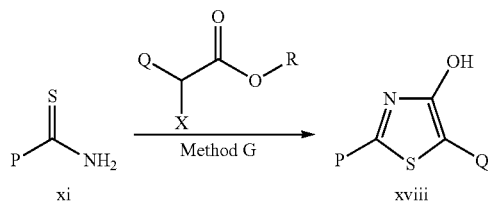

As shown in scheme 4, thioamides xi can be condensed with alpha-halogenated esters in a similar manner as reported by Rzasa, R. M. et al, Bioorg. Med. Chem. 2007, 15, 6574 to obtain 4-hydroxythiazole derivatives xviii. The reaction can be carried out in a suitable solvent, such as ethanol, in the presence of an appropriate base, i.e., pyridine, under elevated temperature (Method G).

Schemes 5-19 describe procedures for basic functional group transformations on thiophene/thiazole central core scaffolds.

In the schemes 5-8, general functional group transformation procedures for introduction of the HY group are described.

Scheme 5: Introduction of HY to 3-cyanothiophenes

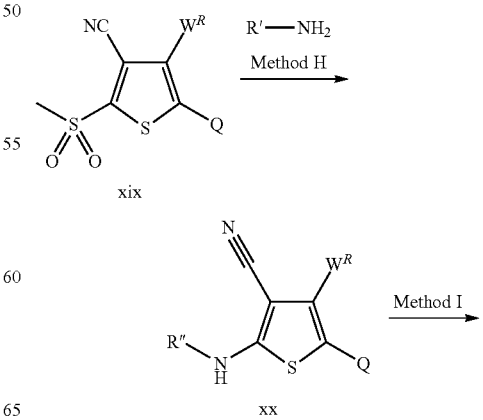

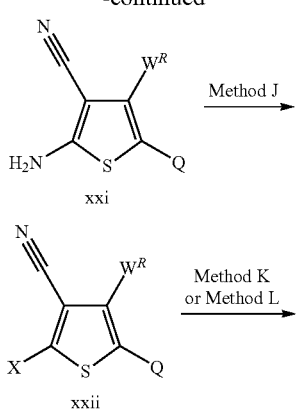

Deprotection of R″ group may be carried out using a standard procedure, in the case of dimethoxybenzyl group with an acid, such as TFA in DCM, to afford amines xxi (Method I).

Amines xxi can then be subjected to Sandmeyer reaction using appropriate reagents, such as methylene iodide and amyl nitrite in ACN (Method J).

The resulting halogenated thiophenes xxii can be coupled with aryl stannanes under suitable conditions, for example Pd(PPh$_3$)$_4$, CuI, LiCl in a suitable solvent, such as dioxane, at elevated temperature to give compounds of formula xxiii (Method K). Alternatively, boronic acids or esters can be used for such coupling reactions, for example Pd(PPh$_3$)$_4$, Na$_2$CO$_3$, DME/water, elevated temperature or microwave irradiation (Method L).

A conversion reaction from xxiii to compounds xxiv can be performed, for example, by a combination of generally known functional group conversion reactions shown below.

Scheme 6: General method for the introduction of HY to 2-unsubstituted thiophenes.

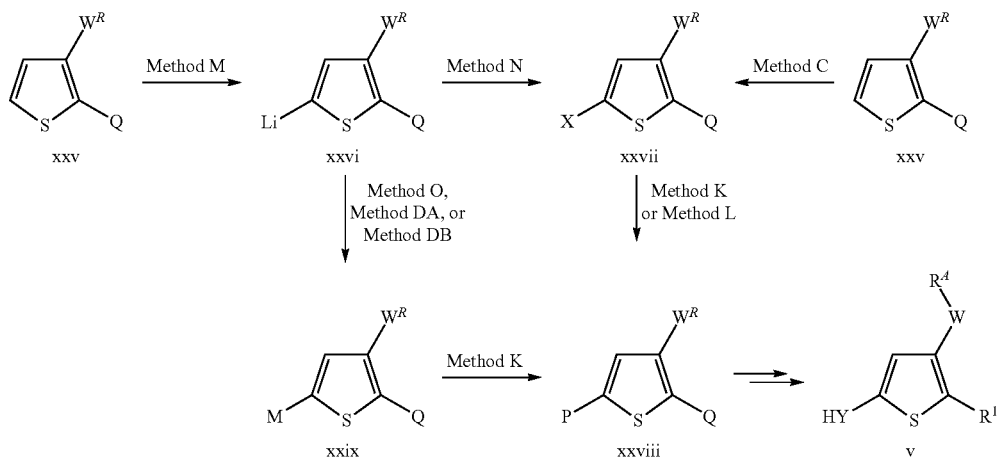

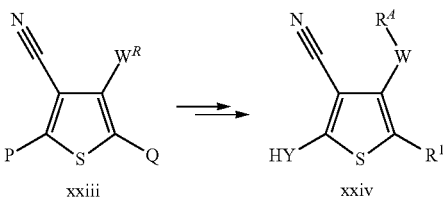

Scheme 5 describes the procedure for the introduction of HY to 3-cyanothiophene analogs by a known functional group transformation reaction.

As shown in Scheme 5, sulfones of formula xix (synthetic examples given in Mansanet et al, WO 2005070916) may be treated with amines R′—NH$_2$, such as 2,4-dimethoxybenzylamine, in a suitable solvent, e.g., THF, at elevated temperature (Method H) to give xx.

Scheme 6 shows a general route for introducing HY to unsubstituted 2-position of thiophene core.

2-unsubstituted thiophenes xxv can be treated with suitable base, such as n-BuLi in THF at low temperature, to produce lithiated thiophene intermediates xxvi (Method M). The intermediate organolithium species can be quenched with halogen molecule, for example iodine in a suitable solvent, such as THF, to afford halogenated compounds of formula xxvii (Method N). Alternatively, thiophenes xxv can be directly halogenated using suitable conditions, for example NBS in DCM to afford halogenated compounds of formula xxvii (Method C). Halides xxvii can be coupled with aryl stannanes under suitable conditions, for example Pd(PPh$_3$)$_4$, CuI, LiCl in a suitable solvent, such as dioxane at elevated temperature to give compounds of formula xxviii (Method K), or boronic acids or esters. with an appropriate catalyst, for example Pd(PPh$_3$)$_4$, in the presence of a suitable base, such as sodium carbonate, in DME-water mixture at elevated temperature (Method L) to afford compounds of formula xxviii. Alternatively, lithium intermediates xxvi can be transformed to organometallic reagents, such as stannanes by quenching with suitable tin halide, such as tributyltin chloride (Method O), or boronic esters, such as alkoxy-tetramethyl-1,3,2-dioxaborolane (method DA), or trifluoroborates by the subsequent treatment of boronic esters with a suitable fluorine source, such as KHF$_2$ (Method DB). Stannanes xxix may then be coupled with aryl halides, triflates, or mesylates using appropriate conditions, such as Pd(PPh$_3$)$_4$, CuI, LiCl in a suitable solvent, such as dioxane, at elevated temperature to give compounds of formula xxviii (Method K). Boronic acids, esters or trifluoroborates can be then coupled with aryl halides, triflates, or mesylates with an appropriate catalyst, for example Pd(PPh$_3$)$_4$, in the presence of a suitable base, such as sodium carbonate in DME-water mixture at elevated temperature (Method L) to afford compounds of formula xxviii.

A conversion reaction from xxviii to compounds v can be performed, for example, by a combination of generally known functional group conversion reactions shown below.

Scheme 7: General method for introduction of HY to 2-position of thiazole core.

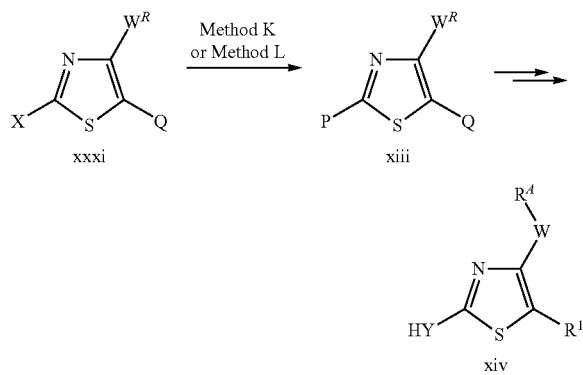

Scheme 7 shows a general route for introducing HY to 2-position of thiazole core scaffold. Halogenated thiazoles xxxi, which may be available as described in scheme 3, can coupled with suitable partners, such as boronic acids, stannanes, etc under standard Suzuki conditions, such as Pd(PPh$_3$)$_4$, Na$_2$CO$_3$, DME/water, elevated temperature or microwave irradiation (Method L), or standard Stille conditions, such as Pd(PPh$_3$)$_4$, CuI, LiCl, dioxane at elevated temperature (Method K) to afford compounds of formula xiii.

A conversion reaction from xiii to compounds xiv can be performed, for example, by a combination of generally known functional group conversion reactions shown below.

Scheme 8: General method for the synthesis of 3-cyanothiophenes

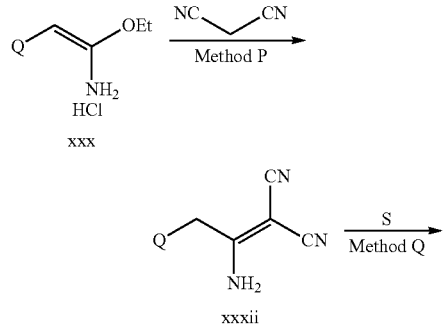

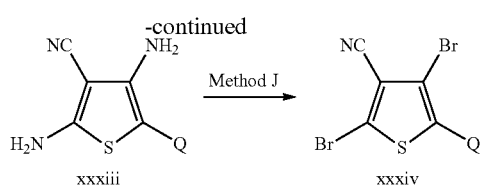

Scheme 8 describes the procedure for the synthesis of 3-cyanothiophenes xxxiv. Substituted alkoxyethenamine xxx may be treated with malononitrile in the presence of a suitable base, such as TEA, in a suitable solvent, like chloroform, at elevated temperature to afford substituted aminoethylene malononitriles xxxii (Method P), that are treated with sulfur under suitable conditions, such as DMF and elevated temperature, to give diaminocyanothiophenes xxxiii (Method Q). Diamines xxxiii may then be subjected to a Sandmeyer reaction using appropriate reagents, such as copper(II)bromide, amyl nitrite in ACN at elevated temperature (Method J) to afford compounds of formula xxxiv.

Schemes 9-21 describe methods for the introduction of R$^1$ and W—R$^A$ groups.

Scheme 9: General method for the synthesis of preparation of 4-alkoxy thiophene/thiazole derivatives.

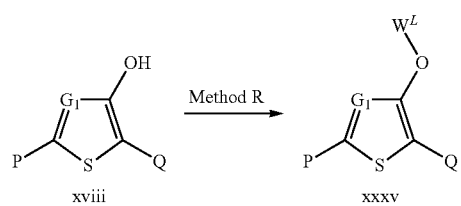

4-Alkoxy thiophenes/thiazoles can be obtained by the conventional alkylation method of 4-hydroxythiazole derivatives obtained in scheme 4.

As shown in scheme 9,4-hydroxy thiophenes/thiazoles xviii can be treated with alkyl halides using a suitable base, such as potassium carbonate, in a suitable solvent, for example DMF, at elevated temperature to afford compounds of formula xxxv (Method R).

Scheme 10: General method for halogenation of thiophenes/thiazoles

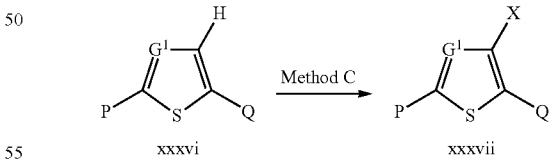

Scheme 10 shows a general route for introducing halogen functionality at the 4-unsubstituted position of thiophene/thiazole core.

Halogenation of thiophene/thiazoles can be achieved in a similar manner as reported in the literature (Takami et al, Tetrahedron 2004, 60, 6155). For example, xxxvi is treated with a generally known halogenating reagent, such as bromine or N-bromosuccinimide, in a suitable solvent, such as DCM, at elevated temperature to afford compounds of formula xxxvii (Method C).

The halogenated thiazole xxxvii can be used for further functional group transformation shown below.

Scheme 11: General method for the preparation of 4-aminothiazoles

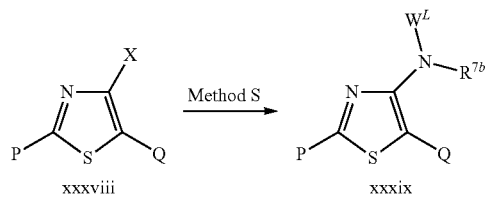

Scheme 11 shows general methods for the synthesis of 4-aminothiazole derivatives xxxix from 4-halogenated thiazoles xxxviii, which can be prepared by the procedure described in scheme 10. Displacement of a halogen group with an amine can be achieved in a similar manner as reported in the literature (J. Med. Chem. 2006, 49, 5769). Treatment of xxxviii with an amine at elevated temperature in a suitable solvent, such as DMF, can lead to amines xxxix (Method S). If necessary a base, such as sodium carbonate, can be added.

Scheme 12: General method for introducing carbon functionality to 4-halogenated thiophenes/thiazoles.

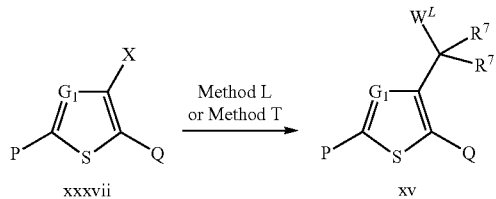

As shown in Scheme 12, carbon functionality can be introduced by the well known cross-coupling technique from the 4-halogenated thiophenes/thiazoles xxxvii which can be prepared by the procedure described in scheme 10.

For example, xv can be obtained from 4-halogenated thiophenes/thiazoles xxxvii by reaction with an organic boronic acid reagent, or an organic zinc reagent in a presence of palladium catalyst. Suzuki couplings with alkyl, alkenyl boronic acids or esters can be performed using Pd(PPh$_3$)$_4$, or a similar palladium catalyst, a suitable base, such as sodium carbonate in an appropriate solvent, such as DME/water, at elevated temperature (Method L), while Pd(tBu$_3$P)$_2$ can be used for Negishi coupling reactions, together with in a suitable solvent, such as THF, at elevated temperature (Method T).

Scheme 13: General method for introducing carbon functionality to 4-halogenated thiophenes/thiazoles.

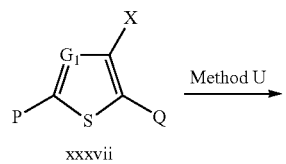

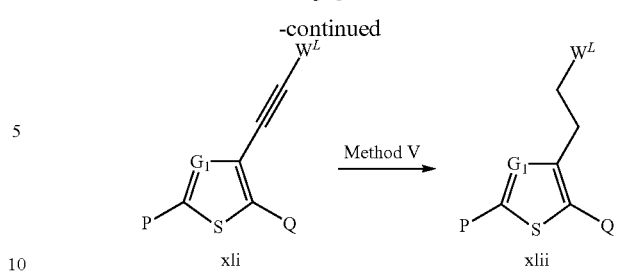

Scheme 13 shows a general method for the synthesis carbon substituted thiophenes/thiazoles. 4-halogenated thiophenes/thiazoles xxxvii can be treated with an alkyne in the presence of a suitable catalyst, for example Pd(PPh$_3$)$_4$, CuI, base, such as TEA in a suitable solvent, like DCM, to afford alkynes xli (Method U). Compounds xli can be then reduced to alkyl substituted thiophenes/thiazoles xlii, for example using hydrogenation with Pd/C in a suitable solvent, such as ethanol (Method V)

Scheme 14: General method for introducing carbon functionality to halogenated thiophenes.

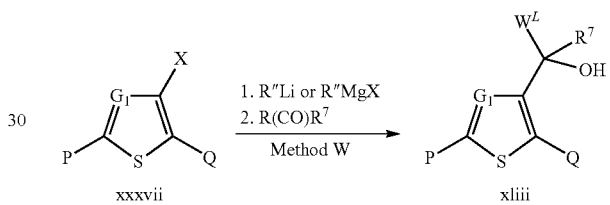

Scheme 14 shows a general method for the synthesis of carbon substituted thiophenes. Halogenated thiophenes xxxvii can be treated with alkyllithium, arryllithium or alkylmagnesium reagents, such as of n-BuLi at low temperature to generate intermediate metallated thiophenes that are subsequently treated with aldehydes or ketones to afford carbinols xliii (Method W).

Scheme 15: General method for introducing carbon functionality to 4-halogenated thiophenes/thiazoles.

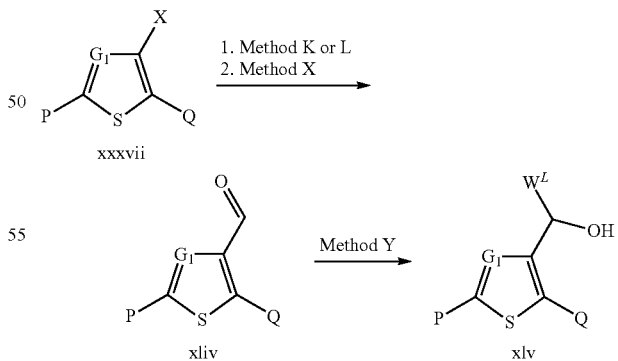

Scheme 15 shows a general method for the synthesis carbon substituted thiophenes/thiazoles. Halogenated thiophenes/thiazoles xxxvii can be treated with vinylorganometallic reagents, for example vinyltributylstannane under Stille conditions (Method K), or vinyltrifluoroborate under Suzuki conditions (Method L) to afford vinyl thiophenes/ thiazoles, that can be oxidized to aldehydes xliv using a suitable method, for example OsO$_4$, sodium periodate in water-dioxane mixture (Method X). Aldehydes xliv can be then treated with organometallic reagents, such as Grignard or alkyl/aryllithium compounds in a suitable solvent, such as THF, at low temperature to afford carbinols of formula xlv (Method Y).

Scheme 16: General method for the synthesis of ethers

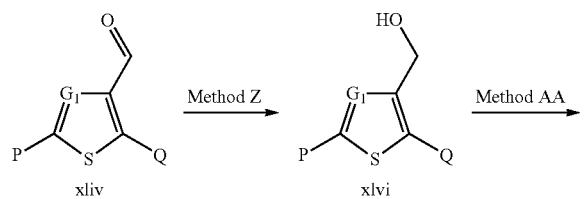

Scheme 16 shows a general method for the synthesis of alcohols xlvi and ethers xlvii. Aldehydes prepared as described in Scheme 15 above can be treated with a suitable reducing agent, such as NaBH$_4$ in an appropriate solvent, for example THF, to afford alcohols of formula xlvi (Method Z). Alcohols xlvi can be then alkylated using standard conditions, for example with alkyl halides in the presence of base, such as K$_2$CO$_3$, in THF to afford ethers xlvii (Method AA).

Scheme 17: General method for the synthesis of amines

Scheme 17 shows a general method for the synthesis of amines xlviii. As shown is Scheme 17, alcohols can be activated via sulfonyl esters, for example by reaction with methanesulfonic chloride and a base, such as pyridine in a suitable solvent, for example DCM. Sulfonyl esters are then treated with amines at elevated temperature to provide target amines xlviii (Method AB).

Scheme 18: General method for the synthesis of ethers

Scheme 18 shows a general method for the synthesis of ethers il when W$^L$ is an aromatic or heteroaromatic group. As shown is Scheme 18, alcohols xlv are treated with an excess of alcohol, such as methanol, in the presence of an acid, like aqueous HCl with an optional co-solvent, for example dioxane at ambient temperature to afford ethers of formula il.

Scheme 19: General method for introducing sulfur functionality

As shown in Scheme 19, sulfur functionality can be introduced to the 4-halogenated thiazoles/thiophenes xxxvii by a similar manner as described by Rossignol et al, US2009036467. Treatment of xxxvii with thiols in the presence of a copper catalyst, like CuI in a suitable solvent, such as DMF, with an appropriate base, for example sodium hydroxide, at elevated temperature gives thioethers of formula l (Method AD). Thioethers 1 can subsequently be oxidized to sulfones li using a suitable oxidating agent, for example mCPBA in DCM (Method AE).

Scheme 20: General method for Pd-catalyzed amination/amidation of 4-halogenated thiophenes/thiazoles

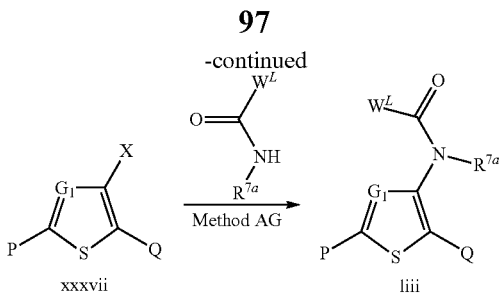

As shown in Scheme 20, amine or amide functionality can be introduced by the well known palladium catalyzed amination/amidation reaction, so called Buchwald coupling, to the 4-halogenated thiophenes/thiazoles xxxvii.

For example, halides xxxvii can be treated with amines using an appropriate Pd catalyst, such as $Pd_2dba_3$/BINAP, with a suitable solvent/base combination, for example NaOtBu in toluene at elevated temperature or using microwave irradiation to afford amines of formula lii (Method AF).

Coupling with amides also can be carried out using a suitable Pd catalyst, for example $Pd_2dba_3$/XantPhos, with a suitable solvent/base combination, like $Cs_2CO_3$ in dioxane at elevated temperature or using microwave irradiation to give amides of formula liii (Method AG).

Scheme 21: General method for the functionalization of 4-hydroxyl group of thiophene/thiazole derivatives

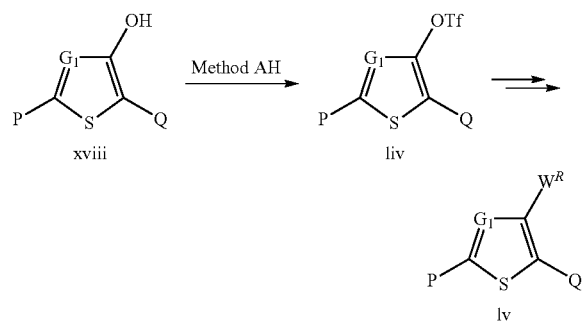

As shown in Scheme 21, 4-hydroxythiazoles or thiophenes xviii can be transformed to various functionalized thiazole/thiophene derivatives via triflate liv.

For example, compounds xviii can be transformed into triflates liv, using, e.g., triflic anhydride, with pyridine as base in DCM (Method U). Triflates liv can be then subjected to coupling reactions with amines, boronic esters, stannanes, or thiols under similar conditions as described for analogous halides in Schemes 11-14 (analogous literature examples include Rzasa, R. et al, Bioorg. Med. Chem. 2007, 15, 6574; Langille, N. F., Org. Lett. 2002, 4, 2485.) to afford compounds of formula lv.

Scheme 22: General method for halogenation of 3-position onto thiophene/thiazoles.

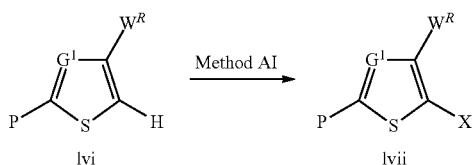

Scheme 22 shows a general route for introducing halogen functionality onto unsubstituted 5-position of thiophene/thiazole core scaffold.

Halogenation of 5-unsubstituted thiazoles/thiophenes can be achieved in a similar manner as reported in the literature (Haelmmerle et al, Synlett 2007, 2975). For example, lvi is treated with a generally known halogenating reagent such as bromine or N-bromosuccinimide in a suitable solvent, such as DCM to afford compounds of formula lvii (Method AI).

The resulting halogenated thiophenes/thiazoles lvii can be used for the further functional group transformation reaction such as described in scheme 11-15.

Scheme 23: General route for the synthesis of carboxamides

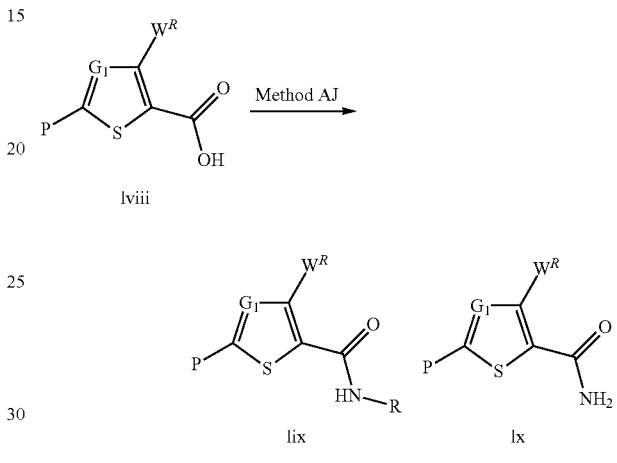

Scheme 23 shows a general route for preparing amide compounds of formula lix. As shown in Scheme 23, acids lviii may be treated with amines using standard coupling conditions, such as EDCI and HOBt in DCM to afford amides lix (Method AJ).

When ammonia is used as an amine source, primary amide derivatives lx may be obtained, which can be used as intermediates for the construction of azoles as described in Schemes 25, 26, 28 and 37.

Scheme 24: General route for the synthesis of 5-halogenated thiophenes/thiazoles by Hunsdiecker reaction

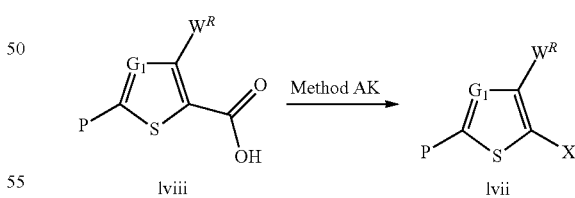

As shown Scheme 24, 5-halogenated thiophenes/thiazoles lvii can be prepared by the Hunsdiecker reaction from thiophene/thiazole carboxylic acid analogs lviii.

As shown in Scheme 24, acids xlviii may be treated with sliver hydroxide to form a silver salt, which is subsequently treated with halogen, for example bromine, in a suitable solvent, such as $CCl_4$ at elevated temperature to form lvii (Method AK).

Scheme 25: General route for the synthesis of 5-cyano thiophenes/thiazoles

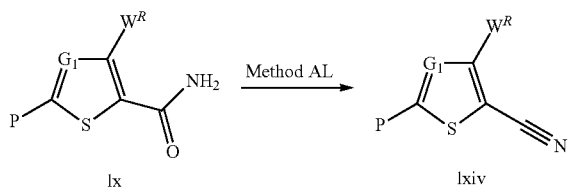

As shown in scheme 25, amides lx, which can be prepared by the procedure described in scheme 23, are treated with phosphoryl chloride, or similar reagents to form 5-cyano thiophenes/thiazoles of formula lxiv (Method AL).

Scheme 26: General route for the synthesis of thioamides

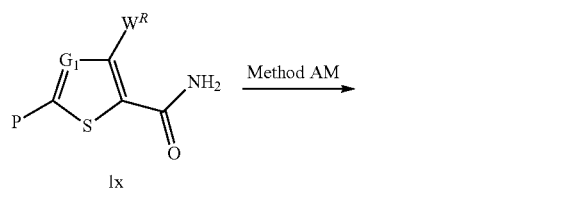

As shown in scheme 26, amides lx, which can be prepared by the procedure described in scheme 23, are treated with a suitable reagent, for example Lawesson's reagent, or $P_2S_5$ in a suitable solvent, such as toluene at elevated temperature to afford thioamides of formula lxv (Method AM).

Scheme 27: Alternative route for the synthesis of thioamides

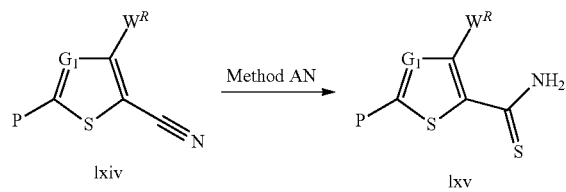

As shown in scheme 27, 5-cyano thiazoles/thiophenes lxiv, which can be prepared by the procedure described in scheme 25, are treated with a suitable reagent, for example ammonium sulfide in a suitable solvent, such as methanol to afford thioamides of formula lxv (method AN).

In the schemes 28-46, general procedures for the construction of the representative azoles as $R^1$ are described.

Schemes 28-30 describe the formation of 1,2,4-triazolyl group as $R^1$.

Scheme 28: General route for the construction of 1,2,4-triazolyl

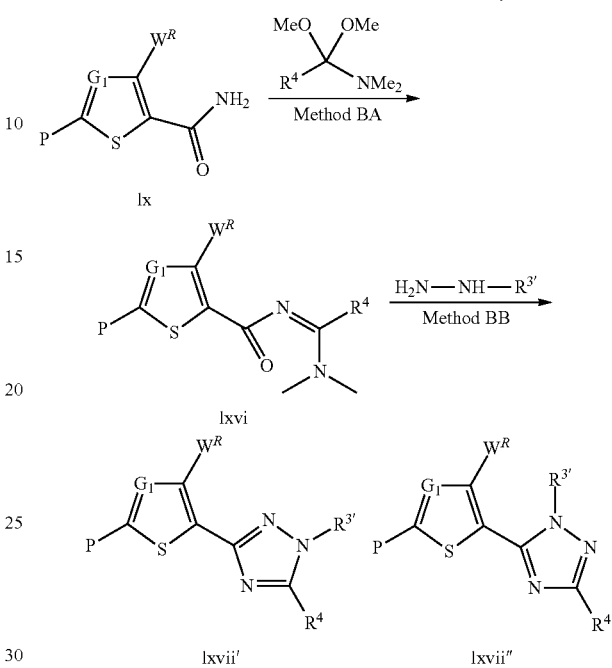

As shown in Scheme 28, amides lx, which can be prepared by the procedure described in scheme 23, can be treated with DMF-DMA at elevated temperature or under microwave irradiation (Method BA) to give intermediate amidines lxvi that are transformed to 1,2,4-triazoles lxvii' and lxvii" using hydrazine or substituted hydrazines in acetic acid at elevated temperature or under microwave irradiation (Method BB).

Scheme 29: General route for the construction of 5-halogenated 1,2,4-triazolyl

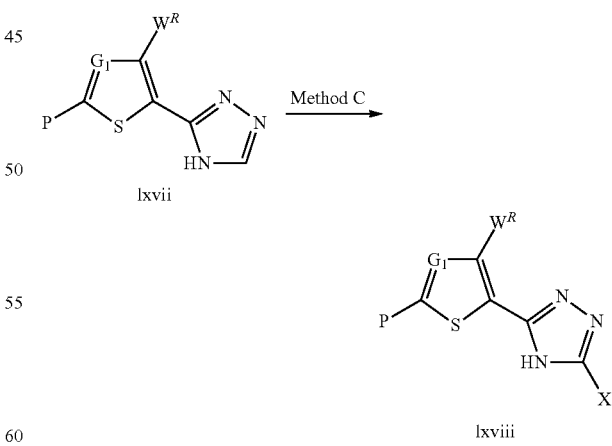

As shown in Scheme 29, 1,2,4-triazoles lxvii, which can be prepared by the procedure described in scheme 28, are treated with a suitable halogenating agent, like NBS, in a suitable solvent, for example tetrachloromethane, to afford compounds of formula lxviii (Method C).

Scheme 30: General route for the construction of 5-amino-1,2,4-triazolyl

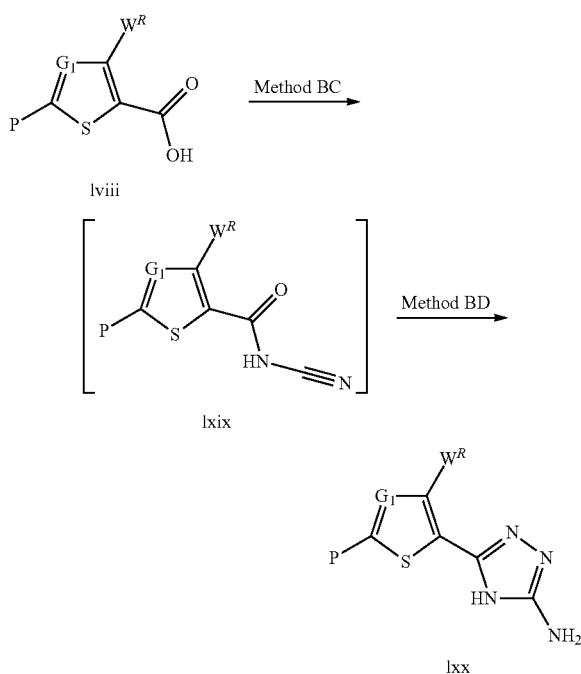

As shown in Scheme 30, acids lviii may be coupled with cyanamide, for example via an intermediate acid halide in a suitable solvent, such as DCM to acylcyanamides lxix (Method BC), that are in turn treated with hydrazine using appropriate conditions, for example acetic acid at elevated temperature to give compounds of formula lxx (Method BD).

Scheme 31-39 describes the formation of 2-imidazolyl group as $R^1$.

Scheme 31: General route for the construction of 2-imidazolyl

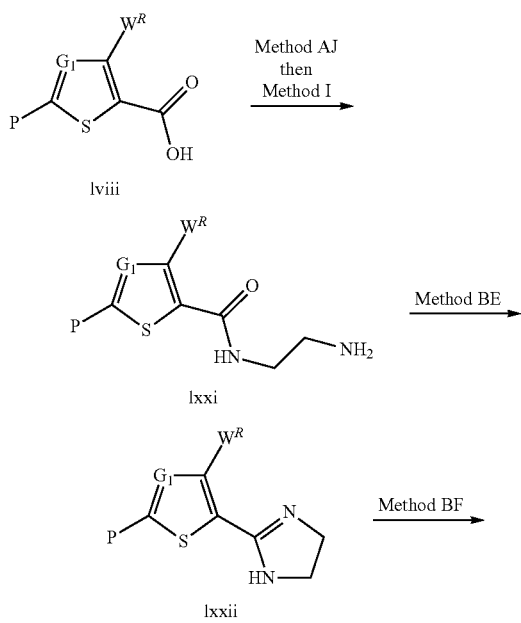

As shown in Scheme 31, acids lviii are treated with Boc protected ethylenediamine using standard coupling conditions, such as EDCI and HOBt in DCM (Method AJ). Protective group is removed using an appropriate acid, for example TFA in DCM to give amide lxxi (Method I). Cyclization of lxxi is achieved using suitable conditions, for example POCl₃ (Method BE) to form dihydroimidazoles lxxii. Dihydroimidazoles lxxii can be oxidized to imidazoles lxxiii using a suitable oxidative method, for example heating with Magtrieve (Method BF).

Scheme 32: Alternative route for the construction of 2-imidazolyl

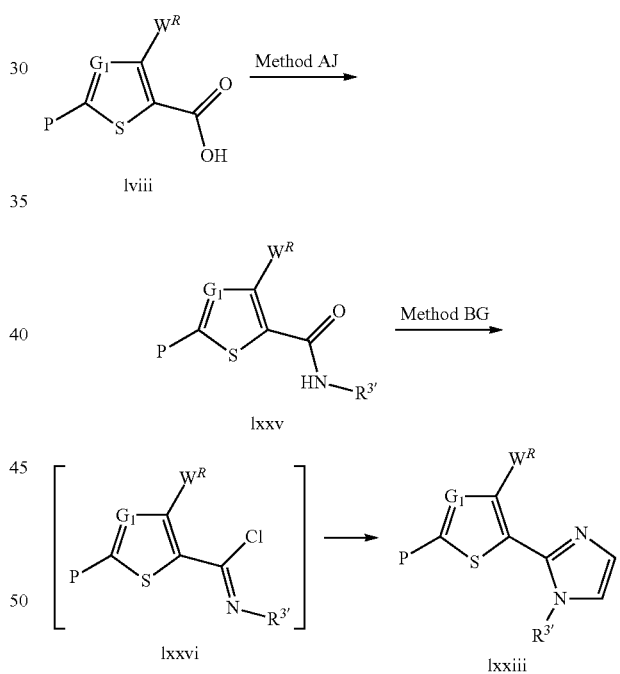

Scheme 32 above shows an alternative route for preparing imidazoles of formula lxxiii. As shown in Scheme 32, acids lviii are treated with amines using standard coupling conditions, such as EDCI and HOBt in DCM to afford amides lxxv (Method AJ). Cyclization to imidazoles may be achieved through a 3-step one pot process that involves treatment with phosphorus pentachloride and HCl in dioxane to afford carbimidoyl chloride intermediates lxxvi, that can be then treated with aminoacetaldehyde dimethylacetal followed by HCl in dioxane at elevated temperature to give lxxiii (Method BG). When $R^{3'}$=allyl, benzyl or substituted benzyl, it can also serve as a protecting group.

Scheme 33: Alternative route for the synthesis of 2-imidazolyl

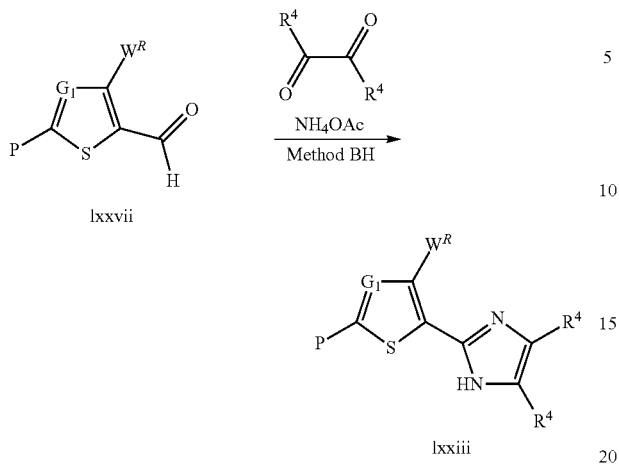

lxxvii lxxiii

As shown in scheme 33, aldehydes lxxvii may be condensed with dicarbonyl compounds, such as diketones, ketoaldehydes, or glyoxal with an appropriate ammonia source, such as ammonium acetate, with suitable acid, such as acetic acid in solvent such as methanol to form imidazoles lxxiii (Method BH).

Scheme 34: Alternative method for the construction of substituted 2-imidazolyl.

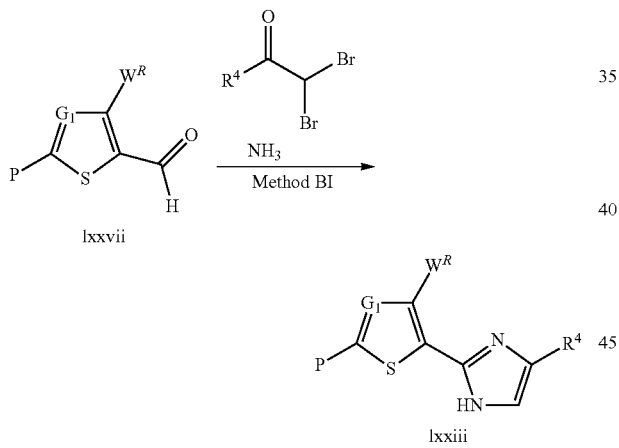

lxxvii lxxiii

As shown in scheme 34, aldehydes of formula lxxvii can be treated with alpha, alpha-dihalo-ketones under suitable conditions, such as ammonium hydroxide, sodium acetate in an appropriate solvent, for example methanol and water to afford imidazoles of formula lxxiii (Method BI).

Scheme 35: Alternative method for the construction of substituted 2-imidazolyl.

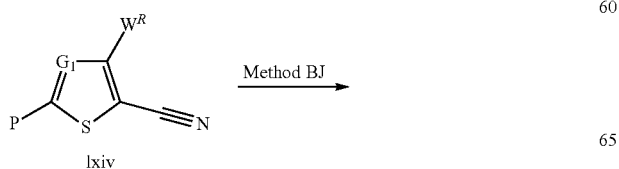

lxiv

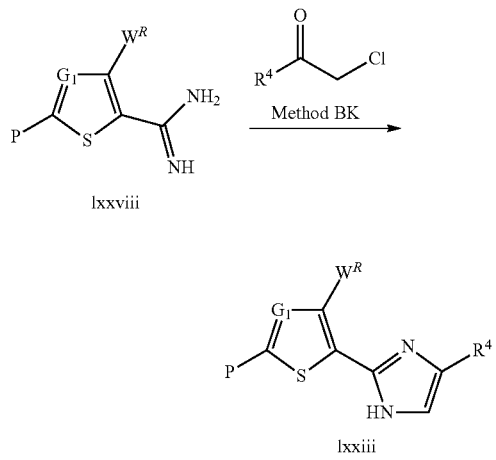

lxxviii lxxiii

As shown in scheme 35, treatment of nitriles lxiv, which can be prepared by the procedure described in scheme 25, with LiHMDS in a suitable solvent mixture, such as THF/ether/hexane gives amidines of formula lxxviii (Method BJ) that can be treated with haloketones in the presence of a suitable base, such as potassium carbonate in an appropriate solvent, such as DCM under elevated temperature to give imidazoles of general formula lxxiii (Method BK).

Scheme 36: Alternative method for the construction of substituted 2-imidazolyl.

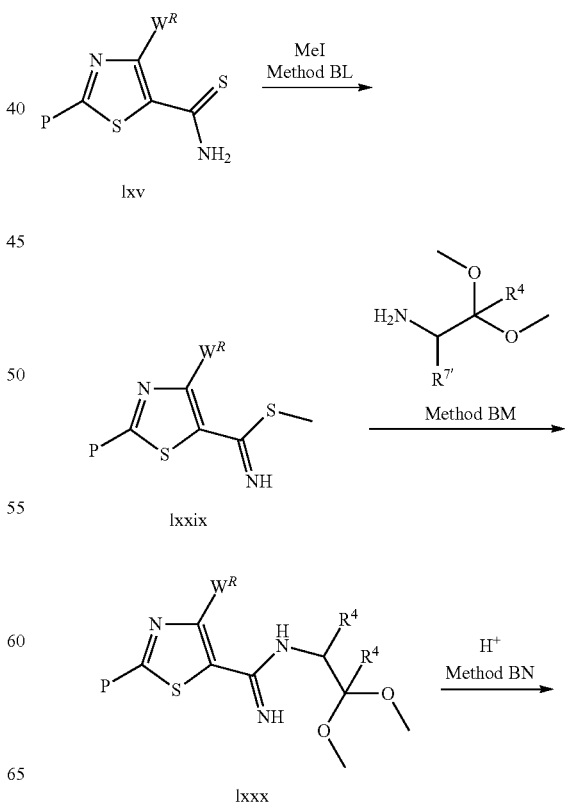

lxv lxxix lxxx

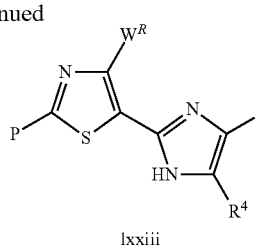

lxxiii

As shown in scheme 36, treatment of thioamides lxv, which can be prepared by the procedure described in scheme 26 or 27, with methyl iodide affords imidothioate intermediates lxxix (Method BL), which may then be treated with optionally substituted aminoacetaldehyde dimethyl acetal in a suitable solvent, like acetic acid, at elevated temperature to afford intermediate amidines lxxx (Method BM). Amidines lxxx can then be treated with an acid, such as aqueous HCl and a suitable co-solvent, like ethanol, at elevated temperature to give imidazoles of formula lxxiii (Method BN).

Scheme 37: Alternative method for the construction of substituted 2-imidazolyl.

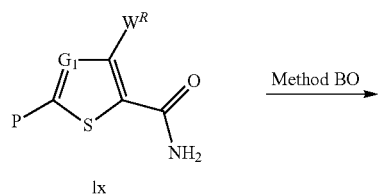

lx

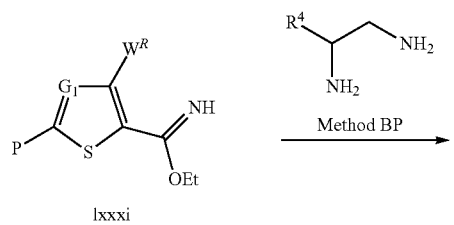

lxxxi

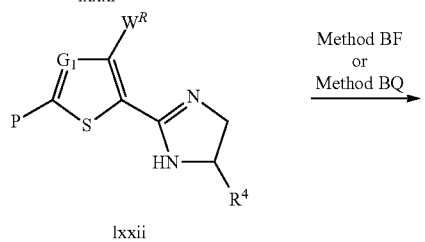

lxxii

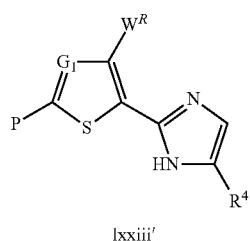

lxxiii'

As shown in scheme 37, treatment of amides lx, which can be prepared by the procedure described in scheme 23, with an alkylating agent, such as Meerwein's reagent, in DCM (Method BO) gives iminoesters lxxxi, which can be then treated with diamines using appropriate conditions, for example ethanol at elevated temperature (Method BP) to forme dihydroimidazoles lxxii, which can be then oxidized in a same manner as in Method BF described in Scheme 31, or when $R^4$ is an appropriate leaving group, elimination can be carried out using a base, such as DBU in DCM (Method BQ).

Scheme 38: General route for the construction of substituted 4 (5)-imidazolyl.

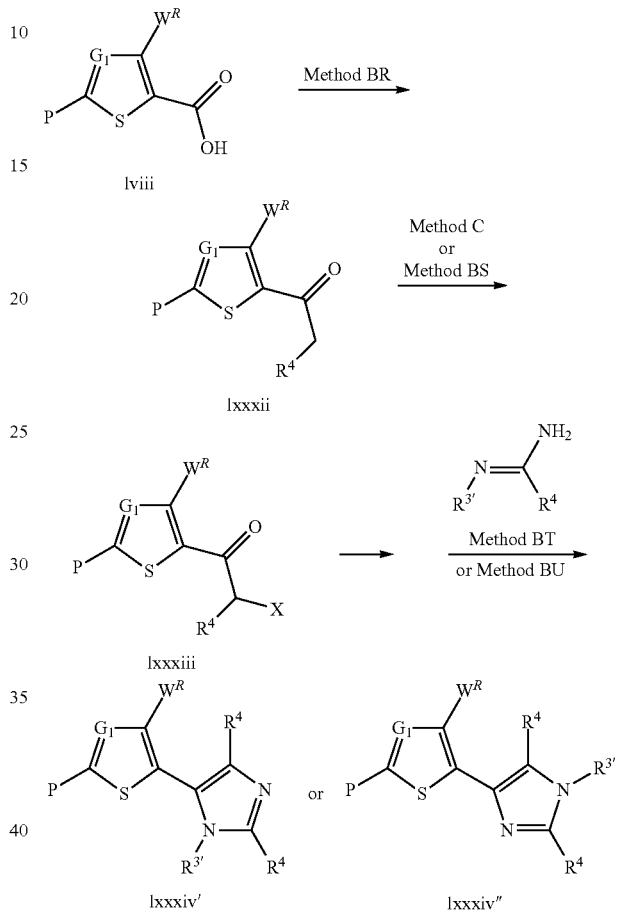

As shown in Scheme 38, acids lviii may be transformed to ketones lxxxii using a suitable synthetic sequence, for example through a coupling with N,O-dimethylhydroxylamine and subsequent treatment of the resulting Weinreb amides with alkyllithium or Grignard reagents in a suitable solvent, like THF (Method BR).

Ketones lxxxii are then halogenated with a suitable reagent, such as bromine or NBS in an appropriate solvent, like DCM (Method C) to form alpha-halogenated ketones lxxxiii (X=halogen). Alternatively, treatment of ketones lxxxii with a suitable oxidative sulfonylating agent, like hydroxy(tosyloxy)iodobenzene using suitable conditions, for example heating in acetonitrile (Method AS) affords sulfonyl esters of formula lxxxiii (X=OSO$_2$R).

Treatment of lxxxiii with amidine reagents in the presence of a suitable base, like potassium carbonate in a suitable solvent, such as THF-water mixture at elevated temperature or microwave irradiation affords the final imidazoles lxxxiv' and lxxxiv" (Method BT). Alternatively, compounds lxxxiii can be treated with large excess of amides, such as formamide using microwave irradiation to afford imidazoles lxxxiv' and lxxxiv" (Method BU).

Scheme 39: Alternative method for the construction of substituted 4 (5)-imidazolyl.

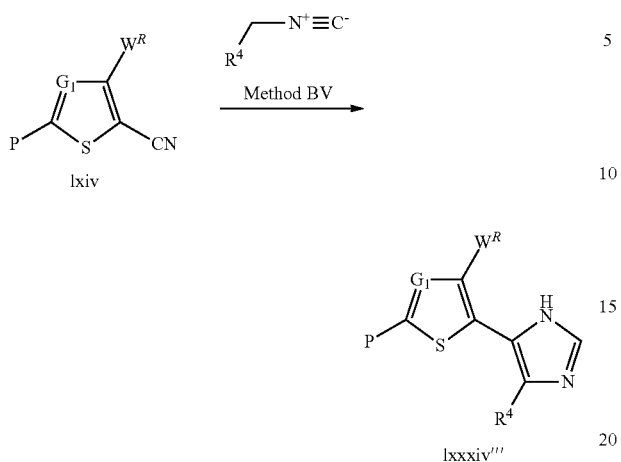

As shown in scheme 39, treatment of nitriles lxiv, which can be prepared by the procedure described in scheme 25, with isocyanates in the presence of a suitable base, such as tOBuK, in a suitable solvent, for example THF gives imidazoles of formula lxxxiv'''. (Method BV).

Scheme 40: Alternative method for the construction of 4-imidazolyl.

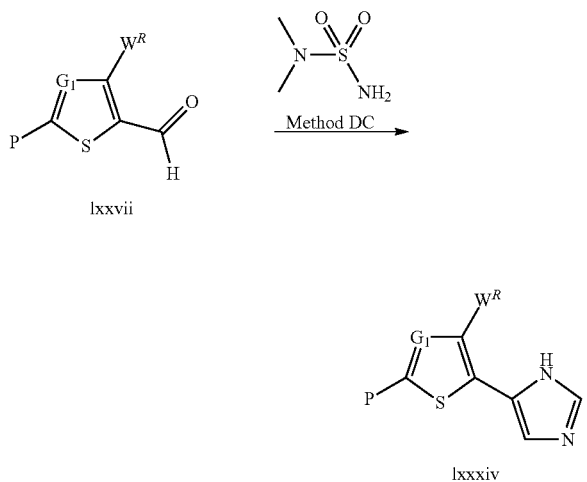

As shown in scheme 40, treatment of aldehydes lxxvii with N,N-dimethylsulfonamide at elevated temperature in a suitable solvent, for example toluene, to allow azeotropic removal of water can afford intermediate imines, that are treated with TOSMIC, a suitable base, like potassium carbonate in a suitable solvent, such as DME at elevated temperature to afford intermediate imidazole sulfonamides, that can be hydrolyzed to imidazoles lxxxiv with an acid, for example aqueous HBr at elevated temperature (Method DC).

Schemes 41 and 42 describe the procedures for introducing a pyrazolyl group.

Scheme 41: General route for the construction of 3 (5)-pyrazolyl.

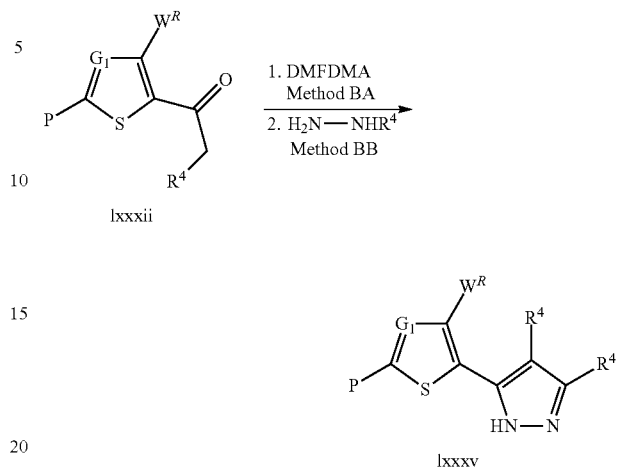

As shown in Scheme 41, ketones lxxxii, which can be prepared by the procedure described in scheme 38, are treated with DMF-DMA to afford an intermediate enamines (Method BA) followed by reaction with substituted hydrazine, or hydrazine hydrate in a suitable solvent, for example acetic acid, to give pyrazoles lxxxv (Method BB).

Scheme 42: General route for the introduction of heteroaromatic group.

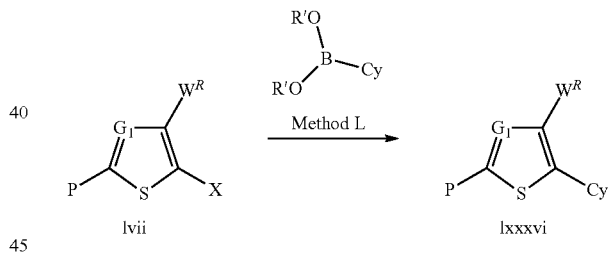

As shown in Scheme 42, halides lvii, which can be prepared by the procedure described in scheme 24, are treated with heteroaryl boronic acids or esters, in the presence of a suitable catalyst, for example Pd(PPh$_3$)$_4$, using a base, such as cesium carbonate in a suitable solvent, like dioxane-water mixture at elevated temperature to afford compounds of formula lxxxvi (Method L).

Scheme 43: General route for the construction of 1,2,3-triazolyl.

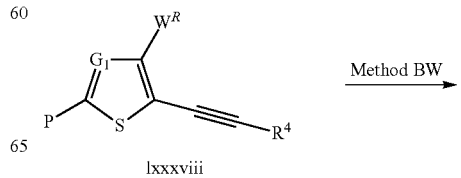

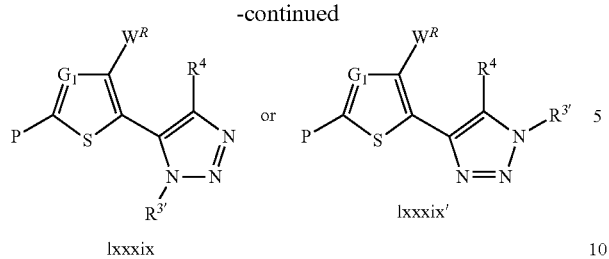

As shown in Scheme 43, alkynes lxxxviii, which can be prepared by the known Stille- or Sonogashira-coupling reaction in which a halide lvii, which can be prepared by the procedure described in scheme 24, and an appropriate alkyne derivative may be treated with azides, inorganic or organic a suitable solvent, such as dioxane, at elevated temperature to afford triazoles of formula lxxxix and lxxxix' (Method BW).

Scheme 44: General route for the construction of tetrazolyl.

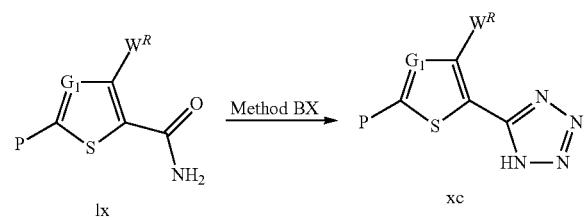

As shown in Scheme 44, amides lx, which can be prepared by the procedure described in scheme 23, may be treated with an azide source, for example sodium azide using a suitable Lewis acid, for example silicon tetrachloride in an appropriate solvent, such as acetonitrile to give tetrazoles xc (Method BX).

Scheme 45: General route for the construction of 2-thiazolyl.

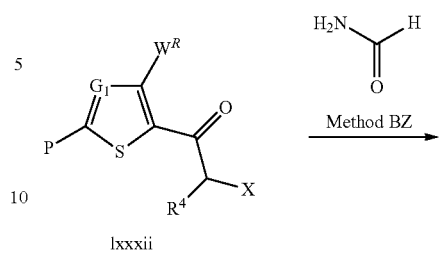

As shown in scheme 45, thioamides lxv, which can be prepared by the procedure described in scheme 26 or 27, are treated with substituted bromoacetaldehyde dimethyl acetals to afford thiazoles of formula xci (Method BY).

Scheme 46: General route for the construction of 4-oxazolyl

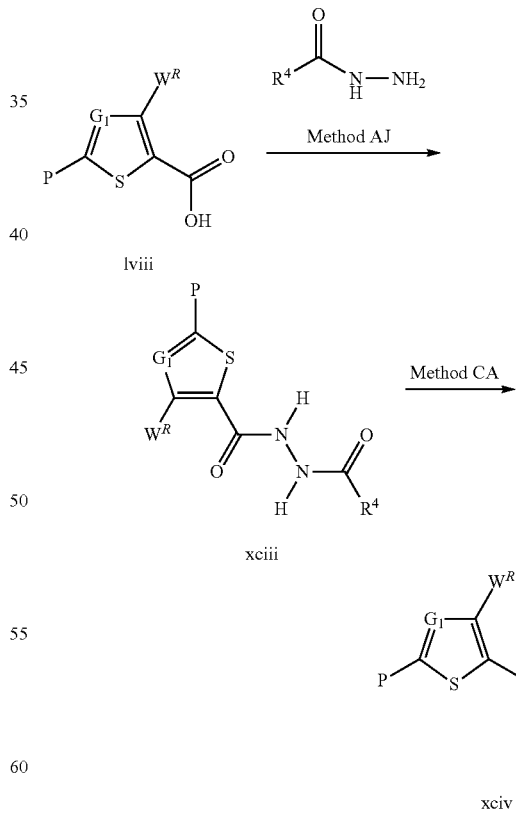

As shown in scheme 46, alpha-halogenated ketones lxxxiii, which can be prepared by the procedure described in scheme 38, may be treated with formamide under elevated temperature or microwave irradiation to afford the final 4-oxazoles xcii (Method BZ).

Scheme 47: General route for the construction of 1,3,4-thiadiazolyl

As shown in scheme 47, acids lviii are coupled with acyl-hydrazines using standard coupling conditions, such as EDCI, HOBt, DMF at elevated temperature to afford intermediates xciii (Method AJ), that are treated with Lawesson's reagent using suitable conditions, for example in toluene under reflux to afford thiadiazoles xciv (Method CA).

Scheme 48-51 describe general procedure for the functional group transformation on HY.

Scheme 48: General method for the introduction of amino group to 2-fluoropyridyl

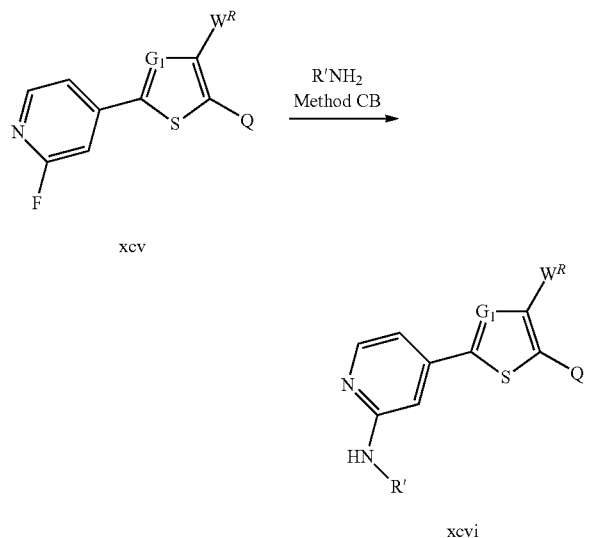

xcv xcvi

Scheme 48 shows a general route for the transformation of 2-fluoropyridyl to 2-substituted aminopyridyl to give the compounds of formula xcvi.

As shown in Scheme 48, compounds xcv can be treated with amines at elevated temperature or under microwave irradiation to give 2-aminopyridines xcvi (Method CB).

Scheme 49: General method for the introduction of 2-acylaminopyridines by Buchwald reaction

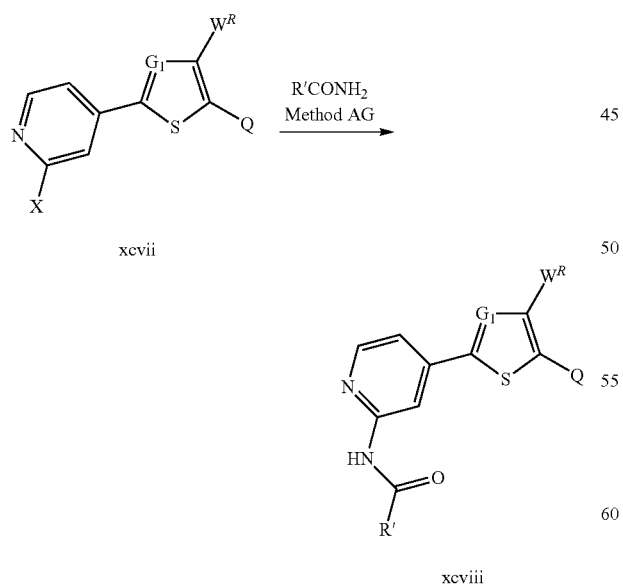

xcvii xcviii

Scheme 49 shows a general route for the transformation of 2-halopyridyl to 2-acylaminopyridyl by Buchwald reaction to give the compounds formula xcviii.

As shown in Scheme 49, compounds xcvii can be treated with amides or carboxamides in the presence of a suitable catalyst, such as $Pd_2dba_3$, XantPhos, base like cesium carbonate in an appropriate solvent, for example dioxane at elevated temperature or under microwave irradiation to give acylaminopyridines xcviii (Method AG).

Scheme 50: General method for the synthesis of 2-aminopyrimidyl thiophene/thiazole

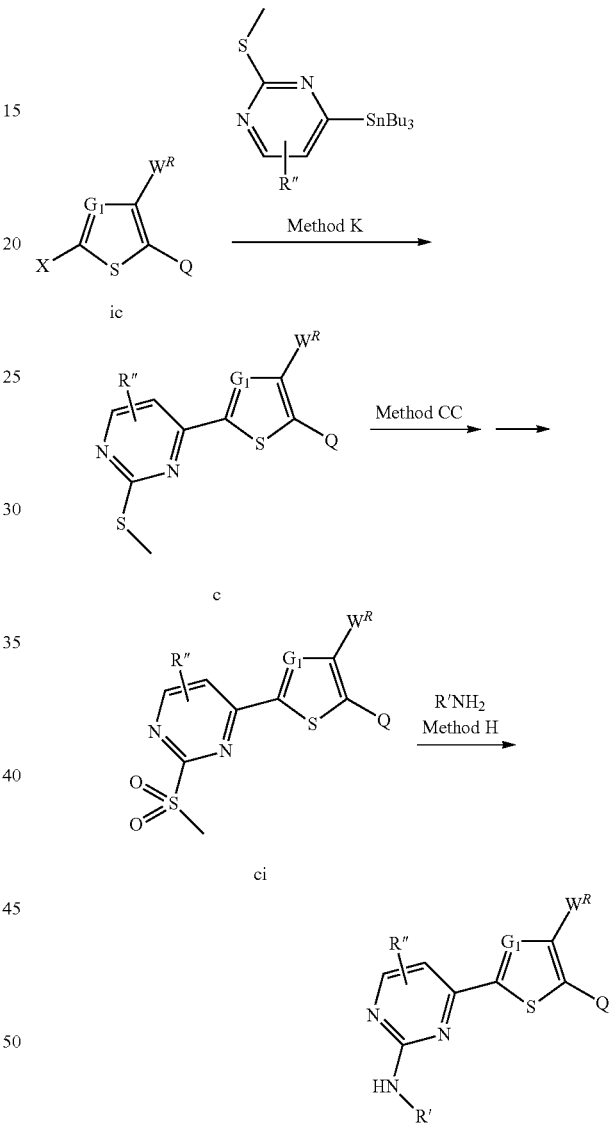

ic c ci cii

As shown in Scheme 50, compounds is can be coupled with stannanes under suitable conditions, for example $Pd(PPh_3)_4$, CuI, LiCl in dioxane at elevated temperature to give compounds c (Method K).

Oxidation of thioethers c to sulfones ci can be achieved using a suitable oxidant, for example mCPBA in DCM (Method CC).

Methanesulfonyl group of sulfones ci can be displaced by treatment with amines in a suitable solvent, for example THF to afford 2-aminopyrimidines cii (method H).

Scheme 51: General method for the introduction of 2-halo substituent on 4-pyridyl group

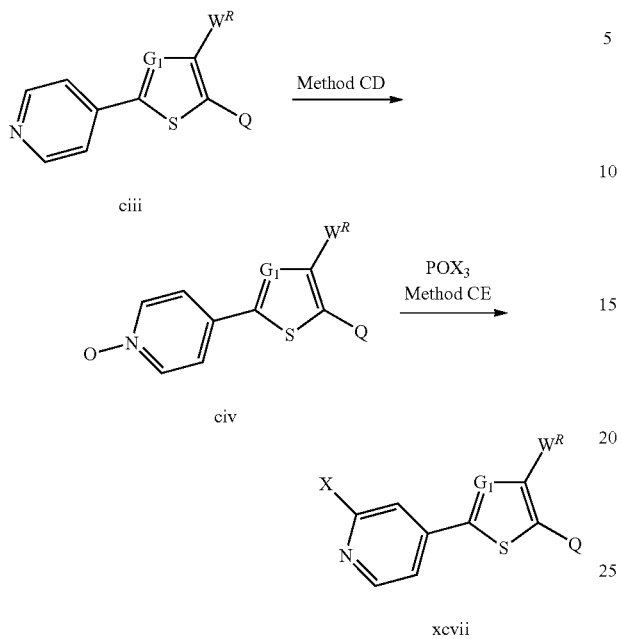

Schemes 52-58 describe the procedures for the synthesis of building blocks for HY.

Scheme 51 shows a general route for the transformation of 4-pyridyl to 2-halo-4-pyridyl compounds formula xcvii. As shown in Scheme 51, compounds ciii can be treated with an oxidant, for example mCPBA in a suitable solvent, such as DCM to afford intermediate N-oxides civ (Method CD), which may be halogenated in 2-position using phosphoryl halides, for example phosphoryl chloride, under elevated temperature to afford compounds of formula xcvii (Method CE).

Schemes 52-58 describe the procedures for the synthesis of building blocks for HY.

Scheme 52: General method for the synthesis of imidazo[1,2-a]pyridine building blocks.

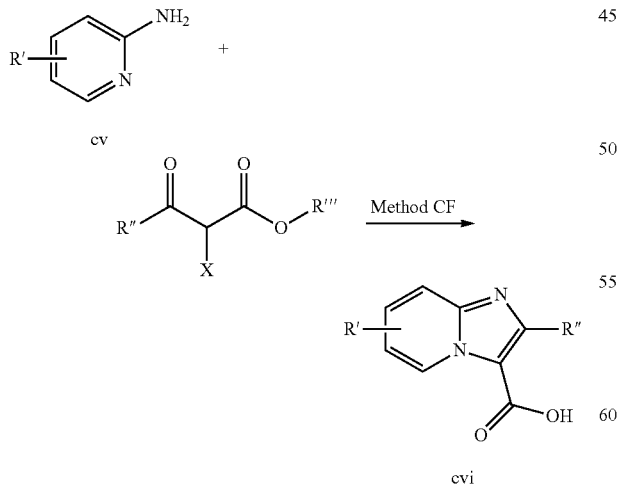

Scheme 52 shows a general method for the synthesis of imidazo[1,2-a]pyridines cvi. As shown in Scheme 52, 2-aminopyridines cv may be condensed with alpha-halogenated beta-ketoesters in a suitable solvent, for example ethanol, at elevated temperature to afford intermediate esters, that are hydrolyzed using standard conditions, such as aqueous sodium hydroxide in THF followed by acidic workup to give acids cvi (Method CF).

Scheme 53: General method for the synthesis of imidazo[1,2-b]pyridine building blocks

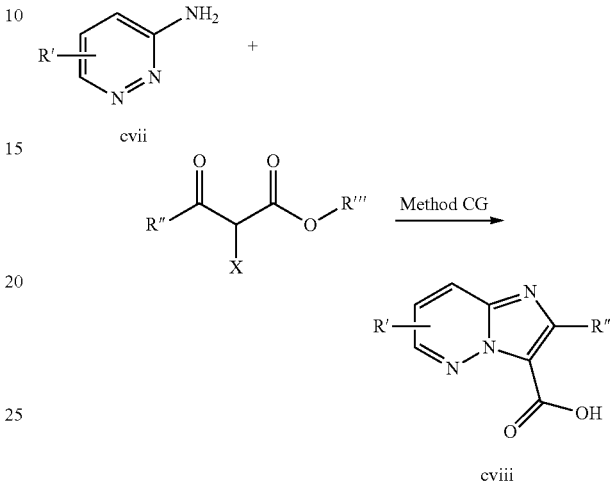

Scheme 53 shows a general method for the synthesis of imidazo[1,2-b]pyridazines cviii. As shown in Scheme 53, 2-aminopyridazines cvii may be condensed with α-halogenated beta-ketoesters in a suitable solvent, for example ethanol at elevated temperature to afford intermediate esters, that are hydrolyzed using standard conditions, such as aqueous sodium hydroxide in THF followed by acidic workup to give acids cviii (Method CG).

Scheme 54: General method for the synthesis of imidazol[2,1-b][1,3]thiazole building blocks

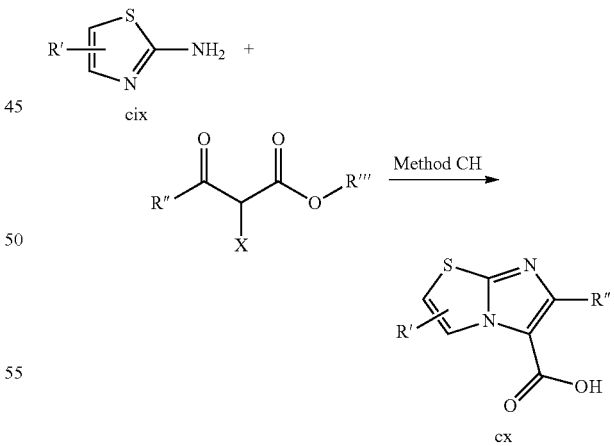

Scheme 54 shows a general method for the synthesis of imidazo[2,1-b][1,3]thiazoles cx. As shown in Scheme 54, 2-aminothiazoles cix may be condensed with α-halogenated β-ketoesters in a suitable solvent, for example ethanol, at elevated temperature to afford intermediate esters, which may be hydrolyzed using standard conditions, such as aqueous sodium hydroxide in THF followed by acidic workup to give acids cx (Method CH).

115

Scheme 55: General method for the synthesis of pyrazolo[1,5-a]pyridine building blocks

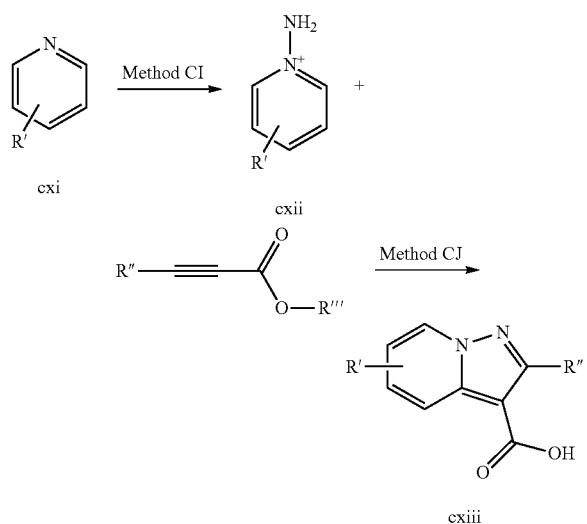

Scheme 55 shows a general method for the synthesis of pyrazolo[1,5-a]pyridines cxiii. As shown in Scheme 55, pyridines cxi may be N-aminated with a suitable agent, such as O-(mesitylsulfonyl)hydroxylamine using appropriate conditions, for example toluene or ethyl acetate as solvent (Method CI).
Resulting N-aminopyridinium salts cxii may then be condensed with alkynylcarboxylic acid esters with a suitable base, such as potassium carbonate in a suitable solvent, for example DMF to afford intermediate esters, which may be hydrolyzed using standard conditions, such as aqueous sodium hydroxide in THF followed by acidic workup to give acids cxiii (Method CJ).

Scheme 56: General method for the synthesis of pyrazolo[5,1-b][1,3]thiazole building blocks

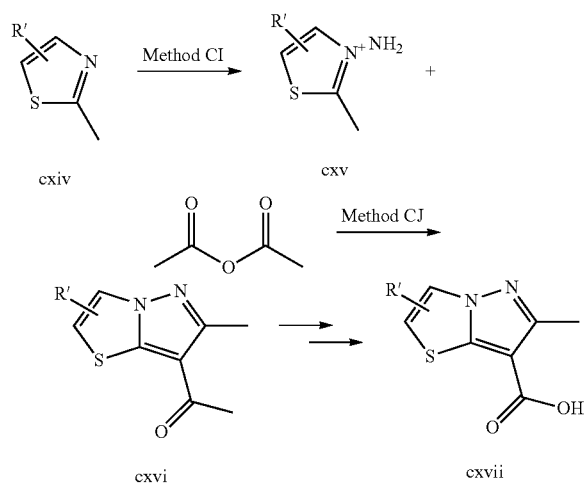

Scheme 56 shows a general method for the synthesis of pyrazolo[5,1-b][1,3]thiazoles cxvii. As shown in Scheme 56, 2-methylthiazoles cxiv may be N-aminated with a suitable agent, such as O-(mesitylsulfonyl)hydroxylamine using appropriate conditions, for example toluene or ethyl acetate as solvent (Method CI).

116

Resulting N-aminothiazolium salts cxv can then be condensed with acetic anhydride and potassium acetate at elevated temperature to afford methyl ketone intermediate cxvi (Method CJ), which can be converted to carboxylic acid cxvii moiety by well known functional transformation of methyl ketone to carboxylic acid.

Scheme 57: Alternative method for the synthesis of pyrazolo[5,1-b][1,3]thiazole derivatives

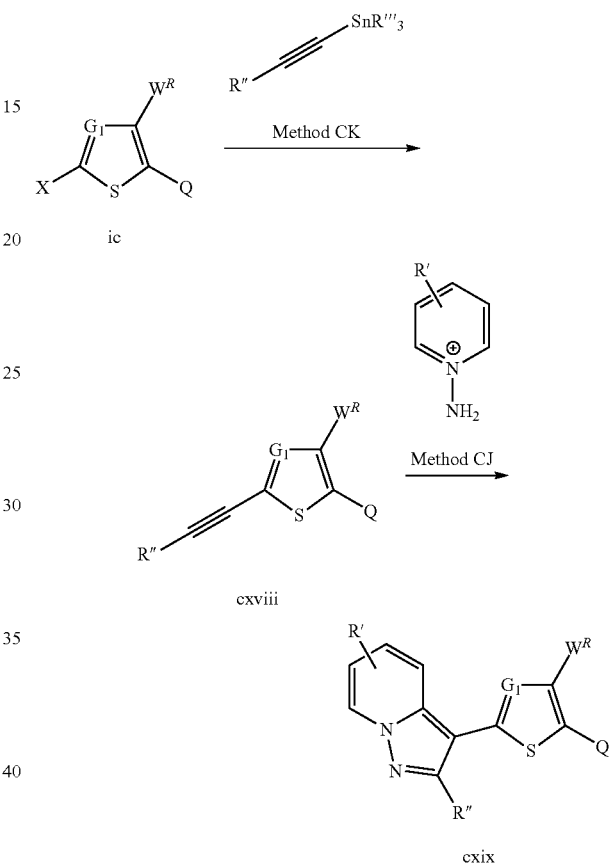

Scheme 57 shows an alternative method for the synthesis of pyrazolopyridines cxix. As shown in Scheme 57, halides is are treated with alkynyl stannanes in the presence of a suitable catalysts, such as $Pd(PPh_3)_4$, CuI, with LiCl in an appropriate solvent, like dioxane at elevated temperature to give alkynes of formula cxviii (Method CK). Alkynes cxviii are then coupled with N-aminopyridinium salts with a base, like potassium carbonate in a suitable solvent, for example DMF to afford compounds of formula cxix (Method CJ).

Scheme 58: Alternative method for the synthesis of imidazo[1,2-a]pyridine building blocks.

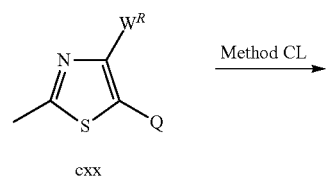

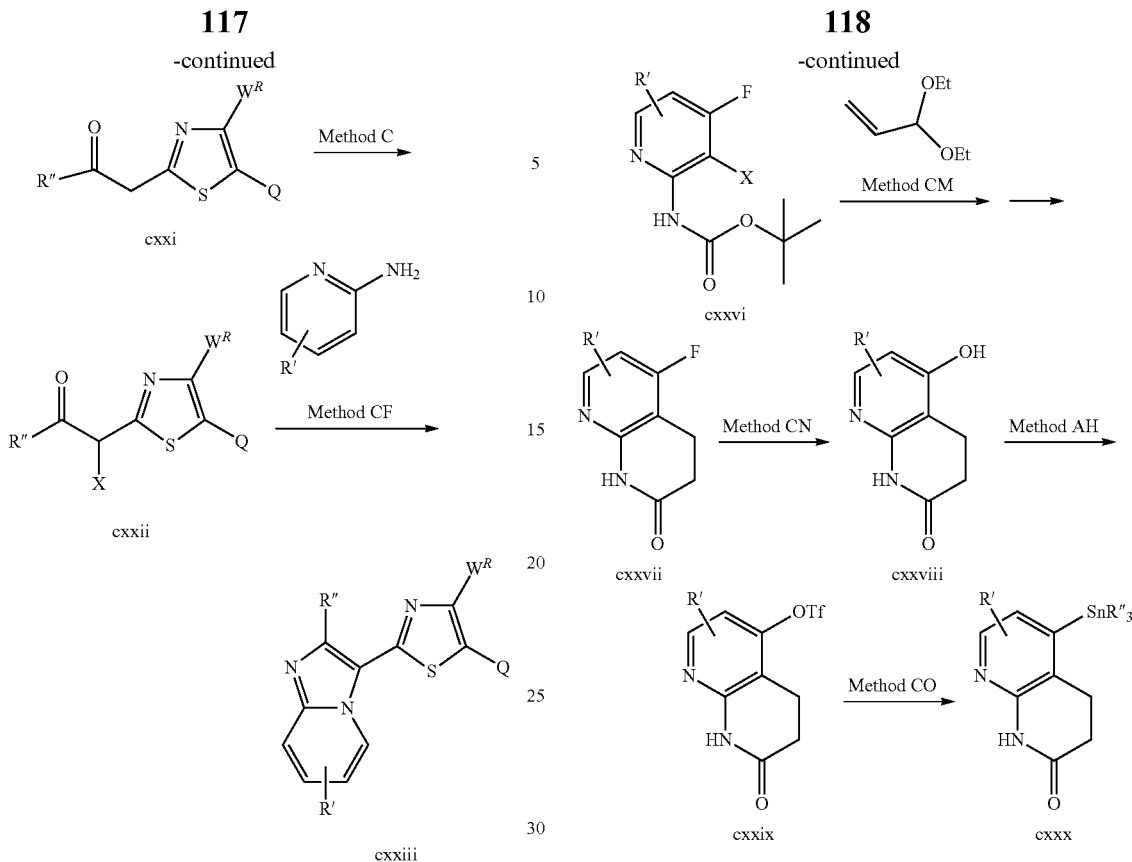

Scheme 58 shows an alternative method for the synthesis of imidazolopyridines cxxiii. As shown in Scheme 58, 2-methylthiazoles cxx may be deprotonated with a suitable reagent, such as n-BuLi and subsequently treated with Weinreb amides in a suitable solvent, such as THF to give ketones cxxi (Method CL). Halogenation of ketones can be achieved using standard conditions, for example NBS in DCM (Method C) and the resulting haloketones cxxii are then treated with aminopyridines in a suitable solvent, for example ethanol at elevated temperature to give compounds of formula cxxiii (Method CF).

Scheme 59: General method for the synthesis of bicyclic lactam building blocks

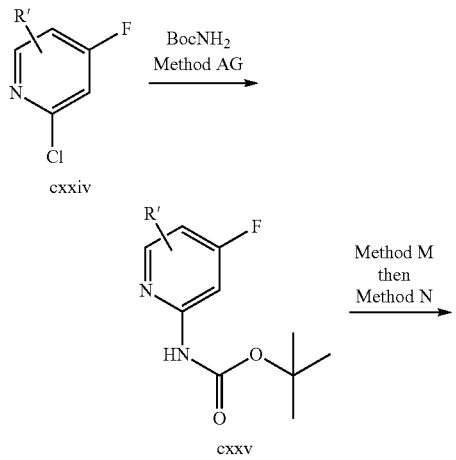

Scheme 59 shows a general method for the synthesis of bicyclic lactam building blocks cxxix and cxxx. As shown in Scheme 59, substituted 2-chloro-4-fluoropyridines can be amidated, for example with $BocNH_2$, $Pd_2dba_3$ and a suitable ligand, such as X-Phos in the presence of a base, for example cesium carbonate in an appropriate solvent, like dioxane to afford Boc-protected 2-aminopyridines cxxv (Method AG). Compounds cxxv can be deprotonated, for example using n-BuLi/TMEDA in THF at low temperature (Method M) and then quenched with a molecule of halogen, such as iodine in THF (Method N) to give halogenated compounds cxxvi. Compounds cxxvi can be coupled with diethoxypropene using a suitable Pd catalyst, such as Di-mu-chlorobis[5-hydroxy-2-[1-(hydroxyimino-kappaN)ethyl]phenyl-kappaC] palladium(II) dimer with an appropriate base, like N,N-diisopropylethylamine in a suitable solvent, for example DMF-water mixture (Method CM) to afford lactams of formula cxxvii. Transformation of fluoro cxxvii into hydroxyl analogs cxxviii can be carried out using a standard procedure, for example treatment with benzyl alcohol in the presence of a base, such as sodium hydride at elevated temperature and subsequent debenzylation, such as using hydrogenation with Pd/C catalyst in a suitable solvent, such as ethanol (Method CN). Triflates cxxix can be formed by treatment of cxxviii with a suitable reagent, for example triflic anhydride using appropriate conditions, such as pyridine as a base in DCM (Method AH). Triflates cxxix can be coupled with stannanes xxix, obtained in Scheme 6 using standard Stille conditions (Method K). Alternatively, triflates cxxix can be transformed into stannanes cxxx using a suitable method, such as heating with hexamethyldistannane, $Pd(PPh_3)_4$ in a suitable solvent, like THF (Method CO). Stannanes cxxx can be then coupled with thiophene/thiazole halides ic, which can be prepared by the procedures described in schemes 3, 5, 6 using standard Stille conditions (Method K).

Scheme 60: Alternative method for the synthesis of bicyclic lactam building blocks

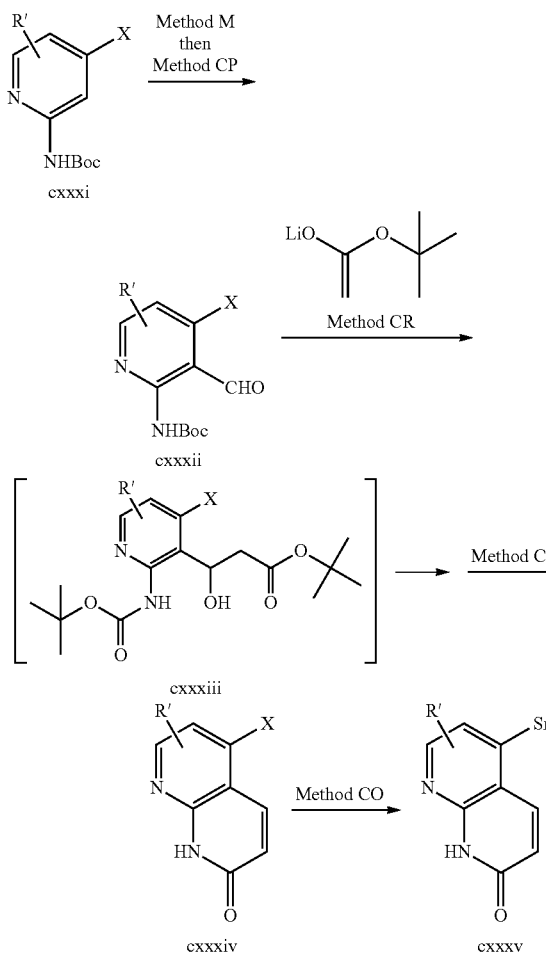

cyclized to lactams cxxxiv using an acid, such as HCl, in water at elevated temperature (Method CS). Halides cxxxiv can be coupled with stannanes xxix, obtained in Scheme 6 using standard Stille conditions (Method K). Alternatively, transformation of aryl halides cxxxiv to stannanes cxxxv can be carried out using hexamethyldistannane, Pd(PPh$_3$)$_4$ in a suitable solvent, like THF (Method CO). Stannanes cxxxv can be then coupled with thiophene/thiazole halides ic, which can be prepared by the procedures described in schemes 3, 5, 6 using standard Stille conditions (Method K).

Scheme 61: General method for the preparation of 2-aminothiazoles

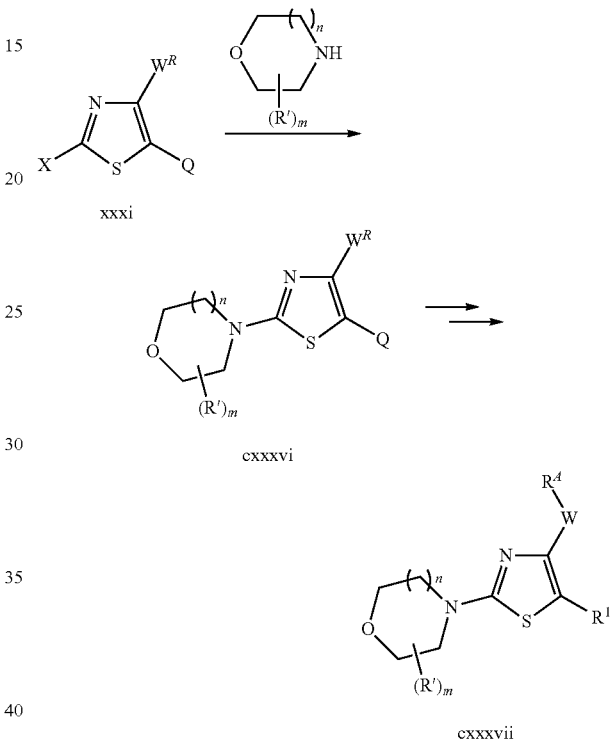

Scheme 60 shows an alternative method for the synthesis of bicyclic lactam building blocks cxxxv. As shown in Scheme 60, compounds cxxxi can be deprotonated with a suitable reagent, such as n-BuLi in THF at low temperature (Method M) and then treated with DMF to produce carbaldehydes cxxxii (Method CP). Aldehyde group in cxxxii can be then treated with enolate generated from t-Butylacetate and LDA in a suitable solvent, such as THF at low temperature (Method CR) to form intermediate β-hydroxyesters cxxxiii that can be Scheme 61 shows a general method for preparation of compounds of formula cxxxvii. As shown in scheme 61, 2-halothiazoles are treated with amines at elevated temperature, either neat, or in a suitable solvent, such as NMP with an appropriate base, for example K$_2$CO$_3$ (Method H) to afford 2-aminothiazoles cxxxvi, that can be further transformed to compounds cxxxvii using generally known methods.

Scheme 62: General method for coupling of halothiazoles with vinylstannanes

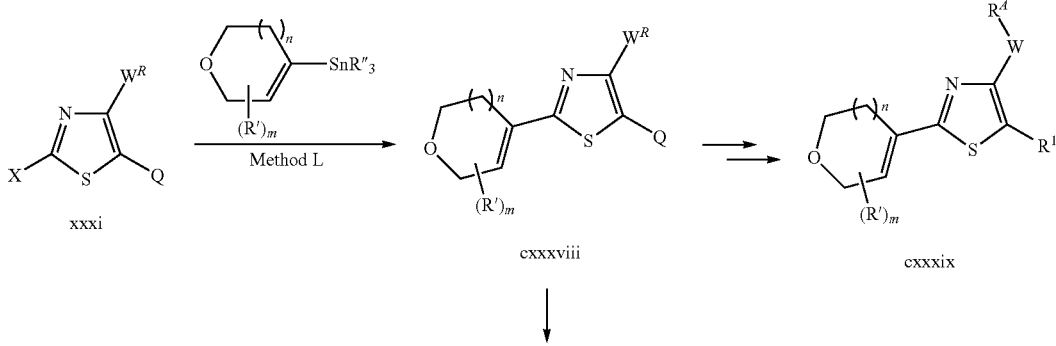

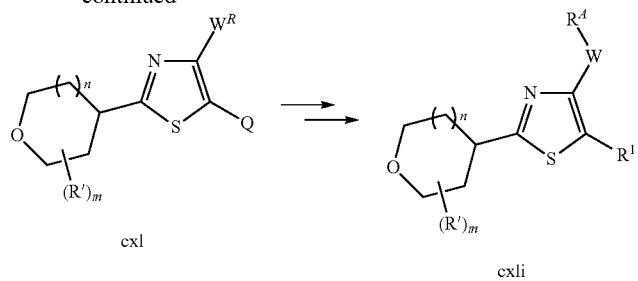

cxl → cxli

Scheme 62 shows a general method for preparation of compounds of formula cxxxix and cxli. As shown in Scheme 62, compounds xxxi can be coupled with vinylstananes under suitable conditions, for example Pd(PPh$_3$)$_4$, CuI, LiCl in dioxane under elevated temperature to give alkenes cxxxviii (Method K), that can be further transformed to compounds cxxxix by generally known methods. Alternatively, hydrogenation of cxxxviii, for example using Pd/C as catalyst in a suitable solvent, such as ethanol (Method V) can afford compounds cxl, that can be further transformed to cxli by generally known methods.

Scheme 71: General method for the synthesis of amines

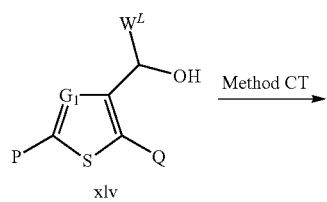

xlv

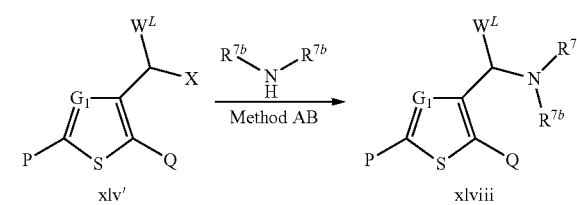

xlv' → xlviii

Scheme 71 shows a general method for the synthesis of amines xlviii. As shown is Scheme 71, alcohols xlv can be transformed to halides xlv' using treatment with a suitable reagent, such as PCl$_5$ in a suitable solvent, such as DCM. Halides xlv' are then treated with amines at elevated temperature to provide target amines xlviii (Method AB).

Scheme 63: General method for the synthesis of substituted thiazoles

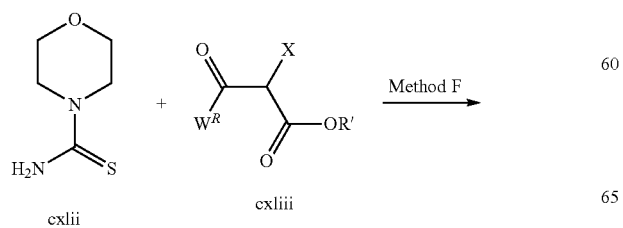

cxlii + cxliii → (Method F)

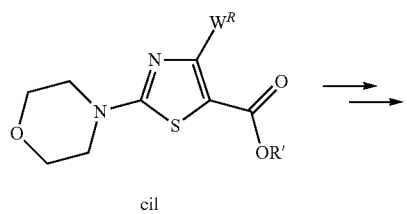

cil

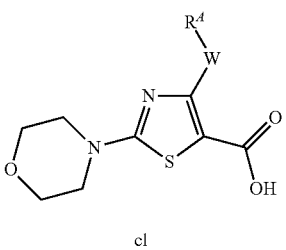

cl

Scheme 63 shows a general route for the synthesis of compounds of formula cl. Thioamide cxiii can be treated with alpha-halogenated carbonyl compounds cxliii in a suitable solvent, such as isopropanol at elevated temperature to give thiazoles cil. (Method F). A conversion reaction from cil to compounds cl can be performed by a combination of generally known functional group conversion reactions.

Scheme 64: General method for introduction of morpholine to 2-position of thiazole core.

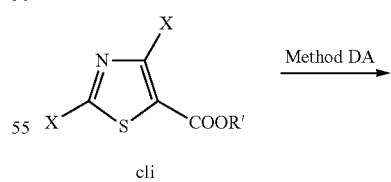

cli

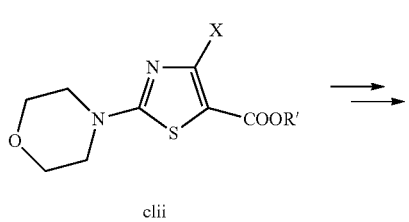

clii

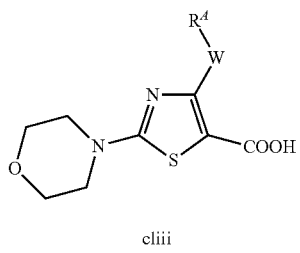

cliii

Scheme 64 shows a general route for introducing morpholine to the 2-position of thiazole core scaffold. Dihalothiazole esters, such as Methyl 2,4-dibromo-5-thiazolecarboxylate can be treated with morpholine at elevated temperature, with a suitable base, such as cesium carbonate in THF or other appropriate solvent (Method DA) to afford compounds of formula clii. Compounds clii can be then transformed into compounds cliii using generally known functional group conversion reactions.

Scheme 65: General method for the synthesis of 3-cyanothiophenes

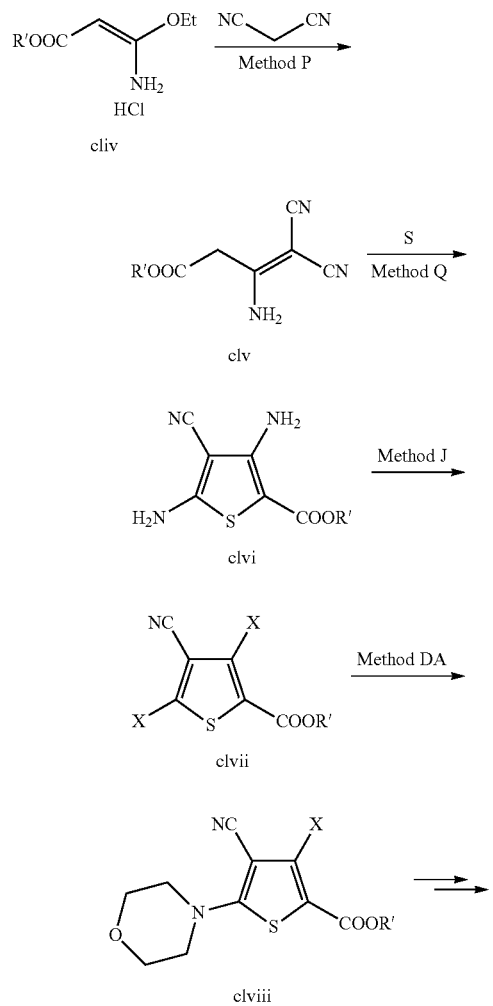

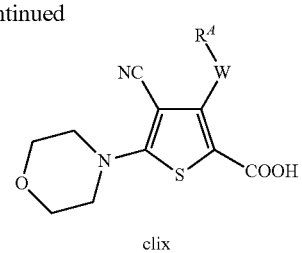

clix

Scheme 65 describes the procedure for the synthesis of 3-cyanothiophenes clix. Substituted alkoxyethenamine cliv can be treated with malononitrile in the presence of a suitable base, such as TEA, in a suitable solvent, like chloroform, at elevated temperature to afford substituted aminoethylene malononitriles clv (Method P), that are treated with sulfur under suitable conditions, such as DMF and elevated temperature, to give diaminocyanothiophenes xclvi (Method Q). Diamines clvi may then be subjected to a Sandmeyer reaction using appropriate reagents, such as copper(II)bromide, amyl nitrite in ACN at elevated temperature (Method J) to afford compounds of formula clvii. Dihalocyanothiophenes can be then treated with morpholine at elevated temperature, with a suitable base, such as cesium carbonate in THF or other appropriate solvent (Method DA) to afford compounds of formula clviii. Compounds clviii can be then transformed into compounds clvix using generally known functional group conversion reactions.

Scheme 66: Alternative method for the synthesis of cyanothiophenes

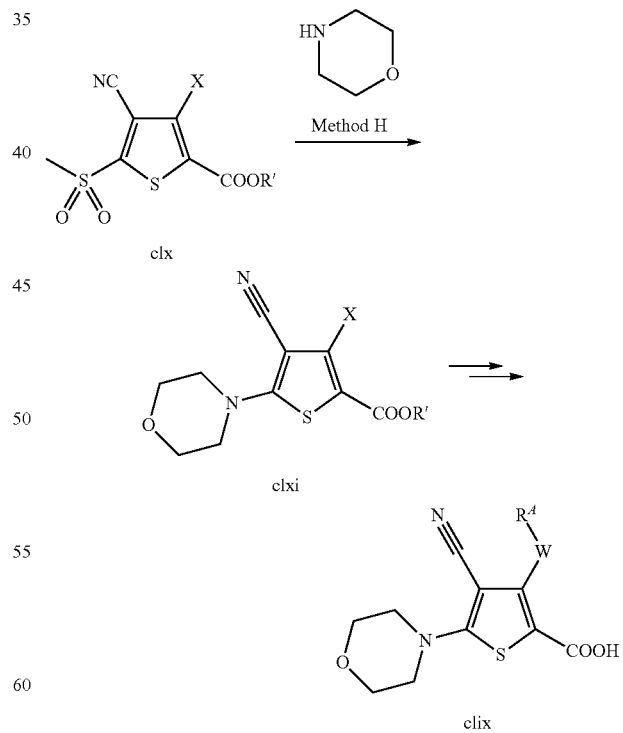

Scheme 66 describes a procedure for the introduction of morpholine to 3-cyanothiophene analogs. As shown in Scheme 66, sulfones of formula clx (synthetic examples given in Mansanet et al, WO 2005070916) can be treated with morpholine in a suitable solvent, e.g., THF, at elevated temperature (Method H) to give clxi. Conversion reactions from clxi to compounds clix can be performed, for example, by a combination of generally known functional group conversion reactions.

Scheme 67: General method for coupling of halothiophenes/thiazoles with vinylstannanes/boronic esters

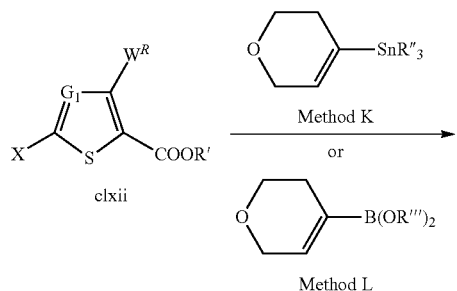

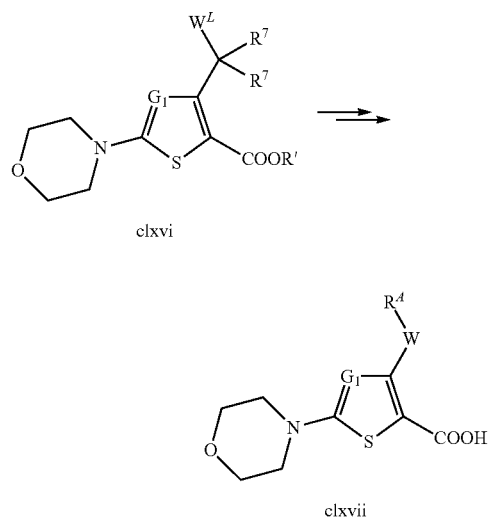

As shown in Scheme 68 carbon functionality can be introduced by the well known Negishi cross-coupling technique. Halogenated thiophenes/thiazoles clxv can be treated with alkyl zinc halides using Pd catalyst, such as $Pd(tBu_3P)_2$ under standard Negishi coupling conditions, such as THF at elevated temperature (Method T) to afford compounds clxvi, that can be further transformed to compounds clxvii using generally known methods.

Scheme 67 shows a general method for preparation of compounds of formula clxiv. As shown in Scheme 67, compounds clxii can be coupled with vinylstananes under suitable conditions, for example $Pd(PPh_3)_4$, CuI, LiCl in dioxane under elevated temperature to give alkenes clxiii (Method K). Alternatively, Suzuki conditions, such as $Pd(PPh_3)_4$, $CsCO_3$, dioxane at elevated temperature (Method L) can be used. Compounds clxiii can be then further transformed to compounds clxiv by generally known methods.

Scheme 69: Alternative method for introducing carbon functionality to thiophenes/thiazoles.

Scheme 68: General method for introducing carbon functionality to halogenated thiophenes/thiazoles.

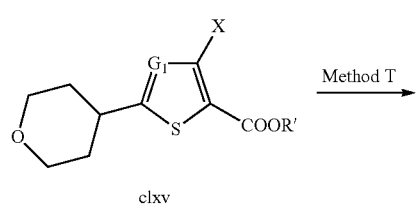

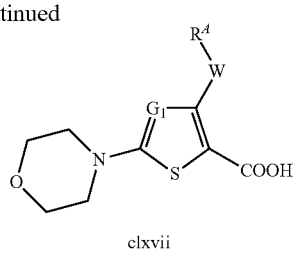

clxvii

As shown in Scheme 69, methyl substituent of thiophenes/thiazoles clxviii can be halogenated using a suitable reagent, for example NBS with a radical source, such as AIBN in an appropriate solvent, like DCM (Method DB) to afford halides clxix. Halides clxix can be then coupled with boronic acids or esters using the well known Suzuki cross-coupling technique, for example $Pd(PPh_3)_4$, $Cs_2CO_3$, dioxane-water at elevated temperature (Method L) to afford compounds clxvi, that can be further transformed to compounds clxvii using generally known methods.

Scheme 70: General method for the synthesis of amino acids

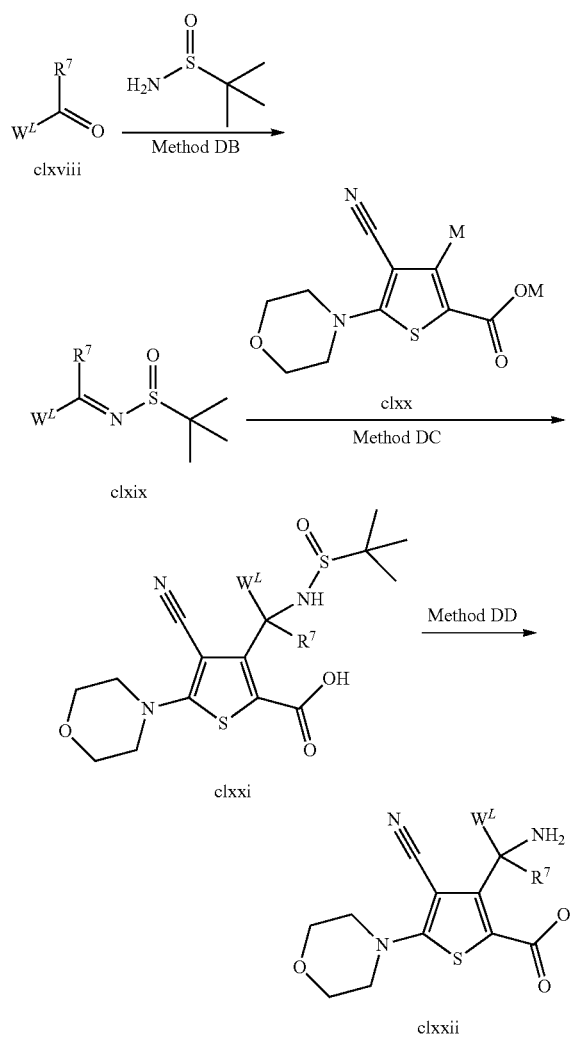

As shown in Scheme 70, aldehydes or ketones clxx can be treated with 2-Methyl-2-propanesulfinamide in the presence of a suitable Lewis acid, such as $Ti(OiPr)_4$ in anhydrous THF, or other suitable solvent to afford sulfinamides clxixi (Method DC), that can be subsequently treated with thiophene metal compounds clxxii (Method DD), obtained from corresponding thiophene halides through halogen-metal exchange, for example from thiophene bromide using an excess of phenyllithium at low temperature. Formed sulfinyl amines clxxiii can be then treated with an acid, such as HCl in dioxane with an optional co-solvent, for example DCM (Method DE) to afford amino acids clxxiv.

Scheme 72: Alternative method for the synthesis of cyanothiophenes

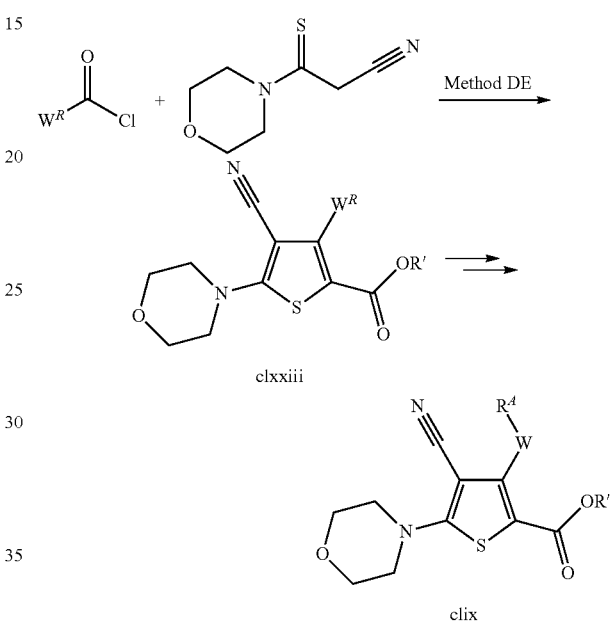

As shown in Scheme 72, acyl halides can be coupled with thiomorpholine and alkylhaloacetate in the presence of a suitable base, such as diisopropylamine in an appropriate solvent, for example MeCN at elevated temperature to afford cyanothiophenes clxxiii (Method DE). A conversion reaction from clxxiii to compounds clix can be performed by a combination of generally known functional group manipulations.

Scheme 73: General method for benzylic alkylation

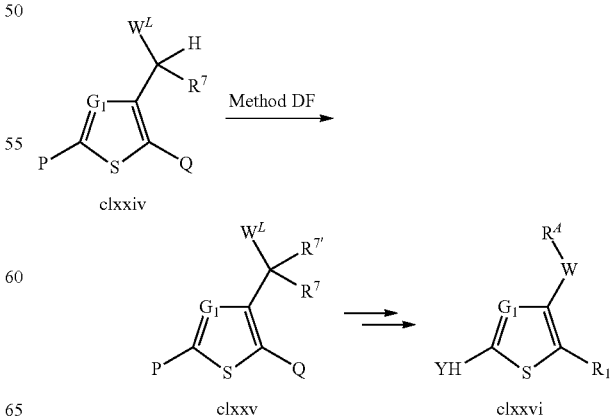

As shown in Scheme 73, compounds clxxiv (where $W^L$ is an aromatic or heteroaromatic group) can be deprotonated using a suitable base, such as KOtBu in an appropriate solvent, for example THF and subsequently alkylated using an alkyl halide $R^{7'}$—X (Method DF) to afford products of benzylic alkylations clxxv. Compounds clxxv can be further transformed to compounds clxxvi using generally known methods.

Scheme 74: General method for the synthesis of substituted selenazoles

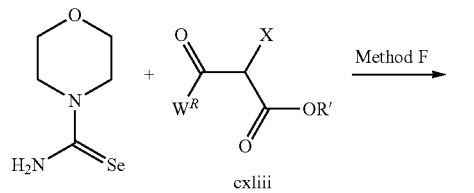

cxliii

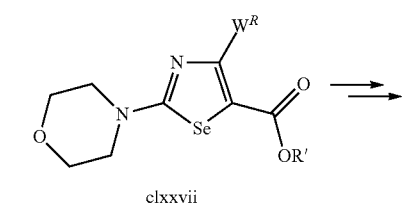

clxxvii

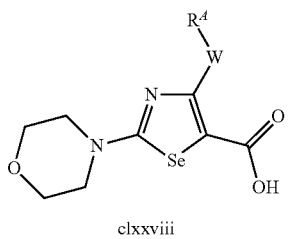

clxxviii

Scheme 74 shows a general route for the synthesis of compounds of formula clxxvii. Selenoamide can be treated with alpha-halogenated carbonyl compounds cxliii in a suitable solvent, such as isopropanol at elevated temperature to give selenazoles clxxvii. (Method F). A conversion reaction from clxxvii to compounds clxxviii can be performed by a combination of generally known functional group manipulations.

Scheme 75: General method for the synthesis of selenophenes

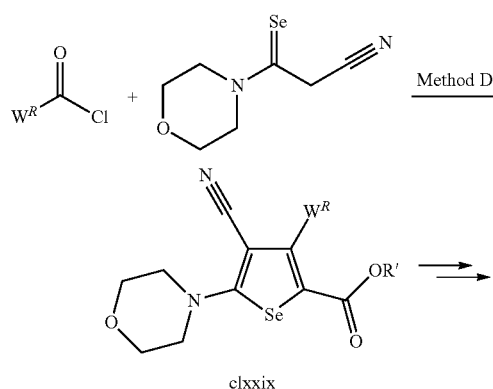

clxxix

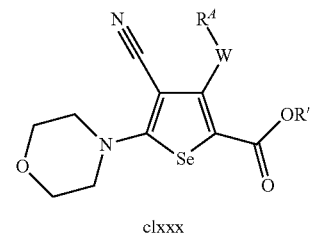

clxxx

As shown in Scheme 75, acyl halides can be coupled with selenomorpholine building block and alkylhaloacetate in the presence of a suitable base, such as diisopropylamine in an appropriate solvent, for example MeCN at elevated temperature to afford selenophenes clxxix (Method DE). A conversion reaction from clxxix to compounds clxxx can be performed by a combination of generally known functional group manipulations.

EXAMPLES

Table 1 below depicts certain compounds represented by compounds of general formula IA and IB.

TABLE 1

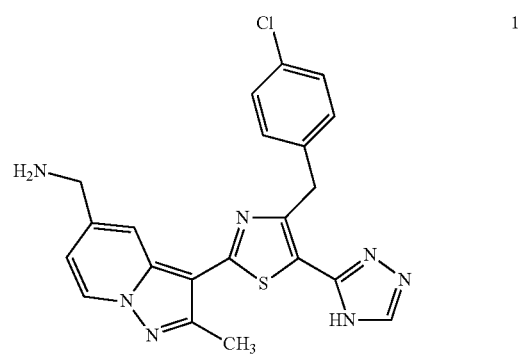

1

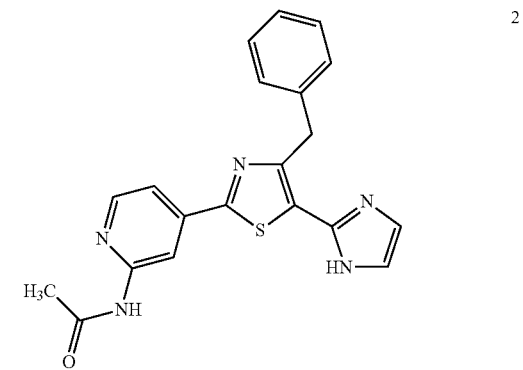

2

TABLE 1-continued
| | |
|---|---|
| 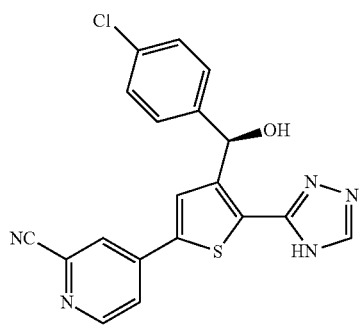 [SMILES: N#Cc1cc(-c2cc([C@H](O)c3ccc(Cl)cc3)c(-c3nnc[nH]3)s2)ccn1] | 3 |
| 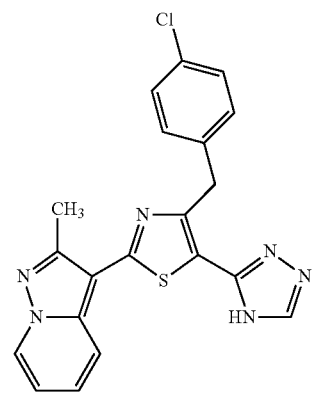 [SMILES: Cc1nn2ccccc2c1-c1nc(Cc2ccc(Cl)cc2)c(-c2nnc[nH]2)s1] | 4 |
| 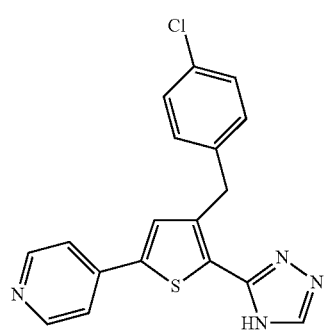 [SMILES: Clc1ccc(Cc2cc(-c3ccncc3)sc2-c2nnc[nH]2)cc1] | 5 |
| 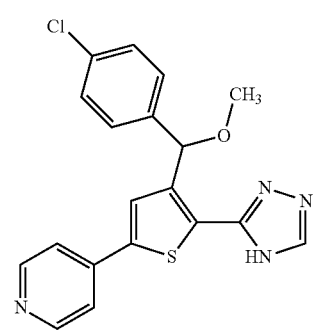 [SMILES: COC(c1ccc(Cl)cc1)c1cc(-c2ccncc2)sc1-c1nnc[nH]1] | 6 |
TABLE 1-continued
| | |
|---|---|
| 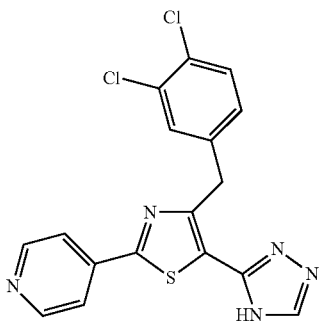 [SMILES: Clc1ccc(Cc2nc(-c3ccncc3)sc2-c2nnc[nH]2)cc1Cl] | 7 |
| 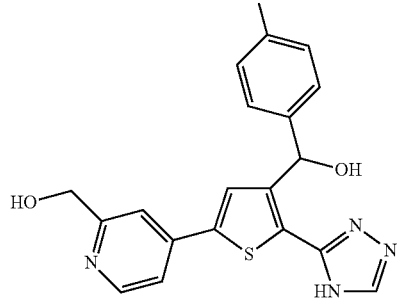 | 8 |
| 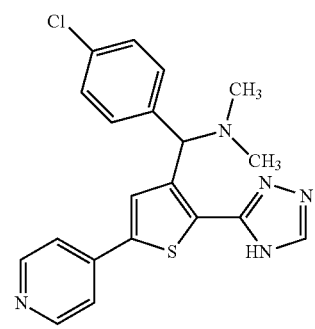 | 9 |
| 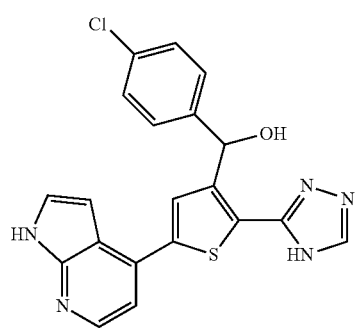 [SMILES: OC(c1ccc(Cl)cc1)c1cc(-c2ccnc3[nH]ccc23)sc1-c1nnc[nH]1] | 10 |
| 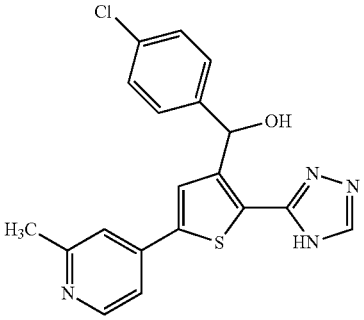 [SMILES: Cc1cc(-c2cc(C(O)c3ccc(Cl)cc3)c(-c3nnc[nH]3)s2)ccn1] | 11 |

TABLE 1-continued
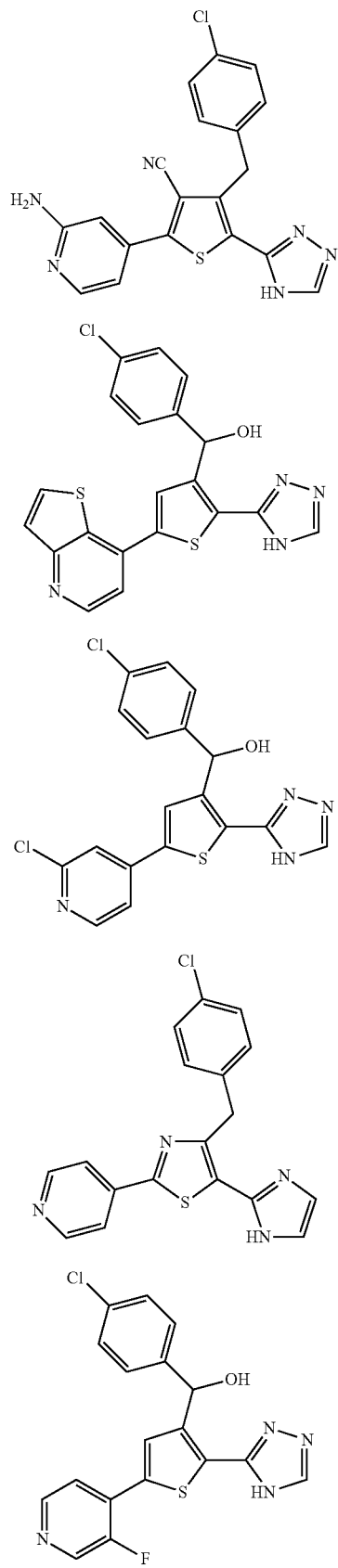
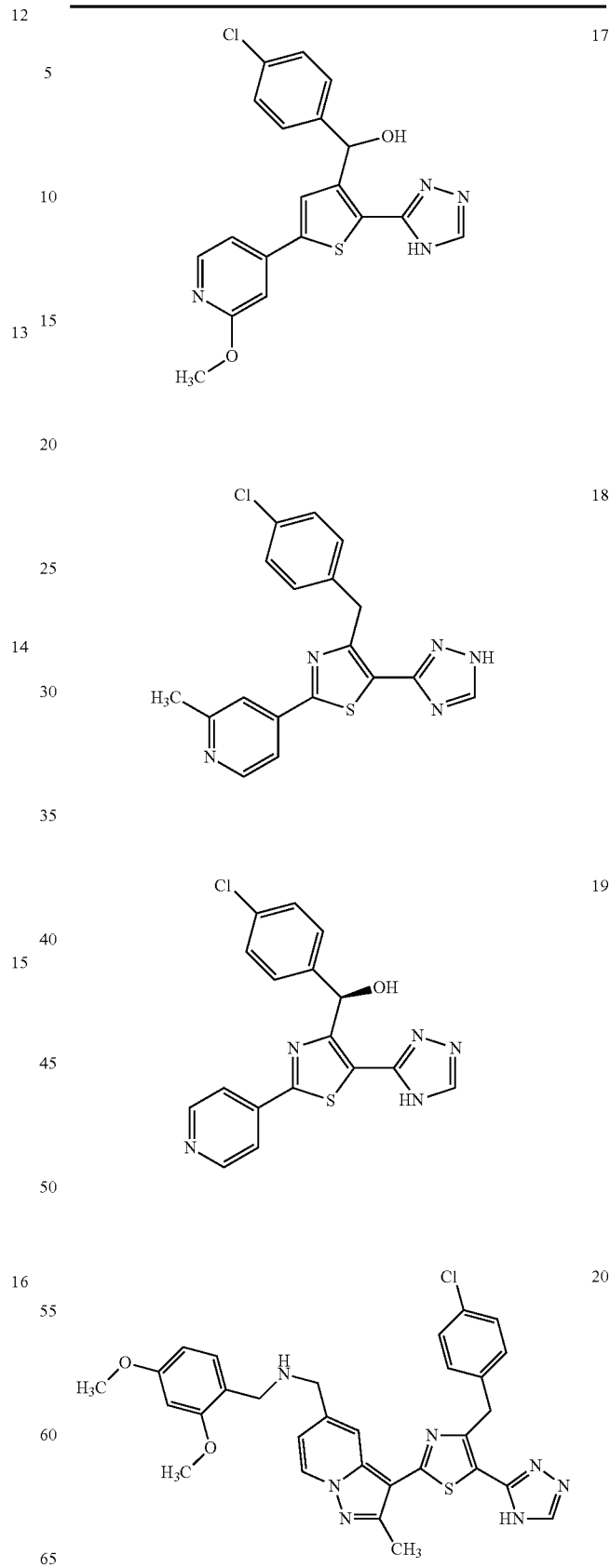

TABLE 1-continued
| | |
|---|---|
| 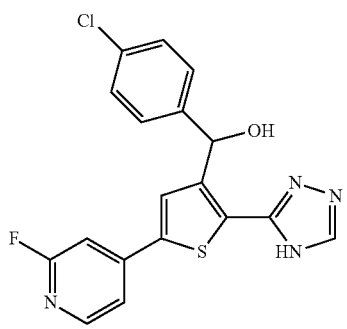 [SMILES: OC(c1ccc(Cl)cc1)c1cc(-c2ccnc(F)c2)sc1-c1nnc[nH]1] 21 | 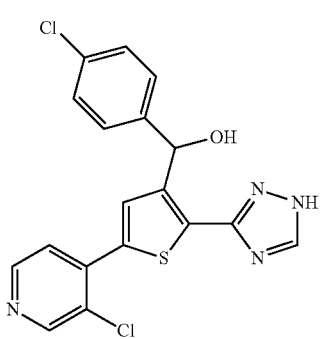 25 |
| 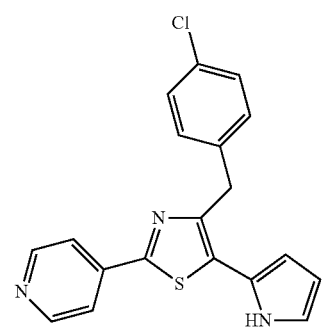 [SMILES: Clc1ccc(Cc2nc(-c3ccncc3)sc2-c2ccc[nH]2)cc1] 22 | 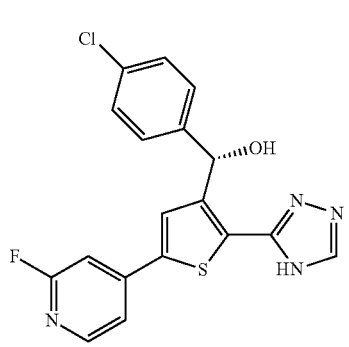 26 |
| 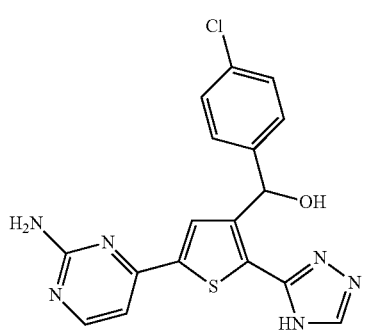 [SMILES: Nc1nccc(-c2cc(C(O)c3ccc(Cl)cc3)c(-c3nnc[nH]3)s2)n1] 23 | 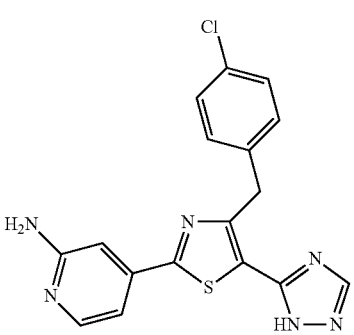 27 |
| 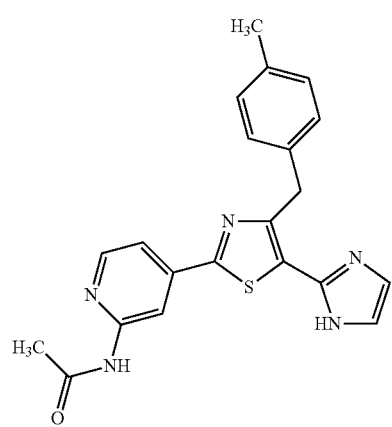 [SMILES: CC(=O)Nc1cc(-c2nc(Cc3ccc(C)cc3)c(-c3ncc[nH]3)s2)ccn1] 24 | 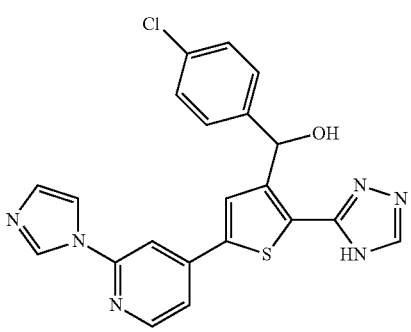 [SMILES: OC(c1ccc(Cl)cc1)c1cc(-c2ccnc(-n3ccnc3)c2)sc1-c1nnc[nH]1] 28 |

TABLE 1-continued

TABLE 1-continued
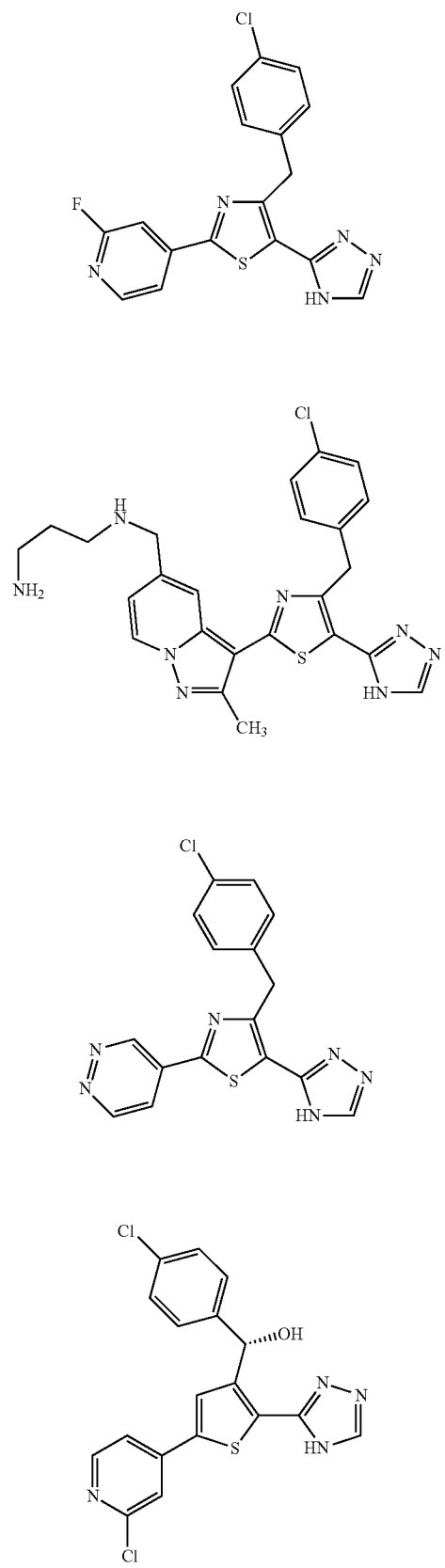
TABLE 1-continued
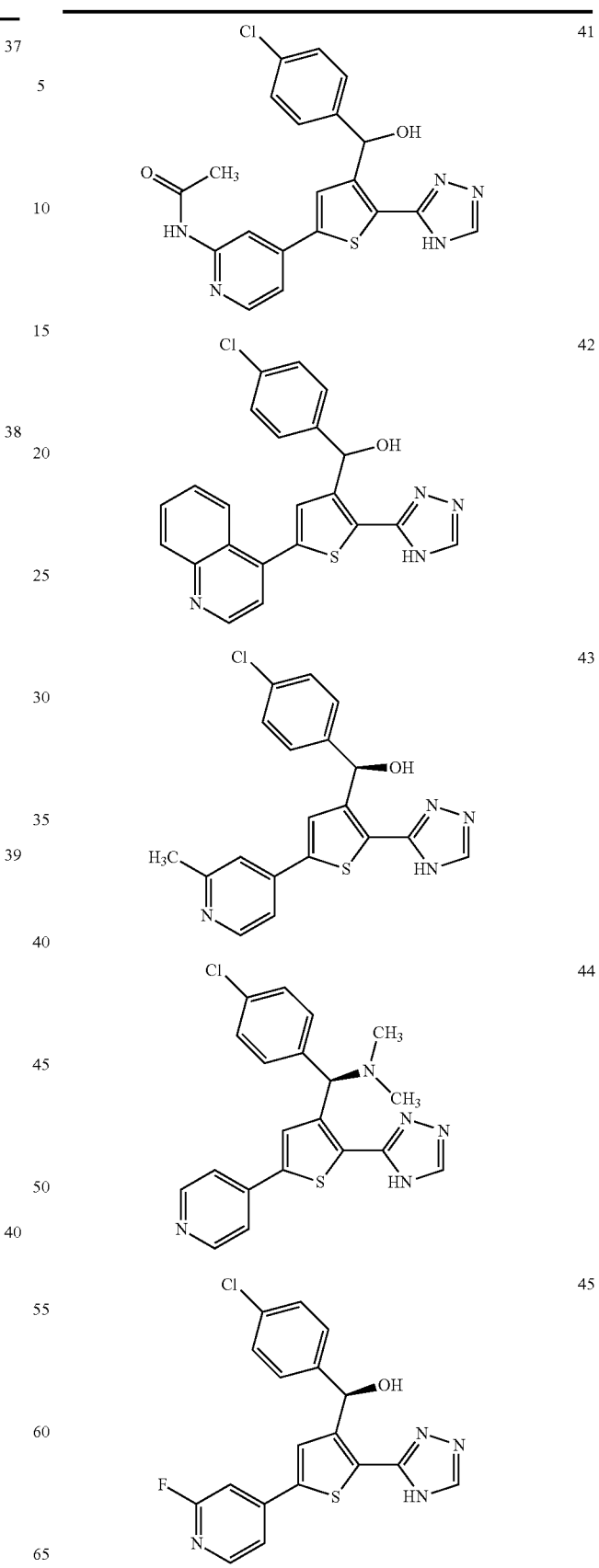

TABLE 1-continued
| | |
|---|---|
| 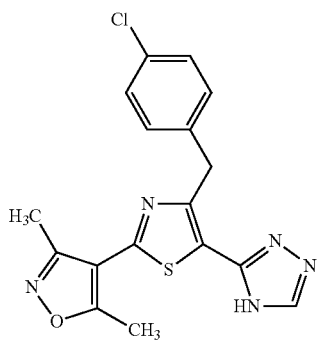 [SMILES: Cc1noc(C)c1-c1nc(Cc2ccc(Cl)cc2)c(-c2nnc[nH]2)s1] 46 | 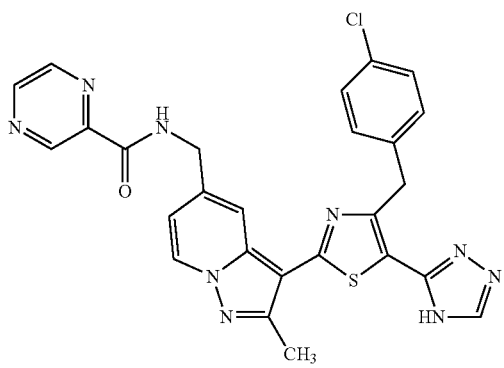 50 |
| 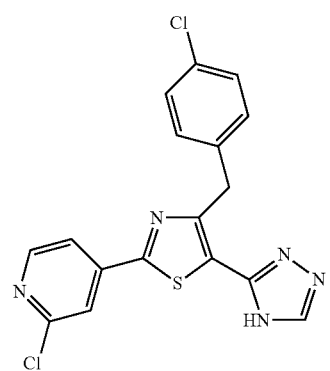 [SMILES: Clc1ccc(Cc2nc(-c3ccnc(Cl)c3)sc2-c2nnc[nH]2)cc1] 47 | 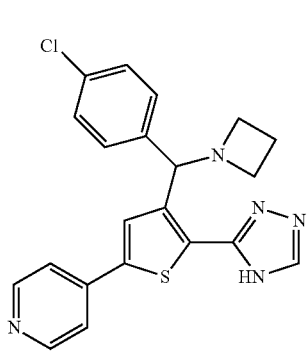 51 |
| 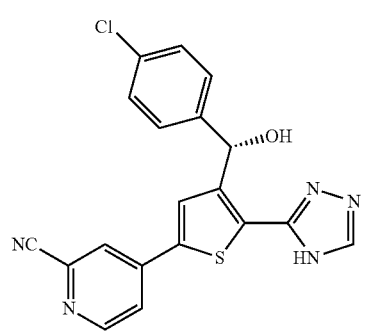 [SMILES: N#Cc1cc(-c2cc([C@@H](O)c3ccc(Cl)cc3)c(-c3nnc[nH]3)s2)ccn1] 48 | 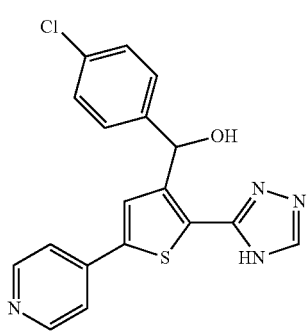 52 |
| 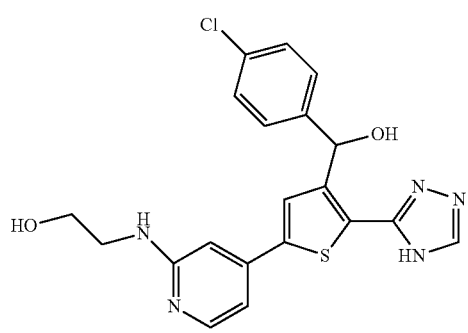 [SMILES: OCCNc1cc(-c2cc(C(O)c3ccc(Cl)cc3)c(-c3nnc[nH]3)s2)ccn1] 49 | 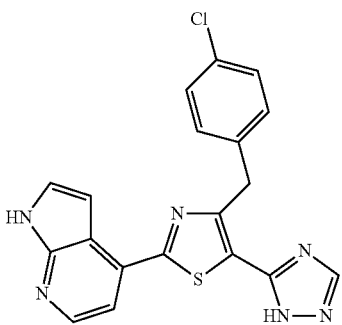 [SMILES: Clc1ccc(Cc2nc(-c3ccnc4[nH]ccc34)sc2-c2ncn[nH]2)cc1] 53 |

TABLE 1-continued
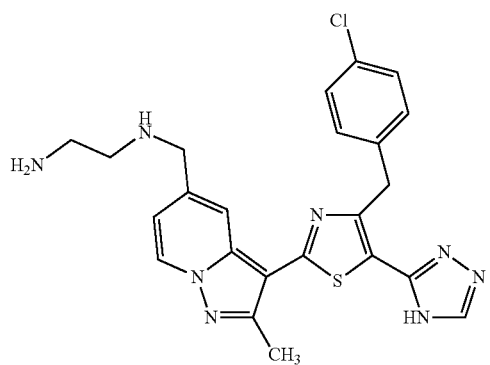 [SMILES: Cc1nn2ccc(CNCCN)cc2c1-c1nc(Cc2ccc(Cl)cc2)c(-c2nnc[nH]2)s1]
54
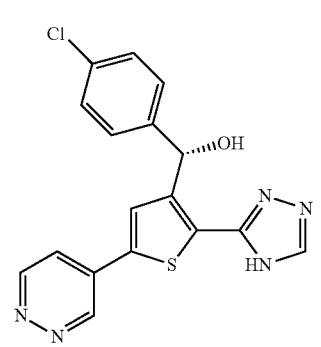 [SMILES: O[C@@H](c1ccc(Cl)cc1)c1cc(-c2ccnnc2)sc1-c1nnc[nH]1]
55
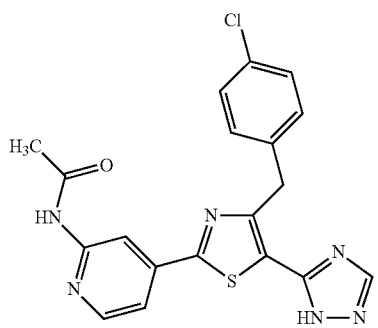 [SMILES: CC(=O)Nc1cc(-c2nc(Cc3ccc(Cl)cc3)c(-c3ncn[nH]3)s2)ccn1]
56
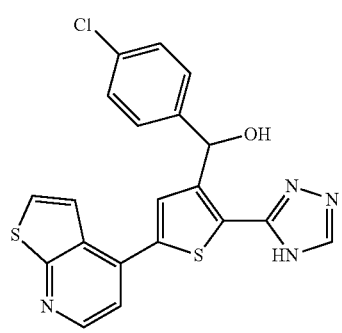 [SMILES: OC(c1ccc(Cl)cc1)c1cc(-c2ccnc3sccc23)sc1-c1nnc[nH]1]
57
TABLE 1-continued
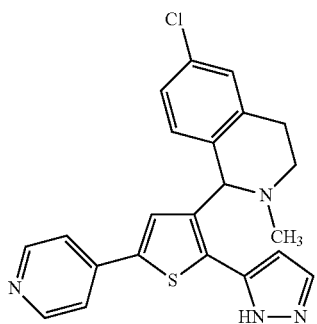 [SMILES: CN1CCc2cc(Cl)ccc2C1c1cc(-c2ccncc2)sc1-c1ccn[nH]1]
58
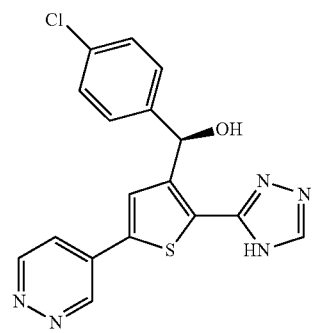 [SMILES: O[C@H](c1ccc(Cl)cc1)c1cc(-c2ccnnc2)sc1-c1nnc[nH]1]
59
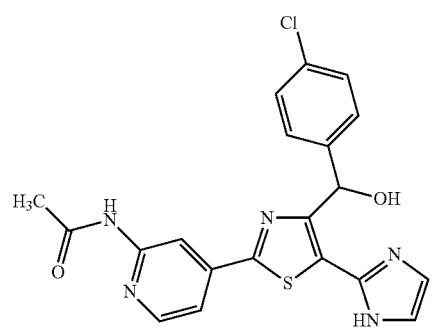 [SMILES: CC(=O)Nc1cc(-c2nc(C(O)c3ccc(Cl)cc3)c(-c3ncc[nH]3)s2)ccn1]
60
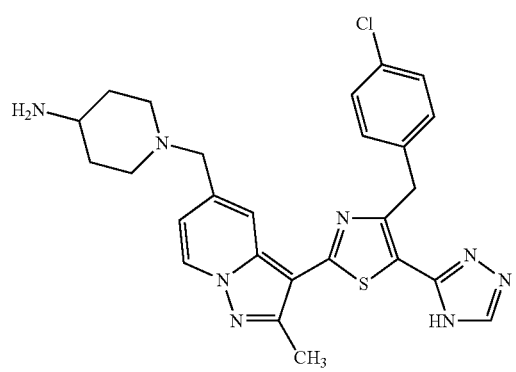 [SMILES: Cc1nn2ccc(CN3CCC(N)CC3)cc2c1-c1nc(Cc2ccc(Cl)cc2)c(-c2nnc[nH]2)s1]
61

TABLE 1-continued
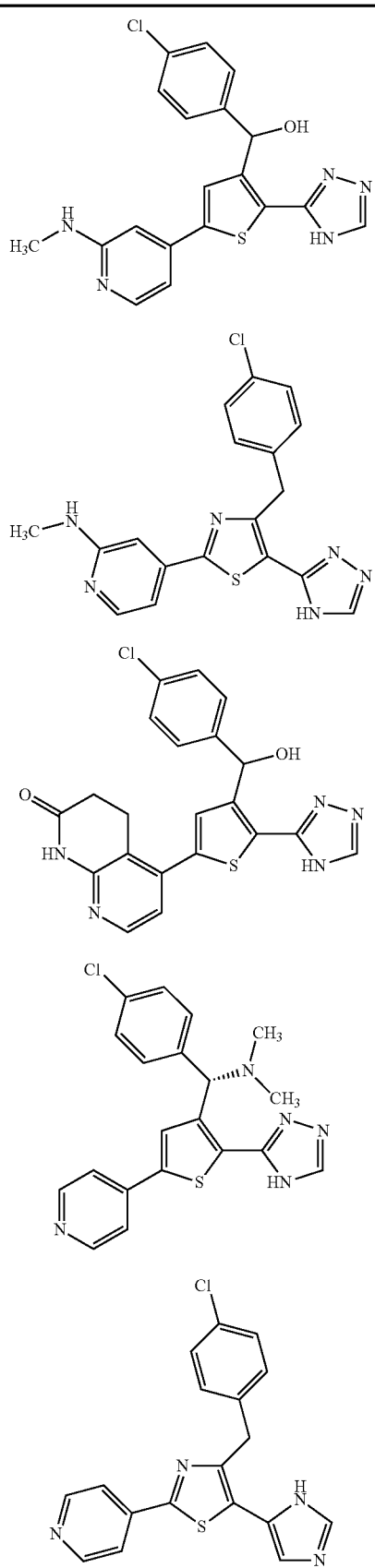
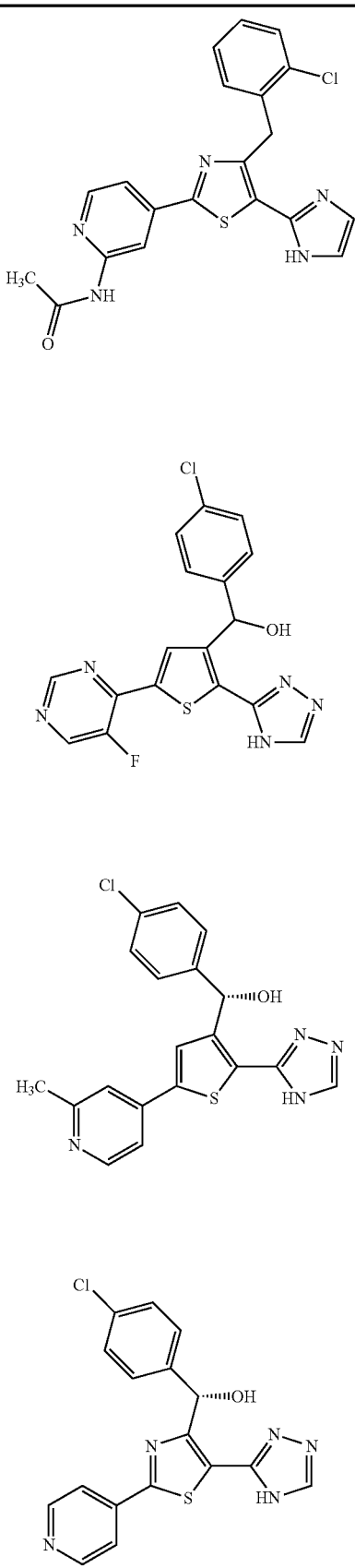

TABLE 1-continued
| | |
|---|---|
| 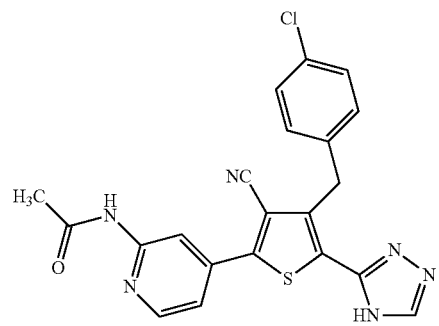 [SMILES: CC(=O)Nc1cc(-c2sc(-c3nnc[nH]3)c(Cc3ccc(Cl)cc3)c2C#N)ccn1] 71 | 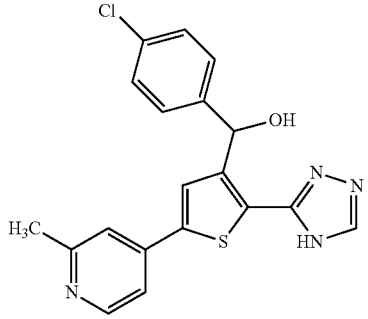 75 |
| 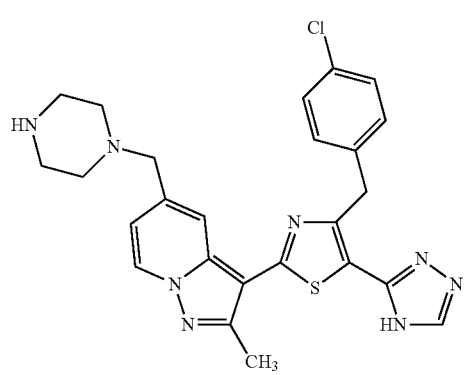 [SMILES: Cc1nn2ccc(CN3CCNCC3)cc2c1-c1nc(Cc2ccc(Cl)cc2)c(-c2nnc[nH]2)s1] 72 | 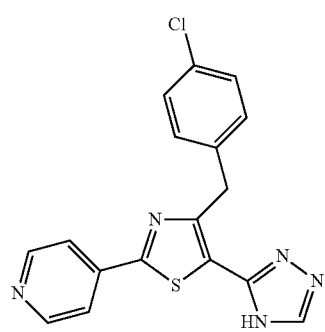 76 |
| 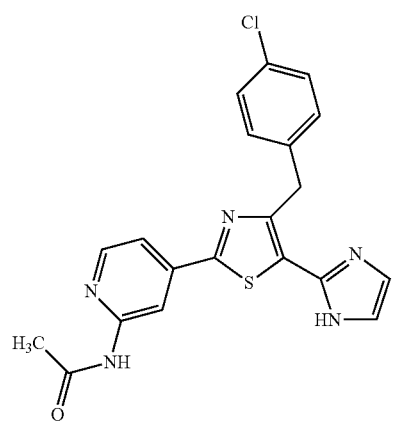 [SMILES: CC(=O)Nc1cc(-c2nc(Cc3ccc(Cl)cc3)c(-c3ncc[nH]3)s2)ccn1] 73 | 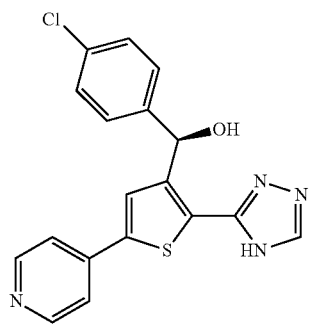 77 |
| | 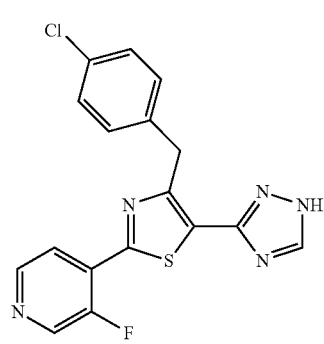 78 |
| 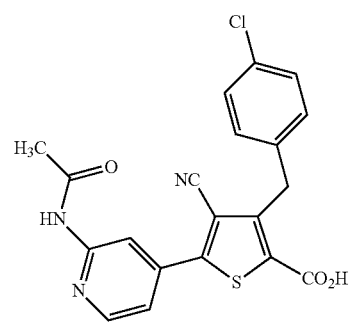 [SMILES: CC(=O)Nc1cc(-c2sc(C(=O)O)c(Cc3ccc(Cl)cc3)c2C#N)ccn1] 74 | 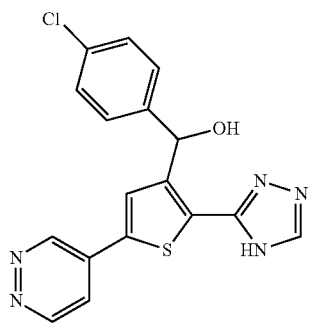 [SMILES: OC(c1ccc(Cl)cc1)c1cc(-c2ccnnc2)sc1-c1nnc[nH]1] 79 |

TABLE 1-continued
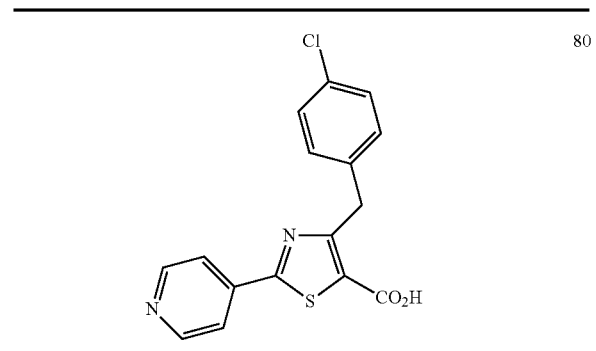
80
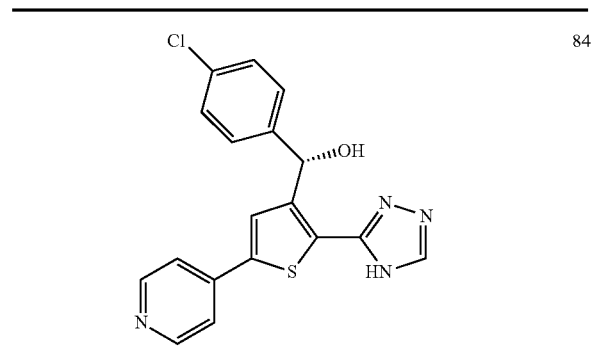
84
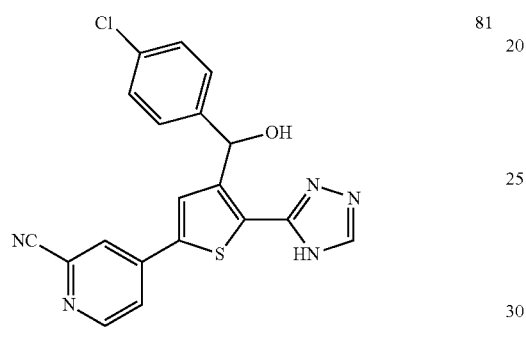
81
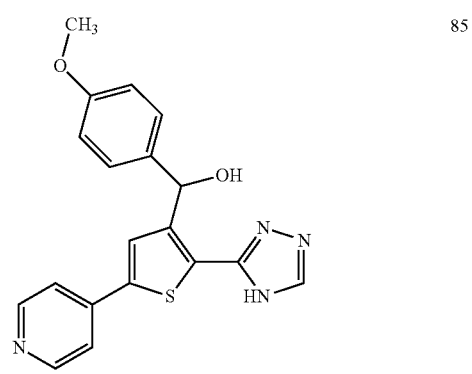
85
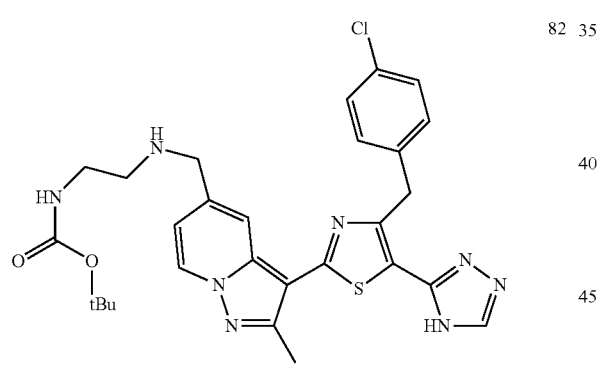
82
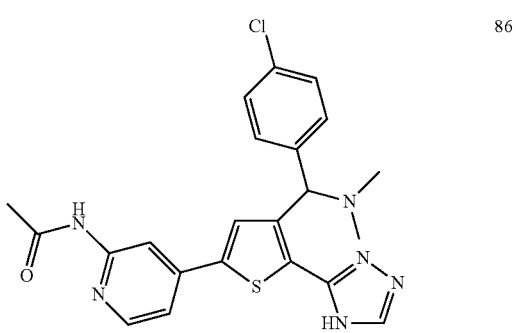
86
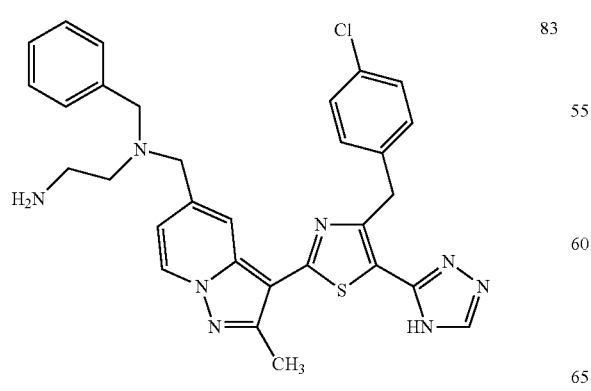
83
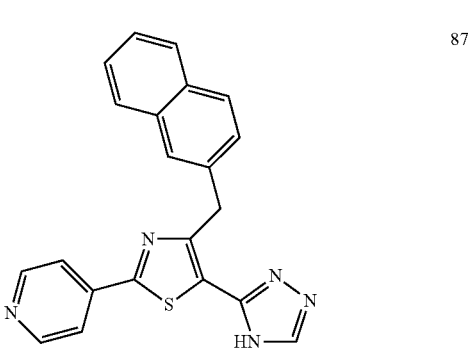
87

TABLE 1-continued
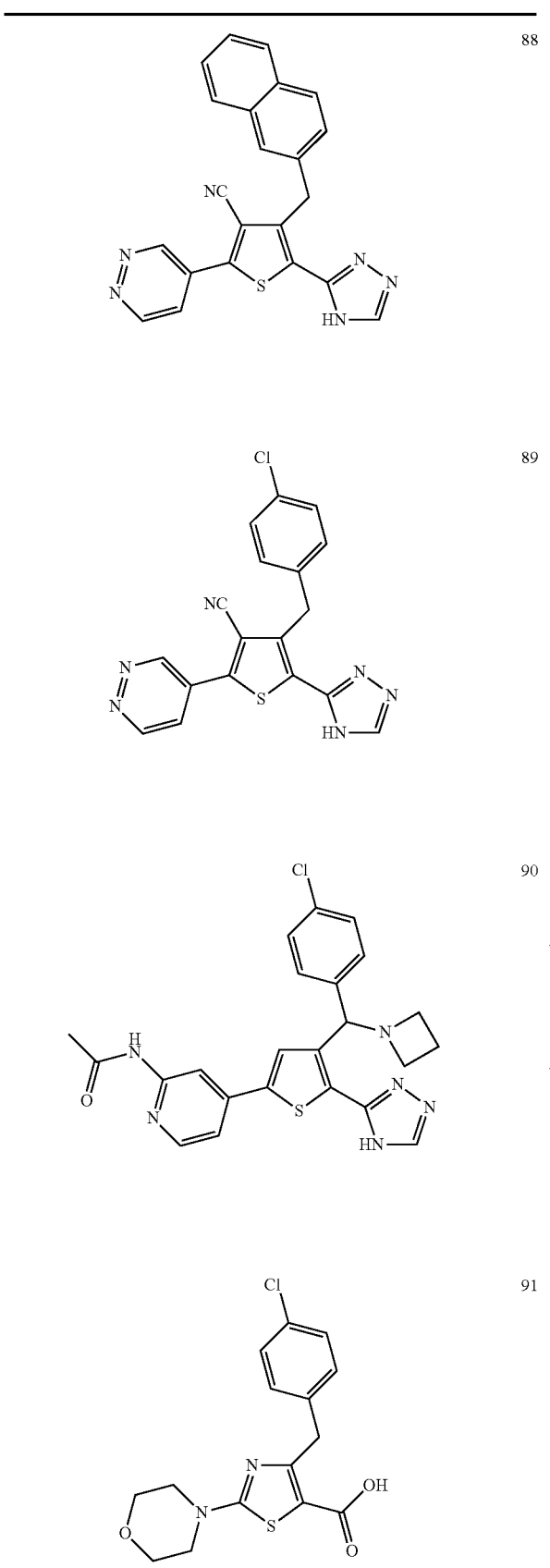
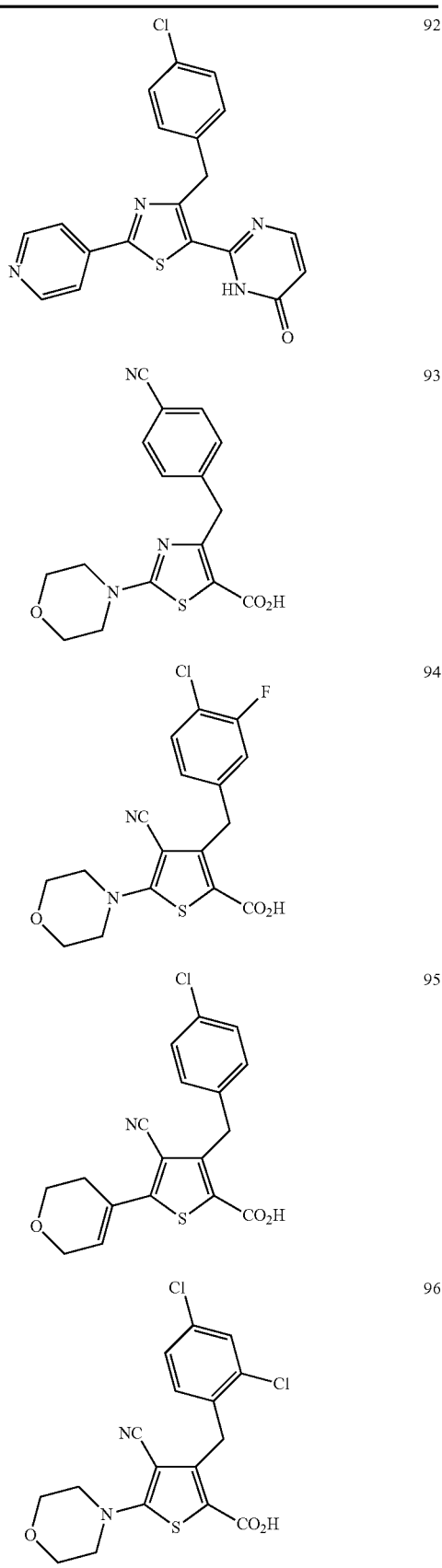

TABLE 1-continued
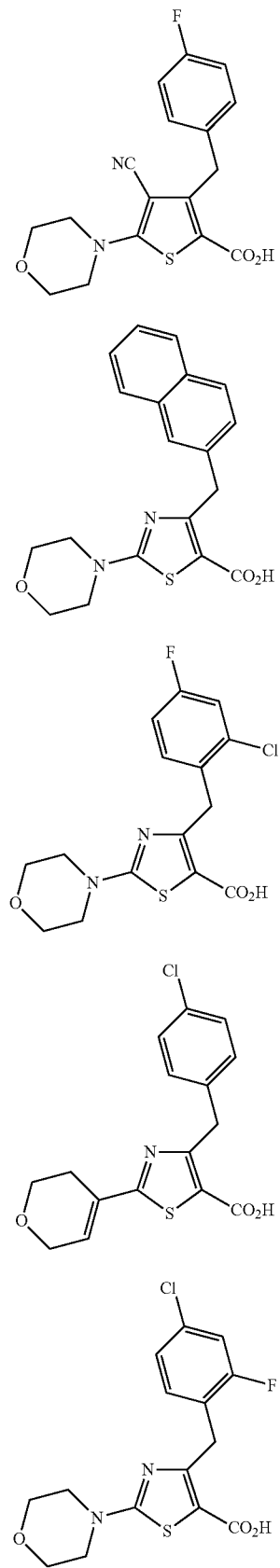
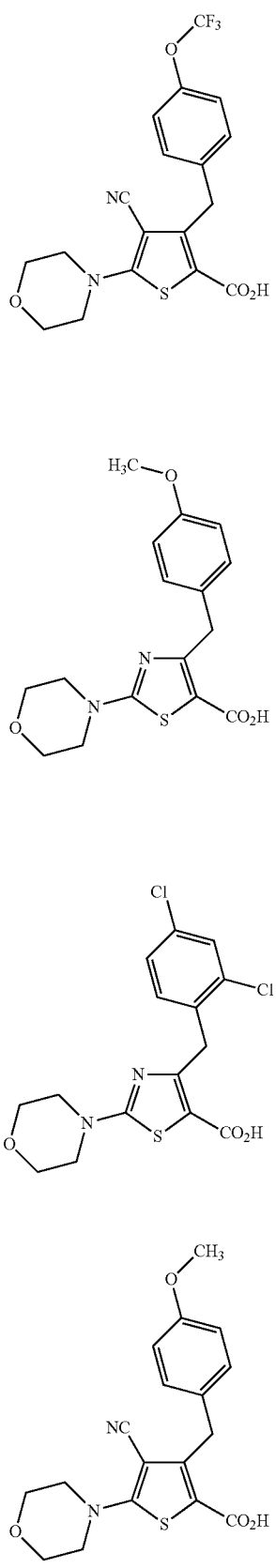

TABLE 1-continued
| | |
|---|---|
| 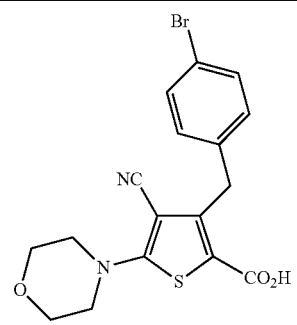 | 106 |
| 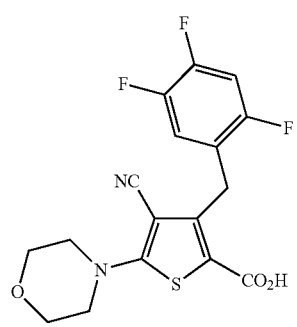 | 107 |
| 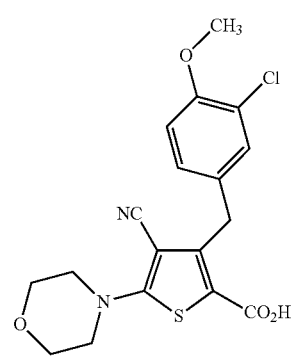 [SMILES: COc1ccc(Cc2c(C(=O)O)sc(N3CCOCC3)c2C#N)cc1Cl] | 108 |
| 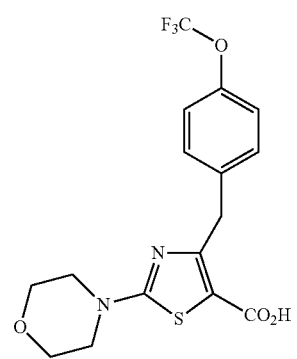 [SMILES: O=C(O)c1sc(N2CCOCC2)nc1Cc1ccc(OC(F)(F)F)cc1] | 109 |
TABLE 1-continued
| | |
|---|---|
| 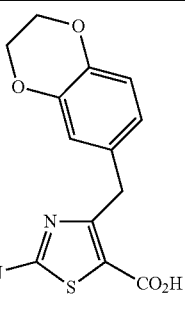 | 110 |
| 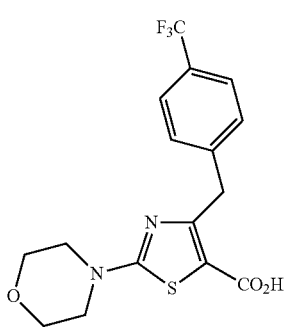 [SMILES: O=C(O)c1sc(N2CCOCC2)nc1Cc1ccc(C(F)(F)F)cc1] | 111 |
| 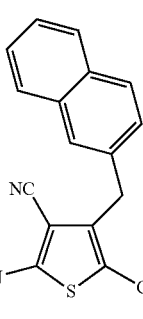 | 112 |
| 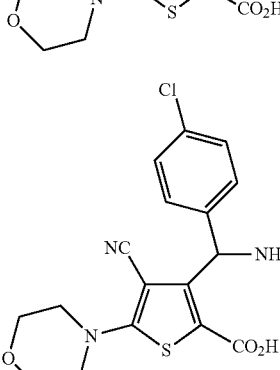 | 113 |
| 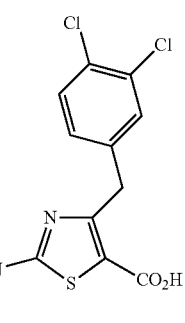 | 114 |

TABLE 1-continued
| | |
|---|---|
| 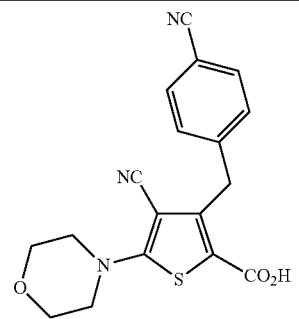 115 | 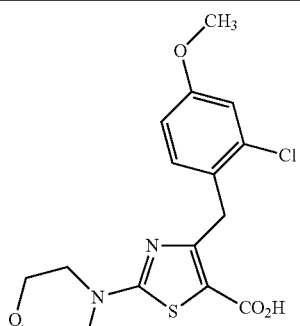 120 |
| 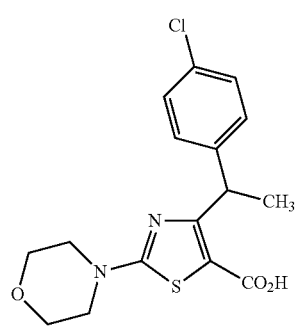 [SMILES: CC(c1ccc(Cl)cc1)c1nc(N2CCOCC2)sc1C(=O)O] 116 | 121 |
| 117 | 122 |
| 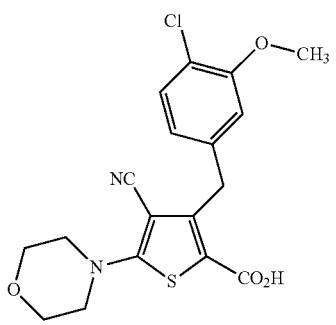 [SMILES: COc1cc(Cc2c(C(=O)O)sc(N3CCOCC3)c2C#N)ccc1Cl] 118 | 123 |
| 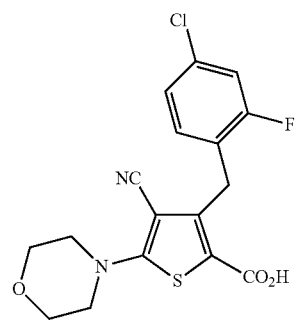 [SMILES: N#Cc1c(N2CCOCC2)sc(C(=O)O)c1Cc1ccc(Cl)cc1F] 119 | 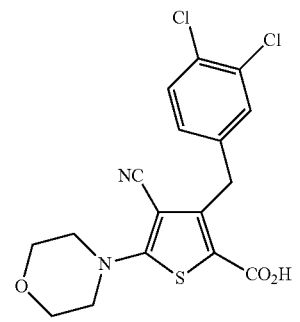 [SMILES: N#Cc1c(N2CCOCC2)sc(C(=O)O)c1Cc1ccc(Cl)c(Cl)c1] 124 |

TABLE 1-continued
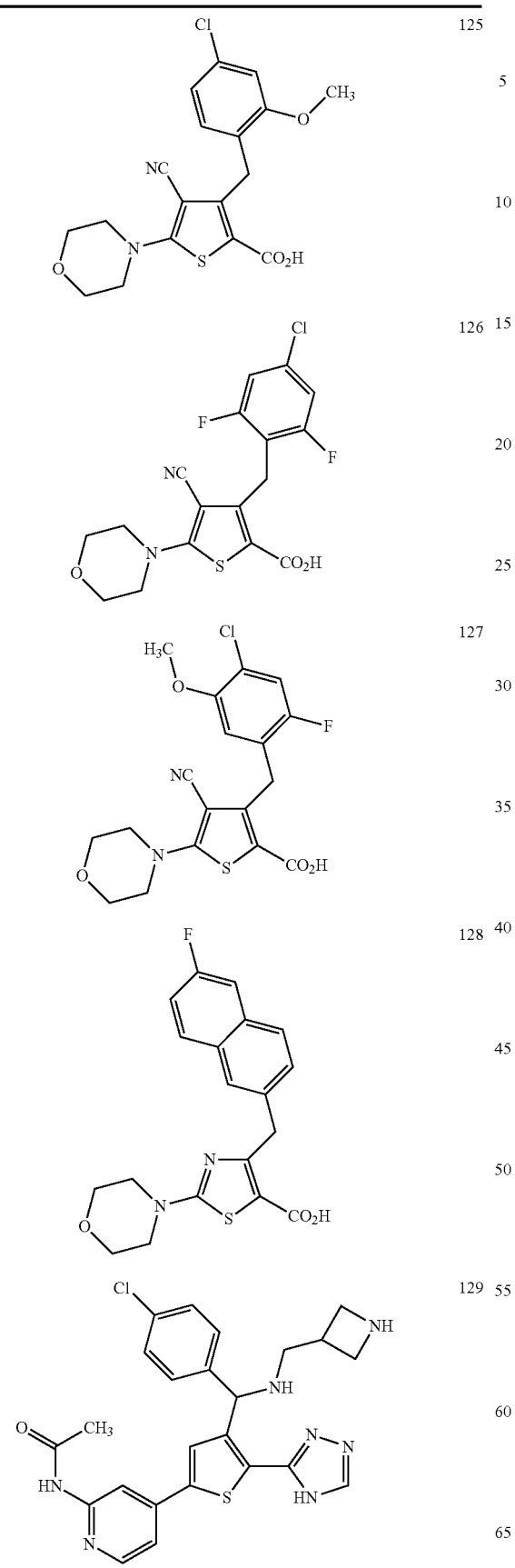
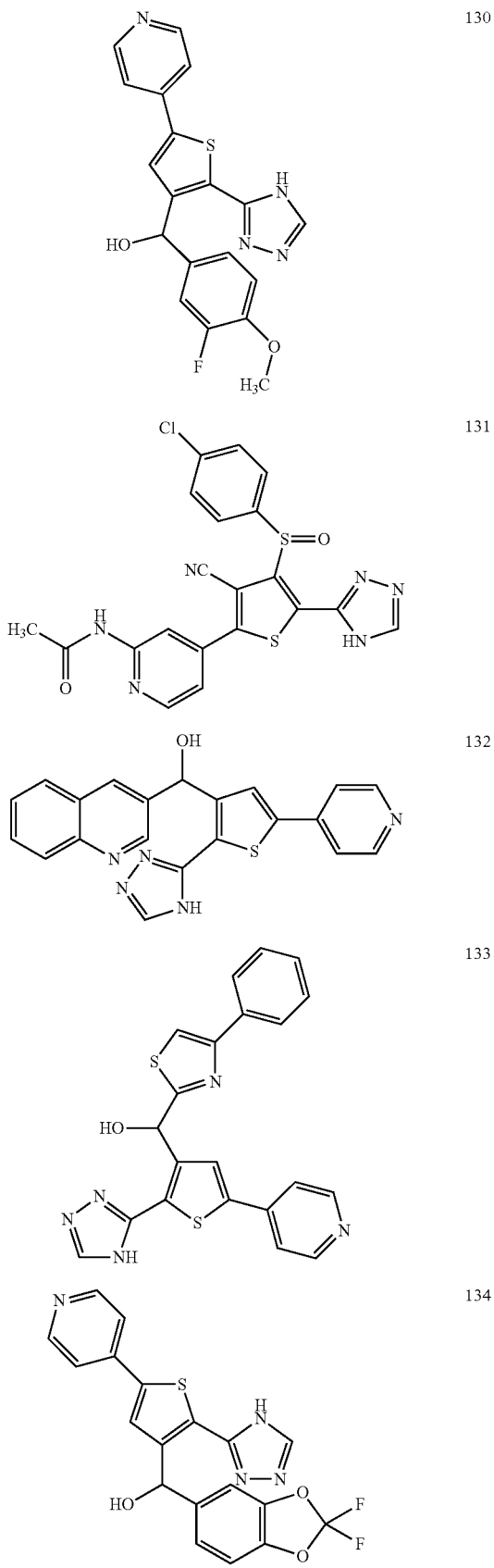

TABLE 1-continued
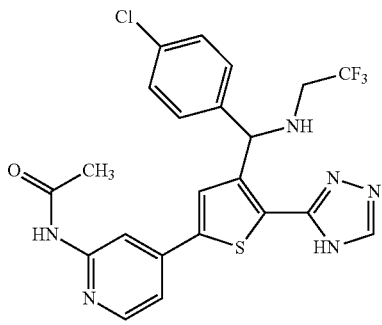 [SMILES: CC(=O)Nc1cc(-c2cc(C(NCC(F)(F)F)c3ccc(Cl)cc3)c(-c3nnc[nH]3)s2)ccn1]
135
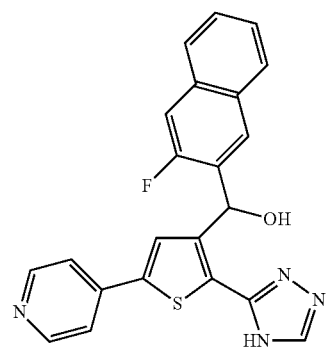 [SMILES: OC(c1cc2ccccc2cc1F)c1cc(-c2ccncc2)sc1-c1nnc[nH]1]
136
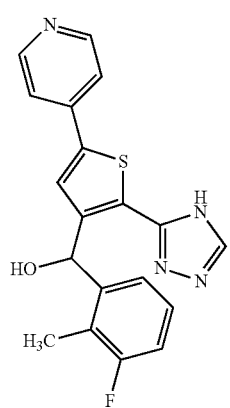 [SMILES: Cc1c(F)cccc1C(O)c1cc(-c2ccncc2)sc1-c1nnc[nH]1]
137
TABLE 1-continued
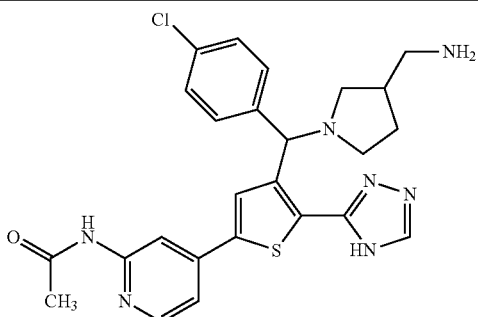
139
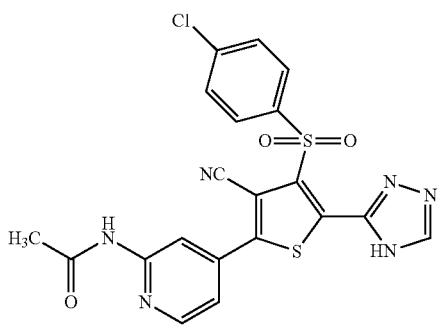 [SMILES: CC(=O)Nc1cc(-c2sc(-c3nnc[nH]3)c(S(=O)(=O)c3ccc(Cl)cc3)c2C#N)ccn1]
140
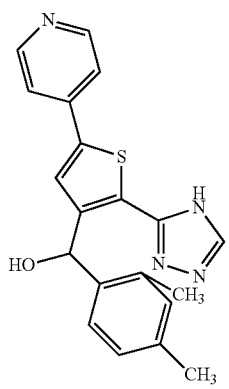 [SMILES: Cc1ccc(C(O)c2cc(-c3ccncc3)sc2-c2nnc[nH]2)c(C)c1]
141
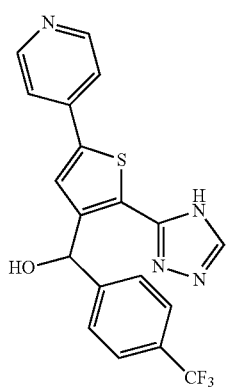 [SMILES: OC(c1ccc(C(F)(F)F)cc1)c1cc(-c2ccncc2)sc1-c1nnc[nH]1]
142

TABLE 1-continued
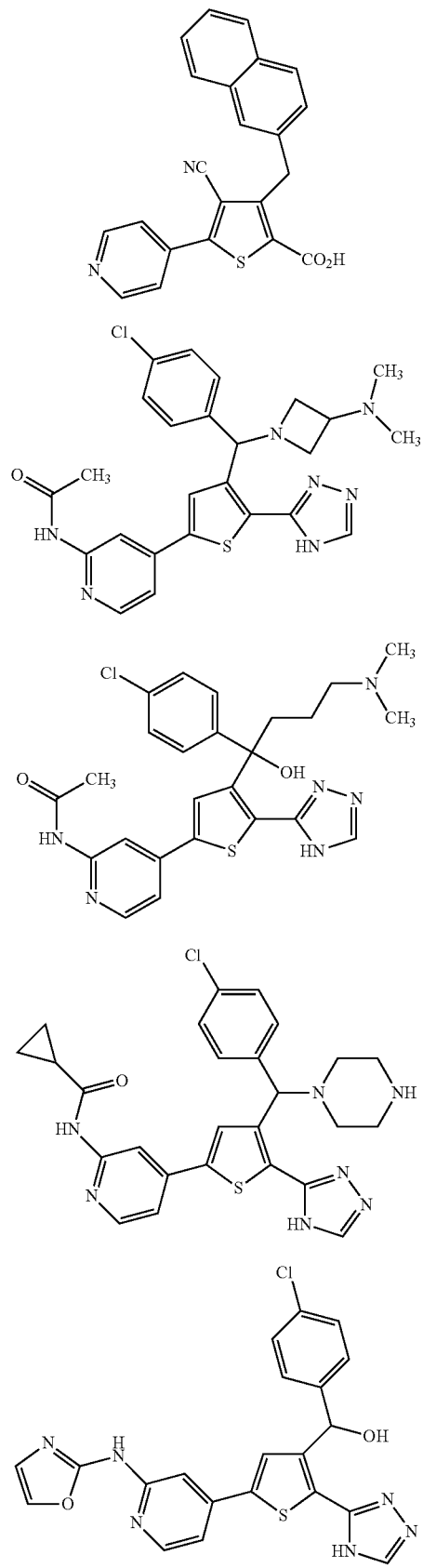
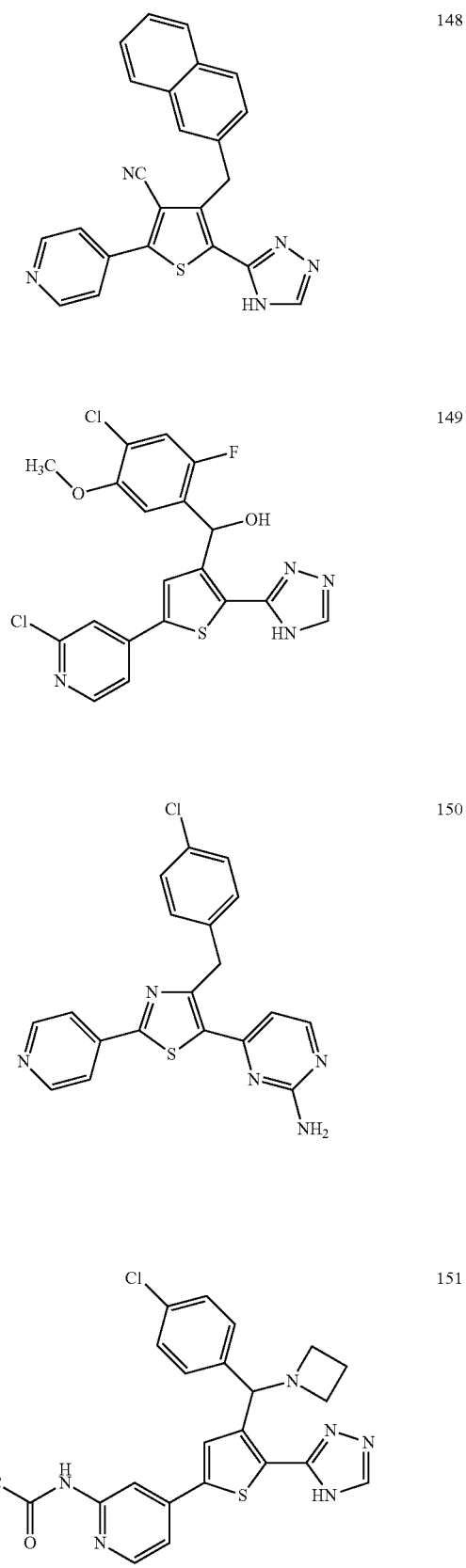

TABLE 1-continued
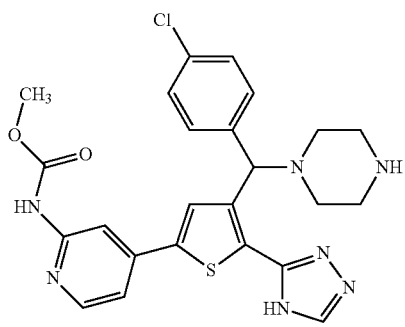 [SMILES: COC(=O)Nc1cc(-c2cc(C(c3ccc(Cl)cc3)N3CCNCC3)c(-c3nnc[nH]3)s2)ccn1]
152
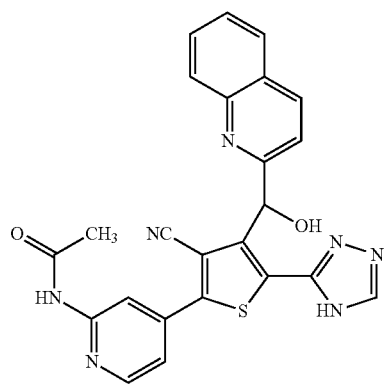 [SMILES: CC(=O)Nc1cc(-c2sc(-c3nnc[nH]3)c(C(O)c3ccc4ccccc4n3)c2C#N)ccn1]
153
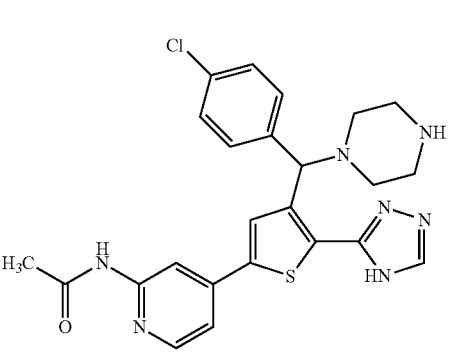 [SMILES: CC(=O)Nc1cc(-c2cc(C(c3ccc(Cl)cc3)N3CCNCC3)c(-c3nnc[nH]3)s2)ccn1]
154
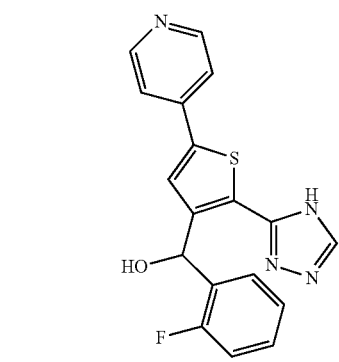 [SMILES: OC(c1ccccc1F)c1cc(-c2ccncc2)sc1-c1nnc[nH]1]
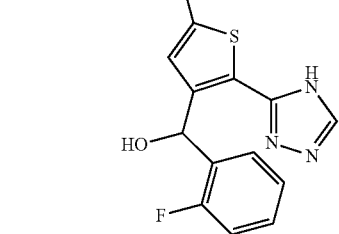
155
TABLE 1-continued
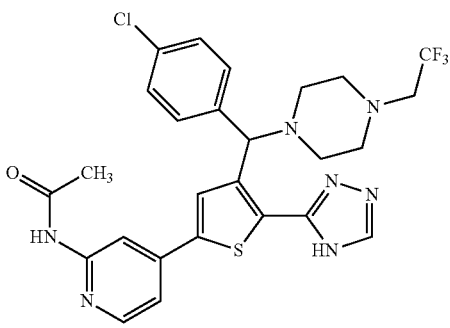 [SMILES: CC(=O)Nc1cc(-c2cc(C(c3ccc(Cl)cc3)N3CCN(CC(F)(F)F)CC3)c(-c3nnc[nH]3)s2)ccn1]
157
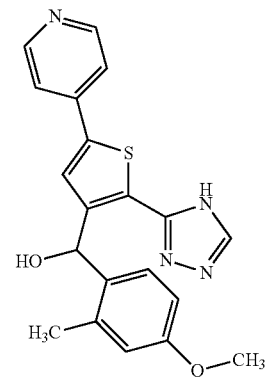 [SMILES: COc1ccc(C(O)c2cc(-c3ccncc3)sc2-c2nnc[nH]2)c(C)c1]
158
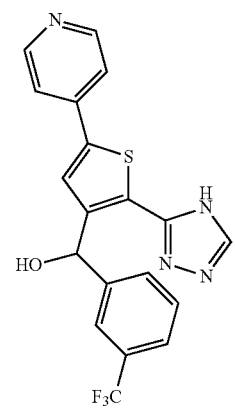 [SMILES: OC(c1cccc(C(F)(F)F)c1)c1cc(-c2ccncc2)sc1-c1nnc[nH]1]
159
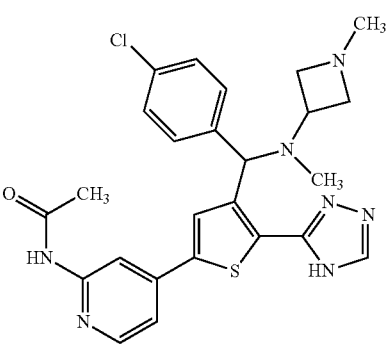 [SMILES: CC(=O)Nc1cc(-c2cc(C(c3ccc(Cl)cc3)N(C)C3CN(C)C3)c(-c3nnc[nH]3)s2)ccn1]
160

TABLE 1-continued
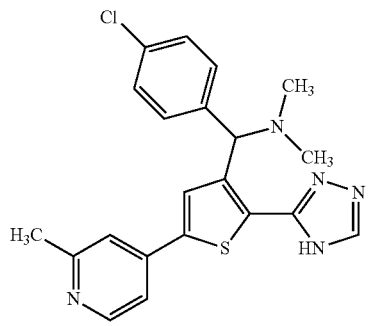
161
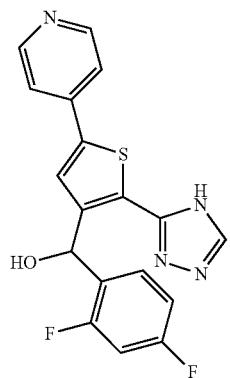 [SMILES: OC(c1ccc(F)cc1F)c1cc(-c2ccncc2)sc1-c1nnc[nH]1]
162
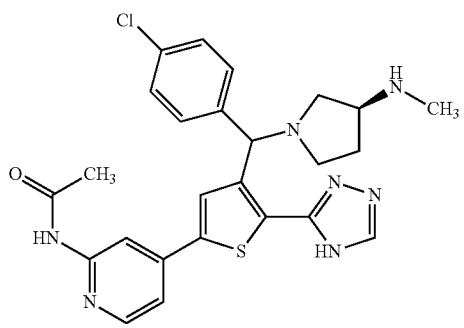 [SMILES: CN[C@H]1CCN(C(c2ccc(Cl)cc2)c2cc(-c3ccnc(NC(C)=O)c3)sc2-c2nnc[nH]2)C1]
163
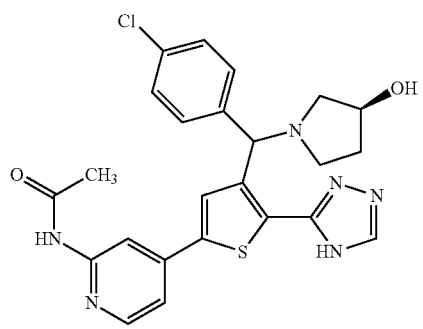 [SMILES: CC(=O)Nc1cc(-c2cc(C(c3ccc(Cl)cc3)N3CC[C@H](O)C3)c(-c3nnc[nH]3)s2)ccn1]
164
TABLE 1-continued
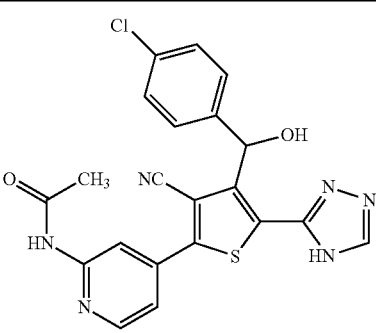
165
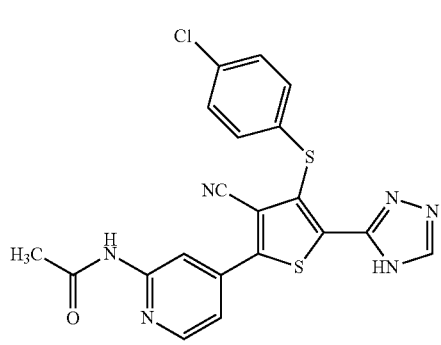 [SMILES: CC(=O)Nc1cc(-c2sc(-c3nnc[nH]3)c(Sc3ccc(Cl)cc3)c2C#N)ccn1]
166
167
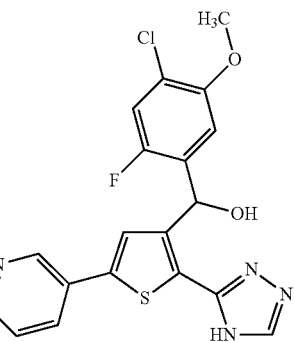
168

TABLE 1-continued
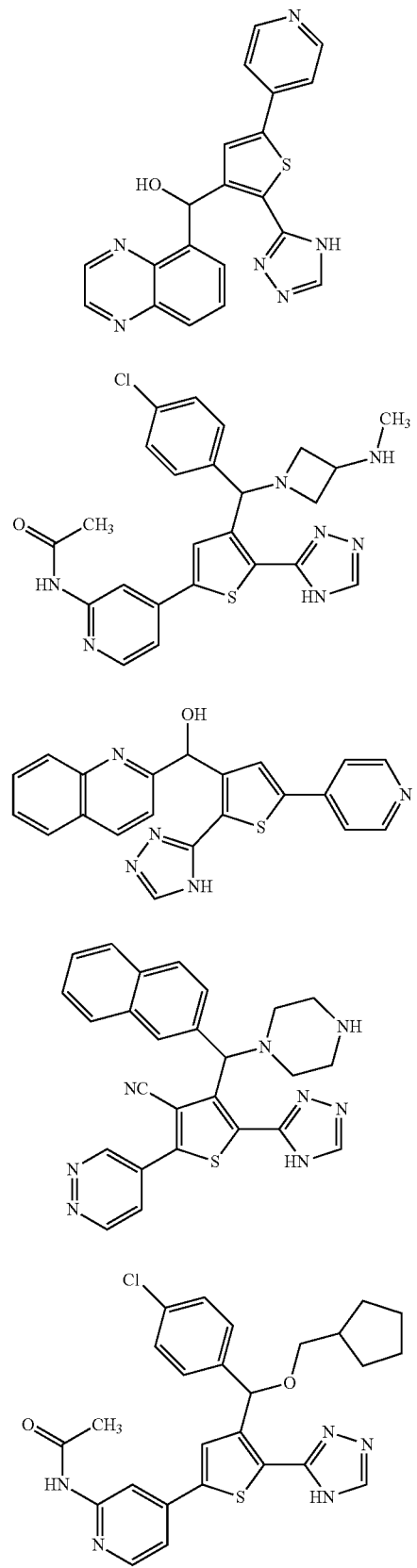
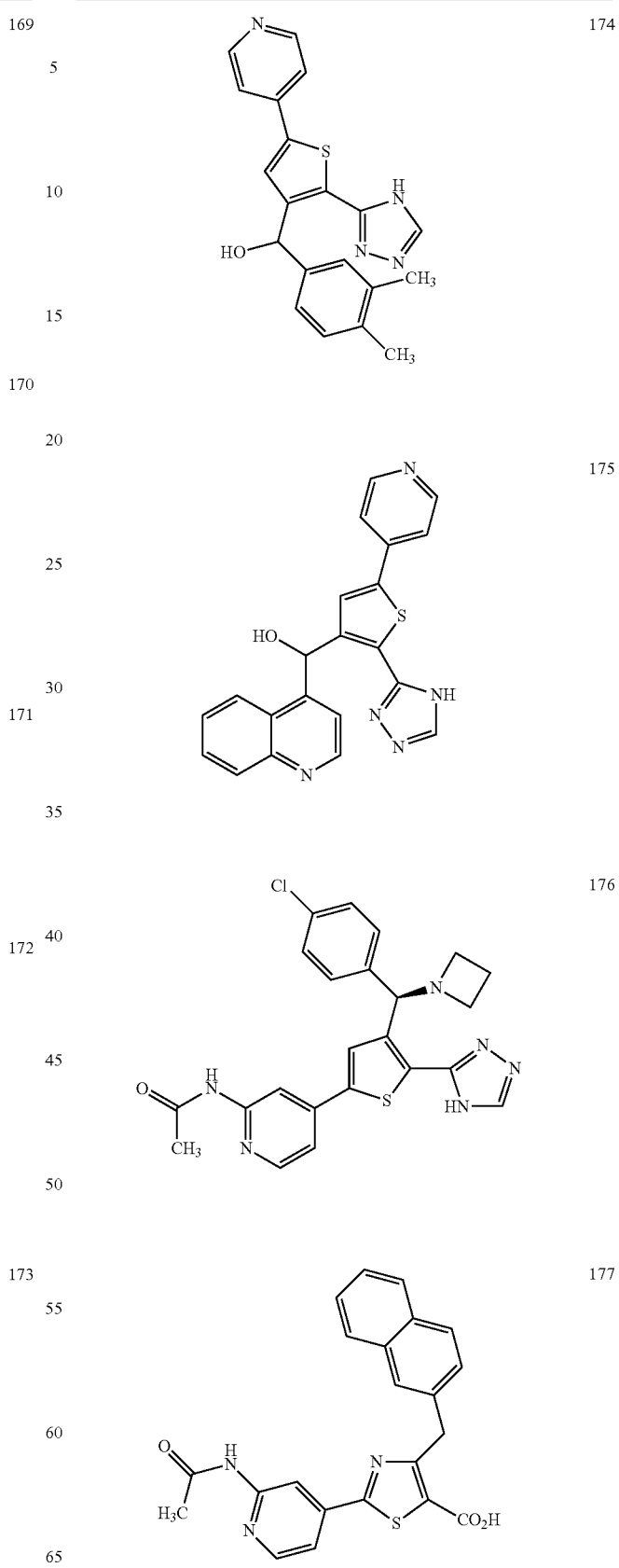

TABLE 1-continued
| 178 | 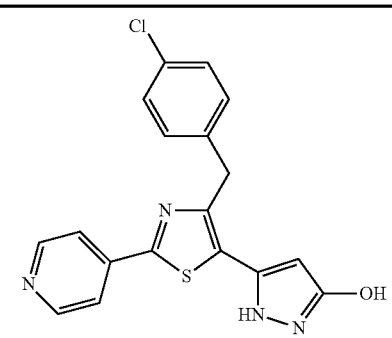 |
| 179 | 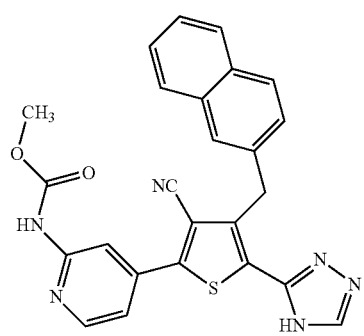 [SMILES: COC(=O)Nc1cc(-c2sc(-c3nnc[nH]3)c(Cc3ccc4ccccc4c3)c2C#N)ccn1] |
| 180 | 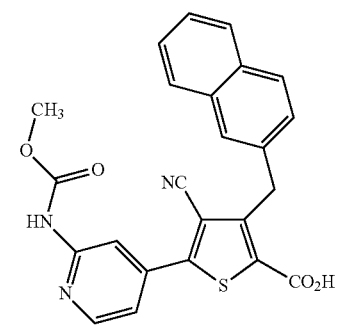 [SMILES: COC(=O)Nc1cc(-c2sc(C(=O)O)c(Cc3ccc4ccccc4c3)c2C#N)ccn1] |
| 181 | 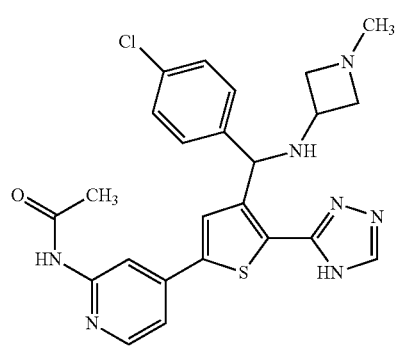 [SMILES: CC(=O)Nc1cc(-c2cc(C(NC3CN(C)C3)c3ccc(Cl)cc3)c(-c3nnc[nH]3)s2)ccn1] |
| 182 | 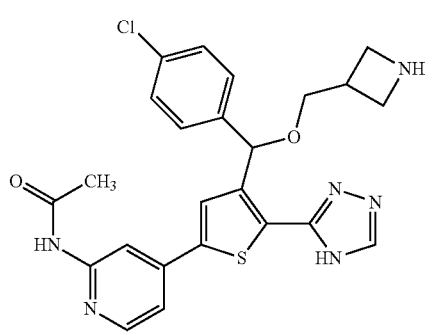 [SMILES: CC(=O)Nc1cc(-c2cc(C(OCC3CNC3)c3ccc(Cl)cc3)c(-c3nnc[nH]3)s2)ccn1] |
TABLE 1-continued
| 183 | 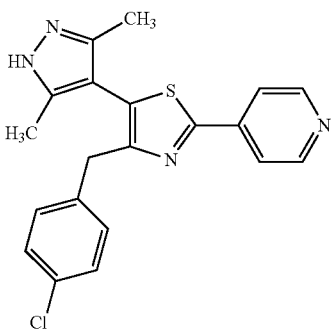 [SMILES: Cc1n[nH]c(C)c1-c1sc(-c2ccncc2)nc1Cc1ccc(Cl)cc1] |
| 184 | 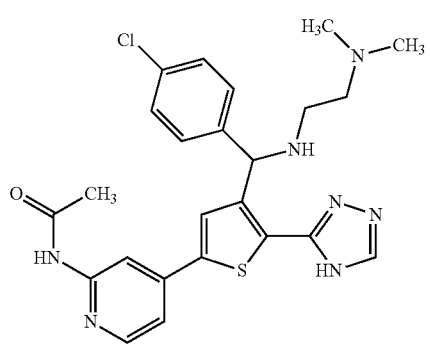 [SMILES: CC(=O)Nc1cc(-c2cc(C(NCCN(C)C)c3ccc(Cl)cc3)c(-c3nnc[nH]3)s2)ccn1] |
| 185 | 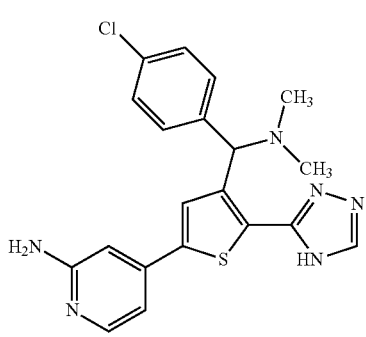 [SMILES: CN(C)C(c1ccc(Cl)cc1)c1cc(-c2ccnc(N)c2)sc1-c1nnc[nH]1] |
| 186 | 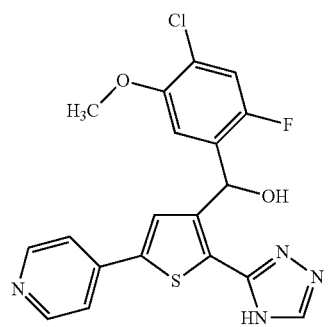 [SMILES: COc1cc(C(O)c2cc(-c3ccncc3)sc2-c2nnc[nH]2)c(F)cc1Cl] |

TABLE 1-continued
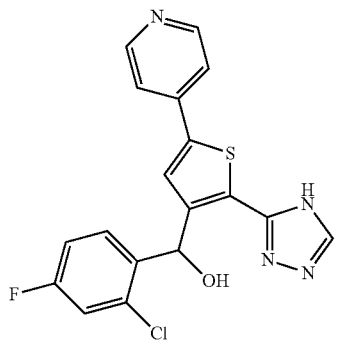 [SMILES: OC(c1ccc(F)cc1Cl)c1cc(-c2ccncc2)sc1-c1nnc[nH]1]
187
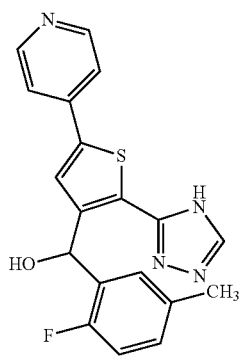 [SMILES: Cc1ccc(F)c(C(O)c2cc(-c3ccncc3)sc2-c2nnc[nH]2)c1]
188
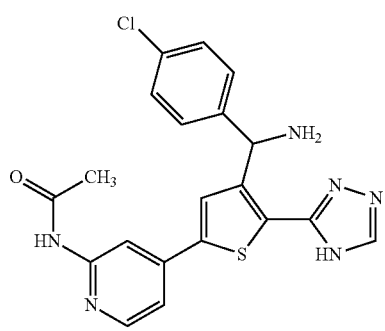 [SMILES: CC(=O)Nc1cc(-c2cc(C(N)c3ccc(Cl)cc3)c(-c3nnc[nH]3)s2)ccn1]
189
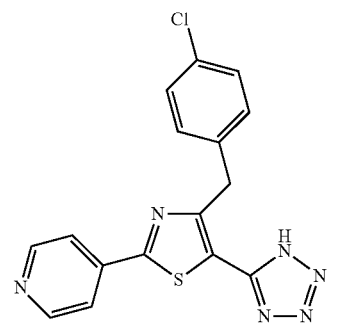 [SMILES: Clc1ccc(Cc2nc(-c3ccncc3)sc2-c2nnn[nH]2)cc1]
190
TABLE 1-continued
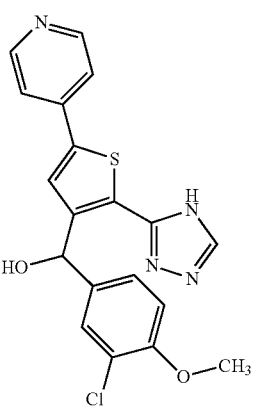 [SMILES: COc1ccc(C(O)c2cc(-c3ccncc3)sc2-c2nnc[nH]2)cc1Cl]
191
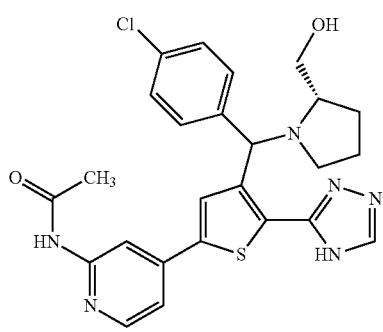 [SMILES: CC(=O)Nc1cc(-c2cc(C(c3ccc(Cl)cc3)N3CCC[C@H]3CO)c(-c3nnc[nH]3)s2)ccn1]
192
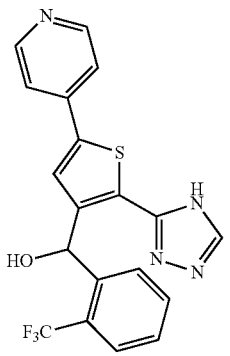 [SMILES: OC(c1ccccc1C(F)(F)F)c1cc(-c2ccncc2)sc1-c1nnc[nH]1]
193
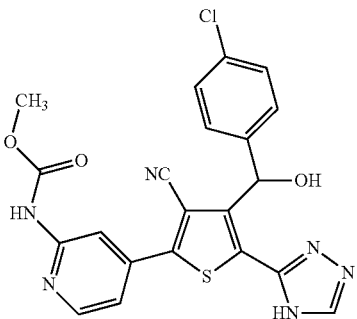 [SMILES: COC(=O)Nc1cc(-c2sc(-c3nnc[nH]3)c(C(O)c3ccc(Cl)cc3)c2C#N)ccn1]
195

TABLE 1-continued
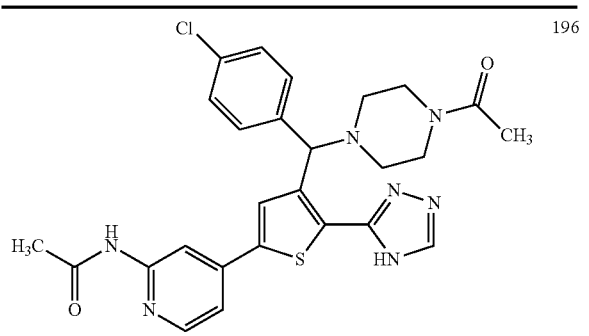 196
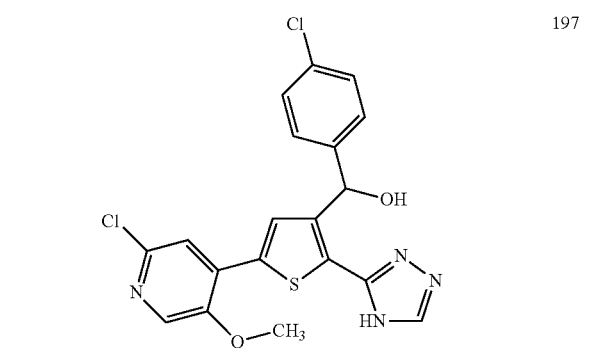 197
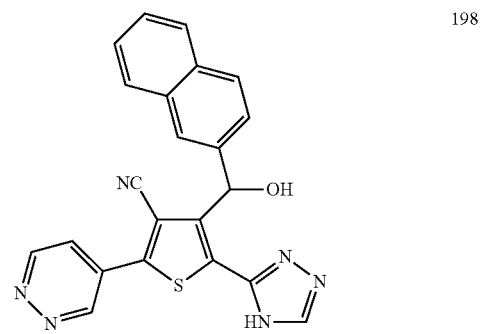 198
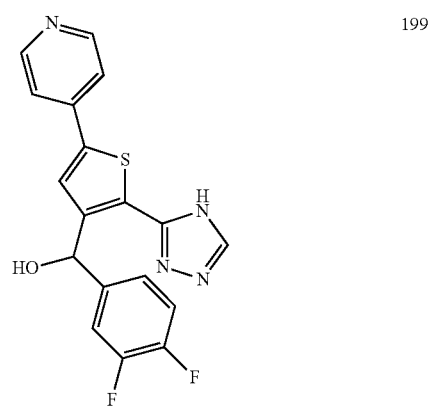 199
TABLE 1-continued
 200
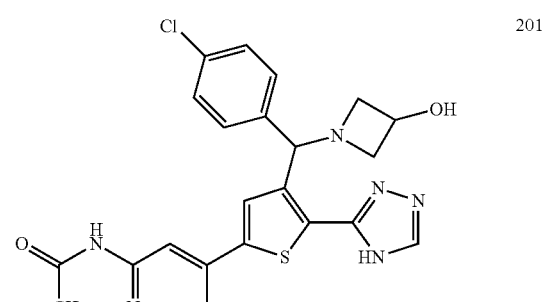 201
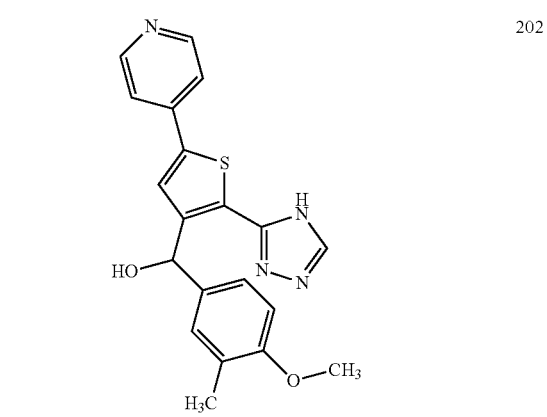 202
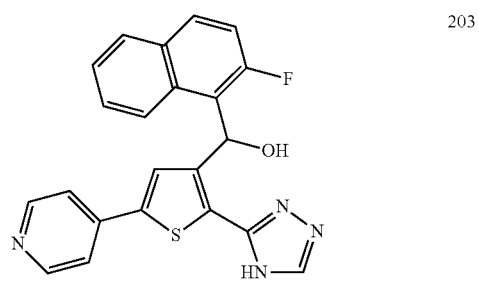 203
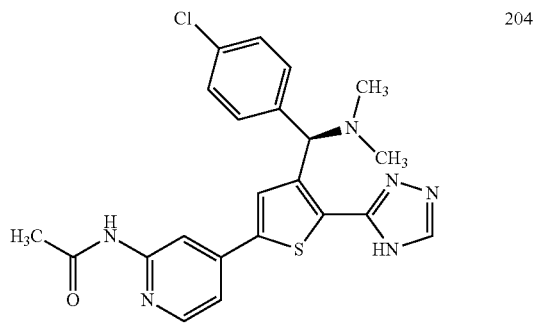 204

TABLE 1-continued
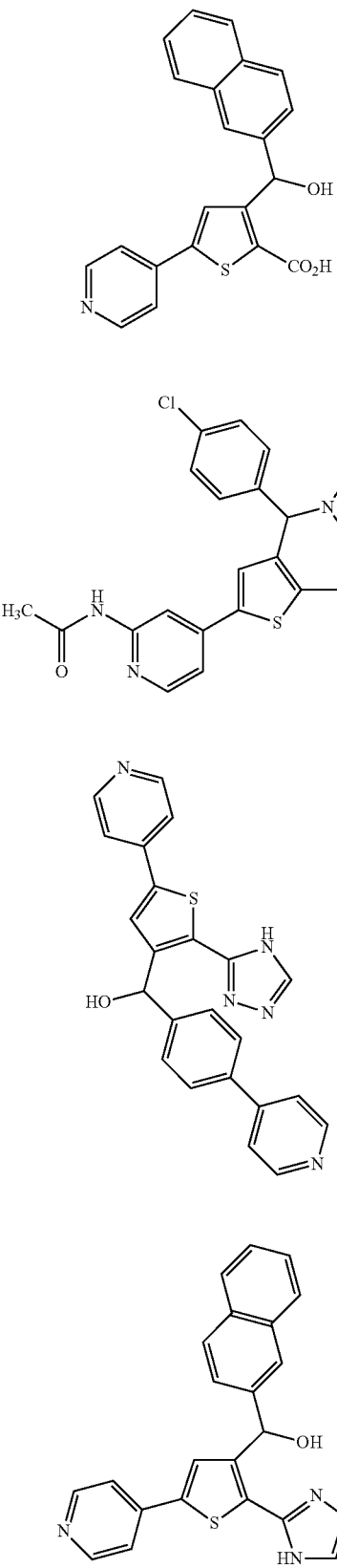
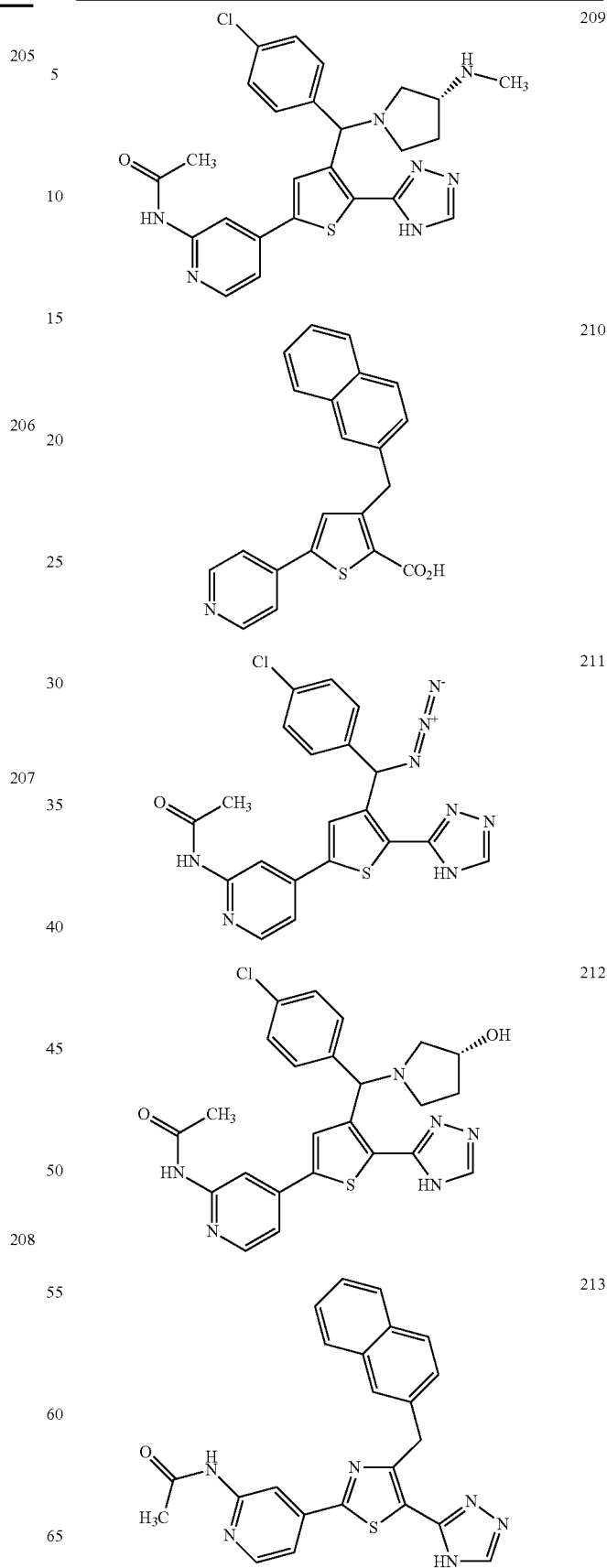

TABLE 1-continued
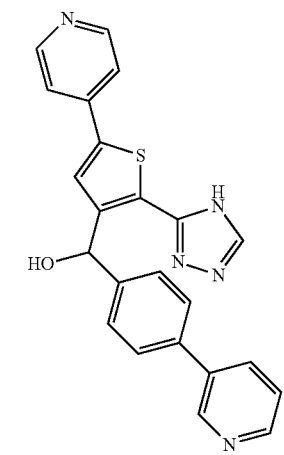 [SMILES: OC(c1ccc(-c2cccnc2)cc1)c1cc(-c2ccncc2)sc1-c1nnc[nH]1] 214
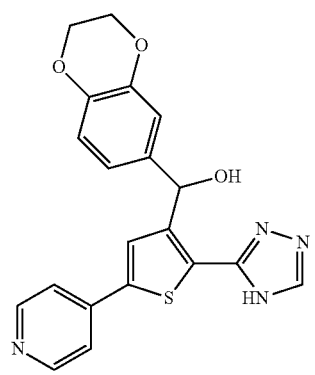 [SMILES: OC(c1ccc2c(c1)OCCO2)c1cc(-c2ccncc2)sc1-c1nnc[nH]1] 215
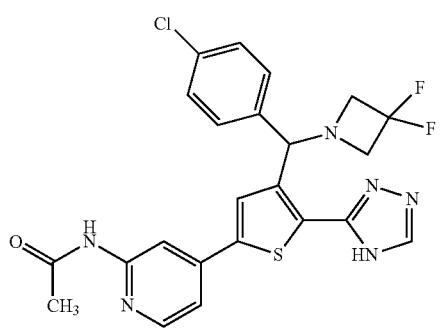 [SMILES: CC(=O)Nc1cc(-c2cc(C(c3ccc(Cl)cc3)N3CC(F)(F)C3)c(-c3nnc[nH]3)s2)ccn1] 216
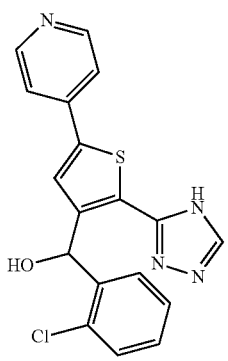 [SMILES: OC(c1ccccc1Cl)c1cc(-c2ccncc2)sc1-c1nnc[nH]1] 217
TABLE 1-continued
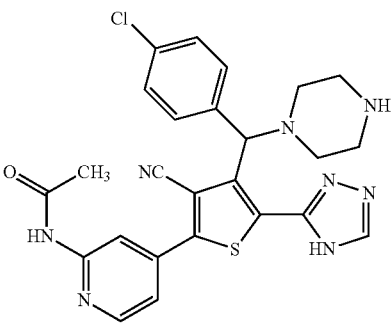 [SMILES: CC(=O)Nc1cc(-c2sc(-c3nnc[nH]3)c(C(c3ccc(Cl)cc3)N3CCNCC3)c2C#N)ccn1] 218
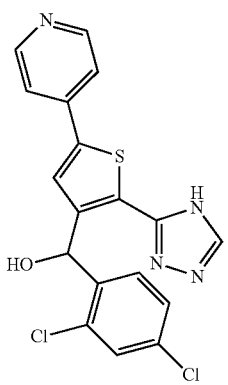 [SMILES: OC(c1ccc(Cl)cc1Cl)c1cc(-c2ccncc2)sc1-c1nnc[nH]1] 219
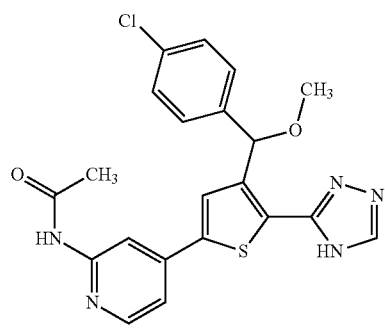 [SMILES: COC(c1ccc(Cl)cc1)c1cc(-c2ccnc(NC(C)=O)c2)sc1-c1nnc[nH]1] 220
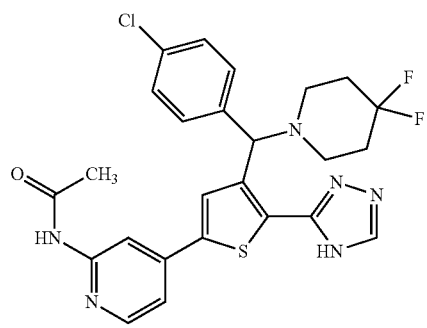 [SMILES: CC(=O)Nc1cc(-c2cc(C(c3ccc(Cl)cc3)N3CCC(F)(F)CC3)c(-c3nnc[nH]3)s2)ccn1] 221

TABLE 1-continued
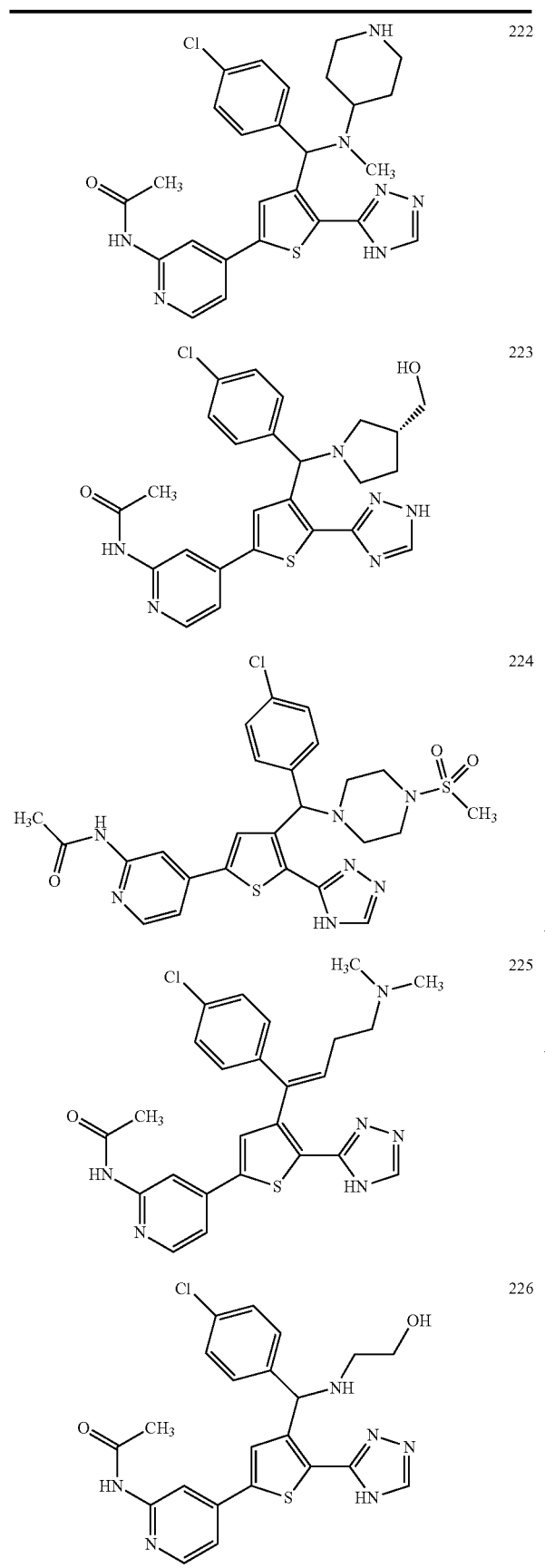
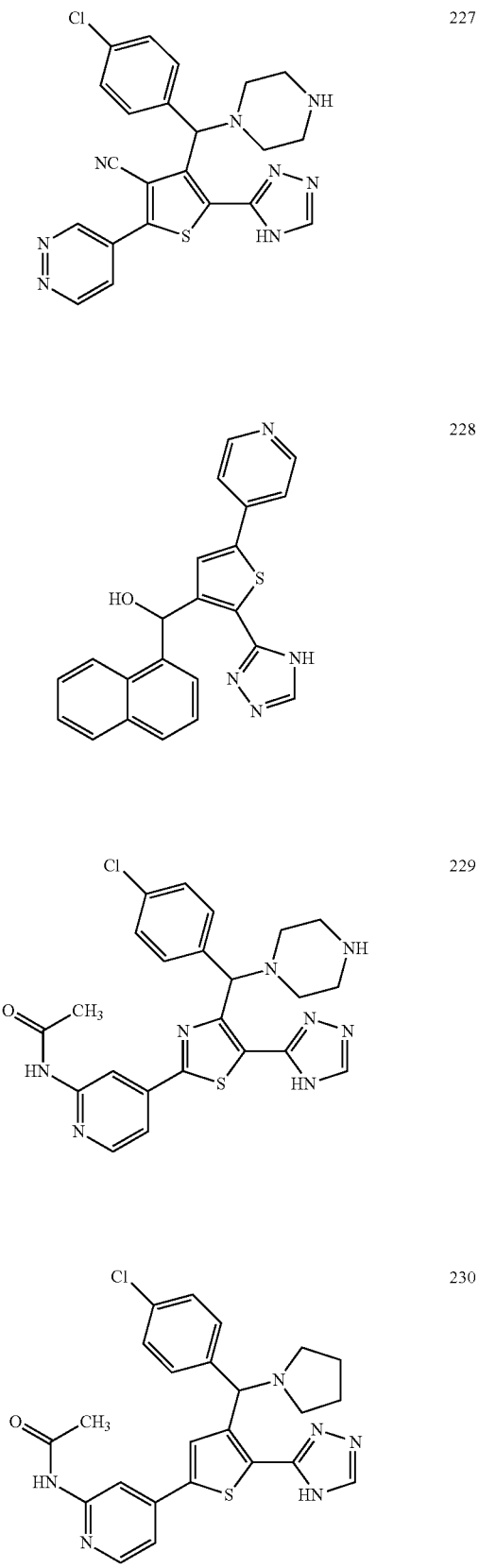

TABLE 1-continued
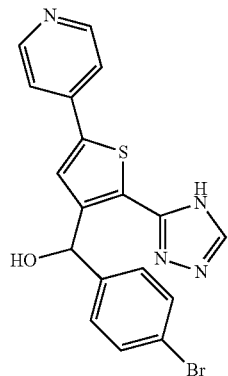 [SMILES: OC(c1ccc(Br)cc1)c1cc(-c2ccncc2)sc1-c1nnc[nH]1] 231
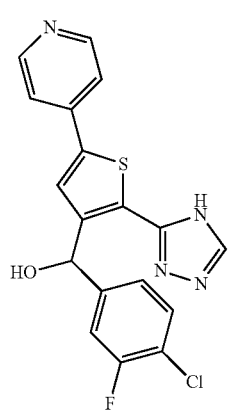 [SMILES: OC(c1ccc(Cl)c(F)c1)c1cc(-c2ccncc2)sc1-c1nnc[nH]1] 232
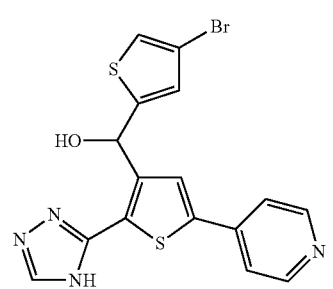 [SMILES: OC(c1cc(Br)cs1)c1cc(-c2ccncc2)sc1-c1nnc[nH]1] 233
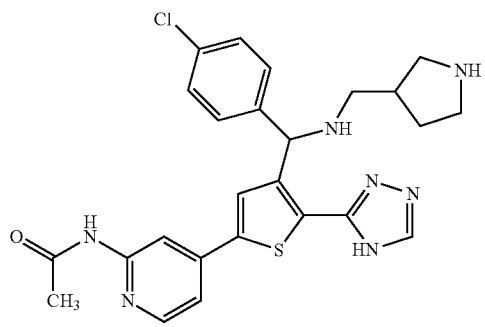 [SMILES: CC(=O)Nc1cc(-c2cc(C(NCC3CCNC3)c3ccc(Cl)cc3)c(-c3nnc[nH]3)s2)ccn1] 234
TABLE 1-continued
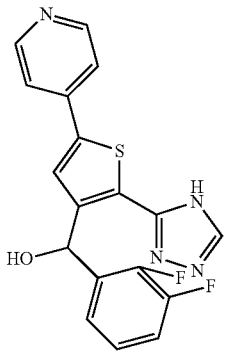 [SMILES: OC(c1cc(-c2ccncc2)sc1-c1nnc[nH]1)c1cccc(F)c1F] 235
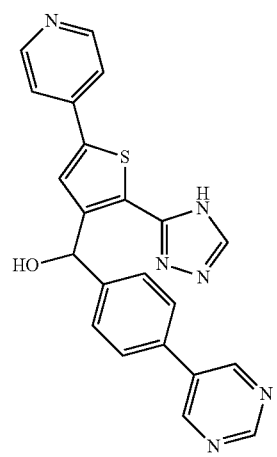 [SMILES: OC(c1ccc(-c2cncnc2)cc1)c1cc(-c2ccncc2)sc1-c1nnc[nH]1] 236
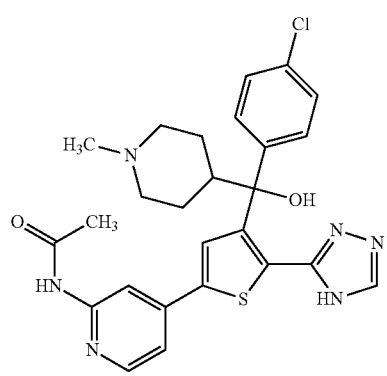 [SMILES: CC(=O)Nc1cc(-c2cc(C(O)(c3ccc(Cl)cc3)C3CCN(C)CC3)c(-c3nnc[nH]3)s2)ccn1] 237
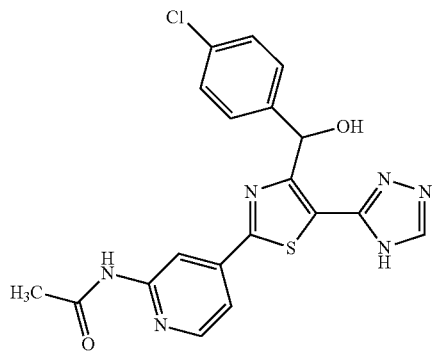 [SMILES: CC(=O)Nc1cc(-c2nc(C(O)c3ccc(Cl)cc3)c(-c3nnc[nH]3)s2)ccn1] 238

TABLE 1-continued
239 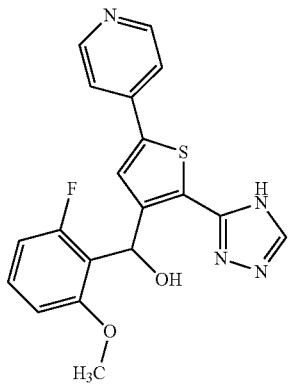 [SMILES: COc1cccc(F)c1C(O)c1cc(-c2ccncc2)sc1-c1nnc[nH]1]
240 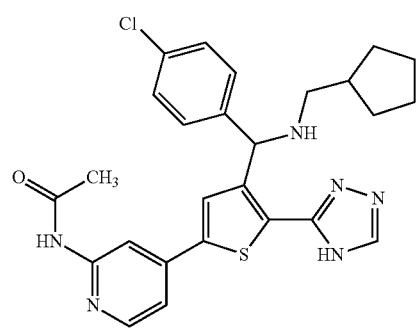 [SMILES: CC(=O)Nc1cc(-c2cc(C(NCC3CCCC3)c3ccc(Cl)cc3)c(-c3nnc[nH]3)s2)ccn1]
241 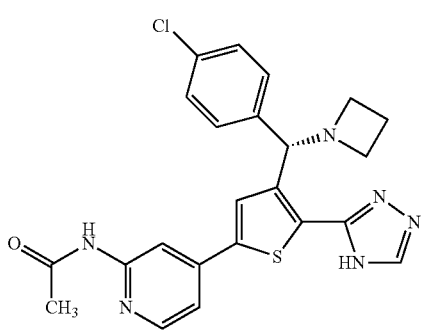 [SMILES: CC(=O)Nc1cc(-c2cc([C@H](c3ccc(Cl)cc3)N3CCC3)c(-c3nnc[nH]3)s2)ccn1]
242 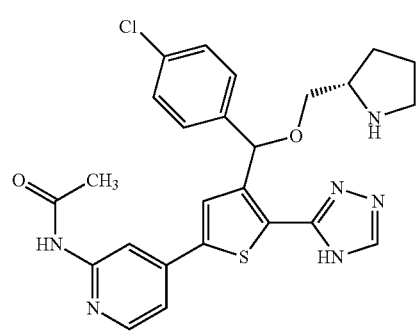 [SMILES: CC(=O)Nc1cc(-c2cc(C(OC[C@@H]3CCCN3)c3ccc(Cl)cc3)c(-c3nnc[nH]3)s2)ccn1]
TABLE 1-continued
243 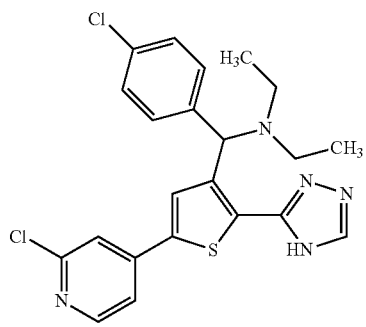 [SMILES: CCN(CC)C(c1ccc(Cl)cc1)c1cc(-c2ccnc(Cl)c2)sc1-c1nnc[nH]1]
244 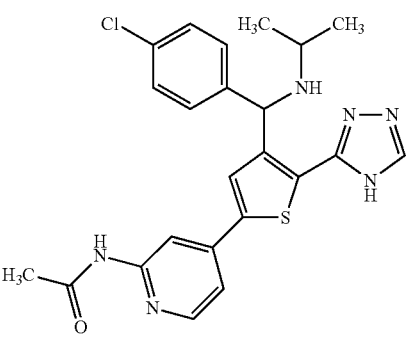 [SMILES: CC(=O)Nc1cc(-c2cc(C(NC(C)C)c3ccc(Cl)cc3)c(-c3nnc[nH]3)s2)ccn1]
245 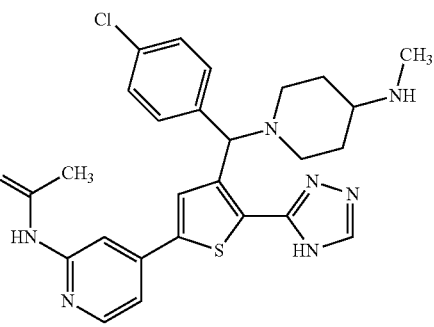
246 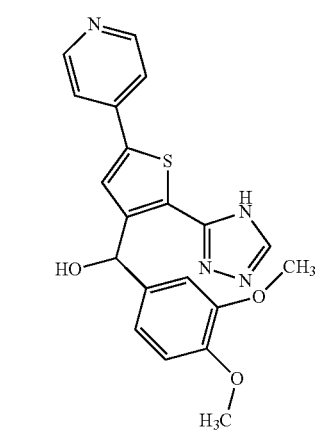 [SMILES: COc1ccc(C(O)c2cc(-c3ccncc3)sc2-c2nnc[nH]2)cc1OC]

TABLE 1-continued
247
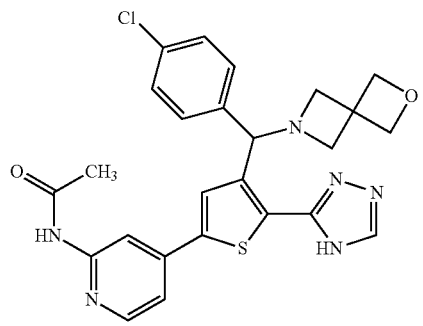 [SMILES: CC(=O)Nc1cc(-c2cc(C(c3ccc(Cl)cc3)N3CC4(COC4)C3)c(-c3nnc[nH]3)s2)ccn1]
248
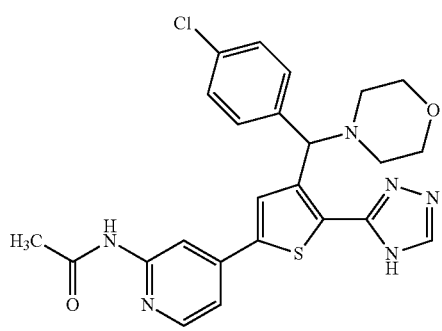 [SMILES: CC(=O)Nc1cc(-c2cc(C(c3ccc(Cl)cc3)N3CCOCC3)c(-c3nnc[nH]3)s2)ccn1]
249
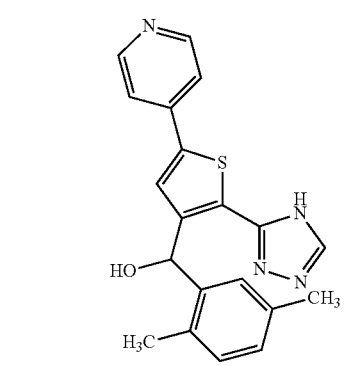 [SMILES: Cc1ccc(C)c(C(O)c2cc(-c3ccncc3)sc2-c2nnc[nH]2)c1]
250
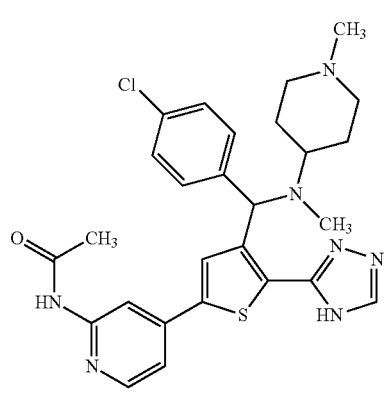 [SMILES: CC(=O)Nc1cc(-c2cc(C(c3ccc(Cl)cc3)N(C)C3CCN(C)CC3)c(-c3nnc[nH]3)s2)ccn1]
251
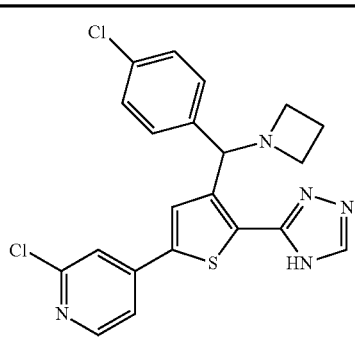
252
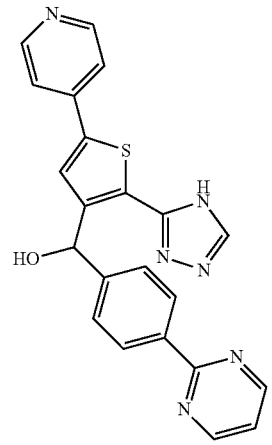 [SMILES: OC(c1ccc(-c2ncccn2)cc1)c1cc(-c2ccncc2)sc1-c1nnc[nH]1]
253
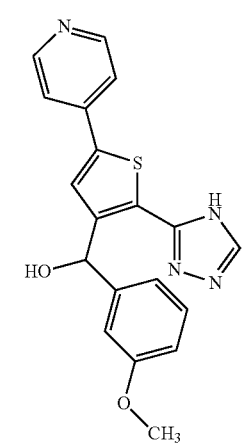 [SMILES: COc1cccc(C(O)c2cc(-c3ccncc3)sc2-c2nnc[nH]2)c1]
254
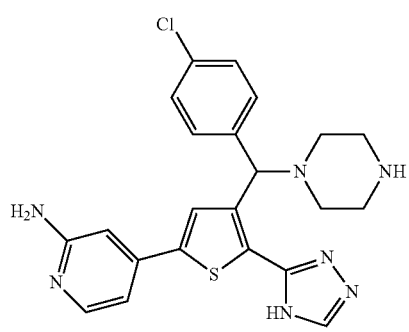 [SMILES: Nc1cc(-c2cc(C(c3ccc(Cl)cc3)N3CCNCC3)c(-c3nnc[nH]3)s2)ccn1]

TABLE 1-continued
255 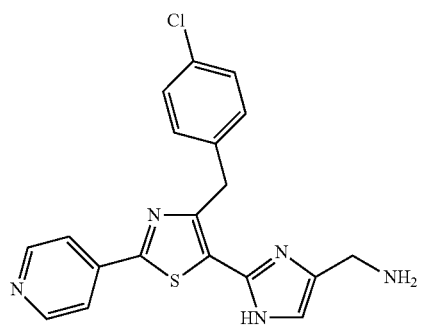 [SMILES: NCc1c[nH]c(-c2sc(-c3ccncc3)nc2Cc2ccc(Cl)cc2)n1]
256 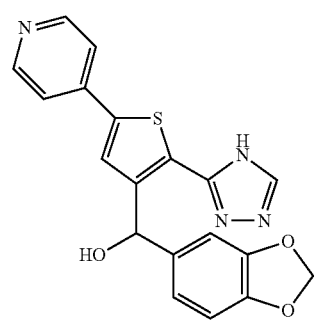 [SMILES: OC(c1ccc2c(c1)OCO2)c1cc(-c2ccncc2)sc1-c1nnc[nH]1]
257 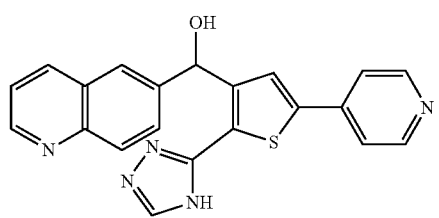 [SMILES: OC(c1ccc2ncccc2c1)c1cc(-c2ccncc2)sc1-c1nnc[nH]1]
258 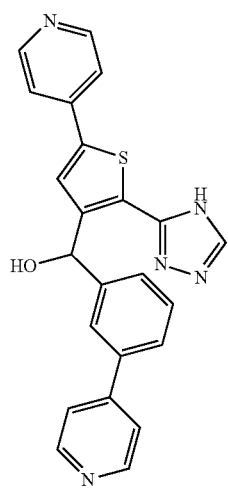 [SMILES: OC(c1cccc(-c2ccncc2)c1)c1cc(-c2ccncc2)sc1-c1nnc[nH]1]
TABLE 1-continued
259 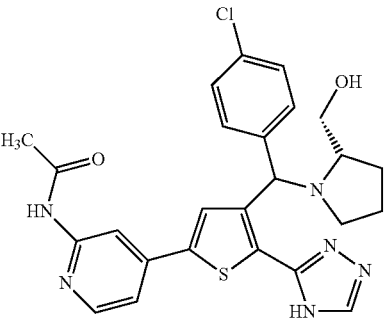
260 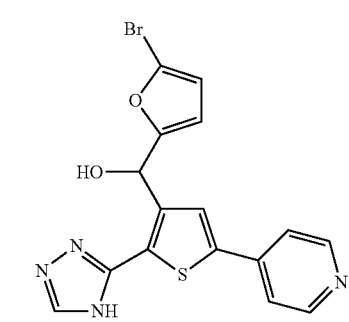 [SMILES: OC(c1ccc(Br)o1)c1cc(-c2ccncc2)sc1-c1nnc[nH]1]
261 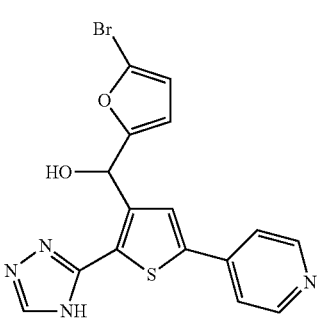
262 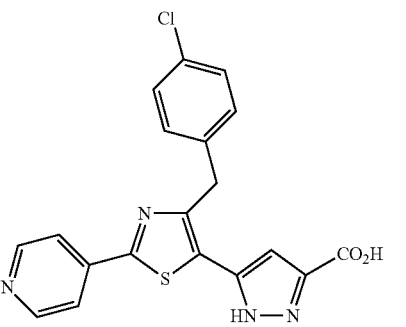 [SMILES: O=C(O)c1cc(-c2sc(-c3ccncc3)nc2Cc2ccc(Cl)cc2)[nH]n1]
263 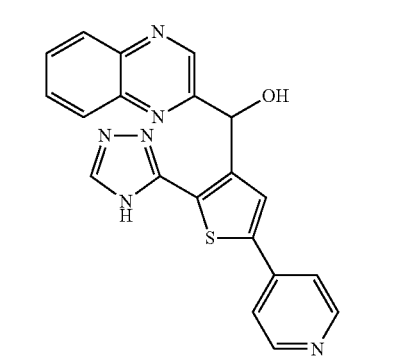 [SMILES: OC(c1cnc2ccccc2n1)c1cc(-c2ccncc2)sc1-c1nnc[nH]1]

TABLE 1-continued
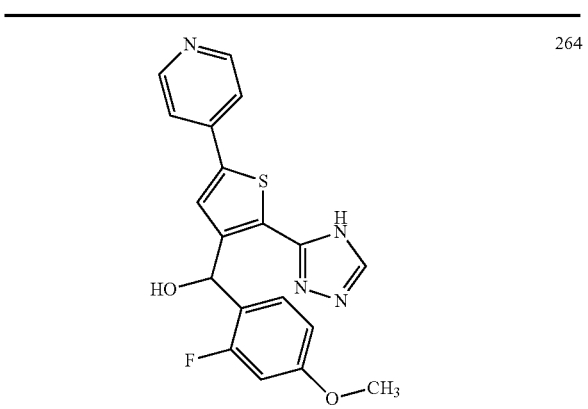
264
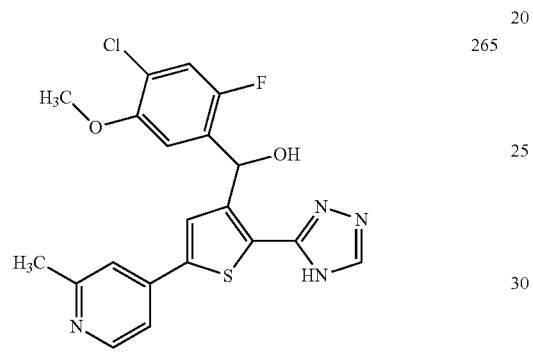
265
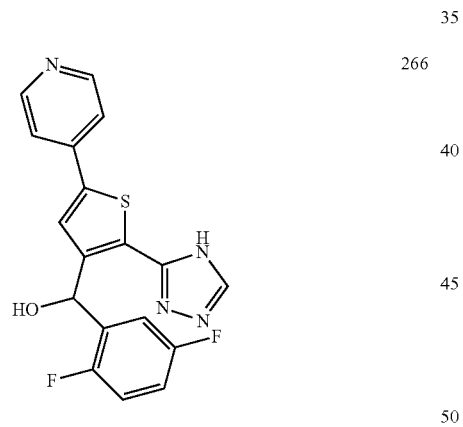
266
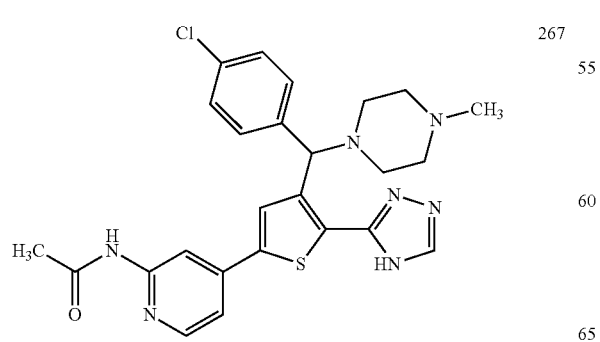
267
TABLE 1-continued
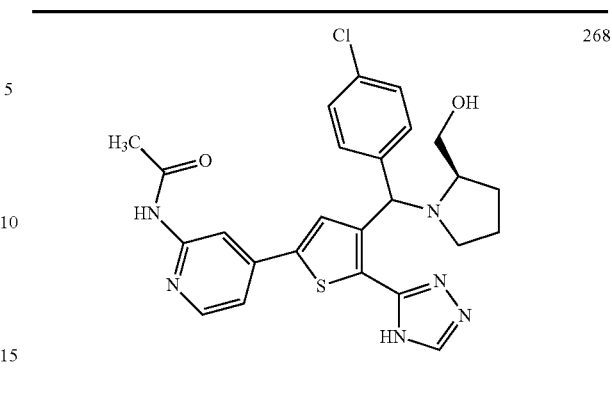
268
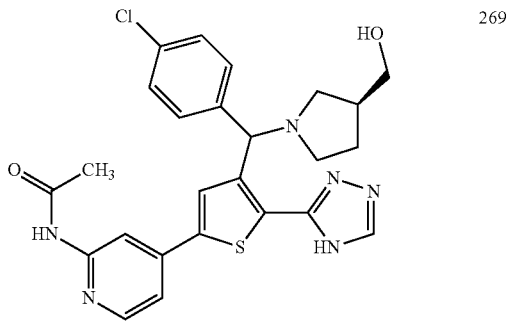
269
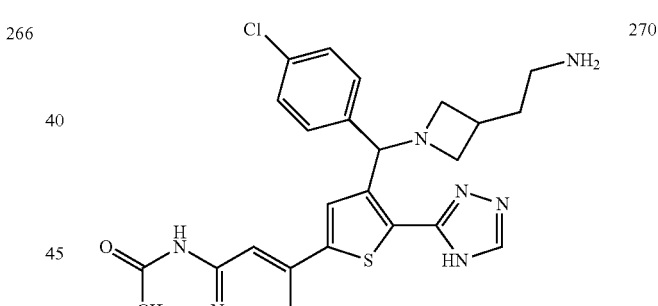
270
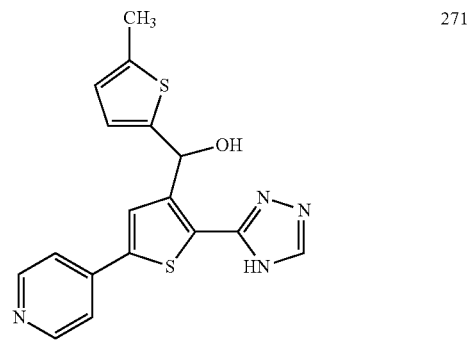
271

TABLE 1-continued
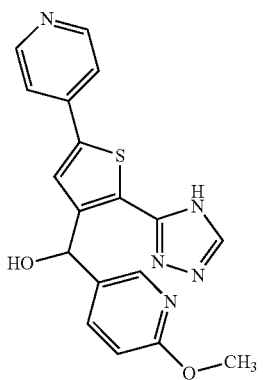 [SMILES: COc1ccc(C(O)c2cc(-c3ccncc3)sc2-c2nnc[nH]2)cn1] 272
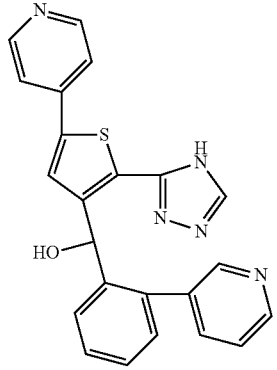 276
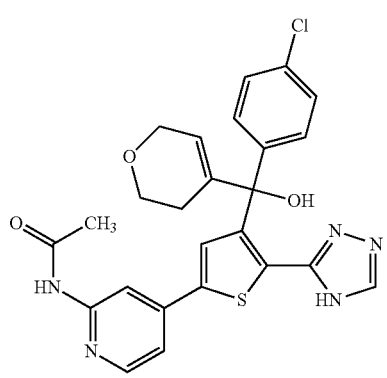 [SMILES: CC(=O)Nc1cc(-c2cc(C(O)(C3=CCOCC3)c3ccc(Cl)cc3)c(-c3nnc[nH]3)s2)ccn1] 273
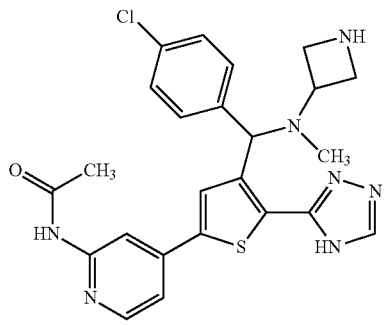 [SMILES: CC(=O)Nc1cc(-c2cc(C(c3ccc(Cl)cc3)N(C)C3CNC3)c(-c3nnc[nH]3)s2)ccn1] 277
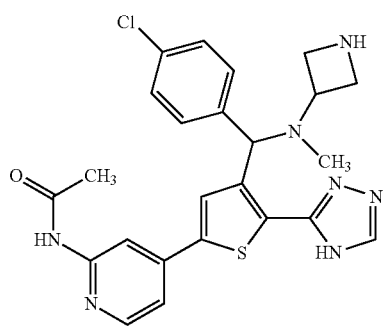 [SMILES: CC(=O)Nc1cc(-c2cc(C(c3ccc(Cl)cc3)N(C)C3CNC3)c(-c3nnc[nH]3)s2)ccn1] 274
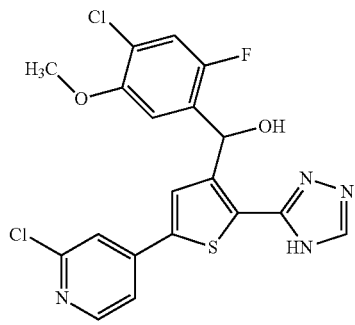 [SMILES: COc1cc(C(O)c2cc(-c3ccnc(Cl)c3)sc2-c2nnc[nH]2)c(F)cc1Cl] 278
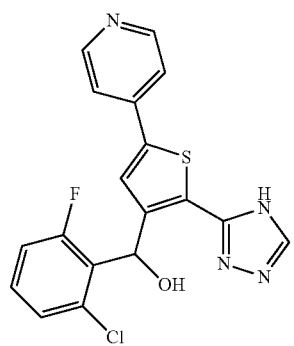 275
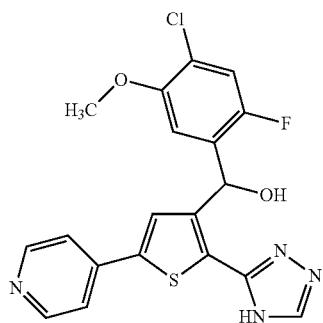 [SMILES: COc1cc(C(O)c2cc(-c3ccncc3)sc2-c2nnc[nH]2)c(F)cc1Cl] 279

TABLE 1-continued
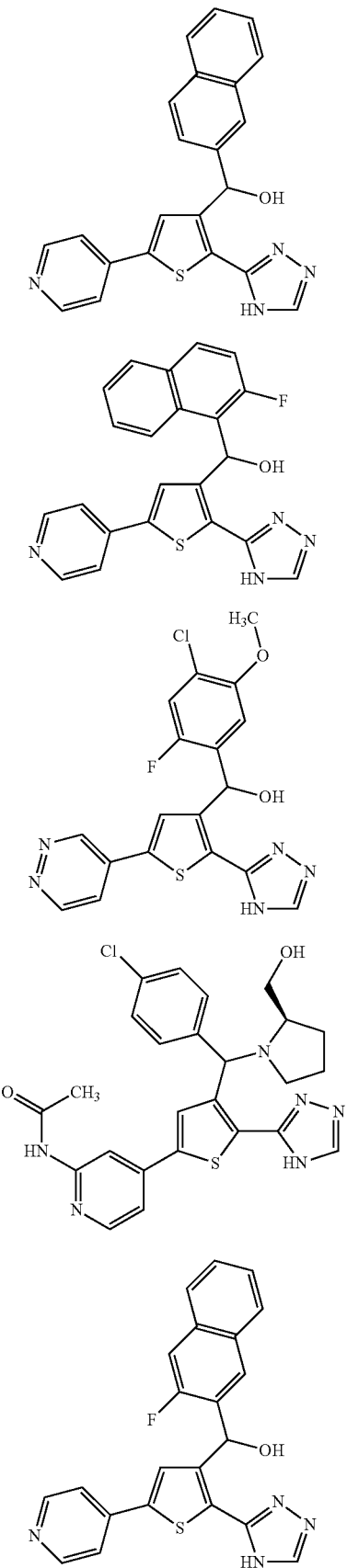
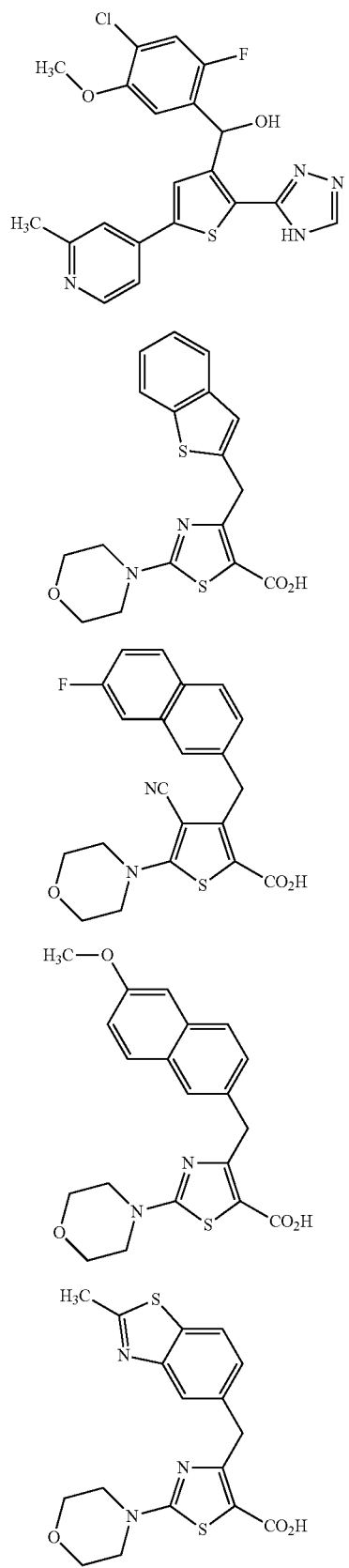

TABLE 1-continued
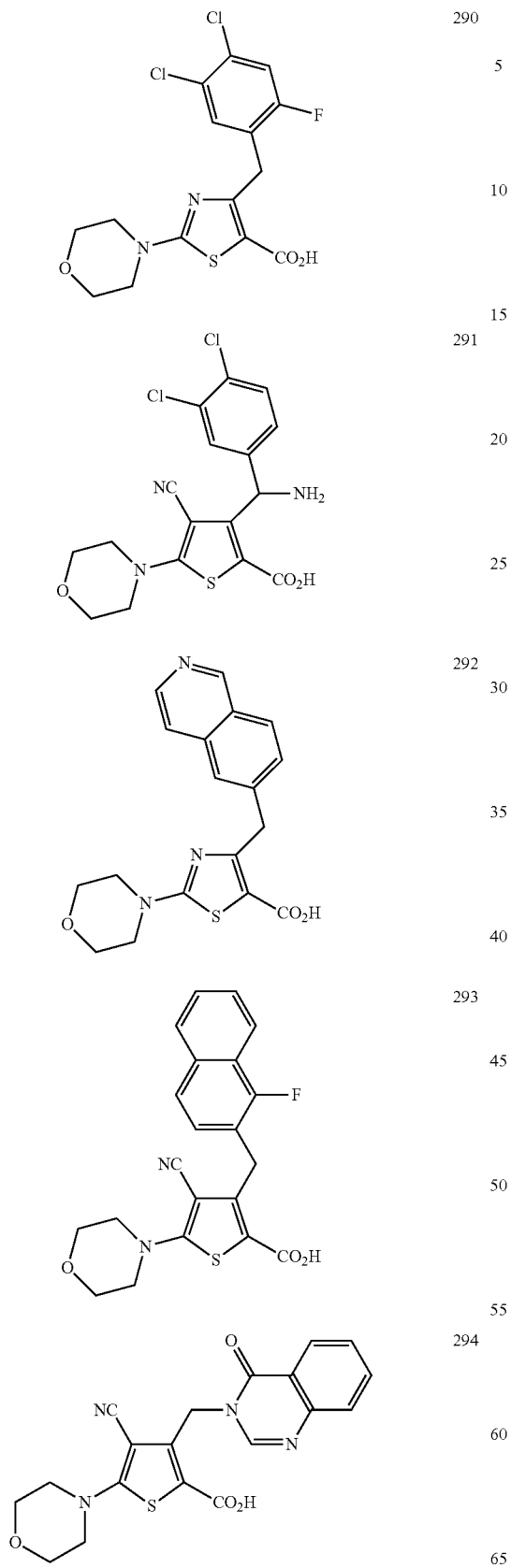
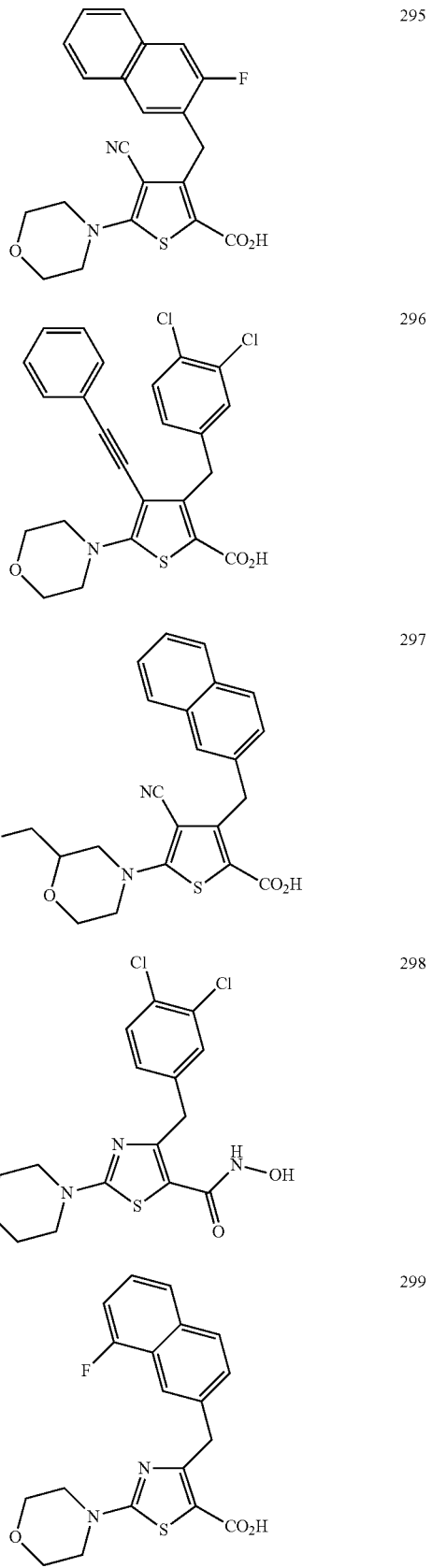

TABLE 1-continued
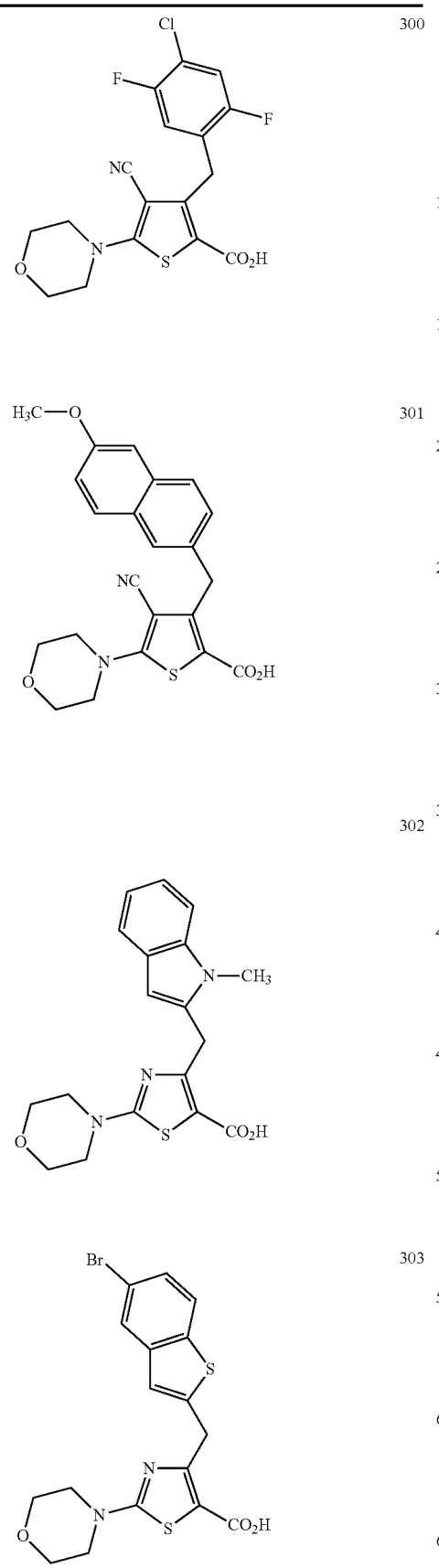
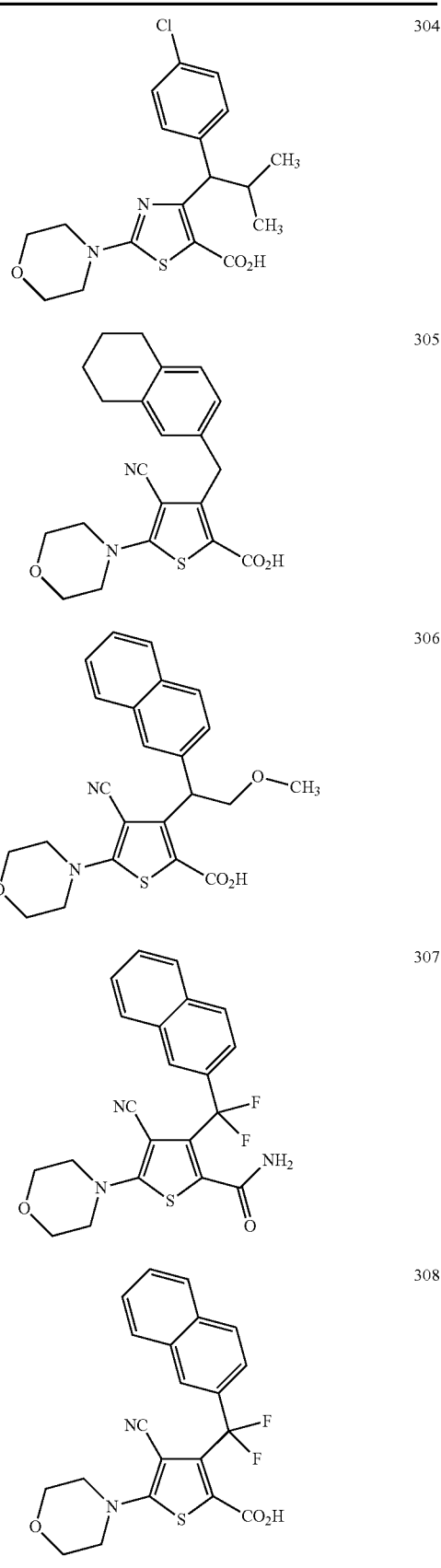

TABLE 1-continued
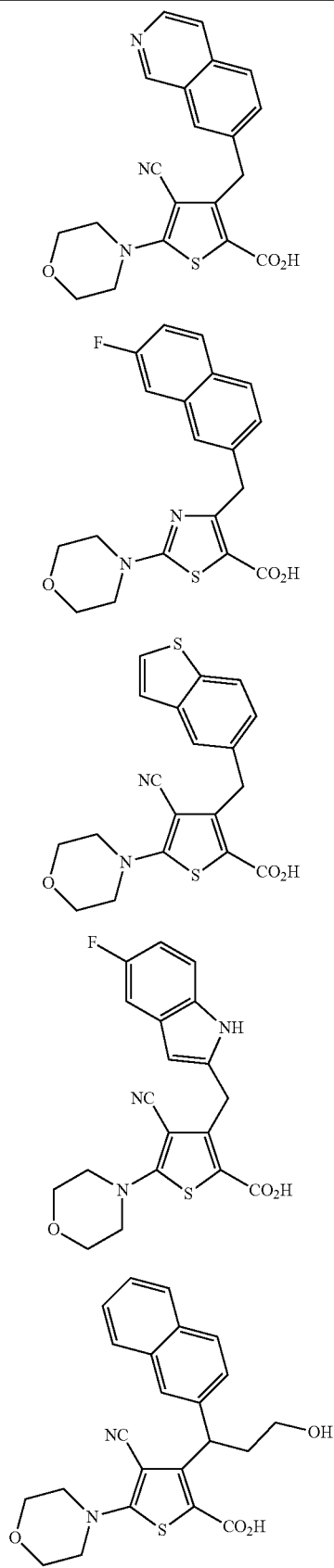
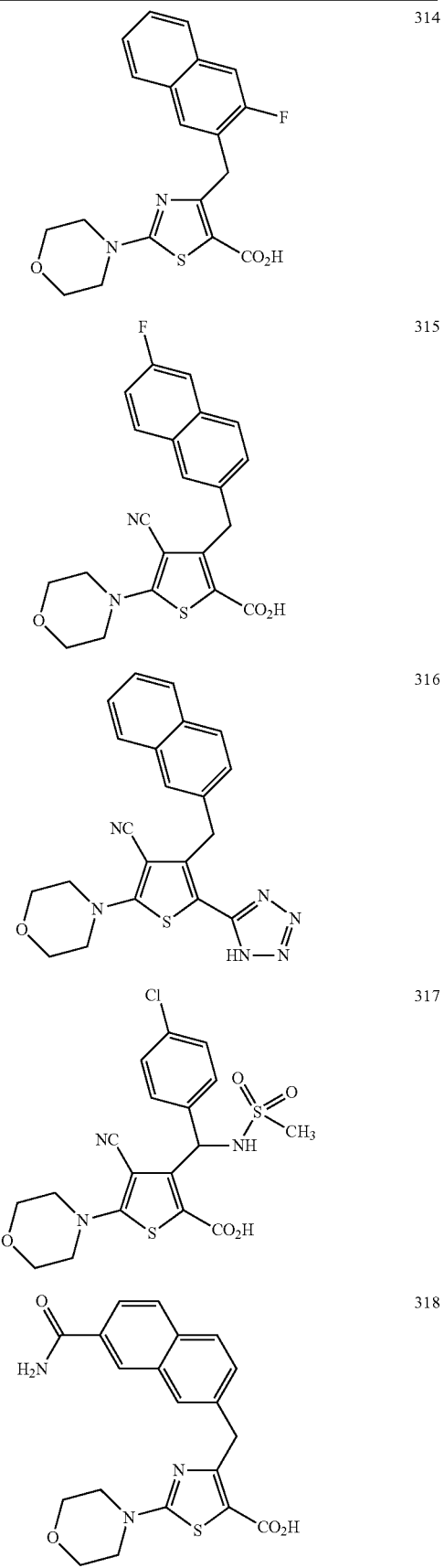

203
TABLE 1-continued
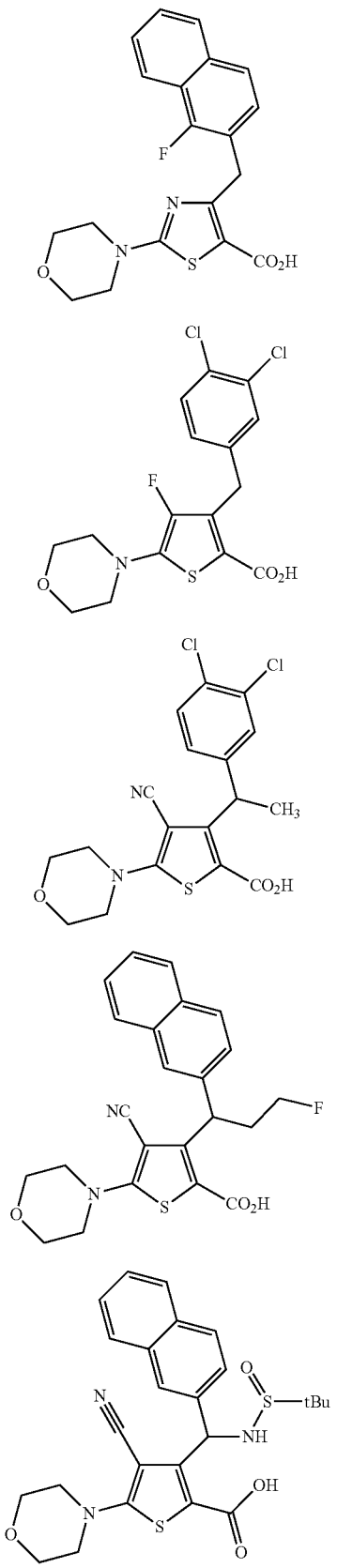
| | |
|---|---|
| 319 | |
| 320 | |
| 321 | |
| 322 | |
| 323 | |
204
TABLE 1-continued
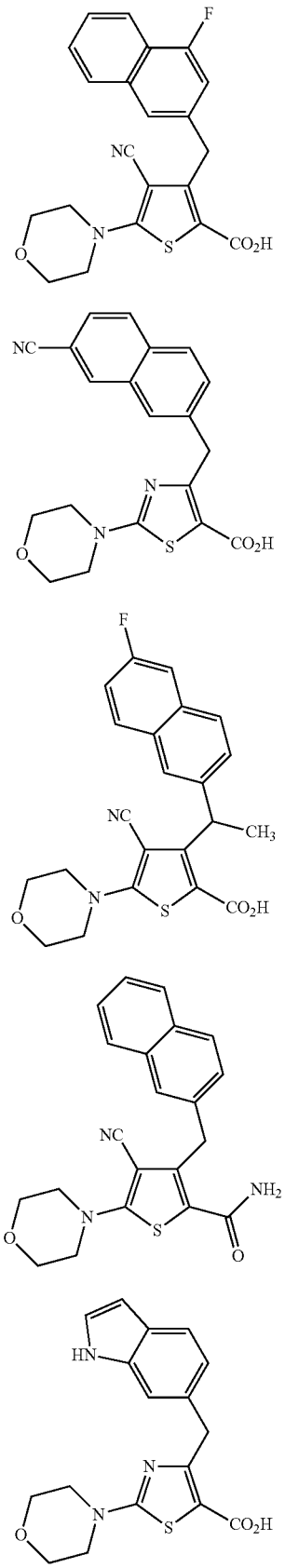
| | |
|---|---|
| 324 | |
| 325 | |
| 326 | |
| 327 | |
| 328 | |

TABLE 1-continued
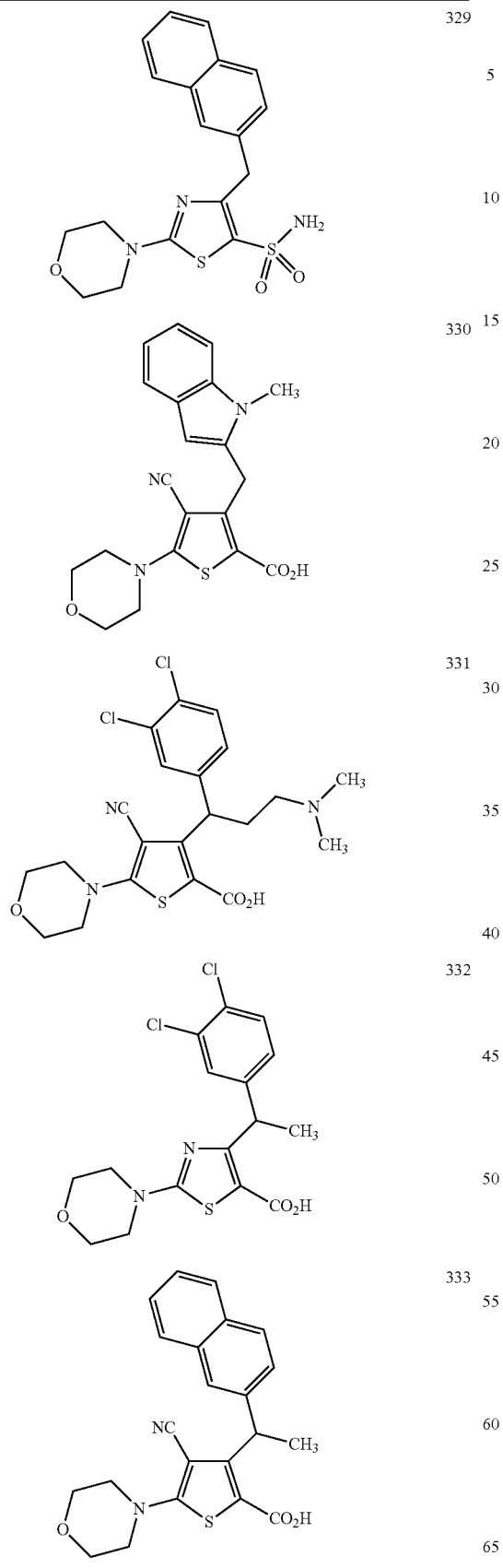
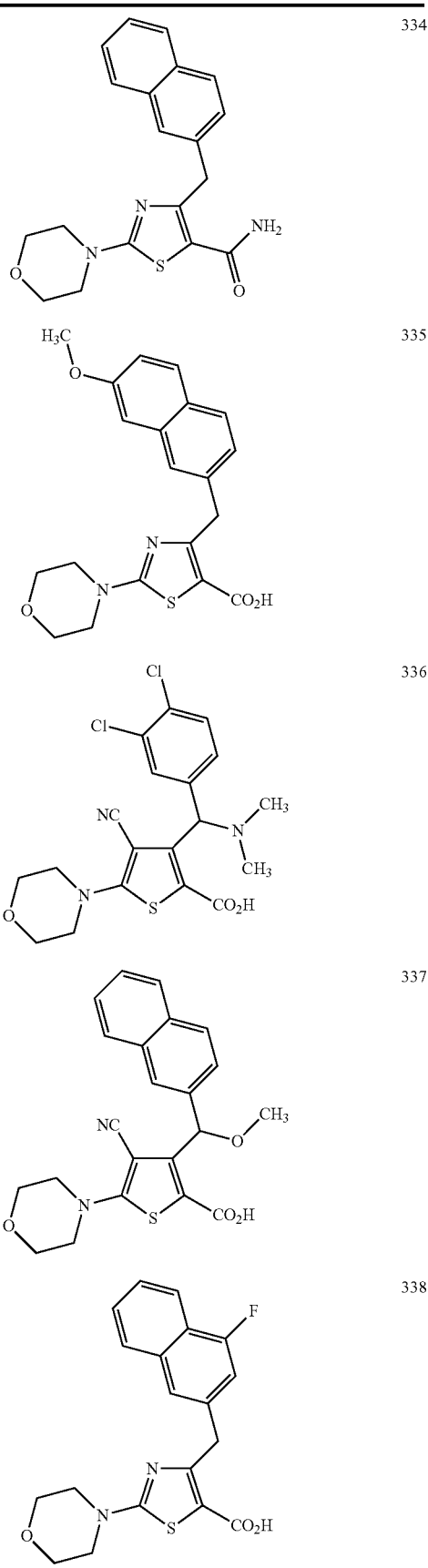

TABLE 1-continued
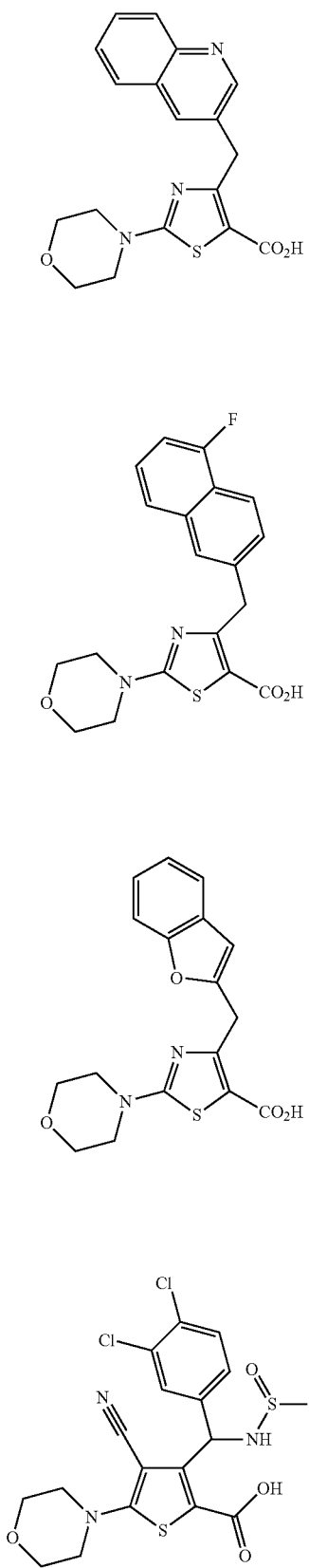
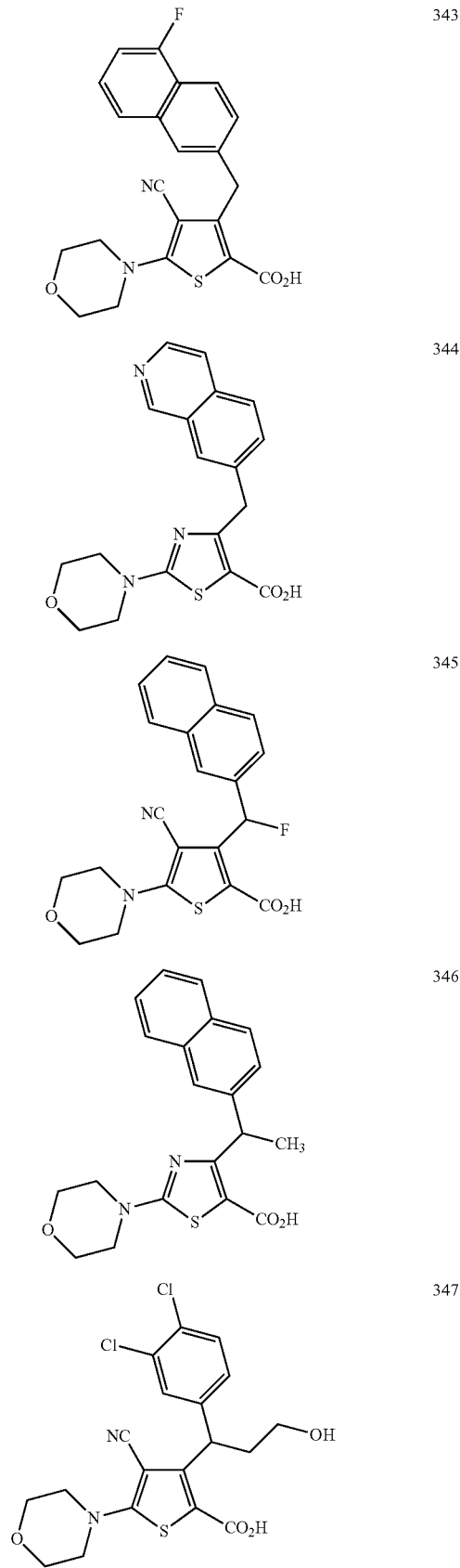

TABLE 1-continued
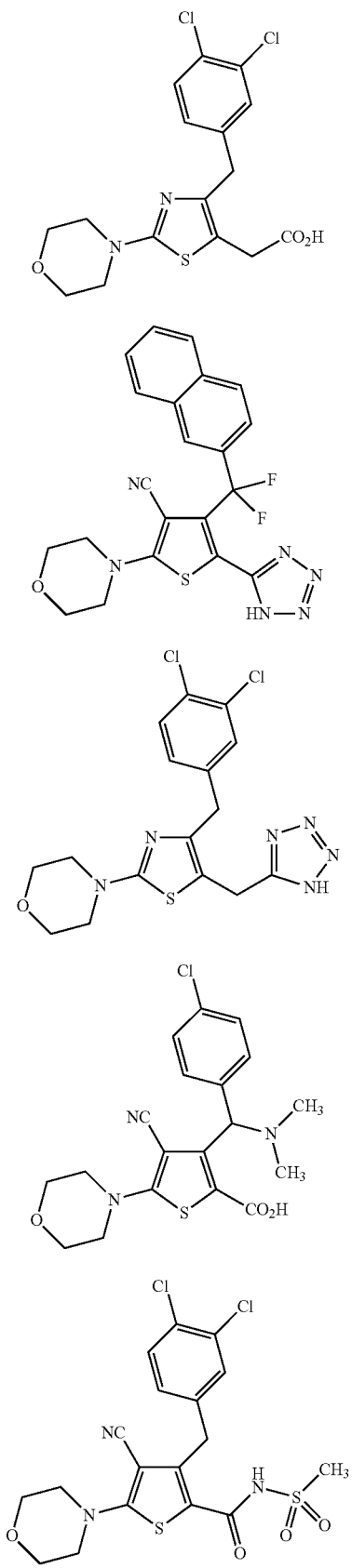
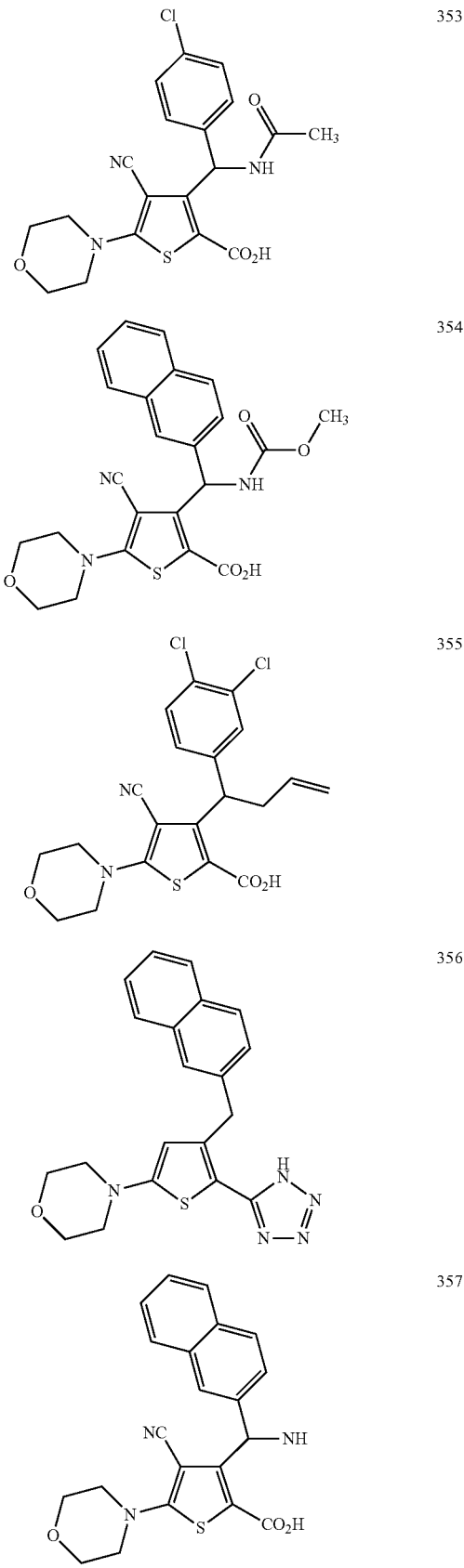

TABLE 1-continued

358

359

360

361

TABLE 1-continued

362

363

364

365

366

TABLE 1-continued

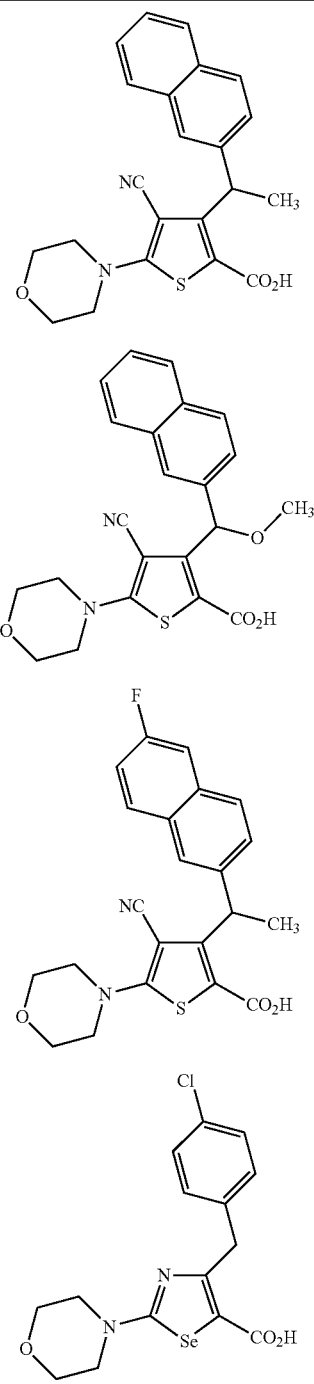

367

368

369

370

DEFINITIONS

AcOH acetic acid
ACN acetonitrile
ATP adenosine triphosphate
br broad
BCA bicinchoninic acid
BSA bovine serum albumin
BOC tert-butoxycarbonyl
BuLi butyllithium
m-CPBA m-chloroperbenzoic acid
d doublet
dd doublet of doublets
DCE dichloroethane
DCM dichloromethane
DDQ 2,3-dichloro-5,6-dicyano-1,4-benzoquinone
DIPEA diisopropylethyl amine
DMAP N,N-dimethylaminopyridine
DME 1,2-Dimethoxyethane
DMEM Dulbecco's Modified Eagle's Medium
DMF N,N-dimethylformamide
DMF-DMA N,N-dimethylformamide dimethyl acetal
DMSO dimethylsulfoxide
DPPA diphenylphosphoryl azide
DTT dithiothreitol
dppf diphenylphosphinoferrocene
EDCI N-(3-dimethylaminopropyl)-N'-ethylcarbodiimide hydrochloride
EDTA ethylenediaminetetraacetic acid
EtOAc ethyl acetate
EtOH ethanol
FA formic acid
FBS fetal bovine serum
J coupling constant
h hours
Hz: hertz
HATU N,N,N',N'-tetramethyl-o-(7-azabenzotriazole-1-yl)uronium hexafluorophosphate
HBTU o-benzotriazol-1-yl-N,N,N',N'-tetramethyluronium hexafluorophosphate
HEPES N-(2-Hydroxyethyl)piperazine-N'-(2-ethanesulfonic acid)
HOBT 1-hydroxybenztriazole hydrate
HRMS high resolution mass spectrum
LAH lithium aluminum hydride
LCMS liquid chromatography mass spectrum
LDA lithium diisopropylamide
LiHMDS Lithium bis(trimethylsilyl)amide
m multiplet
m/z mass to charge
Me methyl
MeOH methanol
min minutes
MS mass spectrum
MTT methylthiazoletetrazolium
MWI microwave irradiation
NBS N-bromosuccinimide
PBS phosphate buffered saline
PKA cAMP-dependent protein kinase
rt room temperature
s singlet
t triplet
TEA triethylamine
TFA: trifluoroacetic acid
TFFA trifluoroacetic anhydride
THF tetrahydrofuran
TMB 3,3',5,5'-Tetramethylbenzidine
TMEDA Tetramethylethylenediamine
q quartet
WST (4-[3-(4-iodophenyl)-2-(4-nitrophenyl)-2H-5-tetrazolio]-1,3-benzene disulfonate sodium salt)

The following analytical methods were used:

LCMS sectra were run on a Phenominex Luna 5 μm C18 50×4.6 mm column on a Hewlett-Packard HP1100 using the following gradients:

Method Formic Acid (FA): Acetonitrile containing 0 to 100 percent 0.1% formic acid in water (2.5 ml/min for a 3 minute run).

Method Ammonium Acetate (AA): Acetonitrile containing 0 to 100 percent 10 mM ammonium acetate in water (2.5 ml/min for a 3 minute run).

Chiral isomers were separated using chiral HPLC on a Chiralpak IC 250×25 mm 5 micron column using hexane/ethanol/diethylamine or hexane/isopropylalcohol/ethanol/diethylamine as mobil phase. Absolute configurations of the separated isomers were unknown, structures were assigned arbitrarily.

NMR spectrum is shown by proton NMR, with tetramethylsilane as the internal standard and using 300 MHz Bruker Avance spectrometer equipped with a 5 mm QNP probe and 400 MHz Bruker Avance II spectrometer equipped with a 5 mm QNP probe for the measurement; δ values are expressed in ppm.

Example 1

Synthesis of N-{4-[4-(4-chlorobenzyl)-3-cyano-5-(4H-1,2,4-triazol-3-yl)-2-thienyl]pyridin-2-yl}acetamide (Compound 71) and 2-(2-aminopyridin-4-yl)-4-(4-chlorobenzyl)-5-(4H-1,2,4-triazol-3-yl)thiophene-3-carbonitrile (Compound 12)

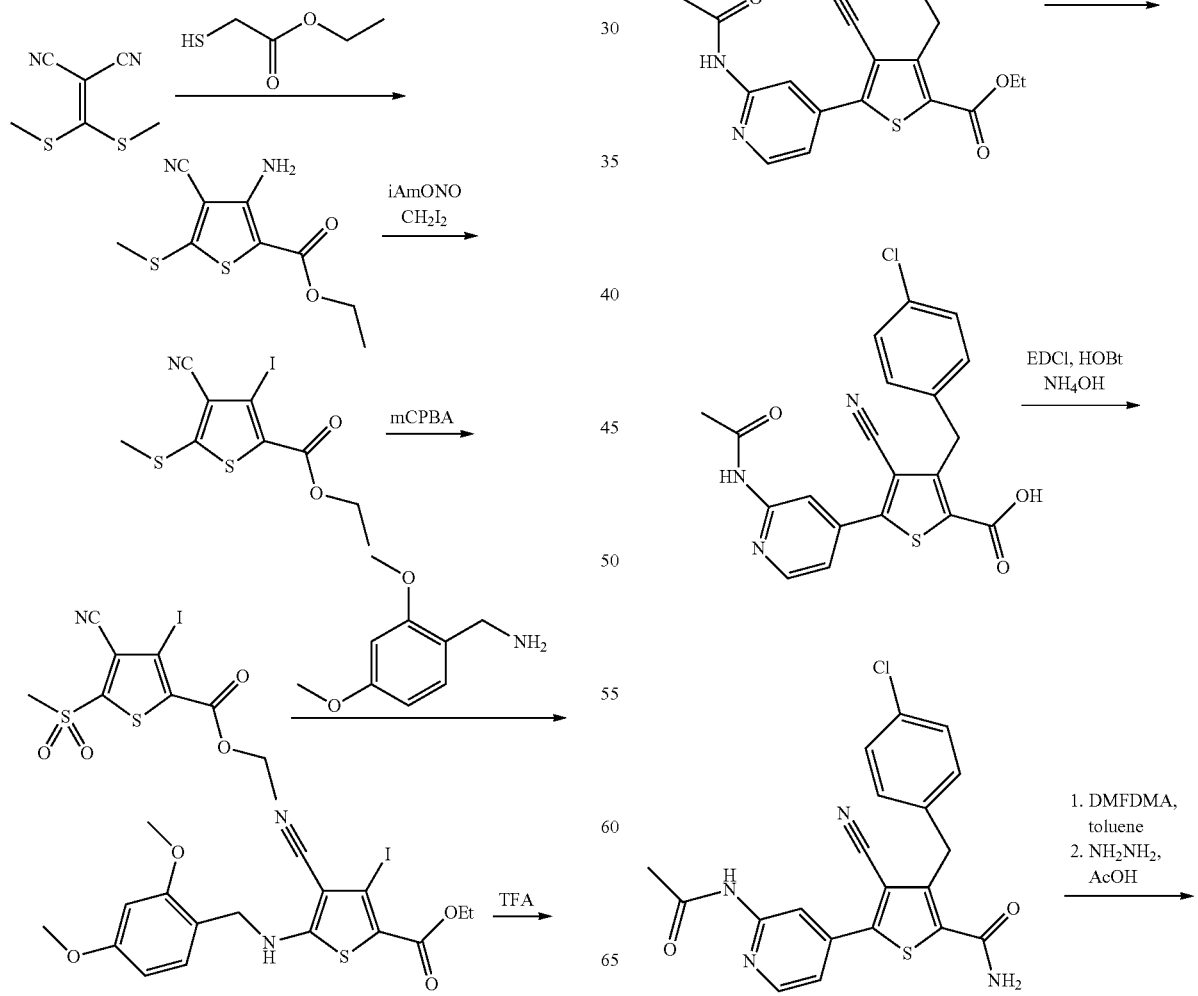

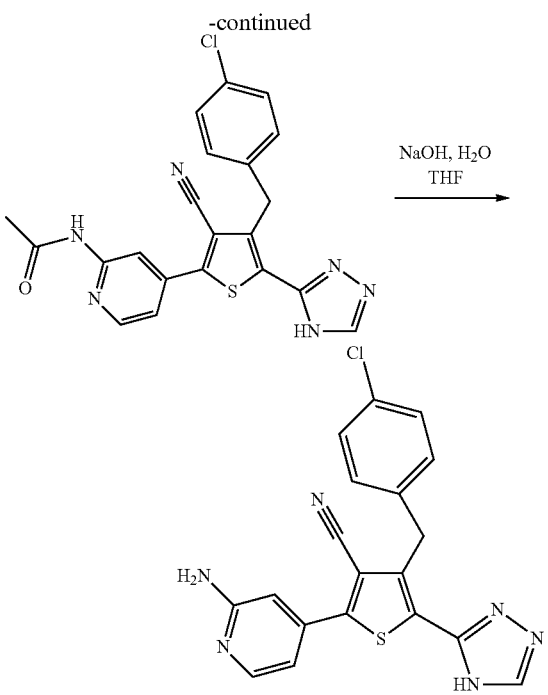

$\xrightarrow{\text{NaOH, H}_2\text{O}}{\text{THF}}$

Step 1: Ethyl 3-amino-4-cyano-5-(methylsulfanyl) thiophene-2-carboxylate

A mixture of [bis(methylsulfanyl)methylene]malononitrile (40 g, 230 mmol), ethylthioglycolate (29 g, 230 mmol) and TEA (24 mL, 173 mmol) in MeOH (600 mL) was allowed to stir at reflux for 2 h. The reaction mixture was allowed to cool overnight and the precipitate was filtered off then washed with cold MeOH (3×50 mL) to give ethyl 3-amino-4-cyano-5-(methylsulfanyl)thiophene-2-carboxylate (52.4 g, 99%). LCMS: (FA) ES+ 275.

Step 2: Ethyl 4-cyano-3-iodo-5-(methylsulfanyl) thiophene-2-carboxylate

Ethyl 3-amino-4-cyano-5-(methylsulfanyl)thiophene-2-carboxylate (10 g, 41.3 mmol) was dissolved in acetonitrile (50 mL) under an atmosphere of argon. Diiodomethane (11.6 mL, 0.144 mol) was added and the mixture was heated at 40° C. Isoamyl nitrite (12.1 g, 0.103 mol) was added and the reaction was allowed to cool to room temperature and stirred for 2 hours. The mixture was cooled down to 0° C., diluted with hexane (50 mL) and the precipitate was filtered off, washed with 10:1 hexane-acetonitrile mixture (10 mL), 3:1 hexane-ether (10 mL) and hexane (10 mL). The precipitate was dried to afford ethyl 4-cyano-3-iodo-5-(methylsulfanyl) thiophene-2-carboxylate (6.90 g, 45%). LCMS: (FA) ES+ 354. $^1$H NMR (400 MHz, CDCl$_3$) δ: 4.38 (q, 2H), 2.70 (s, 3H), 1.40 (t, 3H).

Step 3: Ethyl 4-cyano-3-iodo-5-(methylsulfonyl) thiophene-2-carboxylate

Ethyl 4-cyano-3-iodo-5-(methylsulfanyl)thiophene-2-carboxylate (7.2 g, 20.4 mmol) was dissolved in DCM (200 mL) and THF (100 mL) and m-CPBA (9.14 g, 40.8 mmol) was added. The reaction mixture was stirred at rt overnight. Sodium sulfite (5.14 g, 40.8 mmol) was added and the mixture was stirred for 10 minutes followed by the addition of potassium carbonate (8.45, 61.2 mmol). The suspension was stirred at rt for 1 hour and filtered through celite, washed with DCM and the solvent was evaporated to afford ethyl 3-iodo-4-cyano-5-(methylsulfonyl)thiophene-2-carboxylate (6.80 g, 78%). LCMS: (FA) ES+ 386. $^1$H NMR (400 MHz, CDCl$_3$) δ: 4.45 (q, 2H), 3.38 (s, 3H), 1.43 (t, 3H).

Step 4: Ethyl 4-cyano-5-[(2,4-dimethoxybenzyl) amino]-3-iodothiophene-2-carboxylate Ethyl 4-cyano-3-iodo-5-(methylsulfonyl)thiophene-2-carboxylate (5.60 g, 0.0145 mol) and 2,4-dimethoxybenzylamine (3.51 mL, 0.0234 mol) were combined in tetrahydrofuran (100 mL) and stirred at 60° C. for 3 days. The reaction was concentrated in vacuo, diluted with dichloromethane and hexanes and the resultant precipitate was filtered to yield the title compound (5.56, 81%) as a yellow solid. LCMS: (FA) ES$^+$, 473. $^1$H NMR (400 MHz, d$_6$-DMSO) δ: 9.05 (s, 1H) 7.10 (d, 1H, J=8.57 Hz), 6.60-6.50 (m, 2H), 4.30 (s, 2H), 4.22-4.14 (m, 2H), 3.80 (s, 3H), 3.75 (s, 3H), 1.26-1.21 (m, 3H).

Step 5: Ethyl 4-cyano-3,5-diiodothiophene-2-carboxylate

To a solution of ethyl 4-cyano-5-[(2,4-dimethoxybenzyl) amino]-3-iodothiophene-2-carboxylate (4.50 g, 9.53 mmol) in dichloromethane (100 mL) at room temperature was added trifluoroacetic acid (22.5 mL, 292 mmol). The mixture was then stirred at room temperature for 10 minutes. The solvent was evaporated and the excess trifluoroacetic acid was removed by azeotroping with toluene. The crude material was diluted with ethyl acetate, then treated with saturated sodium bicarbonate solution. The mixture was extracted with ethyl acetate five times and the combined organic extracts were dried over anhydrous sodium sulfate, filtered and concentrated in vacuo. Column chromatography was performed to yield ethyl 5-amino-4-cyano-3-iodothiophene-2-carboxylate (2.85 g, 88%). LCMS: (FA) ES$^+$, 323. $^1$H NMR (400 MHz, d$_6$-DMSO) δ: 8.18 (s, 2H), 4.20-4.16 (m, 2H), 2.50-2.48 (m, 3H). To a suspension of 5-amino-4-cyano-3-iodothiophene-2-carboxylate (2.85 g, 8.85 mmol) in acetonitrile (46.2 mL) under argon was added diiodomethane (2.49 mL, 31.0 mmol). The mixture was heated to 38° C. for 30 minutes, then amyl nitrite (2.59 g, 22.1 mmol) was added dropwise over 5 minutes. The reaction was slowly allowed to cool to room temperature then the mixture was concentrated and column chromatography was performed to yield the title compound (3.20 g, 79%). LCMS: (FA) ES$^+$, 434. $^1$H NMR (400 MHz, d$_6$-DMSO) δ: 4.33-4.27 (m, 2H), 2.51-2.47 (m, 3H).

Step 6: Ethyl 5-[2-(acetylamino)pyridin-4-yl]-4-cyano-3-iodothiophene-2-carboxylate To a solution of ethyl 4-cyano-3,5-diiodothiophene-2-carboxylate (0.473 g, 1.09 mmol) and N-[4-(trimethylstannyl) pyridin-2-yl]acetamide (0.392 g, 1.31 mmol) in dioxane (10.2 mL) was added lithium chloride (0.139 g, 3.28 mmol), copper(I) iodide (0.0624 g, 0.328 mmol), and tetrakis(triphenylphosphine)palladium(0) (0.0947 g, 0.0819 mmol). The reaction flask was evacuated and backfilled with argon, then the solution was heated at 110° C. for 2 hours. The mixture was cooled to room temperature and a mixture of dichloromethane and methanol was added until almost all solids had dissolved. The suspension was filtered through celite and the filtrate was evaporated. Column chromatography was performed to yield the title compound (0.312 g, 65%). LCMS: (FA) ES+ 442. $^1$H NMR (400 MHz, d$_6$-DMSO) δ: 8.54-8.49 (m, 2H), 8.31 (s, 1H), 4.38-4.32 (m, 2H), 2.13 (s, 3H), 1.36-1.29 (m, 3H).

Step 7: Ethyl 5-[2-(acetylamino)pyridin-4-yl]-3-(4-chlorobenzyl)-4-cyanothiophene-2-carboxylate To a solution of ethyl 5-[2-(acetylamino)pyridin-4-yl]-4-cyano-3-iodothiophene-2-carboxylate (0.209 g, 0.474 mmol) in tetrahydrofuran (3.3 mL) was added 4-chlorobenzylzinc chloride (0.50M solution in tetrahydrofuran, 1.89 mL, 0.947 mmol) and bis(tri-t-butylphosphine)palladium(0) (0.0182 g, 0.0355 mmol) under argon. The solution was stirred at 60° C. for 3 hours. The reaction was allowed to cool to room temperature and then the solvent was evaporated in vacuo. Column chromatography was performed to yield the title compound (0.159 g, 76%). LCMS: (FA) ES+, 440. $^1$H NMR (400 MHz, CDCl$_3$) δ: 8.66 (br s, 1H), 8.60 (br s, 1H), 8.38 (d, J=5.27 Hz, 1H), 7.51-7.47 (m, 1H), 7.33-7.23 (m, 4H), 4.51 (s, 2H), 4.39 (q, J=7.03 Hz, 2H), 2.24 (s, 3H), 1.39 (t, J=7.03 Hz, 3H).

Step 8: 5-[2-(Acetylamino)pyridin-4-yl]-3-(4-chlorobenzyl)-4-cyanothiophene-2-carboxylic acid To a solution of ethyl 5-[2-(acetylamino)pyridin-4-yl]-3-(4-chlorobenzyl)-4-cyanothiophene-2-carboxylate (0.080 g, 0.18 mmol) in tetrahydrofuran (1.28 mL) and water (0.85 mL) was added lithium hydroxide (1.0M solution in water, 0.236 mL, 0.236 mmol). The reaction mixture was stirred at room temperature for 16 hours. The mixture was acidified to pH 6 using aqueous 1N HCl (0.300 mL). The mixture was extracted with ethyl acetate. The combined organic extracts were washed with brine, and then dried over anhydrous sodium sulfate, filtered and concentrated in vacuo. Column chromatography was performed to yield the title compound (0.058 g, 78%). LCMS: (FA) ES+, 412. $^1$H NMR (400 MHz, d$_6$-DMSO) δ: 10.72 (s, 1H), 8.46-8.41 (m, 2H), 7.42-7.39 (m, 1H), 7.36-7.32 (m, 4H) 4.53 (s, 2H), 2.11 (s, 3H).

Step 9: 5-[2-(Acetylamino)pyridin-4-yl]-3-(4-chlorobenzyl)-4-cyanothiophene-2-carboxamide To a solution of 5-[2-(acetylamino)pyridin-4-yl]-3-(4-chlorobenzyl)-4-cyanothiophene-2-carboxylic acid (0.0710 g, 0.172 mmol) in dichloromethane (5.0 mL) was added N-(3-dimethylaminopropyl)-N'-ethylcarbodiimide hydrochloride (0.0991 g, 0.517 mmol) and 1-hydroxybenzotriazole hydrate (0.0528 g, 0.345 mmol). The solution was stirred at room temperature for 30 minutes, then added 33% ammonium hydroxide (33:67 ammonia:water, 0.298 mL, 3.45 mmol) was added. The solution was then stirred at room temperature for 16 hours, then the mixture was concentrated and column chromatography was performed to yield the title compound (0.031 g, 42%). LCMS: (FA) ES+, 411. $^1$H NMR (400 MHz, d$_6$-DMSO) δ: 10.79 (s, 1H), 8.50-8.46 (m, 2H), 8.14 (br s, 1H), 7.85 (br s, 1H), 7.47-7.43 (m, 1H), 7.39-7.34 (m, 2H), 7.29-7.24 (m, 2H), 4.41 (s, 2H), 2.12 (s, 3H).

Step 10: N-{4-[4-(4-chlorobenzyl)-3-cyano-5-(4H-1,2,4-triazol-3-yl)-2-thienyl]pyridin-2-yl}acetamide (Compound 71)

To a solution of 5-[2-(acetylamino)pyridin-4-yl]-3-(4-chlorobenzyl)-4-cyanothiophene-2-carboxamide (0.030 g, 0.073 mmol) in toluene (0.75 mL) was added 1,1-dimethoxy-N,N-dimethylmethanamine (0.0970 mL, 0.730 mmol), and the mixture was stirred at 100° C. for 90 minutes. The mixture was concentrated and the residue was dissolved in acetic acid (0.75 mL). Hydrazine (0.0114 mL, 0.365 mmol) was added and the mixture was stirred at 100° C. for 1 hour. The mixture was concentrated and the residue was treated with water. The precipitate was collected, washed with water and dried in a vacuum oven to yield the title compound (0.016 g, 48%). LCMS: (FA) ES+, 435. $^1$H NMR (400 MHz, d$_6$-DMSO) δ: 10.76 (s, 1H), 8.77 (s, 1H), 8.54-8.46 (m, 2H), 7.50-7.47 (m, 1H), 7.37-7.26 (m, 4H), 4.63 (s, 2H), 2.12 (s, 3H).

Step 11: 2-(2-Aminopyridin-4-yl)-4-(4-chlorobenzyl)-5-(4H-1,2,4-triazol-3-yl)thiophene-3-carbonitrile (Compound 12)

To a solution of N-{4-[4-(4-chlorobenzyl)-3-cyano-5-(4H-1,2,4-triazol-3-yl)-2-thienyl]pyridin-2-yl}acetamide (0.020 g, 0.046 mmol) in tetrahydrofuran (5.0 mL) was added sodium hydroxide (1.0M solution in water, 2.0 mL, 2.0 mmol). The solution was stirred at room temperature for 48 hours. The mixture was extracted with ethyl acetate three times, and the combined organic extracts were then dried over anhydrous sodium sulfate, filtered and concentrated in vacuo. Column chromatography was performed to yield the title compound (0.007 g, 30%). LCMS: (FA) ES+, 393. $^1$H NMR (400 MHz, d$_6$-DMSO) δ: 8.75 (s, 1H), 8.07-8.03 (m, 1H), 7.36-7.26 (m, 4H), 6.83-6.79 (m, 1H), 6.78-6.76 (m, 1H), 6.34-6.29 (m, 1H), 4.61 (s, 2H), 4.04 (s, 2H).

Compounds in the following table were prepared from the appropriate starting materials in a method analogous to that of Example 1:

| | |
|---|---|
| 36 | LCMS: (FA) ES+ 355, 357 |
| 74 | LCMS: (FA) ES+, 412, 414. |
| 143 | LC/MS: (FA) ES+ 371; ES− 369 |
| 148 | LCMS: (FA) ES+ 394 |
| 179 | LC/MS: (FA) ES+ 467 |
| 180 | LC/MS: (FA) ES+ 444; ES− 442 |

Example 2

Synthesis of 4-(4-((4-chlorophenyl)(hydroxy)methyl)-5-(4H-1,2,4-triazol-3-yl)thiophen-2-yl)picolinonitrile (Compound 81)

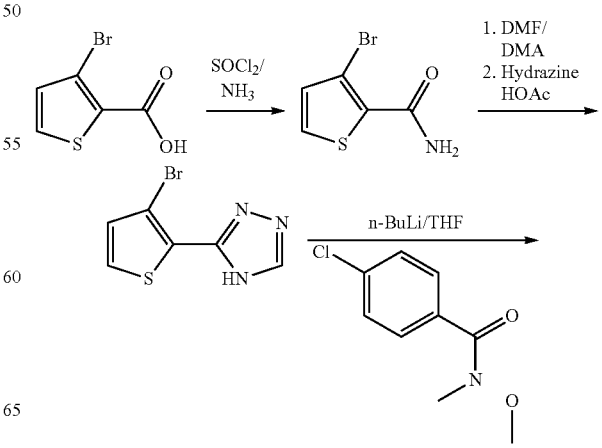

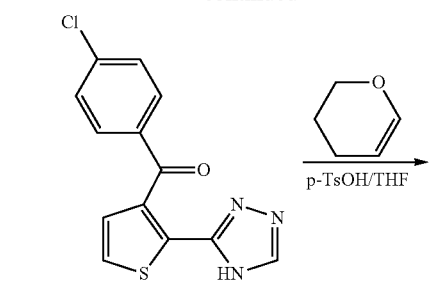

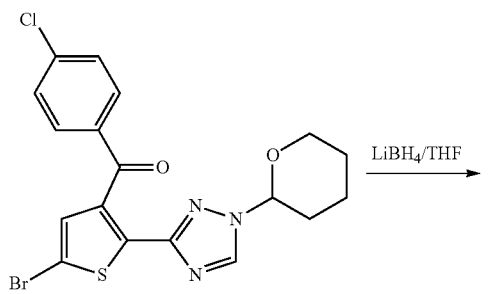

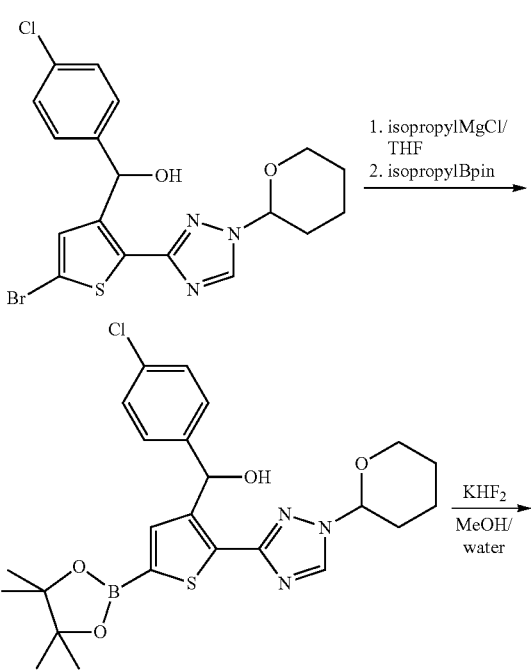

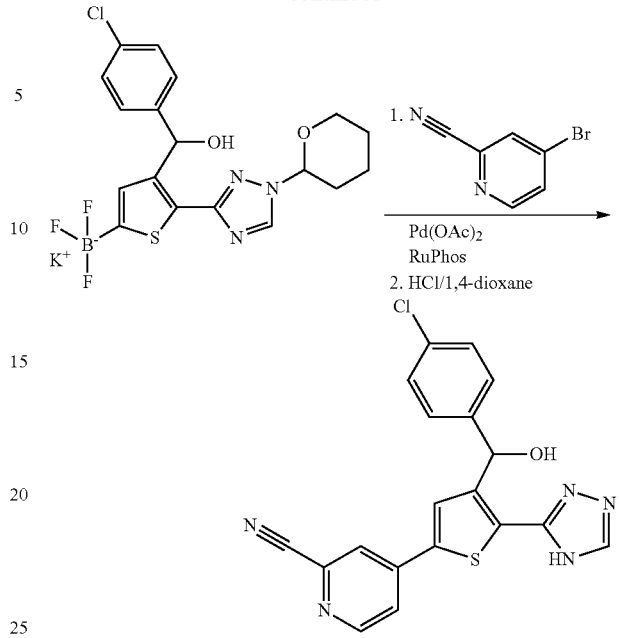

Step 1: 3-Bromothiophene-2-carboxamide

3-Bromothiophene-2-carboxylic acid (63.61 g, 307.2 mmol) was weighed into a 1 L round bottom flask equipped with reflux condenser and the flask was purged with argon. To this flask was added toluene (636.1 mL, 5972 mmol) and thionyl chloride (44.82 mL, 614.4 mmol) at room temperature, and the resulting mixture was stirred for 3 h at 100° C. The reaction mixture was evaporated and the residue was azeotroped with toluene (2×100 mL). The resulting residue was dissolved in tetrahydrofuran (954.1 mL, 11760 mmol) then 10 M ammonia in water (170 mL, 2500 mmol) was added slowly into the solution. The mixture was stirred for 5 h at room temperature. Thin-layer chromatography showed complete reaction. The reaction mixture was rotovaped to remove THF and the solid residue in water was filtered through a glass frit funnel then washed with water and dried under vacuum to give 3-bromothiophene-2-carboxamide as a white solid (33.26 g, 52.5%). LCMS: (FA) ES+ 206.0, 208.0

Step 2: 3-(3-Bromothiophen-2-yl)-4H-1,2,4-triazole

3-Bromothiophene-2-carboxamide (33.2 g, 161 mmol) in 1,1-dimethoxy-N,N-dimethylmethanamine (100 mL, 800 mmol) and toluene (100 mL, 900 mmol) was heated at 90° C. for 2 h. The solvent was evaporated off and the residue was dissolved in acetic acid (183 mL, 3220 mmol). Hydrazine (20 mL, 600 mmol) was added and the mixture was heated at 90° C. again. After 40 min, LCMS showed complete reaction. The reaction mixture was evaporated to remove most of the acetic acid. Water was added and the precipitate was collected and dried in air overnight to afford 3-(3-bromothiophen-2-yl)-4H-1,2,4-triazole as a white powder (31.7 g, 85.6%). LCMS: (FA) ES+ 230.0, 232.0

Step 3: (4-Chlorophenyl)[2-(4H-1,2,4-triazol-3-yl)-3-thienyl]methanone

To a solution of 3-(3-bromo-2-thienyl)-4H-1,2,4-triazole (15.05 g, 65.41 mmol) in Tetrahydrofuran (500 mL, 6000 mmol) was added dropwise 2.5M BuLi in hexanes (104 mL, 262 mmol) at −70° C. (internal temperature) and the solution was stirred for 30 min at −78° C. A solution of 4-chloro-N-methoxy-N-methylbenzamide (41.24 g, 206.6 mmol) in tetrahydrofuran (80 mL, 1000 mmol) was then added dropwise into the suspension. The resulting mixture was stirred for 60 min at −78° C. Ammonium chloride (17.49 g, 327.0 mmol) in water (100 mL, 6000 mmol) was added to the mixture at −78° C. and the mixture was stirred for 15 min before being warmed to rt. The organic layer was separated and the aqueous layer was extracted with EtOAc. The combined organic layers were washed with brine, dried over sodium sulfate, and then filtered to remove drying agent. The solvent was evaporated and the residue was purified by chromatography to afford (4-chlorophenyl)[2-(4H-1,2,4-triazol-3-yl)-3-thienyl]methanone as white solid (16.8 g, 88.5%). LCMS: (FA) ES+ 289.9, 291.8

Step 4: (4-Chlorophenyl)(2-(1-(tetrahydro-2H-pyran-2-yl)-1H-1,2,4-triazol-3-yl)thiophen-3-yl)methanone In a 500 mL, round bottomed flask, (4-chlorophenyl)[2-(4H-1,2,4-triazol-3-yl)-3-thienyl]methanone (16.89 g, 58.29 mmol) was dissolved in tetrahydrofuran (500.0 mL, 6164 mmol). To the solution were added dihydropyran (31.9 mL, 3.50E2 mmol) and p-toluenesulfonic acid monohydrate (16.6 g, 87.4 mmol). The mixture was stirred for 3 h at rt. The reaction was quenched by the addition of saturated aqueous solution of sodium bicarbonate (200 mL). The aqueous phase was separated and then extracted with EtOAc (300 mL). The combined organic phases were dried over anhydrous sodium sulfate. The drying agent was removed by filtration and the filtrate was concentrated under reduced pressure. The residue was purified by chromatography to afford (4-chlorophenyl)(2-(1-(tetrahydro-2H-pyran-2-yl)-1H-1,2,4-triazol-3-yl)thiophen-3-yl)methanone as an oil which was dried under high vacuum overnight (19.4, 89.1%). LCMS: (FA) ES+ 374.2, 376.1.

Step 5: (5-Bromo-2-(1-(tetrahydro-2H-pyran-2-yl)-1H-1,2,4-triazol-3-yl)thiophen-3-yl)(4-chlorophenyl)methanone To a mixture of (4-chlorophenyl){2-[1-(tetrahydro-2H-pyran-2-yl)-1H-1,2,4-triazol-3-yl]-3-thienyl}methanone (20.2 g, 54.0 mmol) in N,N-dimethylformamide (350 mL, 4500 mmol) was added dropwise a solution of N-bromosuccinimide (14.42 g, 81.05 mmol) in N,N-dimethylformamide (50 mL, 600 mmol) under argon. The mixture was stirred at rt with care taken to block the reaction from exposure to ambient light. After 3 h reaction, LCMS showed both starting material and product. Additional N-bromosuccinimide (6.732 g, 37.82 mmol) was added and the mixture was stirred at rt again. After stirring overnight, the mixture was diluted with water and sodium bicarbonate solution and then the mixture was extracted with EtOAc. The organic layer was washed with water and brine. The EtOAc layer was dried and evaporated in vacuum to a residue, which was purified by chromatography to afford (5-bromo-2-(1-(tetrahydro-2H-pyran-2-yl)-1H-1,2,4-triazol-3-yl)thiophen-3-yl)(4-chlorophenyl)methanone as a white solid (18.0, 73.5%). LCMS: (FA) ES+ 451.9, 453.9

Step 6: (5-Bromo-2-(1-(tetrahydro-2H-pyran-2-yl)-1H-1,2,4-triazol-3-yl)thiophen-3-yl)(4-chlorophenyl)methanol To a solution of {5-bromo-2-[1-(tetrahydro-2H-pyran-2-yl)-1H-1,2,4-triazol-3-yl]-3-thienyl}(4-chlorophenyl)methanone (11.81 g, 26.08 mmol) in tetrahydrofuran (300 mL, 4000 mmol) was added lithium tetrahydroborate (52.17 mmol, 52.17 mmol) in tetrahydrofuran (26 mL, 320 mmol) under argon. The mixture was stirred at rt for 3 h and then cooled down in dry ice-acetone bath. Acetic acid (7.1 mL, 120 mmol) was added. The mixture was stirred for 5 min and saturated aqueous sodium bicarbonate solution was added, followed by EtOAc. The organic layer was separated and washed with brine, then dried over sodium sulfate. The solvent was removed and the residue was purified by column chromatography to afford (5-bromo-2-(1-(tetrahydro-2H-pyran-2-yl)-1H-1,2,4-triazol-3-yl)thiophen-3-yl)(4-chlorophenyl)methanol as a white powder (11.2, 94.2%). LCMS: (FA) ES+ 454.0, 456.0

Step 7: (4-chlorophenyl)(2-(1-(tetrahydro-2H-pyran-2-yl)-1H-1,2,4-triazol-3-yl)-5-(4,4,5,5-tetramethyl-1,3,2-dioxaborolan-2-yl)thiophen-3-yl)methanol To a mixture of {5-bromo-2-[1-(tetrahydro-2H-pyran-2-yl)-1H-1,2,4-triazol-3-yl]-3-thienyl}(4-chlorophenyl)methanol (5.19 g, 11.4 mmol) in tetrahydrofuran (146.9 mL, 1811 mmol) was added isopropylmagnesium chloride (1M in THF, 34.2 mL, 34.2 mmol) at −40° C. under argon. After addition, the reaction temperature was raised to rt for 15 min. The mixture was then cooled to −78° C. and 2-isopropoxy-4,4,5,5-tetramethyl-1,3,2-dioxaborolane (8.149 mL, 39.94 mmol) was added. After the addition, the mixture was brought to rt. After 1 h, the mixture was heated at 75° C. overnight. The mixture was cooled to rt and quenched with saturated ammonium chloride solution. The mixture was stirred for 10 min then extracted with EtOAc. The organic layer was dried and evaporated in vacuum. The mixture was purified by chromatography to afford (4-chlorophenyl)(2-(1-(tetrahydro-2H-pyran-2-yl)-1H-1,2,4-triazol-3-yl)-5-(4,4,5,5-tetramethyl-1,3,2-dioxaborolan-2-yl)thiophen-3-yl)methanol as a thick oil (5.32 g, 65.0%). LCMS: (FA) ES+ 502.2, 504.1.

Step 8: Potassium (4-((4-chlorophenyl)(hydroxy)methyl)-5-(1-(tetrahydro-2H-pyran-2-yl)-1H-1,2,4-triazol-3-yl)thiophen-2-yl)trifluoroborate To a suspension of (4-chlorophenyl)(2-(1-(tetrahydro-2H-pyran-2-yl)-1H-1,2,4-triazol-3-yl)-5-(4,4,5,5-tetramethyl-1,3,2-dioxaborolan-2-yl)thiophen-3-yl)methanol in methanol (3.5 mL, 87 mmol) under argon was added potassium hydrogen fluoride (3.13 g, 40.0 mmol) in one portion at 0° C. Water (8.06 mL, 447 mmol) was added dropwise. After the addition, the ice-water bath was removed and the mixture was stirred at rt over the weekend. The mixture was evaporated and the residue was dried under high vacuum. The crude mixture was extracted with hot actone 3 times. The extracts were combined and evaporated to dryness to afford potassium (4-((4-chlorophenyl)(hydroxy)methyl)-5-(1-(tetrahydro-2H-pyran-2-yl)-1H-1,2,4-triazol-3-yl)thiophen-2-yl)trifluoroborate as a white powder (6.34 g, 100%). LCMS: (AA) ES− 442.2, 444.2, $^1$H NMR (400 MHz, d$_6$-DMSO) δ: 8.71 (d, J=2.81 Hz, 1H), 7.35-7.24 (m, 2H), 7.45 (td, J=4.77, 2.42, 2.42 Hz, 2H), 6.69-6.59 (m, 1H), 6.80 (d, J=4.16 Hz, 1H), 5.81 (dd, J=4.74, 1.41 Hz, 1H), 5.57 (td, J=9.49, 2.15, 2.15 Hz, 1H), 4.02-3.89 (m, 1H), 3.74-3.59 (m, 1H), 2.21-1.88 (m, 3H), 1.76-1.47 (m, 3H).

Step 9: 4-(4-((4-Chlorophenyl)(hydroxy)methyl)-5-(4H-1,2,4-triazol-3-yl)thiophen-2-yl)picolinonitrile
(Compound 81)

A mixture of potassium (4-((4-chlorophenyl)(hydroxy)methyl)-5-(1-(tetrahydro-2H-pyran-2-yl)-1H-1,2,4-triazol- 3-yl)thiophen-2-yl)trifluoroborate (0.133 g, 0.276 mmol), 4-bromo-pyridine-2-carbonitrile (60.6 mg, 0.331 mmol), 2-dicyclohexylphosphino-2',6'-di-1-propoxy-1,1'-biphenyl (24.8 mg, 0.0533 mmol), palladium acetate (4.6 mg, 0.020 mmol) and sodium carbonate (77 mg, 0.73 mmol) in ethanol (6.2 mL, 110 mmol) was degassed with argon and then heated at 85° C. for 13 h. The mixture was absorbed on silica gel and purified by chromatography to afford an intermediate. LCMS: (AA) ES+ 478.1, 480.0. This intermediate in 1,4-dioxane (2.0 mL, 26 mmol), tert-butyl alcohol (2.0 mL, 21 mmol) and 4.00 M HCl in dioxane (3.0 mL, 14 mmol) was heated at 60° C. for 1 h. The mixture was evaporated to dryness and then purified by HPLC to afford 4-(4-((4-chlorophenyl)(hydroxy)methyl)-5-(4H-1,2,4-triazol-3-yl)thiophen-2-yl)picolinonitrile (12.4 mg, 11.4%). LCMS: (FA) ES+ 394.3, 396.1. $^1$H NMR (400 MHz, d$_6$-DMSO) δ: 14.69-13.48 (br, 1H), 8.69 (d, J=6.79 Hz, 2H), 8.45 (s, 1H), 8.08-7.88 (m, 2H), 7.56 (d, J=8.39 Hz, 2H), 7.35 (d, J=8.40 Hz, 2H), 6.79 (s, 1H).

Compounds in the following table were prepared from the appropriate starting materials in a method analogous to that of Example 2:

| | |
|---|---|
| 3 | LCMS: (AA) ES+ 394, 396. |
| 8 | LCMS: (FA) ES+ 399, 401. |
| 10 | LCMS: (AA) ES+ 408, 410. |
| 13 | LCMS: (AA) ES+ 425, 427. |
| 16 | LCMS: (AA) ES+ 387, 389. |
| 17 | LCMS: (AA) ES+ 399, 401. |
| 23 | LCMS: (FA) ES+ 385, 387. |
| 25 | LCMS: (AA) ES+ 403, 405, 407. |
| 42 | LCMS: (AA) ES+ 419, 421. |
| 48 | LCMS: (AA) ES+ 394, 396. |
| 57 | LCMS: (AA) ES+ 425, 427. |
| 64 | LCMS: (AA) ES+ 438, 440. |
| 68 | LCMS: (FA) ES+ 388, 390. |
| 147 | LCMS: (AA) ES+ 451, 453 |
| 197 | LCMS: (AA) ES− 431, 433, 435 |

Example 3

Synthesis of (4-chlorophenyl)[5-(2-fluoropyridin-4-yl)-2-(4H-1,2,4-triazol-3-yl)-3-thienyl]methanol (Compound 21)

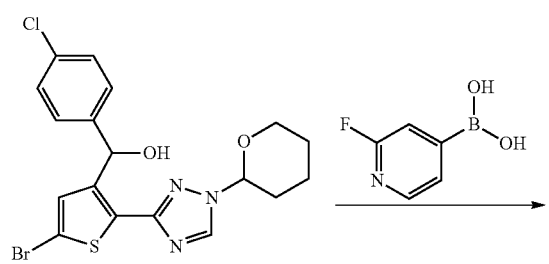

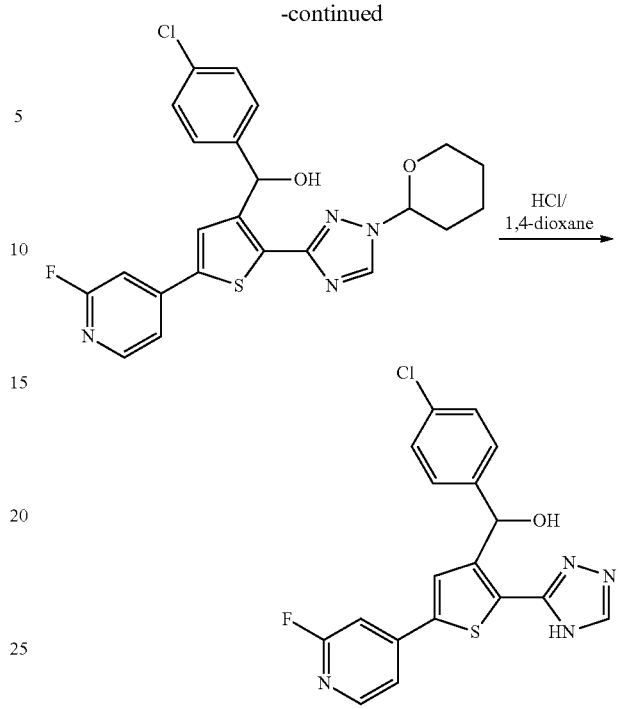

Step 1: (4-Chlorophenyl){5-(2-fluoropyridin-4-yl)-2-[1-(tetrahydro-2H-pyran-2-yl)-1H-1,2,4-triazol-3-yl]-3-thienyl}methanol A mixture of {5-bromo-2-[1-(tetrahydro-2H-pyran-2-yl)-1H-1,2,4-triazol-3-yl]-3-thienyl}(4-chlorophenyl)methanol (734 mg, 1.61 mmol), 2-fluoro-4-pyridinylboronic acid (455 mg, 3.23 mmol), tetrakis(triphenylphosphine)palladium(0) (93.3 mg, 0.0807 mmol) and cesium carbonate (1.58 g, 4.84 mmol) in 1,4-dioxane (10.1 mL, 129 mmol) and water (1.45 mL, 80.7 mmol) was irradiated in a microwave oven at 140° C. under argon for 20 min. The reaction mixture was dry loaded onto silica gel and purified by column chromatography (SiO$_2$, elution with EtOAc in hexanes, 0-80% gradient) to afford (4-chlorophenyl) {5-(2-fluoropyridin-4-yl)-2-[1-(tetrahydro-2H-pyran-2-yl)-1H-1,2,4-triazol-3-yl]-3-thienyl}methanol as a white solid (0.71 g, 92.8%). LCMS: (AA) ES+ 471.1, 473.1

Step 2: (4-chlorophenyl)[5-(2-fluoropyridin-4-yl)-2-(4H-1,2,4-triazol-3-yl)-3-thienyl]methanol (Compound 21)

A mixture of (4-Chlorophenyl){5-(2-fluoropyridin-4-yl)-2-[1-(tetrahydro-2H-pyran-2-yl)-1H-1,2,4-triazol-3-yl]-3-thienyl}methanol (0.261 g, 0.554 mmol), tert-butyl alcohol (3.9 mL, 41 mmol), 1,4-dioxane (2.6 mL, 33 mmol) and 4.00 M HCl in dioxane (3.66 mL, 16.6 mmol) was heated at 70° C. for 2 h. The mixture was cooled down. A small amount of water was added, followed by the addition of sodium bicarbonate (0.745 g, 8.87 mmol). The mixture was stirred for 10 min and then evaporated in vacuum. The residue was purified by (HPLC to afford 4-chlorophenyl)[5-(2-fluoropyridin-4-yl)-2-(4H-1,2,4-triazol-3-yl)-3-thienyl]methanol as a white solid. LCMS: (AA) ES+ 387.2, 389.1; $^1$H NMR (300 MHz, d$_4$-methanol) δ: 8.51 (s, 1H), 8.18 (d, J=5.41 Hz, 1H), 7.73 (s, 1H), 7.60-7.44 (m, 3H), 7.37-7.23 (m, 3H), 6.76 (s, 1H).

Compounds in the following table were prepared from the appropriate starting materials in a method analogous to that of Example 3:

| | |
|---|---|
| 11 | LCMS: (AA) ES+ 383, 385. |
| 14 | LCMS: (AA) ES+ 403, 405, 407. |
| 26 | LCMS: (AA) ES+ 387, 389. |
| 30 | LCMS: (AA) ES+ 403, 405, 407. |
| 34 | LCMS: (AA) ES+ 387, 389. |
| 40 | LCMS: (AA) ES+ 403, 405, 407. |
| 41 | LCMS: (AA) ES+ 426, 428. |
| 43 | LCMS: (AA) ES+ 383, 385. |
| 45 | LCMS: (AA) ES+ 387, 389. |
| 52 | LCMS: (AA) ES+ 369, 371. |
| 55 | LCMS: (AA) ES+ 370, 372. |
| 59 | LCMS: (AA) ES+ 370, 372. |
| 69 | LCMS: (AA) ES+ 383, 385. |
| 75 | LCMS: (AA) ES+ 384, 386. |
| 77 | LCMS: (AA) ES+ 369, 371. |
| 79 | LCMS: (AA) ES+ 370, 372. |
| 84 | LCMS: (AA) ES+ 369, 371. |

Example 4

Synthesis of 4-[4-[(4-chlorophenyl)(methoxy)methyl]-5-(4H-1,2,4-triazol-3-yl)-2-thienyl]pyridine (Compound 6)

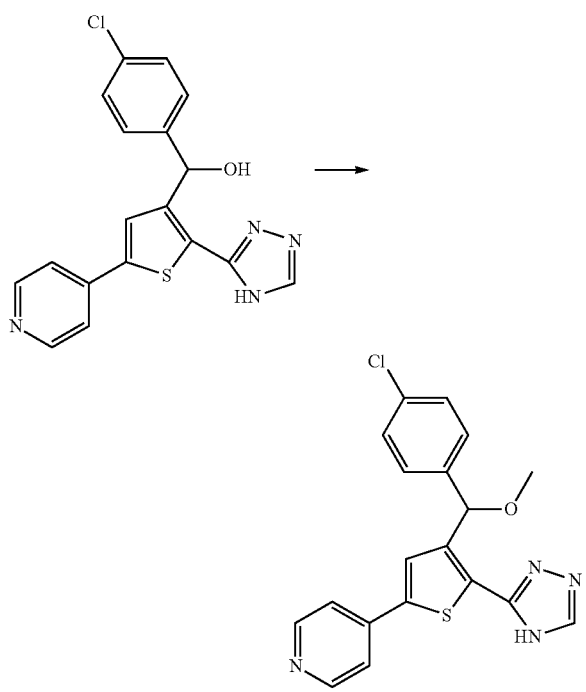

To a solution of (4-chlorophenyl)[5-pyridin-4-yl-2-(4H-1,2,4-triazol-3-yl)-3-thienyl]methanol (100 mg, 0.271 mmol) in methanol (10 mL) was added conc. HCl (2.0 mL, 24 mmol) and the mixture was stirred at rt overnight. The reaction mixture was concentrated and basified by sodium bicarbonate, loaded on silica gel and purified by column chromatography (SiO2, elution with 0-5% MeOH in DCM) to afford the title compound (80 mg, 78%). LCMS: (AA) ES+ 383.3, 385.2; $^1$H NMR (300 MHz, $d_6$-DMSO) δ: 8.70 (s, 1H), 8.57 (d, J=4.80 Hz, 2H), 7.79 (s, 1H), 7.68 (d, J=4.79 Hz, 2H), 7.56 (d, J=8.25 Hz, 2H), 7.38 (d, J=8.30 Hz, 2H), 6.50 (s, 1H), 3.31 (d, J=9.06 Hz, 3H).

Compounds in the following table were prepared from the appropriate starting materials in a method analogous to that of Example 4:

| | |
|---|---|
| 220 | LCMS: (AA) ES+ 440, 442. |

Example 5

Synthesis of 1-(4-chlorophenyl)-N,N-dimethyl-1-[5-pyridin-4-yl-2-(4H-1,2,4-triazol-3-yl)-3-thienyl]methanamine (Compound 9)

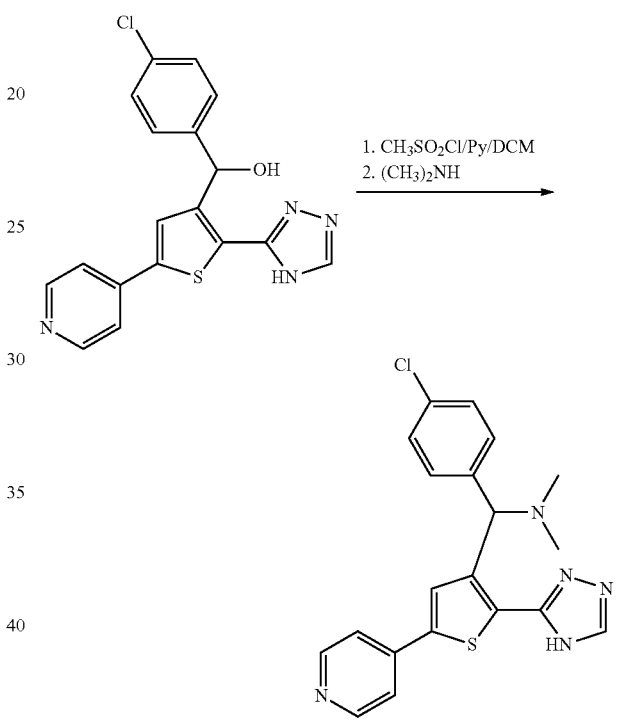

To a mixture of (4-chlorophenyl)[5-pyridin-4-yl-2-(4H-1,2,4-triazol-3-yl)-3-thienyl]methanol (141 mg, 0.382 mmol) (synthesized in an analogous way as described in Example 3) in methylene chloride (2.8 mL) was added pyridine (6.0 mL, 74 mmol) and methanesulfonyl chloride (0.148 mL, 1.91 mmol) at 0° C. After the addition, the mixture was warmed to rt and stirred for 30 min and then heated at 60° C. for 20 min. The mixture was cooled in an ice bath and dimethylamine (0.553 mL, 11.5 mmol) in THF was added to the mixture. After the addition, the ice bath was removed and the mixture was stirred at rt for 30 min and then heated at 55° C. for 2 h. The mixture was cooled, concentrated, and the residue was purified by HPLC to afford 1-(4-chlorophenyl)-N,N-dimethyl-1-[5-pyridin-4-yl-2-(4H-1,2,4-triazol-3-yl)-3-thienyl]methanamine as white powder (115 mg, 76%). LCMS: (AA) ES+ 396.3, 398.1; $^1$H NMR (400 MHz, $d_6$-DMSO) δ: 14.48-14.27 (m, 1H), 8.71 (s, 1H), 8.57 (dd, J=4.55, 1.62 Hz, 2H), 7.95 (s, 1H), 7.73-7.63 (m, 4H), 7.39-7.30 (m, 2H), 5.53 (s, 1H), 2.13 (s, 6H).

Compounds in the following table were prepared from the appropriate starting materials in a method analogous to that of Example 5:

| | |
|---|---|
| 33 | LCMS: (AA) ES+ 410, 412. |
| 44 | LCMS: (AA) ES+ 396, 398. |
| 51 | LCMS: (AA) ES+ 408, 410. |
| 65 | LCMS: (AA) ES+ 396, 398. |
| 86 | LCMS: (AA) ES+ 453, 455. |
| 90 | LCMS: (AA) ES+ 465, 467 |
| 135 | LCMS: (AA) ES+ 507, 509. |
| 139 | LCMS: (AA) ES+ 508, 510 |
| 146 | LCMS: (FA) ES+ 520, 522 |
| 151 | LCMS: (AA) ES+ 465, 467 |
| 152 | LCMS: (FA) ES+ 510, 512 |
| 154 | LCMS: (FA) ES+ 494, 496 |
| 161 | LCMS: (AA) ES+ 410, 412. |
| 163 | LCMS: (AA) ES+ 508, 510 |
| 164 | LCMS: (AA) ES+ 495, 497. |
| 167 | LCMS: (AA) ES+ 476, 478 |
| 173 | LCMS: (AA) ES+ 508, 510 |
| 176 | LCMS: (AA) ES+ 465, 467 |
| 182 | LCMS: (AA) ES+ 495, 497. |
| 183 | LCMS: (AA) ES+ 496, 498. |
| 185 | LCMS: (AA) ES+ 411, 413 |
| 192 | LCMS: (AA) ES+ 509, 511. |
| 196 | LCMS: (AA) ES+ 536, 538 |
| 200 | LCMS: (AA) ES+ 480, 482 |
| 201 | LCMS: (AA) ES+ 481, 483 |
| 204 | LCMS: (AA) ES+ 453, 455 |
| 206 | LCMS: (AA) ES+ 476, 478 |
| 208 | LCMS: (AA) ES+ 508, 510 |
| 209 | LCMS: (AA) ES+ 508, 510 |
| 212 | LCMS: (AA) ES+ 495, 497. |
| 216 | LCMS: (AA) ES+ 501, 503 |
| 221 | LCMS: (AA) ES+ 529, 531 |
| 224 | LC/MS: (FA) ES+ 572, 574; ES− 570, 572. |
| 229 | LCMS: (AA) ES+ 495, 497. |
| 234 | LCMS: (AA) ES+ 508, 510 |
| 240 | LCMS: (AA) ES+ 507, 509 |
| 241 | LCMS: (AA) ES+ 465, 467 |
| 242 | LCMS: (AA) ES+ 507, 509 |
| 243 | LCMS: (AA) ES+ 458, 460 |
| 247 | LCMS: (AA) ES+ 507, 509 |
| 248 | LCMS: (AA) ES+ 495, 497 |
| 251 | LCMS: (AA) ES+ 442, 444 |
| 254 | LCMS: (FA) ES+ 452, 454 |
| 259 | LCMS: (AA) ES+ 509, 511. |
| 261 | LCMS: (AA) ES+ 453, 455 |
| 267 | LCMS: (AA) ES+ 508, 510 |
| 268 | LCMS: (AA) ES+ 509, 511. |
| 270 | LCMS: (AA) ES+ 508, 510 |
| 283 | LCMS: (AA) ES+ 509, 511. |

Example 6

Synthesis of 2-({4-[4-[(4-chlorophenyl)(hydroxy)methyl]-5-(4H-1,2,4-triazol-3-yl)-2-thienyl]pyridin-2-yl}amino)ethanol (Compound 49)

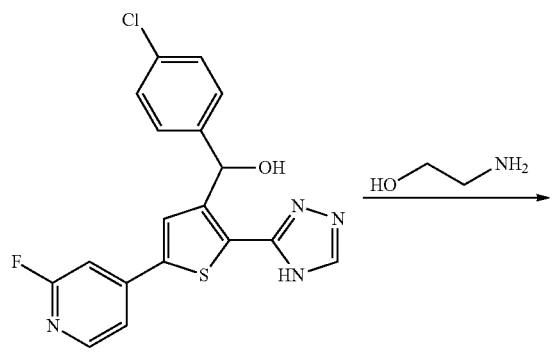

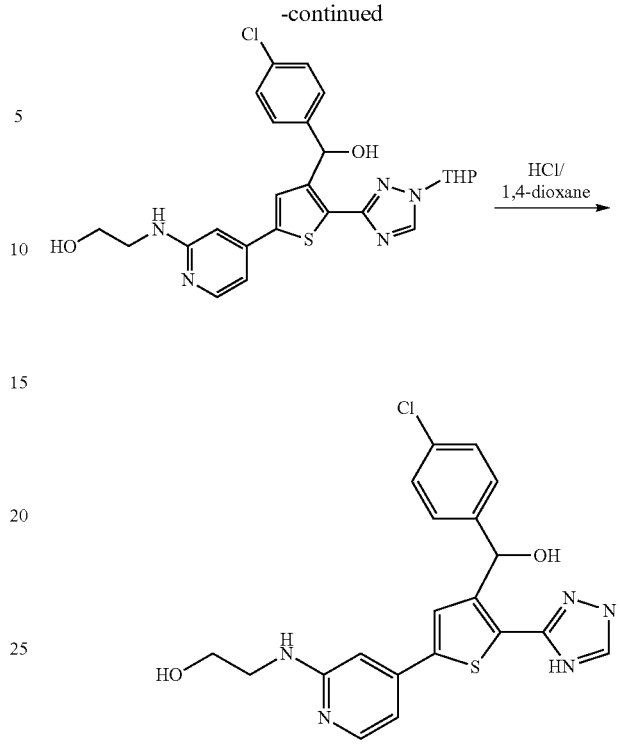

A mixture of (4-chlorophenyl){5-(2-fluoropyridin-4-yl)-2-[1-(tetrahydro-2H-pyran-2-yl)-1H-1,2,4-triazol-3-yl]-3-thienyl}methanol (80.0 mg, 0.170 mmol), ethanolamine (0.104 g, 1.70 mmol) and N,N-diisopropylethylamine (0.118 mL, 0.679 mmol) in dimethylsulfoxide (0.5 mL, 7 mmol) was heated at 200° C. for 1 h under argon. The reaction mixture was cooled, diluted with water and extracted with butanol. The butanol layer was collected and evaporated to a residue which was purified by chromatography (SiO$_2$, elution with 0-20% MeOH in DCM) to afford the intermediate. The intermediate in 1,4-dioxane (1.0 mL, 13 mmol) and conc HCl (1.0 mL, 12 mmol) was stirred at rt for 1 h. The solvent was evaporated and the residue was purified by chromatography (SiO$_2$, elution with 0-70% (MeOH/DCM/NH4OH, 13/85/2) in DCM) to afford 2-({4-[4-[(4-chlorophenyl)(hydroxy)methyl]-5-(4H-1,2,4-triazol-3-yl)-2-thienyl]pyridin-2-yl}amino)ethanol (17.6 mg, 24.2%). LCMS: (AA) ES+ 428.2, 430.0; $^1$H NMR (400 MHz, d$_6$-DMSO) δ: 14.66-14.13 (m, 1H), 8.68 (s, 1H), 7.94 (d, J=5.30 Hz, 1H), 7.58-7.48 (m, 3H), 7.38-7.30 (m, 2H), 6.81-6.68 (m, 3H), 6.60 (s, 1H), 4.72 (s, 1H), 3.57-3.45 (m, 2H), 3.34 (d, J=5.88 Hz, 3H).

Compounds in the following table were prepared from the appropriate starting materials in a method analogous to that of Example 6:

| | |
|---|---|
| 28 | LCMS: (AA) ES+ 435, 437. |
| 62 | LCMS: (AA) ES+ 398, 400. |

Example 7

Synthesis of (4-methoxyphenyl)[5-pyridin-4-yl-2-(4H-1,2,4-triazol-3-yl)-3-thienyl]methanol (Compound 85)

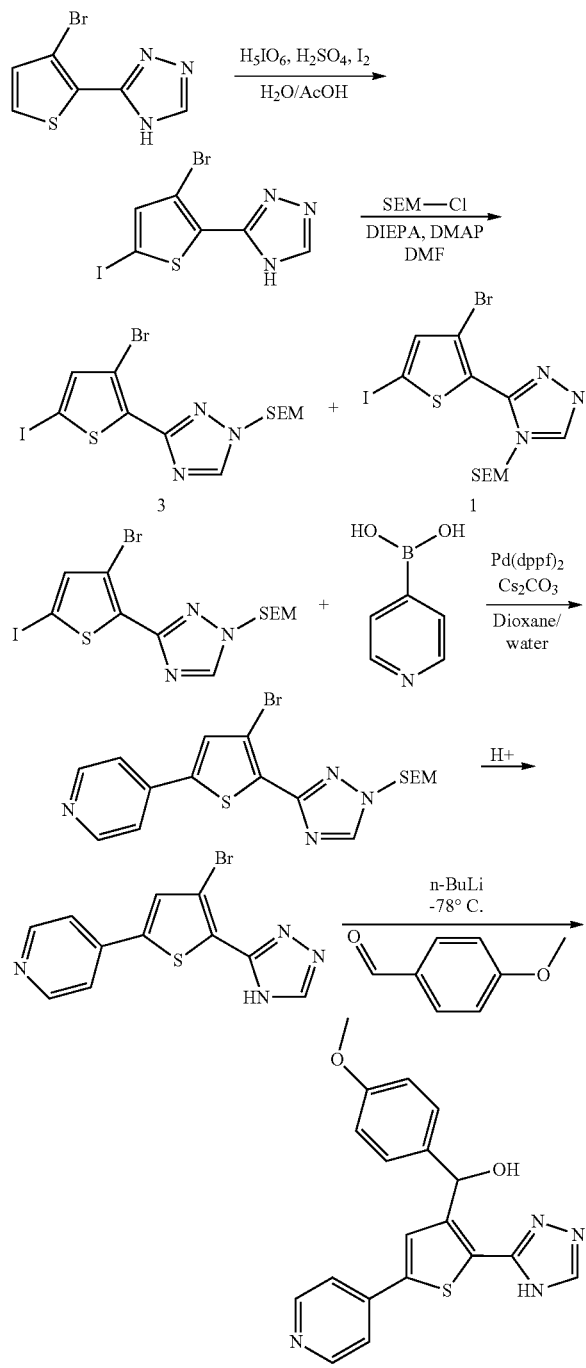

Step 1: 3-(3-Bromo-5-iodo-2-thienyl)-4H-1,2,4-triazole

To a mixture of 3-(3-bromo-2-thienyl)-4H-1,2,4-triazole (1.12 g, 4.87 mmol), iodine (1.12 g, 4.41 mmol) and periodic acid (4.80 g, 24.8 mmol) in acetic acid (11.0 mL, 200 mmol) were added water (8.0 mL, 400 mmol) and sulfuric acid (2.0 mL, 40 mmol) and the reaction mixture was stirred at rt for two days. The resulting white precipitate was collected by filtration. The solid cake was washed with water and dried under high vacuum at 40° C. to yield product as a white solid (1.74 g, 100% yield, as a white solid). LCMS: (FA) ES$^+$, 357.7. $^1$H NMR (400 MHz, d$_6$-DMSO) δ: 8.63 (s, 1H), 7.43 (s, 1H)

Step 2: 3-(3-Bromo-5-iodo-2-thienyl)-1-{[2-(trimethylsilyl)ethoxy]methyl}-1H-1,2,4-triazole Into a solution of 3-(3-bromo-5-iodo-2-thienyl)-4H-1,2,4-triazole (500.0 mg, 1.40 mmol), N,N-dimethylaminopyridine (17.2 mg, 0.140 mmol) and N,N-diisopropylethylamine (0.32 mL, 1.83 mmol) in N,N-dimethylformamide (17.0 mL, 220 mmol) was added [β-(Trimethylsilyl)ethoxy]methyl chloride (0.270 mL, 1.55 mmol) was added and the solution was stirred for 2 h at rt. Water (5.0 mL) and EtOAc (5 mL) were added, the organic layer was separated, washed with brine, dried over MgSO$_4$, filtered, concentrated and the obtained residue was purified by column chromatography (SiO$_2$, elution with 0-30% EtOAc in hexane) to give the title compound as a yellowish oil (653 mg, (87% major isomer, 13% minor isomer) LCMS: (FA) ES$^+$, 486, 488. (major isomer) $^1$H NMR (400 MHz, d$_6$-DMSO) δ: 8.81 (s, 1H), 7.45 (s, 1H), 5.540-5.545 (s, br, 2H), 3.62-3.66 (m, 2H), 0.840-0.880 (m, 2H), −0.05 (s, 9H). LCMS: (FA) ES$^+$, 486, 488. (minor isomer) $^1$H NMR (400 MHz, d$_6$-DMSO) δ: 8.215 (s, 1H), 7.615 (s, 1H), 5.48 (s, br, 2H), 3.44-3.50 (m, 2H), 0.75-0.80 (m, 2H), −0.08 (s, 9H).

Step 3: 4-[4-Bromo-5-(1-{[2-(trimethylsilyl)ethoxy]methyl}-1H-1,2,4-triazol-3-yl)-2-thienyl]pyridine A mixture of 3-(3-bromo-5-iodo-2-thienyl)-1-{[2-(trimethylsilyl)ethoxy]methyl}-1H-1,2,4-triazole (653.0 mg, 1.34 mmol), pyridine-4-boronic acid (248 mg, 2.02 mmol), [1,1'-bis(diphenylphosphino)ferrocene]palladium(II)dichloride (55.2 mg, 0.067 mmol) and cesium carbonate (1.80 g, 5.37 mmol) in 1,4-dioxane (8.40 mL, 107 mmol) and water (1.2 mL, 67.1 mmol) was heated at 110° C. under an atmosphere of argon overnight. Water (3 mL) and EtOAc (3 mL) were added, the organic layer was separated, washed with brine, dried over MgSO$_4$, filtered, concentrated and the obtained residue was purified by column chromatography (SiO$_2$, elution with 0-10% MeOH in DCM) to give the title compound as a white solid (438 mg, 74.6%). LCMS: (FA) ES$^+$, 438, 440. $^1$H NMR (400 MHz, d$_6$-DMSO) δ: 8.87 (s, 1H), 8.62-8.64 (dd, J=1.5 Hz, 2H), 7.98 (s, 1H), 7.30-7.75 (dd, J=1.5, 2H), 5.58-5.59 (s, br, 2H), 3.40-3.69 (m, 2H), 0.840-0.890 (m, 2H), −0.04 (s, 9H).

Step 4: 4-[4-Bromo-5-(4H-1,2,4-triazol-3-yl)-2-thienyl]pyridine

4-[4-Bromo-5-(1-{[2-(trimethylsilyl)ethoxy]methyl}-1H-1,2,4-triazol-3-yl)-2-thienyl]pyridine (111.0 mg, 0.224 mmol) was dissolved in methylene chloride (3.0 mL, 47 mmol). Trifluoroacetic acid (3.0 mL, 39 mmol) was added and the solution was stirred at rt overnight. After the reaction was completed saturated NaHCO$_3$ (1 mL) was added and the reaction was stirred at rt for 20 min. EtOAc (5 mL) was added, the organic layer was separated, washed with brine, dried over MgSO$_4$, filtered, concentrated and the obtained residue was purified by column chromatography (SiO$_2$, elution with 2-20% MeOH in DCM) to give the title compound as a yellow solid (222 mg, 54%). LCMS: (FA) ES+, 307, 309. ¹H NMR (400 MHz, d₆-DMSO)) δ: 14.5 (s, br, 1H), 8.70-8.72 (dd, J=1.5 Hz, 2H), 8.10 (s, 1H), 7.90-7.94 (dd, J=1.5 Hz, 2H)

Step 5: (4-Methoxyphenyl)[5-pyridin-4-yl-2-(4H-1,2,4-triazol-3-yl)-3-thienyl]methanol (Compound 85)

To a mixture of 4-[4-bromo-5-(4H-1,2,4-triazol-3-yl)-2-thienyl]pyridine (222.0 mg, 0.730 mmol) in tetrahydrofuran (5.9 mL, 72.3 mmol) cooled to −78° C. was added dropwise n-BuLi in hexanes (2.50 M, 1.2 mL, 2.90 mmol) under an atmosphere of argon and the mixture was stirred at −78° C. for 30 min. To the solution was added dropwise a solution of 4-methoxybenzaldehyde (0.53 mL, 4.34 mmol) in tetrahydrofuran (5.0 mL, 60 mmol) and the resulting solution was stirred for 30 min at −78° C. The reaction mixture was quenched by the addition of water (2 mL) and the resulting mixture was warmed to room temperature and stirred for 30 min. The mixture was extracted with EtOAc (5 mL) then the organic layer was separated, washed with brine, dried over MgSO₄, filtered, and concentrated under the reduced pressure. The obtained residue was purified by prep HPLC to yield 62.0 mg as a yellow solid (23.5%). LCMS: (FA) ES+, 365. ¹H NMR (400 MHz, d₆-DMSO) δ: 8.68 (s, 1H), 8.55-8.57 (dd, J=1.5 Hz, 2H), 7.81 (s, br, 1H), 7.63-7.65 (dd, J=1.5 Hz, 2H), 7.40-7.44 (d, J=8.78 Hz, 2H), 6.82-6.84 (d, J=8.78 Hz, 2H), 6.72 (s, br, 1H), 3.68-3.69 (s, br, 3H).

Compounds in the following table were prepared from the appropriate starting materials in a method analogous to that of Example 7:

| 130 | LCMS: (FA) ES+ 383.4 |
| 132 | LCMS: (FA) ES+ 386.3 |
| 133 | LCMS: (FA) ES+ 418.3 |
| 134 | LCMS: (FA) ES+ 415.3 |
| 136 | LCMS: (FA) ES+ 403 |
| 138 | LCMS: (FA) ES+ 367.4 |
| 141 | LCMS: (FA) ES+ 363.3 |
| 142 | LCMS: (FA) ES+ 403.3 |
| 155 | LCMS: (FA) ES+ 353.4 |
| 158 | LCMS: (FA) ES+ 379.4 |
| 159 | LCMS: (FA) ES+ 403.3 |
| 162 | LCMS: (FA) ES+ 371.3 |
| 169 | LCMS: (FA) ES+ 387.3 |
| 171 | LCMS: (FA) ES+ 386.4 |
| 174 | LCMS: (FA) ES+ 363.5 |
| 175 | LCMS: (FA) ES+ 386.4 |
| 183 | LCMS: (FA) ES+ 381.4 |
| 186 | LCMS: (FA) ES+ 417, 419. |
| 187 | LCMS: (FA) ES+ 387.3 |
| 188 | LCMS: (FA) ES+ 367.4 |
| 191 | LCMS: (FA) ES+ 399.4 |
| 193 | LCMS: (FA) ES+ 403.4 |
| 198 | LCMS: (FA) ES+ 411. |
| 199 | LCMS: (FA) ES+ 371.4 |
| 202 | LCMS: (FA) ES+ 379.4 |
| 203 | LCMS: (FA) ES+ 403. |
| 207 | LCMS: (FA) ES+ 412.3 |
| 208 | LCMS: (FA) ES+ 385. |
| 214 | LCMS: (FA) ES+ 412.4 |
| 215 | LCMS: (FA) ES+ 393. |
| 217 | LCMS: (FA) ES+ 369.4 |
| 219 | LCMS: (FA) ES+ 403.4 |
| 228 | LCMS: (FA) ES+ 385.4 |
| 231 | LCMS: (FA) ES+ 413.3 |
| 232 | LCMS: (FA) ES+ 387.3 |
| 233 | LCMS: (FA) ES+ 419.2 |
| 235 | LCMS: (FA) ES+ 371.3 |
| 236 | LCMS: (FA) ES+ 413.4 |
| 239 | LCMS: (FA) ES+ 383.4 |
| 246 | LCMS: (FA) ES+ 395.4 |
| 249 | LCMS: (FA) ES+ 365.3 |
| 252 | LCMS: (FA) ES+ 413.4 |
| 253 | LCMS: (FA) ES+ 363.3 |
| 256 | LCMS: (FA) ES+ 379.4 |
| 257 | LCMS: (FA) ES+ 386.4 |
| 258 | LCMS: (FA) ES+ 412.3 |
| 260 | LCMS: (FA) ES+ 403.2 |
| 263 | LCMS: (FA) ES+ 387.3 |
| 264 | LCMS: (FA) ES+ 383.4 |
| 266 | LCMS: (FA) ES+ 371.3 |
| 271 | LCMS: (FA) ES+ 355.4 |
| 272 | LCMS: (FA) ES+ 366.3 |
| 275 | LCMS: (FA) ES+ 387.4 |
| 276 | LCMS: (FA) ES+ 412.3 |
| 279 | LCMS: (FA) ES+ 417, 419. |
| 280 | LCMS: (FA) ES+ 385. |
| 281 | LCMS: (FA) ES+ 403. |
| 284 | LCMS: (FA) ES+ 403 |

Example 8

Synthesis of 4-[4-(4-chlorobenzyl)-5-(4H-1,2,4-triazol-3-yl)-2-thienyl]pyridine (Compound 5)

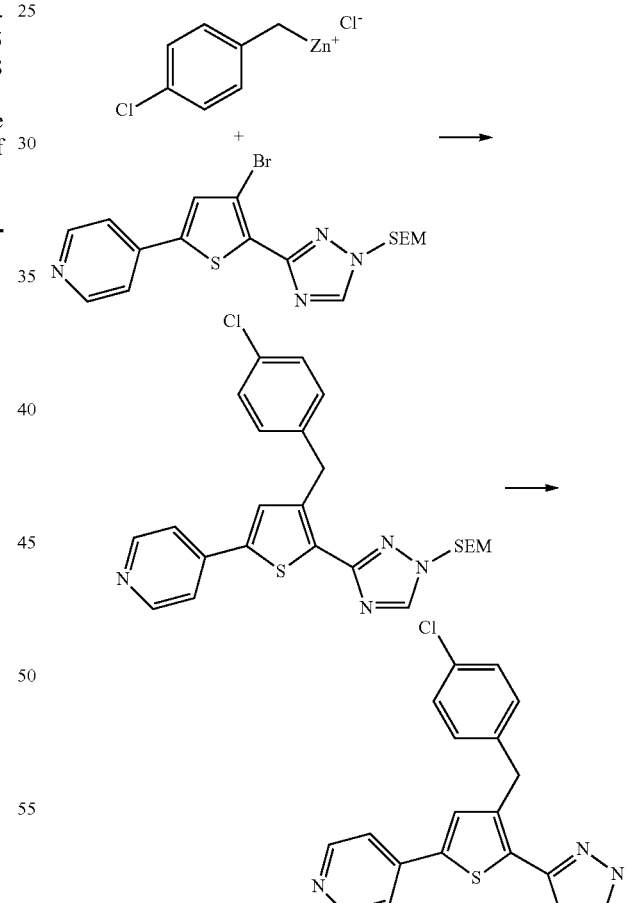

Step 1: 4-[4-(4-Chlorobenzyl)-5-(1-{[2-(trimethylsilyl)ethoxy]methyl}-1H-1,2,4-triazol-3-yl)-2-thienyl]pyridine Bis(tri-t-butylphosphine)palladium(0) (4.38 mg, 0.00857 mmol) and 4-[4-bromo-5-(1-{[2-(trimethylsilyl)ethoxy]methyl}-1H-1,2,4-triazol-3-yl)-2-thienyl]pyridine (0.075 g, 0.17 mmol) were combined in a dry round bottomed flask fitted with a stirbar and sealed with a septum. The flask was evacuated/refilled with nitrogen three times then a solution of 4-chlorobenzylzinc chloride in tetrahydrofuran (0.50M, 0.720 mL, 0.360 mmol) was added dropwise via a syringe. A nitrogen line was attached and the reaction was stirred at rt for 30 minutes, then at 60° C. for ~2 hours. The reaction was cooled to rt, diluted with EtOAc and saturated ammonium chloride solution, then the mixture was transferred to a separatory funnel. The organic layer was separated and the aqueous layer was extracted twice more with EtOAc. The organics were combined, washed with bicarbonate solution, then brine, then dried over sodium sulfate. The mixture was filtered then evaporated in vacuo and the residue was purified by column chromatography on silica, elution 100% hexane to 100% EtOAc to afford the title compound as a light yellow oil. Yield 63 mg (76% yield). LCMS: (FA) ES+, 483, 485.

Step 2: 4-[4-(4-Chlorobenzyl)-5-(4H-1,2,4-triazol-3-yl)-2-thienyl]pyridine (Compound 5)

The 4-[4-(4-chlorobenzyl)-5-(1-{[2-(trimethylsilyl)ethoxy]methyl}-1H-1,2,4-triazol-3-yl)-2-thienyl]pyridine (58 mg, 0.12 mmol) and methylene chloride (4.0 mL, 62 mmol) were combined in a round bottomed flask equipped with a stirbar. The mixture was stirred and trifluoroacetic acid (1.1 mL, 14 mmol) was added in one portion. The resulting yellow solution was stirred overnight at rt under an atmosphere of nitrogen. Excess solvent was removed on the rotovap and the residue was digested in a mixture of EtOAc and aqueous sodium bicarbonate solution. The mixture was stirred then transferred to a separatory funnel. The organic layer was separated and the aqueous layer was extracted twice more with EtOAc. The organics were combined, washed with bicarbonate solution, then saline, and then dried over sodium sulfate. The mixture was filtered then evaporated in vacuo and the residue was purified by column chromatography on silica, elution 100% DCM to 100% EtOAc to afford the title compound as an off-white powder. Yield 41 mg (97% yield). LCMS: (FA) ES+, 353, 355. $^1$H NMR (400 MHz, $d_6$-DMSO) δ: 14.31 (1H, br s), 8.67 (1H, br s), 8.55 (2H, d, J=6.3 Hz), 7.69 (1H, s), 7.63 (2H, d, J=6.3 Hz), 7.36-7.30 (4H, m), 4.47 (2H, s).

Compounds in the following table were prepared from the appropriate starting materials in a method analogous to that of Example 8:

| 87 | LCMS: (FA) ES+ 370. |
|---|---|

Example 9

Synthesis of 6-chloro-2-methyl-1-[2-(1H-pyrazol-5-yl)-5-pyridin-4-yl-3-thienyl]-1,2,3,4-tetrahydroisoquinoline (Compound 58)

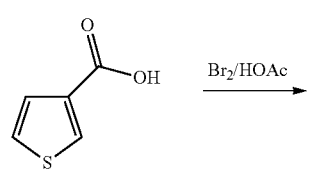

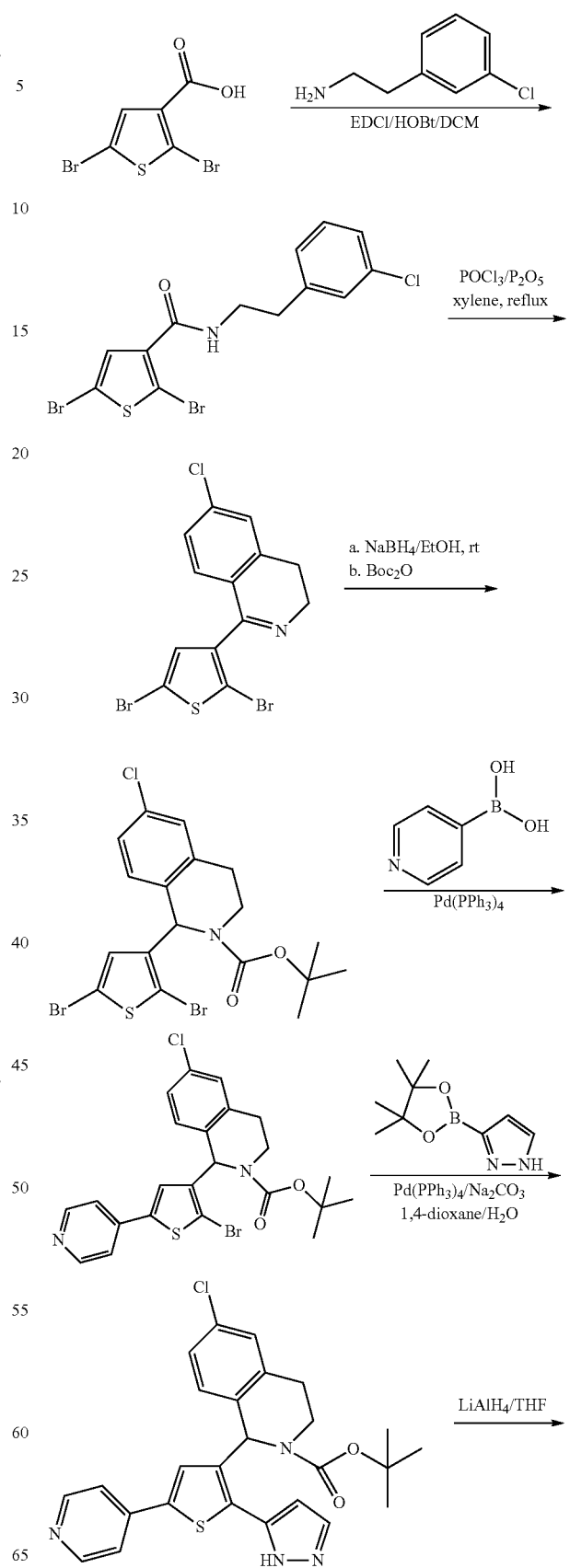

-continued

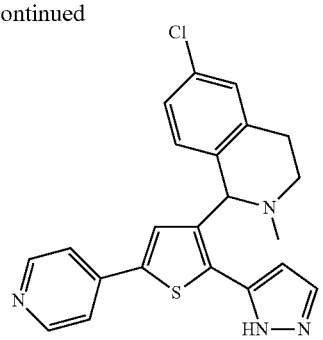

Step 1: 2,5-Dibromo-3-thenoic Acid

In a 500 mL round bottomed flask was placed 3-thenoic acid (16.04 g, 125.2 mmol) and acetic acid (200 mL, 4000 mmol). To the mixture was added bromine (32.24 mL, 625.8 mmol) and the mixture was stirred for 18 h at 60° C. The mixture was allowed to cool to rt then was diluted with ice-water. Sodium bisulfite (52.10 g, 500.7 mmol) was added. The resulting precipitate was collected by filtration and then washed with water to give 5-dibromo-3-thenoic acid as an off-white powder (33.4, 93.3%). LCMS (FA) ES+ 284.9, 286.9.

Step 2: 2,5-dibromo-N-[2-(3-chlorophenyl)ethyl]thiophene-3-carboxamide

To a mixture of 2,5-dibromo-3-thenoic Acid (10.0 g, 35.0 mmol), 2-(3-chlorophenyl)ethanamine (7.08 g, 45.5 mmol) and 1-hydroxybenzotriazole hydrate (5.89 g, 38.5 mmol) in methylene chloride (291 mL, 4550 mmol) was added N-(3-dimethylaminopropyl)-N'-ethylcarbodiimide hydrochloride (12.1 g, 62.9 mmol). The mixture was stirred at rt overnight. The reaction mixture was washed with 1NHCl, water, saturated sodium bicarbonate and brine. The DCM layer was dried and evaporated to afford 5-dibromo-N-[2-(3-chlorophenyl)ethyl]thiophene-3-carboxamide (14.7, 99.2%). LCMS (FA) ES+ 423.9, 425.9.

Step 3: 6-chloro-1-(2,5-dibromo-3-thienyl)-3,4-dihydroisoquinoline

To a mixture of 2,5-dibromo-N-[2-(3-chlorophenyl)ethyl]thiophene-3-carboxamide (5.15 g, 12.2 mmol) in xylenes (25.98 mL, 70.32 mmol) at 70° C. was added phosphorus pentoxide (13.0 g, 45.8 mmol) and then phosphoryl chloride (12.0 mL, 129 mmol). The mixture was heated at 150° C. for 60 h, then the mixture was cooled to rt. The solution was removed by decantation and washed with toluene twice. Water (20 mL) and 20% NaOH (20 mL) were added and the mixture was sonicated. The mixture was extracted with EtOAc. The organic layer was washed with water, dried over MgSO4, and evaporated in vacuo to give a residue which was purified by chromatography to afford 6-chloro-1-(2,5-dibromo-3-thienyl)-3,4-dihydroisoquinoline as foam solid (2.8 g, 57%).

Step 4: tert-Butyl 6-chloro-1-(2,5-dibromo-3-thienyl)-3,4-dihydroisoquinoline-2(1H)-carboxylate To a mixture of 6-chloro-1-(2,5-dibromo-3-thienyl)-3,4-dihydroisoquinoline (2.60 g, 6.41 mmol) in ethanol (37.43 mL, 641.1 mmol) was added di-tert-butyldicarbonate (2.80 g, 12.8 mmol) and sodium tetrahydroborate (0.485 g, 12.8 mmol) at 0° C. The mixture was stirred for 20 min at 0° C. and then overnight at rt. The reaction mixture was concentrated and the residue was extracted with EtOAc. The organic layer was separated, washed with water, washed with brine, and then dried over MgSO4. The solvent was evaporated and the residue was purified by chromatography to afford tert-butyl 6-chloro-1-(2,5-dibromo-3-thienyl)-3,4-dihydroisoquinoline-2(1H)-carboxylate as a white powder (2.45 g, 75.3%).

Step 5: tert-Butyl 1-(2-bromo-5-pyridin-4-yl-3-thienyl)-6-chloro-3,4-dihydroisoquinoline-2(1H)-carboxylate A mixture of tert-butyl 6-chloro-1-(2,5-dibromo-3-thienyl)-3,4-dihydroisoquinoline-2(1H)-carboxylate (177.0 mg, 0.3486 mmol), pyridine-4-boronic acid (51.43 mg, 0.4184 mmol) tetrakis(triphenylphosphine)palladium(0) (20.1 mg, 0.0174 mmol) and cesium carbonate (0.341 g, 1.04 mmol) in 1,4-dioxane (6.0 mL, 77 mmol) and water (2.0 mL, 110 mmol) was degassed and heated at 100° C. for 1 h. The mixture was extracted with EtOAc. The organic layer was separated and washed with water. The organic layer was dried and evaporated to leave a residue which was purified by chromatography to afford tert-butyl 1-(2-bromo-5-pyridin-4-yl-3-thienyl)-6-chloro-3,4-dihydroisoquinoline-2(1H)-carboxylate as a white solid (72 mg, 41%). LCMS AA ES+ 505.1, 507.1

Step 6: tert-Butyl 6-chloro-1-[2-(1H-pyrazol-5-yl)-5-pyridin-4-yl-3-thienyl]-3,4-dihydroisoquinoline-2(1H)-carboxylate A mixture of tert-butyl 1-(2-bromo-5-pyridin-4-yl-3-thienyl)-6-chloro-3,4-dihydroisoquinoline-2(1H)-carboxylate (72.0 mg, 0.142 mmol), 3-(4,4,5,5-tetramethyl-1,3,2-dioxabolone)-pyrrazole (27.6 mg, 0.142 mmol), [1,1'-bis(diphenylphosphino)ferrocene]palladium(II)dichloride (11.7 mg, 0.0142 mmol) and sodium carbonate (29 mg, 0.27 mmol) in 1,2-dimethoxyethane (3.0 mL, 29 mmol) and water (1.0 mL, 56 mmol) was heated at 95° C. for 4.5 h. A LCMS showed the desired product together with unreacted starting material. Additional [1,1'-bis(diphenylphosphino)ferrocene]palladium(II)dichloride (11.7 mg, 0.0142 mmol) 3-(4,4,5,5-Tetramethyl-1,3,2-dioxabolone)-pyrrazole (56 mg, 0.29 mmol), tetrakis(triphenylphosphine)palladium(0) (15 mg, 0.013 mmol), sodium carbonate (100 mg, 0.9 mmol) and 1,2-dimethoxyethane (3.0 mL, 29 mmol) were added. The mixture was heated at 100° C. for another 4 h. The mixture was dry-loaded onto silica gel and purified by chromatography to afford tert-butyl 6-chloro-1-[2-(1H-pyrazol-5-yl)-5-pyridin-4-yl-3-thienyl]-3,4-dihydroisoquinoline-2(1H)-carboxylate (41 mg, 58%). LCMS AA ES+ 493.2, 495.1.

Step 7: 6-Chloro-2-methyl-1-[2-(1H-pyrazol-5-yl)-5-pyridin-4-yl-3-thienyl]-1,2,3,4-tetrahydroisoquinoline (Compound 58)

To a solution of tert-butyl 6-chloro-1-[2-(1H-pyrazol-5-yl)-5-pyridin-4-yl-3-thienyl]-3,4-dihydroisoquinoline-2(1H)-carboxylate (41 mg, 0.083 mmol) in tetrahydrofuran (3.0 mL, 37 mmol) was added lithium tetrahydroaluminate (0.249 mmol, 0.249 mmol) in THF (2.0 mM) at −78° C. After the addition, the temperature of the reaction was raised to rt for 30 min and then heated at 85° C. for 5 h. The mixture was quenched with water, diluted with methanol, and extracted with ethyl acetate. The organic phase was dried, filtered and evaporated. The residue was loaded onto silica gel and purified by chromatography to afford 6-chloro-2-methyl-1-[2-(1H-pyrazol-5-yl)-5-pyridin-4-yl-3-thienyl]-1,2,3,4-tetrahydroisoquinoline (5.1 mg, 15%). LCMS AA ES+ 407.2, 409.1; $^1$H NMR (400 MHz, d$_4$-methanol) δ: 8.48 (d, J=5.06 Hz, 2H), 7.89-7.66 (m, 1H), 7.61 (s, 2H), 7.50-7.31 (br, 1H), 7.17 (s, 1H), 7.00 (d, J=7.98 Hz, 1H), 6.87-6.48 (m, 2H), 5.16-4.94 (m, 1H), 3.34 (s, 1H), 3.28-3.10 (m, 2H), 2.94-2.79 (m, 1H), 2.72-2.56 (m, 1H), 2.26 (s, 3H)
Example 10
Synthesis of 4-(4-chlorobenzyl)-2-(pyridin-4-yl)-5-(4H-1,2,4-triazol-3-yl)thiazole (Compound 76)
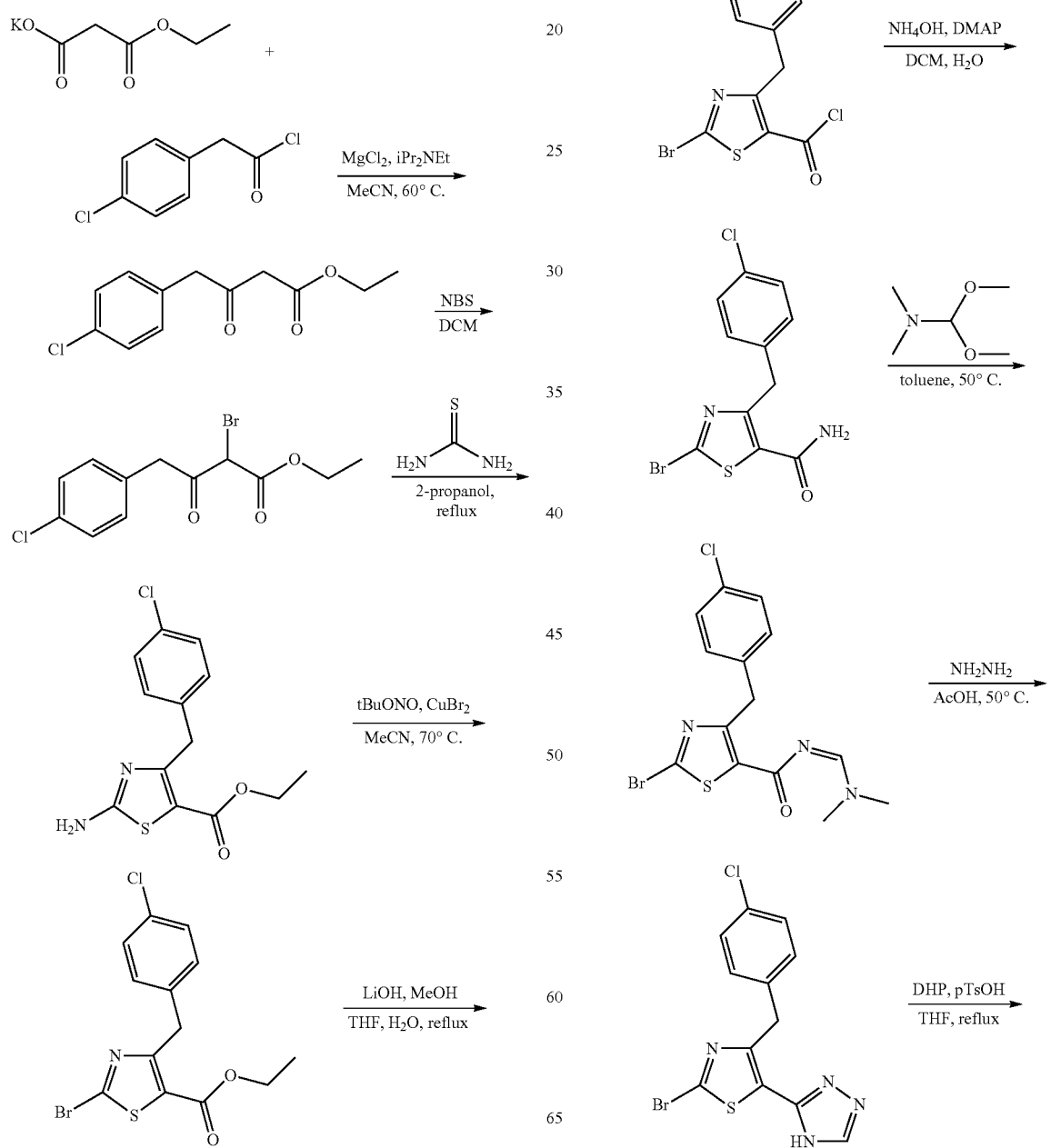
-continued
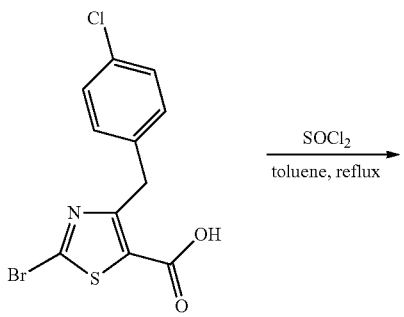

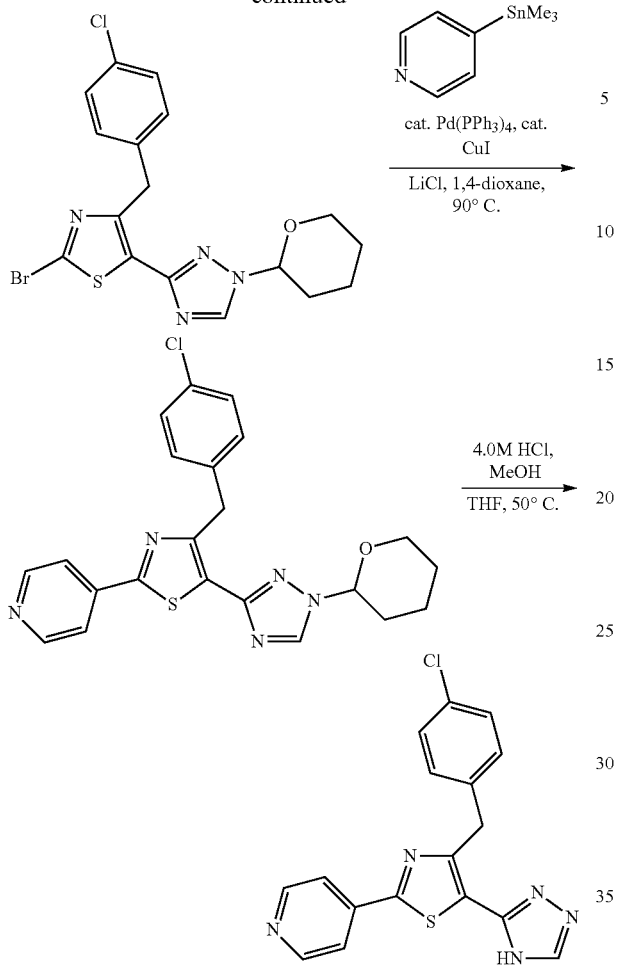

Step 1: Ethyl 4-(4-chlorophenyl)-3-oxobutanoate

To a suspension of potassium ethyl malonate (17.12 g, 100.6 mmol) in acetonitrile (150 mL) were added N,N-diisopropylethylamine (28 mL, 160 mmol) and magnesium chloride (12.11 g, 127.2 mmol). The resulting mixture was stirred for 1 hour. A solution of 4-chlorophenylacetyl chloride (10.12 g, 53.53 mmol) in acetonitrile (100 mL) was then added and the mixture was heated to 60° C. and stirred for 20 hours. The mixture was cooled to room temperature and concentrated under reduced pressure. The residue was suspended in 1N aqueous HCl (250 mL) and was extracted with EtOAc (100 mL×2). The combined organic phases were dried over anhydrous MgSO4 and insoluble materials were removed by filtration. The filtrate was concentrated under reduced pressure and the residue was purified by column chromatography on silica, elution with a 0%-80% mixture of EtOAc in hexane (linear gradient, 45 min) to obtain ethyl 4-(4-chlorophenyl)-3-oxobutanoate (5.0 g, 39%) as a yellow oil. LC/MS (FA) ES– 239. $^1$H NMR ($d_6$-DMSO, 400 MHz): δ: 7.37 (2H, d, J=13.8 Hz), 7.20 (2H, d, J=13.8 Hz), 4.07 (2H, q, J=7.2 Hz), 3.89 (2H, s), 3.66 (2H, s), 1.17 (3H, t, J=7.2 Hz).

Step 2: Ethyl 2-bromo-4-(4-chlorophenyl)-3-oxobutanoate

In a 250 mL round bottomed flask were placed ethyl 4-(4-chlorophenyl)-3-oxobutanoate (4.04 g, 16.8 mmol) and methylene chloride (100 mL). To the solution was added N-bromosuccinimide (3.13 g, 17.6 mmol) and the mixture was stirred for 3 h at rt. To the mixture was added a freshly prepared 10% aqueous solution of NaHSO3 (5 g NaHSO$_3$ dissolved in 50 mL water) and the resulting biphasic mixture was vigorously stirred for 15 min at rt. The organic phase was separated and the aqueous phase was extracted with DCM (30 mL). The organic phases were combined and washed with a saturated aqueous solution of NaHCO$_3$ (50 mL) and dried over anhydrous MgSO$_4$. Insoluble materials were removed by filtration and the filtrate was concentrated under reduced pressure. The residual yellow oil was essentially pure and was used in the next step without further purification. LC/MS (FA) ES– 319.

Step 3: Ethyl 2-amino-4-(4-chlorobenzyl)thiazole-5-carboxylate

In a 100 mL round bottomed flask were placed ethyl 2-bromo-4-(4-chlorophenyl)-3-oxobutanoate (990 mg, 3.1 mmol) and isopropyl alcohol (20 mL). To the mixture was added thiourea (590 mg, 7.8 mmol) and the reaction was then refluxed for 16 h with stirring. The mixture was allowed to cool to rt and was then concentrated under reduced pressure. The residue was suspended in EtOAc (50 mL) and then washed with a saturated aqueous solution of NaHCO$_3$ (50 mL), brine (50 mL), and dried over anhydrous MgSO4. Insoluble materials were removed by filtration and the filtrate was concentrated under reduced pressure. The residual off-white yellowish crystalline solid was essentially pure by LCMS and was used in the next step without further purification. LC/MS (FA) ES+ 296. $^1$H NMR ($d_6$-DMSO, 400 MHz): δ: 7.80 (2H, br s), 7.32 (2H, d, J=8.8 Hz), 7.23 (2H, d, J=8.8 Hz), 4.14-4.20 (4H, m), 1.22 (3H, t, J=7.1 Hz).

Step 4: Ethyl 2-bromo-4-(4-chlorobenzyl)thiazole-5-carboxylate

In a 250 mL round bottomed flask were placed ethyl 2-amino-4-(4-chlorobenzyl)-1,3-thiazole-5-carboxylate (786 mg, 2.65 mmol) and acetonitrile (75 mL). To the mixture was added copper (II) bromide (963 mg, 4.31 mmol). The suspension was stirred for 15 min at rt. To the mixture was added tert-butyl nitrite (0.630 mL, 5.30 mmol) and the stirring was continued for an additional 1.5 h at 70° C. The reaction mixture was allowed to cool to rt and was then concentrated under reduced pressure. The residue was purified by column chromatography on silica, elution with a 10%-50% mixture of EtOAc in hexane to obtain ethyl 2-bromo-4-(4-chlorobenzyl)-1,3-thiazole-5-carboxylate (820 mg; 86%) as an yellow syrup, which spontaneously solidified on standing at rt to afford off-white crystalline solid. LC/MS (FA) ES+ 362. NMR (CDCl3, 400 MHz): δ: 7.29 (2H, d, J=8.8 Hz), 7.24 (2H, d, J=8.8 Hz), 4.44 (2H, s), 4.35 (2H, q, J=7.3 Hz), 1.36 (3H, t, J=7.3 Hz).

Step 5: Ethyl 2-bromo-4-(4-chlorobenzyl)thiazole-5-carboxylic acid

In a 100 mL round bottomed flask were placed ethyl 2-bromo-4-(4-chlorobenzyl)-1,3-thiazole-5-carboxylate (955 mg, 2.65 mmol) and tetrahydrofuran (50 mL, 600 mmol). To this solution was added a freshly prepared aqueous solution of lithium hydroxide [(lithium hydroxide.H$_2$O (177 mg, 4.22 mmol) and water (15 mL, 830 mmol)). The mixture was stirred for 4 h at rt then MeOH (20 mL) was added and the mixture was refluxed for 3 h. The mixture was allowed to cool to rt and then acidified by the addition of 1.0N HCl aq (4.5 mL). The mixture was stirred for 1 h at rt. The mixture was then concentrated under reduced pressure until reduced to ca 5 mL volume. EtOAc (50 mL) was added and the mixture was washed with water (50 mL), then brine (50 mL), then was dried over anhydrous MgSO4. Insoluble materials were removed by filtration and the filtrate was concentrated under reduced pressure. The residual yellow crystalline solid was used in the next step without further purification. LC/MS (FA) ES+ 332.

Steps 6 and 7:
2-Bromo-4-(4-chlorobenzyl)thiazole-5-carboxamide

In a 250 mL round bottomed flask were placed 2-bromo-4-(4-chlorobenzyl)-1,3-thiazole-5-carboxylic acid (800 mg, 2 mmol) and toluene (30 mL, 300 mmol). To the suspension was added thionyl chloride (700 uL, 10 mmol) and the mixture was refluxed for 2 h during which time the suspension turned into a solution. The reaction was allowed to cool to rt and then was concentrated under reduced pressure. The residue was co-evaporated with toluene (10 mL). The residual orange oil was dissolved in methylene chloride (30 mL, 500 mmol) then N,N-dimethylaminopyridine (21.2 mg, 0.174) was added. To the mixture was added ammonium hydroxide in water (8.5 M, 20 mL) and the mixture was stirred for 1.5 h at rt. The organic phase was separated and the aqueous phase was extracted with DCM (30 mL). The organic phase and extract were combined and dried over anhydrous MgSO4. Insoluble materials were removed by filtration and the filtrate was concentrated under reduced pressure. The residual yellow syrup was used in the next step without further purification. LC/MS (FA) ES+ 333.

Step 8: (Z)-2-bromo-4-(4-chlorobenzyl)-N-((dimethylamino)methylene)thiazole-5-carboxamide In a 250 mL round bottomed flask were placed 2-bromo-4-(4-chlorobenzyl)-1,3-thiazole-5-carboxamide (0.66 g, 2.0 mmol) and toluene (30 mL, 300 mmol). The mixture was turned into a suspension by ultrasonication. To the suspension was added 1,1-dimethoxy-N,N-dimethylmethanamine (80 uL, 6.0 mmol) and the mixture was stirred for 2 h at 50° C. The mixture was allowed to cool to rt then was concentrated under reduced pressure. The residue was used in the next step without further purification. LC/MS (FA) ES+ 388.

Step 9: 2-Bromo-4-(4-chlorobenzyl)-5-(4H-1,2,4-triazol-3-yl)thiazole

In a 250 mL round bottomed flask were placed 2-bromo-4-(4-chlorobenzyl)-N-[(1Z)-(dimethylamino)methylene]-1,3-thiazole-5-carboxamide and acetic acid (50 mL, 900 mmol). Hydrazine hydrate (490 uL, 10 mmol) was added and the mixture was stirred for 1 h at 50° C. The mixture was allowed to cool to rt, then was concentrated under reduced pressure to obtain 3-[2-bromo-4-(4-chlorobenzyl)-1,3-thiazol-5-yl]-4H-1,2,4-triazole as a yellowish off-white crystalline solid. The crude material was used in the next step without further purification. LC/MS (FA) ES+ 357.

Step 10: 2-Bromo-4-(4-chlorobenzyl)-5-(1-(tetrahydro-2H-pyran-2-yl)-1H-1,2,4-triazol-3-yl)thiazole In a 250 mL round bottomed flask were placed 3-[2-bromo-4-(4-chlorobenzyl)-1,3-thiazol-5-yl]-4H-1,2,4-triazole (0.7 g, 2 mmol) and tetrahydrofuran (50 mL, 600 mmol). To the mixture were added dihydropyran (2 mL, 20 mmol) and p-toluenesulfonic acid monohydrate (911.3 mg, 4.791 mmol). The mixture was refluxed for 2 h then was allowed to cool to rt and then a saturated aqueous solution of NaHCO$_3$ (50 mL) was added. The resulting biphasic mixture was vigorously stirred for 30 min at rt. The aqueous phase was separated then was extracted with EtOAc (50 mL×2). The combined organic phases were dried over anhydrous MgSO$_4$. Insoluble materials were removed by filtration and the filtrate was concentrated under reduced pressure. The residue was purified by column chromatography on silica, elution with a 10%-80% mixture of EtOAc in hexane (linear gradient, 30 min) to afford 3-[2-bromo-4-(4-chlorobenzyl)-1,3-thiazol-5-yl]-1-(tetrahydro-2H-pyran-2-yl)-1H-1,2,4-triazole (778 mg; 67% six steps) as a yellow syrup which spontaneously solidified on standing at rt for 2 days. LC/MS (FA) ES+ 441. $^1$H NMR (d$_6$-DMSO, 400 MHz): δ: 8.89 (1H, s), 7.28-7.34 (4H, m), 5.62 (1H, dd, J=2.8 and 9.6 Hz), 4.52 (2H, s), 3.92-3.96 (1H, m), 3.63-3.70 (1H, m), 1.91-2.14 (3H, m), 1.52-1.72 (3H, m)

Step 11: 4-(4-Chlorobenzyl)-2-(pyridin-4-yl)-5-(1-(tetrahydro-2H-pyran-2-yl)-1H-1,2,4-triazol-3-yl)thiazole To a 20 mL vial was added a solution of 3-[2-bromo-4-(4-chlorobenzyl)-1,3-thiazol-5-yl]-1-(tetrahydro-2H-pyran-2-yl)-1H-1,2,4-triazole (0.1500 g, 0.3411 mmol) and 4-(tributylstannyl)pyridine (0.2511 g, 0.6822 mmol) in anhydrous 1,4-dioxane (5.000 mL). The solution was degassed for 10 minutes. Lithium chloride (0.108 g, 2.56 mmol) and copper (I) iodide (0.0487 g, 0.256 mmol) were added followed by tetrakis(triphenylphosphine)palladium(0) (0.0492 g, 0.0426 mmol). The reaction mixture was heated to 90° C. and allowed to stir for 18 h. The reaction was cooled to ambient temperature and quenched by the addition of a saturated aqueous solution of sodium bicarbonate (10 mL). The quench mixture was extracted with EtOAc (10 mL×3). The combined organic layers were dried over anhydrous Na$_2$SO$_4$, filtered and concentrated under reduced pressure. The crude material was purified by column chromatography on silica (gradient DCM to 10% MeOH over 30 min) to afford the product (0.2245 g, 73%) as a yellow solid. LC/MS (AA) ES+ 438. $^1$H NMR (400 MHz, d$_6$-DMSO) δ: 8.92 (s, 1H), 7.90 (d, J=4.8 Hz, 2H), 7.65 (d, J=1.2 Hz, 2H), 7.38-7.32 (m, 4H), 5.66 (dd, J=9.6, 2.8 Hz, 1H), 4.65 (s, 2H), 3.97-3.94 (m, 1H), 3.72-3.66 (m, 1H), 1.59-1.48 (m, 2H), 1.32-1.23 (m, 2H), 1.10-1.06 (m, 2H).

Step 12: 4-(4-Chlorobenzyl)-2-(pyridin-4-yl)-5-(4H-1,2,4-triazol-3-yl)thiazole (Compound 76)

To a 20 mL vial was added a solution of 4-{4-(4-chlorobenzyl)-5-[1-(tetrahydro-2H-pyran-2-yl)-1H-1,2,4-triazol-3-yl]-1,3-thiazol-2-yl}pyridine (0.2245 g, 0.635 mmol) in anhydrous tetrahydrofuran (2.000 mL) and methanol (2.000 mL). 4.0 M Hydrochloric acid in 1,4-dioxane (1.0 mL, 4.0 mmol) was added and the reaction mixture was allowed to stir at 50° C. for 18 hours. The reaction was cooled to ambient temperature and quenched by the addition of a saturated aqueous solution of sodium bicarbonate (10 mL) and extracted with EtOAc (10 mL×3). The combined organic phases were dried over anhydrous Na$_2$SO$_4$, filtered and concentrated under reduced pressure. The crude material was purified by HPLC to afford the product (0.0423 g, 45%) as an off white solid. LC/MS (AA) ES+ 354. $^1$H NMR (400 MHz, d₆-DMSO) δ: 14.48 (s, 1H), 8.71 (dd, J=4.4, 1.2 Hz, 2H), 7.89-7.87 (m, 2H), 7.38-7.32 (m, 4H), 4.67 (s, 2H).

Compounds in the following table were prepared from the appropriate starting materials in a method analogous to that of Example 10:

| | |
|---|---|
| 37 | LCMS: (FA) ES+ 372, 374. |
| 39 | LCMS: (AA) ES+ 355, 357. |
| 46 | LCMS: (AA) ES− 370, 372. |
| 63 | LCMS: (FA) ES+ 383, 385. |
| 78 | LCMS: (AA) ES+ 372, 374. |

Example 11

Synthesis of 4-(4-Chlorobenzyl)-2-(2-methylpyridin-4-yl)-5-(4H-1,2,4-triazol-3-yl)thiazole (Compound 18)

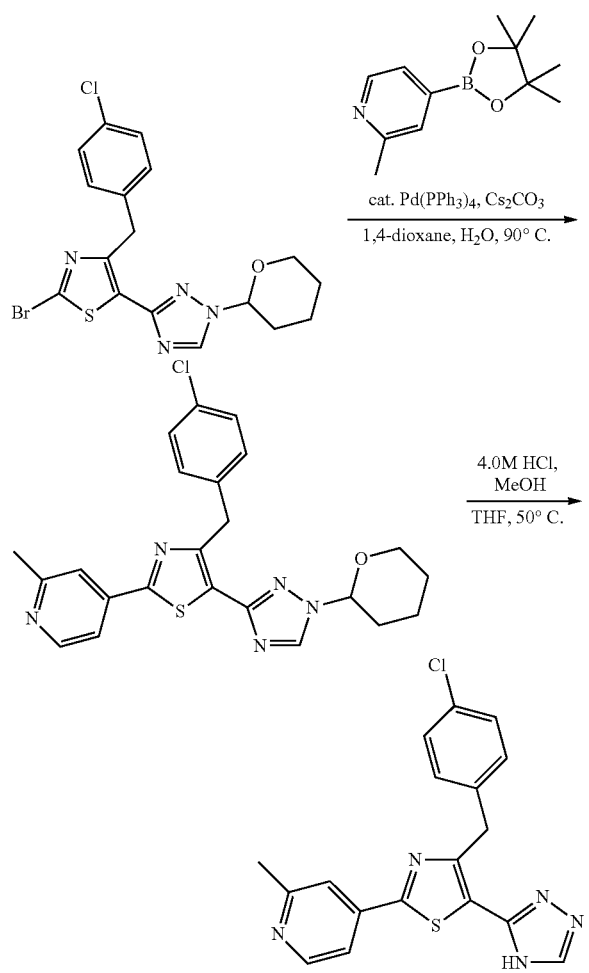

Step 1: 4-(4-chlorobenzyl)-2-(2-methylpyridin-4-yl)-5-(1-(tetrahydro-2H-pyran-2-yl)-1H-1,2,4-triazol-3-yl)thiazole To a 20 mL vial was added a solution of 3-[2-bromo-4-(4-chlorobenzyl)-1,3-thiazol-5-yl]-1-(tetrahydro-2H-pyran-2-yl)-1H-1,2,4-triazole (0.1000 g, 0.2274 mmol) and 2-methyl-4-(4,4,5,5-tetramethyl-[1,3,2]dioxaborolan-2-yl)pyridine (0.0931 g, 0.425 mmol) in a solution of 1,4-dioxane (2.5000 mL, 32.036 mmol) and water (0.2500 mL). Cesium carbonate (0.2223 g, 0.6822 mmol) was added followed by tetrakis(triphenylphosphine)palladium(0) (0.031533 g, 0.027288 mmol). The reaction mixture was heated to 90° C. and allowed to stir for 18 h. The reaction was cooled to ambient temperature and quenched by the addition of a saturated aqueous solution of sodium bicarbonate (10 mL) and extracted with EtOAc (10 mL×3). The combined organic phases were dried over anhydrous Na₂SO₄, filtered and concentrated under reduced pressure. The crude material was dry loaded onto silica gel then was purified by column chromatography on silica (gradient DCM to 10% MeOH over 30 min) to afford the product with Ph₃PO impurities (0.1654 g, 96.6%) as a brown oil. LC/MS (AA) ES+ 452. ¹H NMR (400 MHz, d₆-DMSO) δ: 8.91 (s, 1H), 7.64-7.53 (m, 3H), 7.37-7.31 (m, 4H), 5.66 (dd, J=9.6, 2.8 Hz, 1H), 4.61 (s, 2H), 3.72-3.66 (m, 2H), 2.55 (s, 3H), 1.70-1.68 (m, 2H), 1.62-1.48 (m, 2H), 1.45-1.38 (m, 2H).

Step 2: 4-(4-Chlorobenzyl)-2-(2-methylpyridin-4-yl)-5-(4H-1,2,4-triazol-3-yl)thiazole (Compound 18)

To a 20 mL vial was added a solution of 4-{4-(4-chlorobenzyl)-5-[1-(tetrahydro-2H-pyran-2-yl)-1H-1,2,4-triazol-3-yl]-1,3-thiazol-2-yl}-2-methylpyridine (0.1654 g, 0.365 mmol) in anhydrous tetrahydrofuran (2.000 mL) and methanol (2.000 mL). 4.0 M hydrochloric acid in 1,4-dioxane (1.0 mL, 4.0 mmol) was added and the reaction mixture was allowed to stir at 50° C. for 18 hours. The reaction was cooled to ambient temperature and quenched by the addition of a saturated aqueous solution of sodium bicarbonate (10 mL) then was extracted with EtOAc (10 mL×3). The combined organic layers were dried over anhydrous Na₂SO₄, filtered and concentrated under reduced pressure. The crude material was purified by HPLC to afford the product (0.0351 g, 39.9%) as a white solid. LC/MS (AA) ES+ 368, 370. ¹H NMR (400 MHz, d₆-DMSO) δ: 8.73 (s, 1H), 8.56 (d, J=5.2 Hz, 1H), 7.75 (s, 1H), 7.67 (dd, J=5.2, 1.6 Hz, 1H), 7.37-7.32 (m, 4H), 4.65 (s, 2H) 2.55 (s, 3H).

Compounds in the following table were prepared from the appropriate starting materials in a method analogous to that of Example 11:

| | |
|---|---|
| 137 | LCMS: (FA) ES+ 354, 356. |
| 213 | LCMS: (FA) ES+ 427. |

Example 12

Synthesis of 4-(4-chlorobenzyl)-2-(pyridin-4-yl)thiazole-5-carboxylic acid (Compound 80)

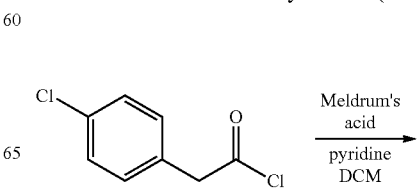

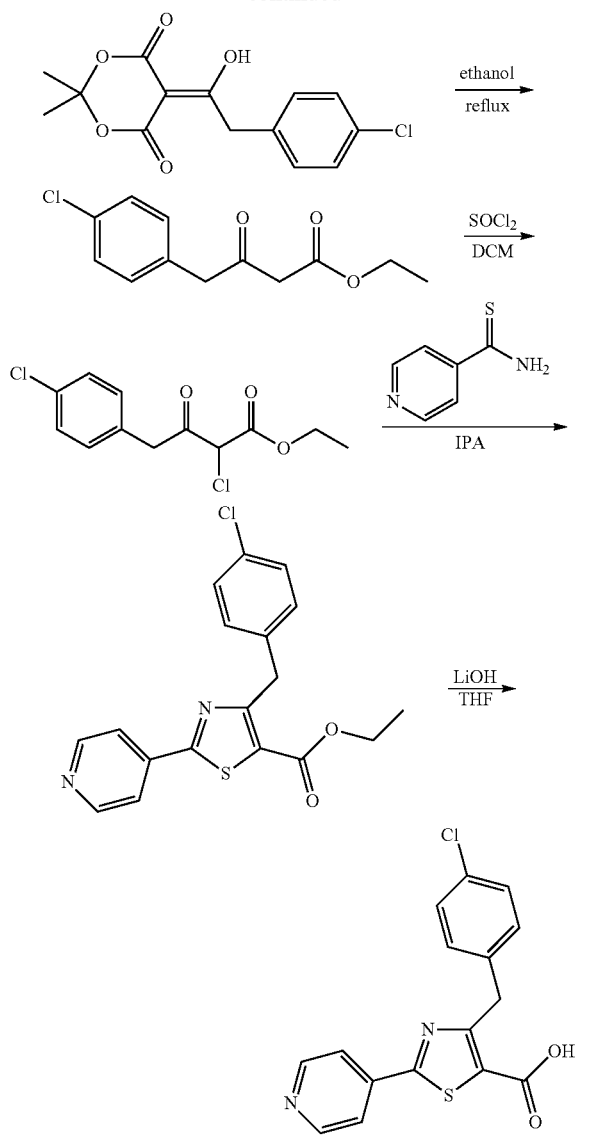

Step 1: 5-(2-(4-Chlorophenyl)-1-hydroxyethylidene)-2,2-dimethyl-1,3-dioxane-4,6-dione To a mixture of 2,2-dimethyl-1,3-dioxane-4,6-dione (52.7 g, 366 mmol) in DCM (205 mL) at −10° C. in an ice/methanol bath was added pyridine (72.5 mL, 897 mmol) over 10 minutes. To the resulting solution at −10° C. was added a solution of 2-(4-chlorophenyl)acetyl chloride (69.1 g, 366 mmol) in DCM (144 mL) dropwise over 1 hour. The mixture was stirred at −10° C. for 1 hour, then at room temperature for 1 hour. The mixture was poured into a mixture of 2 M HCl (820 mL) and ice (400 mL) and the aqueous layer was extracted with DCM (2×200 mL). The combined DCM layers were washed with 1 N HCl (100 mL) and brine (100 mL). The combined organic layers were dried over MgSO$_4$, filtered, and concentrated in vacuo to give 103 g of title compound. (95% yield). LC/MS (FA) ES− 295. $^1$H NMR (400 MHz, CDCl$_3$) δ: 15.25 (br s, 1H), 7.34-7.26 (m, 4H), 4.37 (s, 2H), 1.72 (s, 6H).

Step 2: Ethyl 4-(4-chlorophenyl)-3-oxobutanoate

A solution of 5-(2-(4-chlorophenyl)-1-hydroxyethylidene)-2,2-dimethyl-1,3-dioxane-4,6-dione (103 g, 347 mmol) in ethanol (718 mL) was refluxed for 3 hours. The reaction was cooled and concentrated in vacuo. The residue was purified by silica gel chromatography (ethyl acetate/hexane=0/100→20/80) to give 61 g of the title compound as an orange oil. (73% yield). LC/MS (FA) ES+ 241. $^1$H NMR (400 MHz, CDCl$_3$) δ: 7.32-7.28 (m, 2H), 7.15-7.11 (m, 2H), 4.17 (q, 2H, J=7.2 Hz), 3.81 (s, 2H), 3.45 (s, 2H), 1.26 (t, 3H, J=7.2 Hz).

Step 3: Ethyl 2-chloro-4-(4-chlorophenyl)-3-oxobutanoate

To a solution of ethyl 4-(4-chlorophenyl)-3-oxobutanoate (61.0 g, 253 mmol) in DCM (811 mL) in an ice bath was added sulfuryl chloride (34.2 g, 253 mmol) and the resulting solution was allowed to stir at room temperature overnight. The reaction was quenched with saturated sodium bicarbonate solution (200 mL) and the layers separated. The organic layer was washed with brine (100 mL), dried over MgSO$_4$, filtered, and concentrated in vacuo to give 70.8 g of title compound. (100% yield). $^1$H NMR (400 MHz, CDCl$_3$) δ: 7.33-7.30 (m, 2H), 7.17-7.14 (m, 2H), 4.85 (s, 1H), 4.26 (dq, 1H, J=7.2, 1.2 Hz), 4.02 (d, 1H, J=16.8 Hz), 3.97 (d, J=16.8 Hz, 1H), 1.29 (t, 3H, J=7.2 Hz).

Step 4: Ethyl 4-(4-chlorobenzyl)-2-(pyridin-4-yl)thiazole-5-carboxylate

To a solution of ethyl 2-chloro-4-(4-chlorophenyl)-3-oxobutanoate (70.8 g, 257 mmol) in IPA (2.96 L) was added thioisonicotinamide (71.1 g, 515 mmol) and the resulting mixture was refluxed for 3 days. The reaction was cooled and concentrated in vacuo and the residue was partitioned between DCM (300 ml) and saturated sodium bicarbonate solution (200 mL). The layers were separated and the aqueous layer was extracted with DCM (100 mL). The combined DCM layers were washed with brine (100 mL), dried over MgSO$_4$, filtered, and concentrated in vacuo to give crude product which was purified by silica gel chromatography (ethyl acetate/DCM=0/100→40/60) followed by recrystallization from ethyl acetate/hexanes to give 33 g of the title compound as yellow crystals. (36% yield). LC/MS (FA) ES+ 359. $^1$H NMR (400 MHz, CDCl$_3$) δ: 8.74-8.72 (m, 2H), 7.81-7.80 (m, 2H), 7.36-7.32 (m, 2H), 7.27-7.23 (m, 2H), 4.54 (s, 2H), 4.38 (q, 2H, J=7.2 Hz), 1.40 (t, 3H, J=7.2 Hz).

Step 5: 4-(4-chlorobenzyl)-2-(pyridin-4-yl)thiazole-5-carboxylic acid (Compound 80)

To a solution of ethyl 4-(4-chlorobenzyl)-2-(pyridin-4-yl)thiazole-5-carboxylate (12.8 g, 35.7 mmol) in THF (200 mL) and water (100 mL) was added 1.0 M LiOH (46.4 mL, 46.4 mmol) and the resulting solution was stirred at room temperature overnight. The mixture was acidified to pH 4 with 1 N HCl. The precipitated solids were filtered, washed with water and dried to give 11 g of the title compound as a white solid. (93% yield). LC/MS (FA) ES+ 331. $^1$H NMR (400 MHz, d$_6$-DMSO) δ: 13.86 (br s, 1H), 8.72-8.71 (m, 2H), 7.89-7.87 (m, 2H), 7.36-7.29 (m, 4H), 4.50 (s, 2H).

Example 13

Synthesis of N-{4-[4-(4-chlorobenzyl)-5-(4H-1,2,4-triazol-3-yl)-1,3-thiazol-2-yl]pyridin-2-yl}acetamide (Compound 56)

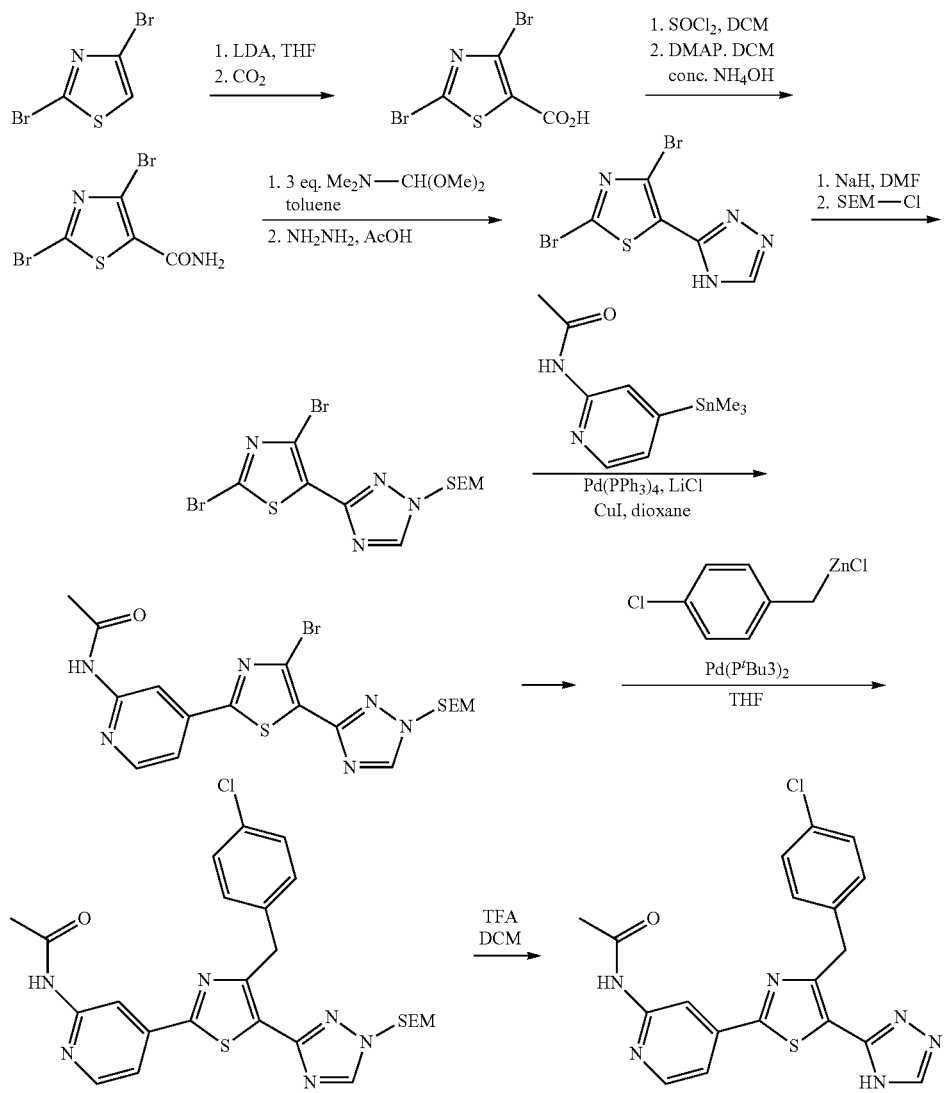

Step 1: 2,4-Dibromo-1,3-thiazole-5-carboxylic acid

To a 500 mL 3-neck round bottom flask equipped with dropping funnel and internal temperature monitor was added THF (200 mL) and N,N-diisopropylamine (14.7 mL, 105 mmol) under atmosphere of argon. After cooling at −75° C., 2.50 M of n-Butyllithium in hexane (41.1 mL, 103 mmol) was added dropwise into the solution over 30 min. The internal temperature was kept below −70° C. and the resulting solution was stirred for 15 min at −75° C. To this LDA solution was added a solution of 2,4-dibromothiazole (25.0 g, 99.8 mmol) in THF (60 mL) via dropping funnel over 40 min and the internal temperature was kept below −70° C., then this solution was stirred for 20 min at −75° C. To this solution was added crushed dry ice at −75° C. and the mixture was stirred for 15 min. At that time, 10 mL water was added dropwise. The cooling bath was removed and the mixture was brought to rt over 1 h with a water bath. The solvent was evaporated under reduced pressure to give a solid residue. The residue was suspended in 100 mL water, basified with 1.00 M of sodium hydroxide in water (110 mL) and extracted with 100 mL ether. The ether layer was washed with 0.5 N NaOH (2×30 mL). The combined aqueous solution was acidified with conc. HCl to ~pH 2, extracted with ether (5×100 mL, adjusting the pH to ~2 each time after separation). The combined ether solutions were washed with brine, dried over $Na_2SO_4$, filtered, evaporated to give a solid product (28.04 g, 98%). LCMS: (FA) ES+ 288, ES− 286.

Step 2: 2,4-Dibromo-1,3-thiazole-5-carboxamide

A suspension of 2,4-dibromo-1,3-thiazole-5-carboxylic acid (16.33 g, 56.91 mmol) in dry DCM (250 mL) and DMF (0.400 mL) was cooled in an ice bath. Thionyl chloride (40.0 mL, 548 mmol) was added dropwise. The cooling bath was removed and the suspension was stirred at rt for 2.5 hours. Toluene (80 mL, 800 mmol) was added and the suspension was heated to reflux for 1 hour. The mixture was cooled to room temperature, the solvent was removed and the residue was azeotroped with toluene (2×100 mL) to give a crude intermediate. This material was suspended in DCM (230 mL) and cooled in an ice bath. N,N-Dimethylaminopyridine (0.70 g, 5.7 mmol) was added, followed by the slow addition of 8.5 M ammonium hydroxide in water (100.0 mL, 850.0 mmol). The mixture was stirred at room temperature overnight. The mixture was filtered and the aqueous layer was separated and extracted with DCM (3×100 mL). The combined DCM layers were washed with water, brine, dried over $Na_2SO_4$, filtered, and evaporated to give a solid product (11.2 g, 69%). LCMS: (FA) ES+ 287 and ES– 285.

Step 3: 3-(2,4-Dibromo-1,3-thiazol-5-yl)-4H-1,2,4-triazole

To a suspension of 2,4-dibromo-1,3-thiazole-5-carboxamide (0.110 g, 0.385 mmol) in dry toluene (8.0 mL, 75 mmol) was added DMF-DMA (0.204 mL, 1.54 mmol). The mixture was stirred at 60° C. under a nitrogen atmosphere for 3 hours. The solvent was removed and to the intermediate was added acetic acid (2.0 mL, 35 mmol), followed by hydrazine (0.0604 mL, 1.92 mmol). The mixture was heated to 120° C. for 30 min. The mixture was cooled to room temperature, the solvent was removed and the residual acetic acid was azeotroped with toluene (2×5 mL) to give an oily material, which was basified with saturated aqueous NaHCO3 to pH~8 and extracted with EtOAc (3×30 mL). The EtOAc layer was washed with water, brine, dried over $Na_2SO_4$, filtered, and evaporated to give a crude product. Chromatography on a silica column using EtOAc/hexane (0/100 to 50/50) gave a solid product (0.073 g, 61%). LCMS: (FA) ES+ 311 and ES– 309. $^1$H NMR (400 MHz, $d_4$-methanol) δ: 8.53 (s, 1H).

Step 4: 3-(2,4-Dbromo-1,3-thiazol-5-yl)-1-{[2-(trimethylsilyl)ethoxy]methyl}-1H-1,2,4-triazole To the solution of 3-(2,4-dibromo-1,3-thiazol-5-yl)-4H-1,2,4-triazole (1.16 g, 3.74 mmol) in dry DMF (5.0 mL) at 0° C. was added portionwise sodium hydride (60%, 0.180 g, 4.49 mmol). The ice bath was removed, mixture was stirred for 5 min at ambient temperature then cooled in an ice bath. [3-(Trimethylsilyl)ethoxy]methyl chloride (0.795 mL, 4.49 mmol) in dry DMF (2.0 mL) was added dropwise and the mixture was stirred at room temperature for 2 hours. The mixture was quenched with ice-water, extracted with EtOAc, washed with brine, dried over $Na_2SO_4$, filtered, evaporated to give a crude oil. The product was purified by column chromatography on silica gel, eluting with EtOAc/hexane (0/100 to 20/80) to afford a white solid product (1.10 g, 67%). LCMS: (FA) ES+ 441. $^1$H NMR (400 MHz, $CDCl_3$) δ: 8.29 (s, 1H), 5.54 (s, 2H), 3.71 (t, J=8.28 Hz, 2H), 0.95 (t, J=8.28 Hz, 2H), 0.00 (s, 9H).

Step 5: N-{4-[4-Bromo-5-(1-{[2-(trimethylsilyl)ethoxy]methyl}-1H-1,2,4-triazol-3-yl)-1,3-thiazol-2-yl]pyridin-2-yl}acetamide The mixture of 3-(2,4-dibromo-1,3-thiazol-5-yl)-1-{[2-(trimethylsilyl)ethoxy]methyl}-1H-1,2,4-triazole (1.10 g, 2.50 mmol), N-[4-(trimethylstannyl)pyridin-2-yl]acetamide (0.896 g, 3.00 mmol), tetrakis(triphenylphosphine)palladium (0) (0.155 g, 0.125 mmol), copper(I) iodide (0.143 g, 0.750 mmol) and lithium chloride (0.318 g, 7.50 mmol) in dry 1,4-dioxane (100 mL) was sonicated for 2 min, degassed and backfilled with nitrogen 5 times. The mixture was heated under nitrogen atmosphere to reflux for 90 min, then cooled to room temperature, filtered through celite and washed with dioxane/DCM. The filtrate was evaporated under reduced pressure to give a crude residue, which was purified by column chromatography on silica gel eluting with MeOH/DCM (0/100 to 5/95) to give a product, which was further purified on a silica column using MeOH/EtOAc/hexane (0/0/100 to 5/45/50) to give pure product (0.150 g, 13%). LCMS: (FA) ES+ 495, 497. $^1$H NMR (400 MHz, $CDCl_3$) δ: 8.72 (s, 1H), 8.37 (m, 1H), 8.33 (s, 1H), 8.26 (s, 1H), 7.68 (m, 1H), 5.57 (s, 2H), 3.73 (t, J=8.28 Hz, 2H), 2.25 (s, 3H), 0.97 (t, J=8.28 Hz, 2H), 0.00 (s, 9H).

Step 6: N-{4-[4-(4-Chlorobenzyl)-5-(1-{[2-(trimethylsilyl)ethoxy]methyl}-1H-1,2,4-triazol-5-yl)-1,3-thiazol-2-yl]pyridin-2-yl}acetamide To a solution of N-{4-[4-bromo-5-(1-{[2-(trimethylsilyl)ethoxy]methyl}-1H-1,2,4-triazol-5-yl)-1,3-thiazol-2-yl]pyridin-2-yl}acetamide (0.292 g, 0.589 mmol) in tetrahydrofuran (4.1 mL) was added 4-chlorobenzylzinc chloride (0.50M solution in tetrahydrofuran, 2.36 mL, 1.18 mmol) and bis(tri-t-butylphosphine)palladium(0) (0.0226 g, 0.0442 mmol) under argon. The solution was stirred at 60° C. for 2 hours. The reaction was incomplete by LCMS, so additional 4-chlorobenzylzinc chloride (0.50M solution in tetrahydrofuran, 2 mL, 1 mmole) was added, then the reaction was stirred at 60° C. for an additional 2 hours. The reaction was allowed to cool to room temperature then the solvent was evaporated in vacuo. Column chromatography was performed to yield the title compound (0.112 g, 35%). LCMS: (FA) ES$^+$, 542. $^1$H NMR (400 MHz, $d_4$-methanol) δ: 8.73-8.69 (m, 1H), 8.42-8.38 (m, 1H), 8.14 (s, 1H), 7.58-7.55 (m, 1H), 7.27-7.20 (m, 4H), 5.52 (s, 2H), 4.32 (s, 2H), 3.68-3.61 (m, 2H), 2.20 (s, 3H), 0.90-0.84 (m, 2H), 0.040 (s, 9H).

Step 7: N-{4-[4-(4-Chlorobenzyl)-5-(4H-1,2,4-triazol-3-yl)-1,3-thiazol-2-yl]pyridin-2-yl}acetamide (Compound 56)

To a solution of N-{4-[4-(4-chlorobenzyl)-5-(1-{[2-(trimethylsilyl)ethoxy]methyl}-1H-1,2,4-triazol-5-yl)-1,3-thiazol-2-yl]pyridin-2-yl}acetamide (0.112 g, 0.207 mmol) in dichloromethane (2.0 mL) at room temperature was added trifluoroacetic acid (3.1 mL, 40 mmol). The mixture was then stirred at room temperature for 4 hours. The solvent was evaporated and the excess trifluoroacetic acid was removed by azeotroping with toluene. Column chromatography was performed to yield the title compound (0.0520 g, 61%). LCMS: (FA) ES$^+$, 411. $^1$H NMR (400 MHz, $d_6$-DMSO) δ: 14.46 (s, 1H), 10.69 (s, 1H), 8.80-8.73 (m, 1H), 8.64-8.60 (m, 1H), 8.43-8.37 (m, 1H), 7.59-7.54 (m, 1H), 7.37-7.28 (m, 4H), 4.66 (s, 2H), 2.12 (s, 3H).

Compounds in the following table were prepared from the appropriate starting materials in a method analogous to that of Example 13:

| | |
|---|---|
| 7 | LCMS: (FA) ES+ 388, 390. |
| 27 | LCMS: (AA) ES+ 369, 371. |
| 53 | LCMS: (AA) ES+ 393, 395. |

Example 14

Synthesis of 3-[4-(4-chlorobenzyl)-5-(4H-1,2,4-triazol-3-yl)-1,3-thiazol-2-yl]-2-methylpyrazolo[1,5-a]pyridine (Compound 4)

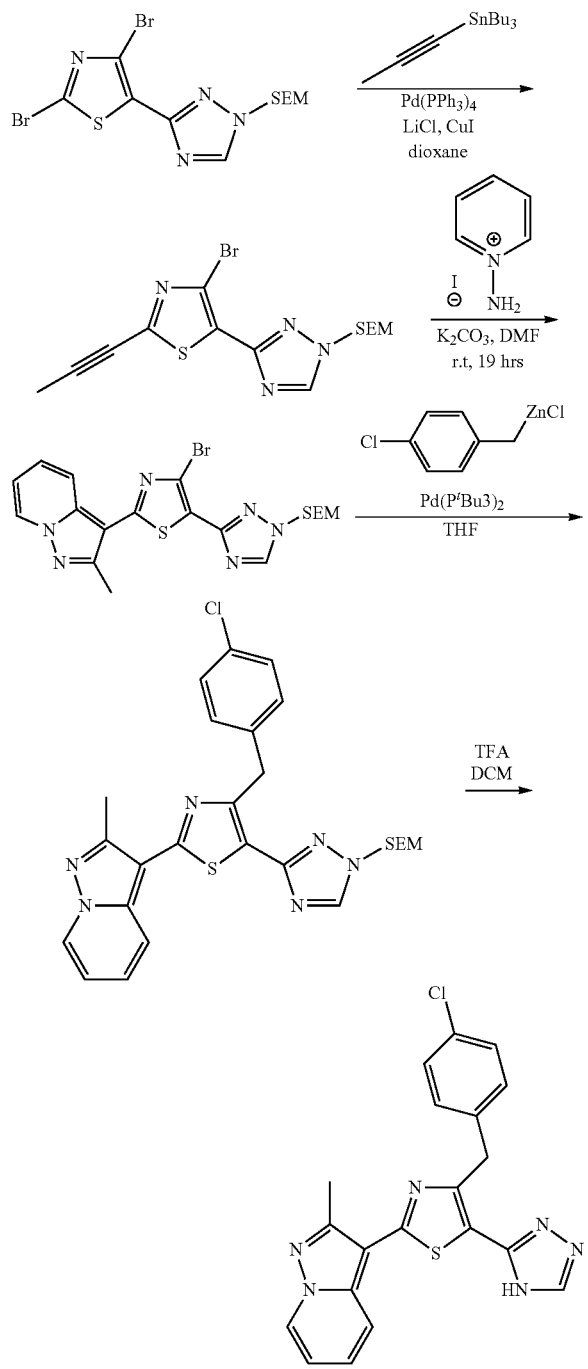

Step 1: 3-(4-Bromo-2-prop-1-yn-1-yl-1,3-thiazol-5-yl)-1-{[2-(trimethylsilyl)ethoxy]methyl}-1H-1,2,4-triazole A mixture of 3-(2,4-dibromo-1,3-thiazol-5-yl)-1-{[2-(trimethylsilyl)ethoxy]methyl}-1H-1,2,4-triazole (6.00 g, 13.6 mmol), lithium chloride (1.73 g, 40.9 mmol), copper(I) iodide (0.779 g, 4.09 mmol) and tetrakis(triphenylphosphine)platinum (O) (0.848 g, 0.681 mmol) in anhydrous 1,4-dioxane (120 mL, 1500 mmol) was sonicated under an argon atmosphere for 2 minutes in a 250 mL RBF. Tributyl(1-propynyl)tin (4.80 mL, 15.0 mmol) was added. The mixture was heated to 100° C. for 1 hour under an argon atmosphere. The mixture was cooled to it, diluted with DCM (~150 mL), filtered through celite, and washed with DCM. The filtrate was rotavaped to give a crude residue which was then purified by column chromatography (SiO2, elution with 0-100% EtOAc in hexane) to afford a pure solid product (4.14 g, 76% yield). LCMS: (FA) ES+ 399, 401. NMR (400 MHz, CDCl$_3$) δ: 8.29 (s, 1H), 5.54 (s, 2H), 3.69-3.74 (m, 2H), 2.15 (s, 3H), 0.93-0.97 (m, 2H), 0.00 (s, 9H).

Step 2: 3-[4-Bromo-5-(1-{[2-(trimethylsilyl)ethoxy]methyl}-1H-1,2,4-triazol-3-yl)-1,3-thiazol-2-yl]-2-methylpyrazolo[1,5-a]pyridine A mixture of 3-(4-bromo-2-prop-1-yn-1-yl-1,3-thiazol-5-yl)-1-{[2-(trimethylsilyl)ethoxy]methyl}-1H-1,2,4-triazole (0.514 g, 1.29 mmol), 1-aminopyridinium iodide (0.343 g, 1.54 mmol) and potassium carbonate (0.231 g, 1.67 mmol) in N,N-dimethylformamide (8.0 mL, 1.0E2 mmol) was stirred at rt for 29 hours. The mixture was quenched with ice water (80 mL) then extracted with EtOAc 3 times. The combined EtOAc solution was washed with water, brine, dried over Na$_2$SO$_4$, filtered and purified by column chromatography (SiO2, elution with 0-100% EtOAc in hexane) to afford a solid product. (0.410 g, 64.8% yield). LCMS: (FA) ES+ 491, 493. $^1$H NMR (400 MHz, CDCl$_3$) δ: 8.43-8.46 (m, 2H), 8.32 (s, 1H), 7.39-7.42 (m, 1H), 6.90-6.93 (m, 1H), 5.57 (m, 2H), 3.72-3.76 (m, 2H), 2.76 (s, 3H), 0.96-1.00 (m, 2H), 0.00 (s, 9H).

Step 3: 3-[4-(4-Chlorobenzyl)-5-(1-{[2-(trimethylsilyl)ethoxy]methyl}-1H-1,2,4-triazol-3-yl)-1,3-thiazol-2-yl]-2-methylpyrazolo[1,5-a]pyridine To a solution of 3-[4-bromo-5-(1-{[2-(trimethylsilyl)ethoxy]methyl}-1H-1,2,4-triazol-3-yl)-1,3-thiazol-2-yl]-2-methylpyrazolo[1,5-a]pyridine (0.200 g, 0.407 mmol) in tetrahydrofuran (2.8 mL) were added 4-chlorobenzylzinc chloride (0.50M solution in tetrahydrofuran, 1.63 mL, 0.814 mmol) and bis(tri-t-butylphosphine)palladium(0) (0.0156 g, 0.0305 mmol) under argon. The solution was stirred at 60° C. for 3 hours. The reaction was incomplete by LCMS, so additional 4-chlorobenzylzinc chloride (0.50M solution in tetrahydrofuran, 1.0 mL, 0.5 mmole) was added then the reaction was stirred at 60° C. for an additional 3 hours. The reaction was cooled to room temperature then the solvent was evaporated in vacuo. The residue was purified by column chromatography (SiO2, elution with EtOAc in hexanes 10-100% gradient) to yield the title compound (0.188 g, 86%). LCMS: (FA) ES+, 538. $^1$H NMR (400 MHz, d$_6$-DMSO) δ: 8.87 (s, 1H), 8.76-8.72 (m, 1H), 8.28-8.24 (m, 1H), 7.54-7.48 (m, 1H), 7.44-7.40 (m, 2H), 7.35-7.30 (m, 2H), 7.09-7.03 (m, 1H), 5.58 (s, 2H), 4.63 (s, 2H), 3.68-3.62 (m, 2H), 2.66 (s, 3H), 0.91-0.84 (m, 2H), 0.050 (s, 9H).

Step 4: 3-[4-(4-Chlorobenzyl)-5-(4H-1,2,4-triazol-3-yl)-1,3-thiazol-2-yl]-2-methylpyrazolo[1,5-a]pyridine (Compound 4)

To a solution of 3-[4-(4-chlorobenzyl)-5-(1-{[2-(trimethylsilyl)ethoxy]methyl}-1H-1,2,4-triazol-3-yl)-1,3-thiazol-2- yl]-2-methylpyrazolo[1,5-a]pyridine (0.182 g, 0.339 mmol) in dichloromethane (3.3 mL) at room temperature was added trifluoroacetic acid (5.1 mL, 66 mmol). The mixture was then stirred at room temperature for 3 hours. The solvent was evaporated and the excess trifluoroacetic acid was removed by azeotroping with toluene. The crude product was purified by column chromatography (SiO2, elution with hexane to 100% ethyl acetate) to yield the title compound (0.0884 g, 64%). LCMS: (FA) ES+, 407. $^1$H NMR (400 MHz, d$_6$-DMSO) δ: 8.76-8.70 (m, 2H), 8.28-8.22 (m, 1H), 7.53-7.46 (m, 1H), 7.45-7.40 (m, 2H), 7.37-7.31 (m, 2H), 7.07-7.01 (m, 1H), 5.55-5.50 (m, 1H), 4.64 (s, 2H), 2.65 (s, 3H).

Example 15

Synthesis of N-{4-[4-benzyl-5-(1H-imidazol-2-yl)-1,3-thiazol-2-yl]pyridin-2-yl}acetamide (Compound 2)

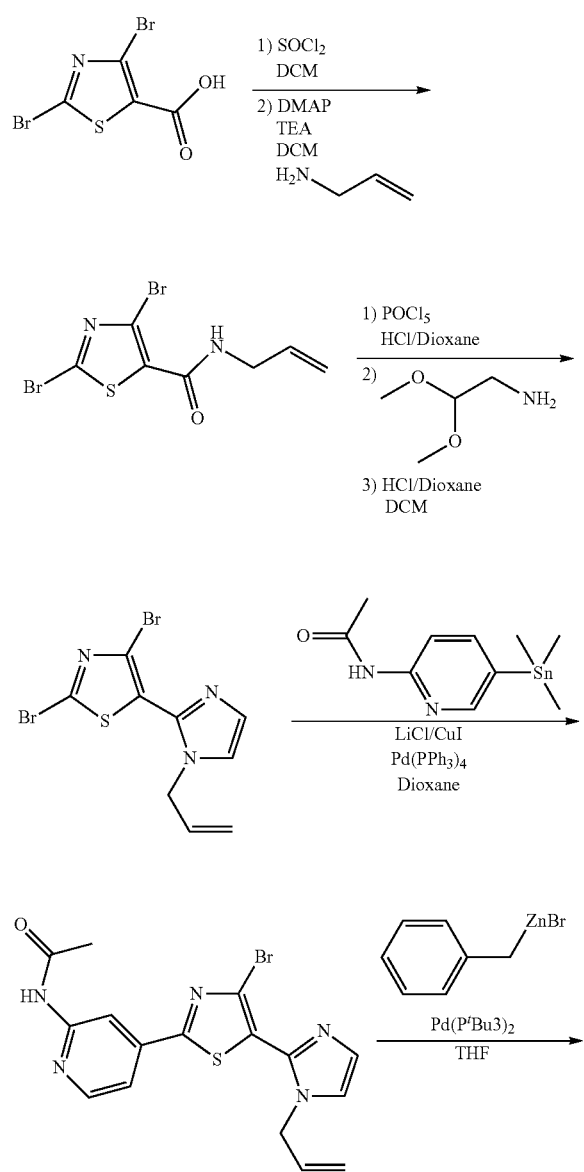

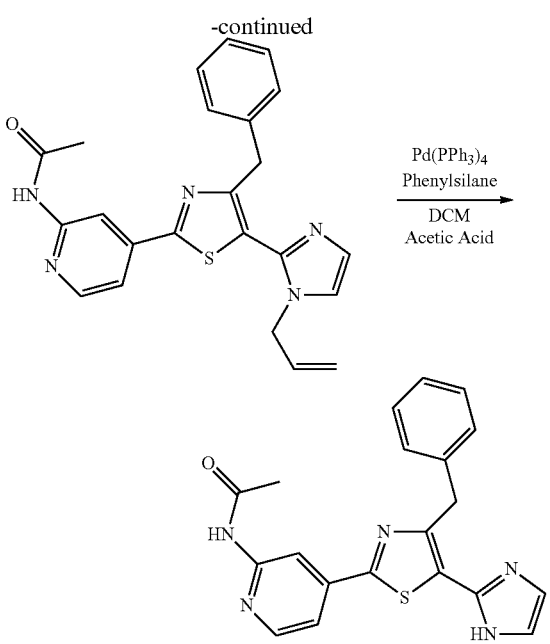

Step 1:
N-allyl-2,4-dibromo-1,3-thiazole-5-carboxamide

To a solution of 2,4-dibromo-1,3-thiazole-5-carboxylic acid (25.0 g, 87.1 mmol) in dichloromethane (600 mL) at 0° C. was added thionyl chloride (66.1 mL, 906 mmol) followed by N,N-dimethylformamide (7.02 mL, 90.6 mmol). The mixture was allowed to warm to room temperature and stir for 2 hours. The solvent was evaporated and the excess thionyl chloride was removed by azeotroping with toluene. The residue was dissolved in dichloromethane (600 mL) and cooled to 0° C., then added triethylamine (63.2 mL, 453 mmol) was added followed by 2-propen-1-amine (23.8 mL, 317 mmol) and N,N-dimethylaminopyridine (1.11 g, 9.06 mmol). The mixture was allowed to warm to room temperature and stirred for 2 hours. The solution was then diluted with dichloromethane and water and the layers were separated. The aqueous phase was then extracted with dichloromethane twice, then the combined organic extracts were washed with brine, dried over anhydrous sodium sulfate, filtered and concentrated in vacuo. Column chromatography was performed to yield the title compound (14.3 g, 50%). LCMS: (FA) ES+, 327. $^1$H NMR (400 MHz, d$_4$-methanol) δ: 5.97-5.85 (m, 1H), 5.32-5.24 (m, 1H), 5.20-5.14 (m, 1H), 4.02-3.95 (m, 2H).

Step 2: 5-(1-allyl-1H-imidazol-2-yl)-2,4-dibromo-1,3-thiazole

To a solution of N-allyl-2,4-dibromo-1,3-thiazole-5-carboxamide (13.0 g, 39.9 mmol) in dichloromethane (260 mL) was added phosphorus pentachloride (9.93 g, 47.7 mmol) and 4M hydrochloric acid in dioxane (1.52 mL, 6.06 mmol). The reaction was heated to 60° C. for 90 minutes under an atmosphere on nitrogen. The reaction was allowed to cool to room temperature and then aminoacetaldehyde dimethyl acetal (47.8 mL, 439 mmol) was added slowly through the condenser. The mixture was heated to 60° C. for 2 hours under an atmosphere of nitrogen then cooled to room temperature, and water was added (200 mL). The layers were separated and the organic phase was washed with water again (2×200 mL). The organic extracts were washed with brine, dried over anhydrous sodium sulfate, filtered and washed with dichloromethane (200 mL). To this dichloromethane solution of the intermediate was added 4M hydrochloric acid in dioxane (120 mL, 480 mmol) and the solution was stirred at 60° C. for 16 hours. The solution was decanted (leaving behind an oily black residue on the flask) then the solvent was evaporated and the residue was diluted with ethyl acetate and saturated sodium bicarbonate solution. The layers were separated and the aqueous phase was extracted three more times with ethyl acetate. The organic extracts were washed with brine, dried over anhydrous sodium sulfate, filtered and concentrated in vacuo. Column chromatography was performed to yield the title compound (8.04 g, 58%). LCMS: (FA) ES+, 306 (parent minus allyl group). $^1$H NMR (300 MHz, $d_4$-methanol) δ: 7.37-7.31 (m, 1H), 7.20-7.16 (m, 1H), 6.02-5.86 (m, 1H), 5.26-5.18 (m, 1H), 5.07-4.96 (m, 1H), 4.68-4.59 (m, 2H).

Step 3: Synthesis of N-{4-[5-(1-allyl-1H-imidazol-2-yl)-4-bromo-1,3-thiazol-2-yl]pyridin-2-yl}acetamide To a solution of 5-(1-allyl-1H-imidazol-2-yl)-2,4-dibromo-1,3-thiazole (5.00 g, 14.3 mmol) in 1,4-dioxane (133 mL) was added N-[4-(trimethylstannyl)pyridine-2-yl]acetamide (5.14 g, 17.2 mmol), lithium chloride (1.82 g, 43.0 mmol), copper (I) iodide (0.818 g, 4.30 mmol) and tetrakis(triphenylphosphine)palladium(0) (1.24 g, 1.07 mmol). The flask was purged with argon and then the mixture was heated at 115° C. for 4 hours. The reaction was allowed to cool to room temperature, and then the solvent was evaporated in vacuo. Column chromatography was performed to yield the title compound (3.13 g, 54%). LCMS: (FA) ES+, 406. $^1$H NMR (400 MHz, $d_6$-DMSO) δ: 10.77 (s, 1H), 8.66-8.61 (m, 1H), 8.49-8.44 (m, 1H), 7.61-7.56 (m, 1H), 7.49-7.45 (m, 1H), 5.98-5.87 (m, 1H), 5.19-5.12 (m, 1H), 4.95-4.88 (m, 1H), 4.70-4.64 (m, 2H), 2.13 (s, 3H).

Step 4: Synthesis of N-{4-[5-(1-allyl-1H-imidazol-2-yl)-4-benzyl-1,3-thiazol-2-yl]pyridin-2-yl}acetamide To a solution of N-{4-[5-(1-allyl-1H-imidazol-2-yl)-4-bromo-1,3-thiazol-2-yl]pyridin-2-yl}acetamide (0.0500 g, 0.124 mmol) in tetrahydrofuran (0.86 mL) was added benzylzinc bromide (0.50M solution in tetrahydrofuran, 0.495 mL, 0.247 mmol) and bis(tri-t-butylphosphine)palladium(0) (0.00474 g, 0.00928 mmol) under argon. The solution was stirred at 60° C. for 2 hours then cooled to room temperature. The solvent was evaporated in vacuo. Column chromatography was performed to yield the title compound (0.0110 g, 21%). LCMS: (FA) ES+, 416. $^1$H NMR (400 MHz, $d_4$-methanol) δ: 8.70-8.65 (m, 1H), 8.41-8.36 (m, 1H), 7.66-7.61 (m, 1H), 7.34-7.05 (m, 7H), 5.81-5.70 (m, 1H), 5.16-5.10 (m, 1H), 4.95-4.88 (m, 1H), 4.38-4.33 (m, 2H), 4.13 (s, 2H), 2.20 (s, 3H).

Step 5: Synthesis of N-{4-[4-benzyl-5-(1H-imidazol-2-yl)-1,3-thiazol-2-yl]pyridin-2-yl}acetamide (Compound 2)

To a solution of N-{4-[5-(1-allyl-1H-imidazol-2-yl)-4-benzyl-1,3-thiazol-2-yl]pyridin-2-yl}acetamide (0.210 g, 0.0505 mmol) in dichloromethane (0.38 mL) and acetic acid (0.13 mL) was added tetrakis(triphenylphosphine)palladium(0) (0.00292 g, 0.00253 mmol) followed by phenylsilane (0.0318 mL, 0.258 mmol). The solution was stirred at 40° C. for 3 hours. The solution was cooled to room temperature then concentrated in vacuo and diluted with ethyl acetate and saturated sodium bicarbonate solution. The layers were separated and the aqueous phase was extracted three more times with ethyl acetate. The organic extracts were washed with brine, dried over anhydrous sodium sulfate, filtered and concentrated in vacuo. Column chromatography was performed to yield the title compound (0.0100 g, 53%). LCMS: (FA) ES+, 376. $^1$H NMR (400 MHz, $d_4$-methanol) δ: 8.67-8.63 (m, 1H), 8.38-8.35 (m, 1H), 7.63-7.59 (m, 1H), 7.25-7.07 (m, 7H), 4.42 (s, 2H), 2.20 (s, 3H).

Compounds in the following table were prepared from the appropriate starting materials in a method analogous to that of Example 15:

| | |
|---|---|
| 24 | LCMS: (FA) ES+ 390 |
| 67 | LCMS: (FA) ES+ 410, 412. |
| 73 | LCMS: (FA) ES+ 410, 412. |

Example 16

Synthesis of (4-chlorophenyl)[2-pyridin-4-yl-5-(1H-1,2,4-triazol-3-yl)-1,3-thiazol-4-yl]methanol (Compounds 19 and 70)

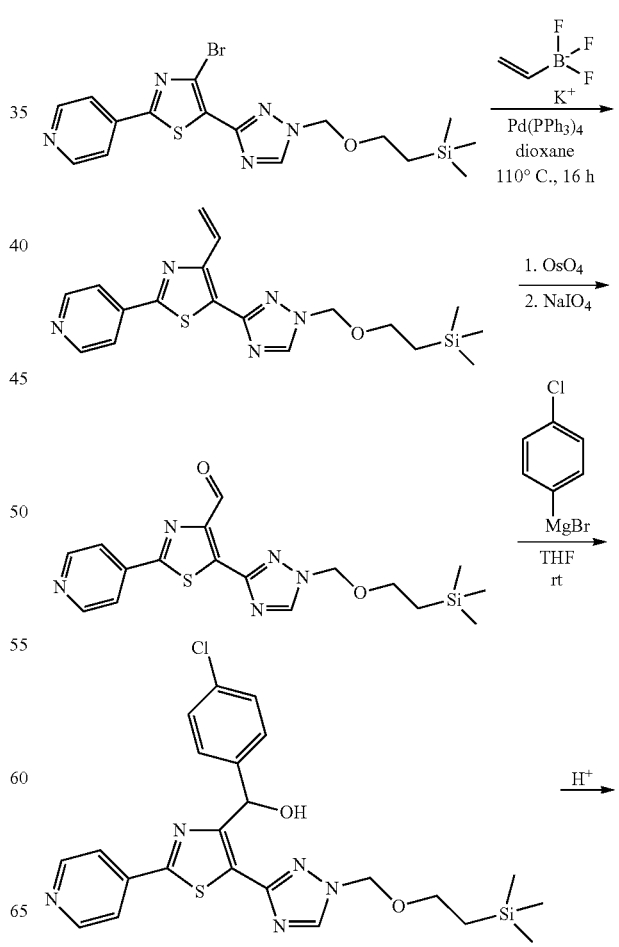

259

-continued

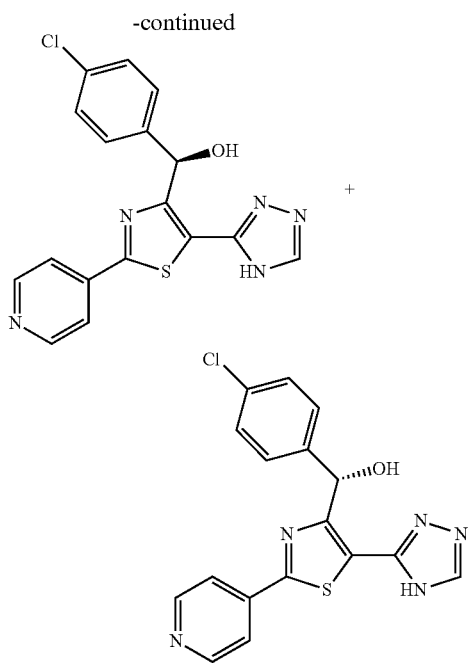

Step 1: 4-[5-(1-{[2-(Trimethylsilyl)ethoxy]methyl}-1H-1,2,4-triazol-3-yl)-4-vinyl-1,3-thiazol-2-yl]pyridine Into a sealed tube was added potassium vinyltrifluoroborate (1.34 g, 10.0 mmol), 1,4-dioxane (21.0 mL, 269 mmol), 4-[4-bromo-5-(1-{[2-(trimethylsilyl)ethoxy]methyl}-1H-1,2,4-triazol-3-yl)-1,3-thiazol-2-yl]pyridine (2.0 g, 4.6 mmol) and 2 M sodium carbonate in water (9.10 mL, 18.2 mmol). The reaction was degassed with nitrogen for 15 min then tetrakis(triphenylphosphine)palladium(0) (527 mg, 0.456 mmol) was added. The tube was sealed and the reaction was heated in an oil bath at 110° C. with stirring overnight. The reaction solution was cooled to room temperature, water (10 mL) and EtOAc (10 mL) were added, and the combined organic layers were washed with brine, dried over MgSO$_4$, filtered and concentrated under reduced pressure. The obtained residue was purified by column chromatography (SiO$_2$, elution with 0-10% MeOH in DCM) to give the title compound as a yellow solid (1.34 g 81%). LCMS: (FA) ES$^+$, 386. $^1$H NMR (400 MHz, d6-DMSO) δ:8.92 (s, 1H), δ 8.74-8.76 (dd, J=1.75 Hz, J=1.5 Hz 2H), 7.96-7.98 (dd, J=1.75 Hz, 2H), 6.34-6.40 (dd, J=2.3 Hz, 12H), 5.62-5.65 (dd, J=2.3 Hz, 1H), 5.60 (s, br, 2H), 3.63-3.68 (m, 2H), 0.86-0.90 (m, 2H), −0.04 (s, 9H).

Step 2: 2-Pyridin-4-yl-5-(1-{[2-(trimethylsilyl)ethoxy]methyl}-1H-1,2,4-triazol-3-yl)-1,3-thiazole-4-carbaldehyde To a solution of 4-[5-(1-{[2-(trimethylsilyl)ethoxy]methyl}-1H-1,2,4-triazol-3-yl)-4-vinyl-1,3-thiazol-2-yl]pyridine (1.43 g, 2.60 mmol) in a 3:1 mixture of 1,4-dioxane (17.5 mL, 224.6 mmol) and water (5.8 mL, 324.25 mmol) was added 2,6-lutidine (1.50 mL, 12.98 mmol) and the mixture was cooled to 0° C. Sodium metaperiodate (2.80 g, 12.98 mmol) was added followed by the addition of 4% osmium tetroxide in water (0.50 mL, 0.080 mmol) and the reaction mixture was slowly warmed to ambient temperature and

260 allowed to stir overnight. Water (10 mL) was added. The resulting yellow precipitate was collected by filtration, washed with water, ether and MeOH. The filtrate was concentrated under reduced pressure and dried on the high vac to give the title compound (1.0 g, yield 99%). LCMS: (FA) ES$^+$, 388. $^1$H NMR (400 MHz, d$_6$-DMSO) δ: 10.70 (s, 1H), δ:9.05 (s, 1H), 8.79-8.80 (dd, J=1.5 Hz, 2H), 7.98-8.0 (dd, J=1.5 Hz, J=1.7 Hz, 2H), 5.64-5.66 (s, br, 2H), 3.64-3.68 (m, 2H), 0.870-0.90 (m, 2H), −0.03 (s, 9H).

Step 3: (4-Chlorophenyl)[2-pyridin-4-yl-5-(1-{[2-(trimethylsilyl)ethoxy]methyl}-1H-1,2,4-triazol-3-yl)-1,3-thiazol-4-yl]methanol To a solution of 2-pyridin-4-yl-5-(1-{[2-(trimethylsilyl)ethoxy]methyl}-1H-1,2,4-triazol-3-yl)-1,3-thiazole-4-carbaldehyde (280.0 mg, 0.722 mmol) in tetrahydrofuran (4.0 mL, 40 mmol), 1 M 4-chlorophenyl magnesium bromide in ether (4.0 mL, 4 mmol) was added and the mixture was stirred for 40 min at rt. After the reaction was completed a 5% aqueous solution of NH$_4$Cl (10 mL) and EtOAc (10 mL) were added and the resulting bi-phasic mixture was vigorously stirred for 15 min then the aqueous phase was discarded. The organic phase was washed with brine (5 mL) then dried over anhydrous MgSO$_4$. Insoluble materials were removed by filtration and the filtrate was concentrated under reduced pressure. The obtained residue was purified by column chromatography (SiO$_2$, elution with 20-80% EtOAc in hexane) to give the title compound as a white solid (230 mg, 73.6%). LCMS: (FA) ES$^+$, 500. $^1$H NMR (400 MHz, d$_6$-DMSO) δ:8.96 (s, 1H), δ 8.70-8.72 (dd, J=1.75 Hz, 2H), 7.87-7.89 (dd, J=1.75, 2H), 7.32-7.37 (m, 2H), 7.55-7.58 (m, 3H), 6.85-6.87 (d, J=5.5 Hz, 1H), 6.15-6.17 (d, J=5.5 Hz, 1H), 5.6 (s, br, 2H), 3.65-3.67 (m, 2H), 0.850-0.90 (m, 2H), −0.05 (s, 9H).

Step 4: (4-Chlorophenyl)[2-pyridin-4-yl-5-(1H-1,2,4-triazol-3-yl)-1,3-thiazol-4-yl]methanol (4-Chlorophenyl)[2-pyridin-4-yl-5-(1-{[2-(trimethylsilyl)ethoxy]methyl}-1H-1,2,4-triazol-3-yl)-1,3-thiazol-4-yl]methanol (266.0 mg, 0.530 mmol) was dissolved in methylene chloride (3.0 mL, 47 mmol). Trifluoroacetic acid (3.0 mL, 39 mmol) was added and the solution was stirred at rt overnight. After the reaction wars completed, saturated NaHCO$_3$ was added and the reaction was stirred at it for 20 min, then EtOAc (5 mL) was added, the organic layer was separated, washed with brine, dried over MgSO$_4$, filtered, concentrated and the obtained residue was purified by column chromatography (SiO$_2$, elution with 2-20% MeOH in DCM) to give the title compound as a white solid (200 mg). The racemic isomers were separated by chiral prep HPLC to yield 17 (34 mg, 12.7%) (peak 1, ret. time 13.04 min). LCMS: (FA) ES$^+$, 370. $^1$H NMR (400 MHz, d$_6$-DMSO) δ: 8.76 (s, 1H), 8.69-8.71 (dd, J=1.5 Hz, 2H), 7.86-7.88 (dd, J=1.5, 2H), 7.55-7.58 (d, J=8.5 Hz, 2H), 7.34-7.38 (d, J=8.5 Hz, 2H), 6.84-6.86 (s, br, 1H) and 70 (34.8 mg, 13.0%) (peak 2, ret. time 13.2 min). LCMS: (FA) ES$^+$, 370. $^1$H NMR (400 MHz, d$_6$-DMSO) δ: 8.68-8.72 (m, 3H), 7.86-7.88 (dd, J=1.69 Hz, J=1.5 Hz, 2H), 7.54-7.58 (d, J=8.47 Hz, 2H), 7.34-7.38 (d, J=8.47 Hz, 2H), 6.81-6.82 (s, br, 1H).

Compounds in the following table were prepared from the appropriate starting materials in a method analogous to that of Example 16:

| | |
|---|---|
| 149 | LCMS: (AA) ES+ 451, 453, 455 |
| 168 | LCMS: (FA) ES+ 418, 420 |
| 238 | LCMS: (AA) ES+ 427, 429 |
| 265 | LCMS: (AA) ES+ 431, 433 |
| 278 | LCMS: (AA) ES+ 451, 453, 455 |
| 282 | LCMS: (FA) ES+ 418, 420 |
| 285 | LCMS: (AA) ES+ 431, 433 |

Example 17

Synthesis of 4-(4-chlorobenzyl)-5-(1H-imidazol-2-yl)-2-(pyridin-4-yl)thiazole (Compound 15)

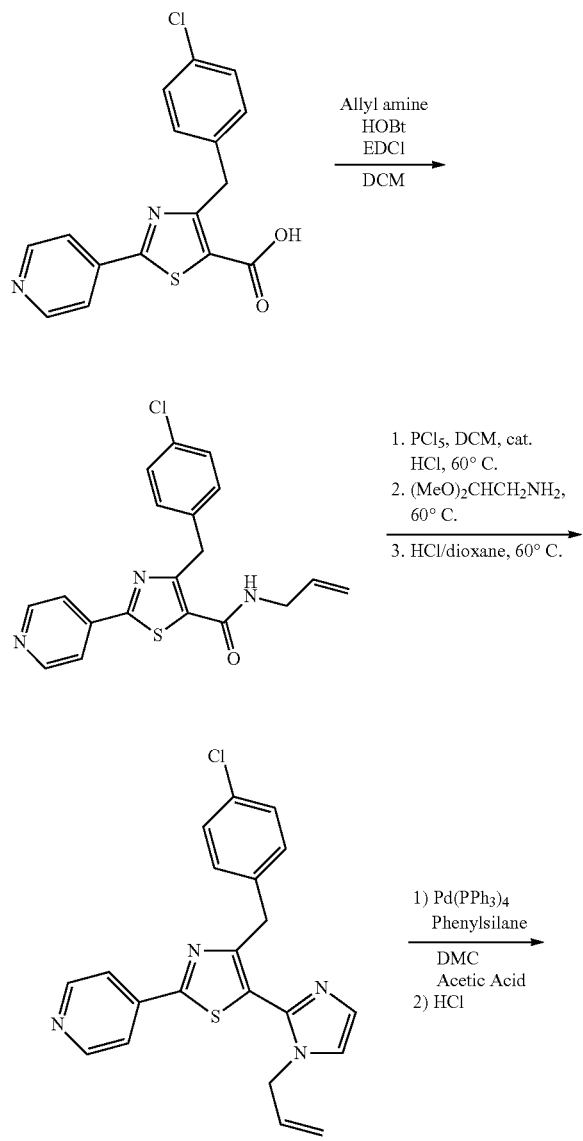

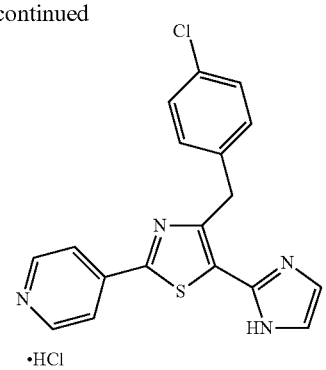

·HCl

Step 1: N-Allyl-4-(4-chlorobenzyl)-2-(pyridin-4-yl)thiazole-5-carboxamide

To a stirred solution of 4-(4-chlorobenzyl)-2-(pyridin-4-yl)thiazole-5-carboxylic acid (220 mg, 0.665 mmol) in DCM (4.05 mL) was added HOBT (98.8 mg, 0.732 mmol) and EDCI (204 mg, 1.06 mmol) at room temperature and the mixture was stirred for 30 min. To the solution was added 2-propen-1-amine (0.200 mL, 2.66 mmol) then the resulting mixture was stirred at room temperature overnight. The reaction mixture was diluted with DCM (10 mL) and washed with water (3 mL) and brine (2 mL), then dried over MgSO$_4$, filtered, and concentrated in vacuo. The residue was purified by silica gel chromatography (ethyl acetate/DCM=0/100→75/25) to give 150 mg of the title compound as a yellow solid (61% yield). LC/MS (FA) ES+ 370. $^1$H NMR (400 MHz, CDCl$_3$) δ: 8.74-8.72 (m, 2H), 7.79-7.77 (m, 2H), 7.35-7.32 (m, 2H), 7.27-7.25 (m, 2H), 5.94-5.80 (m+bs, 2H), 5.25-5.20 (m, 2H), 4.48 (s, 2H), 4.06-4.02 (m, 2H).

Step 2: 5-(1-Allyl-1H-imidazol-2-yl)-4-(4-chlorobenzyl)-2-(pyridin-4-yl)thiazole To a solution of N-allyl-4-(4-chlorobenzyl)-2-(pyridin-4-yl)thiazole-5-carboxamide (150 mg, 0.406 mmol) in DCM (2.64 mL) was added phosphorus pentachloride (101 mg, 0.485 mmol) and 4 M hydrochloric acid in 1,4-dioxane (0.0154 mL, 0.0614 mmol) and the mixture was heated to 60° C. for 1.5 h. The reaction was cooled to room temperature and aminoacetaldehyde dimethyl acetal (0.486 mL, 4.46 mmol) was added. The resulting mixture was heated at 60° C. for 2 h. The mixture was cooled to room temperature, diluted with DCM (10 mL), washed with water (2×2 mL) and brine (2 mL), dried over sodium sulfate, filtered, and concentrated in vacuo. The residue was taken up in DCM (3.0 mL) and 4 M hydrochloric acid in 1,4-dioxane (0.608 mL, 2.43 mmol) was added and the mixture was stirred at 60° C. overnight. The reaction was cooled and concentrated in vacuo. The residue was taken up in ethyl acetate (20 mL) and saturated sodium bicarbonate (5 mL). The layers were separated and the aqueous layer was extracted with ethyl acetate (5 mL). The combined organic layers were dried over MgSO$_4$, filtered, and concentrated in vacuo. The residue was purified by silica gel chromatography (methanol/DCM=0/100→5/95) to give 99 mg of the title compound (62% yield). LC/MS (FA) ES+ 393. $^1$H NMR (300 MHz, CDCl$_3$) δ: 8.72-8.70 (m, 2H), 7.80-7.72 (m, 2H), 7.26 (m, 1H), 7.22-7.14 (m, 4H), 7.06 (m, 1H), 5.84-5.71 (m, 1H), 5.23-5.19 (m, 1H), 5.01-4.96 (m, 1H), 4.38-4.34 (m, 2H), 4.20 (s, 2H).

Step 3: 4-(4-Chlorobenzyl)-5-(1H-imidazol-2-yl)-2-(pyridin-4-yl)thiazole, hydrochloride salt (Compound 15)

To a solution of 5-(1-allyl-1H-imidazol-2-yl)-4-(4-chlorobenzyl)-2-(pyridin-4-yl)thiazole (99.0 mg, 0.252 mmol) and tetrakis(triphenylphosphine)palladium (14.6 mg, 0.0126 mmol) in DCM (3.38 mL) was added acetic acid (0.623 mL, 11.0 mmol) and phenylsilane (0.158 mL, 1.28 mmol) and the mixture was stirred for 2 h at 40° C. The reaction mixture was evaporated to remove volatiles and DCM (10 mL) added. To this solution was added saturated sodium bicarbonate (4 mL) and the resulting mixture was stirred for 30 min. The mixture was extracted with DCM (3×10 mL) and the combined DCM layers were washed with brine. The organics were dried over MgSO$_4$, filtered, and concentrated in vacuo. The residue was purified by silica gel chromatography (methanol/DCM=0/100→10/90) to give 57 mg of the title compound as a yellow solid (64% yield). The HCl salt was made as follows. To a mixture of the free base (57 mg, 0.162 mmol) in ethanol (5 mL) was added 1.0 M HCl in ether (0.178 mL, 0.178 mmol) and the mixture was stirred for 2 hours then concentrated in vacuo. The residue was taken up in a minimum of methanol, and acetonitrile was added to give a precipitate. Ether was added and the precipitate was filtered, washed with ether and dried to give the title compound as an orange solid. LC/MS (FA) ES+ 353. $^1$H NMR (400 MHz, d$_6$-DMSO) δ: 8.78-8.74 (m, 2H), 7.96-7.91 (m, 2H), 7.48-7.43 (m, 2H), 7.34-7.28 (m, 4H), 4.51 (s, 2H).

Example 18

Synthesis of 4-(4-chlorobenzyl)-5-(1H-imidazol-5-yl)-2-(pyridin-4-yl)thiazole (Compound 66)

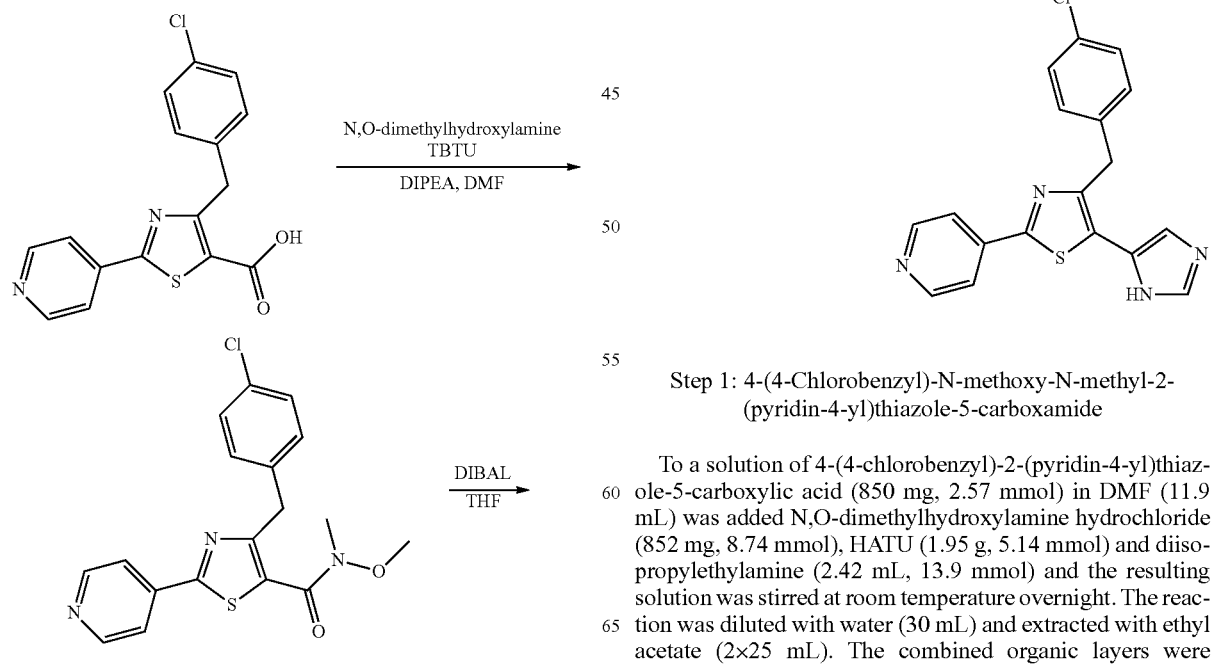

Step 1: 4-(4-Chlorobenzyl)-N-methoxy-N-methyl-2-(pyridin-4-yl)thiazole-5-carboxamide To a solution of 4-(4-chlorobenzyl)-2-(pyridin-4-yl)thiazole-5-carboxylic acid (850 mg, 2.57 mmol) in DMF (11.9 mL) was added N,O-dimethylhydroxylamine hydrochloride (852 mg, 8.74 mmol), HATU (1.95 g, 5.14 mmol) and diisopropylethylamine (2.42 mL, 13.9 mmol) and the resulting solution was stirred at room temperature overnight. The reaction was diluted with water (30 mL) and extracted with ethyl acetate (2×25 mL). The combined organic layers were washed with water (3×30 mL), dried over MgSO$_4$, filtered, and concentrated in vacuo. The residue was purified by silica gel chromatography (ethyl acetate/DCM=0/100→80/20) to give 775 mg of the title compound as a yellow solid (80% yield). LC/MS (FA) ES+ 374. $^1$H NMR (400 MHz, CDCl$_3$) δ: 8.72-8.70 (m, 2H), 7.84-7.82 (m, 2H), 7.37-7.34 (m, 2H), 7.25-7.22 (m, 2H). 4.56 (s, 2H), 3.70 (s, 3H), 3.37 (s, 3H).

Step 2: Preparation of 4-(4-chlorobenzyl)-2-(pyridin-4-yl)thiazole-5-carbaldehyde To a solution of 4-(4-chlorobenzyl)-N-methoxy-N-methyl-2-(pyridin-4-yl)thiazole-5-carboxamide (1.13 g, 3.02 mmol) in THF (36.8 mL) at −50° C. was added 1.0 M diisobutylaluminum hydride in hexane (15.1 mL, 15.1 mmol) and the resulting solution was stirred at −50° C. to −30° C. for 2 hours. The reaction was quenched with saturated ammonium chloride (10 mL) and allowed to warm to room temperature. Water (25 mL) was added and the mixture was extracted with ethyl acetate (2×40 mL). The combined organic layers were dried over MgSO$_4$, filtered, and concentrated in vacuo. The residue was purified by silica gel chromatography (ethyl acetate/DCM=0/100→70/30) to give 699 mg of the title compound as a white solid (73% yield). LC/MS (FA) ES+ 315. NMR (300 MHz, CDCl$_3$) δ: 10.16 (s, 1H), 8.78-8.76 (m, 2H), 7.85-7.83 (m, 2H), 7.30-7.25 (m, 4H), 4.47 (s, 2H).

Step 3: N'-{(1E)-[4-(4-chlorobenzyl)-2-pyridin-4-yl-1,3-thiazol-5-yl]methylene}-N,N-dimethylsulfamide A solution of 4-(4-chlorobenzyl)-2-(pyridin-4-yl)thiazole-5-carbaldehyde (186 mg, 0.591 mmol) and N,N-dimethylsulfonamide ((75.6 mg, 0.608 mmol) (prepared according to Li, *Tetrahedron Letters*, 50(19), 2232-2235) in toluene (5.0 mL) was refluxed overnight using a Dean Stark trap to azeotrope water. The reaction was cooled and concentrated in vacuo. The residue was purified by silica gel chromatography (ethyl acetate/DCM=0/100→60/40) to give 699 mg of the title compound as a yellow solid (60% yield). LC/MS (FA) ES+ 421. $^1$H NMR (300 MHz, CDCl$_3$) δ: 9.08 (s, 1H), 8.78-8.76 (m, 2H), 7.84-7.82 (m, 2H), 7.32-7.22 (m, 4H), 4.38 (s, 2H), 2.86 (s, 6H).

Step 4: 5-(4-(4-Chlorobenzyl)-2-(pyridin-4-yl)thiazol-5-yl)-N,N-dimethyl-1H-imidazole-1-sulfonamide and 4-(4-chlorobenzyl)-5-(1H-imidazol-5-yl)-2-(pyridin-4-yl)thiazole (Compound 66)

A solution of N'-{(1E)-[4-(4-chlorobenzyl)-2-pyridin-4-yl-1,3-thiazol-5-yl]methylene}-N,N-dimethylsulfamide (148 mg, 0.352 mmol), p-tolylsulfonylmethyl isocyanide (75.5 mg, 0.387 mmol) and potassium carbonate (146 mg, 1.05 mmol) in DME (2.50 mL) was heated at 78° C. for 2 hours. The reaction was diluted with DCM (10 mL) and water (5 mL). The layers were separated and the aqueous layer was extracted with DCM (5 mL). The combined organic layers were dried over MgSO$_4$, filtered, and concentrated in vacuo. The residue was purified by silica gel chromatography (methanol/DCM=0/100→15/85) to give 50 mg of 5-(4-(4-chlorobenzyl)-2-(pyridin-4-yl)thiazol-5-yl)-N,N-dimethyl-1H-imidazole-1-sulfonamide. LC/MS (FA) ES+ 460. (Some of the deprotected product, 4-(4-chlorobenzyl)-5-(1H-imidazol-5-yl)-2-(pyridin-4-yl)thiazole, was also obtained (19 mg). This material was combined with the material obtained in the following deprotection step.)

A solution of 5-(4-(4-chlorobenzyl)-2-(pyridin-4-yl)thiazol-5-yl)-N,N-dimethyl-1H-imidazole-1-sulfonamide (50 mg, 0.109 mmol) in 48% HBr in water (3.0 mL) was heated to 90° C. for 2.5 hours. The cooled solution was taken up in DCM (20 mL) and saturated sodium bicarbonate (20 mL). The layers were separated and the aqueous extracted with DCM (20 mL). The combined organic layers were dried over MgSO$_4$, filtered, and concentrated in vacuo. To this crude material was added the 19 mg of deprotected material obtained in the previous step. The combined material was purified by silica gel chromatography (methanol/DCM=0/100→15/85) to give 34 mg of the title compound as a white solid (27% yield). LC/MS (FA) ES+ 353. $^1$H NMR (300 MHz, d$_4$-MeOH) δ: 8.63-8.61 (m, 2H), 7.93-7.91 (m, 2H), 7.80 (d, 1H, J=1.1 Hz), 7.30-7.19 (m, 5H), 4.35 (s, 2H).

Example 19

Synthesis of 4-(4-chlorobenzyl)-2-(pyridin-4-yl)-5-(1H-pyrrol-2-yl)thiazole (Compound 22)

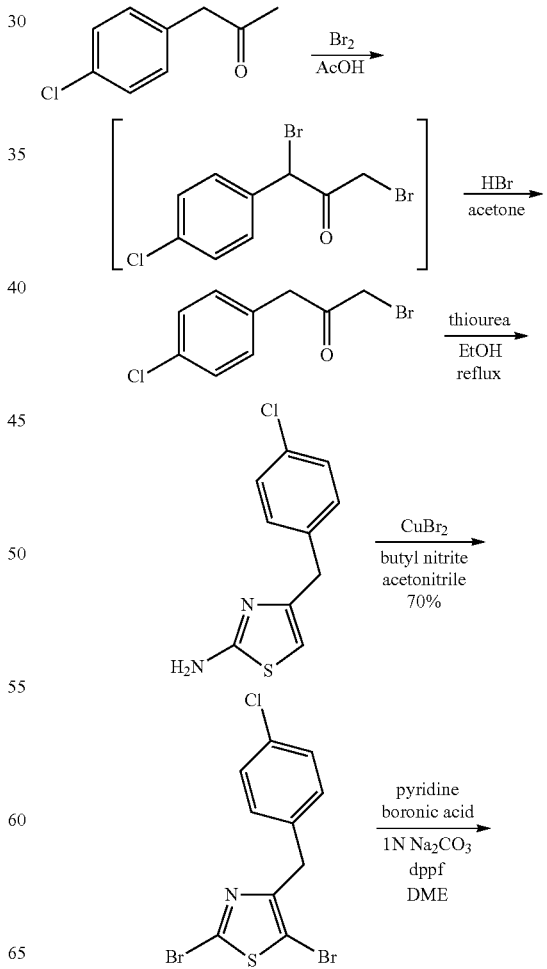

-continued

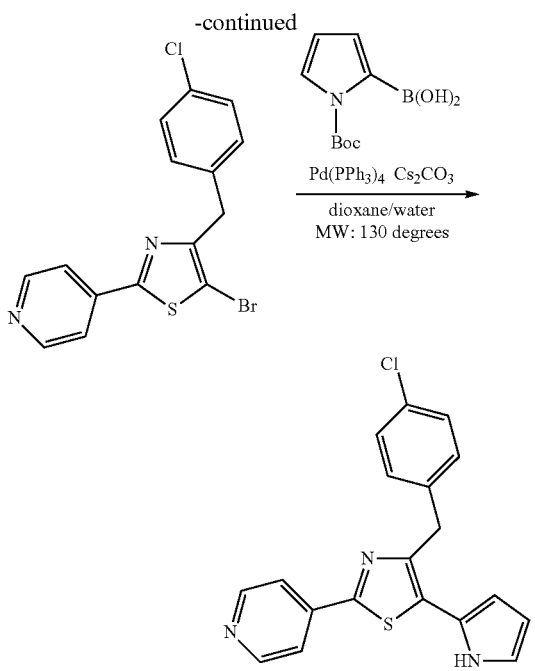

Step 1: 1-Bromo-3-(4-chlorophenyl)propan-2-one

To a solution of 1-(4-chlorophenyl)propan-2-one (25.0 g, 148 mmol) in acetic acid (37.9 mL) was added 48% aqueous HBr (19.0 mL, 168 mmol). A solution of bromine (16.3 mL, 316 mmol) in acetic acid (63.2 mL) was then added over 10 minutes and the resulting solution was stirred for 4 hours at room temperature. Acetone (190 mL) was added and the resulting solution was stirred at room temperature for 3 days. The reaction was concentrated in vacuo and the residue was taken up in DCM (300 mL) and brine (100 mL). The layers were separated and the aqueous layer was extracted with DCM (100 mL). The combined organic layers were dried over MgSO$_4$, filtered, and concentrated in vacuo. The residue was purified by silica gel chromatography (ethyl acetate/hexanes=0/100→15/85) to give 25.4 grams of the title compound as a dark gray solid (69% yield). $^1$H NMR (400 MHz, CDCl$_3$) δ: 7.34-7.31 (m, 2H), 7.18-7.15 (m, 2H), 3.94 (s, 2H), 3.91 (2, 2H).

Step 2: 4-(4-Chlorobenzyl)thiazol-2-amine

A mixture of 1-bromo-3-(4-chlorophenyl)propan-2-one (25.4 grams, 103 mmol) and thiourea (8.59 g, 113 mmol) in ethanol (1.51 L) was heated at 85° C. for 2 hours. The reaction was cooled and concentrated in vacuo and the residue was taken up in ethyl acetate (300 mL) and saturated sodium bicarbonate (100 mL). The layers were separated and the aqueous layer was extracted with ethyl acetate (100 mL). The combined organic layers were washed with brine (50 mL), dried over MgSO$_4$, filtered, and concentrated in vacuo. The residue was recrystallized from ethyl acetate/hexanes to give 19.9 grams of the title compound as a tan powder (86% yield). LC/MS (FA) ES+ 225. $^1$H NMR (300 MHz, CDCl$_3$) δ: 7.29-7.24 (m, 2H), 7.20-7.15 (m, 2H), 6.04 (m, 1H), 5.00 (bs, m, 2H), 3.83 (s, 2H).

Step 3: 2,5-Dibromo-4-(4-chlorobenzyl)thiazole

To a mixture of 4-(4-chlorobenzyl)thiazol-2-amine (6.90 g, 30.7 mmol) in acetonitrile (367 mL) was added copper(II) bromide (10.3 grams, 46.0 mmol) and the resulting mixture was stirred at room temperature for 4 hours. Butyl nitrite (5.21 mL, 46.0 mmol) was added and the mixture was stirred at room temperature for 30 minutes. The reaction was concentrated in vacuo and the residue was slurried in DCM (250 mL) for 30 minutes. The mixture was filtered through Celite and washed with DCM (50 mL). The filtrate was concentrated in vacuo and the residue was purified by silica gel chromatography (ethyl acetate/hexanes=0/100→10/90) to give 8.47 grams of the title compound as an orange oil (75% yield). LC/MS (FA) ES+ 368, 370. $^1$H NMR (300 MHz, CDCl$_3$) δ: 7.30-7.18 (m, 4H), 4.03 (s, 2H).

Step 4: 5-Bromo-4-(4-chlorobenzyl)-2-(pyridin-4-yl)thiazole

To a solution of 2,5-dibromo-4-(4-chlorobenzyl)thiazole (12.9 grams, 35.1 mmol) in DME (365 mL) was added pyridine-4-boronic acid (5.61 g, 45.6 mmol), 1M sodium carbonate (70.2 mL, 70.2 mmol), and PdCl$_2$(dppf) (2.89 g, 3.51 mmol). The reaction was degassed with argon and stirred at 85° C. overnight. The reaction was cooled and taken up in ethyl acetate (400 mL) and saturated sodium bicarbonate (200 mL). The insolubles were filtered through celite and the bed was washed with ethyl acetate (100 mL). The layers were separated and the aqueous layer was extracted with ethyl acetate (100 mL). The combined organic layers were dried over MgSO$_4$, filtered, and concentrated in vacuo. The residue was purified by silica gel chromatography (ethyl acetate/DCM=0/100→70/30) followed by another silica gel chromatography (ethyl acetate/hexanes=0/100→100/0) to give 3.3 grams of the title compound as a brown solid (26% yield). LC/MS (FA) ES+ 365, 367. $^1$H NMR (300 MHz, CDCl$_3$) δ: 8.70-8.67 (m, 2H), 7.70-7.67 (m, 2H), 7.28-7.26 (m, 4H), 4.13 (s, 2H).

Step 5: 4-(4-Chlorobenzyl)-2-(pyridin-4-yl)-5-(1H-pyrrol-2-yl)thiazole (Compound 22)

To a solution of 5-bromo-4-(4-chlorobenzyl)-2-(pyridin-4-yl)thiazole (94.0 mg, 0.257 mmol) in 4:1 dioxane:water (3.0 mL) was added 1-(t-butoxycarbonyl)pyrrole-2-boronic acid (57 mg, 0.27 mmol), cesium carbonate (251 mg, 0.771 mmol), and tetrakis(triphenylphosphine)palladium(0) (30 mg, 0.026 mmol). The solution was degassed with argon and heated in a microwave reactor at 130° C. for 105 minutes. The reaction was concentrated in vacuo and the residue taken up in DCM (25 mL) and water (10 mL). The layers were separated and the aqueous layer was extracted with DCM (2×10 mL). The combined organic layers were dried over MgSO$_4$, filtered, and concentrated in vacuo. The residue was purified by silica gel chromatography (ethyl acetate/DCM=0/100→80/20) followed by HPLC purification (formic acid method) to give 26 mg of the title compound as a yellow solid (29% yield). LC/MS (FA) ES+ 352. $^1$H NMR (300 MHz, d$_4$-MeOH) δ: 8.62-8.60 (m, 2H), 7.90-7.88 (m, 2H), 7.66-

7.55 (m, 1H), 7.26-7.24 (m, 2H), 7.20-7.17 (m, 2H), 6.92 (dd, 1H, J=2.7, 1.5 Hz), 6.32 (dd, 1H, J=3.5, 1.5 Hz), 6.21 (dd, 1H, J=3.5, 2.7 Hz), 4.28 (s, 2H).

Example 20

Synthesis of 4-(4-chlorobenzyl)-2-(2-chloropyridin-4-yl)-5-(4H-1,2,4-triazol-3-yl)thiazole (Compound 47)

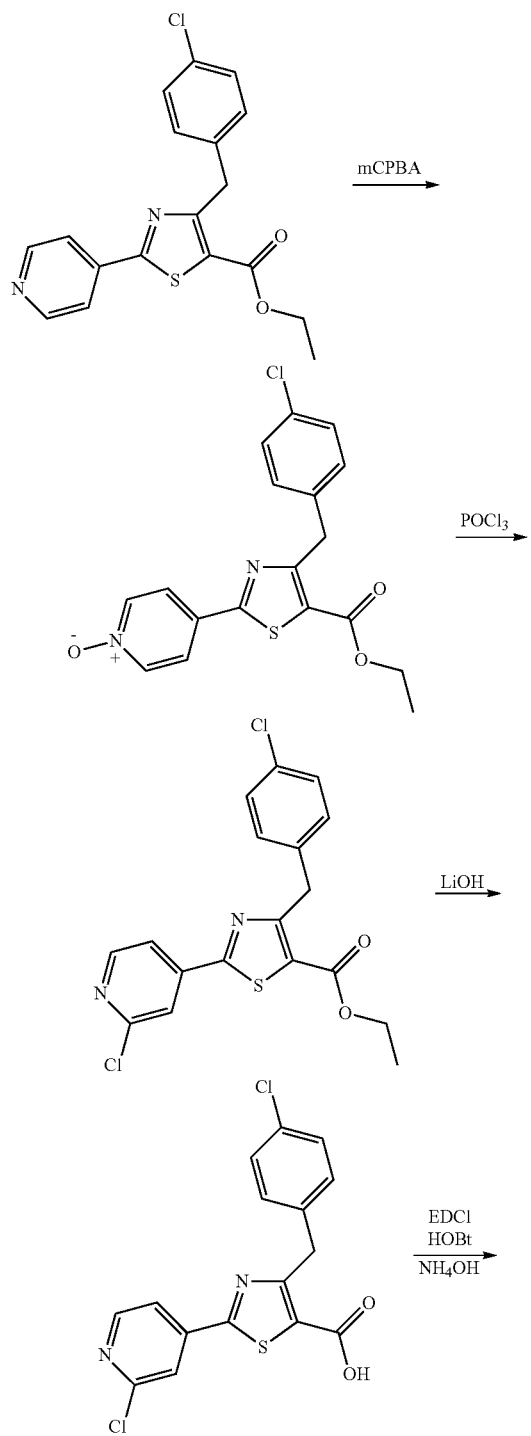

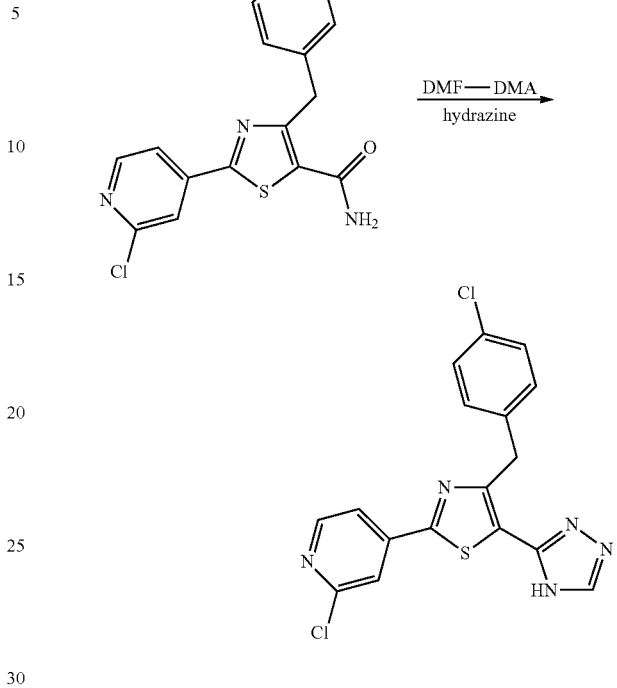

Step 1: 4-(4-(4-Chlorobenzyl)-5-(methoxycarbonyl)thiazol-2-yl)pyridine 1-oxide

To a solution of ethyl 4-(4-chlorobenzyl)-2-(pyridin-4-yl)thiazole-5-carboxylate (430 mg, 1.20 mmol) in DMF (6.0 mL) was added mCPBA (322 mg, 1.44 mmol) and the mixture was stirred at room temperature overnight. To the reaction was added DCM (30 mL) and saturated sodium bicarbonate (25 mL). The layers were separated and the aqueous layer extracted with DCM (20 mL). The combined organic layers were dried over MgSO₄, filtered, and concentrated in vacuo. The residue was purified by silica gel chromatography (ethyl acetate/DCM=50/50→100/0) to give 449 mg of the title compound as a white solid (100% yield). LC/MS (FA) ES+ 375. $^1$H NMR (300 MHz, CDCl₃) δ: 8.23-8.20 (m, 2H), 7.84-7.81 (m, 2H), 7.33-7.23 (m, 4H), 4.51 (s, 2H), 4.38 (q, 2H, J=7.2 Hz), 1.39 (t, 3H, J=7.2 Hz).

Step 2: Ethyl 4-(4-chlorobenzyl)-2-(2-chloropyridin-4-yl)thiazole-5-carboxylate

A solution of 4-(4-(4-chlorobenzyl)-5-(methoxycarbonyl)thiazol-2-yl)pyridine 1-oxide (334 mg, 0.891 mmol) in phosphoryl chloride (1.66 mL, 17.8 mmol) was heated at 100° C. for 2 hours. The reaction was cooled and poured onto ice and saturated sodium bicarbonate (50 mL). The mixture was extracted with ethyl acetate (2×40 mL) and the combined organic layers were washed with water (20 mL), brine (10 mL) and dried over MgSO₄, filtered, and concentrated in vacuo. The residue was purified by silica gel chromatography (DCM/hexanes=50/50→100/0) to give 191 mg of the title compound as a white solid (54% yield). LC/MS (FA) ES+ 393, 395. $^1$H NMR (300 MHz, CDCl₃) δ: 8.49 (dd, 1H, J=5.3, 0.7 Hz), 7.88 (dd, 1H, J=1.5, 0.7 Hz), 7.71 (dd, 1H, J=5.3, 1.5 Hz), 7.36-7.31 (m, 2H), 7.27-7.23 (m, 2H), 4.53 (s, 2H), 4.39 (q, 2H, J=7.2 Hz), 1.40 (t, 3H, J=7.2 Hz).

Step 3: 4-(4-Chlorobenzyl)-2-(2-chloropyridin-4-yl)thiazole-5-carboxylic acid To a solution of ethyl 4-(4-chlorobenzyl)-2-(2-chloropyridin-4-yl)thiazole-5-carboxylate (199 mg, 0.506 mmol) in THF (2.84 mL) and water (1.42 mL) was added 1.0 M LiOH (0.658 mL, 0.658 mmol) and the resulting solution was stirred at room temperature overnight. The mixture was acidified to pH=4 with 1 N HCl. The precipitated solids were filtered, washed with water and dried to give 179 mg of the title compound as an a white solid. (96% yield). LC/MS (FA) ES+ 365, 367.

Step 4: 4-(4-Chlorobenzyl)-2-(2-chloropyridin-4-yl)thiazole-5-carboxamide

To a mixture of 4-(4-chlorobenzyl)-2-(2-chloropyridin-4-yl)thiazole-5-carboxylic acid (179 mg, 0.490 mmol) in DCM (27.5 mL) was added EDCI (282 mg, 1.47 mmol) and 1-hydroxybenzotriazole hydrate (150 mg, 0.980 mmol) and the solution was stirred for 10 minutes. 28% ammonium hydroxide (2.12 mL, 24.5 mmol) was added and the resulting mixture was stirred at room temperature overnight. Water (20 mL) was added and the mixture was extracted with DCM (2×25 mL). The combined organic layers were dried over MgSO$_4$, filtered, and concentrated in vacuo. The residue was purified by silica gel chromatography (methanol/DCM=0/100→15/85) to give 121 mg of the title compound as a white solid (67% yield). LC/MS (FA) ES+ 364, 366. $^1$H NMR (400 MHz, d$_6$-DMSO) δ: 8.54 (dd, 1H, J=5.2, 0.7 Hz), 8.02 (bs, 1H), 7.91 (dd, 1H, J=1.5, 0.7 Hz), 7.84 (dd, 1H, J=5.2, 1.5 Hz), 7.79 (bs, 1H), 7.36-7.29 (m, 4H), 4.43 (s, 2H).

Step 5: 4-(4-Chlorobenzyl)-2-(2-chloropyridin-4-yl)-5-(4H-1,2,4-triazol-3-yl)thiazole (Compound 47)

A solution of 4-(4-chlorobenzyl)-2-(2-chloropyridin-4-yl)thiazole-5-carboxamide (128 mg, 0.351 mmol) and 1,1-dimethoxy-N,N-dimethylmethanamine (0.467 mL, 3.51 mmol) in toluene (3.75 mL) was heated at 100° C. for 1 hour. The reaction was cooled and concentrated in vacuo to give the intermediate, 4-(4-chlorobenzyl)-2-(2-chloropyridin-4-yl)-N-((dimethylamino)methylene)thiazole-5-carboxamide, as a solid. LC/MS (FA) ES+ 419, 421. The intermediate was dissolved in acetic acid (3.60 mL). Hydrazine hydrate (0.0855 mL, 1.76 mmol) was added and the resulting solution was heated at 90° C. for 2 hours. The mixture was cooled and concentrated in vacuo, and the residue was azeotroped with toluene. The residue was slurried in DCM (30 mL) and saturated sodium bicarbonate (20 mL). Some undissolved solids were filtered to give one batch of desired product. The layers of the filtrate were separated and the aqueous layer was extracted with DCM (2×20 mL). The combined organic layers were dried over MgSO$_4$, filtered, and concentrated in vacuo to give another batch of desired product. The two product batches were combined and purified by silica gel chromatography (methanol/DCM=0/100→20/80) to give 85 mg of the title compound as a beige solid (62% yield). LC/MS (FA) ES+ 388, 390. $^1$H NMR (300 MHz, d$_6$-DMSO) δ: 14.48 (bs, 1H), 8.76 (s, 1H), 8.54-8.51 (m, 1H), 7.96-7.95 (m, 1H), 7.92-7.89 (m, 1H), 7.38-7.30 (m, 4H), 4.65 (s, 2H).

Example 21

Synthesis of N-{4-[4-[(4-chlorophenyl)(hydroxy)methyl]-5-(1H-imidazol-2-yl)-1,3-thiazol-2-yl]pyridin-2-yl}acetamide (Compound 60)

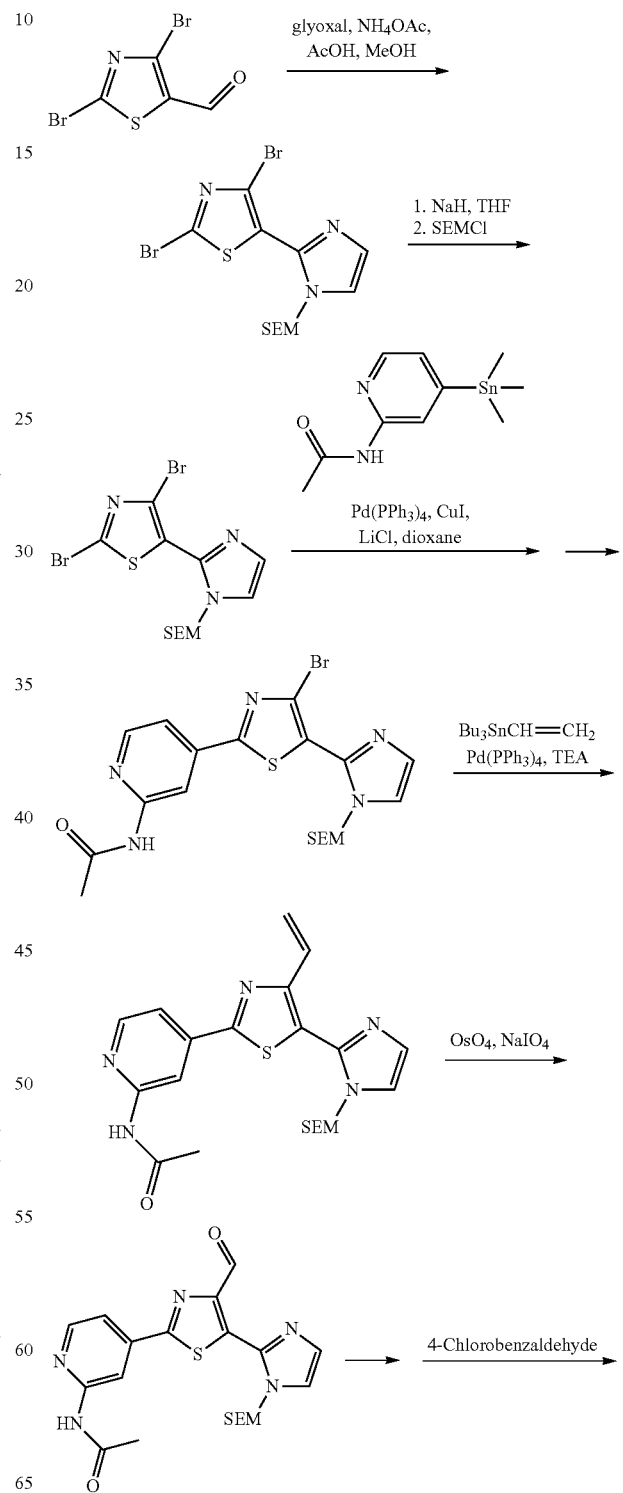

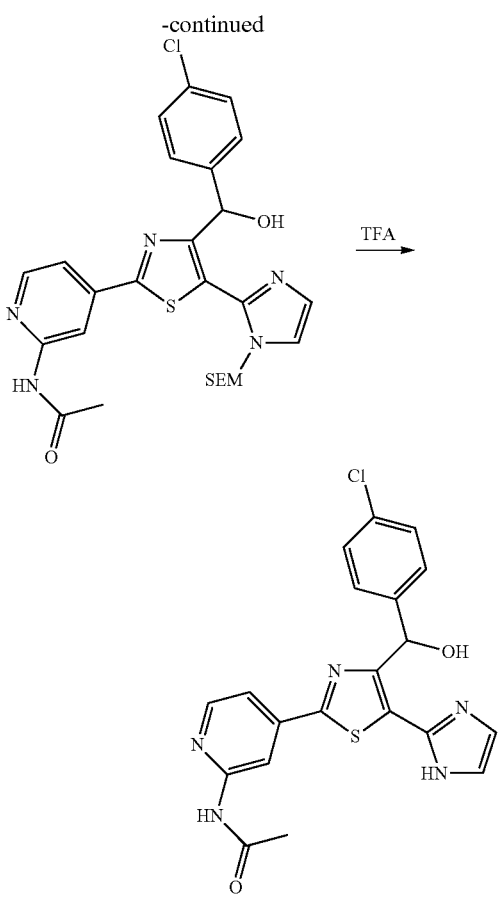

Step 1: 2,4-Dibromo-5-(1H-imidazol-2-yl)thiazole

A mixture of 2,4-dibromo-thiazole-5-carbaldehyde (14.8 g, 54.6 mmol), glyoxal trimer dihydrate (22.96 g, 109.2 mmol) and ammonium acetate (25.26 g, 327.8 mmol) in MeOH (450 mL) and acetic acid (31.06 mL) was stirred at rt overnight. The reaction mixture was concentrated in vacuo to a thick liquid mixture. Remaining acetic acid was removed by azeotroping with toluene (3×100 mL) to afford a dark brown solid. The mixture was purified by column chromatography on silica gel (0 to 25% EtOAc in hexanes) to give pure product (9.12 g, 54%). LCMS: (AA) ES+, 310, 312. $^1$H NMR (400 MHz, $d_6$-DMSO) δ: 12.50 (br, 1H), 7.21 (br, 2H).

Step 2: 2,4-Dibromo-5-(1-((2-(trimethylsilyl)ethoxy)methyl)-1H-imidazol-2-yl)thiazole To a mixture of sodium hydride (2.89 g, 72.2 mmol) in THF (431 mL) was added 2,4-dibromo-5-(1H-imidazol-2-yl)thiazole (18.8 g, 60.9 mmol) in THF (60 mL) at 0° C. After stirring 30 min, 2-(trimethylsilyl)ethoxymethyl chloride (11.8 mL, 66.9 mmol) in THF (24 mL) was slowly added at 0° C. After 30 min at this temperature, the reaction was quenched by the addition of MeOH (20 mL). The solvent was evaporated and the residue was purified by column chromatography on silica gel (0 to 25% EtOAc in hexanes). Product was obtained as colorless oil (21.8 g, 81.6%). LCMS: (AA) ES+, 440, 442. $^1$H NMR (300 MHz, CDCl$_3$) δ: 7.24 (dd, 2H), 5.27 (s, 2H), 3.39 (t, 2H), 0.85 (t, 2H), −0.03 (s, 9H).

Step 3: N-(4-(4-Bromo-5-(1-((2-(trimethylsilyl)ethoxy)methyl)-1H-imidazol-2-yl)thiazol-2-yl)pyridin-2-yl)acetamide A mixture of 2,4-dibromo-5-(1-((2-(trimethylsilyl)ethoxy)methyl)-1H-imidazol-2-yl)thiazole (13.6 g, 31.0 mmol), N-[4-(trimethylstannyl)pyridin-2-yl]acetamide (11.1 g, 37.2 mmol), tetrakis(triphenylphosphine)palladium(0) (1.792 g, 1.550 mmol), copper(I) iodide (1.77 g, 9.30 mmol) and lithium chloride (3.94 g, 93.0 mmol) in 1,4-dioxane (569 mL) was degassed with argon. The mixture was sonicated for 20 min and then heated at 120° C. for 5 h. The solvent was evaporated and the crude reaction mixture was purified by ISCO chromatography (0 to 3% MeOH in DCM). Product was obtained as an orange solid (10.1 g, 66.0%). LCMS: (AA) ES+, 494, 496. $^1$H NMR (300 MHz, CDCl$_3$) δ: 8.65 (s, 1H), 8.44 (br, 1H), 8.34 (d, 1H), 7.60 (dd, 1H), 7.30 (d, 2H), 5.30 (s, 2H), 3.40 (t, 2H), 2.25 (s, 3H), 0.86 (t, 2H), −0.05 (s, 9H).

Step 4: N-{4-[5-(1-{[2-(trimethylsilyl)ethoxy]methyl}-1H-imidazol-2-yl)-4-vinyl-1,3-thiazol-2-yl]pyridin-2-yl}acetamide N-(4-(4-bromo-5-(1-((2-(trimethylsilyl)ethoxy)methyl)-1H-imidazol-2-yl)thiazol-2-yl)pyridin-2-yl)acetamide (0.80 g, 1.6 mmol) and tetrakis(triphenylphosphine)palladium(0) (0.187 g, 0.162 mmol) were placed in a microwave vial and sealed under atmosphere of argon. Triethylamine (7.0 mL, 50 mM), THF (7 mL) and tributylethenyl stannane (0.708 mL, 2.43 mmol) were added and the mixture was irradiated at 95° C. for 3 hours. The solvent was evaporated and the residue was purified using column chromatography on silica gel (0 to 60% EA in hexane) to give the title compound (0.65 g, 72%). LCMS: (FA) ES+, 442. $^1$H NMR (400 MHz, CDCl$_3$) δ: 8.80 (s, 1H), 8.41-8.31 (m, 1H), 8.09 (s, 1H), 7.70-7.40 (m, 3H), 6.81 (dd, J=17.2, 10.7 Hz, 1H), 6.38 (dd, J=17.2, 1.9 Hz, 1H), 5.54 (dd, J=10.7, 1.9 Hz, 1H), 5.27 (s, 2H), 3.48-3.34 (m, 2H), 2.25 (s, 3H), 0.90-0.84 (m, 2H), −0.04 (s, 9H).

Step 5: N-{4-[4-formyl-5-(1-{[2-(trimethylsilyl)ethoxy]methyl}-1H-imidazol-2-yl)-1,3-thiazol-2-yl]pyridin-2-yl}acetamide N-{4-[5-(1-{[2-(trimethylsilyl)ethoxy]methyl}-1H-imidazol-2-yl)-4-vinyl-1,3-thiazol-2-yl]pyridin-2-yl}acetamide (0.650 g, 1.47 mmol) was dissolved in tetrahydrofuran (20 mL) and water (10 mL) at ambient temperature and 0.157 M osmium tetraoxide in water (93 uL, 0.014 mmol) was added. The mixture was stirred at room temperature for 5 minutes. Sodium metaperiodate (0.661 g, 3.09 mmol) was then added in portions over 20 minutes and the mixture was stirred at room temperature overnight. Solids were removed by filtration and washed with THF (2×50 mL) and ethyl acetate (2×5 mL). The filtrate was extracted with ethyl acetate (3×100 mL). The extracts were combined, washed with brine, dried over sodium sulfate, filtered and concentrated under reduced pressure. Crude material was purified by silica gel chromatography (0 to 30% ethyl acetate in hexanes) to afford the title compound (0.25 g, 38%). LCMS: (FA) ES+, 444. $^1$H NMR (400 MHz, CDCl$_3$) δ: 8.75 (s, 1H), 10.21 (s, 1H), 8.41 (d, J=5.18 Hz, 1H), 8.20-8.07 (m, 1H), 7.76 (dd, J=5.21, 1.58 Hz, 1H), 7.30 (dd, J=2.87, 1.21 Hz, 2H), 5.32 (s, 2H), 3.50-3.33 (m, 2H), 2.26 (s, 3H), 0.93-0.78 (m, 2H), −0.04 (s, 9H).

Step 6: N-{4-[4-[(4-chlorophenyl)(hydroxy)methyl]-5-(1-{[2-(trimethylsilyl)ethoxy]methyl}-1H-imidazol-2-yl)-1,3-thiazol-2-yl]pyridin-2-yl}acetamide N-{4-[4-formyl-5-(1-{[2-(trimethylsilyl)ethoxy]methyl}-1H-imidazol-2-yl)-1,3-thiazol-2-yl]pyridin-2-yl}acetamide (0.250 g, 0.564 mmol) was dissolved in tetrahydrofuran (20 mL) and cooled at 0° C. 1.0 M 4-Chlorophenylmagnesium bromide in ether (1.41 mL, 1.41 mmol) was added and the solution was stirred at 0° C. for 30 minutes. The reaction was quenched by the addition of MeOH (10 mL), and was evaporated under reduced pressure. The residue was purified using column chromatography (20 to 100% ethyl acetate in hexane) to give the title compound (0.150 g, 48%). LCMS: (FA) ES+, 556, 558. $^1$H NMR (400 MHz, CDCl$_3$) δ: 8.69 (s, 1H), 8.34 (d, J=5.23 Hz, 1H), 8.21 (s, 1H), 7.65 (dd, J=5.23, 1.55 Hz, 1H), 7.31 (d, J=8.28 Hz, 2H), 7.21-7.16 (m, 3H), 7.07 (d, J=1.31 Hz, 1H), 6.26-6.15 (m, 1H), 5.30 (s, 1H), 3.46-3.36 (m, 2H), 2.24 (s, 3H), 0.94-0.84 (m, 2H), −0.02 (s, 9H).

Step 7: N-{4-[4-[(4-chlorophenyl)(hydroxy)methyl]-5-(1H-imidazol-2-yl)-1,3-thiazol-2-yl]pyridin-2-yl}acetamide (Compound 60)

N-{4-[4-[(4-chlorophenyl)(hydroxy)methyl]-5-(1-{[2-(trimethylsilyl)ethoxy]methyl}-1H-imidazol-2-yl)-1,3-thiazol-2-yl]pyridin-2-yl}acetamide (0.120 g, 0.216 mmol) was dissolved in DCM (5 mL) and trifluoroacetic acid (5.0 mL, 65 mmol) was added. The mixture was stirred at room temperature overnight. The solvent was evaporated, azeotroped with toluene and purified using column chromatography on silica gel (0 to 10% MeOH in DCM) to give the title compound (0.050 g, 50%). LCMS: (FA) ES+, 426, 428. $^1$H NMR (400 MHz, d$_4$-methanol) δ: 8.68 (s, 1H), 8.38 (d, J=5.24 Hz, 1H), 7.64 (dd, J=5.25, 1.60 Hz, 1H), 7.45-7.37 (m, 2H), 7.30-7.23 (m, 2H), 7.25-7.09 (m, 2H), 6.37 (s, 1H), 2.20 (s, 3H).

Example 22

Synthesis of 3-[4-(4-chlorobenzyl)-5-(4H-1,2,4-triazol-3-yl)-1,3-thiazol-2-yl]-2-methyl-5-(piperazin-1-ylmethyl)pyrazolo[1,5-a]pyridine (Compound 72)

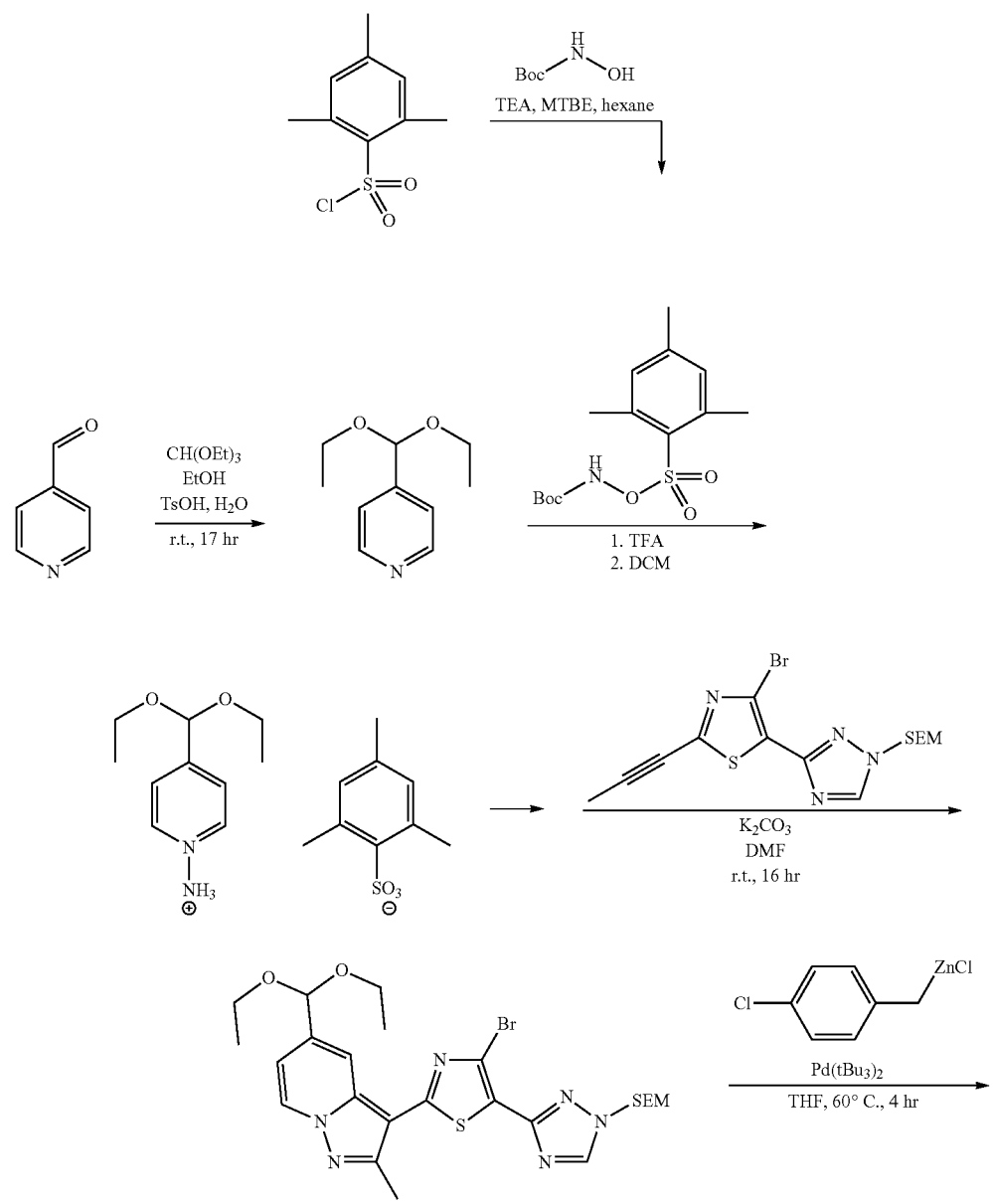

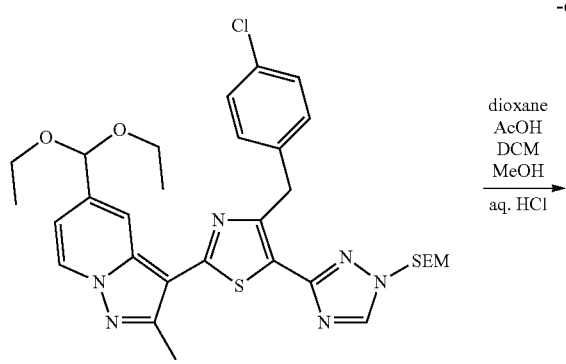

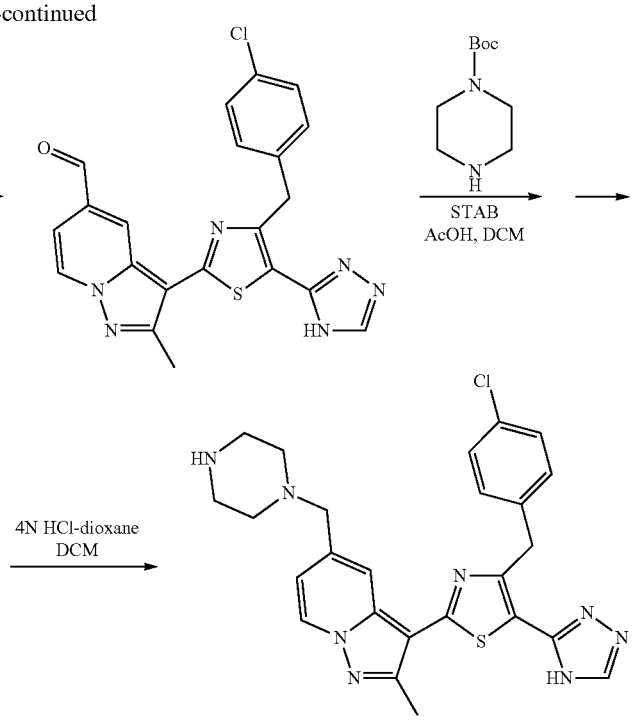

Step 1: 4-(Diethoxymethyl)pyridine p-Toluenesulfonic acid monohydrate (11.8 g, 62.0 mmol) was dissolved in dry ethanol (80 mL) at rt. 4-Pyridinecarboxaldehyde (4.71 mL, 50.0 mmol) was added, followed by ethyl orthoformate (20.79 mL, 125.0 mmol). The mixture was stirred at rt for 17 hours. The mixture was concentrated and the residue was basified with aqueous saturated NaHCO$_3$ solution to ~pH 8, extracted with EtOAc (150 mL), washed with brine, dried over Na$_2$SO$_4$, filtered, evaporated, and dried under high vacuum to give a liquid product. (9.06 g, yield 97.2%). LCMS: (FA) ES$^+$ 182. $^1$H NMR (400 MHz, CDCl$_3$) δ: 8.60-8.62 (m, 2H), 7.38-7.40 (m, 2H), 5.50 (s, 1H), 3.53-3.62 (m, 4H), 1.23-1.27 (m, 6H).

Step 1A: N-tert-Butoxycarbonyl-O-(mesitylsulfonyl)hydroxylamine tert-Butyl-N-hydroxycarbamate (5.00 g, 37.6 mmol) and mesitylenesulfonyl chloride (8.21 g, 37.6 mmol) were dissolved in 2-methoxy-2-methylpropane (90 mL), flushed with nitrogen and cooled in an ice bath to an internal temperature of 1° C. Triethylamine (5.34 mL, 38.3 mmol) was added dropwise over 25 min during which time the temperature, increased to 6° C. The mixture was stirred with cooling for 2 hours at which time the internal reaction temperature was 8° C. The suspension was filtered and the solids were washed with 2-methoxy-2-methylpropane (60 mL). The filtrate was concentrated to ~20 mL volume, diluted with hexane (70 mL) and allowed to sit at rt for 30 min. The resulting crystalline solid was collected by filtration and washed with hexane (20 mL). The mother liquor was evaporated, diluted with hexane (50 mL), and allowed to sit, giving a second crop of crystals. The combined collected solids were dried in vacuum for 1 hour to give a white crystal product (11.06 g, yield 93.4%). LCMS: (AA) ES$^+$ 316 and 333 for M$^+$+NH$_3$. $^1$H NMR (400 MHz, CDCl$_3$) δ: 7.54 (s, 1H), 6.99 (s, 2H), 2.68 (s, 6H), 2.32 (s, 3H), 1.31 (s, 9H).

Step 2: 1-Amino-4-(diethoxymethyl)pyridinium 2,4,6-trimethylbenzenesulfonate Trifluoroacetic acid (12.0 mL, 156 mmol) was cooled in an ice bath. N-tert butoxycarbonyl-O-(mesitylsulfonyl)hydroxylamine (7.91 g, 25.1 mmol) was portionwise added over 15 min. The mixture was stirred with cooling for 2 hours then ~50 g of ice was added, followed by ~100 mL of ice water. The resulting white solid was collected by filtration and washed with water until the washings were ~pH 6. The solid was dried in air for 15 min to afford a still damp intermediate (6.25 g). The solid then was dissolved in methylene chloride (160 mL, 2500 mmol), dried over Na$_2$SO$_4$, and filtered. The filtrate was cooled in an ice bath and a solution of 4-(diethoxymethyl)pyridine (5.91 g, 32.6 mmol) in dry methylene chloride (20 mL, 300 mmol) was slowly added over 10 min. The ice bath was removed and the mixture was stirred at rt for 50 min. The mixture was concentrated to ~30 mL volume. The oily residue was azeotroped with 15 mL of diethyl ether, then the residue was diluted with 250 mL of diethyl ether and cooled in an ice bath for 1 hour, then stored in a freezer (−20° C.) overnight. An oily residue appeared. The clear solution was decanted and the oily residue was dried under high vacuum to give a first crop of oily product (2.15 g). The decanted solution was concentrated to give an oily residue which was triturated with hexane (2×100 mL), then dried under high vacuum to give a second crop of oily product (6.15 g, yield 79.7% for 2 crops). LCMS: (FA) ES$^+$ 197; ES$^-$ 199. $^1$H NMR (400 MHz, CDCl$_3$) δ: 9.00-9.05 (m, 4H), 7.69-7.71 (m, 2H), 6.85 (s, 2H), 5.50 (s, 1H), 3.52-3.57 (m, 4H), 2.67 (s, 6H), 2.25 (s, 3H), 1.22-1.26 (m, 6H).

Step 3: 3-[4-Bromo-5-(1-{[2-(trimethylsilyl)ethoxy] methyl}-1H-1,2,4-triazol-3-yl)-1,3-thiazol-2-yl]-5-(diethoxymethyl)-2-methylpyrazolo[1,5-a]pyridine To a mixture of 3-(4-bromo-2-prop-1-yn-1-yl-1,3-thiazol-5-yl)-1-{[2-(trimethylsilyl)ethoxy]methyl}-1H-1,2,4-triazole [Prepared as described in Example 14 (4.37 g, 10.9 mmol)] and potassium carbonate (3.00 g, 21.7 mmol) in dry N,N-dimethylformamide (20.0 mL) was added a solution of 1-amino-4-(diethoxymethyl)pyridinium 2,4,6-trimethylbenzenesulfonate (6.37 g, 15.6 mmol) in dry N,N-dimethylformamide (20.0 mL) over 10 min. The resulting dark brown solution was stirred at rt for 40 hours. The mixture was added to ~250 mL of ice water with stirring, then was extracted with EtOAc (100 mL×5) until the aqueous layer turned into a clear solution. The combined EtOAc extracts were washed with water, brine, dried over $Na_2SO_4$, filtered, and evaporated. The crude product was purified by column chromatography on silica gel, using EtOAc/hexane (0/100 to 50/50) as an eluant to give a solid product (4.56 g, 70.2%). LCMS: (FA) $ES^+$ 593, 595. $^1H$ NMR (400 MHz, $CDCl_3$) δ: 8.46 (d, J=2.01 Hz, 1H), 8.40-8.42 (d, J=7.28 Hz, 1H), 8.32 (s, 2H), 7.05-7.08 (dd, J=2.01, 7.03 Hz, 1H), 5.57 (s, 2H, 3.68-3.77 (m, 4H), 3.58-3.63 (m, 2H), 2.75 (s, 3H), 1.28-1.32 (m, 6H), 0.95-1.00 (m, 2H), 0.02 (s, 9H)

Step 4: 3-[4-(4-Chlorobenzyl)-5-(1-{[2-(trimethylsilyl)ethoxy]methyl}-1H-1,2,4-triazol-3-yl)-1,3-thiazol-2-yl]-5-(diethoxymethyl)-2-methylpyrazolo[1,5-a]pyridine A mixture of 3-[4-bromo-5-(1-{[2-(trimethylsilyl)ethoxy] methyl}-1H-1,2,4-triazol-3-yl)-1,3-thiazol-2-yl]-5-(diethoxymethyl)-2-methylpyrazolo[1,5-a]pyridine (0.907 g, 1.53 mmol) and bis(tri-t-butylphosphine)palladium(0) (39.0 mg, 0.0764 mmol) in a 40 mL vial was evacuated under low vacuum and backfilled with nitrogen four times. 4-Chlorobenzylzinc chloride in tetrahydrofuran (0.50 M, 7.0 mL, 3.5 mmol) was added and the solution was again evacuated under low vacuum and backfilled with nitrogen twice. The solution was heated to 60° C. for 4 hours. The reaction mixture was cooled to rt, quenched with water, adjusted to ~pH 6 with acetic acid, and extracted with EtOAc (2×). The organic layers were combined, washed with water, brine, dried over $Na_2SO_4$, filtered and evaporated to give a crude residue which was purified by column chromatography on silica gel column using EtOAc/hexane (0/100 to 40/60) as an eluant to give a solid product (0.806 g, 85% pure by $^1H$-NMR, yield 70.5%). LCMS: (FA) $ES^+$ 639, 641. $^1H$ NMR of pure fraction (400 MHz, $CDCl_3$) δ: 8.36-8.39 (m, 2H), 8.27 (s, 1H), 7.45-7.47 (m, 2H), 7.23-7.25 (m, 2H), 6.99-7.01 (m, 1H), 5.54 (s, 2H, 5.50 (s, 1H), 4.67 (s, 2H), 3.66-3.74 (m, 4H), 3.57-3.62 (m, 2H), 2.74 (s, 3H), 1.26-1.30 (m, 6H), 0.95-0.99 (m, 2H), 0.00 (s, 9H).

Step 5: 3-[4-(4-Chlorobenzyl)-5-(4H-1,2,4-triazol-3-yl)-1,3-thiazol-2-yl]-2-methylpyrazolo[1,5-a]pyridine-5-carbaldehyde 3-[4-(4-Chlorobenzyl)-5-(1-{[2-(trimethylsilyl)ethoxy] methyl}-1H-1,2,4-triazol-3-yl)-1,3-thiazol-2-yl]-5-(diethoxymethyl)-2-methylpyrazolo[1,5-a]pyridine (1.17 g, 1.83 mmol) was dissolved in 1,4-dioxane (45 mL) and cooled in a water bath. 12 M hydrochloric acid (15 mL) was added and the mixture was stirred at rt for 15 hours. Acetic acid (40 mL, 700 mmol) was added and the suspension was stirred at rt for 24 hours then heated to 70° C. for 2 hours, then evaporated. The solid residue was stirred with 1.00 hydrochloric acid (100 mL) and methanol (120 mL) at rt for 14 hours. The mixture was evaporated on a rotovap at 45° C. to dryness and then azeotroped with DCM to give a crude product. The crude product was suspended in water, basified with $NaHCO_3$ to ~pH 8, extracted with EtOAc (300 mL, 3×80 mL), washed with brine, dried over $Na_2SO_4$, filtered, and evaporated to afford a yellow solid product (0.773 g, yield 97.2%). LCMS: (FA) $ES^+$ 435, 437. $^1H$ NMR (400 MHz, $CDCl_3$) δ: 10.84 (s, br, 1H), 9.99 (s, 1H), 8.75 (m, 1H), 8.43-8.46 (d, J=7.28 Hz, 1H), 8.36 (s, 1H), 7.41-7.44 (d, J=8.53 Hz, 2H), 7.32-7.35 (dd, J=7.03, 2.01 Hz, 1H), 7.27-7.30 (d, J=8.53 Hz, 2H), 4.69 (s, 2H), 2.79 (s, 3H).

Step 6: tert-Butyl 4-({3-[4-(4-chlorobenzyl)-5-(4H-1,2,4-triazol-3-yl)-1,3-thiazol-2-yl]-2-methylpyrazolo[1,5-a]pyridin-5-yl}methyl)piperazine-1-carboxylate A mixture of 3-[4-(4-chlorobenzyl)-5-(4H-1,2,4-triazol-3-yl)-1,3-thiazol-2-yl]-2-methylpyrazolo[1,5-a]pyridine-5-carbaldehyde (0.0563 g, 0.109 mmol), tert-butyl 1-piperazinecarboxylate (60.8 mg, 0.326 mmol) and acetic acid (0.0800 mL, 1.41 mmol) in dry methylene chloride (10 mL) was stirred at rt for 15 min. Sodium triacetoxyborohydride (69.1 mg, 0.326 mmol) was added and the mixture was stirred at rt for 15 hours. The mixture was washed with saturated $NaHCO_3$ solution and the aqueous layer was extracted with DCM. The DCM extract was washed with water, brine, dried over $Na_2SO_4$, filtered and evaporated to give a crude product which was purified by column chromatography on silica gel column using MeOH/DCM (0/100 to 5/95) to give solid product (0.0464 g, yield 70.5%). LCMS: (FA) $ES^+$ 605, 607; $ES^-$ 603, 605. $^1H$ NMR (400 MHz, $CDCl_3$ and $d_4$-methanol) δ: 8.23-8.25 (d, J=7.03 Hz, 1H), 8.20 (s, 1H), 7.94 (s, 1H), 7.29-7.31 (d, J=8.28 Hz, 2H), 7.15-7.17 (d, J=8.53 Hz, 2H), 6.86-6.89 (dd, J=7.28, 1.76 Hz, 1H), 4.53 (s, 2H), 3.45 (s, 2H), 3.33-3.36 (m, 4H), 2.62 (s, 3H), 2.35 (s, br, 4H), 1.37 (s, 9H).

Step 7: 3-[4-(4-Chlorobenzyl)-5-(4H-1,2,4-triazol-3-yl)-1,3-thiazol-2-yl]-2-methyl-5-(piperazin-1-ylmethyl)pyrazolo[1,5-a]pyridine (Compound 72)

To a solution of tert-butyl 4-({3-[4-(4-chlorobenzyl)-5-(4H-1,2,4-triazol-3-yl)-1,3-thiazol-2-yl]-2-methylpyrazolo[1,5-a]pyridin-5-yl}methyl)piperazine-1-carboxylate (0.0435 g, 0.0719 mmol) in methylene chloride (2.0 mL) and methanol (2.0 mL) was added 4 M hydrochloric acid in 1,4-dioxane (2.0 mL, 7.8 mmol). The mixture was stirred at rt for 5 hours then was evaporated, azeotroped with MeOH, and dried under high vacuum to give a solid (~50 mg). The solid was triturated with diethyl ether (10 ml×2) then dried under high vacuum to give product as a pale yellow powder (0.0424 g, yield 100%) as a bis HCl salt. LCMS: (FA) $ES^+$ 505, 507; $ES^-$ 503, 505. $^1H$ NMR (400 MHz, $d_4$-methanol) δ: 8.71 (s, 1H), 8.62-8.64 (d, J=7.03 Hz, 1H), 8.41 (s, 1H), 7.39-7.41 (d, J=8.78 Hz, 2H), 7.27-7.29 (d, J=8.53 Hz, 2H), 7.20-7.23 (dd, J=7.03, 2.01 Hz, 1H), 4.66 (s, 2H), 4.38 (s, 2H), 3.54 (s, br, 4H), 3.43 (s, br, 4H), 2.73 (s, 3H).

Compounds in the following table were prepared from the appropriate starting materials in a method analogous to that of Example 22:

| | |
|---|---|
| 31 | LCMS: (FA) ES+ 570, 572. |
| 32 | LCMS: (FA) ES+ 526, 528. |
| 38 | LCMS: (FA) ES+ 493, 495. |
| 54 | LCMS: (FA) ES+ 479, 481. |
| 61 | LCMS: (FA) ES+ 519, 521. |
| 82 | LCMS: (FA) ES+ 579, 581. |
| 83 | LCMS: (FA) ES+ 569, 571. |

Example 23

Synthesis of 1-{3-[4-(4-chlorobenzyl)-5-(4H-1,2,4-triazol-3-yl]-1,3-thiazol-2-yl]-2-methylpyrazolo[1,5-a]pyridin-5-yl}methanamine (Compound 1)

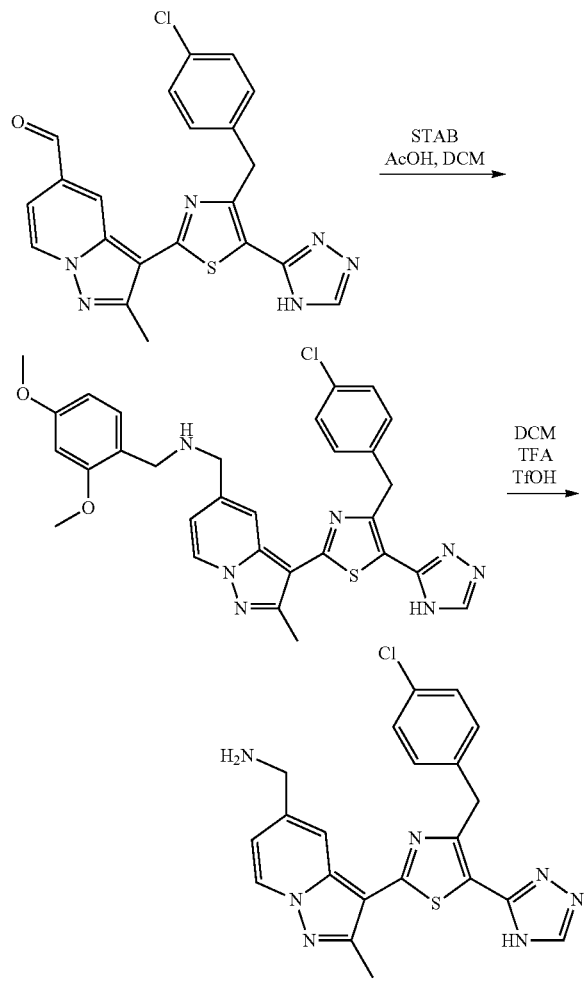

Step 1: 1-{3-[4-(4-Chlorobenzyl)-5-(4H-1,2,4-triazol-3-yl)-1,3-thiazol-2-yl]-2-methylpyrazolo[1,5-a]pyridin-5-yl}-N-(2,4-dimethoxybenzyl)methanamine To a suspension of 3-[4-(4-chlorobenzyl)-5-(4H-1,2,4-triazol-3-yl)-1,3-thiazol-2-yl]-2-methylpyrazolo[1,5-a]pyridine-5-carbaldehyde (0.300 g, 0.690 mmol) in acetic acid (0.20 mL, 3.5 mmol) and dry methylene chloride (10 mL, 200 mmol) was added 2,4-dimethoxybenzylamine (0.207 mL, 1.38 mmol), followed by additional of sodium triacetoxyborohydride (0.363 g, 1.71 mmol). The mixture was stirred at rt. for 16 hours. The mixture was basified with NaHCO₃ solution to ~pH 8 then extracted with DCM. The DCM solution was washed with water. The crude product was purified by column chromatography (SiO2, elution with 0-100% MeOH in DCM) to afford a solid product (0.252 g, yield 62%). LCMS: (FA) ES⁺ 586, 588; ES⁻ 584, 586. ¹H NMR (400 MHz, CDCl₃ and d₄-methanol) δ: 8.23-8.25 (d, J=7.03 Hz, 1H), 8.18 (s, 1H), 8.01 (s, 1H), 7.28-7.30 (d, J=8.53 Hz, 2H), 7.09-7.11 (d, J=8.53 Hz, 2H), 7.01-7.03 (d, J=8.28 Hz, 1H), 6.78-6.80 (d, J=7.03 Hz, 1H), 6.33-6.37 (m, 2H), 4.53 (s, 2H), 3.65 (s, 2H), 3.64 (s, 6H), 3.61 (s, 2H), 2.61 (s, 3H).

Step 2: 1-{3-[4-(4-Chlorobenzyl)-5-(4H-1,2,4-triazol-3-yl)-1,3-thiazol-2-yl]-2-methylpyrazolo[1,5-a]pyridin-5-yl}methanamine (Compound 1)

1-{3-[4-(4-chlorobenzyl)-5-(4H-1,2,4-triazol-3-yl)-1,3-thiazol-2-yl]-2-methylpyrazolo[1,5-a]pyridin-5-yl}-N-(2,4-dimethoxybenzyl)methanamine (0.257 g, 0.438 mmol) was dissolved in methylene chloride (6.0 mL) and trifluoroacetic acid (6.0 mL). Trifluoromethanesulfonic acid (0.050 mL, 0.56 mmol) was added and the mixture was heated to 60° C. for 6 days. The mixture was evaporated in a rotary evaporator, azeotroped with EtOAc (3×), and evaporated to give a crude residue. The residue was suspended in ~1 mL of MeOH and diluted with ~20 mL of Et₂O. The resulting powder was collected by filtration and dried under high vacuum to afford a pale pink solid product. The solid was taken up in EtOAc/water (20 mL/10 mL) and adjusted to ~pH 8 with NaHCO₃ solution. The layers were separated and the aqueous layer was extracted with EtOAc (2×30 mL). The combined EtOAc solutions were washed with water, brine, dried over Na₂SO₄, and filtered. The filtrate was concentrated to ~5 mL volume and the precipitated solid was collected by filtration to give a pure crop of product (0.0069 g). The filtrate was evaporated then dried under high vacuum to afford a second crop of solid product (0.171 g, yield for 2 crops 89.9%). LCMS: (FA) ES⁺ 436, 438; ES⁻ 434, 436. ¹H NMR (400 MHz, d₄-methanol) δ: 8.33-8.35 (d, J=7.29 Hz, 1H), 8.24 (s, 1H), 8.09 (s, 1H), 7.31-7.33 (d, J=8.78 Hz, 2H), 7.20-7.22 (d, J=8.53 Hz, 2H), 6.98-7.00 (m, 1H), 4.59 (s, 2H), 4.06 (s, 2H), 2.67 (s, 3H).

Compound in the following table was prepared from the appropriate starting materials in a method analogous to that of Example 23:

| | | |
|---|---|---|
| 20 | | LCMS: (FA) ES+ 586, 588. |

Example 24

Synthesis of N-({3-[4-(4-chlorobenzyl)-5-(4H-1,2,4-triazol-3-yl)-1,3-thiazol-2-yl]-2-methylpyrazolo[1,5-a]pyridin-5-yl}methyl)guanidine (Compound 35)

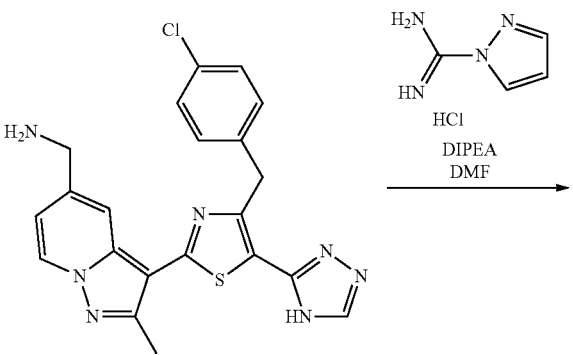

-continued

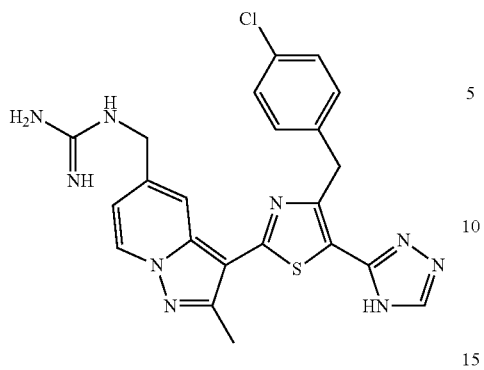

To a mixture of 1-{3-[4-(4-chlorobenzyl)-5-(4H-1,2,4-triazol-3-yl)-1,3-thiazol-2-yl]-2-methylpyrazolo[1,5-a]pyridin-5-yl}methanamine (0.0250 g, 0.0553 mmol) and 1H-pyrazole-1-carboxamidine hydrochloride (8.20 mg, 0.0559 mmol) in dry N,N-dimethylformamide (0.50 mL) was added N,N-diisopropylethylamine (7.15 mg, 0.0553 mmol). The solution was stirred at rt for 23 hours. The reaction mixture was diluted with water (15 mL) and extracted with EtOAc (5×15 mL). The EtOAc solution was washed with brine, dried over $Na_2SO_4$, filtered, and concentrated in a rotary evaporator to give a crude residue. The residue was dissolved in ~0.2 mL of MeOH, then diluted with ~5 mL of EtOAc. The resulting solid was collected by filtration to give a pale yellow powder product (0.008 g, 30%). LCMS: (FA) ES$^+$ 478, 480; ES$^-$ 476, 478. $^1$H NMR (400 MHz, CDCl$_3$ and d$_4$-methanol) δ: 8.25-8.27 (d, J=7.28 Hz, 1H), 8.17 (s, 1H), 7.92 (s, 1H), 7.21-7.23 (d, J=8.53 Hz, 2H), 7.08-7.10 (d, J=8.28 Hz, 2H), 6.72-6.74 (dd, J=7.28, 1.76 Hz, 1H), 4.48 (s, 2H), 4.30 (s, 2H), 2.57 (s, 3H).

Example 25

Synthesis of N-({3-[4-(4-chlorobenzyl)-5-(4H-1,2,4-triazol-3-yl)-1,3-thiazol-2-yl]-2-methylpyrazolo[1,5-a]pyridin-5-yl}methyl)pyrazine-2-carboxamide (Compound 50)

-continued

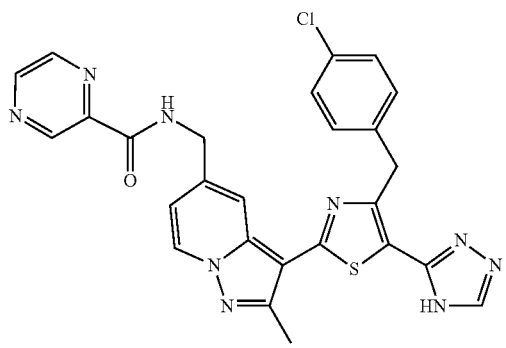

A mixture of 1-{3-[4-(4-chlorobenzyl)-5-(4H-1,2,4-triazol-3-yl)-1,3-thiazol-2-yl]-2-methylpyrazolo[1,5-a]pyridin-5-yl}methanamine (0.0222 g, 0.0491), pyrazine-2-carboxylic acid chloride (8.0 mg, 0.056 mmol) and N,N-diisopropylethylamine (10 mg, 0.08 mmol) in dry Methylene chloride (5.0 mL) in dry N,N-dimethylformamide (1.0 mL) was sonicated for 2 min. The mixture was stirred at rt for 22 hours. N,N-diisopropylethylamine (13 mg, 0.10 mmol) and pyrazine-2-carboxylic acid chloride (9.11 mg, 0.0639 mmol) were added and the mixture was stirred at rt for 3 days. The mixture was quenched with water, then extracted with DCM (3×30 mL). The combined DCM solutions were washed with water, brine, dried over $Na_2SO_4$, filtered, and evaporated to give a crude product (80 mg). The crude product was purified by HPLC to give a solid product (0.0007 g, yield 3%). LCMS: (AA) ES$^+$ 542, 544. $^1$H NMR (400 MHz, d$_6$-DMSO) δ: 9.72-9.74 (d, J=6.53 Hz, 1H), 9.23 (s, 1H), 8.87 (s, 1H), 8.75 (s, 1H), 8.67-8.69 (d, J=6.53 Hz, 1H), 8.63 (s, 1H), 8.22 (s, 1H), 7.24-7.30 (m, 4H), 7.03-7.05 (d, J=7.28 Hz, 1H), 4.62-4.64 (d, J=6.78 Hz, 2H), 4.47 (s, 2H), 2.63 (s, 3H).

Example 26

Synthesis of N-(2-(2-acetamidopyridin-4-yl)-5-(1H-imidazol-2-yl)thiazol-4-yl)benzamide (Compound 29)

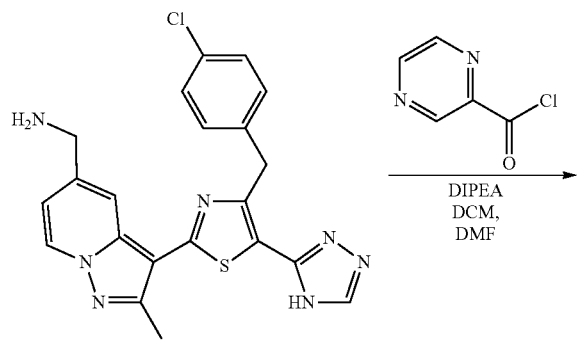

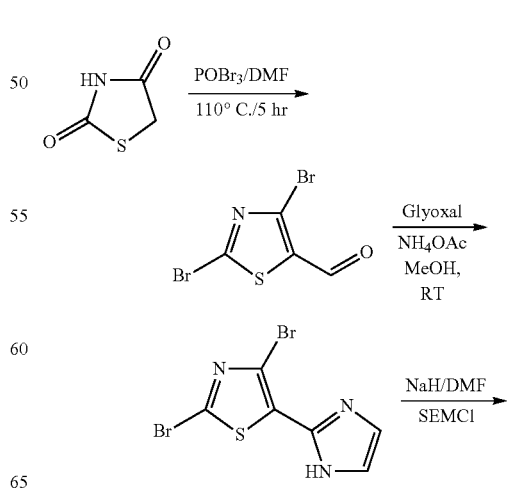

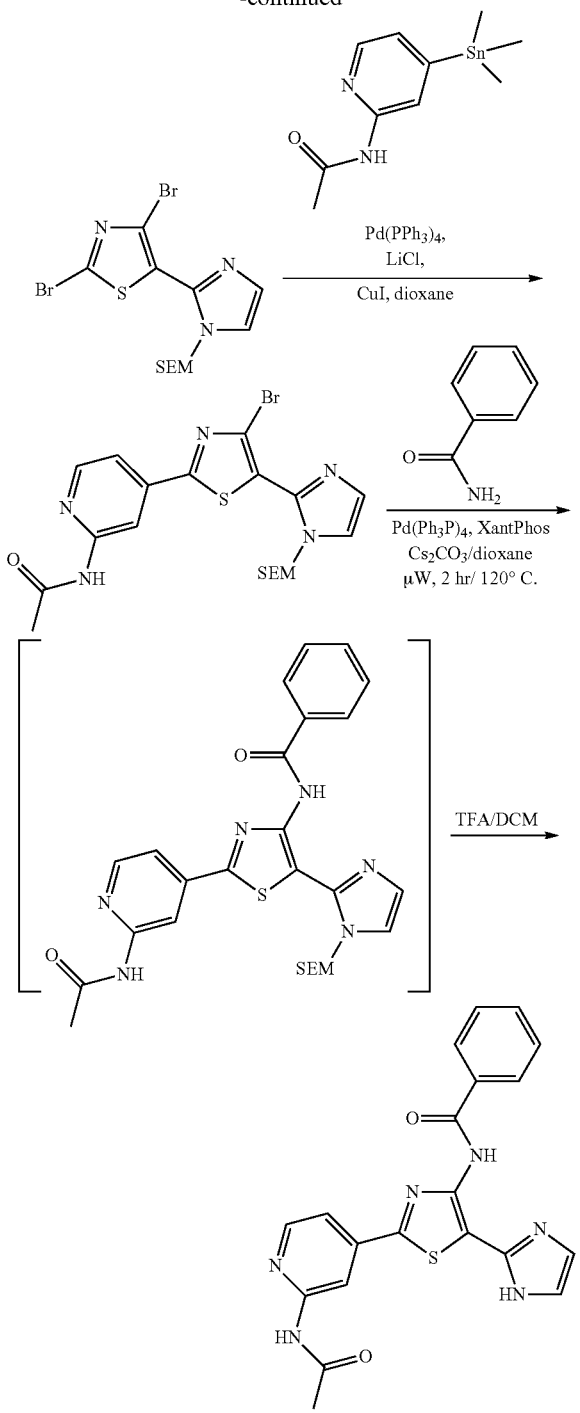

Step 1: 2,4-Dibromo-thiazole-5-carbaldehyde 2,4-Thiazolidinedione (3.50 g, 0.0299 mol) and phosphorus oxybromide (42.76 g, 0.1491 mol) were placed into a two-neck round bottomed flask and the solid mixture was well mixed. The flask was evacuated and filled with argon. N,N-dimethylformamide (2.54 mL, 0.0329 mol) was added via syringe with hand shaking of the flask at the same time. The mixture was stirred at rt for 2 hours and then heated slowly to 105° C., until the evolution of hydrogen bromide had ceased, (approximately 4 h). The reaction was cooled to rt then the mixture was transferred to a beaker containing 200 g of ice. The aqueous mixture was stirred with DCM then filtered. The DCM phase was separated and the aqueous phase was extracted with DCM twice. The DCM layers were combined and washed with saturated sodium bicarbonate solution, then brine, dried over anhydrous sodium sulfate, filtered and concentrated. The mixture was dry loaded on silica gel and purified by chromatography to afford 2,4-dibromo-thiazole-5-carbaldehyde (2.50 g, 30.9%). LCMS (FA) ES+ 272, 274.

Step 2: 2,4-Dibromo-5-(1H-imidazol-2-yl)thiazole 2,4-Dibromo-thiazole-5-carbaldehyde (14.8 g, 54.6 mmol), hexahydro-[1,4]dioxino[2,3-b][1,4]dioxine-2,3,6,7-tetraol (22.96 g, 109.2 mmol), and ammonium acetate (25.26 g, 327.8 mmol) were added to a round bottomed flask followed by methanol (450 mL, 11000 mmol). The mixture was stirred and acetic acid (31.06 mL, 546.3 mmol) was added. The reaction was stirred overnight then the reaction mixture was concentrated under vacuum to provide a thick liquid mixture. Toluene (100 mL) was then added and reevaporated and this process was repeated several times to give a dark brown solid. Methanol was added and the mixture was loaded on silica gel. Purification by column chromatography on silica gel afforded 2,4-dibromo-5-(1H-imidazol-2-yl)thiazole (9.12 g, 54%). LCMS (AA) ES+ 310, 312, 308.

Step 3: 2,4-Dibromo-5-(1-((2-(trimethylsilyl)ethoxy)methyl)-1H-imidazol-2-yl)thiazole To a mixture of sodium hydride (2.89 g, 72.2 mmol) in tetrahydrofuran (431 mL, 5310 mmol) was added 2,4-dibromo-5-(1H-imidazol-2-yl)thiazole (18.81 g, 60.88 mmol) in tetrahydrofuran (60 mL, 700 mmol) at 0° C. The mixture was stirred for 30 min before [β-(Trimethylsilyl)ethoxy]methyl chloride (11.85 mL, 66.96 mmol) in tetrahydrofuran (24 mL, 3.0E2 mmol) was added slowly at 0° C. The reaction was quenched with MeOH. The solvent was evaporated and the residue was purified by column chromatography on silica gel to afford 2,4-dibromo-5-(1-((2-(trimethylsilyl)ethoxy)methyl)-1H-imidazol-2-yl)thiazole (13.6 g, 81.7%). LCMS (AA) ES+ 440, 442.

Step 4: N-(4-(4-bromo-5-(1-42-(trimethylsilyl)ethoxy)methyl)-1H-imidazol-2-yl)thiazol-2-yl)pyridin-2-yl)acetamide A mixture of 2,4-dibromo-5-(1-((2-(trimethylsilyl)ethoxy)methyl)-1H-imidazol-2-yl)thiazole (13.62 g, 31.01 mmol), N-[4-(trimethylstannyl)pyridin-2-yl]acetamide (11.1 g, 37.2 mmol), tetrakis(triphenylphosphine)palladium(0) (1.792 g, 1.550 mmol), copper(I) iodide (1.772 g, 9.302 mmol) and lithium chloride (3.944 g, 93.02 mmol) in 1,4-dioxane (569 mL, 7290 mmol) was degassed and filled with argon three times. The mixture was sonicated for 20 min and then heated at 120° C. for 5 h. The reaction mixture was dry loaded onto a silica gel column and purified by chromatography to afford N-(4-(4-bromo-5-(1-((2-(trimethylsilyl)ethoxy)methyl)-1H-imidazol-2-yl)thiazol-2-yl)pyridin-2-yl)acetamide as an orange solid. LCMS (AA) ES+ 494, 496.

Step 5: N-(2-(2-acetamidopyridin-4-yl)-5-(1H-imidazol-2-yl)thiazol-4-yl)benzamide (Compound 29)

A mixture of N-(4-(4-bromo-5-(1-((2-(trimethylsilyl)ethoxy)methyl)-1H-imidazol-2-yl)thiazol-2-yl)pyridin-2-yl)acetamide (80.9 mg, 0.164 mmol), benzamide (99.1 mg, 0.818 mmol), tris(dibenzylideneacetone)dipalladium(0) (21.3 mg, 0.0233 mmol), 4,5-bis(diphenylphosphino)-9,9-dimethylxanthene (39.9 mg, 0.0690 mmol) and cesium carbonate (303 mg, 0.930 mmol) in 1,4-dioxane (7.66 mL, 98.2 mmol) was evacuated then filled with argon and then irradiated in microwave at 130° C. for 3 h. The reaction mixture was filtered and the filtrate was purified by column chromatography to afford the desired intermediate. LCMS (AA) ES+ 535, 536. To the above intermediate were added methylene chloride (1.2 mL, 19 mmol) and trifluoroacetic acid (1.8 mL, 23 mmol). The mixture was stirred at rt for 2 h. The excess trifluoroacetic acid and solvent was evaporated and the residue was purified by HPLC to afford N-(2-(2-acetamidopyridin-4-yl)-5-(1H-imidazol-2-yl)thiazol-4-yl)benzamide (11.3 mg, 17.1%). LCMS (FA) ES+ 406, 407; $^1$H NMR (300 MHz, d$_4$-methanol) δ: 8.67 (d, J=0.45 Hz, 1H), 8.40 (d, J=5.23 Hz, 1H), 8.17-8.07 (m, 2H), 7.84-7.78 (m, 1H), 7.59 (dd, J=13.90, 7.27 Hz, 3H), 7.22 (s, 2H), 2.22 (s, 3H).

Example 27

Synthesis of 4-(2-naphthylmethyl)-2-pyridazin-4-yl-5-(4H-1,2,4-triazol-3-yl)thiophene-3-carbonitrile (Compound 88)

Step 1: Ethyl 3-amino-4,4-dicyano-3-butenoate

Ethyl 3-ethoxy-3-iminopropionate hydrochloride (166 g, 721 mmol.) was suspended in dry methylene chloride (400 mL, 6000 mmol). Malononitrile (46.7 g, 707 mmol) was added, followed by Triethylamine (1.00 mL, 721 mmol). The mixture was heated to reflux for 3 hours. The mixture was cooled to rt then quenched with 200 mL of water. The separated organic layer was washed with 2×200 mL of water. The combined aqueous layers were extracted with DCM (3×30 mL). The combined organic layers were washed with brine, dried over anhydrous Na$_2$SO$_4$, filtered, and concentrated under reduced pressure. The residue was further azeotroped with MTBE (2×200 mL) and ethyl acetate (70 mL). The residue was diluted with 70 mL of EtOAc. A precipitate appeared and the solid was collected by filtration and washed with ~20 mL of EtOAc until the pink-red color of the solid faded to give a first crop of product (32 g). The filtrate was concentrated in rotary evaporator and dried under high vacuum to a weight of ~110 g. More precipitate appeared after the concentrated filtrate sat for 1 hour. Approximately 50

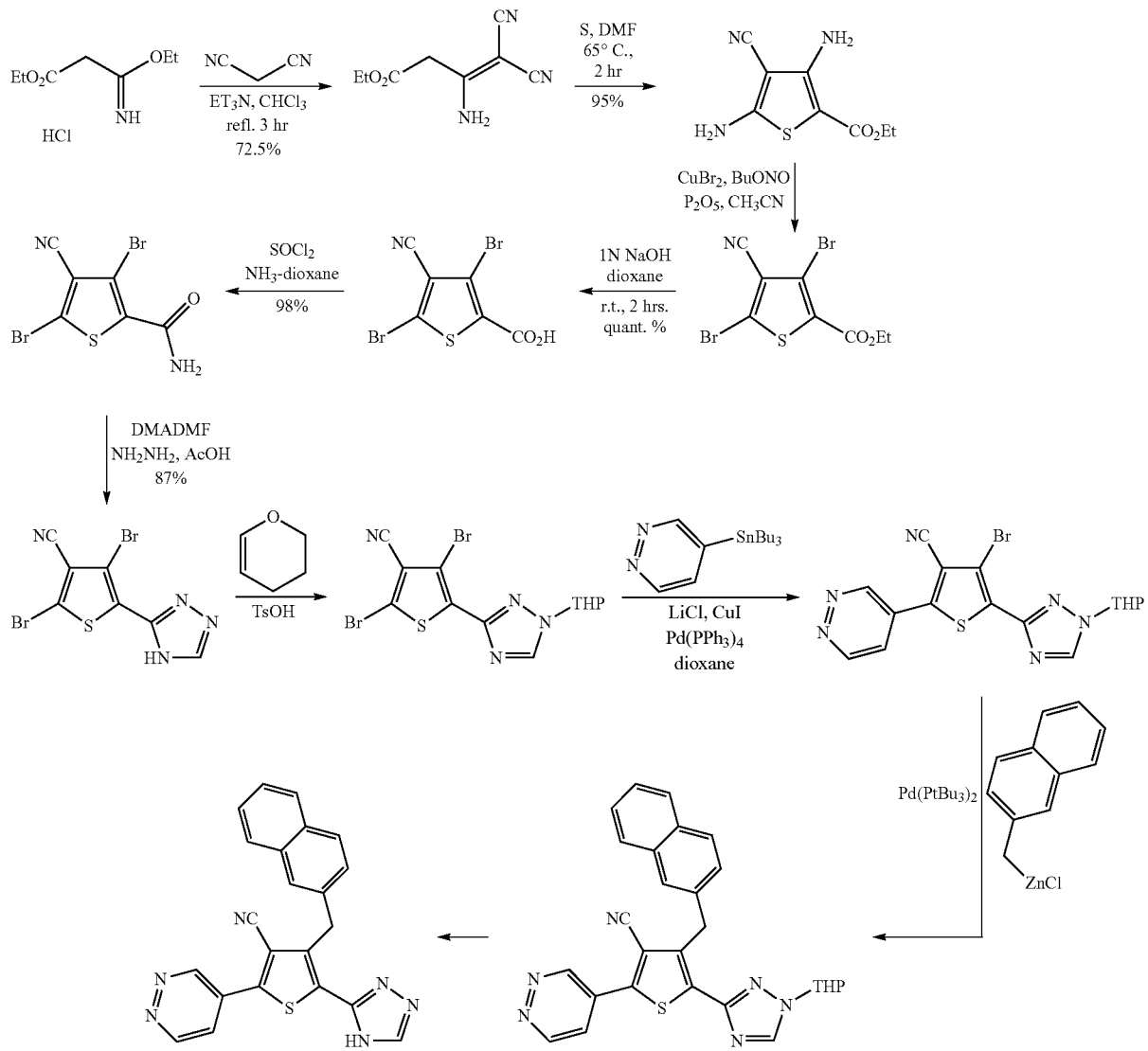

mL of Et$_2$O was added and the mixture was allowed to sit overnight. The resulting precipitate was collected by filtration and washed with Et$_2$O to afford a second crop of solid product (20.59 g). The filtrate was concentrated in a rotary evaporator to give an oily residue. Chromatography on a silica column using EtOAc/hexane (short gradient from 0/100 to 50/50 then stayed on 50/50 for 100 min, with 120 mL/min flow rate) afforded a third crop of pure product (39.3 g, yield for all crops was 72.5%). LCMS: (FA) ES− 178. $^1$H NMR (400 MHz, CDCl$_3$) δ: 7.57 (s, br, 1H), 6.33 (s, br, 1H), 4.24-4.30 (q, 2H), 3.63 (s, 2H), 1.31-1.35 (t, 3H).

Step 2: Ethyl
3,5-diamino-4-cyanothiophene-2-carboxylate

The mixture of ethyl 3-amino-4,4-dicyano-3-butenoate (91.9 g, 513 mmol) and sulfur (16.4 g, 513 mmol) in dry N,N-dimethylformamide (200 mL, 3000 mmol) was cooled in a water bath. Diethylamine (106 mL, 1020 mmol) was slowly added during which time the internal reaction temperature increased to 43° C. The dark-brown solution was then cooled in ice bath to rt (22° C.) then the ice bath was removed. The mixture was stirred at rt for 3 hours. The mixture was poured into ice water (~1.4 L) and the resulting suspension was allowed to sit overnight. The solid was collected by filtration and washed with 200 mL of water thoroughly to give a wet solid. The solid was stirred with 1.5 L of EtOAc at rt overnight, then filtered. The filtrate (EtOAc-water bilayer) was separated. The solid cake was dissolved in 1.2 L of EtOAc. The combined EtOAc solutions were washed with brine, dried over anhydrous Na$_2$SO$_4$, filtered, rotavaped and dried under high-vacuum overnight to give a dry powder product (102.6 g, yield 94.7%). LCMS: (FA) ES+ 212, ES− 210. $^1$H NMR (400 MHz, CDCl$_3$ and d4-methanol) δ: 4.14 (m, 2H), 1.21-1.25 (t, 3H).

Step 3: Ethyl
3,5-dibromo-4-cyanothiophene-2-carboxylate

Ethyl 3,5-diamino-4-cyanothiophene-2-carboxylate (25.0 g, 118 mmol) was dissolved in acetonitrile (500 mL, 10000 mmol). Copper(II) Bromide (105.7 g, 473.4 mmol) was added, followed by phosphorus pentoxide (6.72 g, 23.7 mmol). The mixture was stirred at room temperature for 30 min, then cooled to 0° C. Butyl nitrite (56.4 mL, 473.4 mmol) was slowly added. After the completion of the addition the mixture was heated to reflux for 1 h then cooled to room temperature. The reaction mixture was poured into 500 mL 4N HCl solution, then extracted with 500 mL DCM twice. The insoluble material was filtered off from the organic layer. The organic filtrate was dried over MgSO4, and filtered. The filtrate was concentrated and purified by column chromatograph in silica gel, using the eluent of 0-6% ethyl acetate in hexane. The fractions containing product were collected and concentrated to give a suspension. The solid was collected by filtration to afford a pure product (14.45 g, yield 36.0%). $^1$H NMR (400 MHz, CDCl$_3$) δ: 4.37-4.42 (q, 2H), 1.38-1.41 (t, 3H).

Step 4: 3,5-dibromo-4-cyanothiophene-2-carboxylic acid

Ethyl 3,5-dibromo-4-cyanothiophene-2-carboxylate (6.54 g, 0.0193 mol) was dissolved in a mixture of tetrahydrofuran (40.0 mL, 0.493 mol) and methanol (20.0 mL, 0.494 mol), then sodium hydroxide in water (1.0 M, 60.0 mL, 0.0600 mol) was added at 0° C. The resulting solution was warmed to rt and stirred for 20 min. The mixture was neutralized with hydrochloric acid in water (4.0 M, 20 mL, 0.080 mol) and extracted with 80 mL DCM twice. The combined organic layers were washed with 30 mL water, evaporated in vacuo to yield a white solid product (5.96 g, yield 99.4%). LCMS: (FA) ES−, 307, 309, 311.

Step 5:
3,5-Dibromo-4-cyanothiophene-2-carboxamide 3,5-Dibromo-4-cyanothiophene-2-carboxylic acid (5.90 g, 18.6 mmol) was added to a solution of thionyl chloride (27.1 mL, 371 mmol) in acetonitrile (40.0 mL, 766 mmol). The mixture was refluxed for 30 min then cooled to rt. The solvent was evaporated in vacuo to dryness to yield a lightly yellow solid. Methylene chloride (100 mL, 2000 mmol) was added to dissolve the solid, then the solution was cooled to 0° C. Under a nitrogen atmosphere, a solution of 0.500 M ammonia in 1,4-dioxane (111.5 mL, 55.7 mmol) was slowly added, and the mixture was brought to room temperature for 1 h. The mixture was evaporated in vacuo to give a solid residue. 100 mL of 1N HCl was added and the suspension was stirred for 1 h at room temperature. The solid product was collected by filtration and dried under high vacuum to give product (5.64 g, yield 98%). LCMS: (FA) ES−, 308, 310, 312.

Step 6: 2,4-Dibromo-5-(4H-1,2,4-triazol-3-yl) thiophene-3-carbonitrile 3,5-Dibromo-4-cyanothiophene-2-carboxamide (5.90 g, 19.0 mmol) was suspended in dry Toluene (250 mL, 2300 mmol). 1,1-Dimethoxy-N,N-dimethylmethanamine (10.1 mL, 76.1 mmol) was added and the mixture was heated to 90° C. for 1 hour. The mixture was cooled to rt then rotavaped to dryness to give a crude intermediate. The intermediate was suspended in acetic acid (150 mL, 2600 mmol). Hydrazine hydrate (5.78 mL, 76.1 mmol) was added dropwise and the temperature was raised to 55° C. The mixture was stirred at the same temperature for 2 hours. The suspension was then evaporated to remove most of acetic acid. The resulting solid was collected by filtration and dried under vacuum to give a product (5.54 g, yield 87.2%). LCMS: (FA) ES−, 331, 333, 335. $^1$H NMR (300 MHz, d6-dmso) δ: 14.2 (s, br, 1H), 8.65 (s, 1H).

Step 7: 2,4-Dibromo-5-[1-(tetrahydro-2H-pyran-2-yl)-1H-1,2,4-triazol-3-yl]thiophene-3-carbonitrile 2,4-Dibromo-5-(4H-1,2,4-triazol-3-yl)thiophene-3-carbonitrile (0.80 g, 2.4 mmol) was placed in a 500 mL round bottom flask and tetrahydrofuran (50 mL, 600 mmol) was added. To the resulting solution were added dihydropyran (1.31 mL, 14.4 mmol) and p-toluenesulfonic acid monohydrate (0.683 g, 3.59 mmol). The mixture was stirred for 3 h at rt. The solution was then poured into 20 mL water and extracted with 40 mL ethyl acetate twice. The combined organic layers were evaporated in vacuo. The residue was purified by column chromatography using 0-35% EtOAc in hexane to afford a solid product (0.842 g, yield 84%). LCMS: (AA) ES+, 417, 419, 421. $^1$H NMR (300 MHz, CDCl$_3$) δ: 8.38 (s, 1H), 5.55-5.60 (m, 1H), 4.06-4.10 (m, 1H), 3.68-3.78 (m, 1H), 2.15-2.28 (m, 1H), 2.01-2.13 (m, 2H), 1.66-1.80 (m, 3H).

Step 8: 4-Bromo-2-pyridazin-4-yl-5-[1-(tetrahydro-2H-pyran-2-yl)-1H-1,2,4-triazol-3-yl]thiophene-3-carbonitrile A mixture of 2,4-dibromo-5-[1-(tetrahydro-2H-pyran-2-yl)-1H-1,2,4-triazol-3-yl]thiophene-3-carbonitrile (0.248 g, 0.594 mmol), 4-(tributylstannyl)pyridazine (2.30 mg, 0.624 mmol), copper(I) iodide (34.0 mg, 0.178 mmol), lithium chloride (75.6 mg, 1.78 mmol) and tetrakis(triphenylphosphine)palladium(0) (34.3 mg, 0.0297 mmol) in dry 1,4-dioxane (5.0 mL, 64 mmol) was sonicated under a nitrogen atmosphere for 2 min then heated in a capped vial to 130° C. in microwave machine for 20 mins. The suspension was cooled to rt, diluted with 20% MeOH/DCM (~100 mL), treated with 12 g of silica gel then rotavaped and dried under high vacuum. The coated silica gel was chromatographed on a silica column eluting with MeOH/DCM (0/100 to 5/95) to afford a solid product (0.143 g, yield 57.7%). LCMS: (AA) ES+, 417, 419. $^1$H NMR (300 MHz, CDCl$_3$) δ: 9.55 (s, 1H), 9.37-9.39 (m, 1H), 8.40 (s, 1H), 7.69-8.00 (m, 1H), 5.55-5.60 (m, 1H), 4.08-4.13 (m, 1H), 3.73-3.81 (m, 1H), 2.18-2.30 (m, 1H), 2.03-2.16 (m, 2H), 1.68-1.82 (m, 3H).

Step 9: 4-(2-Naphthylmethyl)-2-pyridazin-4-yl-5-[1-(tetrahydro-2H-pyran-2-yl)-1H-1,2,4-triazol-3-yl]thiophene-3-carbonitrile Bis(tri-t-butylphosphine)palladium(0) (4.92 mg, 0.00963 mmol), 4-bromo-2-pyridazin-4-yl-5-[1-(tetrahydro-2H-pyran-2-yl)-1H-1,2,4-triazol-3-yl]thiophene-3-carbonitrile (0.0402 g, 0.0963 mmol), 2-naphthylmethylzinc bromide in tetrahydrofuran (0.50M, 0.578 mL, 0.289 mmol) and tetrahydrofuran (4.0 mL, 49 mmol) were added to a microwave tube. The tube was sealed under a nitrogen atmosphere and heated at 70° C. for 2 h then cooled to rt. The mixture was concentrated in vacuo and the residue was purified by chromatography on a silica gel column eluting with 0-100% EtOAc in hexane to afford a solid product (0.0332 g, yield 72%). LCMS: (AA) ES+, 479. $^1$H NMR (300 MHz, d4-methanol) δ: 9.63 (s, 1H), 9.28-9.35 (m, 1H), 8.68 (s, 1H), 8.13-8.15 (m, 1H), 7.69-8.00 (m, 4H), 7.37-7.48 (m, 3H), 5.62-5.66 (m, 1H), 3.94-4.08 (m, 1H), 3.69-3.80 (m, 1H), 3.30 (s, 2H), 2.07-2.22 (m, 1H), 1.95-2.07 (m, 2H), 1.61-1.79 (m, 3H).

Step 10: 4-(2-naphthylmethyl)-2-pyridazin-4-yl-5-(4H-1,2,4-triazol-3-yl)thiophene-3-carbonitrile (Compound 88)

4-(2-Naphthylmethyl)-2-pyridazin-4-yl-5-[1-(tetrahydro-2H-pyran-2-yl)-1H-1,2,4-triazol-3-yl]thiophene-3-carbonitrile (0.03178 g, 0.06641 mmol) was dissolved in methanol (3.00 mL, 74.0 mmol). HCl in water (12 M, 3.00 mL, 36.0 mmol) was added. The solution was heated at 50° C. for 60 min then cooled to rt. The mixture was evaporated in vacuo to remove the most of methanol. To the residue was added 30 mL saturated sodium bicarbonate solution, extracted with 40 mL ethyl acetate twice. The combined EtOAc layers were washed with 20 mL water then concentrated in vacuo. The resulting crystalline solid was collected by filtration to afford a pure product (0.0158 g, yield 60.3%). LCMS: (AA) ES+ 395. NMR (300 MHz, d4-methanol) δ: 9.60 (s, 1H), 9.27-9.29 (m, 1H), 8.47 (s, 1H), 8.09-8.11 (m, 1H), 7.69-7.77 (m, 4H), 7.37-7.47 (m, 3H), 3.30 (s, 2H).

The compound in the following table was prepared from the appropriate starting materials in a method analogous to that of Example 27:

| | |
|---|---|
| 89 | LCMS: (FA) ES+ 379, 381. |

Example 28

Synthesis of 4-(4-chlorobenzyl)-2-morpholinothiazole-5-carboxylic acid (Compound 91)

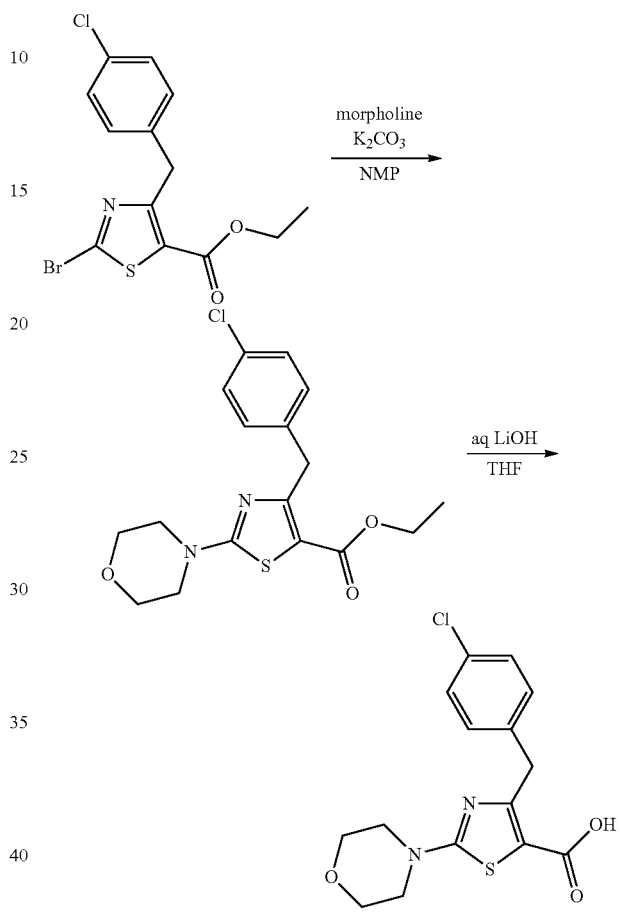

Step 1, Preparation of ethyl 4-(4-chlorobenzyl)-2-morpholinothiazole-5-carboxylate To a solution of ethyl 2-bromo-4-(4-chlorobenzyl)thiazole-5-carboxylate (4.19 g, 11.6 mmol, prepared as described in Example 10) in N-methylpyrrolidinone (12.2 mL) was added potassium carbonate (3.21 g, 23.2 mmol) and morpholine (1.52 mL, 17.4 mmol) and the resulting mixture was heated to 130 degrees for 90 minutes. The reaction was cooled and the volatiles were removed by concentration at 65 degrees under oil pump vacuum. The residue was taken up in DCM (100 mL) and water (50 mL). The layers were separated and the aqueous layer was extracted with DCM (50 mL). The combined DCM layers were dried over MgSO$_4$, filtered, and concentrated to give the crude product, which was purified by silica gel chromatography (ethyl acetate/hexane=0/100→35/65) to give 3.44 g of the title compound as a white solid. (80% yield). LC/MS (FA) ES+ 367. $^1$H NMR (300 MHz, CDCl$_3$) δ: 7.32-7.27 (m, 2H), 7.24-7.20 (m, 2H), 4.28 (s, 2H), 4.27 (q, 2H, J=7.2 Hz), 3.80-3.76 (m, 4H), 3.53-3.48 (m, 4H), 1.32 (t, 3H, J=7.2 Hz).

Step 2, Preparation of 4-(4-chlorobenzyl)-2-morpholinothiazole-5-carboxylic acid. (Compound 91)

To a solution of ethyl 4-(4-chlorobenzyl)-2-morpholinothiazole-5-carboxylate (3.44 g, 9.38 mmol) in THF (53 mL) was added water (26 mL) and 1 N LiOH (28.2 mL, 28.2 mmol) and the resulting mixture was heated to 40 degrees overnight. The reaction was cooled, acidified with 1 N HCl, and extracted with ethyl acetate (3×50 mL). The combined ethyl acetate layers were dried over $MgSO_4$, filtered, and concentrated to give the crude product, which was purified by silica gel chromatography (methanol/DCM=0/100→20/80). Recrystallization from ethyl acetate/hexanes gave 1.3 g of the title compound as a white solid. (41% yield). LC/MS (FA) ES+ 339. $^1$H NMR (400 MHz, DMSO-$d_6$) δ: 12.74 (s, 1H), 7.33-7.30 (m, 2H), 7.26-7.23 (m, 2H), 4.21 (s, 2H), 3.67-3.64 (m, 4H), 3.42-3.40 (m, 4H).

Example 29

Synthesis of 2-(4-(4-chlorobenzyl)-2-(pyridin-4-yl)thiazol-5-yl)pyrimidin-4(3H)-one (Compound 92)

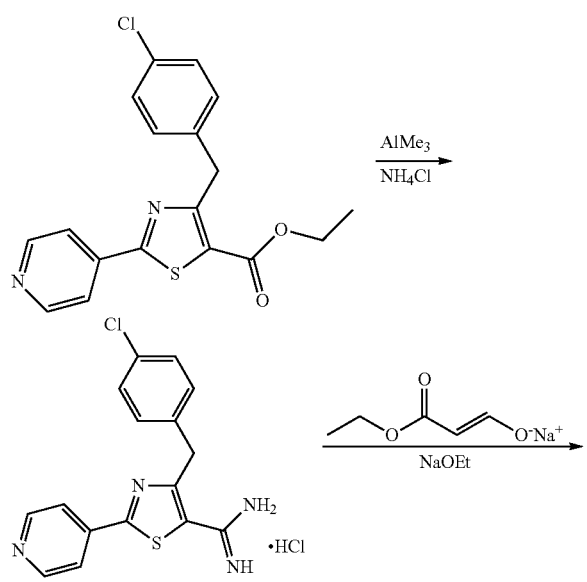

Step 1, Preparation of 4-(4-chlorobenzyl)-2-(pyridin-4-yl)thiazole-5-carboximidamide hydrochloride To a suspension of ammonium chloride (2.25 g, 42.1 mmol) in toluene (21.0 mL) in an ice bath was added 2.0 M trimethylaluminum in toluene (21.1 mL, 42.2 mmol) dropwise (gas evolution). The mixture was then stirred at room temperature for 30 minutes, during which time the solids dissolved. Ethyl 4-(4-chlorobenzyl)-2-morpholinothiazole-5-carboxylate (4.11 g, 11.4 mmol) was added in one portion and the resulting solution was heated slowly to 110° C. over 1 hour, then kept at 110° C. for 2.5 hours. The reaction was allowed to cool to room temperature overnight. The reaction was poured into a slurry of silica gel (10 grams) in chloroform (100 mL) and stirred 10 minutes. Methanol (20 mL) was added (bubbling occurs), and the mixture was filtered through a short silica gel bed in a sintered glass funnel, eluting with 1:1 methanol/chloroform to remove product. The filtrate was concentrated to give the crude product, which was purified by silica gel chromatography (methanol/chloroform=50/50) to give 1.9 g of the title compound as a light yellow solid, which is the HCl salt. (45% yield). (1.6 grams (45%) of 4-(4-chlorobenzyl)-2-(pyridin-4-yl)thiazole-5-carbonitrile was also recovered) LC/MS (FA) ES+ 329. $^1$H NMR (400 MHz, DMSO-$d_6$) δ: 9.73, (bs, 4H), 8.76-8.74 (m, 2H), 7.90-7.88 (m, 2H), 7.39-7.35 (m, 2H), 7.31-7.27 (m, 2H), 4.30 (s, 2H).

Step 2, Preparation of 2-(4-(4-chlorobenzyl)-2-(pyridin-4-yl)thiazol-5-yl)pyrimidin-4(3H)-one (Compound 92)

To a solution of 4-(4-chlorobenzyl)-2-(pyridin-4-yl)thiazole-5-carboximidamide hydrochloride (188 mg, 0.515 mmol) in ethanol (8.0 mL) was added 21% sodium ethoxide in ethanol (0.192 mL, 0.515 mmol) and sodium 2-ethoxycarbonyl ethenolate (284 mg, 2.06 mmol) (prepared as in J. Med. Chem., (2001), 44(17), 2695-2700), and the reaction was heated to reflux overnight. The reaction was cooled and concentrated. The residue was slurried DCM (15 mL) and water (15 mL) for 20 minutes. The solids were filtered, dried and purified by silica gel chromatography (methanol/DCM=0/100→15/85) to give the product. HPLC gave 23 mg of the title compound as a yellow solid. (12% yield). LC/MS (FA) ES+ 381. $^1$H NMR (300 MHz, DMSO-$d_6$) δ: 8.72-8.60 (m, 2H), 8.41 (d, 1H, J=5.7 Hz), 7.88-7.85 (m, 2H), 7.40-7.36 (m, 2H), 7.32-7.28 (m, 2H), 6.58 (d, 1H, J=5.7 Hz), 4.80 (s, 2H).

Example 30

Synthesis of N-{4-[4-{(4-chlorophenyl)[3-(dimethylamino)azetidin-1-yl]methyl}-5-(4H-1,2,4-triazol-3-yl)-2-thienyl]pyridin-2-yl}acetamide (Compound 181)

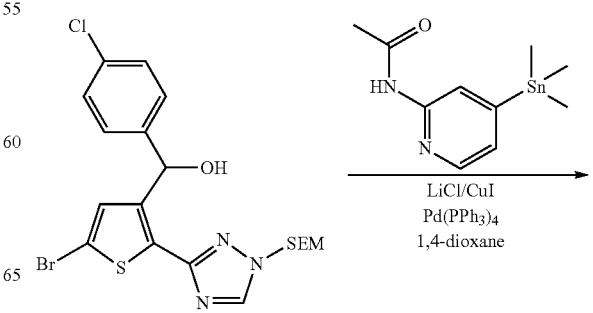

Step 1: Preparation of N-{4-[4-[(4-chlorophenyl)(hydroxy)methyl]-5-(1-{[2-(trimethylsilyl)ethoxy]methyl}-1H-1,2,4-triazol-3-yl)-2-thienyl]pyridin-2-yl}acetamid A mixture of [5-bromo-2-(1-{[2-(trimethylsilyl)ethoxy]methyl}-1H-1,2,4-triazol-3-yl)-3-thienyl](4-chlorophenyl)methanol (3.07 g, 5.52 mmol)) (synthesized in an analogous way as described in Example 2), N-[4-(trimethylstannyl)pyridin-2-yl]acetamide (1.81 g, 6.07 mmol), tetrakis(triphenylphosphine)palladium(0) (319 mg, 0.28 mmol), copper(I) iodide (315 mg, 1.65 mmol) and lithium chloride (702 mg, 16.5 mmol) in 1,4-dioxane (25.0 mL) was stirred at 100° C. for 2 hours under an atmosphere of nitrogen. The reaction was cooled to room temperature and concentrated with Celite. The crude mixture was purified by column chromatography ($SiO_2$, eluent with methanol in dichloromethane, 0-5% gradient) to afford a yellow solid (2.48 g, 80%). LCMS: (AA) ES+ 556, 558; $^1$H NMR (400 MHz, $CDCl_3$) δ: 8.48 (br s, 1H), 8.43 (br s, 1H), 8.25 (s, 1H), 8.19 (d, J=5.6 Hz, 1H), 7.41 (d, J=8.4 Hz, 2H), 7.33-7.24 (m, 2H), 7.19 (s, 1H), 7.16 (dd, J=1.2, 5.6 Hz, 1H), 6.22 (s, 1H), 6.05 (br s, 1H), 5.51 (s, 2H), 3.66 (t, J=8.4 Hz, 2H), 2.22 (s, 3H), 0.94 (t, J=8.4 Hz, 2H), −0.01 (s, 9H).

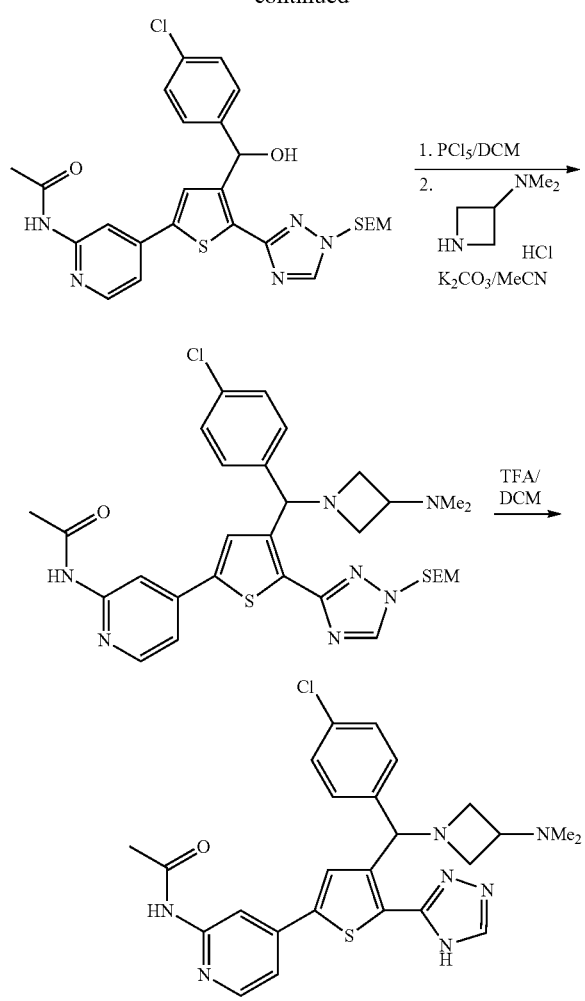

Step 2: Preparation of N-{4-[4-{(4-chlorophenyl)[3-(dimethylamino)azetidin-1-yl]methyl}-5-(1-{[2-(trimethylsilyl)ethoxy]methyl}-1H-1,2,4-triazol-3-yl)-2-thienyl]pyridin-2-yl}acetamide To a solution of N-{4-[4-[(4-chlorophenyl)(hydroxy)methyl]-5-(1-{[2-(trimethylsilyl)ethoxy]methyl}-1H-1,2,4-triazol-3-yl)-2-thienyl]pyridin-2-yl}acetamide (100 mg, 0.18 mmol) in dichloromethane (2.00 mL) was added phosphorus pentachloride (112 mg, 0.54 mmol) at room temperature. The mixture was stirred for 15 min and then water (10 mL) was added. The mixture was stirred vigorously for 10 min. The layers were separated and the aqueous layer was extracted with dichloromethane twice. The combined organic layers were washed with saturated $NaHCO_3$ solution, dried over $Na_2SO_4$, filtered, and concentrated in vacuo to give an intermediate as a yellow solid. This intermediate was dissolved in acetonitrile (1.66 mL) and potassium carbonate (124 mg, 0.90 mmol) and 1-azetidin-3-yl-dimethylamine hydrochloride (130 mg, 0.54 mmol) were added. The mixture was stirred at 80° C. for 5 hours. After cooling to room temperature, the mixture was diluted with dichloromethane and filtered through a glass filter. The filtrate was concentrated in vacuo and the residue was purified by column chromatography ($SiO_2$, elution with methanol in dichloromethane, 0-10% gradient) to afford a solid product (103 mg, 52.3%). LCMS: (AA) ES+ 638, 640; $^1$H NMR (400 MHz, $CDCl_3$) δ: 8.48 (s, 1H), 8.26 (s, 1H), 8.22 (d, J=5.2 Hz, 1H), 8.10 (s, 1H), 7.80 (s, 1H), 7.62 (d, J=8.4 Hz, 2H), 7.25-7.21 (m 3H), 5.61 (s, 1H), 5.56 (s, 2H), 3.72 (dd, J=8.8, 7.6 Hz, 2H), 3.43-3.32 (m, 2H), 2.93-2.80 (m, 3H), 2.24 (s, 3H), 2.06 (s, 6H), 0.99 (dd, J=8.8, 7.6 Hz, 2H), 0.02 (s, 9H).

Step 3: Preparation of N-{4-[4-{(4-chlorophenyl)[3-(dimethylamino)azetidin-1-yl]methyl}-5-(4H-1,2,4-triazol-3-yl)-2-thienyl]pyridin-2-yl}acetamide (Compound 181)

N-{4-[4-{(4-chlorophenyl)[3-(dimethylamino)azetidin-1-yl]methyl}-5-(1-{[2-(trimethylsilyl)ethoxy]methyl}-1H-1,2,4-triazol-3-yl)-2-thienyl]pyridin-2-yl}acetamide (60 mg, 0.094 mmol) was dissolved in dichloromethane (1.19 mL) and trifluoroacetic acid (0.30 mL, 3.85 mmol) was added. The mixture was stirred at room temperature overnight. The mixture was concentrated in vacuo and distributed between EtOAc and saturated $NaHCO_3$ solution. The aqueous layer was extracted with EtOAc twice. The combined organic layers were dried over $Na_2SO_4$, filtered, and concentrated. The residue was purified by column chromatography ($SiO_2$, elution with methanol in dichloromethane, 0-20% gradient) to afford the title compound as a white solid (34.2 mg, 71.6%). LCMS: (AA) ES+ 508, 510; 1H NMR (400 MHz, $d_4$-methanol): 8.51 (s, 1H), 8.39 (s, 1H), 8.24 (br s, 1H), 7.78 (s, 1H), 7.59 (d, J=8.4 Hz, 2H), 7.32 (br s, 1H), 7.26 (d, J=8.4 Hz, 2H), 5.71 (s, 1H), 3.45-3.36 (m, 2H), 3.00-2.83 (m, 3H), 2.19 (s, 3H), 2.06 (s, 6H).

The compounds in the following table were prepared from the appropriate starting materials in a method analogous to that of Example 30:

| | |
|---|---|
| 129 | LCMS: (AA) ES+ 494, 496. |
| 144 | LCMS: (AA) ES+ 508, 510. |
| 157 | LCMS: (AA) ES+ 576, 578. |
| 160 | LCMS: (AA) ES+ 508, 510. |
| 170 | LCMS: (AA) ES+ 494, 496. |
| 172 | LCMS: (AA) ES+ 479. |

-continued

| 189 | LCMS: (AA) ES+ 450, 452. |
| 211 | LCMS: (AA) ES+ 451, 453. |
| 218 | LCMS: (AA) ES+ 519, 521. |
| 222 | LCMS: (AA) ES+ 522, 524. |
| 223 | LCMS: (AA) ES+ 509, 511. |
| 226 | LCMS: (AA) ES+ 469, 471. |
| 227 | LCMS: (AA) ES+ 463, 465. |
| 230 | LCMS: (AA) ES+ 479, 481. |
| 244 | LCMS: (FA) ES+ 467, 469. |
| 245 | LCMS: (AA) ES+ 536, 538. |
| 250 | LCMS: (AA) ES+ 408, 410. |
| 269 | LCMS: (AA) ES+ 509, 511. |
| 274 | LCMS: (AA) ES+ 494, 496. |
| 277 | LCMS: (AA) ES+ 494, 496. |

Example 31

Synthesis of N-(4-{4-[(4-chlorophenyl)(hydroxy)(1-methylpiperidin-4-yl)methyl]-5-(4H-1,2,4-triazol-3-yl)-2-thienyl}pyridin-2-yl)acetamide (Compound 237)

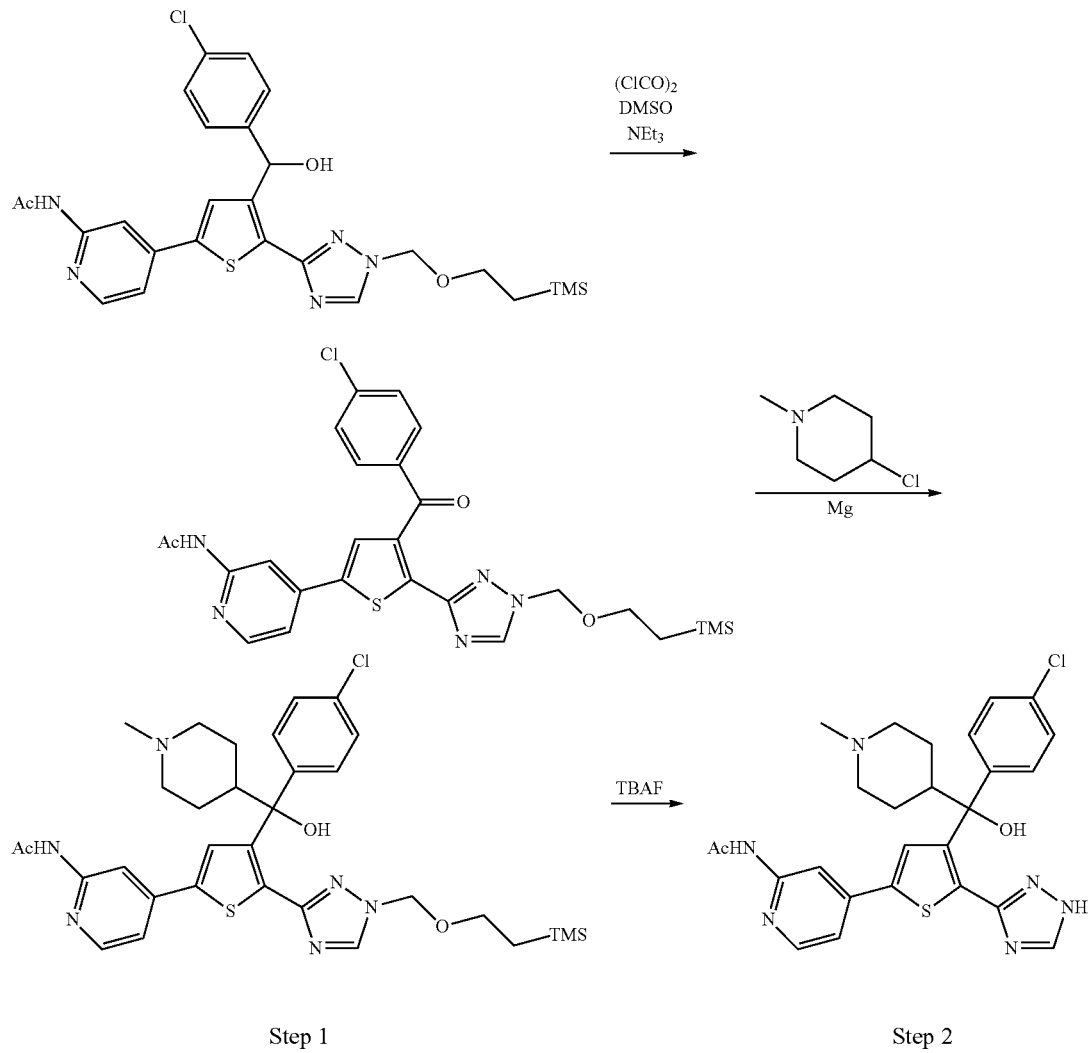

0.918 mmol) in methylene chloride (1.00 mL) dropwise. The reaction was stirred for 10 min under an atmosphere of Nitrogen. To this mixture was added a solution of N-{4-[4-[(4-chlorophenyl)(hydroxy)methyl]-5-(1-{[2-(trimethylsilyl)ethoxy]methyl}-1H-1,2,4-triazol-3-yl)-2-thienyl]pyridin-2-yl}acetamide (319 mg, 0.574 mmol) in methylene chloride (1.50 mL) dropwise. In 1 hr, triethylamine (0.400 mL, 2.87 mmol) was added dropwise to the reaction and the resulting mixture was warmed to rt. In 1 hr, the solution was diluted with $CH_2Cl_2$ and washed with water. The aqueous layer was extracted with $CH_2Cl_2$(×2). The combined org layer was washed with $NaHCO_3$(aq) saturated solution, dried, and concentrated to provide N-{4-[4-(4-chlorobenzoyl)-5-(1-{[2-(trimethylsilyl)ethoxy]methyl}-1H-1,2,4-triazol-3-yl)-2-thienyl]pyridin-2-yl}acetamide as a yellow solid (325 mg, quantitative). LCMS: (AA) 554, 556; $^1$H NMR (400 MHz, $CDCl_3$) δ 8.56-8.47 (s, 1H), 8.32-8.24 (m, 1H), 8.11-8.03 (s, 1H), 8.03-7.92 (s, 1H), 7.87-7.77 (m, 2H), 7.63-7.57 (s, 1H), 7.42-7.32 (m, 3H), 5.37-5.32 (s, 2H), 3.53-3.40 (t, J=8.1 Hz, 2H), 2.27-2.19 (s, 3H), 0.94-0.80 (t, J=8.1 Hz, 2H), 0.02-1-0.04 (s, 9H).

A solution of oxalyl chloride (63.1 uL, 0.746 mmol) in methylene chloride (1.50 mL, 23.4 mmol) was cooled to −78° C. To this solution was added dimethyl sulfoxide (65.1 uL, A 25 mL round bottom flask charged with magnesium turnings (23.0 mg, 0.947 mmol) was flame-dried. To the flask was added tetrahydrofuran (1.00 mL) and a drop of 1,2-dibromoethane. The mixture was heated to 45° C. for 10 min and cooled to rt. To the mixture was added 4-chloro-N-methylpiperidine (126 mg, 0.947 mmol). The reaction was stirred at 35° C. under an atmosphere of nitrogen for 12 hrs. The mixture turned cloudy, and magnesium turnings eventually disappeared, as the reaction progressed. To a solution of N-{4-[4-(4-chlorobenzoyl)-5-(1-{[2-(trimethylsilyl)ethoxy]methyl}-1H-1,2,4-triazol-3-yl)-2-thienyl]pyridin-2-yl}acetamide (113 mg, 0.204 mmol) in tetrahydrofuran (1.00 mL) was added the pre-prepared Grignard reagent solution dropwise at 0° C. In 3 hrs, the reaction was warmed to rt. In another 3 hrs, the reaction was quenched with water and distributed between NaHCO$_3$(aq) saturated solution and EtOAc. The aqueous layer was extracted with EtOAc (×2). The combined organic layer was dried and concentrated. Purification on a silica gel column (gradient elution, 1-20% MeOH) provided N-(4-{4-[(4-chlorophenyl)(hydroxy)(1-methylpiperidin-4-yl)methyl]-5-(1-{[2-(trimethylsilyl)ethoxy]methyl}-1H-1,2,4-triazol-3-yl)-2-thienyl}pyridin-2-yl)acetamide as a yellow solid (59.0 mg, 44.3% yield). LCMS: (AA) ES+ 653, 655; NMR (400 MHz, CDCl$_3$) δ 8.77-8.66 (s, 1H), 8.60-8.49 (s, 1H), 8.31-8.23 (d, J=5.3 Hz, 1H), 8.15-8.08 (m, 2H), 7.66-7.60 (s, 1H), 7.34-7.23 (m, 3H), 7.17-7.08 (d, J=8.7 Hz, 2H), 5.45-5.38 (s, 2H), 3.63-3.51 (m, 2H), 3.49-3.44 (s, 3H), 3.02-2.90 (d, J=10.8 Hz, 1H), 2.90-2.78 (d, J=11.2 Hz, 1H), 2.28-2.20 (m, 4H), 2.20-2.09 (m, 1H), 2.07-1.95 (m, 1H), 1.96-1.78 (m, 2H), 1.76-1.58 (qd, J=12.7, 3.8 Hz, 1H), 1.16-1.07 (d, J=12.5 Hz, 1H), 0.99-0.85 (m, 2H), 0.02-1-0.04 (s, 9H).

Step 3

A 5 mL microwave tube was charged with N-(4-{4-[(4-chlorophenyl)(hydroxy)(1-methylpiperidin-4-yl)methyl]-5-(1-{[2-(trimethylsilyl)ethoxy]methyl}-1H-1,2,4-triazol-3-yl)-2-thienyl}pyridin-2-yl)acetamide (10.0 mg, 0.0153 mmol) and tetrahydrofuran (0.500 mL, 6.16 mmol). To the solution was added 1.00 M of tetra-n-butylammonium fluoride in tetrahydrofuran (61.2 uL). The tube was sealed and heated to 80° C. in an oil bath for 4 hrs. The resulting mixture was cooled to rt and distributed between NaHCO$_3$(aq) saturated solution and EtOAc. The aqueous layer was extracted with EtOAc (×2). The combined org layer was dried and concentrated. Purification on HPLC (reverse phase, AA) provided N-(4-{4-[(4-chlorophenyl)(hydroxy)(1-methylpiperidin-4-yl)methyl]-5-(4H-1,2,4-triazol-3-yl)-2-thienyl}pyridin-2-yl)acetamide as a white solid. (2.0 mg, 25% yield) LCMS (AA) ES+ 523, 525; $^1$H NMR (400 MHz, MeOD) δ 8.50-8.42 (s, 1H), 8.41-8.36 (s, 1H), 8.36-8.29 (d, J=5.3 Hz, 1H), 7.92-7.83 (s, 1H), 7.50-7.43 (m, 1H), 7.43-7.34 (d, J=8.6 Hz, 2H), 7.25-7.14 (d, J=8.6 Hz, 2H), 2.91-2.76 (m, 1H), 2.65-2.55 (m, 4H), 2.26-2.15 (s, 3H), 2.11-2.01 (m, 2H), 1.88-1.72 (m, 2H), 1.70-1.57 (s, 1H), 1.47-1.35 (dd, J=15.0, 7.4 Hz, 1H), 1.31-1.20 (m, 2H).

The compounds in the following table were prepared from the appropriate starting materials in a method analogous to that of Example 31:

| | |
|---|---|
| 145 | LCMS: (AA) ES+ 511, 513 |
| 225 | LCMS: (AA) ES+ 493, 495. |
| 273 | LCMS: (AA) ES+ 508, 510. |

Example 32

Synthesis of 4-(4-(4-chlorobenzyl)-2-(pyridin-4-yl)thiazol-5-yl)pyrimidin-2-amine (Compound 150)

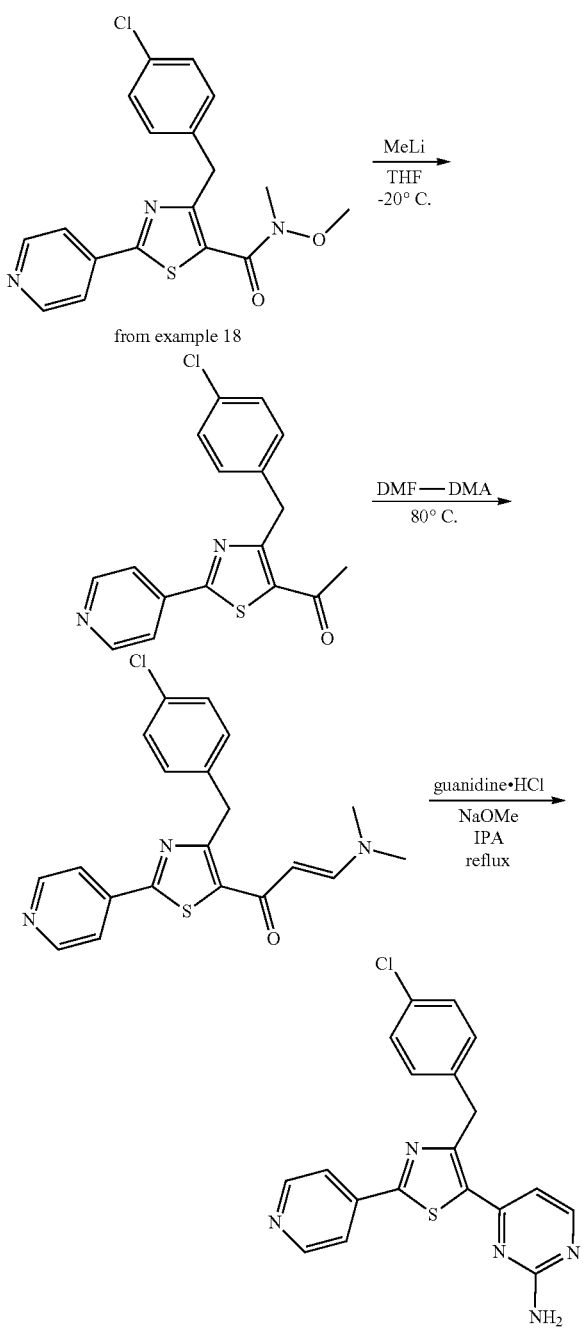

Step 1, Preparation of 1-(4-(4-chlorobenzyl)-2-(pyridin-4-yl)thiazol-5-yl)ethanone To a solution of 4-(4-chlorobenzyl)-N-methoxy-N-methyl-2-(pyridin-4-yl)thiazole-5-carboxamide (1.79 g, 4.79 mmol) in THF (97 mL) at −20° C. was added a 1.60 M solution of MeLi in ether (4.19 mL, 6.70 mmol). The reaction was stirred for 30 minutes at −20° C. An additional portion of a 1.60 M solution of MeLi in ether (0.838 mL, 1.34 mmol) was added and the reaction was stirred for 30 more minutes at −20° C. The reaction was quenched by adding saturated ammonium chloride (25 mL) followed by water (35 mL). The mixture was extracted with ethyl acetate (2×150 mL) and the combined organic layers were dried, filtered and concentrated in vacuo. The residue was purified by silica gel chromatography (EA/DCM=0/100-40/20) to give 1.27 g (81% yield) of the title compound as a light yellow solid. LC/MS (FA) ES+ 329, 331. $^1$H NMR (300 MHz, CDCl$_3$) δ: 8.75-8.73 (m, 2H), 7.83-7.81 (m, 2H), 7.34-7.31 (m, 2H). 7.26-7.23 (m, 2H), 4.53 (s, 2H), 2.59 (s, 3H).

Step 2, Preparation of (E)-1-(4-(4-chlorobenzyl)-2-(pyridin-4-yl)thiazol-5-yl)-3-(dimethylamino)prop-2-en-1-one A solution of 1-(4-(4-chlorobenzyl)-2-(pyridin-4-yl)thiazol-5-yl)ethanone (370 mg, 1.12 mmol) in 1,1-dimethoxy-N,N-dimethylmethanamine (10.0 mL, 75.3 mmol) was heated to 80 degrees for 6 hours. The reaction was cooled and concentrated in vacuo. The residue was purified by silica gel chromatography (EA/DCM=0/100→100/0) to give 389 mg (90% yield) of the title compound. as a yellow solid. LC/MS (FA) ES+ 384, 386. $^1$H NMR (300 MHz, CDCl$_3$) δ: 8.70-8.68 (m, 2H), 7.81-7.75 (m, 3H), 7.36-7.33 (m, 2H), 7.26-7.24 (m, 2H), 5.41 (d, 1H, J=12.3 Hz), 4.55 (s, 2H), 3.16 (s, 3H), 2.88 (s, 3H).

Step 3, Preparation of 4-(4-(4-chlorobenzyl)-2-(pyridin-4-yl)thiazol-5-yl)pyrimidin-2-amine To a solution of (E)-1-(4-(4-chlorobenzyl)-2-(pyridin-4-yl)thiazol-5-yl)-3-(dimethylamino)prop-2-en-1-one (93.0 mg, 0.242 mmol) in isopropyl alcohol (1.0 mL) was added guanidine hydrochloride (34.7 mg, 0.363 mmol) and sodium ethoxide (65.4 mg, 1.21 mmol) and the resulting mixture was heated to reflux for 3 days. The reaction was cooled and concentrated in vacuo. The residue was slurried in DCM (10 mL) and water (10 mL). The undissolved solids were filtered. This material was purified by preparative reverse phase chromatography to give 57 mg (62% yield) of the title compound as a white solid. LC/MS (FA) ES+ 380, 382. $^1$H NMR (300 MHz, DMSO-d$_6$) δ 8.73-8.71 (m, 2H), 8.31 (d, 1H, J=5.1 Hz), 7.88-7.86 (m, 2H), 7.36-7.30 (m, 4H), 6.86 (bs, 2H), 6.84 (d, 1H, J=5.1 Hz), 4.56 (s, 2H).

Example 33

Synthesis of Methyl {4-[4-[(4-chlorophenyl)(hydroxy)methyl]-3-cyano-5-(4H-1,2,4-triazol-3-yl)-2-thienyl]pyridin-2-yl}carbamate (Compound 195)

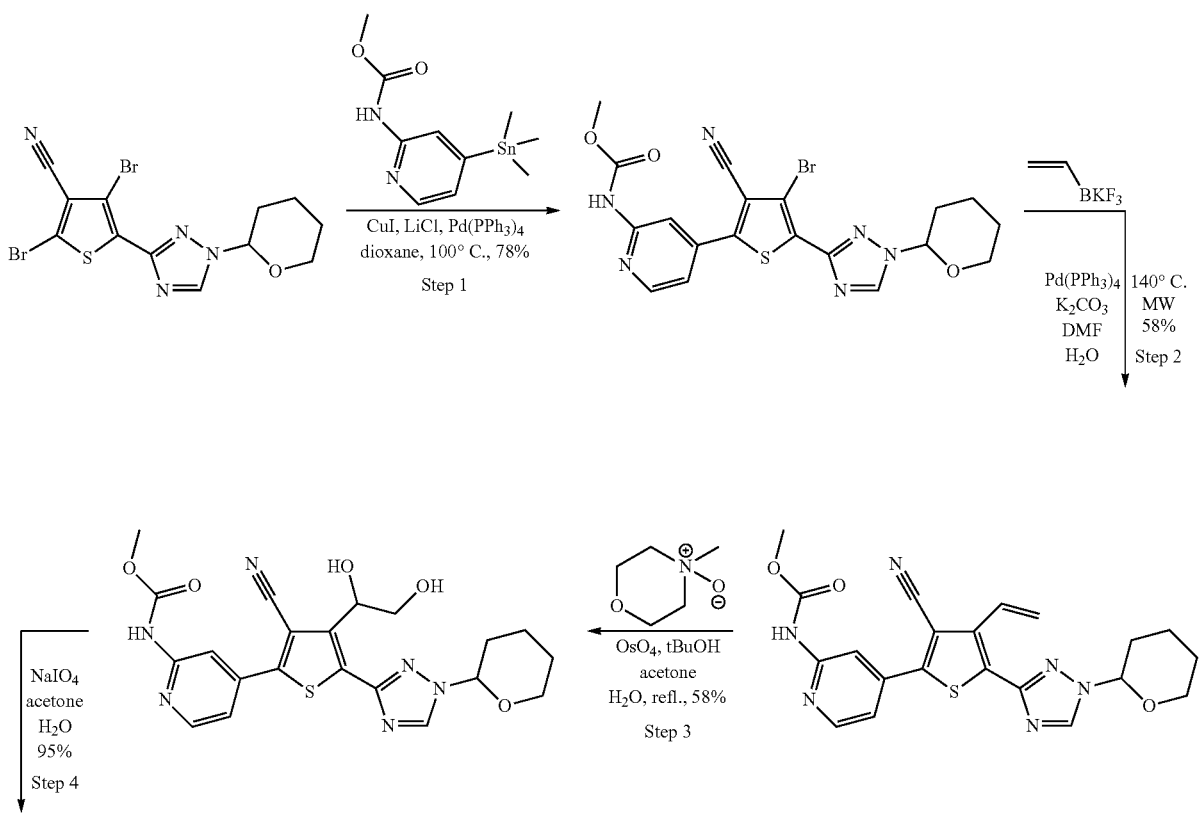

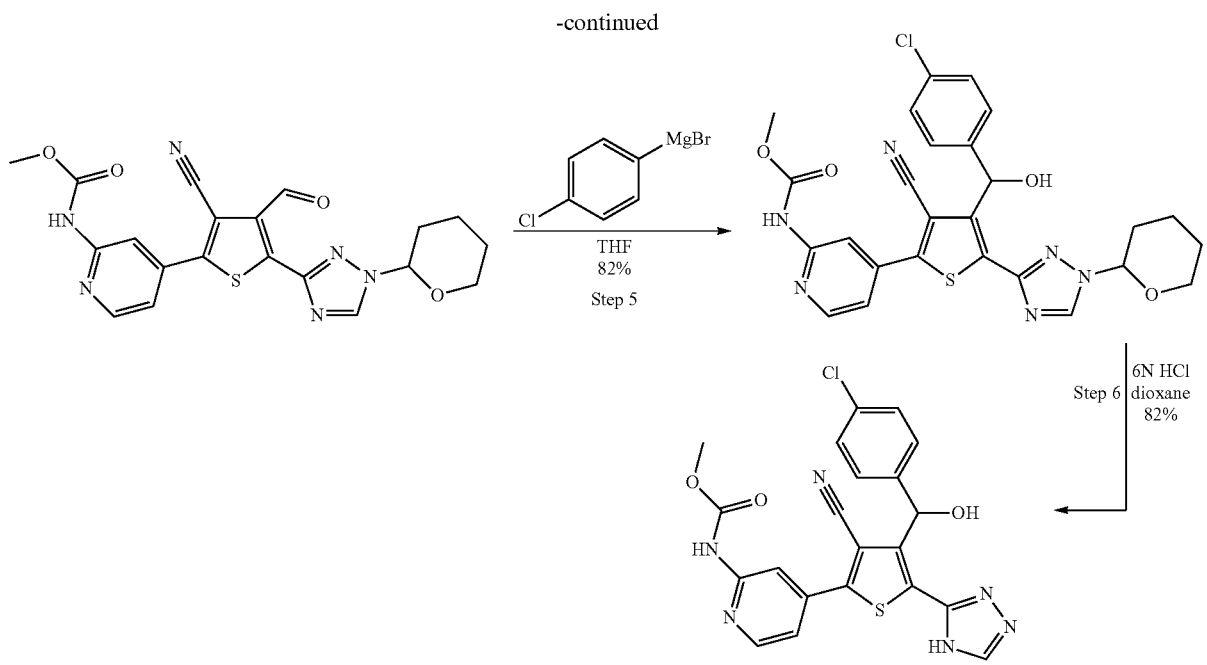

Step 1: Methyl (4-{4-bromo-3-cyano-5-[1-(tetrahydro-2H-pyran-2-yl)-1H-1,2,4-triazol-3-yl]-2-thienyl}pyridin-2-yl)carbamate A mixture of 2,4-dibromo-5-[1-(tetrahydro-2H-pyran-2-yl)-1H-1,2,4-triazol-3-yl]thiophene-3-carbonitrile (1.27 g, 3.05 mmol), methyl [4-(trimethylstannyl)pyridin-2-yl]carbamate (0.960 g, 3.05 mmol), lithium chloride (0.388 g, 9.14 mmol), copper(I) iodide (0.174 g, 0.914 mmol) and tetrakis(triphenylphosphine)platinum (0) (0.190 g, 0.152 mmol) in anhydrous 1,4-dioxane (45 mL) was degassed by evacuation in vacuum and backfilling with $N_2$ 4 times, then heated to 100° C. under $N_2$ for 8 hours, then cooled to room temperature. The suspension was filtered and washed with dioxane. The solid was suspended in 20% MeOH in DCM (300 mL), and washed with water (2×). The organic suspension was concentrated in a rotavapor to give a solid residue. The residue was stirred in DMF/DCM (10 mL/10 mL) at room temperature for 20 min, filtered and washed with DCM to give a solid product (1.16 g, yield 77.8%). LC/MS: (FA) ES+ 489, 491. $^1$H NMR (400 MHz, $d_4$-MeOH/d-chloroform) δ 8.26-8.35 (m, 3H), 7.34 (m, 1H), 5.48 (m, 1H), 4.00 (m, 1H), 3.73 (s, 3H), 3.64-3.69 (m, 1H), 1.97-2.14 (m, 3H), 1.58-1.68 (m, 3H).

Step 2: Methyl (4-{3-cyano-5-[1-(tetrahydro-2H-pyran-2-yl)-1H-1,2,4-triazol-3-yl]-4-vinyl-2-thienyl}pyridin-2-yl)carbamate A mixture of methyl (4-{4-bromo-3-cyano-5-[1-(tetrahydro-2H-pyran-2-yl)-1H-1,2,4-triazol-3-yl]-2-thienyl}pyridin-2-yl)carbamate (1.14 g, 2.33 mmol), potassium vinyltrifluoroborate (0.624 g, 4.66 mmol), tetrakis(triphenylphosphine)platinum (0) (0.145 g, 0.116 mmol) and potassium carbonate (0.967 g, 7.00 mmol) in N,N-dimethylformamide (14.0 mL) and water (5.0 mL) in a microwave vial was heated under nitrogen atmosphere at 140° C. in a microwave for 15 min. The mixture was cooled to room temperature, quenched with water, extracted with DCM, washed with water then brine, dried over $Na_2SO_4$, filtered and rotavaped to give a crude product. Purification on a silica gel column using MeOH/DCM (0/100 to 5/95) afforded the desired product (1.16 g, with PPh3 and O=PPh3 contaminated) with Rf on TLC (MeOH/DCM 5/95) of 0.4, and de-carbamide product (0.627 g, yield 58%). LC/MS: (FA) ES+ 437. $^1$H NMR (400 MHz, d-chloroform) δ 8.52 (s, 1H), 8.45 (s, 1H), 8.41 (m, 1H), 8.33 (s, 1H), 7.51-7.59 (m, 1H), 7.46-7.49 (m, 1H), 6.28-6.33 (m, 1H), 5.66-5.69 (m, 1H), 5.51-5.54 (m, 1H), 4.09-4.12 (m, 1H), 3.86 (s, 3H), 3.75-3.78 (m, 1H), 2.00-2.20 (m, 3H), 1.68-1.77 (m, 3H).

Step 3: Methyl (4-{3-cyano-4-(1,2-dihydroxyethyl)-5-[1-(tetrahydro-2H-pyran-2-yl)-1,1-1,2,4-triazol-3-yl]-2-thienyl}pyridin-2-yl)carbamate To the suspension of methyl (4-{3-cyano-5-[1-(tetrahydro-2H-pyran-2-yl)-1H-1,2,4-triazol-3-yl]-4-vinyl-2-thienyl}pyridin-2-yl)carbamate (0.625 g, 1.34 mmol) in tert-butyl alcohol (3.0 mL) and acetone (30 mL) was added N-methylmorpholine N-oxide (0.315 g, 2.69 mmol), followed by water (1.0 mL) then 0.157 M of osmium tetraoxide in Water (0.257 mL, 0.0404 mmol). The pale yellow suspension was stirred at room temperature for 17 hours. N-Methylmorpholine N-oxide (0.315 g, 2.69 mmol) was added and the suspension was stirred for 3 more hours, then heated to reflux for 7 hours. The mixture was cooled to room temperature, rotavaped and azeotroped with MeOH to give a solid crude residue. The crude solid was partially dissolved in DCM-MeOH, coated on silica gel, evaporated in rotavapor and chromatographed in a silica gel column using an elution of MeOH/DCM (0/100 to 5/95) to afford a solid product (0.365 g, yield 57.6%). LC/MS: (FA) ES+ 471; ES− 469. $^1$H NMR (400 MHz, d-chloroform/d4-methanol) δ 8.35 (m, 2H), 8.30 (m, 1H), 7.40 (m, 1H), 5.47-5.49 (m, 1H), 5.31-5.33 (m, 1H), 4.03-4.07 (m, 1H), 3.87 (m, 1H), 3.79 (s, 3H), 3.71-3.81 (m, 2H), 2.13 (m, 1H), 2.00-2.02 (m, 2H), 1.65-1.70 (m, 3H).

Step 4: Methyl (4-{3-cyano-4-formyl-5-[1-(tetrahydro-2H-pyran-2-yl)-1H-1,2,4-triazol-3-yl]-2-thienyl}pyridin-2-yl)carbamate Methyl (4-{3-cyano-4-(1,2-dihydroxyethyl)-5-[1-(tetrahydro-2H-pyran-2-yl)-1H-1,2,4-triazol-3-yl]-2-thienyl}pyridin-2-yl)carbamate (0.362 g, 0.769 mmol) was dissolved in acetone (40 mL) and water (10 mL). Sodium metaperiodate (0.494 g, 2.31 mmol) was added and the mixture was stirred at room temperature for 6 hours. Sodium metaperiodate (0.329 g, 1.54 mmol) was added and the mixture was stirred for 16 more hours. The mixture was concentrated in rotavapor. The residue was triturated with water, filtered and washed thoroughly with water, then dried in lyophilizer to give a dry solid product (0.320 g, yield 94.8%). LC/MS: (FA) ES+ 439. $^1$H NMR (400 MHz, d6-dmso) δ 10.67 (s, 1H), 10.57 (s, 1H), 9.05 (s, 1H), 8.49 (m, 1H), 8.28 (s, 1H), 7.50 (m, 1H), 5.69-5.73 (m, 1H), 3.94-3.98 (m, 1H), 3.73 (s, 3H), 3.66-3.71 (m, 1H), 1.93-2.12 (m, 3H), 1.58-1.71 (m, 3H).

Step 5: Methyl (4-{4-[(4-chlorophenyl)(hydroxy)methyl]-3-cyano-5-[1-(tetrahydro-2H-pyran-2-yl)-1H-1,2,4-triazol-3-yl]-2-thienyl}pyridin-2-yl)carbamate To a suspension of methyl (4-{3-cyano-4-formyl-5-[1-(tetrahydro-2H-pyran-2-yl)-1H-1,2,4-triazol-3-yl]-2-thienyl}pyridin-2-yl)carbamate (0.1077 g, 0.2456 mmol) in anhydrous Tetrahydrofuran (6.0 mL) cooled with ice bath was added slowly 1.0 M of 4-chlorophenylmagnesium bromide in ether (2.50 mL, 2.50 mmol). The resulting clear solution was stirred with cooling for 30 min, then the mixture was quenched with methanol (0.5 mL), then with acetic acid (148 mg, 2.46 mmol). The mixture was warmed to room temperature, then rotavaped to give crude product, which was chromatograph in a silica gel column using MeOH/DCM (0/100 to 3/97) to afford a solid product (0.116 g, yield 82%). LC/MS: (FA) ES+ 551; ES− 549. $^1$H NMR (400 MHz, d-chloroform/d4-methanol) δ 8.36 (s, 1H), 8.29 (m, 2H), 7.43 (m, 1H), 7.34 (m, 2H), 7.19 (m, 2H), 6.37 (s, 1H), 5.41-5.46 (m, 1H), 3.99-4.04 (m, 1H), 3.79 (s, 3H), 3.68-3.72 (m, 1H), 2.13 (m, 1H), 1.97-2.00 (m, 2H), 1.55-1.70 (m, br, 3H).

Step 6: Methyl {4-[4-[(4-chlorophenyl)(hydroxy)methyl]-3-cyano-5-(4H-1,2,4-triazol-3-yl)-2-thienyl]pyridin-2-yl}carbamate To a suspension of methyl (4-{4-[(4-chlorophenyl)(hydroxy)methyl]-3-cyano-5-[1-(tetrahydro-2H-pyran-2-yl)-1H-1,2,4-triazol-3-yl]-2-thienyl}pyridin-2-yl)carbamate (0.0450 g, 0.0817 mmol) in 1,4-dioxane (4.0 mL, 51 mmol) and cooled in an ice bath was added 6.0 M hydrochloric acid in water (4.0 mL, 24 mmol). The resulting solution was brought to room temperature. Hexane (5.0 mL) was added and the bi layer mixture was stirred for 4 hours. The hexane was separated and the aqueous layer was washed with hexane twice. The aqueous layer was concentrated on a rotavapor to ~half volume; diluted with ice and water, basified with saturated aqueous NaHCO$_3$ to pH ~7.5, extracted with EtOAc (4×). The combined EtOAc solutions were washed with brine, dried over Na$_2$SO$_4$, filtered, and rotavaped to give a crude solid. The crude solid was chromatographed on a silica gel column using MeOH/DCM (0/100 to 5/95) to afford a solid product (33 mg, yield 82%). LC/MS: (FA) ES+ 467, 469. $^1$H NMR (400 MHz, d6-dmso) δ 10.50 (s, 1H), 8.82 (s, 1H), 8.41 (m, 1H), 8.20 (s, 1H), 7.57 (m, 2H), 7.39 (m, 3H), 7.06 (s, 1H), 6.59 (s, br, 1H), 3.69 (s, 3H).

The compounds in the following table were prepared from the appropriate starting materials in a method analogous to that of Example 33:

| 153 | LCMS: (AA) ES+ 468. |
| 165 | LCMS: (AA) ES+ 451, 453. |

Example 34

Synthesis of N-{4-[4-[(4-chlorophenyl)sulfinyl]-3-cyano-5-(4H-1,2,4-triazol-3-yl)-2-thienyl]pyridin-2-yl}acetamide (Compound 131) and N-{4-[4-[(4-chlorophenyl)sulfonyl]-3-cyano-5-(4H-1,2,4-triazol-3-yl)-2-thienyl]pyridin-2-yl}acetamide (Compound 140)

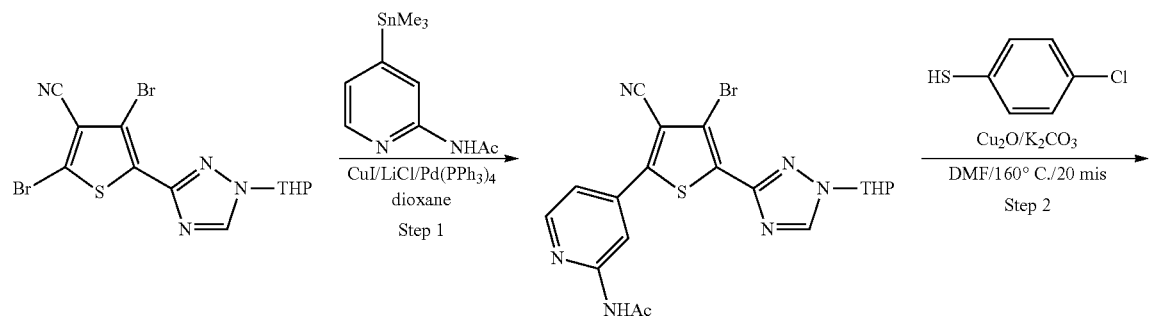

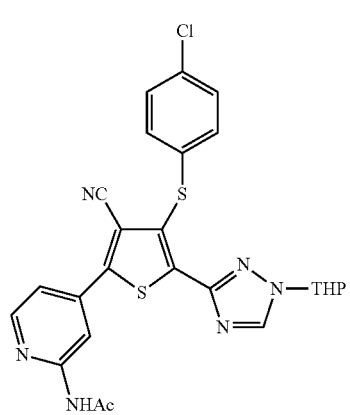
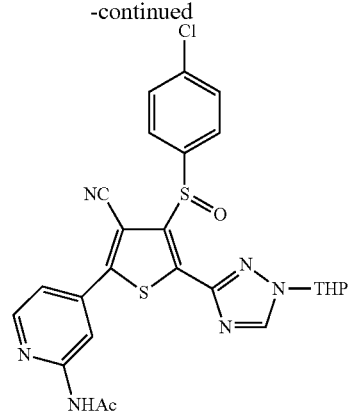
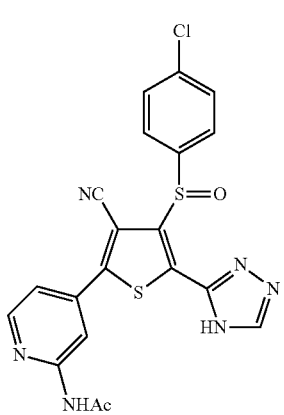

-continued

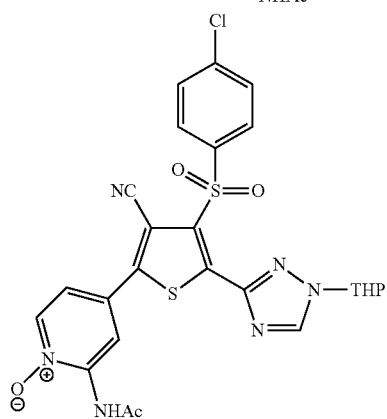
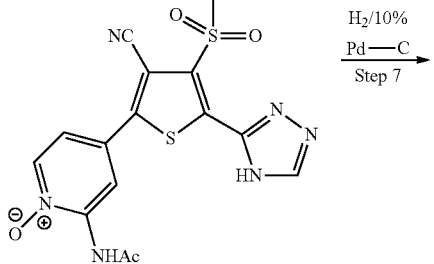
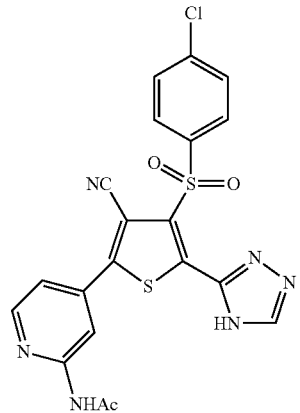

Step 1: N-(4-{4-bromo-3-cyano-5-[1-(tetrahydro-2H-pyran-2-yl)-1H-1,2,4-triazol-3-yl]-2-thienyl}pyridin-2-yl)acetamide A mixture of 2,4-dibromo-5-[1-(tetrahydro-2H-pyran-2-yl)-1H-1,2,4-triazol-3-yl]thiophene-3-carbonitrile (1.3809 g, 3.3027 mmol), [B]N-[4-(trimethylstannyl)-pyridin-2-yl]acetamide (987.38 mg, 3.3028 mmol), copper(I) iodide (188.70 mg, 0.99082 mmol), lithium chloride (420.04 mg, 9.9082 mmol) and tetrakis(triphenylphosphine)-palladium (0) (190.82 mg, 0.16514 mmol) in dry 1,4-Dioxane (20.0 mL) was sonicated under $N_2$ for 2 min, then heated in a capped vial to 130° C. in microwave machine for 20 mins. The suspension was cooled to room temperature, and the residue was purified using silica gel chromatography. The eluent was 40-100% ethyl acetate in hexane, affording a solid product (0.8802 g, yield 56.3%) LCMS: (AA) ES+ 473, 475. $^1$H NMR (300 MHz, CDCl$_3$) δ: 8.61 (s, 1H), 8.41 (d, 1H), 8.39 (s, 1H), 8.10 (s, 1H), 7.53 (d, 1H), 5.55-5.60 (dd, 1H), 4.06-4.10 (m, 1H), 3.68-3.78 (m, 1H), 2.35 (s, 3H), 2.15-2.28 (m, 1H), 2.01-2.13 (m, 2H), 1.66-1.80 (m, 3H).

Step 2: N-(4-{4-[(4-chlorophenyl)sulfanyl]-3-cyano-5-[1-(tetrahydro-2H-pyran-2-yl)-1H-1,2,4-triazol-3-yl]-2-thienyl}pyridin-2-yl)acetamide N-(4-{4-bromo-3-cyano-5-[1-(tetrahydro-2H-pyran-2-yl)-1H-1,2,4-triazol-3-yl]-2-thienyl}pyridin-2-yl)acetamide (0.2601 g, 0.5495 mmol), copper(I) oxide (0.1572 g, 1.099 mmol), 4-chlorobenzenethiol (0.3179 g, 2.198 mmol) and potassium carbonate (0.2278 g, 1.648 mmol) were added to a microwave vial followed by DMF (15.00 mL). The reaction was irradiated at 150° C. for 15 mins. The solid was filtered and washed with DCM. The solution was diluted with 80 ml water, and extracted with 100 ml DCM for two times. The organic layer was concentrated, and purified by column. The eluent was 50-100% ethyl acetate in hexane to yield a solid product (0.224 g, yield 76.0%) LCMS: (AA) ES+ 537, 539. $^1$H NMR (300 MHz, CDCl$_3$) δ: 8.59 (s, 1H), 8.37 (d, 1H), 8.36 (s, 1H), 8.03 (s, 1H), 7.53 (d, 1H), 7.32 (d, 2H), 7.22 (d, 2H), 5.50-5.55 (dd, 1H), 4.02-4.08 (m, 1H), 3.68-3.78 (m, 1H), 2.25 (s, 3H), 2.10-2.18 (m, 1H), 2.00-2.07 (m, 2H), 1.66-1.80 (m, 3H).

Step 3: N-(4-(4-(4-chlorophenylsulfinyl)-3-cyano-5-(1-(tetrahydro-2H-pyran-2-yl)-1H-1,2,4-triazol-3-yl)thiophen-2-yl)pyridin-2-yl)acetamide N-(4-{4-[(4-chlorophenyl)sulfanyl]-3-cyano-5-[1-(tetrahydro-2H-pyran-2-yl)-1H-1,2,4-triazol-3-yl]-2-thienyl}pyridin-2-yl)acetamide (0.0575 g, 0.107 mmol) was dissolved in methylene chloride (5.00 mL), followed by addition of m-chloroperbenzoic acid (0.0194 g, 0.112 mmol). The reaction mixture was stirred at room temperature for 1 hr. The solution was concentrated, and purified by column chromatography. The eluent was 50-100% ethyl acetate in hexane to yield a solid product (0.0324 g, 54.7%) LCMS: (AA) ES+ 553, 555. $^1$H NMR (300 MHz, CDCl$_3$) δ: 8.47 (m, 2H), 8.41 (s, 1H), 8.36 (d, 1H), 8.06 (dd, 2H), 7.46 (dd, 2H), 7.45 (d, 1H), 5.53-5.59 (dd, 1H), 4.08-4.16 (m, 1H), 3.73-3.81 (m, 1H), 2.25 (s, 3H), 2.10-2.18 (m, 1H), 2.00-2.07 (m, 2H), 1.69-1.80 (m, 3H).

Step 4: N-{4-[4-[(4-chlorophenyl)sulfinyl]-3-cyano-5-(4H-1,2,4-triazol-3-yl)-2-thienyl]pyridin-2-yl}acetamide (Compound 131)

N-(4-(4-(4-chlorophenylsulfinyl)-3-cyano-5-(1-(tetrahydro-2H-pyran-2-yl)-1H-1,2,4-triazol-3-yl)thiophen-2-yl)pyridin-2-yl)acetamide (0.0315 g, 0.0570 mmol) was dissolved in TFA (5.00 mL, 64.9 mmol). The mixture was stirred at room temperature for 1 hr, and the solvent was evaporated. 10 ml DCM was added to redissolve the material followed by the addition of triethylamine (1 mL). The solvent was evaporated off, and the mixture was purified by silica gel column. The eluent was 0-6% methanol in hexane to yield a solid product (0.0112 g, yield 41.9%) LCMS: (AA) ES+ 469, 471. 1H NMR (300 MHz, MeOD) δ: 8.65 (s, 1H), 8.51 (s, 1H), 8.42 (d, 1H), 8.06 (d, 2H), 7.58 (d, 2H), 7.44 (dd, 1H), 2.25 (s, 3H).

Step 5: N-(4-{4-[(4-chlorophenyl)sulfonyl]-3-cyano-5-[1-(tetrahydro-2H-pyran-2-yl)-1H-1,2,4-triazol-3-yl]-2-thienyl}-1-oxidopyridin-2-yl)acetamide N-(4-{4-[(4-chlorophenyl)sulfanyl]-3-cyano-5-[1-(tetrahydro-2H-pyran-2-yl)-1H-1,2,4-triazol-3-yl]-2-thienyl}pyridin-2-yl)acetamide (0.0698 g, 0.130 mmol) was dissolved in methylene chloride (6.00 mL) followed by addition of m-Chloroperbenzoic acid (0.08971 g, 0.5199 mmol). The mixture was stirred for 30 mins at room temperature. The solvent was evaporated, and the residue was purified by column chromatography. The eluent was 0-7% methanol in ethyl acetate to yield a solid product (0.0654 g, yield 86.0%) LCMS: (AA) ES+ 585, 587. 1H NMR (300 MHz, CDCl$_3$) δ: 8.76 (s, 1H), 8.41 (s, 1H), 8.37 (d, 2H), 8.26 (d, 1H), 7.50 (d, 2H), 7.43 (d, 1H), 5.50-5.57 (dd, 1H), 4.03-4.10 (m, 1H), 3.70-3.78 (m, 1H), 2.25 (s, 3H), 2.10-2.18 (m, 1H), 2.00-2.07 (m, 2H), 1.69-1.80 (m, 3H).

Step 6: N-{4-[4-[(4-chlorophenyl)sulfonyl]-3-cyano-5-(4H-1,2,4-triazol-3-yl)-2-thienyl]-1-oxidopyridin-2-yl}acetamide N-(4-{4-[(4-chlorophenyl)sulfanyl]-3-cyano-5-[1-(tetrahydro-2H-pyran-2-yl)-1H-1,2,4-triazol-3-yl]-2-thienyl}-1-oxidopyridin-2-yl)acetamide (0.0742 g, 0.127 mmol) was dissolved in trifluoroacetic acid (4.00 mL, 51.9 mmol). The mixture was stirred at room temperature for 4 hrs, solvent was evaporated and the residue was purified by HPLC to yield a solid product (0.0421 g, yield 66.3%) LCMS: (AA) ES+ 501, 503. $^1$H NMR (300 MHz, MeOD) δ: 8.90 (s, 1H), 8.60 (s, 1H), 8.43 (d, 1H), 8.35 (d, 2H), 7.67 (d, 2H), 7.59 (d, 1H), 2.28 (s, 3H).

Step 7: N-{4-[4-[(4-chlorophenyl)sulfonyl]-3-cyano-5-(4H-1,2,4-triazol-3-yl)-2-thienyl]pyridin-2-yl}acetamide (Compound 140)

N-{4-[4-[(4-chlorophenyl)sulfonyl]-3-cyano-5-(4H-1,2,4-triazol-3-yl)-2-thienyl]-1-oxidopyridin-2-yl}acetamide (0.0229 g, 0.0457 mmol) was dissolved in methanol (3.00 mL), followed by the addition of 10% Pd—C (5 mg). The flask was filled with hydrogen at 40 psi, and the suspension was stirred at room temperature for overnight. The solid was filtered off, and the residue was concentrated followed by purification by column chromatography. The eluent was 0-8% methanol in ethyl acetate to yield a solid product (0.0142 g, yield 64.0%). LCMS: (AA) ES+ 485, 487. 1H NMR (300 MHz, MeOD) δ: 8.60 (s, 1H), 8.53 (s, 1H), 8.45 (d, 1H), 8.35 (d, 2H), 7.66 (d, 2H), 7.48 (d, 1H), 2.20 (s, 3H).

The compound in the following table was prepared from the appropriate starting materials in a method analogous to that of Example 34:

| 166 | LCMS: (AA) ES+ 454 |
| --- | --- |

Example 35

Synthesis of 5-(4-(4-chlorobenzyl)-2-(pyridin-4-yl)thiazol-5-yl)-1H-pyrazol-3-ol (Compound 178)

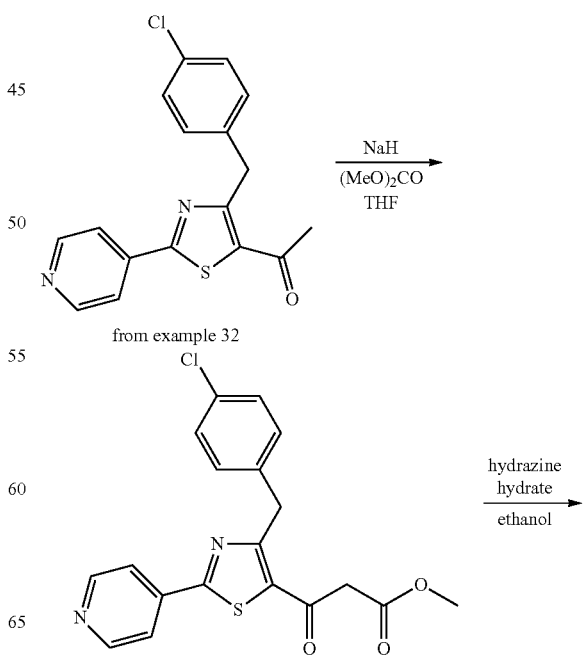

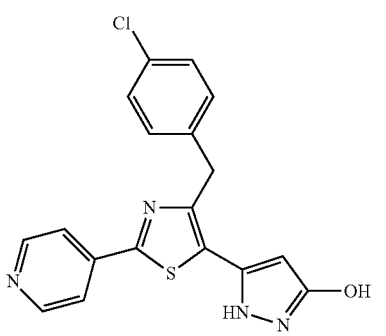

Step 1, Preparation of ethyl 3-(4-(4-chlorobenzyl)-2-(pyridin-4-yl)thiazol-5-yl)-3-oxopropanoate To a flask containing 60% NaH in mineral oil (213 mg, 5.32 mmol) under nitrogen was added THF (31.7 mL) and carbonic acid, dimethyl ester (0.448 mL, 5.32 mmol). The mixture was heated to 60 degrees and a solution of 1-(4-(4-chlorobenzyl)-2-(pyridin-4-yl)thiazol-5-yl)ethanone (875 mg, 2.66 mmol) in THF (12.7 mL) was then added. The mixture was heated at 60 degrees for 1 hour. The reaction was cooled and quenched with methanol (5 mL), then saturated NH₄Cl (10 mL). The organic solvents were concentrated in vacuo, and the aqueous residue was diluted with water (10 mL) and extracted with ethyl acetate (2×20 mL). The combined organic layers were dried, filtered and concentrated in vacuo. The residue was purified by silica gel chromatography (EA/DCM=0/100→40/60) to give 253 mg (25% yield) of the title compound. as an oil. LC/MS (FA) ES+ 387, 389. $^1$H NMR (300 MHz, CDCl₃) δ: 8.76-8.74 (m, 2H), 7.83-7.81 (m, 2H), 7.35-7.32 (m, 2H), 7.26-7.23 (m, 2H), 4.53 (s, 2H), 3.89 (s, 2H), 3.77 (s, 3H).

Step 2, Preparation of 5-(4-(4-chlorobenzyl)-2-(pyridin-4-yl)thiazol-5-yl)-1H-pyrazol-3-ol To a solution of ethyl 3-(4-(4-chlorobenzyl)-2-(pyridin-4-yl)thiazol-5-yl)-3-oxopropanoate (253 mg, 0.631 mmol) in ethanol (16 mL) was added hydrazine hydrate (0.123 mL, 2.52 mmol) and the resulting solution was heated to 80 degrees for 3 hours. The reaction was cooled and concentrated in vacuo. The residue was purified by silica gel chromatography (MeOH/DCM=0/100→10/90) to give 118 mg of the product. This material was purified by preparative reverse phase chromatography to give 63 mg (27% yield) of the title compound. as a white solid. LC/MS (FA) ES+ 369, 371. $^1$H NMR (300 MHz, DMSO-d₆) δ: 12.44 (bs, 1H), 8.68 (bs, 2H), 7.83-7.81 (m, 2H), 7.35-7.32 (m, 2H), 7.27-7.24 (m, 2H), 5.60 (s, 1H), 4.34 (s, 2H).

Example 36

Synthesis of (2-(4-(4-chlorobenzyl)-2-(pyridin-4-yl)thiazol-5-yl)-1H-imidazol-4-yl)methanamine (Compound 255)

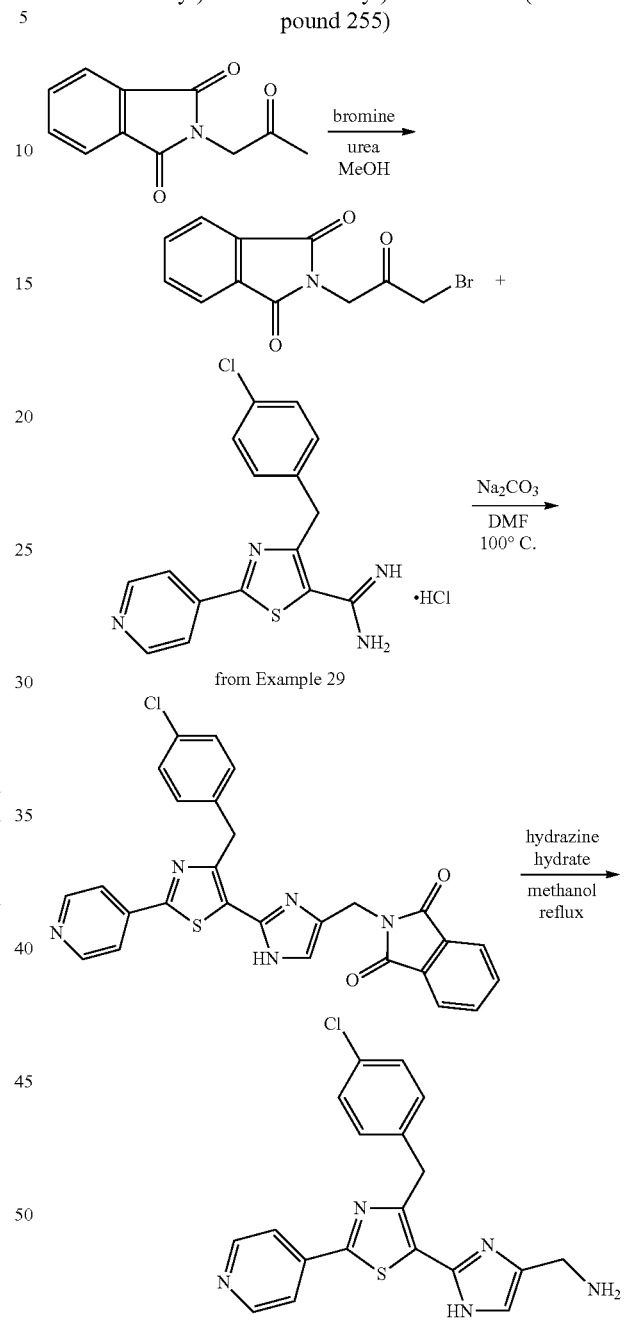

Step 1, Preparation of 2-(3-bromo-2-oxopropyl)isoindoline-1,3-dione

To a solution of phthalimidoacetone (4.04 g, 19.9 mmol) in methanol (100 mL) was added urea (1.19 g, 19.9 mmol) and bromine (3.18 g, 19.9 mmol) and the resulting solution was stirred at room temperature overnight. The reaction was concentrated in vacuo and the residue taken up in DCM (150 mL) and water (50 mL). The layers were separated and the organic layer was dried, filtered, and concentrated in vacuo. The residue was purified by silica gel chromatography (EA/hexanes=0/100→50/50) to give 159 mg (3% yield) of the title compound. ¹H NMR (300 MHz, CDCl₃) δ: 7.90-7.86 (m, 2H), 7.79-7.73 (m, 2H), 4.78 (s, 2H), 4.01 (s, 2H).

Step 2, Preparation of 2-42-(4-(4-chlorobenzyl)-2-(pyridin-4-yl)thiazol-5-yl)-1,1-imidazol-4-yl)methyl) isoindoline-1,3-dione To a mixture of 4-(4-chlorobenzyl)-2-(pyridin-4-yl)thiazole-5-carboximidamide hydrochloride (112 mg, 0.306 mmol) in DMF (2.96 mL) was added sodium carbonate (162 mg, 1.53 mmol) and 2-(3-bromo-2-oxopropyl)isoindoline-1,3-dione (95.0 mg, 0.337 mmol) and the resulting mixture was heated at 100 degrees for 4 hours. The reaction was cooled and taken up in ethyl acetate (30 mL) and water (5 mL). The layers were separated and the organic layer was washed with water (3×5 mL). The organic layer was dried, filtered and concentrated in vacuo. The residue was purified by silica gel chromatography (MeOH/DCM=0/100→10/90) to give 47 mg (30% yield) of the title compound. LC/MS (FA) ES+ 512. 514. ¹H NMR (300 MHz, DMSO-d₆) δ: 12.67 (bs, 1H), 8.69-8.67 (m, 2H), 7.91-7.79 (m, 6H), 7.27-7.24 (m, 3H), 7.11-7.08 (m, 2H), 4.77 (s, 2H), 4.45 (s, 2H).

Step 3, Preparation of (2-(4-(4-chlorobenzyl)-2-(pyridin-4-yl)thiazol-5-yl)-1H-imidazol-4-yl)methanamine To a solution of 24(2-(4-(4-chlorobenzyl)-2-(pyridin-4-yl) thiazol-5-yl)-1H-imidazol-4-yl)methyl)isoindoline-1,3-dione (45 mg, 0.0879 mmol) in methanol (2.0 mL) was added hydrazine hydrate (0.0086 mL, 0.176 mmol) and the resulting solution was heated to reflux for 1 hour. The reaction was cooled and concentrated in vacuo. The residue was taken up in ethyl acetate and water. The layers were separated and the organic layer was dried, filtered and concentrated in vacuo. The residue was purified by silica gel chromatography (MeOH/DCM=0/100-440/60) to give 13 mg (39% yield) of the title compound. LC/MS (FA) ES+ 382, 384. ¹H NMR (300 MHz, MeOH-d₄) δ: 8.71-8.68 (m, 2H), 7.82-7.80 (m, 2H), 7.35-7.29 (m, 4H), 7.22 (s, 1H), 4.53 (s, 2H), 3.86 (s, 2H).

Example 37

Synthesis of 5-(4-(4-chlorobenzyl)-2-(pyridin-4-yl) thiazol-5-yl)-1H-pyrazole-3-carboxylic acid (Compound 262)

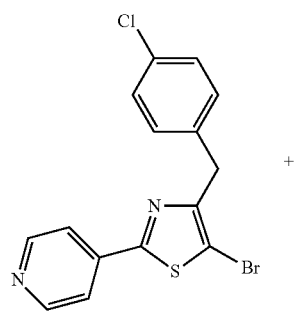

from Example 19

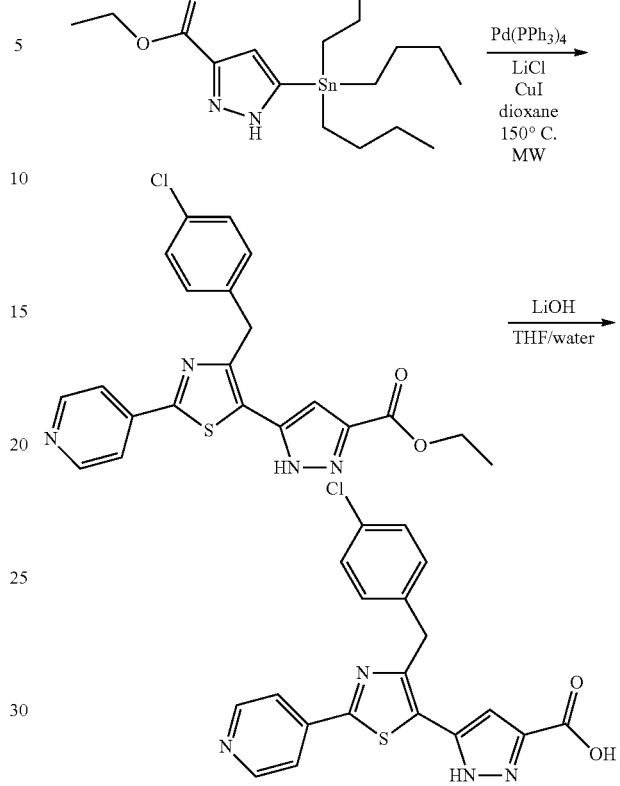

Step 1, Preparation of ethyl 5-(4-(4-chlorobenzyl)-2-(pyridin-4-yl)thiazol-5-yl)-1H-pyrazole-3-carboxylate An argon degassed mixture of 5-bromo-4-(4-chlorobenzyl)-2-(pyridin-4-yl)thiazole (583 mg, 1.59 mmol), ethyl 5-(tributylstannyl)-1H-pyrazole-3-carboxylate (456 mg, 1.06 mmol), tetrakis(triphenylphosphine)palladium(0) (61.4 mg, 0.0531 mmol), copper(I) iodide (60.7 mg, 0.319 mmol), and lithium chloride (135 mg, 3.19 mmol) in dioxane (7.46 mL) was heated in a microwave at 150 degrees for 30 minutes. The reaction mixture was slurried in ethyl acetate (100 mL) and water (2 mL) and the mixture was filtered and concentrated in vacuo. The residue was purified by silica gel chromatography (EA/DCM=0/100→100/0) to give the crude product. This material was purified by preparative reverse phase chromatography to give 55 mg (12% yield) of the title compound as a white solid. LC/MS (FA) ES+ 425, 427. ¹H NMR (300 MHz, DMSO-d₆) δ: 8.71-8.69 (m, 2H), 7.85-7.83 (m, 2H), 7.36-7.33 (m, 2H), 7.28-7.25 (m, 2H), 7.09 (s, 1H), 4.41 (s, 2H), 4.34 (q, 1H, J=7.2 Hz), 1.31 (t, 1H, J=7.2 Hz).

Step 2, Preparation of 5-(4-(4-chlorobenzyl)-2-(pyridin-4-yl)thiazol-5-yl)-1H-pyrazole-3-carboxylic acid A solution of ethyl 5-(4-(4-chlorobenzyl)-2-(pyridin-4-yl) thiazol-5-yl)-1H-pyrazole-3-carboxylate (16.1 mg, 0.0379 mmol) in THF (0.50 mL) was treated with 1.0 M aqueous LiOH (0.0568 mL, 0568 mmol) and the solution was stirred at 40 degrees for 3 days. The reaction was then heated at 65 degrees for 6 hours. The reaction mixture was cooled and acidified with 1N HCl. The solution was extracted with EA (3×25 mL) and the combined organic layers were dried, filtered and concentrated in vacuo. The residue was purified by preparative reverse phase chromatography to give 1 mg (7% yield) of the title compound as a white solid. LC/MS (FA) ES+ 397, 399.

Example 38

Synthesis of 4-(4-chlorobenzyl)-2-(pyridin-4-yl)-5-(1H-tetrazol-5-yl)thiazole (Compound 190)

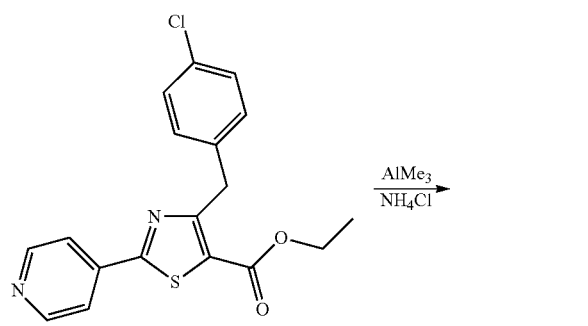

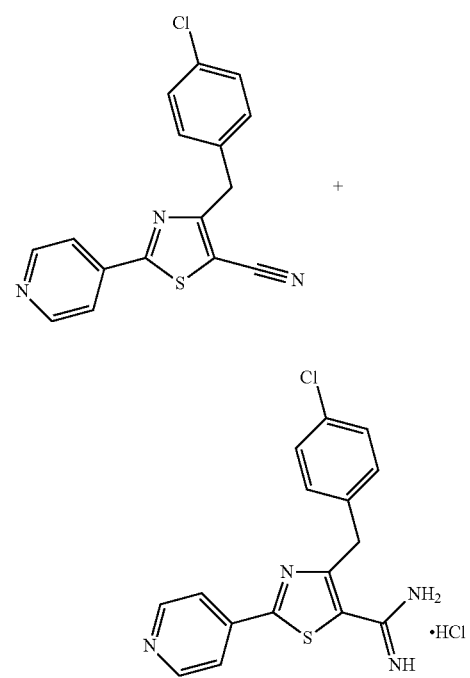

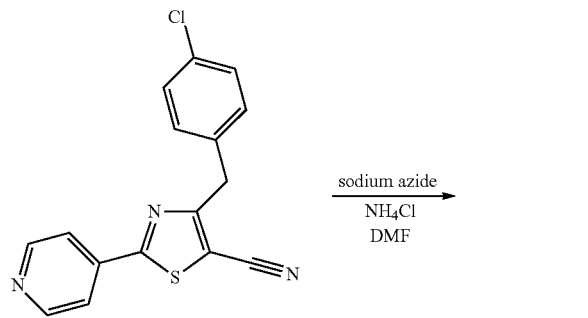

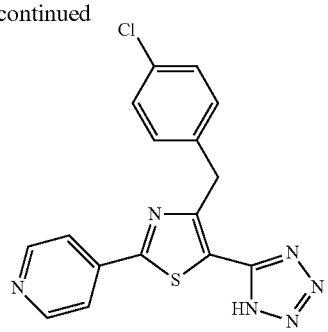

Step 1, Preparation of 4-(4-chlorobenzyl)-2-(pyridin-4-yl)thiazole-5-carboximidamide hydrochloride and 4-(4-chlorobenzyl)-2-(pyridin-4-yl)thiazole-5-carbonitrile To a suspension of ammonium chloride (2.25 g, 42.1 mmol) in toluene (21.0 mL) in an ice bath was added 2.0 M trimethylaluminum in toluene (21.1 mL, 42.2 mmol) dropwise (gas evolution was observed). The mixture was then stirred at room temperature for 30 minutes, during which time the solids dissolved. Ethyl 4-(4-chlorobenzyl)-2-morpholinothiazole-5-carboxylate (4.11 g, 11.4 mmol) was added in one portion and the resulting solution was heated slowly to 110° C. over 1 hour, then kept at 110° C. for 2.5 hours. The reaction was allowed to cool to room temperature overnight. The reaction was poured into a slurry of silica gel (10 grams) in chloroform (100 mL) and stirred 10 minutes. Methanol (20 mL) was added (bubbling occurred), and the mixture was filtered through a short silica gel bed in a sintered glass funnel, eluting with 1:1 methanol/chloroform to remove product. The filtrate was concentrated to give the crude product, which was purified by silica gel chromatography (MeOH/DCM=0/100→50/0) to give 1.6 grams (45% yield) of the nitrile, which eluted first, and 1.9 g (45% yield) of the guanidine, which is the HCl salt. Guanidine: LC/MS (FA) ES+ 329. 331. $^1$H NMR (400 MHz, DMSO-d$_6$) δ: 9.73, (bs, 4H), 8.76-8.74 (m, 2H), 7.90-7.88 (m, 2H), 7.39-7.35 (m, 2H), 7.31-7.27 (m, 2H), 4.30 (s, 2H). Nitrile: LC/MS (FA) ES+ 312, 314. $^1$H NMR (400 MHz, DMSO-d$_6$) δ: 8.77-8.75 (m, 2H), 7.78-7.76 (m, 2H), 7.34-7.29 (m, 4H), 4.29 (s, 2H).

Step 2, Preparation of 4-(4-chlorobenzyl)-2-(pyridin-4-yl)-5-(1H-tetrazol-5-yl)thiazole To a solution 4-(4-chlorobenzyl)-2-(pyridin-4-yl)thiazole-5-carbonitrile (167 mg, 0.536 mmol) in DMF (3.5 mL) was added sodium azide (104 mg, 1.61 mmol) and ammonium chloride (86 mg, 1.61 mmol) and the resulting mixture was heated at 100 degrees overnight. The reaction was cooled and taken up in ethyl acetate and water. The aqueous layer was concentrated in vacuo, and the residue was purified by silica gel chromatography (MeOH/DCM=0/100→10/90) to give 9 mg (5% yield) of the title compound. LC/MS (FA) ES+ 355, 357. $^1$H NMR (400 MHz, DMSO-d$_6$) δ: 8.74-8.73 (m, 2H), 7.93-7.92 (m, 2H), 7.38-7.32 (m, 4H), 4.62 (s, 2H).

Example 39

Preparation of 3-[hydroxy(2-naphthyl)methyl]-5-pyridin-4-ylthiophene-2-carboxylic acid
(Compound 205)

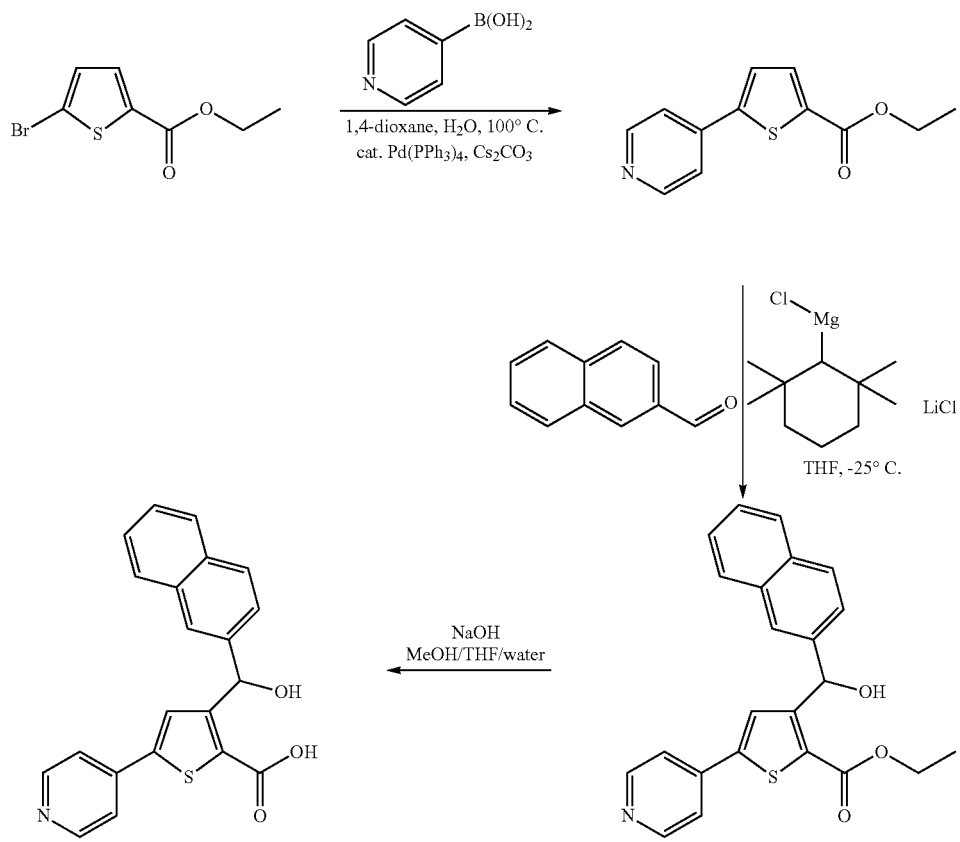

Step 1: Ethyl 5-pyridin-4-ylthiophene-2-carboxylate

A mixture of ethyl 5-bromothiophene-2-carboxylate (1.560 g, 6.65 mmol), pyridine-4-boronic acid (0.98 g, 7.98 mmol), tetrakis(triphenylphosphine)palladium(0) (768 mg, 0.665 mmol) and cesium carbonate (6.50 g, 19.9 mmol) in 1,4-dioxane (20 mL) and water (3.35 mL) was stirred and heated at 100° C. under an atmosphere of nitrogen overnight. The reaction was a clear light orange with a small amount of a second liquid phase on the bottom of the flask. An aliquot was taken, quenched into water, and extracted with ethyl acetate. A TLC on silica gel (1:1 DCM:hexane) indicated that all of the starting material had been consumed. A major new product with Rf ~0.4 was seen. The reaction was cooled to room temperature then was quenched into stirring water and extracted with ethyl acetate. The ethyl acetate extracts were washed with saline, dried over sodium sulfate, filtered, and evaporated to leave crude product as an off-white solid. The crude product was dissolved in minimal DCM then was purified by column chromatography on silica gel (gradient 100% DCM to 50% ethyl acetate) to afford product 1.02 g (66% yield) as white solid. LC/MS (FA) ES+ 234. NMR (400 MHz, DMSO)S 8.68-8.60 (m, 2H), 7.91-7.83 (m, 2H), 7.78-7.71 (m, 2H), 4.37-4.27 (d, J=7.1 Hz, 2H), 1.35-1.27 (t, J=7.1 Hz, 3H).

Step 2: Ethyl 3-[hydroxy(2-naphthyl)methyl]-5-pyridin-4-ylthiophene-2-carboxylate A dry, nitrogen flushed flask, equipped with a stirbar and septum, was charged with 2,2,6,6-tetramethylpiperidinylmagnesium chloride.lithium chloride in tetrahydrofuran (1.0M, 1.21 mL, 1.21 mmol). The flask was cooled to −25° C. and a solution of ethyl 5-pyridin-4-ylthiophene-2-carboxylate (0.257 g, 1.10 mmol) in tetrahydrofuran (1.0 mL, 12 mmol) was added dropwise with stirring. The resulting dark reddish orange solution was stirred at −25° C. for 30 minutes. 2-Naphthalenecarboxaldehyde (0.172 g, 1.10 mmol) was then added dropwise (as a solution in 1.5 ml THF)— the reaction mixture became purple. The reaction was stirred at −25° for 5 minutes, then the cooling bath was removed and the reaction was allowed to warm to room temperature with stirring. An aliquot was removed from the reaction and quenched into sat. NH4Cl solution, then extracted with ethyl acetate. A LCMS of this extract indicated that all starting material had been consumed and that the major peak had correct mass for the desired product. The reaction was quenched by the slow dropwise addition of a saturated ammonium chloride solution (5 ml). The resulting yellow-orange mixture was transferred to a reparatory funnel and diluted further with water and ethyl acetate. The organic layer was separated and the aqueous layer was further extracted with ethyl acetate. The extracts were combined, washed with saline, dried, and evaporated to leave crude product as an orange oil which was dissolved in minimal dichloromethane then was purified by column chromatography on silica gel (gradient 100% DCM to 5% MeOH in ethyl acetate) to afford product 210 mg (49% yield) as a white foam. LC/MS (FA) ES+ 390. ¹H NMR (400 MHz, DMSO) δ 8.63-8.58 (dd, J=4.6, 1.6 Hz, 2H), 8.04-8.00 (s, 1H), 8.00-7.96 (s, 1H), 7.87-7.81 (d, J=8.7 Hz, 3H), 7.76-7.71 (dd, J=4.6, 1.7 Hz, 2H), 7.62-7.58 (d, J=1.6 Hz, 1H), 7.50-7.45 (t, J=3.0 Hz, 2H), 6.74-6.69 (d, J=4.2 Hz, 1H), 6.33-6.28 (d, J=4.2 Hz, 1H), 4.37-4.31 (dd, J=7.1, 4.3 Hz, 2H), 1.35-1.27 (t, J=7.1 Hz, 3H).

Step 3: 3-[Hydroxy(2-naphthyl)methyl]-5-pyridin-4-ylthiophene-2-carboxylic acid (Compound 205)

Ethyl 3-[hydroxy(2-naphthyl)methyl]-5-pyridin-4-ylthiophene-2-carboxylate (70.0 mg, 0.180 mmol) was placed in a round bottomed flask equipped with a stirbar. Tetrahydrofuran (2.00 mL), methanol (1.00 mL), and water (1.50 mL) were added with stirring—all solids dissolved. Sodium hydroxide (1.0 M, 1.50 mL, 1.50 mmol) was added in a single portion and the resulting solution was stirred under an atmosphere of nitrogen overnight, resulting in a clear light yellow solution. The reaction was quenched into water and the pH of the mixture was adjusted the pH to ~6-6.5 with sodium bicarbonate solution. The mixture was extracted with ethyl acetate, the extracts were combined and then rotovapped to leave crude product as a light yellow solid. The crude product was purified by HPLC to yield 9 mg (14% yield) product as a pale yellow powder. LC/MS (FA) ES+ 362. ¹H NMR (400 MHz, DMSO) δ 8.60-8.51 (d, J=6.1 Hz, 2H), 7.98-7.94 (s, 2H), 7.91-7.75 (m, 4H), 7.68-7.58 (m, 3H), 7.53-7.37 (m, 2H), 6.64-6.36 (s, 1H).

Example 40

Preparation of 3-(2-naphthylmethyl)-5-pyridin-4-ylthiophene-2-carboxylic acid (Compound 210)

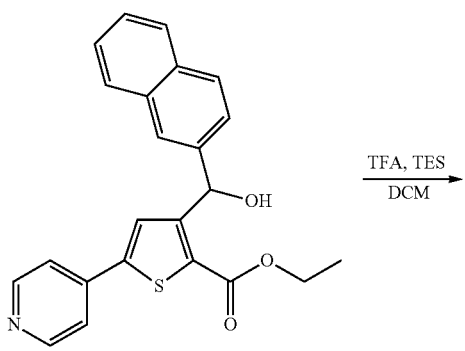

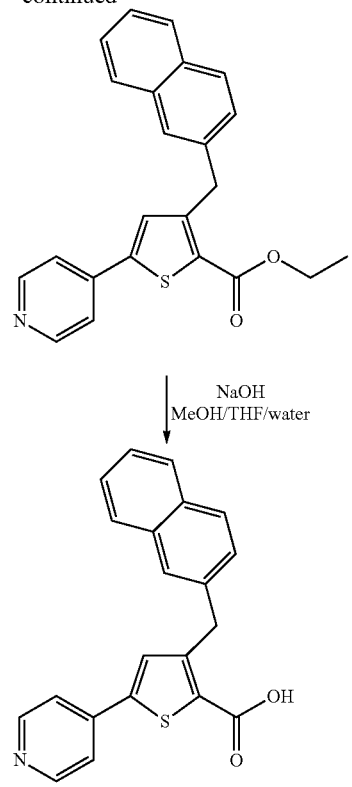

Step 1: Ethyl 5-pyridin-4-ylthiophene-2-carboxylate

Ethyl 3-[hydroxy(2-naphthyl)methyl]-5-pyridin-4-ylthiophene-2-carboxylate (118.0 mg, 0.3030 mmol), methylene chloride (2.4 mL), trifluoroacetic acid (140.0 uL, 1.818 mmol), and triethylsilane (84.7 uL, 0.530 mmol) were combined in a round bottomed flask equipped with a stirbar. The reaction was stirred overnight at room temperature under an atmosphere of nitrogen. An aliquot was taken from the reaction, quenched into water, basified with sodium carbonate, and extracted with ethyl acetate. TLC analysis (2:1 ethyl acetate:DCM) indicated that the starting ester was ~50% converted to a slightly higher Rf product. Additional trifluoroacetic acid (300 uL, 4 mmol) and triethylsilane (200 uL, 1 mmol) were added and the reaction was stirred at room temperature under an atmosphere of nitrogen for another 4 hours. LCMS analysis showed one major peak with correct ES+ for product with a small amount of SM remaining. The reaction was quenched into water, basified, and extracted into ethyl acetate. The extract was washed with saline, dried over sodium sulfate, filtered, and evaporated to leave crude product as an oil. The crude product was dissolved in minimal DCM then was purified by column chromatography on silica gel (gradient 100% DCM to 50% ethyl acetate) to afford product 86 mg (76% yield) as a white solid. LC/MS (FA) ES+ 374. ¹H NMR (400 MHz, DMSO) δ 8.64-8.55 (m, 2H), 7.90-7.80 (m, 4H), 7.80-7.75 (s, 1H), 7.73-7.66 (m, 2H), 7.52-7.40 (m, 3H), 4.57-4.49 (s, 2H), 4.39-4.27 (q, J=7.1 Hz, 2H), 1.35-1.25 (t, J=7.1 Hz, 3H).

Step 2: 3-(2-naphthylmethyl)-5-pyridin-4-ylthiophene-2-carboxylic acid (Compound 210)

Ethyl 3-(2-naphthylmethyl)-5-pyridin-4-ylthiophene-2-carboxylate (80.0 mg, 0.214 mmol) was placed in a round bottomed flask equipped with a stirbar. Methanol (3 mL, 70 mmol) and tetrahydrofuran (3 mL, 40 mmol) were added followed by water (2 mL, 100 mmol). The resulting solution was stirred and lithium hydroxide in water (1.0 M, 0.643 mL, 0.643 mmol) was added. The flask was sealed and stirred overnight at RT. LCMS of an aliquot indicated that all starting material had been consumed to give a single product with the correct mass for the desired product. To the stirring reaction was added ~30 mL water and a few mL saline. The mixture was stirred and acidified to ~pH 1 with 1N HCl—a gelatinous precipitate formed. The mixture was stirred rapidly and diethyl ether (10 mL) was added—the precipitate became more granular and became suspended mostly in the organic layer. The quench mixture was stirred at room temperature for ~30 minutes then the solid was collected on a fritted funnel, washed well with water then diethyl ether, then dried in vacuo to yield product 60 mg (81% yield) as a white powder. LC/MS (FA) ES+ 346. $^1$H NMR (400 MHz, DMSO) δ 13.62-13.20 (s, 1H), 8.63-8.52 (dd, J=4.7, 1.5 Hz, 2H), 7.91-7.80 (m, 3H), 7.80-7.72 (d, J=3.0 Hz, 2H), 7.70-7.63 (dd, J=4.6, 1.5 Hz, 2H), 7.53-7.40 (m, 3H), 4.57-4.48 (s, 2H).

Example 41

Synthesis of 2-(2-acetamidopyridin-4-yl)-4-(naphthalen-2-ylmethyl)thiazole-5-carboxylic acid (Compound 177)

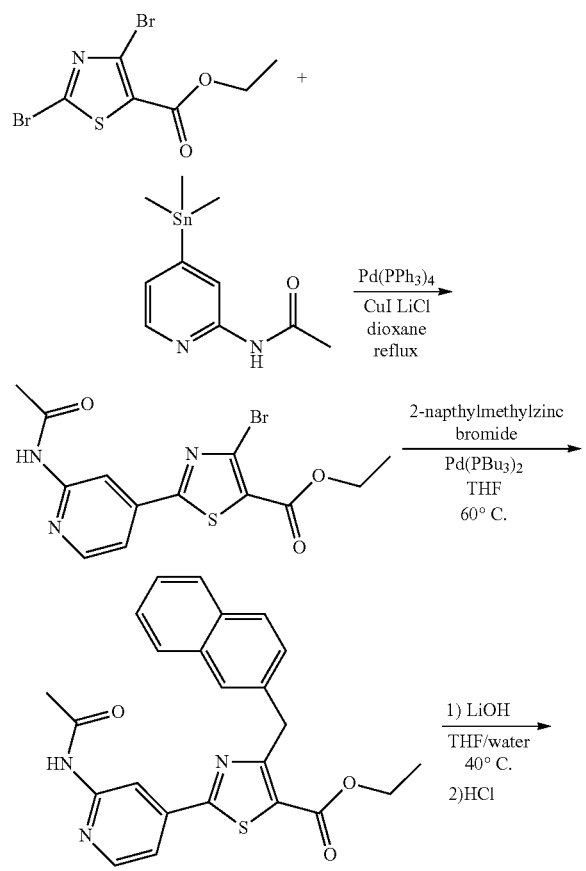

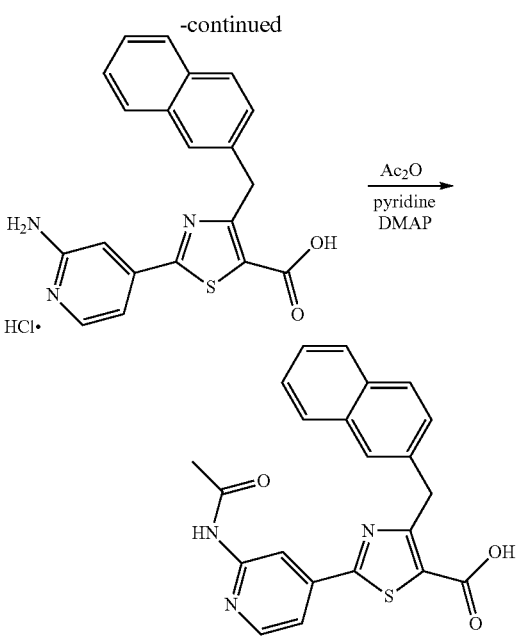

Step 1, Preparation of ethyl 2-(2-acetamidopyridin-4-yl)-4-bromothiazole-5-carboxylate A mixture of ethyl 2,4-dibromothiazole-5-carboxylate (0.500 g, 1.59 mmol), N-(4-(trimethylstannyl)pyridin-2-yl)acetamide (0.569 g, 1.90 mmol), tetrakis(triphenylphosphine)palladium(0) (91.7 mg, 0.0794 mmol), copper(I) iodide (90.7 mg, 0.476 mmol), and lithium chloride (202 mg, 4.76 mmol) in dioxane (29.1 mL) was degassed with nitrogen and heated at reflux for 1 hr. The reaction was cooled and concentrated in vacuo. The residue was purified by silica gel chromatography (ethyl acetate/hexane=0/100→50/50) to give 312 mg of the title compound. (44% yield). LC/MS (FA) ES+ 370, 372. $^1$H NMR (400 MHz, CDCl$_3$) δ: 8.71 (s, 1H), 8.39 (d, 1H, J=5.2 Hz), 8.25 (bs, 1H), 7.68 (dd, 1H, J=5.2, 1.6 Hz), 4.41 (q, 2H, J=7.2 Hz), 2.26 (s, 3H), 1.41 (t, 3H, J=7.2 Hz).

Step 2, Preparation of ethyl 2-(2-acetamidopyridin-4-yl)-4-(naphthalen-2-ylmethyl)thiazole-5-carboxylate To a mixture of ethyl 2-(2-acetamidopyridin-4-yl)-4-bromothiazole-5-carboxylate (190 mg, 0.510 mmol) and bis(tri-t-butylphosphine)palladium(0) (65.6 mg, 0.128 mmol) under nitrogen was added a 0.500 M solution of 2-napthylmethylzinc bromide in THF (3.60 mL, 1.80 mmol). The reaction was stirred at room temperature for 5 minutes, then at 60 degrees for 1 hour. Another portion of bis(tri-t-butylphosphine)palladium(0) (60.0 mg, 0.117 mmol) was added, followed by another portion of 0.500 M solution of 2-napthylmethylzinc bromide in THF (3.00 mL, 1.50 mmol), and the reaction was heated at 60 degrees for an additional 45 minutes. The reaction was cooled to room temperature and quenched with saturated ammonium chloride (10 mL). The mixture was extracted with ethyl acetate (2×20 mL) and the combined organic layers were dried over MgSO$_4$, filtered, and concentrated in vacuo. The residue was purified by silica gel chromatography (ethyl acetate/hexane=0/100→100/0) to give 100 mg of the title compound. (40% yield). LC/MS (FA) ES+ 432.

Step 3, Preparation of 2-(2-aminopyridin-4-yl)-4-(naphthalen-2-ylmethyl)thiazole-5-carboxylic acid, HCl salt To a mixture of ethyl 2-(2-acetamidopyridin-4-yl)-4-(naphthalen-2-ylmethyl)thiazole-5-carboxylate (100 mg, 0.232 mmol) in THF (2.00 mL) was added 1.0 M aqueous LiOH (2.32 mL, 2.32 mmol) and the resulting mixture was heated at 40 degrees for 3 days. The mixture was acidified with 1N HCl and the resulting precipitate was filtered and dried to give the 85 mg of the crude HCl salt (100% yield) which was used as is in the next step. LC/MS (FA) ES+ 362.\

Step 4, Preparation of 2-(2-acetamidopyridin-4-yl)-4-(naphthalen-2-ylmethyl)thiazole-5-carboxylic acid a solution of (2-aminopyridin-4-yl)-4-(naphthalen-2-ylmethyl)thiazole-5-carboxylic acid, HCl salt (85.0 mg, 0.214 mmol) in acetic anhydride (1.15 mL, 12.2 mmol) and pyridine (0.300 mL, 3.71 mmol) was added DMAP (0.30 mg, 0.0024 mmol) and the resulting solution was stirred at room temperature overnight. The reaction was concentrated in vacuo and the residue was purified by silica gel chromatography (MeOH/DCM=0/100→40/60) to give 20 mg of the title compound (23% yield). LC/MS (FA) ES+ 404. NMR (400 MHz, DMSO-$d_6$) δ: 13.84 (bs, 1H), 10.71 (s, 1H), 8.63 (s, 1H), 8.41 (d, 1H, J=5.2 Hz), 7.86-7.82 (m, 3H), 7.76 (s, 1H), 7.57 (dd, 1H, J=5.2, 1.2 Hz), 7.49-7.42 (m, 3H), 4.70 (s, 2H), 2.10 (s, 3H).

The following analytical methods were used for examples below:

LCMS sectra were run on a Phenominex Luna 5 μm C18 50×4.6 mm column on a Hewlett-Packard HP1100 using the following gradients:

Method Formic Acid (FA): Acetonitrile containing 0 to 100 percent 0.1% formic acid in water (2.5 ml/min for a 3 minute run).

Method Ammonium Acetate (AA): Acetonitrile containing 0 to 100 percent 10 mM ammonium acetate in water (2.5 ml/min for a 3 minute run).

Chiral isomers were separated using chiral HPLC on a Chiralpak IC 250×25 mm 5 micron column using hexane/ethanol/diethylamine or hexane/isopropylalcohol/ethanol/diethylamine as mobil phase. Absolute configurations of the separated isomers were unknown, structures were assigned arbitrarily.

NMR spectrum is shown by proton NMR, with tetramethylsilane as the internal standard and using 300 MHz Bruker Avance spectrometer equipped with a 5 mm QNP probe and 400 MHz Bruker Avarice II spectrometer equipped with a 5 mm QNP probe for the measurement; δ values are expressed in ppm.

Example 42

Synthesis of 3-(4-chloro-3-fluorobenzyl)-4-cyano-5-morpholin-4-ylthiophene-2-carboxylic acid (Compound 94)

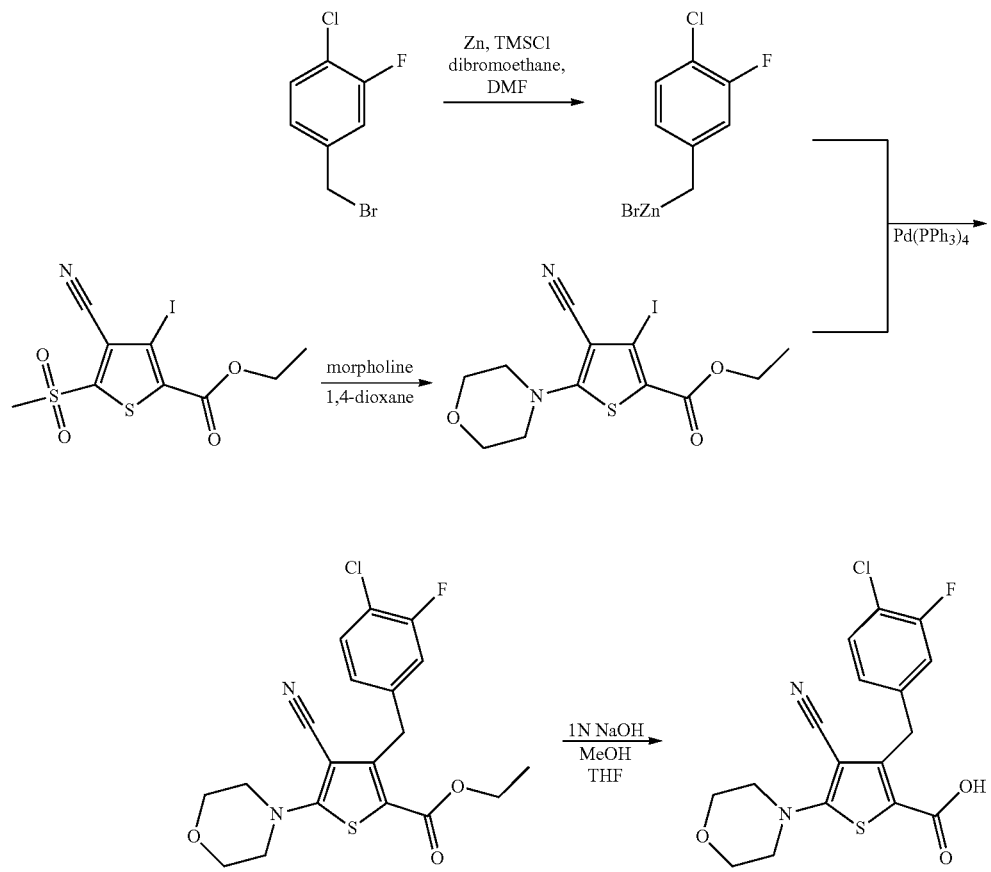

Step 1: Ethyl 4-cyano-3-iodo-5-morpholin-4-ylthiophene-2-carboxylate

To a 500 mL RBF containing ethyl 4-cyano-3-iodo-5-(methylsulfonyl)thiophene-2-carboxylate (17.20 g, 44.65 mmol, prepared as in WO 2009154741) was added anhydrous 1,4-dioxane (172.0 mL, 2204 mmol). To the resulting suspension was added morpholine (8.177 mL, 93.77 mmol). A reflux condenser was attached and the pink/orange heterogeneous suspension was heated to bath temp 90° C. and allowed to stir. Shortly after heating began, reaction mixture became a cherry red, homogenous solution. Reaction was stirred for 16 hours at 90° C. The reaction was then cooled to room temperature and diluted with water (100 mL). Mixture was filtered, and the solid was dried for in vacuo at 40° C. for 5 days to afford ethyl 4-cyano-3-iodo-5-morpholin-4-ylthiophene-2-carboxylate (14.3 grams, 82% yield). LCMS: (FA) ES+ 393; $^1$H NMR (400 MHz, DMSO) δ 4.24 (q, J=7.1, 2H), 3.78-3.70 (m, 4H), 3.63-3.57 (m, 4H), 1.26 (t, J=7.1, 3H).

Step 2: Ethyl 3-(4-chloro-3-fluorobenzyl)-4-cyano-5-morpholin-4-ylthiophene-2-carboxylate In a flame-dried scintillation vial, to a suspension of zinc (0.0998 g, 1.53 mmol) in N,N-dimethylformamide (1.36 mL, 17.6 mmol) were added 1,2-dibromoethane (0.003279 mL, 0.03805 mmol) and chlorotrimethylsilane (0.004830 mL, 0.03805 mmol). Stirred at room temperature for 15 min, at which point a solution of 3-fluoro-4-chlorobenzylbromide (0.341 g, 1.53 mmol) in N,N-dimethylformamide (1.36 mL, 17.6 mmol) was added. The resulting suspension was stirred at room temperature for 16 hours. A scintillation vial containing ethyl 4-cyano-3-iodo-5-morpholin-4-ylthiophene-2-carboxylate (199 mg, 0.507 mmol and bis(tri-t-butylphosphine)palladium(0) (12.96 mg, 0.02537 mmol) was purged via vacuum/backfilling with argon. To this was added the organozinc solution from above, and the resulting solution was stirred at 45° C. for 6 hours, at which point LC/MS showed complete conversion to a single new peak with mass representing desired product. The reaction mixture was transferred to a separatory funnel containing saturated NaHCO$_3$ (aq., 10 mL) and water (10 mL), and then diluted with EtOAc (40 mL). The layers were separated, and the aqueous layer was extracted 2×30 mL with EtOAc. The combined organic layers were washed 1× brine, dried over Na$_2$SO$_4$, filtered, and concentrated in vacuo to afford crude ethyl 3-(4-chloro-3-fluorobenzyl)-4-cyano-5-morpholin-4-ylthiophene-2-carboxylate as a brown oil that was used without further purification. LCMS: (FA) ES+ 409, 411

Step 3: 3-(4-Chloro-3-fluorobenzyl)-4-cyano-5-morpholin-4-ylthiophene-2-carboxylic acid (Compound 94)

To a solution of ethyl 3-(4-chloro-3-fluorobenzyl)-4-cyano-5-morpholin-4-ylthiophene-2-carboxylate in tetrahydrofuran (5.64 mL, 69.6 mmol) was added methanol (2.5 mL, 62 mmol) and 1 M sodium hydroxide in water (4.23 mL, 4.23 mmol) and the resulting suspension was stirred at room temp. The reaction was stirred for 16 hours at room temperature. Volatiles were then removed in vacuo, and the residue diluted with EtOAc (30 mL). Mixture was then transferred to a separatory funnel containing 1N HCl (5.0 mL) and water (10 mL), at which time the pH of aqueous layer was measured at ~2.0. Layers were separated, and the aqueous layer was extracted 3×20 mL with EtOAc. Combined organic layers were dried over Na$_2$SO$_4$, filtered, concentrated in vacuo. Resulting residue was adsorbed to celite, and the resulting solid was placed into a dryload cartridge and purified via column chromatography (gradient elution, 0-5% MeOH:CH$_2$Cl$_2$) to afford 3-(4-chloro-3-fluorobenzyl)-4-cyano-5-morpholin-4-ylthiophene-2-carboxylic acid (94) as a white solid (0.128 g, yield 66.3%). LCMS: (FA) ES+ 381, 383; $^1$H NMR (400 MHz, DMSO) δ 13.25 (s, 1H), 7.52 (dd, J=8.1, 8.1, 1H), 7.22 (dd, J=1.9, 10.5, 1H), 7.05 (dd, J=1.5, 8.3, 1H), 4.31 (s, 2H), 3.80-3.65 (dd, J=4.5, 5.2, 4H), 3.59-3.47 (dd, J=4.5, 5.2, 4H).

Compounds in the following table are prepared from appropriate starting materials in a method analogous to that of Example 42.

| | |
|---|---|
| 96 | LC/MS: (FA) ES– 395, 397 |
| 97 | LC/MS: (AA) ES+ 347 |
| 102 | LC/MS: (FA) ES– 411 |
| 105 | LC/MS: (AA) ES+ 359 |
| 106 | LC/MS: (FA) ES– 405, 407 |
| 107 | LC/MS: (FA) ES– 381 |
| 108 | LC/MS: (FA) ES+ 393, 395 |
| 112 | LC/MS: (FA) ES+ |
| 115 | LC/MS: (FA) ES+ 354 |
| 116 | LC/MS: (FA) ES+ 363 |
| 117 | LC/MS: (FA) ES– 391, 393 |
| 122 | LC/MS: (FA) ES– 391, 393 |
| 123 | LC/MS: (FA) ES+ 381 |
| 124 | LC/MS: (FA) ES– 395, 397 |
| 125 | LC/MS: (FA) ES+ 393, 395 |
| 126 | LC/MS: (FA) ES– 397, 399 |
| 127 | LC/MS: (FA) ES– 409, 411 |
| 300 | LC/MS: (FA) ES– 397 |

Example 43

Synthesis of 3-(4-chlorobenzyl)-4-cyano-5-(3,6-dihydro-2H-pyran-4-yl)thiophene-2-carboxylic acid (Compound 95)

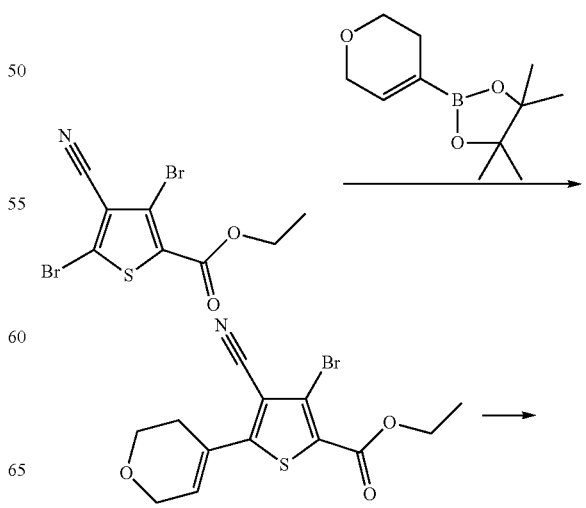

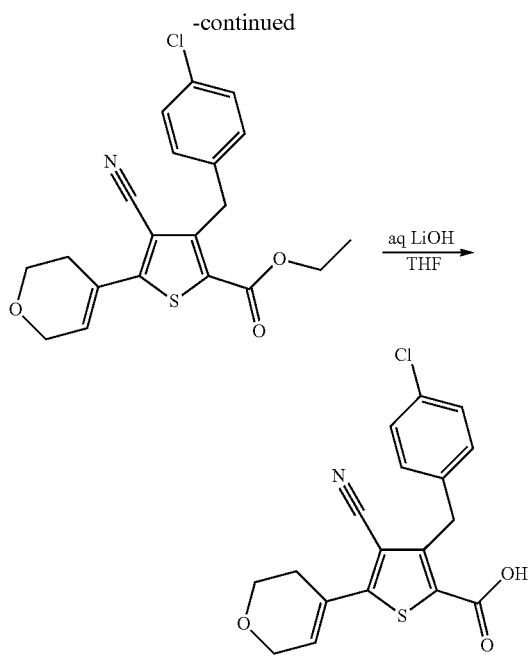

Step 1: Ethyl-3-bromo-4-cyano-5-(3,6-dihydro-2H-pyran-4-yl)thiophene-2-carboxylate To a microwave vial containing a suspension of ethyl 3,5-dibromo-4-cyanothiophene-2-carboxylate (300.0 mg, 0.8849 mmol, prepared as in MPI10-008P1M) and 3,6-dihydro-2h-pyran-4-boronic acid pinacol ester (204 mg, 0.973 mmol) in 1,4-dioxane (8.98 mL, 115 mmol) and water (0.925 mL, 51.3 mmol) were added tetrakis(triphenylphosphine)palladium(0) (102 mg, 0.0885 mmol) and cesium carbonate (865 mg, 2.65 mmol). The vial was sealed, degassed by bubbling argon through for 10 minutes, and then heated at 100° C. with stirring for 24 h. The reaction was then cooled to room temperature and partitioned between EtOAc and water. Layers were separated, and, the aqueous layer was extracted 2× with EtOAc. Combined organic layers were dried over Na$_2$SO$_4$, filtered, and concentrated in vacuo. Residue was subjected to column chromatography as a solution in DCM (40 g column, gradient elution 0 to 25% EtOAc/hexanes) to afford ethyl 3-bromo-4-cyano-5-(3,6-dihydro-2H-pyran-4-yl)thiophene-2-carboxylate as a white solid (183 mg, yield 63%). LCMS: (FA) ES+ 342, 344; $^1$H NMR (400 MHz, DMSO) δ 6.86-6.79 (m, 1H), 4.36-4.27 (m, 4H), 3.82 (dd, J=5.4, 5.4, 2H), 2.53 (ddd, J=2.1, 4.9, 10.0, 2H), 1.30 (dd, J=7.1, 7.1, 3H).

Step 2: Ethyl 3-(4-chlorobenzyl)-4-cyano-5-(3,6-dihydro-2H-pyran-4-yl)thiophene-2-carboxylate In a sealable reaction vial, ethyl 3-bromo-4-cyano-5-(3,6-dihydro-2H-pyran-4-yl)thiophene-2-carboxylate (180.0 mg, 0.5260 mmol) and a stir pea were azeotroped with toluene 3× and dried under high vacuum overnight. To the vial was added bis(tri-t-butylphosphine)palladium(0) (26.88 mg, 0.05260 mmol). Vial was evacuated and then back-filled with argon 2×, at which time was added via syringe 4-chlorobenzylzinc chloride as a 0.50 M solution in tetrahydrofuran (3.682 mL, 1.841 mmol). The reaction was heated with stirring at 60° C. for 2 h. Reaction was cooled to room temperature and then diluted with EtOAc and sat. aq. NH$_4$Cl. Mixture was transferred to a separatory funnel, the layers were separated, and the aqueous layer extracted 2× with EtOAc. The combined organic layers were washed with brine, dried over Na$_2$SO$_4$, filtered through a pad of Celite, and concentrated in vacuo to afford a yellow oil. The residue was dissolved in DCM and loaded onto 40 g ISCO column (gradient elution: 0-25% EtOAc/hexanes) to afford ethyl 3-(4-chlorobenzyl)-4-cyano-5-(3,6-dihydro-2H-pyran-4-yl)thiophene-2-carboxylate (92 mg, 43.6%) as a yellow solid. LC/MS: (AA) ES− 386, 388; $^1$H NMR (400 MHz, DMSO) δ 7.38-7.33 (m, 2H), 7.22 (m, 2H), 6.80-6.76 (m, 1H), 4.40 (s, 2H), 4.34-4.24 (m, 4H), 3.80 (dd, J=5.4, 5.4, 2H), 2.52 (dd, J=2.2, 5.0, 2H), 1.26 (dd, J=7.1, 7.1, 3H).

Step 3: 3-(4-chlorobenzyl)-4-cyano-5-(3,6-dihydro-2H-pyran-4-yl)thiophene-2-carboxylic acid (Compound 95)

To a round bottom flask containing ethyl 3-(4-chlorobenzyl)-4-cyano-5-(3,6-dihydro-2H-pyran-4-yl)thiophene-2-carboxylate (43.0 mg, 0.111 mmol) were added tetrahydrofuran (1.23 mL, 15.2 mmol), sodium hydroxide (1.0N in water, 0.925 mL, 0.925 mmol), and methanol (0.617 mL, 15.2 mmol). The mixture was stirred at room temperature overnight. Reaction was quenched via addition of 1N HCl in water (2 mL), then diluted with EtOAc and transferred to separatory funnel. The layers were separated, and the aqueous layer was extracted 2× with EtOAc. Combined organics were washed with brine, dried over Na$_2$SO$_4$, and filtered, at adsorbed to Celite (10 mL). Column chromatography (40 g ISCO column, gradient elution 0-8% MeOH/DCM afforded 3-(4-chlorobenzyl)-4-cyano-5-(3,6-dihydro-2H-pyran-4-yl)thiophene-2-carboxylic acid (95) (25 mg, 63%) as a white solid. LC/MS: (FA) ES− 358, 360; $^1$H NMR (400 MHz, DMSO) δ 14.04 (br s, 1H), 7.33 (d, J=8.5, 2H), 7.26 (d, J=8.5, 2H), 6.64 (s, 1H), 4.43 (s, 2H), 4.24 (d, J=2.9, 2H), 3.79 (dd, J=5.4, 5.4, 2H), 3.32 (br s, 2H).

Example 44

Synthesis of 4-(4-chloro-3-fluorobenzyl)-2-morpholin-4-yl-1,3-thiazole-5-carboxylic acid (Compound 118)

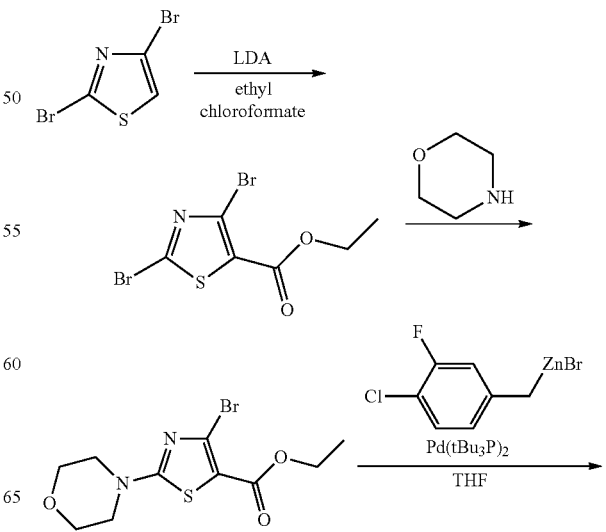

-continued

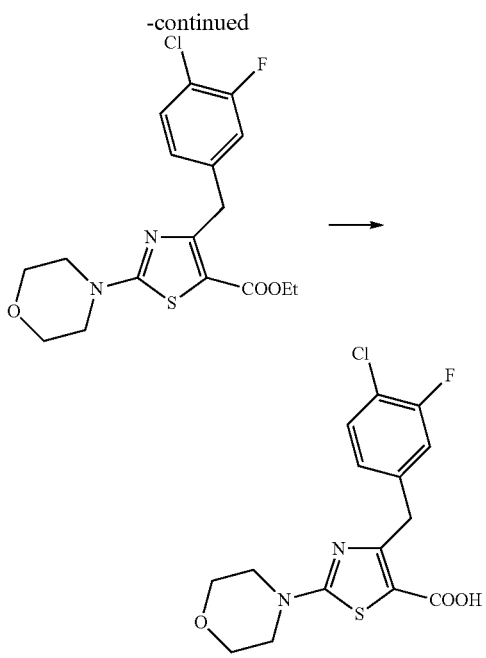

Step 1: Ethyl 2,4-dibromo-1,3-thiazole-5-carboxylate

In a 50 mL 2-neck RBF equipped with septa, a solution of N,N-Diisopropylamine (0.04374 g, 0.4322 mmol) in tetrahydrofuran (1.33 mL, 16.4 mmol) under atmosphere of argon was cooled at −78° C., at which point n-butyllithium (2.50 M in hexane, 0.1647 mL, 0.4116 mmol) was added dropwise and the resulting solution was stirred for 30 minutes at −78° C. To the above solution was added dropwise a solution of 2,4-dibromothiazole (0.100 g, 0.412 mmol) in tetrahydrofuran (1.33 mL, 16.4 mmol) at −78° C., and this solution was stirred for 30 min −78° C. Next, ethyl chloroformate (0.07872 mL, 0.8233 mmol) was added dropwise at −78° C. and the mixture was stirred for 30 minutes. The reaction was quenched by addition of water (20 mL), the layers were separated, and the aqueous layer was extracted with ethyl acetate (3×20 mL). The combined organic layers were washed with brine, dried over Na$_2$SO$_4$, filtered, and concentrated in vacuo. The residue was purified via silica gel column chromatography (12 g Analogix column, gradient elution 5% to 10% EtOAc in hexane) to afford ethyl 2,4-dibromo-1,3-thiazole-5-carboxylate (60 mg, yield 46%). LC/MS: (FA) ES+ 314, 316, 318; $^1$H NMR (400 MHz, CDCl$_3$) δ 4.37 (q, J=7.1, 2H), 1.44-1.33 (m, 3H).

Step 2: Ethyl 4-bromo-2-morpholin-4-yl-1,3-thiazole-5-carboxylate

In a sealable reaction vessel, to a suspension of ethyl 2,4-dibromo-1,3-thiazole-5-carboxylate (2.90 g, 9.21 mmol, prepared as in WO 2005026149) and cesium carbonate (9.00 g, 27.6 mmol) in tetrahydrofuran (24.3 mL, 299 mmol) was added morpholine (0.883 mL, 10.1 mmol), at which point the vessel was sealed and the mixture was heated with stirring at 90° C. for 4 hours. Reaction mixture was diluted with EtOAc and water and transferred to a separatory funnel. Layers were separated, and the organic layer was washed with water, dried over Na$_2$SO$_4$, filtered, and concentrated in vacuo. Residue was subjected to column chromatography (gradient elution, 0 to 50% EA in hexanes) to afford ethyl 4-bromo-2-morpholin-4-yl-1,3-thiazole-5-carboxylate (2.4 g, yield 81%) as a white solid. LC/MS: (FA) ES+ 321, 323; $^1$H NMR (300 MHz, CDCl$_3$) δ 4.30 (dd, J$_7$7.1, 7.1, 2H), 3.82-3.75 (m, 4H), 3.58-3.50 (m, 4H), 1.34 (dd, J=7.1, 7.1, 3H).

Step 3: Ethyl-4-(4-chloro-3-fluorobenzyl)-2-morpholin-4-yl-1,3-thiazole-5-carboxylate In a 50 ml flame-dried round bottom flask, a suspension of zinc (0.183 g, 0.00280 mol), chlorotrimethylsilane (8.9 uL, 0.000070 mol) and 1,2-dibromoethane (6.0 uL, 0.000070 mol) in N,N-dimethylformamide (2.4 mL, 0.031 mol) was stirred for 15 minutes. To this was added a solution of 3-fluoro-4-chlorobenzylbromide (0.626 g, 0.00280 mol) in N,N-dimethylformamide (4.8 mL, 0.062 mol), and the resulting suspension was stirred overnight at room temperature. To a flame-dried 50 ml round bottom flask containing ethyl 4-bromo-2-morpholin-4-yl-1,3-thiazole-5-carboxy late (0.300 g, 0.000934 mol) and bis(tri-t-butylphosphine)palladium(0) (36 mg, 0.000070 mol) was added the organozinc solution from above, and the reaction was heated with stirring at 60° C. for 60 min. Reaction was quenched with saturated ammonium chloride, and then transferred to a separatory funnel containing water (10 mL) and EtOAc (40 mL). The layers were separated, and the aqueous layer was extracted 2×30 mL with EtOAc. The combined organic layers were washed 1× brine, dried over Na$_2$SO$_4$, filtered, and concentrated in vacuo. The resulting residue was dissolved in DCM, adsorbed onto silica gel and purified via column chromotography (24 gram Isco column, gradient elution, 0-50% EtOAc/hexanes) to afford ethyl 4-(4-chloro-3-fluorobenzyl)-2-morpholin-4-yl-1,3-thiazole-5-carboxylate (245 mg, yield 68.2%).

Step 4: 4-(4-chloro-3-fluorobenzyl)-2-morpholin-4-yl-1,3-thiazole-5-carboxylic acid (Compound 118)

In a 50 mL round bottom flask were combined ethyl 4-(4-chloro-3-fluorobenzyl)-2-morpholin-4-yl-1,3-thiazole-5-carboxylate (0.245 g, 0.000637 mol), tetrahydrofuran (5.49 mL, 0.0677 mol) and a solution of lithium hydroxide (2.0 M in water, 3.18 mL, 0.00637 mol). The mixture was heated at 80° C. with stirring for 2 days, and then cooled to room temperature and diluted with water. Reaction mixture was then carefully adjusted to pH 5 via addition of 1N HCl and transferred to a separatory funnel containing EtOAc (40 mL). Layers were separated, and the aqueous layer was extracted 2×30 mL with EtOAc. The combined organic layers were washed 1× brine, dried over Na$_2$SO$_4$, filtered, and concentrated in vacuo to afford a white solid, which was dissolved in DCM and adsorbed onto silica gel. Column chromatography (4 g column, gradient elution 0-20% MeOH in DCM) then afforded 4-(4-chloro-3-fluorobenzyl)-2-morpholin-4-yl-1,3-thiazole-5-carboxylic acid (118) (31 mg, 14%). LC/MS: (FA) ES+ 357, 359; NMR (400 MHz, DMSO) δ 12.79 (s, 1H), 7.48 (t, 0.1=8.1, 1H), 7.24 (dd, J=1.9, 10.5, 1H), 7.08 (dd, J=1.5, 8.3, 1H), 4.24 (s, 2H), 3.71-3.62 (m, 4H), 3.46-3.38 (m, 4H).

Compounds in the following table are prepared from appropriate starting materials in a method analogous to that of Example 44

| 91 | LC/MS: (FA) ES+ 339 |
| 93 | LC/MS: (FA) ES+ 330 |
| 98 | LC/MS: (FA) ES+ 355 |
| 101 | LC/MS: (FA) ES+ 357, 359 |

| | |
|---|---|
| 103 | LC/MS: (FA) ES+ 335 |
| 104 | LC/MS: (FA) ES+ 373, 375, 377 |
| 109 | LC/MS: (FA) ES+ 389 |
| 111 | LC/MS: (FA) ES+ 373 |
| 114 | LC/MS: (FA) ES+ 373, 375, 377 |
| 119 | LC/MS: (FA) ES+ 323 |
| 120 | LC/MS: (FA) ES+ 369, 371 |

Example 45

Synthesis of 4-(2,3-dihydro-1,4-benzodioxin-6-ylm-ethyl)-2-(morpholin-4-yl)-1,3-thiazole-5-carboxylic acid (Compound 110)

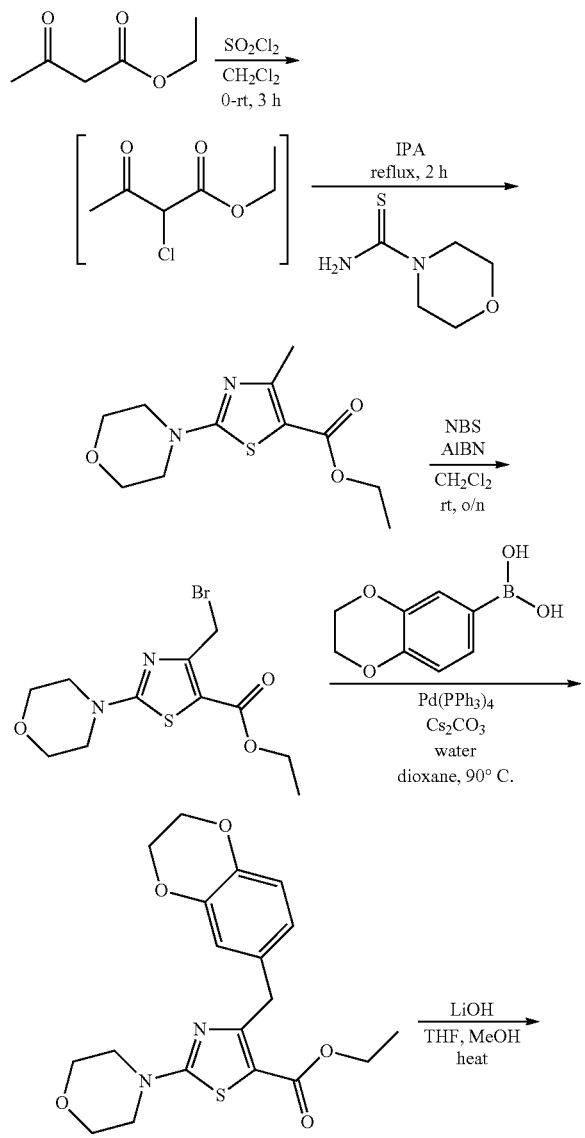

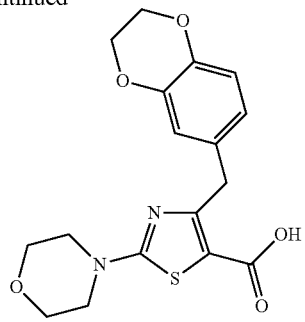

Step 1: Butanoic acid, 2-chloro-3-oxo-, ethyl ester

In a 500 mL round bottomed flask, to a solution of 3-oxobutanoic acid ethyl ester (7.69 mL, 60.3 mmol) in methylene chloride (150 mL, 2300 mmol) at 0° C. was slowly added sulfuryl chloride (6.30 mL, 77.8 mmol). The mixture was stirred for 3 hours, and then quenched with saturated NaHCO₃. Mixture was transferred to a separatory funnel the layers were separated. The organic layer was washed 1× brine, dried with Na₂SO₄, filtered, and concentrated in vacuo to afford butanoic acid, 2-chloro-3-oxo-, ethyl ester which was immediately used without further purification.

Step 2: Ethyl 4-methyl-2-(morpholin-4-yl)-1,3-thiazole-5-carboxylate

In a 100 mL round bottomed flask, to a solution of butanoic acid, 2-chloro-3-oxo-, ethyl ester (11.2 g, 68.4 mmol) in isopropyl alcohol (250 mL, 3300 mmol) was added morpholine-4-carbothioicacidamide (10.0 g, 68.4 mmol). The mixture was stirred at reflux for 1 hour, and then stirred at room temperature for 3 days. Volatiles were removed in vacuo, and the resulting residue was dissolved in ethyl acetate and diluted with saturated, aqueous sodium bicarbonate. The mixture was transferred to a separatory funnel, the layers were separated, and the organic layer dried with Na2SO4, filtered and concentrated in vacuo. The crude product was dissolved in DCM, adsorbed onto silica gel, and purified via column chromatography (120 g Isco column, gradient elution, 0-100% EtOAc/hexanes) to afford ethyl 4-methyl-2-(morpholin-4-yl)-1,3-thiazole-5-carboxylate (14.51 g, yield for 2 steps, 82%). LC/MS: (FA) ES+ 257, 259; $^1$H NMR (400 MHz, CDCl₃) δ 4.26 (dd, J=7.1, 7.1, 2H), 3.87-3.67 (m, 4H), 3.59-3.42 (m, 4H), 2.55 (s, 3H), 1.33 (dd, J=7.1, 7.1, 3H).

Step 3: Ethyl 4-(bromomethyl)-2-(morpholin-4-yl)-1,3-thiazole-5-carboxylate

To a round bottom flask containing a solution of ethyl-4-methyl-2-(morpholin-4-yl)-1,3-thiazole-5-carboxylate (14.50 g, 56.57 mmol) in methylene chloride (400 mL, 6000 mmol) were added N-bromosuccinimide (10.07 g, 56.57 mmol) and 2,2'-azo-bis-isobutyronitrile (464 mg, 2.83 mmol). The mixture was stirred at reflux overnight. Reaction was quenched via addition of 10% aqueous sodium bisulfite (20 g in 200 ml water) and stirred for 20 minutes. Mixture was transferred to a separatory funnel, the layers separated, and the aqueous layer was extracted 2×DCM. Combined organic layers were dried with Na₂SO₄, filtered, and concentrated in vacuo. The resulting residue was dissolved in DCM and adsorbed onto silica gel. Purification via column chromatography (220 g Isco column, gradient elution 0-10% EtOAc in 1:1 DCM:hexanes) afforded ethyl 4-(bromomethyl)-2-(morpholin-4-yl)-1,3-thiazole-5-carboxylate (13.5 g, yield 71.1%). LC/MS: (FA) ES+ 335, 337; NMR (300 MHz, CDCl$_3$) δ 4.76 (s, 2H), 4.30 (dd, J=7.1, 7.1, 2H), 3.88-3.72 (m, 4H), 3.62-3.49 (m, 4H), 1.35 (dd, J=7.1, 7.1, 3H).

Step 4: Ethyl 4-(2,3-dihydro-1,4-benzodioxin-6-ylmethyl)-2-(morpholin-4-yl)-1,3-thiazole-5-carboxylate Ethyl 4-(bromomethyl)-2-(morpholin-4-yl)-1,3-thiazole-5-carboxylate (109.4 mg, 0.326 mmol), 1,4-benzodioxane-6-boronic acid (91.0 mg, 0.506 mmol), tetrakis(triphenylphosphine)palladium(0) (43.0 mg, 0.0372 mmol), cesium carbonate (430 mg, 1.3 mmol), 1,4-dioxane (2.19 mL, 28.0 mmol) and water (43.8 uL, 2.43 mmol) were combined in a vial equipped with a stirbar. The vial was sealed and the atmosphere was replaced with nitrogen. The vial was sonicated for 1 minute then heated at 90° C. (heating block temperature) with stirring for 1 hour. The reaction was cooled to room temperature, the vial was opened and the contents were quenched into stirring saline. The quench mixture was transferred to a separatory funnel and extracted twice with ethyl acetate. The extracts were combined, washed with saline, dried over sodium sulfate, filtered, and concentrated in vacuo to leave an orange oil. The crude residue was purified by silica gel chromatography (gradient elution: ethyl acetate/hexane from 0/100 to 100/0) to give ethyl 4-(2,3-dihydro-1,4-benzodioxin-6-ylmethyl)-2-(morpholin-4-yl)-1,3-thiazole-5-carboxylate (60 mg, 47% yield) as a white powder. LC/MS (FA) ES+ 391; $^1$H NMR (300 MHz, DMSO-d6) δ: 6.67-6.74 (m, 3H), 4.20 (q, 2H, J=7.1 Hz), 4.17 (s, 4H), 4.07 (s, 2H), 3.69-3.65 (m, 4H), 3.46-3.43 (m, 4H), 1.24 (t, 3H, J=7.1 Hz).

Step 5: 4-(2,3-dihydro-1,4-benzodioxin-6-ylmethyl)-2-(morpholin-4-yl)-1,3-thiazole-5-carboxylic acid (Compound 110)

Ethyl 4-(2,3-dihydro-1,4-benzodioxin-6-ylmethyl)-2-(morpholin-4-yl)-1,3-thiazole-5-carboxylate (58.0 mg, 0.000148 mol) was placed in a 50 ml round bottom flask equipped with a stirbar. Tetrahydrofuran (2.25 mL, 0.0277 mol) and methanol (0.50 mL, 0.012 mol) were added and the mixture was stirred to give a clear solution. A solution of lithium hydroxide in water (2.0M, 0.750 mL, 0.00150 mol) was added in a single portion, resulting in a pale yellow solution which was stirred at room temperature under an atmosphere of nitrogen for 15 minutes. The reaction was then heated at reflux for 2.5 hours, cooled to rt, and diluted with water (~25 ml) to give a clear slightly gray solution, which was allowed to stir at room temperature overnight under an atmosphere of nitrogen. 1 N HCl (~1.8 ml) was slowly added to the stirring solution to lower the pH to ~3 (pH paper) whereupon a white precipitate formed. The mixture was stirred for ~15 minutes, at which point the solid was collected on a fritted funnel, washed with water, and dried on the funnel with house vacuum under a stream of nitrogen for several hours to yield 4-(2,3-dihydro-1,4-benzodioxin-6-ylmethyl)-2-(morpholin-4-yl)-1,3-thiazole-5-carboxylic acid (110) (45 mg, 84% yield) as a slightly gray powder. LC/MS (FA) ES+ 363; $^1$H NMR (300 MHz, DMSO) δ 12.65 (s, 1H), 6.76-6.64 (m, 3H), 4.17 (s, 4H), 4.08 (s, 2H), 3.77-3.61 (m, 4H), 3.51-3.34 (m, 4H).

Compounds in the following table are prepared from appropriate starting materials in a method analogous to that of Example 45.

| | |
|---|---|
| 99 | LC/MS: (FA) ES+ 357, 359 |
| 128 | LC/MS: (AA) ES+ 373 |
| 286 | LC/MS: (FA) ES+ 361 |
| 288 | LC/MS: (AA) ES+ 385 |
| 289 | LC/MS: (FA) ES+ 376 |
| 290 | LC/MS: (FA) ES+ 391, 393, 395 |
| 292 | LC/MS: (AA) ES+ 356 |
| 299 | LC/MS: (AA) ES+ 373 |
| 302 | LC/MS: (FA) ES+ 358 |
| 303 | LC/MS: (FA) ES+ 439, 441 |
| 310 | LC/MS: (AA) ES+ 373 |
| 314 | LC/MS: (AA) ES+ 373 |
| 318 | LC/MS: (FA) ES+ 398 |
| 319 | LC/MS: (AA) ES+ 373 |
| 325 | LC/MS: (FA) ES+ 380 |
| 328 | LC/MS: (FA) ES+ 344 |
| 335 | LC/MS: (AA) ES+ 385 |
| 338 | LC/MS: (AA) ES+ 373 |
| 339 | LC/MS: (FA) ES+ 365 |
| 340 | LC/MS: (AA) ES+ 373 |
| 341 | LC/MS: (AA) ES+ 345 |
| 344 | LC/MS: (AA) ES+ 356 |

Example 46

Synthesis of 4-(4-chlorobenzyl)-2-(3,6-dihydro-2H-pyran-4-yl)-1,3-thiazole-5-carboxylic acid (Compound 100)

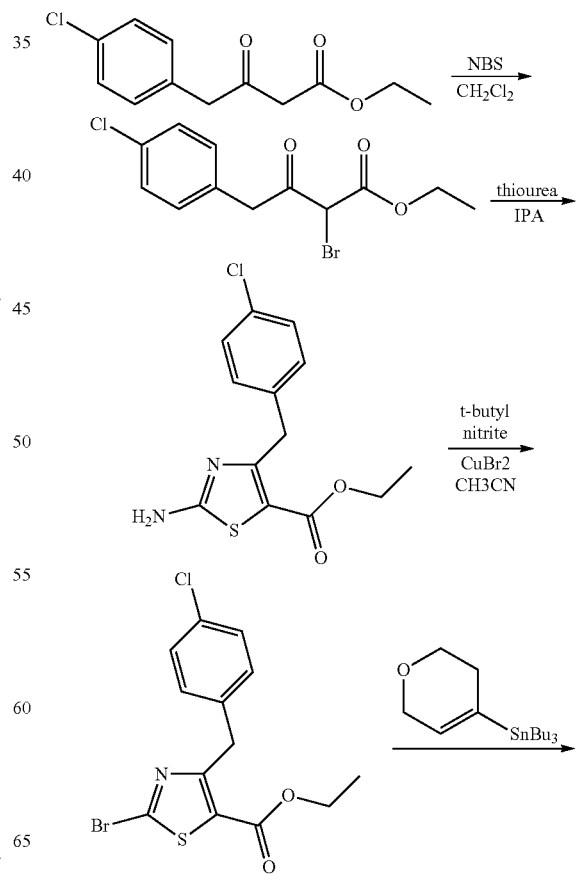

-continued

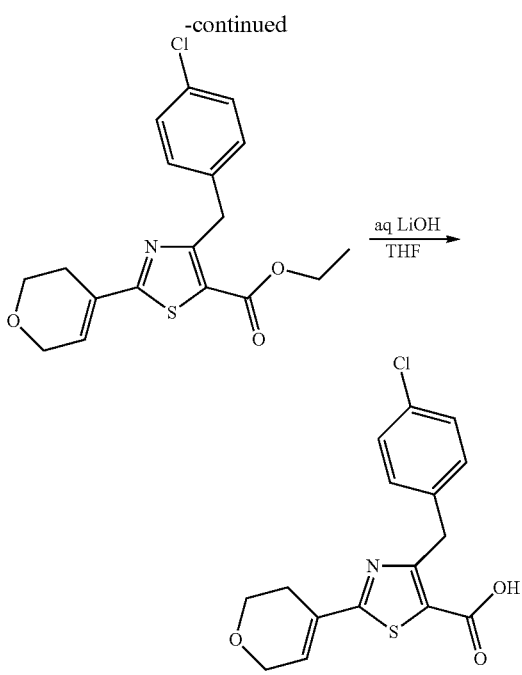

Step 1: Ethyl 2-bromo-4-(4-chlorophenyl)-3-oxobutanoate

In a 250 mL round bottomed flask, to a solution of ethyl 4-(4-chlorophenyl)-3-oxobutanoate (4.04 g, 16.8 mmol) in methylene chloride (100 mL, 2000 mmol) was added N-bromosuccinimide (3.13 g, 17.6 mmol) and the mixture was stirred for 3 h at room temperature. Reaction was quenched via addition of a 10% aqueous solution of NaHSO$_3$ (50 mL), and the resulting biphasic mixture was vigorously stirred for 15 minutes. The reaction mixture was transferred to a separatory funnel, the layers were separated, and the aqueous layer was extracted with CH$_2$Cl$_2$ (30 mL). The combined organic layers were washed with a saturated aqueous solution of NaHCO$_3$ (50 mL), dried over anhydrous MgSO$_4$, filtered, and concentrated in vacuo to afford ethyl 2-bromo-4-(4-chlorophenyl)-3-oxobutanoate (5.23 g, yield 97.5%) as a yellow oil that was used without further purification. LC/MS (FA) ES− 317, 319, 321.

Step 2: Ethyl 2-amino-4-(4-chlorobenzyl)-1,3-thiazole-5-carboxylate

In a 100 mL round bottomed flask, to a solution of ethyl 2-bromo-4-(4-chlorophenyl)-3-oxobutanoate (990 mg, 3.1 mmol) in isopropyl alcohol (20 mL, 300 mmol) was added thiourea (590 mg, 7.8 mmol) and the resulting mixture was stirred at reflux for 16 hours. The mixture was allowed to cool to room temperature and then concentrated under reduced pressure. The residue was suspended in EtOAc (50 mL) and then washed with a saturated aqueous solution of NaHCO$_3$ (50 mL), brine (50 mL). The resulting organic layer was dried over anhydrous MgSO$_4$, filtered, and concentrated to afford ethyl 2-amino-4-(4-chlorobenzyl)-1,3-thiazole-5-carboxylate (900 mg, yield>99%) as a yellowish solid that was used without further purification. LC/MS (FA) ES+ 297, 299.

Step 3: Ethyl 2-bromo-4-(4-chlorobenzyl)-1,3-thiazole-5-carboxylate

In a 250 mL round bottomed flask, to a solution of ethyl 2-amino-4-(4-chlorobenzyl)-1,3-thiazole-5-carboxylate (786 mg, 2.65 mmol) in acetonitrile (75 mL, 1400 mmol) was added copper(II) bromide (963 mg, 4.31 mmol). The suspension was stirred at room temperature for 15 minutes to afford a green solution. To the mixture was added tert-butyl nitrite (0.630 mL, 5.30 mmol) and the reaction was then heated with stirring at 70° C. for 1.5 hours. The reaction mixture was allowed to cool to room temperature and then concentrated under reduced pressure. The residue was purified by column chromatography (80 gram column, gradient elution 10% to 50% EtOAc/hexanes) to afford ethyl 2-bromo-4-(4-chlorobenzyl)-1,3-thiazole-5-carboxylate (820 mg; yield 86%) as a yellow syrup. LC/MS (FA) ES+ 360, 362, 364; $^1$H NMR (400 MHz, CDCl$_3$) δ 7.33-7.20 (m, 4H), 4.44 (s, 2H), 4.34 (dd, J=7.1, 7.1, 2H), 1.36 (dd, J=7.1, 7.1, 3H).

Step 4: Ethyl-4-(4-chlorobenzyl)-2-(3,6-dihydro-2H-pyran-4-yl)-1,3-thiazole-5-carboxylate A mixture of ethyl 2-bromo-4-(4-chlorobenzyl)-1,3-thiazole-5-carboxylate (289 mg, 0.802 mmol), tributyl(3,6-dihydro-2H-pyran-4-yl)stannane (332 mg, 0.890 mmol), tetrakis(triphenylphosphine)palladium(0) (46.4 mg, 0.0401 mmol), lithium chloride (1.20E2 mg, 2.82 mmol) and copper(I) iodide (45.8 mg, 0.241 mmol) in dry 1,4-dioxane (6.26 mL, 80.2 mmol) was degassed by vacuum and backfilling with argon four times, and then heated under argon at reflux for 3 hours. The mixture was filtered thru Celite, washing with 10% MeOH in DCM. Volatiles were removed in vacuo, and the residue was adsorbed to silica gel by concentrating a DCM solution to which silica gel had been added. Column chromatography (gradient elution, 0 to 20% EA in hexanes) afforded ethyl-4-(4-chlorobenzyl)-2-(3,6-dihydro-2H-pyran-4-yl)-1,3-thiazole-5-carboxylate (113 mg, 38.9%) as a white solid. $^1$H NMR (300 MHz, DMSO) δ 7.35-7.31 (m, 2H), 7.27-7.23 (m, 2H), 6.86-6.83 (m, 1H), 4.40 (s, 2H), 4.29 (q, J=6.9, 2H), 4.25-4.22 (m, 2H), 3.78 (t, J=5.4, 2H), 2.51-2.46 (m, 2H), 1.27 (t, J=6.9 Hz, 3H).

Step 5: 4-(4-chlorobenzyl)-2-(3,6-dihydro-2H-pyran-4-yl)-1,3-thiazole-5-carboxylic acid (Compound 100)

In a round bottom flask equipped with a stir bar, a solution of ethyl 4-(4-chlorobenzyl)-2-(3,6-dihydro-2H-pyran-4-yl)-1,3-thiazole-5-carboxylate (109 mg, 0.300 mmol) in tetrahydrofuran (3.33 mL, 41.1 mmol) and methanol (1.67 mL, 41.1 mmol) was treated with lithium hydroxide (1.0M in water, 2.40 mL, 2.40 mmol). The mixture was stirred at room temperature overnight. pH was adjusted to ~3 via addition of 1N aqueous HCl solution, and the reaction was then diluted with EtOAc and transferred to separatory funnel. The layers were separated, and the aqueous layer was extracted 2× with EtOAc. Combined organic layers were washed with brine, dried over Na$_2$SO$_4$, filtered, and concentrated in vacuo. Column chromatography (gradient elution, 0 to 10% MeOH in DCM) afforded 4-(4-chlorobenzyl)-2-(3,6-dihydro-2H-pyran-4-yl)-1,3-thiazole-5-carboxylic acid (100) (53 mg, yield 53% as a white powder. LCMS: (FA) ES+ 336; $^1$H NMR (400 MHz, DMSO) δ 13.52 (bs, 1H), 7.35-7.31 (m, 2H), 7.27-7.23

(m, 2H), 6.82-6.79 (m, 1H), 4.40 (s, 2H), 4.24-4.22 (m, 2H), 3.77 (t, J=5.4, 2H), 2.50-2.45 (m, 2H).

Example 47

Synthesis of 3-[amino(4-chlorophenyl)methyl]-4-cyano-5-(morpholin-4-yl)thiophene-2-carboxylic acid hydrochloride (Compound 113)

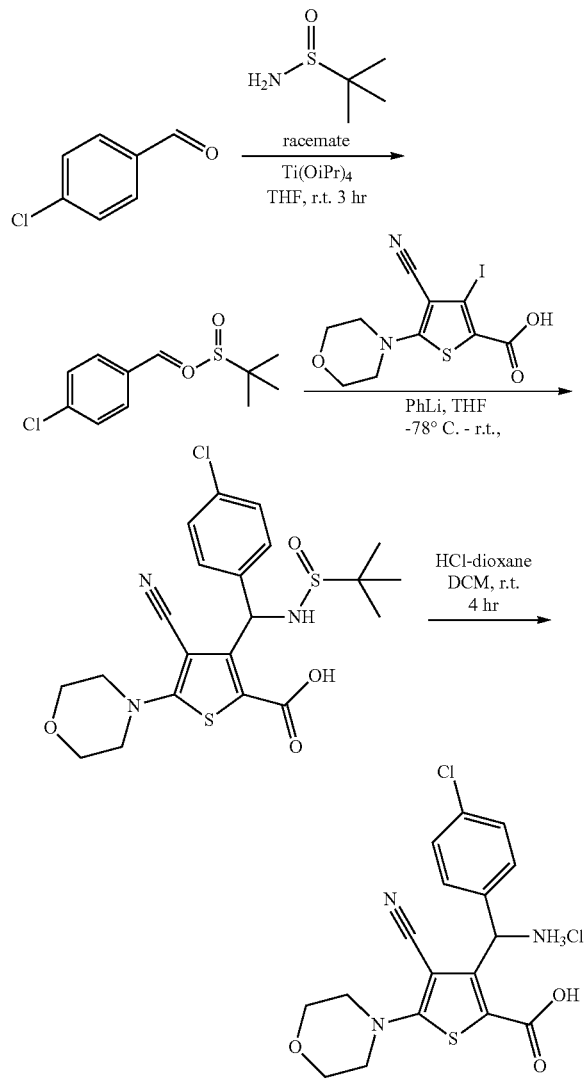

Step 1: N-[(E)-(4-chlorophenyl)methylene]-2-methylpropane-2-sulfinamide

To a solution of 4-chlorobenzaldehyde (2.88 g, 20.5 mmol), (S)-(−)-2-methyl-2-propanesulfinamide (1.40 g, 11.6 mmol), and (R)-(+)-2-methyl-2-propanesulfinamide (1.40 g, 11.6 mmol) in anhydrous tetrahydrofuran (30.0 mL) under nitrogen atmosphere was added titanium tetraisopropoxide (6.00 mL, 20.3 mmol) dropwise. The clear solution was stirred at room temperature for 3 hours. Methylene chloride (200 mL) and water (2.0 mL) were added and the mixture was stirred at room temperature for 1 hour. The suspension was filtered through Celite and washed with DCM. The filtrate was concentrated in vacuo and purified by column chromatography (gradient elution: 0-20% EtOAc/hexane) to afford N-[(E)-(4-chlorophenyl)methylene]-2-methylpropane-2-sulfinamide (3.93 g, yield 78.7%). LCMS: (FA) ES+ 244; $^1$H NMR (400 MHz, CDCl$_3$) δ 8.55 (s, 1H), 7.78-7.80 (d, 2H, J=8.53 Hz), 7.44-7.47 (d, 2H, J=8.53 Hz), 1.26 (s, 9H).

Step 2: 3-{[(tert-butylsulfinyl)amino](4-chlorophenyl)methyl}-4-cyano-5-(morpholin-4-yl)thiophene-2-carboxylic acid 4-cyano-3-iodo-5-morpholin-4-ylthiophene-2-carboxylic acid (1.44 g, 3.96 mmol, prepared as in WO2009/154741) was suspended in anhydrous tetrahydrofuran (80.0 mL, 986 mmol), sonicated under nitrogen atmosphere for 10 min, and cooled in an acetone-dry ice bath for 10 minutes. Phenyllithium (1.8M in n-butyl ether, 8.81 mL, 15.9 mmol) was added dropwise over 7 minutes. The suspension was stirred with cooling for 5 minutes, at which point the cooling bath was removed and the suspension was stirred without cooling for 7 minutes. Reaction mixture was recooled in an acetone-dry ice bath for 10 minutes, at which point a solution of N-[(E)-(4-chlorophenyl)methylene]-2-methylpropane-2-sulfinamide (2.91 g, 11.9 mmol) in anhydrous tetrahydrofuran (20.0 mL, 246 mmol) was added dropwise over 8 minutes, and the mixture was stirred with cooling for 30 minutes. The mixture was quenched with methanol (5.0 mL, 120 mmol) and then acetic acid (1.0 mL, 18 mmol), and allowed to warm to room temperature. The volatiles were removed in vacuo, and the residue was diluted with water and EtOAc. The layers were separated, and the aqueous layer was extracted with 2×EtOAc. The combined organic layers were washed with water and brine, dried over Na$_2$SO$_4$, filtered, and concentrated in vacuo. Purification via column chromatography (gradient elution: AcOH/MeOH/DCM, 0/0/100 to 0.5/4.5/95) afforded 3-{[(tert-butylsulfinyl)amino](4-chlorophenyl)methyl}-4-cyano-5-(morpholin-4-yl)thiophene-2-carboxylic acid as a mixture of diastereomers. Major diastereomer: 1.19 g, yield 62.2%. (FA) ES+ 482; ES− 480; $^1$H NMR (400 MHz, CDCl$_3$) δ 7.31-7.33 (m, 2H), 7.15-7.17 (m, 2H), 6.14 (br s, 2H), 3.87-3.89 (m, 4H), 3.60-3.63 (m, 4H), 1.21 (s, 9H). Minor diastereomer: (0.292 g, yield 15.3%). (FA) ES+ 482; ES− 480; $^1$H NMR (400 MHz, CDCl$_3$) δ 7.26-7.34 (m, 4H), 6.29-6.38 (m, br, 2H), 3.84-3.86 (m, 4H), 3.56-3.60 (m, 4H), 1.35 (s, 9H).

Step 3: 3-[amino(4-chlorophenyl)methyl]-4-cyano-5-(morpholin-4-yl)thiophene-2-carboxylic acid hydrochloride (Compound 113)

To a solution of 3-{[(tert-butylsulfinyl)amino](4-chlorophenyl)methyl}-4-cyano-5-(morpholin-4-yl)thiophene-2-carboxylic acid (1.46 g, 3.03 mmol) in methylene chloride (25.0 mL) was slowly added hydrochloric acid (4M in 1,4-dioxane, 15.0 mL), and the resultant suspension was stirred at room temperature for 1 hour. The suspension was filtered through a fine frit funnel. The collected solid was washed with DCM and dried in vacuo to afford 3-[amino(4-chlorophenyl)methyl]-4-cyano-5-(morpholin-4-yl)thiophene-2-carboxylic acid hydrochloride (113) (1.10 g, yield 86.5%) as a white powder. LCMS: (FA) ES+ 378; ES− 376; $^1$H NMR (400 MHz, CD3OD) δ 7.44-7.90 (m, 4H), 5.84 (s, 1H), 3.81-3.84 (m, 4H), 3.64-3.67 (m, 4H).

Compounds in the following table are prepared from appropriate starting materials in a method analogous to that of Example 47.

| 291 | LC/MS: (FA) ES+ 412, 413; ES− 410, 412 |
| 317 | LC/MS: (FA) ES− 454, 456 |
| 323 | LCMS: (FA) ES+ 498; ES− 496 |
| 342 | LC/MS: (FA) ES+ 516, 518; ES− 514, 516 |
| 353 | LC/MS: (FA) ES+ 420 |
| 354 | LC/MS: (FA) ES+ 452 |
| 357 | LC/MS: (FA) ES+ 394; ES− 392 |

Example 48

Synthesis of 4-[1-(4-chlorophenyl)ethyl]-2-(morpholin-4-yl)-1,3-thiazole-5-carboxylic acid (Compound 121)

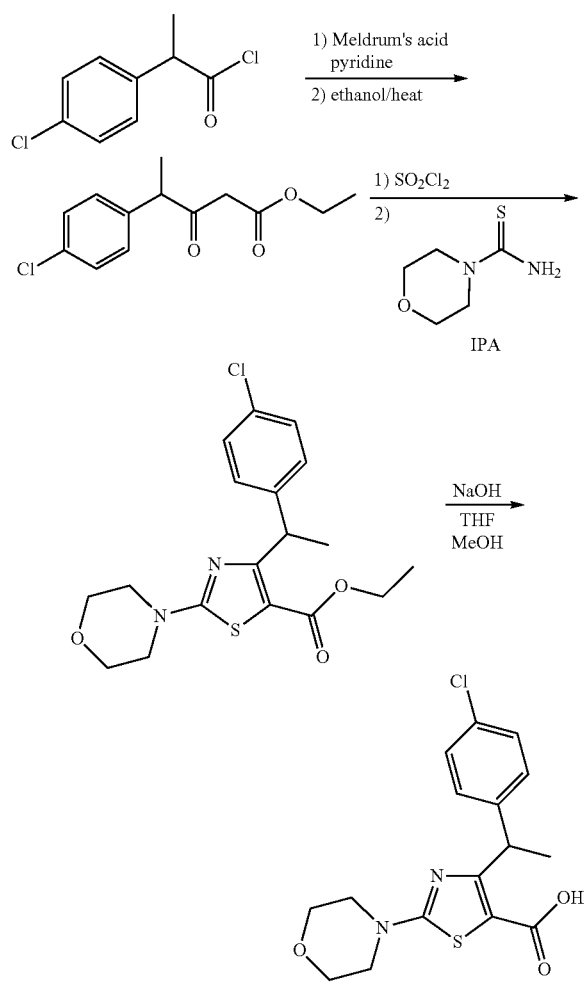

Step 1: Ethyl 4-(4-chlorophenyl)-3-oxopentanoate

In a round bottomed flask, to a suspension of 2,2-dimethyl-1,3-dioxane-4,6-dione (Meldrum's acid, 2.91 g, 20.2 mmol) in methylene chloride (11.3 mL, 177 mmol) at −10° C. (internal temp) was added pyridine (4.00 mL, 49.5 mmol) over 10 minutes. To the resulting clear solution at −10° C., was added dropwise a solution of 2-(4-chlorophenyl)propanoyl chloride (4.10 g, 20.2 mmol) in methylene chloride (7.93 mL, 124 mmol) over 1 h. The reaction mixture was then stirred for 1 h at −10° C., and then for 1 hour at room temperature. The mixture was poured into hydrochloric acid (2.00M in water, 45.3 mL, 90.6 mmol) and ice, the layers were separated, and the aqueous phase was extracted with $CH_2Cl_2$. The combined organic layers were washed with 1N HCl and brine, dried over anhydrous $MgSO_4$, filtered, and concentrated in vacuo. To the crude residue was added ethanol (39.6 mL, 679 mmol) and the mixture was heated at reflux (89 degree bath temp) for 3 hours. After cooling to room temp, the volatiles were removed in vacuo. Residue was adsorbed onto silica using DCM and purified via column chromatography (gradient elution: 0 to 20% EtOAc/hexanes to afford ethyl 4-(4-chlorophenyl)-3-oxopentanoate (2.94 g, 92%) as a yellow oil. LCMS: (FA) ES+ 255; $^1$H NMR (400 MHz, DMSO) δ 7.34-7.30 (m, 2H), 7.17-7.13 (m, 2H), 4.16-4.09 (m, 2H), 3.90 (q, J=7.2, 1H), 3.40 (d, J=15.6, 1H), 3.30 (d, J=15.6, 1H), 1.40 (d, J=6.8, 3H), 1.23 (t, J=7.2, 3H).

Step 2: Ethyl 4-[1-(4-chlorophenyl)ethyl]-2-(morpholin-4-yl)-1,3-thiazole-5-carboxylate To a solution of ethyl 4-(4-chlorophenyl)-3-oxopentanoate (1.78 g, 6.99 mmol) in methylene chloride (22.4 mL, 349 mmol) at 0° C. was added sulfuryl chloride (566 uL, 6.99 mmol) and the mixture was stirred overnight at room temperature. The reaction was quenched with a saturated aqueous solution of $NaHCO_3$ and transferred to a separatory funnel. The layers were separated and the organic layer was washed with brine, dried over anhydrous $MgSO_4$, filtered, and concentrated in vacuo. The resulting residue was used immediately without further purification.
In a round bottomed flask, to a solution of the crude residue from above in isopropyl alcohol (50.3 mL, 657 mmol) was added morpholine-4-carbothioicacidamide (1.44 g, 9.86 mmol). The reaction mixture was heated with stirring at 90° C. for 90 minutes. Volatiles were removed in vacuo and the residue was redissolved in DCM and treated with saturated aqueous $NaHCO_3$ with stirring for 30 minutes. The layers were separated, and the aqueous layer was extracted with DCM. The combined organic layers were washed with brine, dried over $Mg_2SO_4$, filtered, and concentrated in vacuo. Purification by column chromatography (gradient elution: 0 to 25% EtOAc in hexanes) afforded ethyl 4-[1-(4-chlorophenyl)ethyl]-2-(morpholin-4-yl)-1,3-thiazole-5-carboxylate (1.45 g, 57.9%) as a white solid. LCMS: (FA) ES+ 381; NMR (400 MHz, DMSO) δ 7.41-7.37 (m, 2H), 7.24-7.21 (m, 2H), 5.12 (q, J=7.2, 1H), 4.33-4.20 (m, 2H), 3.81-3.78 (m, 4H), 3.57-3.48 (m, 4H), 1.57 (d, J=6.8, 3H), 1.33 (t, J=7.2, 3H).

Step 3: 4-[1-(4-Chlorophenyl)ethyl]-2-(morpholin-4-yl)-1,3-thiazole-5-carboxylic acid (Compound 121)

To a solution of ethyl 4-[1-(4-chlorophenyl)ethyl]-2-(morpholin-4-yl)-1,3-thiazole-5-carboxylate (1.42 g, 0.00373 mol) in tetrahydrofuran (30.2 mL, 0.373 mol) and methanol (6.04 mL, 0.149 mol) was added sodium hydroxide (1.0N in water, 29.8 mL, 0.0298 mol), and the resulting cloudy mixture was heated at 65° C. for 5 hours. The reaction was cooled to room temperature, diluted with water, and adjusted to pH 3.0 via addition of 1N aqueous HCl. The mixture was transferred to a separatory funnel and the layers separated. The aqueous layer was extracted with EtOAc, and the combined organic layers were dried over $MgSO_4$, filtered, and concentrated in vacuo to afford 4-[1-(4-chlorophenyl)ethyl]-2-(morpholin-4-yl)-1,3-thiazole-5-carboxylic acid (121) (1.21 g, yield 92%) as a white solid. LCMS: (FA) ES+ 353; NMR (400

MHz, DMSO) δ 12.70 (bs, 1H), 7.37-7.34 (m, 2H), 7.33-7.30 (m, 2H), 5.09 (q, J=7.2, 1H), 3.69-3.76 (m, 4H), 3.48-3.39 (m, 4H), 1.49 (d, J=6.8, 3H).

Compounds in the following table are prepared from appropriate starting materials in a method analogous to that of Example 48.

| 304 | LC/MS: (AA) ES+ 381, 383 |
| 332 | LC/MS: (AA) ES+ 387, 389 |

Example 49

Synthesis of 4-cyano-3-[(3,4-dichlorophenyl)(dimethylamino)methyl]-5-(morpholin-4-yl)thiophene-2-carboxylic acid (Compound 362)

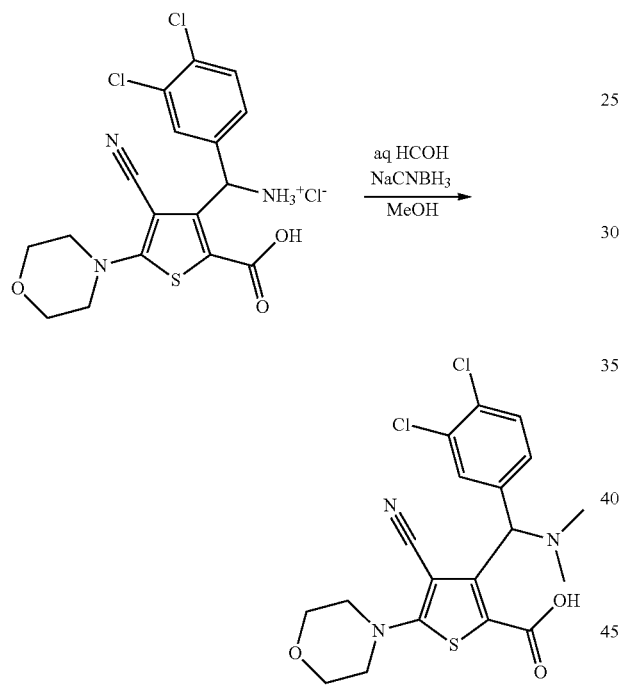

Step 1: 4-cyano-3-[(3,4-dichlorophenyl)(dimethylamino)methyl]-5-(morpholin-4-yl)thiophene-2-carboxylic acid To a suspension of 3-[amino(3,4-dichlorophenyl)methyl]-4-cyano-5-(morpholin-4-yl)thiophene-2-carboxylic acid.HCl (186.0 mg, 0.4145 mmol, prepared according to Example 6) in methanol (8.09 mL, 0.101 mol) was added 10 M of formaldehyde in water (74.00 uL, 0.9119 mmol), and sodium cyanoborohydride (130 mg, 2.07 mmol). Stirred at rt under argon for 16 hours. Added 10 M of formaldehyde in water soln (74.00 uL, 0.919 mmol) and sodium cyanoborohydride (0.130 g, 2.07 mmol) and stirred at rt for 72 hours. Quenched reaction with saturated aqueous sodium bicarbonate solution, added EtOAc, separated layers, extracted again w/EtOAc, combined organics, washed organics with saturated sodium bicarbonate, brine, dried over Na$_2$SO$_4$, filtered, added Celite to filtrate, and concentrated in vacuo. Purification of dry load via silica gel column chromatography (gradient elution: 100% DCM to 8% MeOH in DCM) afforded racemic 4-cyano-3-[(3,4-dichlorophenyl)(dimethylamino)methyl]-5-(morpholin-4-yl)thiophene-2-carboxylic acid (134 mg, 68%) as an off-white solid. LC/MS: (FA) 440, 442, 444; $^1$H NMR (400 MHz, DMSO) δ 7.80-7.76 (m, 2H), 7.53 (dd, J=8.4, 2.1 Hz, 1H), 5.26 (s, 1H), 3.74-3.64 (m, 4H), 3.53-3.38 (m, 4H), 2.76 (s, 3H), 2.42 (s, 3H). Combined with another batch of 134 mg racemate for chiral HPLC to obtain pure enantiomers. Purified on IC 4.6×250 mm with 90/10/0.1 HEX/ETOH/DEA 10 uL Injection at 1.0 mL/min for 70 min. CD AT 254 nm to obtain separated enantiomers as the diethylamine salts. Each compound Peak1 and Peak2 were separately dissolved in water, acidified to pH of 2 with aqueous 1N HCl solution, extracted w/EtOAc, 3×, combined organics and washed w/brine, dried over Na$_2$SO$_4$, filtered, concentrated in vacuo, added water, freeze-dried, lyophilized overnight to recover parent compound. Peak 1 (103 mg, tan solid, overall 27% yield) LC/MS: (FA) 440, 442, 444; $^1$H NMR (400 MHz, DMSO) δ 7.80-7.76 (m, 2H), 7.53 (dd, J=8.4, 2.1 Hz, 1H), 5.26 (s, 1H), 3.74-3.64 (m, 4H), 3.53-3.38 (m, 4H), 2.76 (s, 3H), 2.42 (s, 3H). Peak 2 (80 mg, beige solid, overall 20% yield) LC/MS: (FA) 440, 442, 444; $^1$H NMR (400 MHz, DMSO) δ 7.80-7.76 (m, 2H), 7.53 (dd, J=8.4, 2.1 Hz, 1H), 5.26 (s, 1H), 3.74-3.64 (m, 4H), 3.53-3.38 (m, 4H), 2.76 (s, 3H), 2.42 (s, 3H).

Compounds in the following table are prepared from appropriate starting materials in a method analogous to that of Example 49.

| 336 | LC/MS: (FA) ES+ 440, 442, 444 |
| 351 | LC/MS: (FA) ES+ 406, 408 |

Example 50

Synthesis of 4-cyano-5-[2-(hydroxymethyl)morpholin-4-yl]-3-(2-naphthylmethyl)thiophene-2-carboxylic acid (Compound 297)

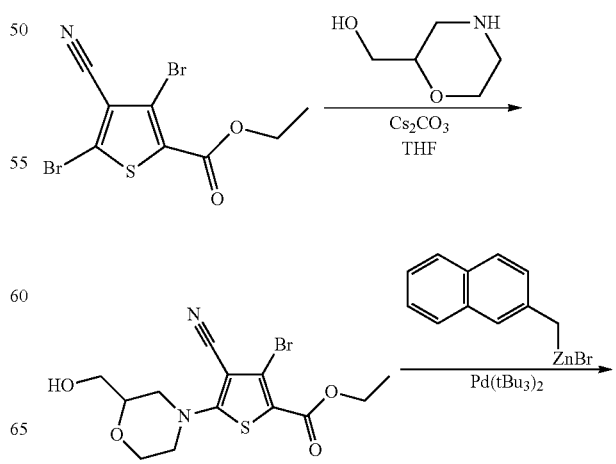

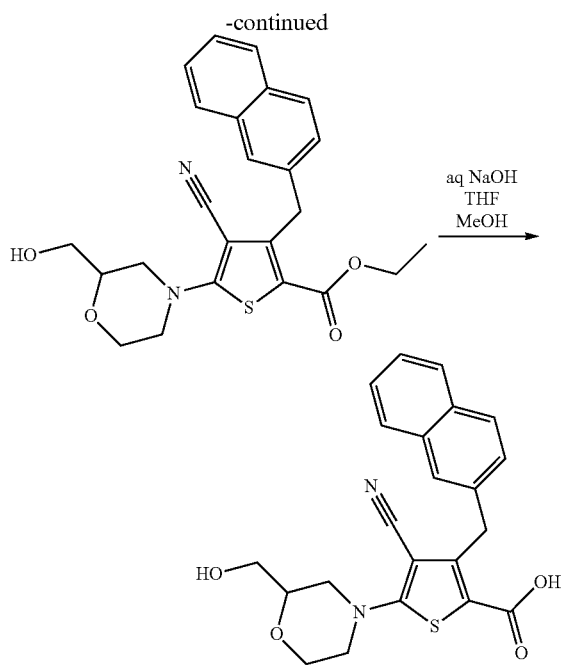

Step 1: ethyl 3-bromo-4-cyano-5-[2-(hydroxymethyl)morpholin-4-yl]thiophene-2-carboxylate Ethyl 3,5-dibromo-4-cyanothiophene-2-carboxylate (0.360 g, 1.06 mmol), cesium carbonate (1.05 g, 3.21 mmol), 2-hydroxymethylmorpholine (137 mg, 1.17 mmol), and tetrahydrofuran (4.5 mL, 36 mmol) were combined in a 15 mL pressure vessel equipped with a stir bar. The vessel was sealed, and the rxn was heated @ 90° C. with stirring for 4 hours. The reaction was cooled to rt. The rxn was poured into water/saline. The reaction vessel was washed out with additional water, then ethyl acetate, and these were added to the quench which was then transferred to a separatory funnel. The aqueous layer was extracted 3× with EtOAc. The extracts were combined, washed with saline, dried over $Na_2SO_4$, filtered, added Celite, concentrated in vacuo, and dried on high vac 30 min. Purified dry load via silica gel chromatography (gradient elution: 0-60% EtOAc/hexanes) to give 163 mg solid (41% yield). $^1$H NMR (400 MHz, DMSO) δ 4.91 (t, J=5.7 Hz, 1H), 4.25 (q, J=7.1 Hz, 2H), 3.99-3.92 (m, 3H), 3.69-3.58 (m, 2H), 3.50 (dt, J=10.5, 5.2 Hz, 1H), 3.41 (dt, J=11.5, 5.8 Hz, 1H), 3.37-3.27 (m, 1H, under H2O peak), 3.15-3.08 (m, 1H), 1.26 (t, J=7.1 Hz, 3H).

Step 2: ethyl 4-cyano-5-[2-(hydroxymethyl)morpholin-4-yl]-3-(2-naphthylmethyl)thiophene-2-carboxylate and 4-cyano-5-[2-(hydroxymethyl)morpholin-4-yl]-3-(2-naphthylmethyl)thiophene-2-carboxylic acid Bis(tri-t-butylphosphine)palladium(0) (16.44 mg, 0.03218 mmol) and ethyl 3-bromo-4-cyano-5-[2-(hydroxymethyl)morpholin-4-yl]thiophene-2-carboxylate (161.0 mg, 0.4290 mmol) were combined in a dry round bottom flask equipped with a stirbar and septum. Evacuated/refilled with argon 3×, then added 0.50 M solution of 2-naphthylmethylzinc bromide in tetrahydrofuran (1.72 mL, 0.858 mmol) via a syringe to give a brown soln. The reaction was stirred at rt for 5 minutes, then at 60° C. for 1.5 h. Bis(tri-t-butylphosphine)palladium (0) (38.4 mg, 0.0751 mmol) and 0.50 M solution of 2-naphthylmethylzinc bromide in tetrahydrofuran (1.29 mL, 0.644 mmol) was added, degassed 2× and flushed w/argon, heated at 60° C. 1 h. The reaction was cooled to rt, diluted with EtOAc, and then quenched with sat. NH4Cl solution. Transferred quenched mixture to a separatory funnel, separated layers, and extracted the aqueous layer once more with EtOAc, combined organics, washed w/brine, dried over Na2SO4, filtered, and concentrated in vacuo. Added EtOAc and Celite, rotovapped, dried on high vac 30 min. Purified dry load onto 40 g ISCO column (gradient elution: 0-55% EtOAc/hexanes) to obtain 119 mg yellow oil (64% yield). LC/MS (AA) ES+ 437.

To ethyl-4-cyano-5-[2-(hydroxymethyl)morpholin-4-yl]-3-(2-naphthylmethyl)thiophene-2-carboxylate (0.116 g, 0.266 mmol) in a rbf equipped with a stirbar was added tetrahydrofuran (2.96 mL, 36.4 mmol) and 1.000 M of sodium hydroxide in water (2.22 mL, 2.22 mmol) and methanol (1.48 mL, 36.5 mmol). The resulting yellow mixture was stirred at rt for 16 h. The reaction was quenched with the addition of 2.5 mL of 1N HCl in water to pH of 2, and added EtOAc Transferred to separatory funnel, separated layers, extracted aqueous 2× w/EtOAc, combined organics, washed w/brine, dried over Na2SO4, filtered, added Celite, and concentrate in vacuo. Purified dry load via silica gel chromatography on 40 g ISCO column (gradient elution 0-20% MeOH/DCM) to give 66 mg white solid (61% yield). LC/MS (FA) ES+ 409; ES− 407; $^1$H NMR (400 MHz, DMSO) δ 13.45 (br s, 1H), 7.88-7.77 (m, 3H), 4.7 Hz, 3H), 7.69 (s, 1H), 7.51-7.42 (m, 3H), 4.87 (s, 1H), 4.57-4.47 (m, 2H), 3.94-3.77 (m, 3H), 3.65-3.53 (m, 2H), 3.60-3.52 (m, 1H), 3.47 (dd, J=11.3, 5.0 Hz, 1H), 3.37 (dd, J=11.3, 5.8 Hz, 1H, overlaps with H$_2$O peak), 3.15 (td, J=12.1, 3.4 Hz, 1H), 2.99-2.89 (m, 1H).

Example 10

Synthesis of 2-morpholino-4-(naphthalen-2-ylmethyl)thiazole-5-sulfonamide (Compound 329)

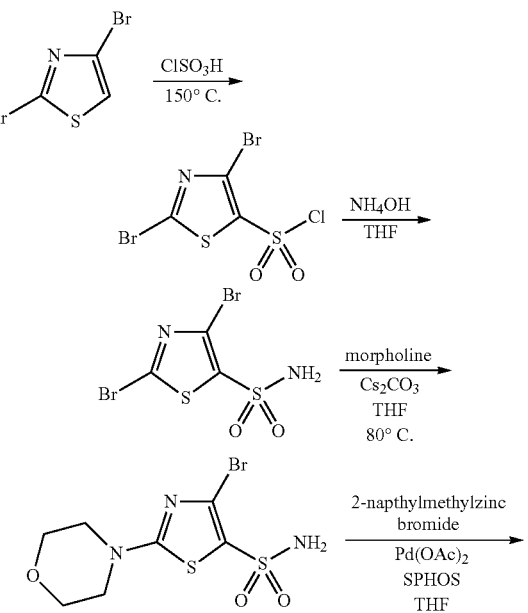

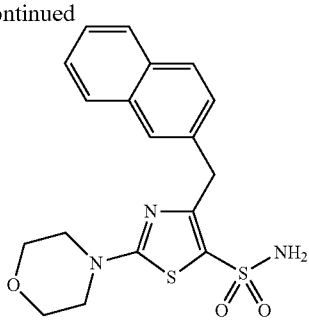

Step 1, Preparation of 2,4-dibromothiazole-5-sulfonyl chloride

To a flask containing chlorosulfonic acid (51.0 mL, 767 mmol) was added 2,4-dibromothiazole (10.2 g, 42.0 mmol) with stirring over 15 minutes. The resulting solution was heated to 150 degrees overnight. The reaction was quenched by carefully and slowly pouring onto ice (500 mL). The resulting precipitate was extracted with ethyl acetate (2×200 mL) and the combined organic layers were washed with water, dried, and concentrated in vacuo. The residue was purified by silica gel chromatography (ethyl acetate/hexane=0/100→15/85) to give 8.1 g (56% yield) of the title compound as a yellow oil which partially solidified. $^{13}$C NMR (400 MHz, CDCl$_3$) δ: 145.04, 138.78, 131.81.

Step 2, Preparation of 2,4-dibromothiazole-5-sulfonamide

To a mixture of 2,4-dibromothiazole-5-sulfonyl chloride (3.17 g, 9.28 mmol) in THF (51.4 mL) was added 33% aqueous NH$_4$OH (24.1 mL, 278 mmol) and the reaction was stirred at room temperature for 30 minutes. The reaction was concentrated in vacuo and the residue was taken up in ethyl acetate (100 mL) and water (100 mL). The aqueous layer was extracted with ethyl acetate (50 mL) and the combined organic layers were washed with water (50 mL) and brine (50 mL), then dried and concentrated in vacuo. The residue was purified by silica gel chromatography (ethyl acetate/DCM=0/100→20/80) to give 1.7 g (57% yield) of the title compound. as a white solid. LC/MS (FA) ES+ 321, 323, 325. $^1$H NMR (400 MHz, DMSO-d$_6$) δ: 8.33 (s, 2H).

Step 3, Preparation of 4-bromo-2-morpholinothiazole-5-sulfonamide

A mixture of 2,4-dibromothiazole-5-sulfonamide (0.515 g, 1.60 mmol), morpholine (0.153 mL, 1.76 mmol), THF (4.22 mL) and cesium carbonate (1.56 g, 4.80 mmol) in a sealed tube was heated to 80 degrees for 4 hours. The cooled reaction was concentrated in vacuo and the residue was taken up in ethyl acetate (50 mL) and water (25 mL). The layers were separated and the organic layer was washed with water (15 mL), dried and concentrated in vacuo. The residue was purified by silica gel chromatography (ethyl acetate/DCM=0/100→50/50) to give 230 mg (44% yield) of the title compound as a white solid. LC/MS (FA) ES+ 328, 330. $^1$H NMR (400 MHz, DMSO-d$_6$) δ: 7.76 (s, 2H), 3.69-3.66 (m, 4H), 3.43-3.40 (m, 4H).

Step 4, Preparation of 2-morpholino-4-(naphthalen-2-ylmethyl)thiazole-5-sulfonamide To a dried flask was added 4-bromo-2-morpholinothiazole-5-sulfonamide (194 mg, 0.591 mmol), THF (4.79 mL), palladium(II) acetate (1.33 mg, 0.00591 mmol) and dicyclohexyl(2',6'-dimethoxybiphenyl-2-yl)phosphine (4.85 mg, 0.0118 mmol). The mixture was stirred for 5 minutes, and a 0.500 M solution of 2-napthylmethylzinc bromide in THF (4.14 mL, 2.04 mmol) was then added dropwise over 30 minutes. The reaction was stirred at room temperature for 1 hour and quenched with saturated ammonium chloride (10 mL). The reaction was extracted with ethyl acetate (2×25 mL) and the combined organic layers were washed with water (15 mL), dried and concentrated in vacuo. The residue was purified by silica gel chromatography (ethyl acetate/DCM=0/100→40/60) which gave a mixture of the desired product with residual 4-bromo-2-morpholinothiazole-5-sulfonamide. This material was purified by preparative reverse phase chromatography to give 51 mg (22% yield) of the title compound as a white solid. LC/MS (FA) ES+ 390. $^1$H NMR (400 MHz, DMSO-d$_6$) δ: 7.85-7.77 (m, 4H), 7.71 (bs, 2H), 7.50-7.42 (m, 3H), 4.25 (s, 2H), 3.64-3.61 (m, 4H), 3.35-3.32 (m, 4H).

Example 51

Synthesis of 4-cyano-3-[1-(3,4-dichlorophenyl)but-3-en-1-yl]-5-(morpholin-4-yl)thiophene-2-carboxylate (Compound 355)

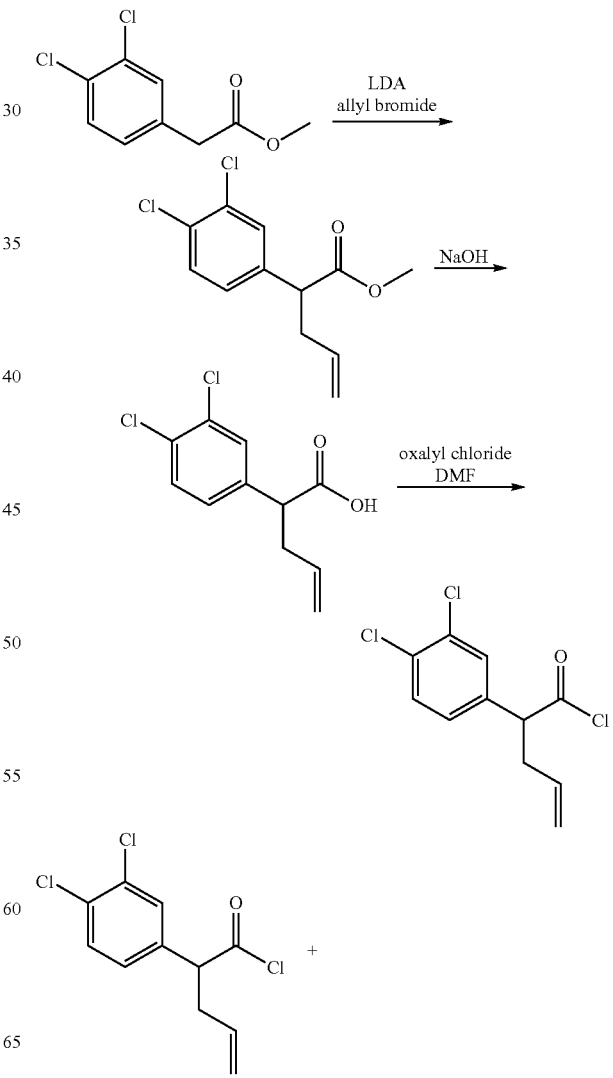

Step 1

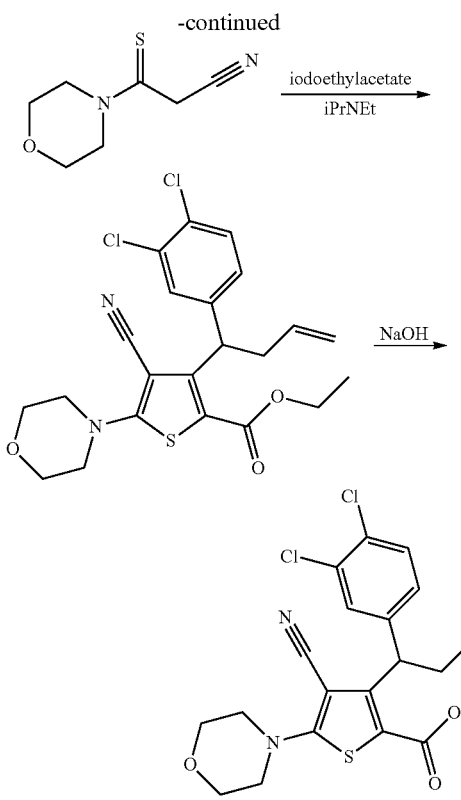

To a solution of N,N-diisopropylamine (1.79 mL, 12.8 mmol) in tetrahydrofuran (10.0 mL, 123 mmol) was added 2.50 M of n-butyllithium in hexane (4.68 mL, 11.7 mmol) dropwise at 0° C. The solution was stirred under an atmosphere of Nitrogen for 10 min, and then cooled to −78° C. A solution of methyl 3,4-dichlorophenylacetate (2.27 g, 10.4 mmol) in tetrahydrofuran (10.0 mL) was added to the LDA solution dropwise via cannula. After 10 min of stirring, the reaction was warmed to 0° C. for 1 hr. The solution was cooled back to −78° C., and allyl bromide (2.24 mL, 25.9 mmol) was added in one portion. In 10 min, the reaction was warmed back to 0° C. After 1 hr of stirring, the reaction was quenched with NH₄Cl sat soln and extracted with EtOAc (×3). The combined organic layer was dried and concentrated to provide an orange oil. Further purification on a silica gel column (gradient elution, 0-10% EtOAc/hexanes) provided methyl 2-(3,4-dichlorophenyl)pent-4-enoate as a colorless oil (2.47 g, 92.0% yield). $^1$H NMR (400 MHz, CDCl$_3$) δ 7.43-7.37 (m, 2H), 7.18-7.12 (dd, J=8.3, 2.1 Hz, 1H), 5.73-5.60 (ddt, J=17.1, 10.2, 6.8 Hz, 1H), 5.12-4.98 (m, 2H), 3.70-3.64 (s, 3H), 3.63-3.55 (t, J=7.8 Hz, 1H), 2.85-2.71 (m, 1H), 2.55-2.43 (m, 1H).

Step 2

To a solution of methyl 2-(3,4-dichlorophenyl)pent-4-enoate (2.47 g, 9.53 mmol) in tetrahydrofuran (15.0 mL) was added a solution of lithium hydroxide monohydrate (2.00 g, 47.6 mmol) in water (15.0 mL). The mixture was vigorously stirred at rt for 12 hrs. The resulting mixture was acidified by addition of 12.0 M of hydrochloric acid in water (3.97 mL, 47.6 mmol) at 0° C., and extracted with EtOAc (×3). The combined organic layer was dried and concentrated to provide 2-(3,4-dichlorophenyl)pent-4-enoic acid as a yellow syrup (2.65 g, quantitative). $^1$H NMR (400 MHz, CDCl$_3$) δ 7.45-7.35 (m, 2H), 7.21-7.11 (dd, J=8.3, 2.1 Hz, 1H), 5.76-5.59 (ddt, J=17.0, 10.2, 6.8 Hz, 1H), 5.14-4.99 (m, 2H), 3.65-3.56 (t, J=7.7 Hz, 1H), 2.88-2.74 (dt, J=14.8, 7.5 Hz, 1H), 2.58-2.43 (dt, J=14.3, 6.9 Hz, 1H).

Step 3

To a soln of 2-(3,4-dichlorophenyl)pent-4-enoic acid (2.34 g, 9.53 mmol) in methylene chloride (25.0 mL) was added oxalyl chloride (1.61 mL, 19.0 mmol) followed by N,N-dimethylformamide (73.8 uL, 0.953 mmol) After 1 hr of stirring at rt, the solution was concentrated to provide 2-(3,4-dichlorophenyl)pent-4-enoyl chloride as a yellow oil (2.70 g, quantitative). $^1$H NMR (400 MHz, CDCl$_3$) δ 7.49-7.42 (d, J=8.3 Hz, 1H), 7.40-7.36 (d, J=2.2 Hz, 1H), 7.17-7.10 (dd, J=8.3, 2.2 Hz, 1H), 5.73-5.57 (ddt, J=17.1, 10.2, 6.9 Hz, 1H), 5.15-5.06 (m, 2H), 4.06-3.97 (t, J=7.6 Hz, 1H), 2.97-2.83 (m, 1H), 2.61-2.49 (m, 1H).

Step 4

To a solution of 2-(3,4-dichlorophenyl)pent-4-enoyl chloride (2.51 g, 9.53 mmol) and 3-morpholin-4-yl-3-thioxopropanenitrile (1.62 g, 9.53 mmol) in acetonitrile (40.0 mL) in a 100 mL round bottom flask was added N,N-diisopropylethylamine (1.82 mL, 10.5 mmol), and the resulting deep orange/red solution was stirred at room temp for 1 hr. To the resulting mixture was added N,N-diisopropylethylamine (4.15 mL, 23.8 mmol) and then ethyl iodoacetate (1.24 mL, 10.5 mmol). The flask was fitted with a reflux condenser and the reaction was heated to reflux over 48 hrs. The mixture was concentrated and distributed between NaHCO$_3$(aq) saturated solution and EtOAc. The aqueous layer was extracted with EtOAc (×2). The combined org layer was washed with brine, dried, and concentrated to provide a dark syrup. Purification on a silica gel column (gradient elution 3-30% EtOAc/hexanes) provided ethyl 4-cyano-3-[1-(3,4-dichlorophenyl)but-3-en-1-yl]-5-(morpholin-4-yl)thiophene-2-carboxylate (704 mg, 15.9% yield). LCMS: (AA) ES+ 465, 467, 469; $^1$H NMR (400 MHz, CDCl$_3$) δ 7.49-7.42 (m, 1H), 7.41-7.33 (m, 1H), 7.31-7.27 (m, 1H), 5.82-5.66 (ddt, J=17.2, 10.1, 6.8 Hz, 1H), 5.62-5.50 (t, J=8.2 Hz, 1H), 5.16-5.08 (dd, J=17.1, 1.6 Hz, 1H), 5.04-4.94 (dd, J=10.2, 1.5 Hz, 1H), 4.35-4.27 (q, J=7.1 Hz, 2H), 3.86-3.78 (m, 4H), 3.59-3.48 (m, 4H), 3.10-2.99 (h, J=6.9 Hz, 2H), 1.40-1.31 (m, 3H).

Step 5

To a solution of ethyl 4-cyano-3-[1-(3,4-dichlorophenyl)but-3-en-1-yl]-5-(morpholin-4-yl)thiophene-2-carboxylate (0.211 g, 0.453 mmol) in tetrahydrofuran (8.00 mL) was added 1.000 M of sodium hydroxide in water (10.0 mL) and methanol (4.00 mL). The resulting mixture was stirred at room temp over 3 hrs. The volatiles were removed under reduced pressure, and the resulting mixture was acidified with conc. HCl soln to pH~2, and extracted with EtOAc (×3). The combined org layer was dried and concentrated to provide a purple syrup. Purification of the crude mixture on HPLC (AA, reverse phase) provided 4-cyano-3-[1-(3,4-dichlorophenyl)but-3-en-1-yl]-5-(morpholin-4-yl)thiophene-2-carboxylic acid as a white solid (63 mg, 31.8% yield). LCMS:

(AA) ES– 391, 393, 395; $^1$H NMR (400 MHz, MeOD) δ 7.54-7.46 (d, J=1.6 Hz, 1H), 7.45-7.35 (d, J=8.4 Hz, 1H), 7.34-7.24 (dd, J=8.4, 1.6 Hz, 1H), 5.88-5.68 (m, 2H), 5.16-5.05 (dd, J=17.1, 1.7 Hz, 1H), 5.00-4.92 (m, 1H), 3.82-3.71 (t, J=4.8 Hz, 4H), 3.51-3.40 (t, J=4.8 Hz, 4H), 3.05-2.95 (m, 2H).

Compounds in the following table are prepared from appropriate starting materials in a method analogous to that of Example 51.

| | |
|---|---|
| 307 | LC/MS: (FA) ES– 412 |
| 308 | LC/MS: (FA) ES– 413 |
| 321 | LC/MS: (AA) ES+ 411, 413 |
| 326 | LC/MS: (AA) ES+ 411 |
| 345 | LC/MS: (FA) ES– 395 |
| 349 | LC/MS: (FA) ES– 437 |
| 358 | LC/MS: (FA) ES+ 399, 401 |
| 364 | LC/MS: (FA) ES– 395 |
| 369 | LC/MS: (AA) ES+ 411 |

Example 52

Synthesis of 4-cyano-3-(isoquinolin-7-ylmethyl)-5-(morpholin-4-yl)thiophene-2-carboxylic acid (Compound 309)

Step 1:
5-Amino-4-cyano-3-methyl-thiophene-2-carboxylic acid ethyl ester

To a solution of 3-oxobutanoic acid, methyl ester (8.25 mL, 76.4 mmol), malononitrile (5.05 g, 76.4 mmol) and sulfur (2.45 g, 76.4 mmol) in anhydrous ethanol (100 mL, 2000 mmol) was added triethylamine (10.7 mL, 76.8 mmol). The mixture was heated to reflux for 30 min. The mixture was cooled to room temperature. The resulted crystal was collected by filtration and washed with MeOH, dried in vacuum to afford the product (9.25 g, yield 61.7%). LC/MS: (FA) ES– 195. NMR (400 MHz, d-chloroform) δ 5.13 (s, br, 2H), 3.82 (s, 3H), 2.52 (s, 3H).

Step 2 Methyl 5-bromo-4-cyano-3-methylthiophene-2-carboxylate

To a dark solution of Methyl 5-amino-4-cyano-3-methylthiophene-2-carboxylate (6.65 g, 33.9 mmol) and copper (II) bromide (15.1 g, 67.8 mmol) in anhydrous acetonitrile (260 mL) was added slowly butyl nitrite (7.26 mL, 61.0 mmol) over 8 min. The mixture was stirred at room temperature for 70 min. The mixture was concentrated in rotavapor to give a black residue. The residue was dissolved in DCM, filtered through Celite. The filtrate was rotavaped with Celite.

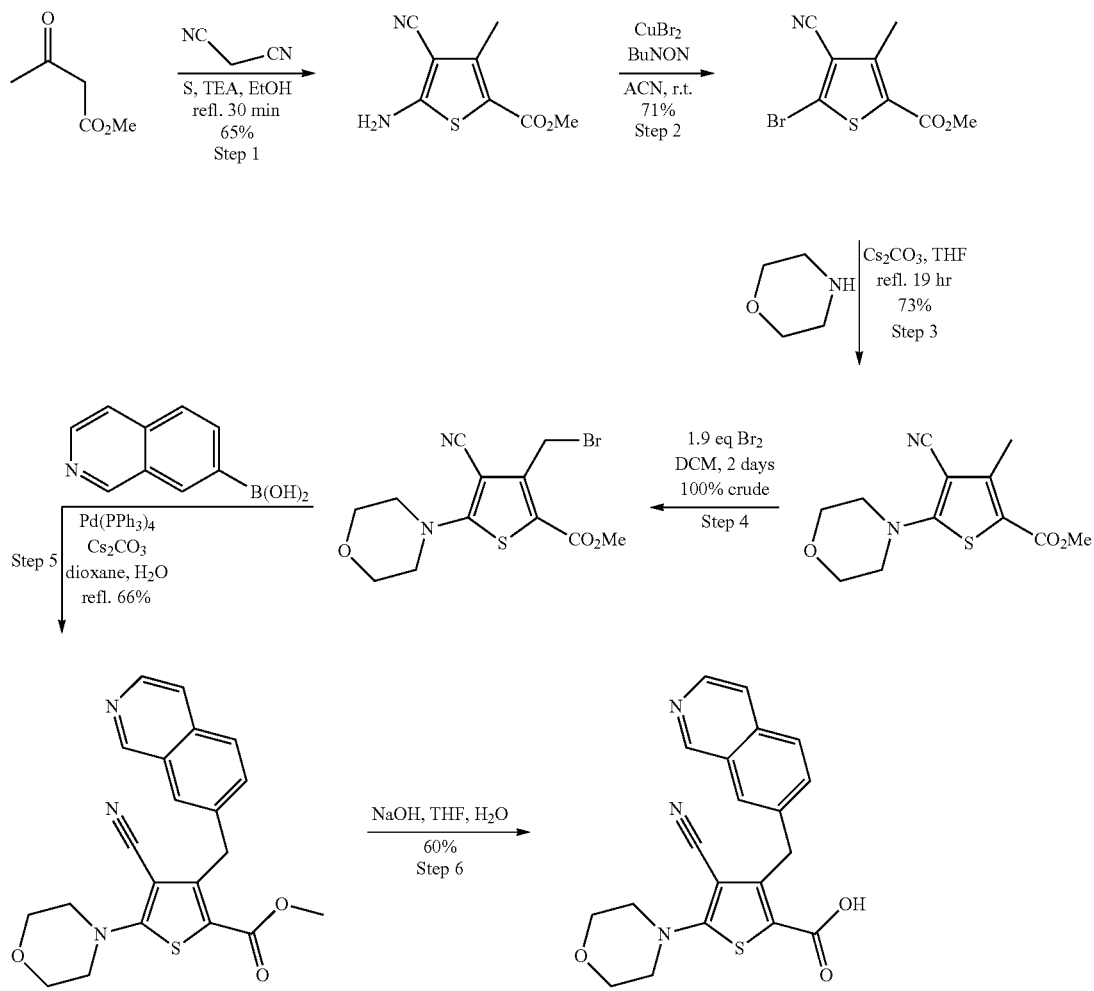

The Celite coated residue was dry loaded into a silica gel column and chromatographed using EtOAc/hexane (0/100 to 10/90) to give a white solid product (6.29 g, yield 71.4%). $^1$H NMR (400 MHz, d-chloroform) δ 3.89 (s, 3H), 2.67 (s, 3H)

Step 3: Methyl 4-cyano-3-methyl-5-(morpholin-4-yl)thiophene-2-carboxylate

A mixture of methyl 5-bromo-4-cyano-3-methylthiophene-2-carboxylate (6.29 g, 24.2 mmol), morpholine (2.53 g, 29.0 mmol) and cesium carbonate (15.8 g, 48.4 mmol) in anhydrous Tetrahydrofuran (110 mL) was heated to reflux for 19 hours, and then cooled to room temperature. The mixture was filtered and washed with DCM. The filtrate was rotavaped with Celite. The coated Celite was dry loaded in a silica gel cartridge and chromatographed using MeOH/DCM (1/99) to give a white solid product (4.70 g, yield 73%). LC/MS: (FA) ES$^+$ 267. $^1$H NMR (400 MHz, d-chloroform) δ 3.85 (m, 4H), 3.82 (s, 3H), 3.58 (m, 4H), 2.56 (s, 3H).

Step 4: Methyl 3-(bromomethyl)-4-cyano-5-(morpholin-4-yl)thiophene-2-carboxylate To the solution of methyl 4-cyano-3-methyl-5-(morpholin-4-yl)thiophene-2-carboxylate (0.500 g, 1.88 mmol) in anhydrous methylene chloride (15 mL, 230 mmol) was added a solution of bromine (0.409 g, 2.56 mmol) in anhydrous methylene chloride (5.0 mL, 78 mmol). The mixture was stirred at room temperature for 4 days. The mixture was evaporated under reduced pressure and dried in vacuum to give a crude product that was used without further purification (0.658 g, contained 3.4% starting material, yield 96.6%). LC/MS: (FA) ES$^+$ 345, 347. $^1$H NMR (400 MHz, d-chloroform) δ 4.83 (s, 2H), 3.87 (s, 3H), 3.85 (m, 4H), 3.62 (m, 4H).

Step 5: Methyl 4-cyano-3-(isoquinolin-7-ylmethyl)-5-(morpholin-4-yl)thiophene-2-carboxylate A mixture of methyl 3-(bromomethyl)-4-cyano-5-(morpholin-4-yl)thiophene-2-carboxylate (0.128 g, 0.371 mmol), isoquinoline-7-boronic acid (101 mg, 0.584 mmol), tetrakis(triphenylphosphine)palladium(0) (21.4 mg, 0.0185 mmol) and cesium carbonate (0.242 g, 0.742 mmol) was suspended in 1,4-dioxane (8.0 mL, 100 mmol) and Water (0.60 mL, 33 mmol) under N$_2$ atmosphere in a 20 mL vial. The vial was capped and heated to 90° C. for 1 hour. The mixture was cooled to room temperature and concentrated in vacuum. The residue was suspended in DCM and filtered over a celite pad. The filtrate was chromatographed in a silica gel column using MeOH/DCM (0/100 to 3/97) to afford a solid product (103 mg, 66.4%). LC/MS: (FA) ES$^+$ 394. $^1$H NMR (400 MHz, d-chloroform) δ 9.20 (s, 1H), 8.47 (d, J=5.77 Hz, 1H), 7.87 (s, 1H), 7.73 (d, J=5.77 Hz, 1H), 7.60 (d, J=5.77 Hz, 1H), 7.44-7.48 (m, 1H), 4.60 (s, 2H), 3.86 (s, 3H), 3.84 (m, 4H), 3.59 (m, 4H).

Step 6: 4-cyano-3-(isoquinolin-7-ylmethyl)-5-(morpholin-4-yl)thiophene-2-carboxylic acid To the solution of methyl 4-cyano-3-(isoquinolin-7-ylmethyl)-5-(morpholin-4-yl)thiophene-2-carboxylate (0.103 g, 0.246 mmol) in tetrahydrofuran (15.0 mL, 185 mmol) was added 1.00 M of sodium hydroxide in water (3.80 mL, 3.80 mmol), followed by water (4.0 mL, 220 mmol) and methanol (4.0 mL, 99 mmol). The homogeneous solution was stirred at room temperature for 18 hours. Acetic acid (270 mg, 4.5 mmol) was added and the mixture was concentrated in rotavapor. The residue was dissolved in DCM-MeOH and then concentrated with celite. The mixture was loaded in a cartridge and chromatographed in a silica gel column using AcOH/MeOH/DCM (0/0/100 to 0.5/4.5/95) to afford a white solid product (56.5 mg, yield 60.3%). LC/MS: (FA) ES$^+$ 380; ES$^-$ 378. $^1$H NMR (400 MHz, d-chloroform) δ 9.23 (s, 1H), 8.45 (d, J=5.77 Hz, 1H), 7.90 (d, J=8.53 Hz, 1H), 7.84 (s, 1H), 7.76 (d, J=5.77 Hz, 1H), 7.65 (dd, J=8.53, 1.76 Hz, 1H), 4.53 (s, 2H), 3.72 (m, 4H), 3.52 (m, 4H).

Compounds in the following table are prepared from appropriate starting materials in a method analogous to that of Example 52.

| | |
|---|---|
| 287 | LC/MS: (AA) ES– 395 |
| 293 | LC/MS: (AA) ES– 395 |
| 295 | LC/MS: (AA) ES– 395 |
| 301 | LC/MS: (AA) ES+ 409 |
| 305 | LC/MS: (FA) ES– 381 |
| 311 | LCMS: (FA) ES+ 385; ES– 383 |
| 312 | LC/MS: (FA) ES+ 386, 388; ES– 384, 386 |
| 315 | LC/MS: (FA) ES+ 397 |
| 324 | LC/MS: (AA) ES– 395 |
| 330 | LC/MS: (FA) ES+ 382; ES– 380 |
| 343 | LC/MS: (AA) ES– 395 |
| 359 | LC/MS: (FA) ES+ 402, 404; ES– 401, 403 |
| 361 | LC/MS: (AA) ES+ 409 |

Example 53

Synthesis Example 3

Synthesis of 4-cyano-3-[methoxy(2-naphthyl)methyl]-5-(morpholin-4-yl)thiophene-2-carboxylic acid (Compound 368)

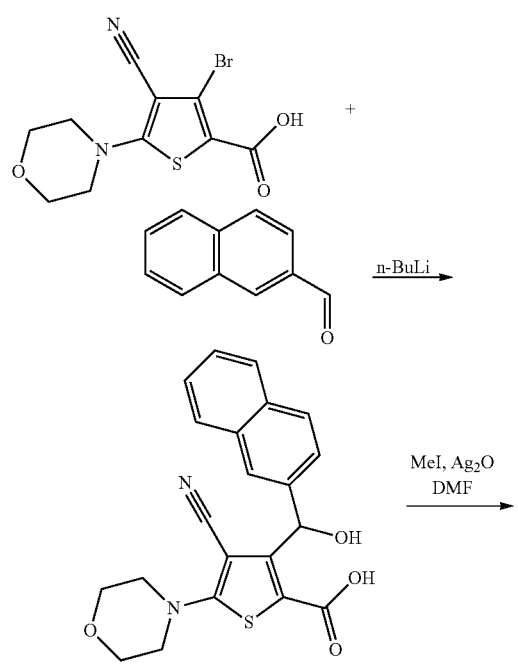

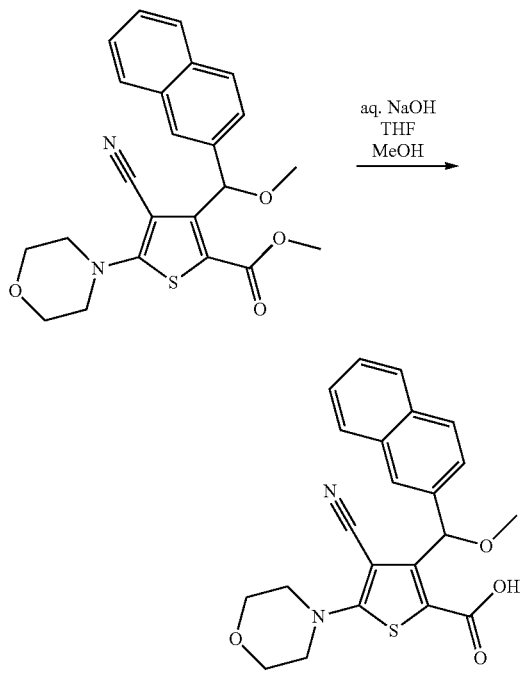

Step 1: 4-cyano-3-[hydroxy(2-naphthyl)methyl]-5-(morpholin-4-yl)thiophene-2-carboxylic acid A solution of 3-bromo-4-cyano-5-morpholinothiophene-2-carboxylic acid (5.50 g, 17.3 mmol) and 2-naphthalenecarboxaldehyde (8.12 g, 52.0 mmol) in tetrahydrofuran (550 mL) was cooled at −78° C. for 10 min, resulting in a white suspension. 2.5 M of n-butyllithium in hexane (27.7 mL, 69.4 mmol) was added dropwise, resulting in an orange solution. The solution was stirred at −78° C. for 10 min, then the cold bath was removed and the orange solution was stirred at ambient temperature for 40 minutes. The solution was quenched by the addition of methanol (21 mL) and acetic acid (3.9 mL), and the resulting mixture was let to warm up to rt O/N. The mixture was combined with a previous run on 2.86 g scale of the carboxylic acid, concentrated in vacuo, and azeotroped with toluene (2×50 mL). The crude solid was dissolved in MeOH, added Celite, rotavapped, dried on high vac O/N. The crude product was purified using dry load via silica gel chromatography on 330 g ISCO column (gradient elution 0-20% of (10% AcOH in MeOH) in DCM) to give 15.2 g solid containing 37 wt % AcOH, for overall 92% yield. LC/MS (AA) ES− 393; $^1$H NMR (400 MHz, DMSO) δ 10.86 (d, J=9.9 Hz, 1H), 7.86-7.81 (m, 4H), 7.70 (dd, J=8.6, 1.6 Hz, 1H), 7.51-7.42 (m, 2H), 5.69 (d, J=9.4 Hz, 1H), 3.73-3.68 (m, 4H), 3.39-3.33 (m, 4H).

Step 2: methyl 4-cyano-3-[methoxy(2-naphthyl)methyl]-5-(morpholin-4-yl)thiophene-2-carboxylate To a round bottom flask was added silver(I) oxide (56.15 g, 0.2423 mol), 4-cyano-3-[hydroxy(2-naphthyl)methyl]-5-(morpholin-4-yl)thiophene-2-carboxylic acid (15.17 g, 0.02423 mol), and N,N-dimethylformamide (66.2 mL), followed by methyl iodide (53.7 mL, 0.863 mol). Added another 10 mL DMF, sonicated to suspend/mix all solid. The reaction mixture was stirred at room temperature for 26 hours, then was diluted with EtOAc, filtered through a pad of Celite, concentrated filtrate in vacuo, azeotroped w/toluene (10×10 mL), DCM (20 mL), dried on high vacuum pump. The crude material was used directly in the next step. LC/MS (AA) ES+ 423, ES+Na+445; $^1$H NMR (400 MHz, DMSO) δ 7.97 (s, 1H), 7.91-7.86 (m, 3H), 7.53-7.48 (m, 3H), 6.62 (s, 1H), 3.85 (s, 3H), 3.72-3.69 (m, 4H), 3.52-3.50 (m, 4H), 3.43 (s, 3H).

Step 3: 4-cyano-3-[methoxy(2-naphthyl)methyl]-5-(morpholin-4-yl)thiophene-2-carboxylic acid To methyl 4-cyano-3-[methoxy(2-naphthyl)methyl]-5-(morpholin-4-yl)thiophene-2-carboxylate (10.56 g, 25 mmol) in a round bottom flask equipped with a stirbar was added tetrahydrofuran (278 mL) and 1.000 M of sodium hydroxide in water (208 mL, 208 mmol). Methanol (139 mL) was added to the mixture, and the resulting yellow mixture was stirred at room temperature for 16 h. The reaction mixture was quenched by the addition of 1N HCl aqueous solution to adjust the pH to 2 and EtOAc was added. The mixture was transferred to a separatory funnel, separated layers, extracted aqueous 2× w/EtOAc, combined organics, washed w/brine, dried over Na$_2$SO$_4$, filtered, added celite, rotavapped, dried on high vacuum for 45 min. The crude material was purified using a dry load on 330 g silica gel ISCO column (gradient elution: 0-20% MeOH/DCM) to obtain the product as an impure beige solid (9.8 g). Took 2 g, redissolved in DCM, added Celite, rotovapped, dried on high vac 45 min. Repurified this portion of product on 120 g ISCO silica gel column (gradient elution: 0-12% MeOH/DCM) to obtain 2.0 g beige foam product (racemate). LC/MS (FA) ES− 407; NMR (400 MHz, DMSO) δ 13.57 (s, 1H), 7.96 (s, 1H), 7.89-7.86 (m, 3H), 7.53-7.46 (m, 3H), 6.68 (s, 1H), 3.73-3.67 (m, 4H), 3.50-3.45 (m, 4H), 3.43 (s, 3H). Enantiomeric separation of the enantiomers was performed by chiral HPLC on CHIRALPAK IC 4.6×250 mm with 85/5/10/0.1% HEX/IPA/ETOH/DEA 10 uL Injection at 1.0 mL/min for 50 min.

Step 4: 4-cyano-3-[methoxy(2-naphthyl)methyl]-5-(morpholin-4-yl)thiophene-2-carboxylic acid.Na 4-cyano-3-[methoxy(2-naphthyl)methyl]-5-(morpholin-4-yl)thiophene-2-carboxylic acid (313.0 mg, 0.7663 mmol) was suspended in ethanol (7.159 mL, 122.6 mmol) and water (2.071 mL, 114.9 mmol) at room temperature. 1.030 M of sodium hydroxide in water (744.0 uL, 0.7663 mmol) was added slowly and the resulting solution was stirred for 10 min. The organic solvent was removed in vacuo. Added 40 ml water, freeze-dried, and lyophilized over night to give 322 mg amber solid (98% yield). LC/MS (FA) ES− 407.5; NMR (400 MHz, DMSO) δ 7.99 (s, 1H), 7.88-7.76 (m, 3H), 7.61 (dd, J=8.6, 1.3 Hz, 1H), 7.50-7.42 (m, 2H), 7.24 (s, 1H), 3.68-3.65 (m, 4H), 3.37 (s, 3H), 3.26-3.33 (m, 4H).

Compounds in the following table are prepared from appropriate starting materials in a method analogous to that of Example 53.

| | |
|---|---|
| 337 | LC/MS: (FA) ES− 407 |

Example 54

Synthesis of Ethyl 4-cyano-5-(morpholin-4-yl)-3-[1-(2-naphthyl)ethyl]thiophene-2-carboxylate (Compound 367)

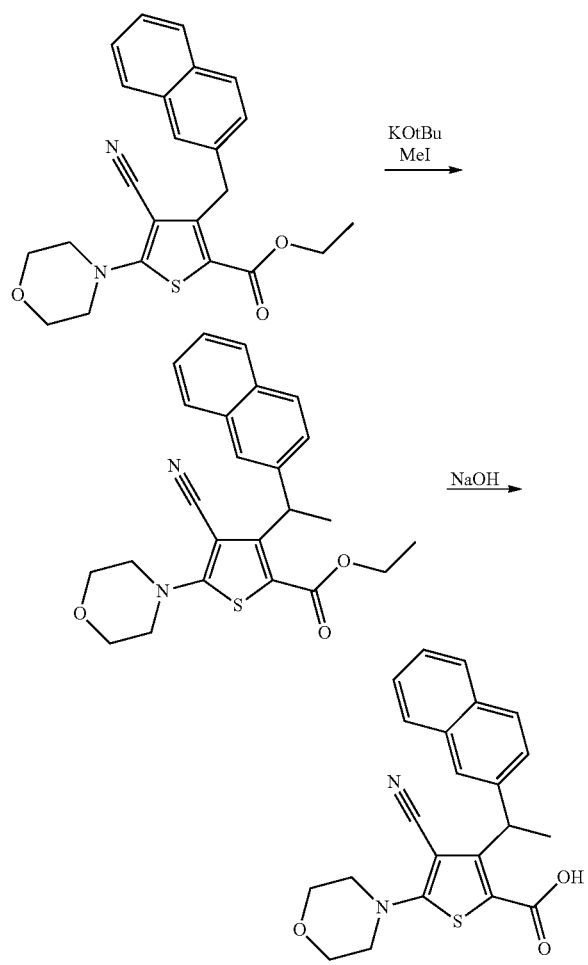

Step 1

A 1 L flask was charged with a big egg-shape stirring bar and ethyl 4-cyano-5-morpholin-4-yl-3-(2-naphthylmethyl)thiophene-2-carboxylate (14.5 g, 35.7 mmol). To the flask was added N,N-dimethylformamide (240 mL) and the mixture was evacuated and purged with nitrogen (×3). To the flask was added tetrahydrofuran (60 mL), and the mixture was stirred until it became a clear yellow solution. The solution was cooled to ~−25° C. in a dry ice-acetone bath (the temperature was actively controlled by slow addition of dry ice between −30~−40° C.). 1 M of Potassium tert-butoxide in tetrahydrofuran (42.8 mL) was added dropwise over 3 min. The mixture turned deep purple immediately. After the addition the mixture was stirred for 10 min at this temperature. Methyl iodide (11.1 mL, 178 mmol) was added over 1 min. By the end of addition the mixture turned light red. After stirring the resulting mixture at 0° C. for 10 min, the reaction was quenched by addition of 10 mL of water. All volatiles were removed under reduced pressure and the resulting mixture was distributed between brine and EtOAc. The aqueous layer was extracted with EtOAc (×2). The combined organic layers were washed with 10% LiCl (aq) soln (×3), then brine, dried, and concentrated to provide a yellow syrup. Purification on a silica gel column (gradient elution 5-20% EtOAc/hexanes) provided Ethyl 4-cyano-5-(morpholin-4-yl)-3-[1-(2-naphthyl)ethyl]thiophene-2-carboxylate as a white solid (11.8 g, 78.7% yield). LCMS: (AA) ES+ 421; $^1$H NMR (400 MHz, CDCl$_3$) δ 7.90-7.82 (m, 2H), 7.82-7.70 (dd, J=15.4, 8.1 Hz, 2H), 7.50-7.37 (m, 3H), 5.82-5.67 (q, J=7.3 Hz, 1H), 4.40-4.25 (qd, J=6.1, 5.0, 3.1 Hz, 2H), 3.86-3.72 (t, J=4.8 Hz, 4H), 3.54-3.44 (t, J=4.8 Hz, 4H), 1.95-1.85 (d, J=7.3 Hz, 3H), 1.42-1.31 (t, J=7.1 Hz, 3H).

Step 2

Ethyl 4-cyano-5-(morpholin-4-yl)-3-[1-(2-naphthyl)ethyl]thiophene-2-carboxylate (13.3 g, 31.6 mmol) in tetrahydrofuran (200 mL) and methanol (150 mL) was stirred until the mixture turned into a clear solution. To the solution was added 1.000 M sodium hydroxide in water (158 mL). The resulting turbid mixture was vigorously stirred at rt for 12 h. The volatiles were removed under reduced pressure, and the resulting aqueous solution was acidified by addition of 12.0 M of hydrochloric acid in water (15.9 mL, 191 mmol) at 0° C., and then extracted with EtOAc (×3). The combined organic layers were washed with 1M HCl soln, dried, and concentrated to provide 4-cyano-5-(morpholin-4-yl)-3-[1-(2-naphthyl)ethyl]thiophene-2-carboxylic acid as a white solid (12.1 g, 97.5% yield). 250 mg of the racemic mixture was purified on chiral prep HPLC to provide each enantiomer (115 mg each, >95% ee) (OJ column, elution with 85/5/10/0.1% hexane/iPrOH/EtOH/Et$_2$NH). LCMS: (AA) ES+ 393; $^1$H NMR (400 MHz, MeOD) δ 7.85-7.76 (m, 3H), 7.76-7.71 (d, J=8.6 Hz, 1H), 7.49-7.38 (m, 2H), 7.38-7.29 (dd, J=8.5, 1.7 Hz, 1H), 5.90-5.74 (q, J=7.3 Hz, 1H), 3.82-3.69 (m, 4H), 3.52-3.43 (dd, J=5.8, 4.0 Hz, 4H), 1.91-1.80 (d, J=7.3 Hz, 3H).

Step 3

The active enantiomer 4-cyano-5-(morpholin-4-yl)-3-[1-(2-naphthyl)ethyl]thiophene-2-carboxylic acid (780 mg, 1.99 mmol) was suspended in ethanol (10.0 mL, 171 mmol). To the mixture was added 1.030 M of sodium hydroxide in water (2.00 mL, 2.06 mmol). The mixture was swirled and sonicated until it turned homogeneous. The solution was concentrated to provide 4-cyano-5-(morpholin-4-yl)-3-[1-(2-naphthyl)ethyl]thiophene-2-carboxylic acid.Na as a yellow solid (785 mg, 95% yield). LCMS: (AA) ES+ 393; $^1$H NMR (400 MHz, MeOD) δ 7.85-7.72 (m, 3H), 7.72-7.66 (d, J=8.6 Hz, 1H), 7.45-7.30 (ddd, J=12.6, 4.9, 2.2 Hz, 3H), 6.20-6.06 (q, J=7.0 Hz, 1H), 3.81-3.70 (t, J=4.8 Hz, 4H), 3.40-3.32 (t, J=4.8 Hz, 4H), 1.88-1.78 (d, J=7.4 Hz, 3H).

Compounds in the following table are prepared from appropriate starting materials in a method analogous to that of Example 54.

| | |
|---|---|
| 306 | LC/MS: (FA) ES+ 423 |
| 313 | LC/MS: (FA) ES+ 423 |
| 322 | LC/MS: (FA) ES+ 425 |
| 333 | LC/MS: (AA) ES+ 393 |
| 346 | LC/MS: (FA) ES+ 369 |
| 363 | LC/MS: (FA) ES+ 423 |
| 365 | LC/MS: (FA) ES+ 425 |
| 366 | LC/MS: (AA) ES− 409, 411, 413 |

Example 55

Synthesis of 4-(5-((1H-tetrazol-5-yl)methyl)-4-(3,4-dichlorobenzyl)thiazol-2-yl)morpholine (Compound 350)

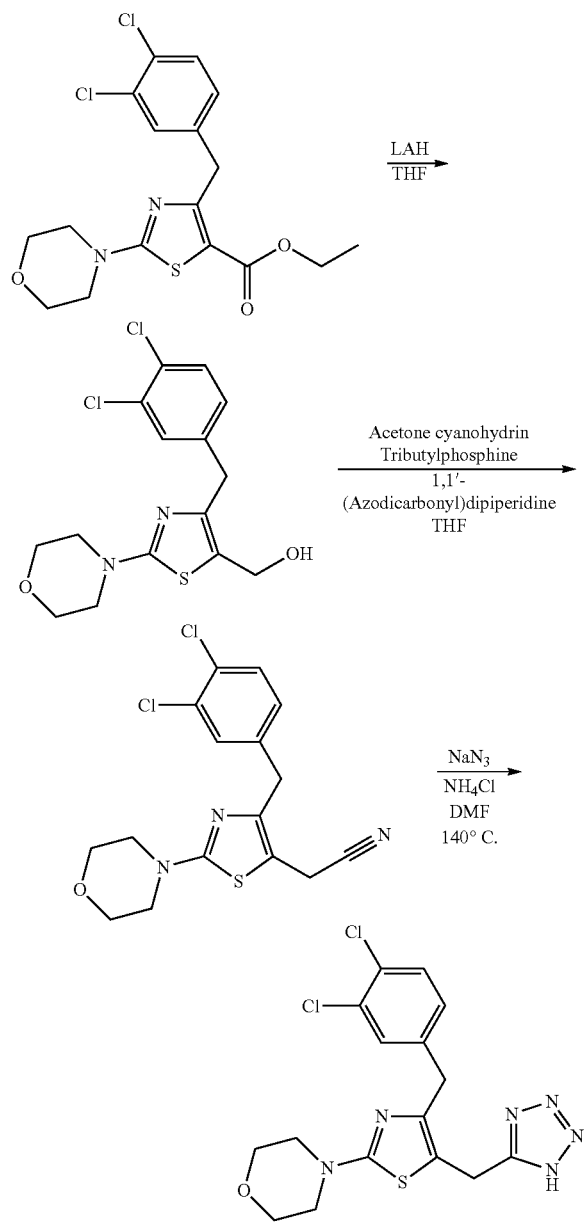

Step 1, Preparation of (4-(3,4-dichlorobenzyl)-2-morpholinothiazol-5-yl)methanol To a solution of ethyl 4-(3,4-dichlorobenzyl)-2-morpholinothiazole-5-carboxylate (4.92 g, 12.2 mmol) in THF (100 mL) was added a 2.00 M solution of LAH in THF (12.9 mL, 25.8 mmol) and the resulting solution was stirred for 2 hours at room temperature. The reaction was quenched by adding saturated NH$_4$Cl (26 mL) followed by 1M HCl (26 mL). Water (100 mL) and ethyl acetate (200 mL) were then added. The layers were separated and the organic layer was washed with brine (50 mL). The organic layer was dried and concentrated in vacuo. The residue was purified by silica gel chromatography (ethyl acetate/DCM=0/100→100/0) to give 2.87 g (65% yield) of the title compound. as a white solid. LC/MS (FA) ES+ 359, 361. $^1$H NMR (400 MHz, CDCl$_3$) δ: 7.34-7.31 (m, 2H), 7.09 (dd, 1H, J=6.0, 2.0 Hz), 4.66 (d, 2H, J=1.2 Hz), 3.84 (s, 2H), 3.79-3.77 (m, 4H), 3.42-3.39 (m, 4H).

Step 2, Preparation of 2-(4-(3,4-dichlorobenzyl)-2-morpholinothiazol-5-yl)acetonitrile To a solution of (4-(3,4-dichlorobenzyl)-2-morpholinothiazol-5-yl)methanol (1.19 g, 3.31 mmol) in THF (58.6 mL) was added acetone cyanohydrin (0.454 mL, 4.97 mmol), 1,1'-(azodicarbonyl)dipiperidine (1.67 g, 6.62 mmol) and tributylphosphine (1.65 mL, 6.62 mmol) and the reaction was stirred for 3 hours at room temperature. The reaction was concentrated in vacuo. The residue was purified by silica gel chromatography (ethyl acetate/DCM=0/100→20/80) to give 551 mg (45% yield) of the title compound as a beige solid. LC/MS (FA) ES+ 368, 370. NMR (400 MHz, CDCl$_3$) δ: 7.35 (d, 1H, J=6.0 Hz), 7.32 (d, 1H, J=2.0 Hz), 7.07 (dd, 1H, J=6.0, 2.0 Hz), 3.82 (s, 2H), 3.80-3.77 (m, 4H), 3.66 (s, 2H), 3.42-3.40 (m, 4H).

Step 3, Preparation of 4-(5-((1H-tetrazol-5-yl)methyl)-4-(3,4-dichlorobenzyl)thiazol-2-yl)morpholine To a solution of 2-(4-(3,4-dichlorobenzyl)-2-morpholinothiazol-5-yl)acetonitrile (87.0 mg, 0.236 mmol) in DMF (0.74 mL) was added sodium azide (21.6 mg, 0.332 mmol) and NH$_4$Cl (17.8 mg, 9.53 mmol) and the resulting mixture was heated to 140 degrees overnight. More sodium azide (43 mg, 0.66 mmol) and NH$_4$Cl (36 mg, 19 mmol) were added and the reaction was heated to 120 degrees overnight. The reaction was cooled and taken up in ethyl acetate (25 mL) and water (5 ml). The layers were separated and the organic layer was washed with water (3×5 mL).). The organic layer was dried and concentrated in vacuo. The residue was purified by preparative reverse phase chromatography to give 5 mg (5% yield) of the title compound. as a white solid. LC/MS (FA) ES+ 411. 413. $^1$H NMR (400 MHz, DMSO-d$_6$) δ: 7.50 (d, 1H, J=8.0 Hz), 7.46 (d, 1H, J=2.0 Hz), 7.20 (dd, 1H, J=8.0, 2.0 Hz), 4.41 (s, 2H), 3.88 (s, 2H), 3.65-3.62 (m, 4H), 3.32 (bs, 1H), 3.26-3.24 (m, 4H).

Example 56

Synthesis of 4-cyano-3-[1-(3,4-dichlorophenyl)-3-hydroxypropyl]-5-(morpholin-4-yl)thiophene-2-carboxylic acid (Compound 347)

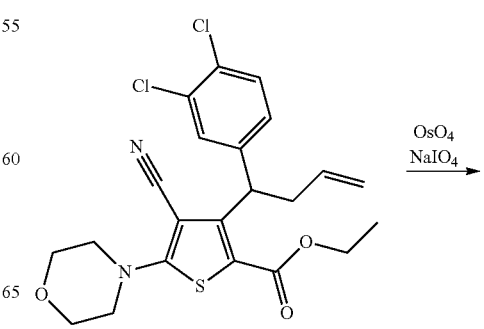

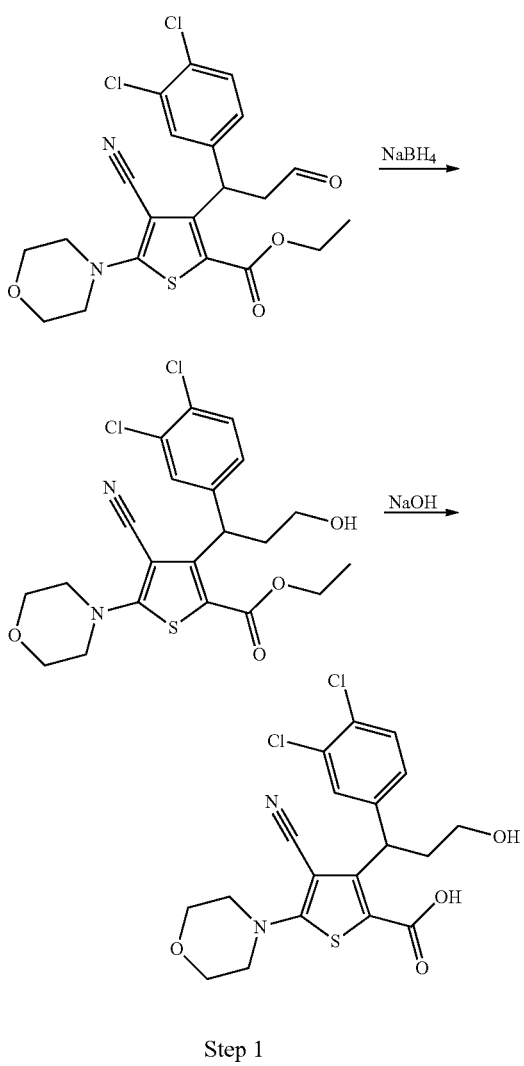

Step 1

To a suspension of ethyl 4-cyano-3-[1-(3,4-dichlorophenyl)but-3-en-1-yl]-5-(morpholin-4-yl)thiophene-2-carboxylate (247 mg, 0.531 mmol) in 1,4-dioxane (6.00 mL) and water (2.00 mL) was added sodium metaperiodate (454 mg, 2.12 mmol), 2,6-lutidine (246 uL, 2.12 mmol), and 4% osmium tetroxide in water (4:96, osmium tetraoxide:water, 64.9 uL, 0.0106 mmol). The reaction was vigorously stirred at rt for 5 hrs. The mixture was filtered over a celite pad and the filtered solid was rinsed with EtOAc. The filtrate was washed with NaHCO₃(aq) saturated solution and the aqueous layer was extracted with EtOAc (×2). The combined organic layer was washed with 1N HCl soln and brine, dried, and concentrated. Purification on a silica gel column (gradient elution 5-50% EtOAc/hexanes) provided ethyl 4-cyano-3-[1-(3,4-dichlorophenyl)-3-oxopropyl]-5-(morpholin-4-yl)thiophene-2-carboxylate as a yellow syrup (108 mg, 43.5% yield). $^1$H NMR (400 MHz, CDCl$_3$) δ 9.84-9.73 (d, J=1.3 Hz, 1H), 7.48-7.42 (d, J=2.1 Hz, 1H), 7.42-7.32 (d, J=8.4 Hz, 1H), 7.30-7.18 (m, 1H), 6.06-5.94 (t, J=-7.7 Hz, 1H), 4.38-4.26 (q, J=7.1 Hz, 2H), 3.86-3.77 (t, J=4.9 Hz, 4H), 3.62-3.51 (dd, J=5.7, 4.0 Hz, 4H), 3.50-3.42 (m, 2H), 1.41-1.29 (m, 3H).

Step 2

To a solution of ethyl 4-cyano-3-[1-(3,4-dichlorophenyl)-3-oxopropyl]-5-(morpholin-4-yl)thiophene-2-carboxylate (50.0 mg, 0.107 mmol) in ethanol (1.00 mL) was added sodium tetrahydroborate (4.05 mg, 0.107 mmol). The mixture was stirred at rt for 1 hr. The reaction was quenched with 1.00 M of hydrochloric acid in water (0.428 mL) and distributed between NaHCO₃(aq) saturated solution and EtOAc. The aqueous layer was extracted with EtOAc (×2). The combined organic layer was dried and concentrated to provide a white solid. Purification on a silica gel column (gradient elution 0-5% MeOH) provided ethyl 4-cyano-3-[1-(3,4-dichlorophenyl)-3-hydroxypropyl]-5-(morpholin-4-yl)thiophene-2-carboxylate as a colorless syrup (38 mg, 75.7% yield). $^1$H NMR (400 MHz, CDCl$_3$) δ 7.46-7.35 (dd, J=5.2, 3.1 Hz, 2H), 7.30-7.19 (m, 1H), 5.65-5.52 (t, J=8.0 Hz, 1H), 4.42-4.26 (q, J=7.1 Hz, 2H), 3.85-3.77 (t, J=4.9 Hz, 4H), 3.76-3.65 (ddt, J=13.0, 9.0, 4.6 Hz, 1H), 3.57-3.44 (t, J=4.8 Hz, 5H), 2.69-2.58 (dd, J=8.4, 4.1 Hz, 1H), 2.56-2.43 (dt, J=8.1, 4.9 Hz, 2H), 1.44-1.32 (t, J=7.1 Hz, 3H).

Step 3

To a solution of ethyl 4-cyano-3-[1-(3,4-dichlorophenyl)-3-hydroxypropyl]-5-(morpholin-4-yl)thiophene-2-carboxylate (38.0 mg, 0.0810 mmol) in tetrahydrofuran (1.00 mL) was added NaH 60% in mineral oil (60:40, Sodium hydride:mineral Oil, 3.56 mg, 0.0890 mmol). The mixture was heated to 60° C. for 3 hrs. The reaction was cooled to rt and distributed between brine and EtOAc. The aqueous layer was extracted with EtOAc (×2). The combined organic layer was washed with brine, dried, and concentrated to provide a yellow solid. Purification on HPLC (reverse phase, AA) provided 4-cyano-3-[1-(3,4-dichlorophenyl)-3-hydroxypropyl]-5-(morpholin-4-yl)thiophene-2-carboxylic acid as a white solid (6.5 mg, 18.2% yield). LCMS: (AA) ES+ 441, 443, 445; $^1$H NMR (400 MHz, MeOD) δ 7.50-7.45 (s, 1H), 7.45-7.37 (d, J=8.4 Hz, 1H), 7.30-7.22 (m, 1H), 5.79-5.63 (m, 1H), 3.83-3.71 (t, J=4.8 Hz, 4H), 3.60-3.50 (q, J=6.9, 6.0 Hz, 2H), 3.50-3.41 (d, J=3.2 Hz, 4H), 2.52-2.37 (m, 2H).

Example 57

Synthesis of 4-cyano-3-[1-(3,4-dichlorophenyl)-3-(dimethylamino)propyl]-5-(morpholin-4-yl)thiophene-2-carboxylic acid (Compound 331)

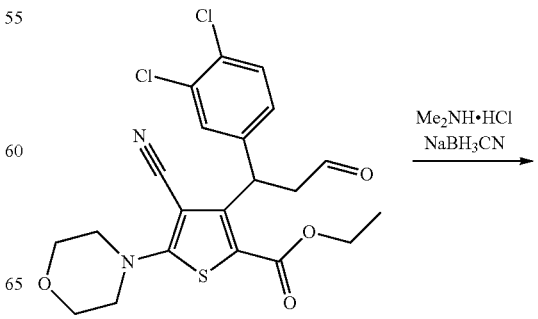

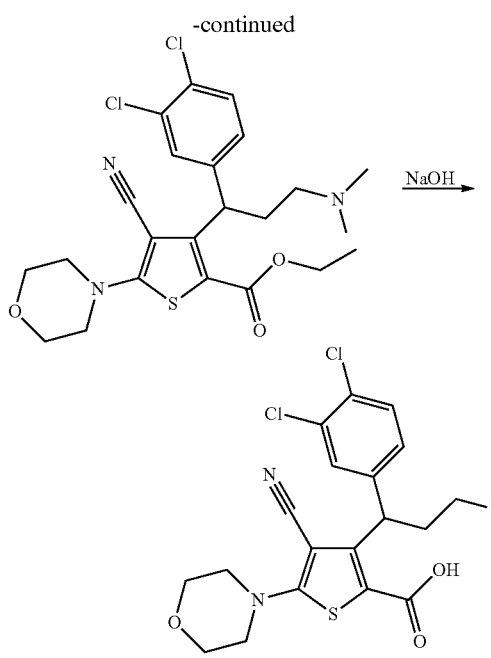

Step 1

To a solution of ethyl 4-cyano-3-[1-(3,4-dichlorophenyl)-3-oxopropyl]-5-(morpholin-4-yl)thiophene-2-carboxylate (38.0 mg, 0.0813 mmol) (from example 56, step 1) in methanol (1.00 mL) was added dimethylamine hydrochloride (9.94 mg, 0.122 mmol), sodium acetate (8.00 mg, 0.0976 mmol), and sodium cyanoborohydride (6.13 mg, 0.0976 mmol). The reaction was stirred at rt for 2 h. The mixture was distributed between NaHCO$_3$(aq) saturated solution and EtOAc. The aqueous layer was extracted with EtOAc (×2). The combined organic layer was dried and concentrated. Purification on a silica gel column (gradient elution, 0-15% MeOH/CH$_2$Cl$_2$) provided ethyl 4-cyano-3-[1-(3,4-dichlorophenyl)-3-(dimethylamino)propyl]-5-(morpholin-4-yl)thiophene-2-carboxylate as a yellow syrup (29.0 mg, 71.8% yield). LCMS: (AA) ES+ 496, 498, 500; $^1$H NMR (400 MHz, CDCl$_3$) δ 7.52-7.44 (d, J=1.9 Hz, 1H), 7.41-7.34 (m, 1H), 7.33-7.27 (m, 1H), 5.54-5.40 (t, J=7.7 Hz, 1H), 4.38-4.27 (q, J=7.1 Hz, 2H), 3.88-3.76 (t, J=4.9 Hz, 4H), 3.58-3.49 (dd, J=5.7, 4.0 Hz, 4H), 2.57-2.31 (m, 3H), 2.29-2.24 (s, 6H), 2.24-2.16 (m, 1H), 1.41-1.30 (t, J=7.1 Hz, 3H).

Step 2

To a solution of ethyl 4-cyano-3-[1-(3,4-dichlorophenyl)-3-(dimethylamino)propyl]-5-(morpholin-4-yl)thiophene-2-carboxylate (29.0 mg, 0.0584 mmol) in methanol (0.500 mL) was added 1.030 M of sodium hydroxide in water (284 uL, 0.284 mmol). The reaction was stirred at rt over 2 days. The mixture was neutralized with 1.00 M of hydrochloric acid in water (0.292 mL), diluted with 5 mL of water and extracted with 10% MeOH/CHCl$_3$ (×5). The combined organic layer was dried and concentrated, and the resulting white syrup/solid was lyophilized to provide 4-cyano-3-[1-(3,4-dichlorophenyl)-3-(dimethylamino)propyl]-5-(morpholin-4-yl) thiophene-2-carboxylic acid as a white solid (26 mg, 95% yield). LCMS: (AA) ES+ 468, 470, 472; $^1$H NMR (400 MHz, DMSO) δ 7.63-7.52 (d, J=8.4 Hz, 1H), 7.44-7.37 (s, 1H), 7.15-7.02 (d, J=8.1 Hz, 1H), 5.49-5.34 (d, J=9.4 Hz, 1H), 3.73-3.63 (t, J=4.8 Hz, 4H), 3.38-3.31 (dd, J=6.2, 4.0 Hz, 4H), 3.13-2.97 (s, 1H), 2.85-2.73 (s, 1H), 2.72-2.60 (s, 6H), 2.56-2.52 (m, 1H).

Example 58

Synthesis of 3-(3,4-dichlorobenzyl)-4-fluoro-5-morpholinothiophene-2-carboxylic acid (Compound 320)

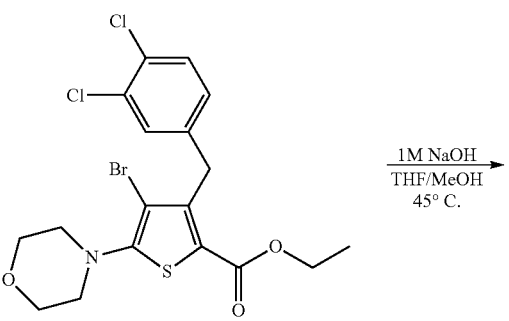

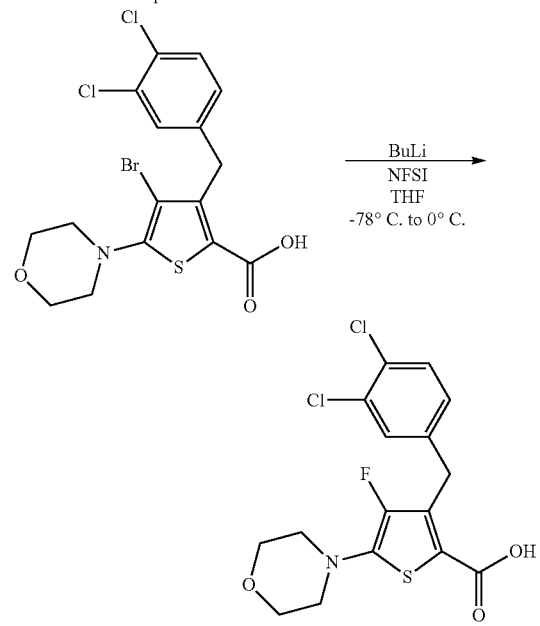

Step 1, Preparation of 4-bromo-3-(3,4-dichlorobenzyl)-5-morpholinothiophene-2-carboxylic acid To a solution of ethyl 4-bromo-3-(3,4-dichlorobenzyl)-5-morpholinothiophene-2-carboxylate (109 mg, 0.227 mmol) in THF (1.8 mL) and MeOH (0.37 mL) was added 1.00 M aqueous NaOH (1.82 mL, 1.82 mmol) and the resulting mixture was stirred at 45° C. overnight. The reaction was diluted with water (5 mL) and acidified to pH=3 with 1 N HCl. The mixture was extracted with ethyl acetate (2×20 mL) and the combined organic layers were dried, filtered and concentrated in vacuo to give 92 mg (90% yield) of a white solid which was used as is in the next step. LC/MS (AA) ES+ 450, 452, 454. $^1$H NMR (400 MHz, DMSO-d$_6$) δ: 13.21 (bs, 1H), 7.52 (d, 1H, J=8.0 Hz), 7.39 (d, 1H, 2.0 Hz), 7.09 (dd, 1H, J=8.0, 2.0 Hz), 4.36 (s, 2H), 3.74-3.71 (m, 4H), 3.13-3.11 (m, 4H).

Step 2, Preparation of 3-(3,4-dichlorobenzyl)-4-fluoro-5-morpholinothiophene-2-carboxylic acid To a solution of 4-bromo-3-(3,4-dichlorobenzyl)-5-morpholinothiophene-2-carboxylic acid (89.0 mg, 0.197 mmol) in THF (3.00 mL) in a dry-ice/acetone bath was added 1.60 M BuLi in hexanes (0.271 mL, 0.434 mmol) and the resulting solution was stirred for 10 minutes at −78° C. A solution of N-fluoro-N-(phenylsulfonyl)benzenesulfonamide (93.3 mg, 0.296 mmol) in THF (0.70 mL) was then added and the reaction was allowed to warm to 0° C. The reaction was quenched with saturated NH4Cl (5 mL) and ethyl acetate (15 mL) was then added. The layers were separated and the aqueous layer was acidified to pH=3 with 1N HCl. The acidic aqueous layer was extracted with ethyl acetate (2×20 mL) and the combined organic layers were dried, filtered and concentrated in vacuo. The residue was purified by silica gel chromatography (MeOH/DCM=0/100→15/85) to give 31 mg of product. This material was purified by preparative reverse phase chromatography to give 9 mg (10% yield) of the title compound. as a white solid. LC/MS (FA) ES+ 390, 392. $^1$H NMR (400 MHz, DMSO-d$_6$) δ: 13.04 (bs, 1H), 7.54 (d, 1H, J=8.0 Hz), 7.44 (d, 1H, J=1.6 Hz), 7.16 (dd, 1H, J=8.0, 1.6 Hz), 4.21 (s, 2H), 3.71-3.68 (m, 4H), 3.14-3.12 (m, 4H).

Example 59

Synthesis of 4-cyano-5-(morpholin-4-yl)-3-[(4-oxoquinazolin-3(4H)-yl)methyl]thiophene-2-carboxylic acid (Compound 294)

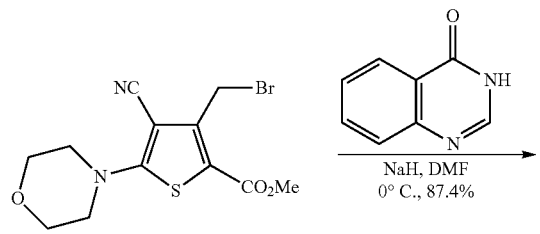

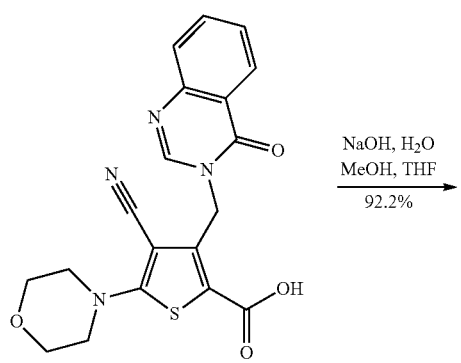

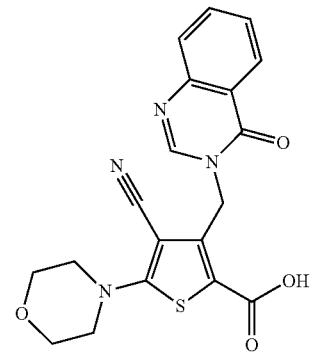

Step 1: Methyl 4-cyano-5-(morpholin-4-yl)-3-[(4-oxoquinazolin-3(4H)-yl)methyl]thiophene-2-carboxylate Under N$_2$ atmosphere Sodium hydride (23.0 mg, 0.910 mmol) was suspended in anhydrous N,N-Dimethylformamide (3.0 mL, 39 mmol), cooled with ice bath and stirred for 10 min. 4-hydroxyquinazoline (0.120 g, 0.821 mmol) was added and the clear solution was stirred at r.t. for 10 min, cooled with ice bath. Methyl 3-(bromomethyl)-4-cyano-5-(morpholin-4-yl)thiophene-2-carboxylate (0.203 g, 0.588 mmol) was added and the reddish-brown solution was stirred with cooling for 40 min. The mixture was quenched with saturated NH4Cl aqueous solution, extracted with EtOAc. The EtOAc solution was washed with water (3x) then brine, dried over Na$_2$SO$_4$, filtered, rotavaped to give a crude solid. Chromatograph in a silica gel column using MeOH/DCM (0/100 to 5/95) afforded a solid product (0.211 g, yield 87.4%). LC/MS: (FA) ES$^+$ 411. $^1$H NMR (400 MHz, d-chloroform) δ 8.30 (m, 1H), 8.26 (s, 1H), 7.68-7.76 (m, 2H), 7.45-7.49 (m, 1H), 5.43 (s, 2H), 3.83-3.85 (m, 4H), 3.82 (s, 3H), 3.59-3.62 (m, 4H).

Step 2: 4-Cyano-5-(morpholin-4-yl)-3-[(4-oxoquinazolin-3(4H)-yl)methyl]thiophene-2-carboxylic acid sodium salt Methyl 4-cyano-5-(morpholin-4-yl)-3-[(4-oxoquinazolin-3(4H)-yl)methyl]thiophene-2-carboxylate (0.139 g, 0.339 mmol) was dissolved in Tetrahydrofuran (15.0 mL), Water (2.0 mL) and Methanol (5.0 mL). 1.00 M of Sodium hydroxide in Water (1.0 mL, 1.0 mmol) was added and the homogeneous solution was stirred at room temperature for 24 hours. The solution was concentrated in rotavapor to give a white crude solid, dissolved in H2O/MeOH (1/10, ~20 mL) and concentrated in rotavapor until a white suspension (~2 mL volume). The suspension was filtered to collect the solid, dried in lypholizer to give a white solid product (0.132 g, yield 92.2%). LC/MS: (FA) ES$^+$ 397; ES$^-$ 395. $^1$H NMR (400 MHz, d4-methanol) δ 8.37 (s, 1H), 8.22 (d, J=8.03 Hz, 1H), 7.78-

7.82 (m, 1H), 7.65 (d, J=7.28 Hz, 1H), 7.51-7.55 (m, 1H), 5.99 (s, 2H), 3.78-3.81 (m, 4H), 3.47-3.50 (m, 4H).

Example 60

Synthesis of 4-(3,4-dichlorobenzyl)-N-hydroxy-2-(morpholin-4-yl)-1,3-thiazole-5-carboxamide (Compound 298)

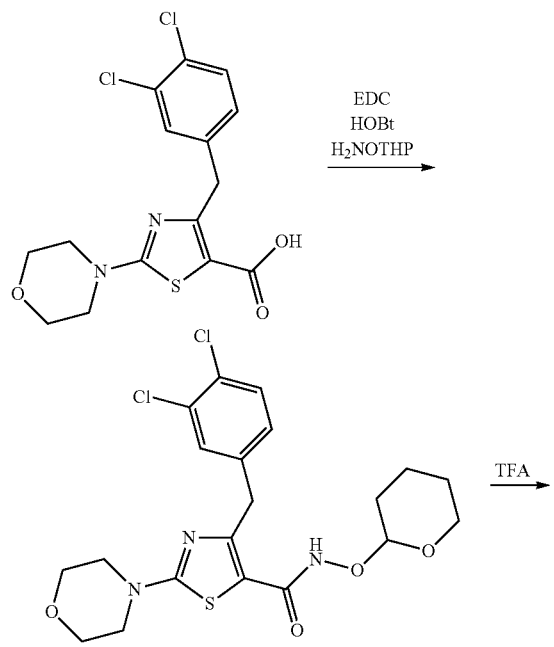

Step 1

To a suspension of 4-(3,4-dichlorobenzyl)-2-morpholin-4-yl-1,3-thiazole-5-carboxylic acid.Na (125 mg, 0.316 mmol), N-(3-dimethylaminopropyl)-N'-ethylcarbodiimide hydrochloride (72.8 mg, 0.380 mmol), and 1-hydroxybenzotriazole (51.3 mg, 0.380 mmol) in N,N-dimethylformamide (1.50 mL) was added O-(tetrahydropyran-2-yl)hydroxylamine (55.6 mg, 0.474 mmol). The reaction was stirred at rt for 15 hrs. The mixture was distributed between water and EtOAc, and the aqueous layer was extracted with EtOAc (×2). The combined organic layer was washed with NaHCO$_3$(aq) saturated solution and 10% LiCl (aq) soln (×2), dried over Na$_2$SO$_4$, and concentrated to provide 4-(3,4-dichlorobenzyl)-2-(morpholin-4-yl)-N-(tetrahydro-2H-pyran-2-yloxy)-1,3-thiazole-5-carboxamide as a white solid (153 mg, quantitative). LCMS: (AA) ES+ 472, 474, 476; $^1$H NMR (400 MHz, CDCl$_3$) δ 7.49-7.43 (d, J=1.9 Hz, 1H), 7.30-7.26 (m, 1H), 7.26-7.17 (m, 1H), 5.01-4.89 (d, J=2.8 Hz, 1H), 4.31-4.21 (m, 2H), 3.96-3.86 (td, J=10.4, 9.1, 2.8 Hz, 1H), 3.80-3.70 (t, J=4.9 Hz, 4H), 3.66-3.56 (m, 1H), 3.51-3.42 (t, J=4.9 Hz, 4H), 1.90-1.73 (m, 3H), 1.69-1.49 (m, 3H).

Step 2

To a solution of 4-(3,4-dichlorobenzyl)-2-(morpholin-4-yl)-N-(tetrahydro-2H-pyran-2-yloxy)-1,3-thiazole-5-carboxamide (153 mg, 0.324 mmol) in methylene chloride (1.50 mL) was added trifluoroacetic Acid (1.50 mL, 19.5 mmol). The reaction was stirred at rt for 12 hrs. The resulting solution was concentrated and distributed between NaHCO$_3$(aq) saturated solution and CH$_2$Cl$_2$. The aqueous layer was extracted with CH$_2$Cl$_2$(×2). The combined org layer was washed with water, dried, and concentrated. Purification on a silica gel column (gradient elution, 0-8% MeOH/CH$_2$Cl$_2$) provided 4-(3,4-dichlorobenzyl)-N-hydroxy-2-(morpholin-4-yl)-1,3-thiazole-5-carboxamide as a yellow solid (53 mg, 42.1% yield). LCMS: (AA) ES+ 388, 390, 392; $^1$H NMR (400 MHz, MeOD) δ 7.47-7.41 (d, J=1.8 Hz, 1H), 7.38-7.29 (d, J=8.3 Hz, 1H), 7.25-7.14 (dd, J=8.3, 1.9 Hz, 1H), 4.28-4.21 (s, 2H), 3.79-3.71 (t, J=4.9 Hz, 4H), 3.50-3.43 (t, J=4.9 Hz, 4H), 3.33-3.27 (t, J=1.6 Hz, 1H).

Compounds in the following table are prepared from appropriate starting materials in a method analogous to that of Example 60.

| | |
|---|---|
| 334 | LC/MS: (AA) ES+ 354 |

Example 61

Synthesis of 2-(morpholin-4-yl)-4-(2-naphthylmethyl)-5-(1H-tetrazol-5-yl)thiophene-3-carbonitrile (Compound 316)

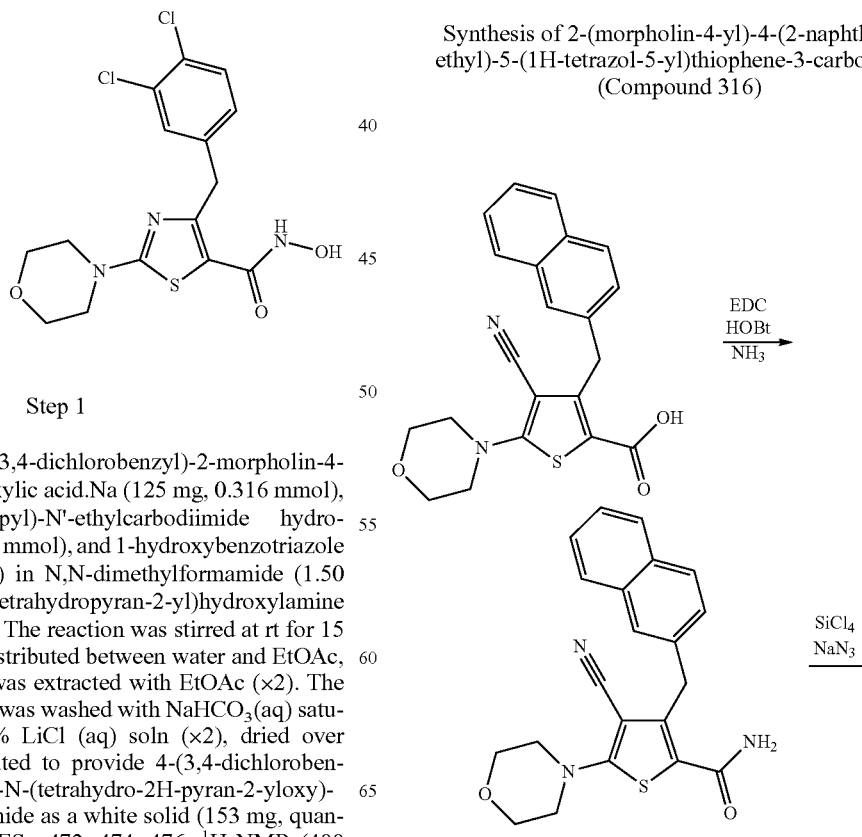

367
-continued

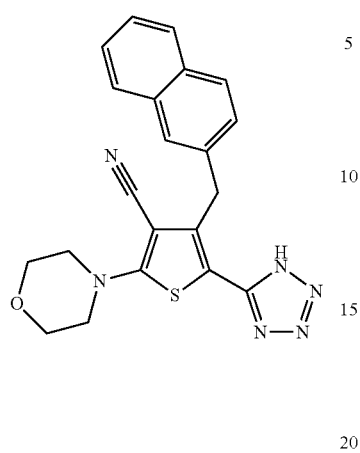

Step 1:

To a mixture of 4-cyano-5-morpholin-4-yl-3-(2-naphthylmethyl)thiophene-2-carboxylic acid.Na (255 mg, 0.637 mmol) in N,N-dimethylformamide (6.00 mL) was added 1-hydroxybenzotriazole hydrate (117 mg, 0.764 mmol), N-(3-dimethylaminopropyl)-N'-ethylcarbodiimide hydrochloride (146 mg, 0.764 mmol), and 0.500 M of ammonia in 1,4-dioxane (3.18 mL, 1.59 mmol). The reaction was vigorously stirred at rt for 5 hrs. The mixture was distributed between brine and EtOAc, and the aqueous layer was extracted with EtOAc (×2). The combined organic layers were washed with 10% LiCl (aq) solution (×2), dried, and concentrated to provide 4-cyano-5-(morpholin-4-yl)-3-(2-naphthylmethyl)thiophene-2-carboxamide (Compound 327) as a white solid (224 mg, 93.2% yield). LCMS: (AA) ES+ 378; $^1$H NMR (400 MHz, DMSO)δ 7.89-7.76 (td, J=11.0, 6.6 Hz, 3H), 7.68-7.62 (s, 1H), 7.51-7.44 (td, J=6.8, 6.0, 3.7 Hz, 3H), 7.43-7.34 (m, 1H), 4.50-4.42 (s, 2H), 3.78-3.69 (t, J=4.9 Hz, 4H), 3.50-3.40 (t, J=4.9 Hz, 4H).

Step 2:

To a mixture of sodium azide (153 mg, 2.35 mmol) in acetonitrile (2.50 mL) in a 20 mL microwave tube was added silicon(IV) chloride (89.9 uL, 0.783 mmol). The mixture was stirred at rt under an atmosphere of Nitrogen for 20 min, then 4-cyano-5-(morpholin-4-yl)-3-(2-naphthylmethyl) thiophene-2-carboxamide (197 mg, 0.522 mmol) was added. The tube was sealed and the reaction was heated to 90° C. for 12 hrs. The mixture was cooled and distributed between water and EtOAc. The aqueous layer was extracted with EtOAc (×2). The combined organic layer was washed with brine, dried, and concentrated to provide a purple syrup. Purification on HPLC (reverse phase, AA) provided 2-(morpholin-4-yl)-4-(2-naphthylmethyl)-5-(1H-tetrazol-5-yl)thiophene-3-carbonitrile as a yellow solid (44 mg, 20.9% yield). LCMS: (AA) ES+ 403; $^1$H NMR (400 MHz, MeOD) δ 7.78-7.73 (m, 1H), 7.73-7.67 (d, J=7.8 Hz, 2H), 7.67-7.61 (s, 1H), 7.42-7.36 (m, 2H), 7.36-7.30 (m, 1H), 4.63-4.57 (s, 2H), 3.85-3.76 (t, J=4.9 Hz, 4H), 3.57-3.48 (t, J=4.8 Hz, 4H).

368

Example 62

Synthesis of 4-[4-(2-naphthylmethyl)-5-(1H-tetrazol-5-yl)-1,3-thiazol-2-yl]morpholine (Compound 360)

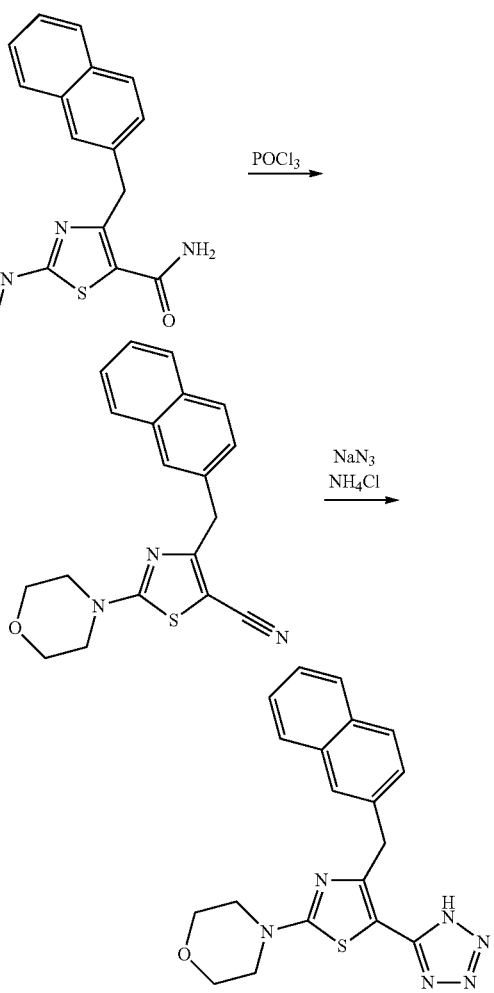

Step 1

A mixture of 2-(morpholin-4-yl)-4-(2-naphthylmethyl)-1,3-thiazole-5-carboxamide (229 mg, 0.648 mmol) (for amide coupling, see example 61-step 1) and phosphoryl chloride (4.00 mL, 42.9 mmol) was stirred at 80° C. for 30 min. The reaction slowly turned homogeneous. The resulting solution was concentrated under reduced pressure and carefully quenched with 1N NaOH solution at 0° C. The resulting mixture was distributed between 1N NaOH solution and EtOAc. The aqueous layer was extracted with EtOAc. The combined organic layer was dried and concentrated to provide 2-(morpholin-4-yl)-4-(2-naphthylmethyl)-1,3-thiazole-5-carbonitrile as a yellow solid (213 mg, 98.0% yield). LCMS: (AA) ES+ 336; $^1$H NMR (400 MHz, DMSO) δ 7.90-7.83 (dd, J=9.0, 1.9 Hz, 3H), 7.80-7.72 (s, 1H), 7.53-7.46 (m, 2H), 7.46-7.38 (m, 1H), 4.18-4.09 (s, 2H), 3.70-3.60 (t, J=4.9 Hz, 4H), 3.51-3.41 (t, J=4.9 Hz, 4H).

Step 2

To a solution of 2-(morpholin-4-yl)-4-(2-naphthylmethyl)-1,3-thiazole-5-carbonitrile (213 mg, 0.635 mmol) in N,N-dimethylformamide (3.00 mL) was added sodium azide (61.9 mg, 0.952 mmol) and ammonium chloride (102 mg, 1.90 mmol). The mixture was heated to 100° C. and stirred for 24 hrs. The resulting mixture was cooled to rt and distributed between water and EtOAc. The aqueous layer was extracted with EtOAc (×2). The combined organic layer was washed with 10% LiCl (aq) solution (×2), dried, and concentrated. Purification on HPLC (reverse phase, AA) provided 4-[4-(2-naphthylmethyl)-5-(1H-tetrazol-5-yl)-1,3-thiazol-2-yl]morpholine as a yellow solid (105 mg, 43.7% yield). LCMS: (AA) ES+ 379; $^1$H NMR (400 MHz, MeOD) δ 7.79-7.61 (m, 4H), 7.43-7.31 (m, 3H), 4.57-4.45 (s, 2H), 3.82-3.68 (t, J=4.9 Hz, 4H), 3.53-3.43 (t, J=4.9 Hz, 4H).

Compounds in the following table are prepared from appropriate starting materials in a method analogous to that of Example 62.

| 356 | LC/MS: (AA) ES+ 378 |
|---|---|

Example 63

Synthesis of 4-cyano-3-(3,4-dichlorobenzyl)-N-(methylsulfonyl)-5-morpholinothiophene-2-carboxamide (Compound 352)

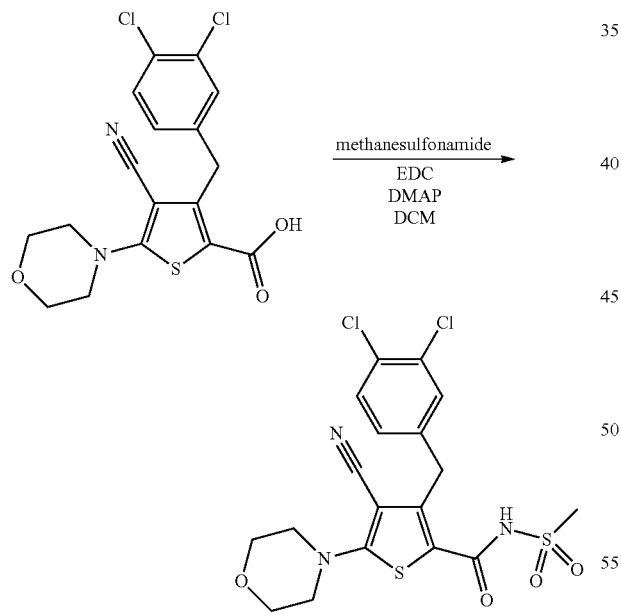

To a mixture of 4-cyano-3-(3,4-dichlorobenzyl)-5-morpholinothiophene-2-carboxylic acid (291 mg, 0.732 mmol), in DCM (5.0 mL) was added methanesulfonamide (87.1 mg, 0.916 mmol), N-(3-dimethylaminopropyl)-N'-ethylcarbodiimide hydrochloride (176 mg, 0.916 mmol), and N,N-dimethylaminopyridine (103 mg, 0.842 mmol) and the resulting solution was stirred at room temperature overnight. The reaction was diluted with DCM (10 mL), 1N HCl (3 mL) and with water (3 mL). The organic layer was dried, filtered and concentrated in vacuo. The residue was purified by silica gel chromatography (MeOH/DCM=0/100→20/80) to give 250 mg of crude product. This material was purified by preparative reverse phase chromatography to give 70 mg (20% yield) of the title compound. as a white solid. LC/MS (FA) ES+ 474, 476. $^1$H NMR (400 MHz, MeOH-d$_4$) δ: 7.45 (d, 1H, J=2.0 Hz)), 7.38 (d, 1H, J=8.4 Hz), 7.25 (dd, 1H, J=8.0, 2.0 Hz), 4.38 (s, 2H), 3.82-3.80 (m, 4H), 3.57-3.55 (m, 4H), 3.18 (s, 3H).

Example 64

Synthesis of 3-(3,4-dichlorobenzyl)-5-(morpholin-4-yl)-4-(phenylethynyl)thiophene-2-carboxylic acid (Compound 296)

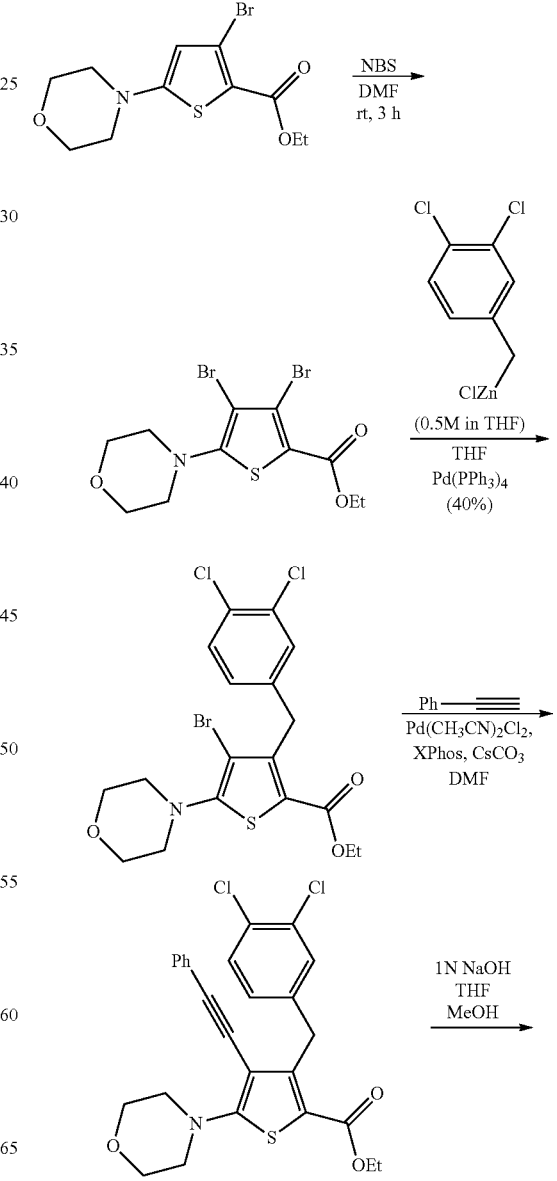

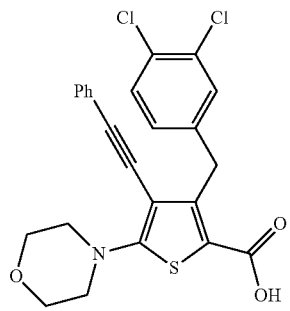

Step 1: Ethyl 3,4-dibromo-5-(morpholin-4-yl) thiophene-2-carboxylate

To a degassed solution of ethyl 3-bromo-5-morpholin-4-ylthiophene-2-carboxylate (0.688 g, 2.15 mmol) in DMF (14 mL, 180 mmol) was added N-bromosuccinimide (0.7648 g, 4.297 mmol) dropwise as a solution in degassed DMF (4.1 mL, 52 mmol). The mixture was wrapped in foil to protect from ambient light, and the reaction was stirred under argon at room temperature for 2 hours. The reaction mixture was quenched via addition of 10% sodium thiosulfate solution (10 mL) and then diluted with EtOAc (30 mL). The layers were separated, and the aqueous layer was extracted with EtOAc (10 mL). The combined organic layers were washed with brine, dried over $Na_2SO_4$, filtered, and concentrated in vacuo. Flash chromatography (eluent: 0-25% EtOAc:hexane) afforded ethyl 3,4-dibromo-5-(morpholin-4-yl)thiophene-2-carboxylate (593 mg, yield 69%). LCMS: (FA) ES+ 398, 400, 402; $^1$H NMR (400 MHz, DMSO) δ 4.26 (q, J=7.1 Hz, 2H), 3.75 (dd, J=5.5, 3.8 Hz, 4H), 3.24-3.10 (m, 4H), 1.27 (t, J=7.1 Hz, 3H).

Step 2: Ethyl 4-bromo-3-(3,4-dichlorobenzyl)-5-(morpholin-4-yl)thiophene-2-carboxylate A sealable reaction vessel containing a suspension of ethyl 3,4-dibromo-5-(morpholin-4-yl)thiophene-2-carboxylate (0.560 g, 1.40 mmol), 0.500 M 3,4-dichlorobenzylzinc chloride in THF (3.368 mL, 1.684 mmol) and THF (2.06 mL, 25.4 mmol) was purged via vacuum/backfilling with argon. To this suspension was added tetrakis(triphenylphosphine)palladium(0) (81.07 mg, 0.07016 mmol), the vial was capped, and the resulting black suspension was stirred at 95° C. overnight. The reaction mixture was adsorbed to celite in vacuo, and the solid thus obtained was purified via column chromatography (eluent: 0-15% EtOAc:hexane) to afford ethyl 4-bromo-3-(3,4-dichlorobenzyl)-5-(morpholin-4-yl)thiophene-2-carboxylate (323 mg, 50%). LCMS: (FA) ES+ 478, 480, 482; $^1$H NMR (400 MHz, DMSO) δ 7.53 (d, J=8.3 Hz, 1H), 7.39 (d, J=2.0 Hz, 1H), 7.07 (dd, J=8.3, 2.1 Hz, 1H), 4.36 (s, 2H), 4.22 (q, J=7.1 Hz, 2H), 3.75-3.70 (m, 4H), 3.17-3.12 (m, 4H), 1.22 (t, J=7.1 Hz, 3H).

Step 3: Ethyl 3-(3,4-dichlorobenzyl)-5-(morpholin-4-yl)-4-(phenylethynyl)-thiophene-2-carboxylate To a suspension of ethyl 4-bromo-3-(3,4-dichlorobenzyl)-5-(morpholin-4-yl)thiophene-2-carboxylate (0.125 g, 0.000222 mol), XPhos (0.0172 g, 0.0000362 mol), CsCO3 (0.199 g, 0.000612 mol) and phenylacetylene (0.146 mL, 0.00133 mol) in DMF (1.2 mL, 0.015 mol) was added bis(acetonitrile)palladium(II) chloride (0.00288 g, 0.0000111 mol) and the mixture was heated at 50° C. overnight. The reaction mixture was diluted with EtOAc (30 mL) and water (15 mL), and the layers were separated. The aqueous layer was extracted with EtOAc (2×15 mL). Combined organic layers were dried over $Na_2SO_4$, filtered, and concentrated. The crude residue was purified using a dry load on a silica gel column (eluent: 0-30% EtOAc:hexane), affording ethyl 3-(3,4-dichlorobenzyl)-5-(morpholin-4-yl)-4-(phenylethynyl) thiophene-2-carboxylate (45 mg, 40% yield). LCMS: (FA) ES+ 500, 501, 502; $^1$H NMR (400 MHz, DMSO) δ 7.55-7.51 (m, 2H), 7.43-7.37 (m, 5H), 7.20 (dd, J=8.3, 2.0 Hz, 1H), 4.38 (s, 2H), 4.22 (q, J=7.1 Hz, 2H), 3.79-3.74 (m, 4H), 3.57-3.52 (m, 4H), 1.23 (t, J=7.1 Hz, 3H).

Step 4: 3-(3,4-dichlorobenzyl)-5-(morpholin-4-yl)-4-(phenylethynyl)-thiophene-2-carboxylic acid To a suspension of ethyl 3-(3,4-dichlorobenzyl)-5-(morpholin-4-yl)-4-(phenylethynyl)thiophene-2-carboxylate (0.041 g, 0.082 mmol in THF (2.00 mL, 24.6 mmol) and methanol (0.37 mL, 9.1 mmol) was added 1.000 M of sodium hydroxide in water (1.684 mL, 1.684 mmol) and the resulting biphasic mixture was stirred at room temp for 2 days. The pH was carefully adjusted to 3.0 via addition of 1N HCl (monitored in real time with a pH meter), and the reaction mixture was transferred to a separatory funnel. The mixture was diluted with EtOAc (40 mL) and water (15 mL), and the layers were separated. The aqueous layer was extracted with EtOAc (2×30 mL). The combined organic layers were washed with brine, then dried over $Na_2SO_4$, filtered, and concentrated. Column chromatography (eluent: 0-5% MeOH:DCM) afforded 3-(3,4-dichlorobenzyl)-5-(morpholin-4-yl)-4-(phenylethynyl)thiophene-2-carboxylic acid (30 mg, 78% yield). LCMS: (FA) ES+ 472, 473, 474; $^1$H NMR (400 MHz, DMSO) δ 12.92 (s, 1H), 7.55-7.50 (m, 2H), 7.43-7.34 (m, 5H), 7.21 (dd, J=8.3, 2.0 Hz, 1H), 4.39 (s, 2H), 3.81-3.68 (m, 4H), 3.56-3.42 (m, 4H).

Example 65

Synthesis of 2-(4-(3,4-dichlorobenzyl)-2-morpholinothiazol-5-yl)acetic acid (Compound 348)

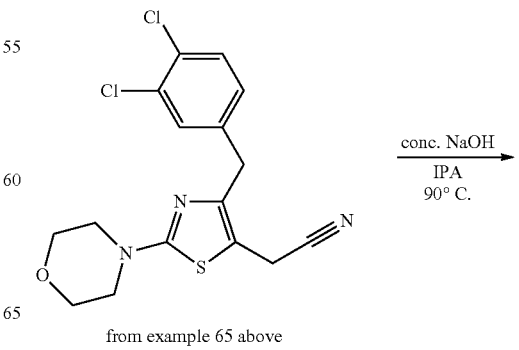

from example 65 above

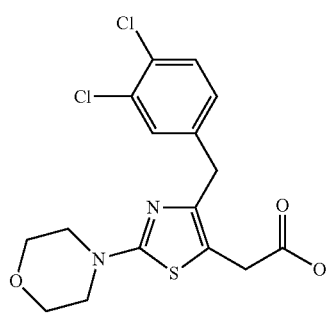

To a solution of 2-(4-(3,4-dichlorobenzyl)-2-morpholinothiazol-5-yl)acetonitrile (165 mg, 0.448 mmol) in IPA (4.88 mL) was added 50% aqueous NaOH (1.68 mL, 44.8 mmol) and the resulting solution was heated to 90 degrees for 3 hours. The reaction was cooled and concentrated in vacuo. The residue was acidified with 1 N HCl and extracted with ethyl acetate (2×25 mL). The combined organic layers were dried, filtered and concentrated in vacuo. The residue was purified by silica gel chromatography (MeOH/DCM=0/100→20/80) to give 120 mg of product. This material was purified by preparative reverse phase chromatography to give 16 mg (9% yield) of the title compound. as a white solid. LC/MS (FA) ES+ 387, 389. $^1$H NMR (400 MHz, DMSO-$d_6$) δ: 7.49 (d, 1H, J=8.0 Hz), 7.47 (d, 1H, J=2.0 Hz), 7.21 (dd, 1H, J=8.0, 2.0 Hz), 3.78 (s, 2H), 3.67 (s, 2H), 3.66-3.63 (m, 4H), 3.26-3.24 (m, 4H).

Example 66

Synthesis of 4-(4-chlorobenzyl)-2-morpholino-1,3-selenazole-5-carboxylic acid (Compound 370)

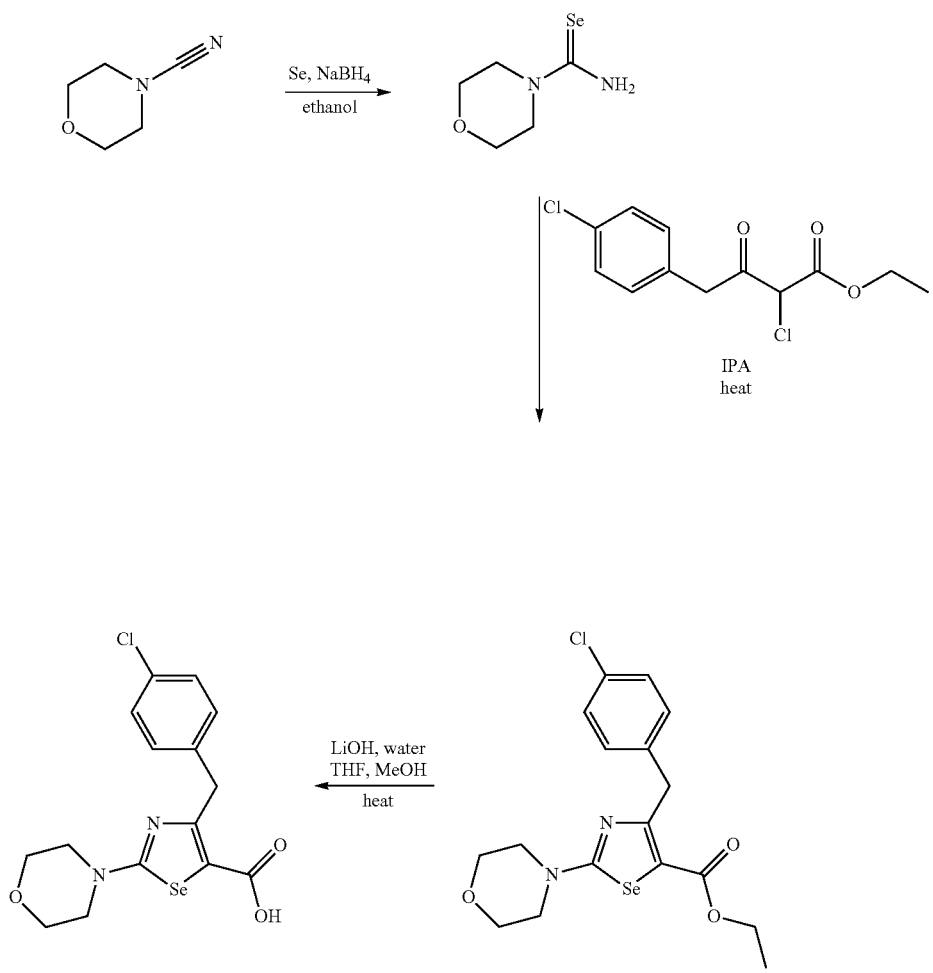

Step 1: Morpholine-4-carboselenoamide

In a round bottomed flask equipped with a stir bar were added selenium metal (4.00 g, 49.4 mmol) and ethanol (50 mL). The mixture was cooled in an ice bath and stirred under a nitrogen atmosphere while sodium tetrahydroborate (2.01 g, 53.1 mmol) was slowly added. Gas was evolved and the selenium slowly dissolved. After gas evolution had ceased, 4-morpholinecarbonitrile (2.77 g, 24.7 mmol) was slowly added followed by pyridine hydrochloride (11.4 g, 98.7 mmol). The resulting dark mixture was stirred overnight at room temperature. The grayish reaction mixture was quenched with water (~250 mL) and the mixture was stirred briefly then transferred to a separatory funnel. The mixture was extracted with dichloromethane (3×). The extracts were combined and dried over sodium sulfate. The insolubles were filtered off and the filtrate was evaporated to leave a light pink solid which was stirred with water then filtered. The collected solid was washed with ethyl acetate and the washings were combined then evaporated to leave 80 mg (2% yield) product as a light pink solid. LC/MS (FA) ES+ 195. $^1$H NMR (400 MHz, DMSO) δ 8.15-7.71 (br s, 2H), 3.94-3.61 (br s, 4H), 3.60-3.51 (t, J=4.9 Hz, 4H).

Step 2: Ethyl 4-(4-chlorobenzyl)-2-morpholino-1,3-selenazole-5-carboxylate

In a round bottomed flask were placed ethyl 2-chloro-4-(4-chlorophenyl)-3-oxobutanoate (84.4 mg, 0.3069 mmol), isopropyl alcohol (5 mL), and morpholine-4-carboselenoamide (80.0 mg, 0.414 mmol). The resulting mixture was brought to reflux under an atmosphere of nitrogen (all solids dissolved to give a clear pale pink solution). After ~1 hour reflux, TLC analysis indicated that all starting materials had been consumed with the production of one major product. The reaction was allowed to cool to room temperature and stir overnight. The solvent was removed on the rotovap then the residue was dissolved in minimal dichloromethane and purified by column chromatography on silica gel (gradient 100% hexane to 35% ethyl acetate) to afford 35 mg (28% yield) product as a white solid. LC/MS (FA) ES+ 413/415/417. NMR (400 MHz, DMSO) δ 7.37-7.23 (m, 4H), 4.25-4.14 (m, 4H), 3.72-3.62 (t, J=4.9 Hz, 4H), 3.50-3.41 (t, J=4.8 Hz, 4H), 1.27-1.20 (t, J=7.1 Hz, 3H).

Step 3: 4-(4-chlorobenzyl)-2-morpholino-1,3-selenazole-5-carboxylic acid

The ethyl 4-(4-chlorobenzyl)-2-(morpholin-4-yl)-1,3-selenazole-5-carboxylate (35.0 mg, 0.0846 mmol) was placed in a round bottomed flask equipped with a stirbar. Tetrahydrofuran (1.00 mL) and methanol (0.1 mL) were added and the mixture was stirred to give a light yellow solution. A solution of lithium hydroxide in water (2.0 M, 0.423 mL, 0.846 mmol) was added in a single portion, and the resulting mixture was stirred under an atmosphere of nitrogen at room temperature overnight. LCMS analysis of the reaction indicated that starting material still remained; only a small amount of it had been hydrolyzed to the product. Additional tetrahydrofuran (2 mL) and lithium hydroxide in water (2.0 M, 0.423 mL, 0.846 mmol) were added and the reaction was heated overnight at 50° C. under an atmosphere of nitrogen. LCMS analysis indicated that the reaction was 90% complete. The reaction was heated at 60° C. for a further 8 hours. LCMS analysis indicated complete hydrolysis. The reaction was cooled to room temperature, diluted with 10 ml saline, and acidified with dilute acetic acid with good stirring. A white precipitate formed which became granular with stirring. The product was isolated on a fitted funnel, washed with water, and dried at 40° C. overnight to yield 29.2 mg (89% yield) product as a white powder. LC/MS (FA) ES+ 385/387/389. $^1$H NMR (400 MHz, DMSO) δ 12.73-12.44 (br s, 1H), 7.36-7.24 (m, 4H), 4.26-4.18 (s, 2H), 3.74-3.63 (t, J=4.8 Hz, 4H), 3.49-3.39 (t, J=4.7 Hz, 4H).

Formulation Example 1

Amount Per Tablet

| | |
|---|---|
| (1) Compound obtained in Example 1 | 10.0 mg |
| (2) Lactose | 60.0 mg |
| (3) Corn starch | 35.0 mg |
| (4) Gelatin | 3.0 mg |
| (5) Magnesium stearate | 2.0 mg |

A mixture of 10.0 mg of the compound obtained in Example 1, 60.0 mg of lactose and 35.0 mg of corn starch is granulated through a 1 mm-mesh sieve using 0.03 ml of a 10% by weight aqueous solution of gelatin (3.0 mg of gelatin), after which the granules are dried at 40° C. and filtered again. The granules obtained are mixed with 2.0 mg of magnesium stearate and compressed. The core tablets obtained are coated with a sugar coat comprising a suspension of sucrose, titanium dioxide, talc and gum arabic and polished with beeswax to yield sugar-coated tablets.

Formulation Example 2

Dose Per Tablet

| | |
|---|---|
| (1) Compound obtained in Example 1 | 10.0 mg |
| (2) Lactose | 70.0 mg |
| (3) Corn starch | 50.0 mg |
| (4) Soluble starch | 7.0 mg |
| (5) Magnesium stearate | 3.0 mg |

10.0 mg of the compound obtained in Example 1 and 3.0 mg of magnesium stearate are granulated using 0.07 ml of an aqueous solution of soluble starch (7.0 mg of soluble starch), after which these granules are dried and mixed with 70.0 mg of lactose and 50.0 mg of corn starch. This mixture is compressed to yield tablets.

Biological Data:
PI3K and VPS34 Enzyme Assays
Cloning, Expression, and Purification of PI3Ks and VPS34

The catalytic subunits of PI3Ks are cloned into either pDEST8 (p110 alpha) or pDEST10 (p110beta, p110delta, and p110gamma) as N-terminal His tagged fusion proteins using the Gateway system (Invitrogen, catalog #11804-010 for pDEST8 and 11806-015 for pDEST10). The sequences are verified before recombinant protein expression using the Baculovirus Expression System with Gateway® Technology. The accession numbers for the subunits are as follows:

p110 alpha (GB:U79143)
p110beta (GB: 567334)
p110delta (GB: U86453)
p110gamma (GB: X83368)

The regulatory subunits of PI3Ks are cloned into pDEST8 as un-tagged protein using the Gateway system (Catalog

11804-010). The sequences are verified before recombinant protein expression using the Baculovirus Expression System with Gateway® Technology. The accession numbers for the subunits are as following:

p85 alpha (GB: BC030815)
p101(GB: AB028925)

VPS34 (accession number GB:BC033004) is cloned into pDEST20-Thombin as N-terminal GST tagged fusion proteins using the Gateway system (Invitrogen, catalog #11804-013). The sequences are verified before recombinant protein expression using the Baculovirus Expression System with Gateway® Technology.

For expression of the p110 complexes, the p85 (MOI of 4) is co-infected with p110 alpha, beta, and delta respectively (1MOI) in SF9 cells and harvested at 60 hours post co-infection. P110 gamma was infected at 1 MOI and harvested at 60 hours post infection.

For purification, PI3Ks are purified by Ni-NTA Agarose (Qiagen #30250) followed by Mono Q 10/100 GL (Ge Healthcare #17-5167-01). VPS34 is purified by Glutathione Sepharose 4 Fast Flow (GE Healthcare #17-5132-03) followed by HiTrap Q (GE Healthcare #17-1153-01).

For expression VPS34 was infected at 1MOI in SF9 cells and harvested 72 hours post infection.

For purification, VPS34 is purified by Glutathione Sepharose 4 Fast Flow (GE Healthcare #17-5132-03) followed by HiTrap Q (GE Healthcare #17-1153-01).

PI3K and VPS34 Assay Conditions

1) Human PI3K Alpha Enzyme Assay Method 0.5 uL compounds in DMSO are added to wells of a 384-well microtitre plate (Corning 3575). At room temperature: 10 ul PI3K reaction buffer (50 mM Hepes, 5 mM DTT, 150 mM NaCl, 10 mM beta-glycerophosphate, 10 mM MgCl2, 0.25 mM sodium cholate and 0.001% CHAPS, pH 7.00) containing ATP (25 uM, Promega) is added followed immediately by 10 ul PI3K reaction buffer containing di-C8 PI(4,5)P2 (3.5 uM, CellSignals) and PI3Kalpha (0.4875 nM, Millennium Protein Sciences Group) and the mixture is incubated with shaking at room temperature for 30 minutes. Then 5 ul PI3K stop mix (50 mM Hepes, 5 mM DTT, 150 mM NaCl, 0.01% Tween-20, 15 mM EDTA and 25 nM biotin-PI(3,4,5)P3 (Echelon) is added to quench the reaction followed immediately by addition of 5 ul HTRF detection mix (50 mM Hepes, 5 mM DTT, 150 mM NaCl, 0.01% Tween-20, 40 mM KF, 10 nM GST:GRP-1 PH domain (Millennium Protein Sciences Group), 15 nM Streptavidin-XL (CisBio) and 0.375 nM anti-GST Eu++ antibody (CisBio) at pH 7.00). The plates are then incubated for 1 hour at room temperature with shaking and then read on a BMG PheraStar Plus reader.

2) Human PI3K beta, delta and gamma isoforms are tested using the procedure described for PI3K alpha above but with the following changes: PI3K beta (5.25 nM), PI3K delta (0.75 nM) and PI3K gamma (5 nM). All isoforms supplied by Millennium Protein Science Group.

3) VPS34 is assayed using Adapta™ Universal Kinase Assay Kit (Invitrogen).

4) Human VPS34 enzyme assay method 100 nL compounds in DMSO are added to wells of a 384 well microtitre plate (Greiner 780076). At room temperature: 5 ul VPS34 reaction buffer (Invitrogen Assay Buffer Q (diluted 1 in 5 with nanopure water) plus 2 mM DTT and 2 mM MnCl2) containing ATP (20 uM, Promega) and 200 uM PI-PS substrate (Invitrogen PV5122) is added followed immediately by 5 ul VPS34 reaction buffer (as above) containing VPS34 (5 nM, Millennium Protein Sciences Group) and the mixture is incubated with shaking at room temperature for 1 hour. Then 5 ul VPS34 stop-detect mix (as per Invitrogen Adapta Assay kit (PV5009) instructions (contains kinase quench buffer, TR-FRET buffer, Adapta Eu anti-ADP antibody and Alexa Fluor 647 ADP tracer)) is added to quench the reaction. The plates are then incubated for 30 minutes at room temperature with shaking and then read on a BMG PheraStar Plus reader.

For the assay methods described above, test compound percent inhibition, at various concentrations, is calculated relative to control (DMSO and EDTA) treated samples. Compound concentration versus percent inhibition curves are fitted to generate $IC_{50}$ values. One skilled in the art will appreciate that the values generated either as percentage inhibition at a single concentration or $IC_{50}$ values are subject to experimental variation.

PI3K Cell Assays

1) In-Cell Western Assay

The pSer473 AKT LI-COR In-Cell Western Assay is a quantitative immunofluorescent assay that measures phosphorylation of serine 473 AKT (pSer473 AKT) in WM266.4 and SKOV3 tumor cell lines grown in cell culture.

WM266.4 cells are propagated in Minimum Essential Media (MEM) (Invitrogen) containing L-glutamine, 10% Fetal Bovine Serum, 1 mM MEM Sodium Pyruvate, and 0.1 mM MEM Non-Essential Amino Acids and SKOV3 cells are propagated in McCoy's 5A Media (modified) (Invitrogen) containing L-Glutamine and 10% Fetal Bovine Serum. Both cell lines are kept in a humidified chamber at 37° C. with 5% $CO_2$. For the pSer473 AKT LI-COR In-Cell Western Assay, $1.5 \times 10^4$ WM266.4 and $1.5 \times 10^4$ SKOV3 cells are cultured in 100 µl of media per well in tissue culture-treated black-walled, clear bottom Optilux 96-well plates (BD Biosciences) for 16-20 hours. Prior to addition of compounds, cell media is removed and replaced with 75 µl of fresh media. Test compounds in DMSO are diluted 1:100 in media. The diluted test compounds are added to the cells (25 µl per well) in 3-fold dilutions with a final concentration range of 0.0015 to 10 µM. The cells are incubated for 2 hours in a humidified chamber at 37° C. with 5% $CO_2$. Immediately following compound incubation, all liquid is removed from the wells and cells are fixed with 4% paraformaldehyde in PBS (150 µl per well) for 20 minutes at room temperature. The paraformaldehyde solution is removed from wells and the cells are permeabilized with 200 µl 0.1% Triton X-100 in PBS per well for 10 min×3 at room temperature. After removal of PBS+0.1% Triton X-100, 150 µl Odyssey blocking buffer (LI-COR Biosciences) is added to each well and plates are incubated at room temperature for 1.5 h. Blocking buffer is removed from the wells and primary antibodies (Phospho-AKT (Ser473) (D9E) XP™ Rabbit mAb and AKT (pan) (40D4) Mouse mAb, Cell Signaling Technology) diluted in Odyssey blocking buffer are added (50 µl per well). Plates are incubated at 4° C. overnight. The cells are washed for 20 min×3 with PBS+0.1% Tween-20 (200 µl per well). Secondary antibodies (IRDye 680 Goat anti-Rabbit IgG (H+L) and IRDye 800CW Goat anti-Mouse IgG (H+L), LI-COR Biosciences) are diluted in Odyssey blocking buffer and added to wells (50 µl per well) followed by a 1 h incubation at room temperature, protected from light. Cells are washed for 20 min×3 with PBS+0.1% Tween-20 (200 µl per well). Wash buffer is completely removed from wells after last wash, plates are protected from light until scanned and analyzed with the Odyssey Infrared Imaging System (LI-COR Biosciences). Both pS473 AKT and AKT are simultaneously visualized with the 680 nm fluorophore indicated by a red color and the 800 nm fluorophore indicated by a green color. Relative fluorescence units derived from the scans allow for quantitative analyses of both labeled proteins and the ratio of pS473 AKT to AKT is calculated. Concentration response curves are generated by plotting the average ratios of PI3K inhibitor-treated samples relative to DMSO-treated controls to determine percent change in expression of pS473 AKT, and percentage inhibition values at a single concentration or growth inhibition ($IC_{50}$) values are determined from those curves. One skilled in the art will appreciate that the values generated either as percentage inhibition at a single concentration or $IC_{50}$ values are subject to experimental variation.

2) ATPlite Viability Assay

The ATPLite™ Assay (Perkin-Elmer) measures cellular adenosine-triphosphate (ATP) through the generation of a luminescent signal formed from the ATP-dependent enzyme firefly luciferase. The luminescent signal intensity can be used as a measure of cellular proliferation, and can be used to assess the anti-proliferative effects of PI3K inhibitors.

WM266.4 cells propagated in Minimum Essential Media (MEM) (Invitrogen) containing L-Glutamine, 10% Fetal Bovine Serum, 1 mM MEM Sodium Pyruvate, and 0.1 mM MEM Non-Essential Amino Acids are cultured in 384-well tissue culture-treated Black/Clear plates (Falcon) at $1 \times 10^3$ cells per well in a volume of 75 μl in a humidified chamber at 37° C. with 5% $CO_2$ for 24 h. Test compounds (2 μl in 100% DMSO) are diluted in 95 μl of cell culture media. The diluted test compounds are added (8 ml per well) to 384-well plates. Final concentration range of 3-fold serial dilution of compounds is 0.001 to 20 μM. Plates are incubated for 72 h in a humidified chamber at 37° C. with 5% $CO_2$. One control plate without compound addition is processed at the start of the 72 h incubation as a "Time Zero" reading for quantitative evaluation of cell viability at start of assay. After 72 h, all but 25 μl of cell culture media is removed from each well, followed by the addition of 25 μl of ATPlite 1 step reagent (Perkin Elmer) to each well. Luminescence is measured on a LEADSeeker Luminescence Counter (GE Healthcare Life Sciences). Concentration response curves are generated by calculating the luminescence decrease in test compound-treated samples relative to DMSO-treated controls, and percentage inhibition values at a single concentration or growth inhibition ($IC_{50}$) values are determined from the curves. One skilled in the art will appreciate that the values generated either as percentage inhibition at a single concentration or $IC_{50}$ values are subject to experimental variation.

Vps34 Cell Assays

1) FYVE Domain Redistribution Assay

The FYVE domain redistribution assay monitors translocation of EGFP-2XFYVE from its initial location bound to (PtdIns(3)P) in early endosomes to the cytoplasm in response to test compounds. Recombinant U2OS cells stable expressing the FYVE finger from the human homologue of the hepatocyte growth factor-regulated tyrosine kinase substrate Hrs, duplicated in tanden (GenBank Acc. NM_004712) and fused to the C-terminus of enhanced green fluorescent protein (EGFP). U2OS cells are adherent epithelial cells derived from human osteosarcoma. Expression of EGFP-2X-FYVE is controlled by a standard CMV promoter and continuos expression is maintained by addition of geneticin to the culture medium. Localization of the fusion protein within the cells is imaged on the Evotec Technologies OPERA Confocal Imager and Integrated Spot Signal Per Cellular Signal is quantified using Acapella software. Using this information, percentage inhibition values at a single concentration or $IC_{50}$ values for inhibitors can be determined U2OS EGFP-2×FYVE cells are propagated in Dulbecco's Modified Eagle Media High glucose (D-MEM) (Invitrogen cat. 11995) containing 10% Fetal Bovine Serum (HyClone cat. SH30071.02) and 0.5 mg/ml Geneticin (Invitrogen) and kept in a humidified chamber at 37° C. with 5% $CO_2$. $8 \times 10^3$ cells are cultured in 100 μl of media per well in tissue culture-treated black-walled, clear bottom Optilux 96-well plates (BD Biosciences) for 16-24 hours.

Prior to addition of compounds, cell media is removed and replaced with 75 μl of fresh media. Test compounds in DMSO are diluted 1:100 in media. The diluted test compounds are added to the cells (25 μl per well) in 3-fold dilutions with a final concentration range of 0.0015 to 10 μM. The cells are incubated for 30 minutes in a humidified chamber at 37° C. with 5% $CO_2$. Immediately following compound incubation, all liquid is removed from the wells and cells are fixed with 4% paraformaldehyde in PBS (75 μl per well) for 15 minutes at room temperature. The paraformaldehyde solution is removed from wells and washed once with PBS (100 μl per well). The PBS is removed and cells are incubated with DRAQ5 Nucleur Dye (Alexis/Biostatus) (85 μl per well). The plates are covered with Flash Plate plastic adhesive foil and imaged on the Evotec Technologies OPERA Confocal Imager Opera after at least a 30 minute incubation. Concentration curves are generated by calculating the Integrated Spot Intensity Per Cellular Signal decrease in test-compound treated samples relative to DMSO-treated controls and a 100% control inhibitor, and percentage inhibition values at a single concentration or growth inhibition ($IC_{50}$) values are determined from the curves. One skilled in the art will appreciate that the values generated either as percentage inhibition at a single concentration or $IC_{50}$ values are subject to experimental variation.

As detailed above, compounds of the invention inhibit PI3K and/or VPS34. Examples of class I PI3-kinase isoforms are PI3K α, β, γ and δ. In certain embodiments, the compounds of the invention inhibit one or more isoforms of PI3K. In certain other embodiments, the compounds of the invention selectively inhibit one particular isoform of PI3K. For example, in some embodiments the compounds of the invention selectively inhibit PI3Kα. In some embodiments the compounds of the invention selectively inhibit PI3Kβ.

As used herein, selective inhibitor refers to compounds that inhibit one or more of the particular PI3K isoforms with at least about >10-fold, or at least about >20-fold, or at least about >30-fold selectivity for the one or more particular PI3K isoforms relative to other class I PI3-kinase isoforms in a biochemical assay. By way of example, compounds that inhibit PI3Kβ with at least about >10-fold, or at least about >20-fold, or at least about >30-fold selectivity relative to PI3K α, γ or δ are selective inhibitors of PI3Kβ. Alternatively, compounds that inhibit PI3K β and δ with at least about >10-fold, or at least about >20-fold, or at least about >30-fold selectivity relative to PI3K α or γ are selective inhibitors of PI3K β and δ.

As detailed above, compounds of the invention inhibit PI3K. In certain embodiments, compounds inhibit one or more isoforms of PI3K. In other embodiments, compounds of the invention inhibit PI3Kalpha and have an $IC_{50}>1.0$ μM. For example, these compounds include 2, 3, 5, 6, 7, 8, 9, 11, 12, 15, 16, 17, 18, 19, 21, 22, 23, 25, 26, 27, 33, 34, 36, 37, 39, 43, 44, 45, 46, 47, 49, 51, 52, 55, 58, 59, 60, 62, 63, 65, 66, 68, 69, 70, 73, 75, 76, 77, 78, 79, 80, 81, 84, 85, 87, 88, 89, 91, 92. In other embodiments, compounds of the invention have an $IC_{50}<1.0$ μM but >0.1 μM. For example, these compounds include compounds 1, 4, 10, 14, 20, 24, 28, 30, 31, 32, 35, 38, 40, 42, 48, 53, 54, 56, 57, 61, 64, 67, 71, 72, 74, 82, 83, 86, 90. In still other embodiments, compounds of the invention have an $IC_{50}<0.1$ μM. For example, these compounds include compounds 13, 29, 41, 50. In still other embodiments, compounds of the invention inhibit PI3 Kbeta and have an IC$_{50}$>1.0 µM. For example, these compounds include 2, 18, 22, 24, 29, 49, 55, 63, 67, 78. In other embodiments, compounds of the invention have an IC$_{50}$<1.0 µM but >0.1 µM. For example, these compounds include compounds 1, 4, 6, 8, 10, 12, 15, 17, 23, 25, 26, 27, 28, 32, 33, 34, 35, 37, 38, 39, 40, 42, 46, 47, 48, 53, 54, 56, 57, 58, 60, 61, 62, 64, 68, 69, 70, 71, 72, 73, 74, 76, 79, 82, 83, 84, 89. In still other embodiments, compounds of the invention have an IC$_{50}$<0.1 µM. For example, these compounds include compounds 3, 5, 7, 9, 11, 13, 14, 16, 19, 20, 21, 30, 31, 36, 41, 43, 44, 45, 50, 51, 52, 59, 65, 66, 75, 77, 80, 81, 85, 86, 87, 88, 90, 91, 92.

In some embodiments, compounds of the invention inhibit PI3K α and β at a 1.1 µM concentration with the percent inhibition as shown in the table below.

| Compound | PI3Kα Percent Inhibition | PI3Kβ Percent Inhibition |
| --- | --- | --- |
| 91 | 27 | 105 |
| 93 | 9 | 80 |
| 94 | 58 | 97 |
| 95 | 68 | 101 |
| 96 | 58 | 109 |
| 97 | 53 | 101 |
| 98 | 58 | 111 |
| 99 | 12 | 72 |
| 100 | 20 | 98 |
| 101 | 30 | 105 |
| 102 | 30 | 78 |
| 103 | 2 | 71 |
| 104 | 26 | 109 |
| 105 | 21 | 98 |
| 106 | 58 | 103 |
| 107 | 49 | 103 |
| 108 | 44 | 100 |
| 109 | 6 | 76 |
| 110 | 5 | 41 |
| 111 | 7 | 77 |
| 112 | 95 | 110 |
| 113 | 25 | 100 |
| 114 | 40 | 106 |
| 115 | 45 | 97 |
| 116 | 46 | 98 |
| 117 | 48 | 94 |
| 118 | 28 | 104 |
| 119 | 9 | 88 |
| 120 | 18 | 97 |
| 121 | 11 | 59 |
| 122 | 49 | 106 |
| 123 | 64 | 105 |
| 124 | 79 | 109 |
| 125 | 46 | 99 |
| 126 | 42 | 103 |
| 127 | 40 | 110 |
| 128 | 46 | 106 |

In some embodiments, compounds of the invention inhibit PI3K δ and γ at a 1.0 µM concentration with the percent inhibition as shown in the table below.

| Compound | PI3Kδ Percent Inhibition | PI3Kγ Percent Inhibition |
| --- | --- | --- |
| 91 | 84.8 | 15.4 |
| 93 | 46.0 | 9.5 |
| 94 | 102.4 | 52.6 |
| 95 | 86.1 | 23.9 |
| 96 | 96.0 | 36.2 |
| 97 | 89.8 | 17.8 |
| 98 | 108.5 | 67.6 |
| 99 | 55.4 | 6.4 |
| 100 | 65.5 | 13.2 |
| 102 | 38.1 | 6.8 |
| 103 | 38.6 | 6.4 |
| 104 | 93.0 | 28.8 |
| 105 | 51.2 | 9.8 |
| 106 | 88.8 | 51.8 |
| 107 | 87.3 | 20.2 |
| 108 | 99.6 | 38.1 |
| 109 | 35.4 | 3.9 |
| 111 | 60.5 | 6.9 |
| 112 | 114.5 | 69.0 |
| 113 | 78.8 | 32.5 |
| 114 | 112.8 | 56.9 |
| 115 | 63.0 | 12.0 |
| 116 | 83.0 | 36.7 |
| 117 | 78.5 | 14.7 |
| 118 | 89.3 | 27.5 |
| 119 | 62.6 | 7.6 |
| 120 | 77.0 | 11.0 |
| 121 | 77.3 | 7.3 |
| 122 | 96.2 | 49.6 |
| 123 | 96.8 | 36.6 |
| 124 | 112.0 | 74.2 |
| 125 | 85.1 | 25.9 |
| 126 | 100.4 | 37.6 |
| 127 | 100.4 | 55.0 |
| 128 | 114.2 | 63.4 |

In some embodiments, compounds of the invention inhibit VPS34 at a 1.0 µM concentration with the percent inhibition as shown in the tables below.

| Compound | VPS34 Percent Inhibition |
| --- | --- |
| 93 | 19.2 |
| 94 | 30.6 |
| 95 | 167.0 |
| 96 | 47.8 |
| 97 | 45.0 |
| 98 | 68.9 |
| 99 | 46.7 |
| 100 | 36.6 |
| 102 | 28.2 |
| 103 | 7.2 |
| 104 | 63.2 |
| 105 | 22.6 |
| 106 | 34.4 |
| 107 | 45.8 |
| 108 | 62.4 |
| 109 | 24.0 |
| 111 | 46.8 |
| 112 | 37.8 |
| 113 | 18.1 |
| 114 | 131.4 |
| 115 | 39.7 |
| 116 | 54.2 |
| 117 | 28.6 |
| 118 | 68.2 |
| 119 | 19.5 |
| 120 | 38.3 |
| 121 | 64.8 |
| 122 | 55.2 |
| 123 | 45.1 |
| 124 | 78.8 |
| 125 | 37.1 |
| 126 | 44.0 |
| 127 | 33.7 |
| 128 | 88.1 |

| Compound | p110 alpha Percent Inhibition | p110 beta Percent Inhibition | p110 gamma Percent Inhibition | p110 delta Percent Inhibition |
|---|---|---|---|---|
| 129 | 83 | 106 | 32 | 109 |
| 130 | 21 | 73 | 22 | 62 |
| 131 | 75 | 78 | 5 | 80 |
| 132 | 45 | 103 | 53 | 77 |
| 133 | 84 | 101 | 26 | 74 |
| 134 | 21 | 72 | 8 | 44 |
| 135 | 78 | 87 | 8 | 99 |
| 136 | 80 | 110 | 67 | 109 |
| 137 | 12 | 54 | 12 | 30 |
| 138 | 43 | 86 | 13 | 69 |
| 139 | 77 | 100 | 24 | 105 |
| 140 | 76 | 47 | 62 | 74 |
| 141 | 17 | 89 | 15 | 66 |
| 142 | 15 | 67 | 7 | 47 |
| 143 | 58 | 115 | 62 | 85 |
| 144 | 63 | 94 | 19 | 111 |
| 145 | 64 | 98 | 9 | 97 |
| 146 | 67 | 103 | 23 | 110 |
| 147 | 83 | 96 | 18 | 107 |
| 148 | 41 | 98 | 34 | 69 |
| 149 | 54 | 109 | 75 | 117 |
| 150 | 2 | 54 | 6 | 35 |
| 151 | 72 | 105 | 17 | 108 |
| 152 | 61 | 97 | 16 | 106 |
| 153 | 75 | 84 | 11 | 87 |
| 154 | 79 | 108 | 39 | 108 |
| 155 | 29 | 64 | 28 | 53 |
| 156 | 13 | 47 | 2 | 33 |
| 157 | 55 | 68 | 7 | 101 |
| 158 | 18 | 94 | 20 | 69 |
| 159 | 18 | 61 | 5 | 31 |
| 160 | 74 | 101 | 20 | 107 |
| 161 | 14 | 60 | 7 | 40 |
| 162 | 38 | 93 | 33 | 83 |
| 163 | 97 | 110 | 25 | 106 |
| 164 | 100 | 107 | 44 | 112 |
| 165 | 64 | 77 | 14 | 87 |
| 166 | 92 | 82 | 3 | 85 |
| 167 | 105 | 103 | 26 | 110 |
| 168 | 23 | 107 | 58 | 110 |
| 169 | 65 | 89 | 7 | 65 |
| 170 | 84 | 106 | 26 | 105 |
| 171 | 59 | 106 | 60 | 99 |
| 172 | 28 | 101 | 6 | 60 |
| 173 | 69 | 67 | 3 | 83 |
| 174 | 15 | 70 | 8 | 59 |
| 175 | 19 | 85 | 7 | 36 |
| 176 | 76 | 109 | 35 | 109 |
| 177 | 79 | 100 | 34 | 106 |
| 178 | 20 | 109 | 38 | 88 |
| 179 | 29 | 60 | 5 | 89 |
| 180 | 60 | 102 | 21 | 102 |
| 181 | 85 | 91 | 35 | 108 |
| 182 | 83 | 100 | 45 | 107 |
| 183 | −2 | 16 | 3 | 9 |
| 184 | 76 | 112 | 16 | 112 |
| 185 | 16 | 97 | 9 | 50 |
| 186 | 68 | 109 | 65 | 92 |
| 187 | 32 | 95 | 25 | 77 |
| 188 | 47 | 94 | 36 | 82 |
| 189 | 89 | 96 | 21 | 106 |
| 190 | 3 | 60 | 7 | 33 |
| 191 | 26 | 97 | 30 | 90 |
| 192 | 48 | 90 | 12 | 100 |
| 193 | 26 | 69 | 13 | 46 |
| 194 | 17 | 18 | | |
| 195 | 52 | 74 | 8 | 88 |
| 196 | 69 | 91 | 12 | 105 |
| 197 | 15 | 23 | 4 | 19 |
| 198 | 18 | 108 | 35 | 70 |
| 199 | 21 | 64 | 16 | 42 |
| 200 | 101 | 118 | 60 | 111 |
| 201 | 74 | 105 | 37 | 110 |
| 202 | 12 | 80 | 8 | 54 |
| 203 | 10 | 88 | 16 | 67 |
| 204 | 70 | 101 | 25 | 90 |
| 205 | 42 | 114 | 64 | 83 |
| 206 | 90 | 96 | 11 | 106 |
| 207 | 27 | 83 | 9 | 51 |
| 208 | 42 | 108 | 47 | 107 |
| 209 | 92 | 107 | 34 | 108 |
| 210 | 52 | 110 | 68 | 92 |
| 211 | 111 | 111 | 13 | 106 |
| 212 | 87 | 109 | 38 | 112 |
| 213 | 57 | 80 | 35 | 109 |
| 214 | 46 | 84 | 14 | 46 |
| 215 | 29 | 85 | 8 | 51 |
| 216 | 64 | 91 | 11 | 99 |
| 217 | 30 | 74 | 24 | 60 |
| 218 | 61 | 102 | 14 | 97 |
| 219 | 32 | 101 | 31 | 107 |
| 220 | 92 | 91 | 9 | 99 |
| 221 | 62 | 94 | 8 | 100 |
| 222 | 68 | 98 | 9 | 102 |
| 223 | 67 | 94 | 21 | 102 |
| 224 | 70 | 92 | 15 | 103 |
| 225 | 51 | 52 | 51 | 84 |
| 226 | 46 | 98 | 14 | 93 |
| 227 | −2 | 76 | 3 | 24 |
| 228 | 24 | 94 | 11 | 57 |
| 229 | 62 | 105 | 16 | 106 |
| 230 | 57 | 93 | 29 | 102 |
| 231 | 34 | 104 | 47 | 77 |
| 232 | 38 | 105 | 26 | 67 |
| 233 | 61 | 97 | 28 | 74 |
| 234 | 60 | 100 | 10 | 104 |
| 235 | 65 | 101 | 17 | 66 |
| 236 | 11 | 53 | 10 | 48 |
| 237 | 61 | 89 | | |
| 238 | 72 | 88 | 11 | 96 |
| 239 | 30 | 68 | 27 | 41 |
| 240 | 52 | 79 | 8 | 98 |
| 241 | 59 | 107 | 27 | 104 |
| 242 | 81 | 104 | 36 | 112 |
| 243 | 12 | 66 | 4 | 45 |
| 244 | 77 | 101 | 14 | 101 |
| 245 | 73 | 109 | 15 | 104 |
| 246 | 15 | 81 | 8 | 43 |
| 247 | 83 | 105 | 21 | 104 |
| 248 | 89 | 106 | 35 | 109 |
| 249 | 51 | 98 | 9 | 56 |
| 250 | 53 | 92 | 5 | 88 |
| 251 | 14 | 96 | 12 | 44 |
| 252 | 58 | 85 | 12 | 60 |
| 253 | 20 | 64 | 2 | 27 |
| 254 | 49 | 96 | 8 | 91 |
| 255 | 0 | 55 | 5 | 39 |
| 256 | 25 | 87 | 8 | 57 |
| 257 | 31 | 97 | 30 | 68 |
| 258 | 18 | 86 | 13 | 47 |
| 259 | 69 | 100 | 25 | 101 |
| 260 | 37 | 74 | 6 | 37 |
| 261 | 79 | 113 | 33 | 105 |
| 262 | 0 | 69 | 4 | 12 |
| 263 | 48 | 105 | 43 | 84 |
| 264 | 32 | 99 | 28 | 100 |
| 265 | 64 | 109 | 64 | 111 |
| 266 | 36 | 90 | 8 | 52 |
| 267 | 100 | 113 | 43 | 111 |
| 268 | 82 | 95 | 16 | 102 |
| 269 | 72 | 100 | 15 | 101 |
| 270 | 81 | 114 | 24 | 111 |
| 271 | 35 | 82 | 8 | 63 |
| 272 | 70 | 96 | 10 | 70 |
| 273 | 88 | 73 | 7 | 98 |
| 274 | 98 | 109 | 38 | 107 |
| 275 | 17 | 47 | 14 | 44 |
| 276 | 4 | 15 | 6 | 12 |
| 277 | 95 | 97 | 55 | 116 |
| 278 | 23 | 98 | 35 | 83 |
| 279 | 19 | 106 | 42 | 78 |
| 280 | 35 | 106 | 34 | 92 |

| Compound | p110 alpha Percent Inhibition | p110 beta Percent Inhibition | p110 gamma Percent Inhibition | p110 delta Percent Inhibition |
|---|---|---|---|---|
| 281 | 52 | 96 | 56 | 97 |
| 282 | 14 | 99 | 21 | 64 |
| 283 | 96 | 98 | 18 | 99 |
| 284 | 39 | 114 | 66 | 110 |
| 285 | 16 | 83 | 18 | 77 |
| 286 | 36 | 92 | 50 | 104 |
| 287 | 84 | 109 | 69 | 112 |
| 288 | 14 | 85 | 19 | 76 |
| 289 | 11 | 32 | 10 | 32 |
| 290 | 23 | 104 | 49 | 104 |
| 291 | 36 | 107 | 57 | 105 |
| 292 | 4 | 82 | 6 | 56 |
| 293 | 98 | 108 | 78 | 110 |
| 294 | 47 | 94 | 35 | 101 |
| 295 | 101 | 111 | 76 | 112 |
| 296 | 37 | 79 | 14 | 107 |
| 297 | 26 | 104 | 33 | 77 |
| 298 | 11 | 95 | 38 | 103 |
| 299 | 39 | 109 | 42 | 108 |
| 300 | 44 | 105 | 46 | 97 |
| 301 | 55 | 107 | 49 | 89 |
| 302 | 21 | 100 | 15 | 97 |
| 303 | 99 | 110 | 69 | 115 |
| 304 | 6 | 25 | 7 | 32 |
| 305 | 37 | 106 | 37 | 74 |
| 306 | 81 | 109 | 51 | 108 |
| 307 | 15 | 84 | 9 | 62 |
| 308 | 41 | 106 | 39 | 92 |
| 309 | 56 | 101 | 66 | 108 |
| 310 | 34 | 106 | 64 | 105 |
| 311 | 55 | 104 | 64 | 105 |
| 312 | 64 | 105 | 47 | 92 |
| 313 | 73 | 117 | 30 | 86 |
| 314 | 42 | 109 | 42 | 104 |
| 315 | 97 | 110 | 75 | 114 |
| 316 | 78 | 106 | 62 | 111 |
| 317 | 20 | 77 | 29 | 70 |
| 318 | 18 | 96 | 14 | 76 |
| 319 | 59 | 105 | 50 | 113 |
| 320 | 16 | 94 | 35 | 97 |
| 321 | 67 | 73 | 59 | 86 |
| 322 | 64 | 104 | 28 | 67 |
| 323 | 66 | 61 | 46 | 97 |
| 324 | 107 | 118 | 67 | 113 |
| 325 | 17 | 89 | 22 | 89 |
| 326 | 79 | 108 | 56 | 96 |
| 327 | 34 | 109 | 22 | 109 |
| 328 | 11 | 98 | 48 | 83 |
| 329 | 39 | 112 | 29 | 80 |
| 330 | 85 | 109 | 61 | 106 |
| 331 | 37 | 105 | 51 | 107 |
| 332 | 11 | 77 | 27 | 91 |
| 333 | 63 | 95 | 55 | 74 |
| 334 | 21 | 103 | 12 | 101 |
| 335 | 54 | 111 | 31 | 107 |
| 336 | 16 | 90 | 10 | 49 |
| 337 | 14 | 60 | 11 | 46 |
| 338 | 67 | 110 | 73 | 109 |
| 339 | 20 | 86 | 12 | 55 |
| 340 | 48 | 113 | 59 | 104 |
| 341 | 30 | 110 | 30 | 98 |
| 342 | 34 | 80 | 12 | 97 |
| 343 | 84 | 110 | 67 | 113 |
| 344 | 24 | 103 | 59 | 102 |
| 345 | 64 | 105 | 62 | 83 |
| 346 | 21 | 98 | 23 | 98 |
| 347 | 71 | 102 | 60 | 111 |
| 348 | 4 | 63 | 4 | 56 |
| 349 | 43 | 108 | 42 | 96 |
| 350 | 6 | 58 | 3 | 41 |
| 351 | 15 | 82 | 46 | 79 |
| 352 | 18 | 85 | 14 | 84 |
| 353 | 19 | 87 | 15 | 80 |
| 354 | 89 | 111 | 40 | 99 |
| 355 | 44 | 100 | 53 | 105 |
| 356 | 11 | 95 | 23 | 72 |
| 357 | 89 | 110 | 79 | 110 |
| 358 | 13 | 43 | 32 | 51 |
| 359 | 90 | 109 | 64 | 102 |
| 360 | 30 | 106 | 49 | 110 |
| 361 | 104 | 115 | 60 | 111 |
| 362 | 80 | 116 | 44 | 104 |
| 363 | 99 | 113 | 65 | 106 |
| 364 | 88 | 109 | 56 | 101 |
| 365 | 105 | 117 | 63 | 112 |
| 366 | 66 | 113 | 77 | 113 |
| 367 | 99 | 110 | 72 | 116 |
| 368 | 89 | 112 | 87 | 113 |
| 369 | 109 | 115 | 65 | 109 |
| 370 | 22 | 98 | 12 | 62 |

While we have described a number of embodiments of this invention, it is apparent that our basic examples may be altered to provide other embodiments, which utilize the compounds and methods of this invention. Therefore, it will be appreciated that the scope of this invention is to be defined by the appended claims rather than by the specific embodiments, which have been represented by way of example.

The invention claimed is:

1. A compound of formula IA-a or IB-a:

IA-a

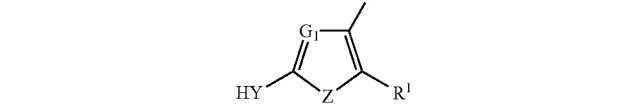

IB-a or a pharmaceutically acceptable salt thereof, wherein:
Z is S or Se;
$R^1$ is CY, —C(O)N($R^3$)$_2$, —C(O)O$R^3$, —C(O)(NH)OH, —C(=NH)NHOH, —C(O)N$R^3$N($R^3$)$_2$, —C(=N—NH$_2$)NH$_2$, or —C(=N)N($R^3$)$_2$, wherein
CY is

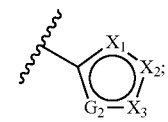

wherein:
$G_2$ is —N=, =N—, or —N($R^{3'}$)—, wherein:
each occurrence of $R^3$ and $R^{3'}$ is independently hydrogen or an optionally substituted $C_{1-6}$ aliphatic, wherein:

$X_1$, $X_2$, and $X_3$, are each independently N, $NR^{3'}$, O, S, or $CR^4$, provided that only one of $X_1$, $X_2$, or $X_3$ may be O, S, or $NR^{3'}$;

each occurrence of $R^4$ is independently hydrogen, —CN, halogen, —$Z_3$—$R^6$, or an optionally substituted group selected from $C_{1-6}$ aliphatic and 3-10-membered cycloaliphatic, wherein:

$Z_3$ is selected from an optionally substituted $C_{1-3}$ alkylene chain, —O—, —$N(R^{4a})$—, —S—, —S(O)—, —$S(O)_2$—, —C(O)—, —$CO_2$—, —$C(O)NR^{4a}$—, —$N(R^{4a})C(O)$—, —$N(R^{4a})CO_2$—, —$S(O)_2NR^{4a}$—, —$N(R^{4a})S(O)_2$—, —$OC(O)N(R^{4a})$—, —$N(R^{4a})C(O)NR^{4a}$—, —$N(R^{4a})S(O)_2N(R^{4a})$—, and —OC(O)—;

$R^{4a}$ is hydrogen or an optionally substituted $C_{1-4}$ aliphatic, and $R^6$ is hydrogen or an optionally substituted group selected from $C_{1-6}$ aliphatic, 3-10-membered cycloaliphatic, 4-10-membered heterocyclyl having 1-5 heteroatoms independently selected from nitrogen, oxygen, and sulfur, 6-10-membered aryl, and 5-10-membered heteroaryl having 1-5 heteroatoms independently selected from nitrogen, oxygen, and sulfur;

or wherein two adjacent occurrences of $R^{3'}$ or $R^4$, taken together with the atom to which they are bound, form an optionally substituted fused group selected from 5-6-membered aryl and 5-6-membered heteroaryl having 1-5 heteroatoms independently selected from nitrogen, oxygen, and sulfur;

Ring A is a group selected from 3-10-membered cycloaliphatic, 4-10-membered heterocyclyl having 1-5 heteroatoms independently selected from nitrogen, oxygen, and sulfur, 6-10-membered aryl, and 5-10-membered heteroaryl having 1-5 heteroatoms independently selected from nitrogen, oxygen, and sulfur;

each occurrence of $R^2$ is independently —$R^{12a}$, -$T_2$-$R^{12d}$, or —$V_2$-$T_2$-$R^{12d}$, and:

each occurrence of $R^{12a}$ is independently halogen, —CN, —$NO_2$, —$R^{12c}$, —$N(R^{12b})_2$, —$OR^{12b}$, —$SR^{12c}$, —$S(O)_2R^{12c}$, —$C(O)R^{12b}$, —$C(O)OR^{12b}$, —$C(O)N(R^{12b})_2$, —$S(O)_2N(R^{12b})_2$, —$OC(O)N(R^{12b})_2$, —$N(R^{12e})C(O)R^{12b}$, —$N(R^{12e})SO_2R^{12c}$, —$N(R^{12e})C(O)OR^{12b}$, —$N(R^{12e})C(O)N(R^{12b})_2$, or —$N(R^{12e})SO_2N(R^{12b})_2$, or two occurrences of $R^{12b}$, taken together with a nitrogen atom to which they are bound, form an optionally substituted 4-7-membered heterocyclyl ring having 0-1 additional heteroatoms selected from nitrogen, oxygen, and sulfur;

each occurrence of $R^{12b}$ is independently hydrogen or an optionally substituted group selected from $C_1$-$C_6$ aliphatic, 3-10-membered cycloaliphatic, 4-10-membered heterocyclyl having 1-5 heteroatoms independently selected from nitrogen, oxygen, and sulfur, 6-10-membered aryl, or 5-10-membered heteroaryl having 1-5 heteroatoms independently selected from nitrogen, oxygen, and sulfur;

each occurrence of $R^{12c}$ is independently an optionally substituted group selected from $C_1$-$C_6$ aliphatic, 3-10-membered cycloaliphatic, 4-10-membered heterocyclyl having 1-5 heteroatoms independently selected from nitrogen, oxygen, and sulfur, 6-10-membered aryl, and 5-10-membered heteroaryl having 1-5 heteroatoms independently selected from nitrogen, oxygen, and sulfur;

each occurrence of $R^{12d}$ is independently hydrogen or an optionally substituted group selected from 3-10-membered cycloaliphatic, 4-10-membered heterocyclyl having 1-5 heteroatoms independently selected from nitrogen, oxygen, and sulfur, 6-10-membered aryl, and 5-10-membered heteroaryl having 1-5 heteroatoms independently selected from nitrogen, oxygen, and sulfur;

each occurrence of $R^{12e}$ is independently hydrogen or an optionally substituted $C_{1-6}$ aliphatic group;

each occurrence of $V_2$ is independently —$N(R^{12e})$—, —O—, —S—, —S(O)—, —$S(O)_2$—, —C(O)—, —C(O)O—, —$C(O)N(R^{12e})$—, —$S(O)_2N(R^{12e})$—, —$OC(O)N(R^{12e})$—, —$N(R^{12e})C(O)$—, —$N(R^{12e})SO_2$—, —$N(R^{12e})C(O)O$—, —$N(R^{12e})C(O)N(R^{12e})$—, —$N(R^{12e})SO_2N(R^{12e})$—, —OC(O)—, or —$C(O)N(R^{12e})$—O—;

$T_2$ is an optionally substituted $C_1$-$C_6$ alkylene chain wherein the alkylene chain optionally is interrupted by —$N(R^{13})$—, —O—, —S—, —S(O)—, —$S(O)_2$—, —C(O)—, —C(O)O—, —$C(O)N(R^{13})$—, —$S(O)_2N(R^{13})$—, —$OC(O)N(R^{13})$—, —$N(R^{13})C(O)$—, —$N(R^{13})SO_2$—, —$N(R^{13})C(O)O$—, —$N(R^{13})C(O)N(R^{13})$—, —$N(R^{13})S(O)_2N(R^{13})$—, —OC(O)—, or —$C(O)N(R^{13})$—O— or wherein $T_2$ or a portion thereof optionally forms part of an optionally substituted 3-7 membered cycloaliphatic or heterocyclyl ring, wherein $R^{13}$ is hydrogen or an optionally substituted $C_{1-4}$ aliphatic group;

n is 0 to 4;

W is —$C(R^7)_2$—, wherein:

each occurrence of $R^7$ is independently hydrogen or an optionally substituted group selected from $C_{1-6}$ aliphatic, 6-10-membered aryl, 5-10-membered heteroaryl having 1-5 heteroatoms independently selected from nitrogen, oxygen, and sulfur, —$N(R^{7b})_2$, —$OR^{7a}$, —$SR^{7a}$, halo, and —CN;

each occurrence of $R^{7a}$ is independently hydrogen or optionally substituted $C_{1-6}$ aliphatic or optionally substituted $C_{3-6}$ cycloaliphatic;

each occurrence of $R^{7b}$ is independently hydrogen, optionally substituted $C_{1-6}$ aliphatic, optionally substituted $C_{3-6}$ cycloaliphatic, —$C(O)R^{7a}$, —$C(O)OR^{7a}$, $S(O)R^{7a}$, or —$S(O)_2R^{7a}$; or wherein any two occurrences of $R^7$, $R^{7a}$, or $R^{7b}$, taken together with the atom to which they are bound, form an optionally substituted group selected from a 3-6-membered cycloaliphatic ring, 6-10-membered aryl, 3-6-membered heterocyclyl having 1-5 heteroatoms independently selected from nitrogen, oxygen, and sulfur, and 5-10-membered heteroaryl having 1-5 heteroatoms independently selected from nitrogen, oxygen, and sulfur;

or wherein any two occurrences of $R^{7a}$ and $R^2$, or $R^{7b}$ and $R^2$ taken together with the nitrogen atom to which they are bound, form an optionally substituted group selected from 3-6-membered heterocyclyl having 1-5 heteroatoms independently selected from nitrogen, oxygen, and sulfur, and 5-10-membered heteroaryl having 1-5 heteroatoms independently selected from nitrogen, oxygen, and sulfur;

$G_1$ is —$CR^8$, wherein $R^8$ is H, —CN, halogen, —$Z_2$—$R^9$, $C_{1-6}$ aliphatic, or 3-10-membered cycloaliphatic, wherein:

$Z_2$ is selected from an optionally substituted $C_{1-3}$ alkylene chain, —O—, —$N(R^{8a})$—, —S—, —S(O)—, $S(O)_2$—, —C(O)—, —$CO_2$—, —$C(O)NR^{8a}$—, —$N(R^{8a})C(O)$—, —$N(R^{8a})CO_2$—, —$S(O)_2$ $NR^{8a}$—, —$N(R^{8a})S(O)_2$—, —$OC(O)N(R^{8a})$—, —$N(R^{8a})C(O)NR^{8a}$—, —$N(R^{8a})S(O)_2N(R^{8a})$—, and —$OC(O)$—;

$R^{8a}$ is hydrogen or an optionally substituted $C_{1-4}$ aliphatic, and $R^9$ is hydrogen or an optionally substituted group selected from $C_{1-6}$ aliphatic, 3-10-membered cycloaliphatic, 4-10-membered heterocyclyl having 1-5 heteroatoms independently selected from nitrogen, oxygen, and sulfur, 6-10-membered aryl, and 5-10-membered heteroaryl having 1-5 heteroatoms independently selected from nitrogen, oxygen, and sulfur; and HY is an optionally substituted group selected from:

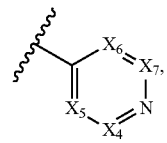

A

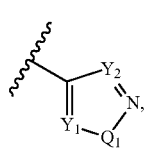

B

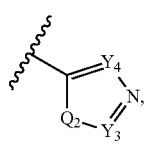

C

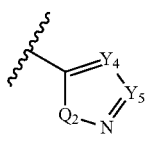

D

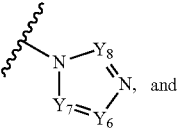

E and

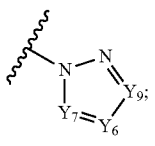

F wherein each occurrence of $X_4$, $X_5$, $X_6$, and $X_7$ is independently —$CR^{10}$ or N, provided no more than two occurrences of $X_4$, $X_5$, $X_6$, and $X_7$ are N;

each occurrence of $Q_1$ and $Q_2$ is independently S, O or —$NR^S$;

each occurrence of $Y_1$, $Y_2$, $Y_3$, $Y_4$, $Y_5$, $Y_6$, $Y_7$, $Y_8$, and $Y_9$ is independently —$CR^{10}$ or N, provided no more than two occurrences of $Y_6$, $Y_7$, $Y_8$, and $Y_9$ are N;

or wherein two adjacent occurrences of $X_4$ and $X_5$, $X_6$ and $X_7$, $Y_1$ and $Q_1$, $Y_3$ and $Q_2$, or $Y_4$ and $Y_5$ taken together with the atom to which they are bound, form an optionally substituted fused group selected from 5-6-membered aryl, and 5-6-membered heteroaryl having 1-5 heteroatoms independently selected from nitrogen, oxygen, and sulfur;

wherein $R^{10}$ is —$R^{10b}$, —$V_1$—$R^{10c}$, -$T_1$-$R^{10b}$, or —$V_1$-$T_1$-$R^{10b}$ wherein:

$V_1$ is —$NR^{11}$—, —$NR^{11}$—C(O)—, —$NR^{11}$—C(S)—, —$NR^{11}$—C($NR^{11}$)—, —$NR^{11}$C(O)$OR^{10a}$—, —$NR^{11}$C(O)$NR^{11}$—, —$NR^{11}$C(O)$SR^{10a}$—, —$NR^{11}$C(S)$OR^{10a}$—, —$NR^{11}$C(S)$NR^{11}$—, —$NR^{11}$C(S)$SR^{10a}$—, —$NR^{11}$C($NR^{11}$)$OR^{10a}$—, —$NR^{11}$C($NR^{11}$)$NR^{11}$—, —$NR^{11}$S(O)_2$—, —$NR^{11}$S(O)_2NR^{11}$—, —C(O)—, —$CO_2$—, —$C(O)NR^{11}$—, —$C(O)NR^{11}O$—, —$SO_2$—, or —$SO_2NR^{11}$—;

each occurrence of $R^{10a}$ is independently hydrogen or an optionally substituted group selected from $C_{1-6}$ aliphatic, 3-10-membered cycloaliphatic, 4-10-membered heterocyclyl having 1-5 heteroatoms independently selected from nitrogen, oxygen, and sulfur, 6-10-membered aryl, and 5-10-membered heteroaryl having 1-5 heteroatoms independently selected from nitrogen, oxygen, and sulfur;

$T_1$ is an optionally substituted $C_1$-$C_6$ alkylene chain wherein the alkylene chain optionally is interrupted by —$N(R^{11})$—, —O—, —S—, —S(O)—, —$S(O)_2$—, —C(O)—, —C(O)O—, —C(O)N($R^{11}$)—, —$S(O)_2N(R^{11})$—, —$OC(O)N(R^{11})$—, —$N(R^{11})C(O)$—, —$N(R^{11})SO_2$—, —$N(R^{11a})C(O)O$—, —$NR^{10a}C(O)N(R^{10a})$—, —$N(R^{10a})S(O)_2N(R^{10a})$—, —$OC(O)$—, or —$C(O)N(R^{11})$—O— or wherein $T_1$ forms part of an optionally substituted 3-7 membered cycloaliphatic or heterocyclyl ring;

each occurrence of $R^{10b}$ is independently hydrogen, halogen, —CN, —$NO_2$, —$N(R^{11})_2$, —$OR^{10a}$, —$SR^{10a}$, —$S(O)_2R^{10a}$, —$C(O)R^{10a}$, —$C(O)OR^{10a}$, —$C(O)N(R^{11})_2$, —$S(O)_2N(R^{11})_2$, —$OC(O)N(R^{11})_2$, —$N(R^{11})C(O)R^{10a}$, —$N(R^{11})SO_2R^{10a}$, —$N(R^{11})C(O)OR^{10a}$, —$N(R^{11})C(O)N(R^{11})_2$, or —$N(R^{11})SO_2N(R^{11})_2$, or an optionally substituted group selected from $C_{1-6}$ aliphatic, 3-10-membered cycloaliphatic, 4-10-membered heterocyclyl having 1-5 heteroatoms independently selected from nitrogen, oxygen, and sulfur, 6-10-membered aryl, and 5-10-membered heteroaryl having 1-5 heteroatoms independently selected from nitrogen, oxygen, and sulfur;

each occurrence of $R^{10c}$ is independently hydrogen or an optionally substituted group selected from $C_{1-6}$ aliphatic, 3-10-membered cycloaliphatic, 4-10-membered heterocyclyl having 1-5 heteroatoms independently selected from nitrogen, oxygen, and sulfur, 6-10-membered aryl, and 5-10-membered heteroaryl having 1-5 heteroatoms independently selected from nitrogen, oxygen, and sulfur, or $R^{10a}$ and $R^{10c}$ taken together with a nitrogen atom to which they are bound form an optionally substituted 4-7-membered heterocyclyl ring having 0-1 additional heteroatoms independently selected from nitrogen, oxygen, and sulfur;

each occurrence of $R^{11}$ is independently hydrogen, —C(O)$R^{11a}$—$CO_2R^{11a}$, —$C(O)N(R^{11a})_2$, —$C(O)N(R^{11a})$—$OR^{11a}$, $SO_2R^{11a}$, —$SO_2N(R^{11a})_2$, or an optionally substituted group selected from $C_{1-6}$ aliphatic, 3-10-membered cycloaliphatic, 4-10-membered heterocyclyl having 1-5 heteroatoms independently selected from nitrogen, oxygen, and sulfur, 6-10-membered aryl, and 5-10-membered heteroaryl having 1-5 heteroatoms independently selected from nitrogen, oxygen, and sulfur;

wherein each occurrence of $R^{11a}$ is independently hydrogen or an optionally substituted group selected from $C_{1-6}$ aliphatic, 3-10-membered cycloaliphatic, 4-10-membered heterocyclyl having 1-5 heteroatoms independently selected from nitrogen, oxygen, and sulfur, 6-10-membered aryl, and 5-10-membered heteroaryl having 1-5 heteroatoms independently selected from nitrogen, oxygen, and sulfur;

each occurrence of $R^5$ is independently hydrogen, —C(O)$R^{5a}$, —CO$_2R^{5a}$, —C(O)N($R^{5b}$)$_2$, —SO$_2R^{5a}$, —SO$_2$N($R^{5b}$)$_2$, or an optionally substituted group selected from $C_{1-6}$ aliphatic, 3-10-membered cycloaliphatic, 4-10-membered heterocyclyl having 1-5 heteroatoms independently selected from nitrogen, oxygen, and sulfur, 6-10-membered aryl, and 5-10-membered heteroaryl having 1-5 heteratoms independently selected from nitrogen, oxygen, and sulfur;

wherein each occurrence of $R^{5a}$ is independently hydrogen or an optionally substituted group selected from $C_{1-6}$ aliphatic, 3-10-membered cycloaliphatic, 4-10-membered heterocyclyl having 1-5 heteroatoms independently selected from nitrogen, oxygen, and sulfur, 6-10-membered aryl, and 5-10-membered heteroaryl having 1-5 heteratoms independently selected from nitrogen, oxygen, and sulfur;

wherein each occurrence of $R^{5b}$ is independently hydrogen or an optionally substituted group selected from $C_{1-6}$ aliphatic, 3-10-membered cycloaliphatic, 4-10-membered heterocyclyl having 1-5 heteroatoms independently selected from nitrogen, oxygen, and sulfur, 6-10-membered aryl, and 5-10-membered heteroaryl having 1-5 heteratoms independently selected from nitrogen, oxygen, and sulfur; or two occurrences of $R^{5b}$ taken together with the nitrogen atom to which they are bound, form an optionally substituted group selected from 3-6-membered heterocyclyl having 1-5 heteroatoms independently selected from nitrogen, oxygen, and sulfur, and 5-10-membered heteroaryl having 1-5 heteroatoms independently selected from nitrogen, oxygen, and sulfur.

2. A compound of formula IA or IB:

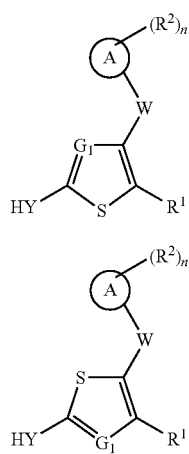

or a pharmaceutically acceptable salt thereof, wherein:

$R^1$ is CY, —C(O)N($R^3$)$_2$, —C(O)O$R^3$, —C(O)(NH)OH, —C(=NH)NHOH, —C(O)N$R^3$N($R^3$)$_2$, —C(=N—NH$_2$)NH$_2$, or —C(=N)N($R^3$)$_2$, wherein:

CY is

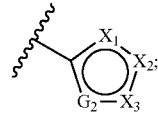

wherein
$G_2$ is —N=, =N—, or —N($R^{3'}$)—, wherein:
each occurrence of $R^3$ and $R^{3'}$ is independently hydrogen or an optionally substituted $C_{1-6}$ aliphatic, wherein:
$X_1$, $X_2$, and $X_3$, are each independently N, $NR^{3'}$, O, S, or $CR^4$, provided that only one of $X_1$, $X_2$, or $X_3$ may be O, S, or $NR^{3'}$;
each occurrence of $R^4$ is independently hydrogen, —CN, halogen, —$Z_3$—$R^6$, or an optionally substituted group selected from $C_{1-6}$ aliphatic and 3-10-membered cycloaliphatic, wherein:
$Z_3$ is selected from an optionally substituted $C_{1-3}$ alkylene chain, —O—, —N($R^{4a}$)—, —S—, —S(O)—, —S(O)$_2$—, —C(O)—, —CO$_2$—, —C(O)N$R^{4a}$—, —N($R^{4a}$)C(O)—, —N($R^{4a}$)CO$_2$—, —S(O)$_2$N$R^{4a}$—, —N($R^{4a}$)S(O)$_2$—, —OC(O)N($R^{4a}$)—, —N($R^{4a}$)C(O)N$R^{4a}$—, —N($R^{4a}$)S(O)$_2$N($R^{4a}$)—, or —OC(O)—;
$R^{4a}$ is hydrogen or an optionally substituted $C_{1-4}$ aliphatic, and
$R^6$ is hydrogen or an optionally substituted group selected from $C_{1-6}$ aliphatic, 3-10-membered cycloaliphatic, 4-10-membered heterocyclyl having 1-5 heteroatoms independently selected from nitrogen, oxygen, and sulfur, 6-10-membered aryl, and 5-10-membered heteroaryl having 1-5 heteroatoms independently selected from nitrogen, oxygen, and sulfur;
or wherein two adjacent occurrences of $R^{3'}$ or $R^4$, taken together with the atom to which they are bound, form an optionally substituted fused group selected from 5-6-membered aryl, and 5-6-membered heteroaryl having 1-5 heteroatoms independently selected from nitrogen, oxygen, and sulfur;
Ring A is a group selected from 3-10-membered cycloaliphatic, 4-10-membered heterocyclyl having 1-5 heteroatoms independently selected from nitrogen, oxygen, and sulfur, 6-10-membered aryl, and 5-10-membered heteroaryl having 1-5 heteroatoms independently selected from nitrogen, oxygen, and sulfur;
each occurrence of $R^2$ is independently —$R^{12a}$, -$T_2$-$R^{12d}$, or —$V_2$-$T_2$-$R^{12d}$, and:
each occurrence of $R^{12a}$ is independently halogen, —CN, —NO$_2$, —N($R^{12b}$)$_2$, —O$R^{12b}$, —S$R^{12c}$, —S(O)$_2R^{12c}$, —C(O)$R^{12b}$, —C(O)O$R^{12b}$, —C(O)N($R^{12b}$)$_2$, —S(O)$_2$N($R^{12b}$)$_2$, —OC(O)N($R^{12b}$)$_2$, —N($R^{12e}$)C(O)$R^{12b}$, —N($R^{12e}$)SO$_2R^{12c}$, —N($R^{12e}$)C(O)O$R^{12b}$, —N($R^{12e}$)C(O)N($R^{12b}$)$_2$, or —N($R^{12a}$)SO$_2$N($R^{12b}$)$_2$, or two occurrences of $R^{12b}$, taken together with a nitrogen atom to which they are bound, form an optionally substituted 4-7-membered heterocyclyl ring having 0-1 additional heteroatoms selected from nitrogen, oxygen, and sulfur;
each occurrence of $R^{12b}$ is independently hydrogen or an optionally substituted group selected from $C_1$-$C_6$ aliphatic, 3-10-membered cycloaliphatic, 4-10-membered heterocyclyl having 1-5 heteroatoms independently selected from nitrogen, oxygen, and sulfur, 6-10-membered aryl, and 5-10-membered heteroaryl having 1-5 heteroatoms independently selected from nitrogen, oxygen, and sulfur;

each occurrence of $R^{12c}$ is independently an optionally substituted group selected from $C_1$-$C_6$ aliphatic, 3-10-membered cycloaliphatic, 4-10-membered heterocyclyl having 1-5 heteroatoms independently selected from nitrogen, oxygen, and sulfur, 6-10-membered aryl, and 5-10-membered heteroaryl having 1-5 heteroatoms independently selected from nitrogen, oxygen, and sulfur;

each occurrence of $R^{12d}$ is independently hydrogen or an optionally substituted group selected from 3-10-membered cycloaliphatic, 4-10-membered heterocyclyl having 1-5 heteroatoms independently selected from nitrogen, oxygen, and sulfur, 6-10-membered aryl, or 5-10-membered heteroaryl having 1-5 heteroatoms independently selected from nitrogen, oxygen, and sulfur;

each occurrence of $R^{12e}$ is independently hydrogen or an optionally substituted $C_{1-6}$ aliphatic group;

each occurrence of $V_2$ is independently —$N(R^{12e})$—, —O—, —S—, —S(O)—, —$S(O)_2$—, —C(O)—, —C(O)O—, —$C(O)N(R^{12e})$—, —$S(O)_2N(R^{12e})$—, —$OC(O)N(R^{12e})$—, —$N(R^{12e})C(O)$—, —$N(R^{12e})SO_2$—, —$N(R^{12e})C(O)O$—, —$N(R^{12e})C(O)N(R^{12e})$—, —$N(R^{12e})SO_2N(R^{12e})$—, —OC(O)—, or —$C(O)N(R^{12e})$—O—; and $T_2$ is an optionally substituted $C_1$-$C_6$ alkylene chain wherein the alkylene chain optionally is interrupted by —$N(R^{13})$—, —O—, —S—, —S(O)—, —$S(O)_2$—, —C(O)—, —C(O)O—, —$C(O)N(R^{13})$—, —$S(O)_2N(R^{13})$—, —$OC(O)N(R^{13})$—, —$N(R^{13})C(O)$—, —$N(R^{13})SO_2$—, —$N(R^{13})C(O)O$—, —$N(R^{13})C(O)N(R^{13})$—, —$N(R^{13})S(O)_2N(R^{13})$—, —OC(O)—, or —$C(O)N(R^{13})$—O— or wherein $T_2$ or a portion thereof optionally forms part of an optionally substituted 3-7 membered cycloaliphatic or heterocyclyl ring, wherein $R^{13}$ is hydrogen or an optionally substituted $C_{1-4}$ aliphatic group;

n is 0 to 4;

W is —$C(R^7)_2$—, wherein:
each occurrence of $R^7$ is independently hydrogen or an optionally substituted group selected from $C_{1-6}$ aliphatic, 6-10-membered aryl, 5-10-membered heteroaryl having 1-5 heteroatoms independently selected from nitrogen, oxygen, and sulfur, —$N(R^{7b})_2$, —$OR^{7a}$, —$SR^{7a}$, halo, and —CN;

each occurrence of $R^{7a}$ is independently hydrogen or optionally substituted $C_{1-6}$ aliphatic or optionally substituted $C_{3-6}$ cycloaliphatic;

each occurrence of $R^{7b}$ is independently hydrogen, optionally substituted $C_{1-6}$ aliphatic, optionally substituted $C_{3-6}$ cycloaliphatic, —$C(O)R^{7a}$, —$C(O)OR^{7a}$, $S(O)R^{7a}$, or —$S(O)_2R^{7a}$; or wherein any two occurrences of $R^7$, $R^{7a}$, or $R^{7b}$, taken together with the atom to which they are bound, form an optionally substituted group selected from a 3-6-membered cycloaliphatic ring, 6-10-membered aryl, 3-6-membered heterocyclyl having 1-5 heteroatoms independently selected from nitrogen, oxygen, and sulfur, and 5-10-membered heteroaryl having 1-5 heteroatoms independently selected from nitrogen, oxygen, and sulfur;

or wherein any two occurrences of $R^{7a}$ and $R^2$, or $R^{7b}$ and $R^2$, taken together with the nitrogen atom to which they are bound, form an optionally substituted group selected from 3-6-membered heterocyclyl having 1-5 heteroatoms independently selected from nitrogen, oxygen, and sulfur, and 5-10-membered heteroaryl having 1-5 heteroatoms independently selected from nitrogen, oxygen, and sulfur;

$G_1$ is —$CR^8$, wherein $R^8$ is H, —CN, halogen, —$Z_2$—$R^9$, $C_{1-6}$ aliphatic, or 3-10-membered cycloaliphatic, wherein:
$Z_2$ is selected from an optionally substituted $C_{1-3}$ alkylene chain, —O—, —$N(R^{8a})$—, —S—, —S(O)—, $S(O)_2$—, —C(O)—, —$CO_2$—, —$C(O)NR^{8a}$—, —$N(R^{8a})C(O)$—, —$N(R^{8a})CO_2$—, —$S(O)_2NR^{8a}$—, —$N(R^{8a})S(O)_2$—, —$OC(O)N(R^{8a})$—, —$N(R^{8a})C(O)NR^{8a}$—, —$N(R^{8a})S(O)_2N(R^{8a})$—, and —OC(O)—;

$R^{8a}$ is hydrogen or an optionally substituted $C_{1-4}$ aliphatic, and $R^9$ is hydrogen or an optionally substituted group selected from $C_{1-6}$ aliphatic, 3-10-membered cycloaliphatic, 4-10-membered heterocyclyl having 1-5 heteroatoms independently selected from nitrogen, oxygen, and sulfur, 6-10-membered aryl, and 5-10-membered heteroaryl having 1-5 heteroatoms independently selected from nitrogen, oxygen, and sulfur; and HY is an optionally substituted group selected from:

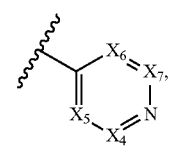

A

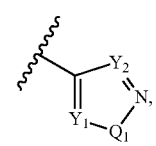

B

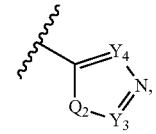

C

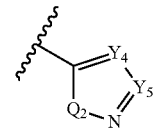

D

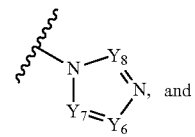

E

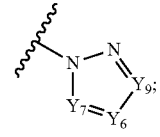

F wherein each occurrence of $X_4$, $X_5$, $X_6$, and $X_7$ is independently —$CR^{10}$ or N, provided no more than two occurrences of $X_4$, $X_5$, $X_6$, and $X_7$ are N;

each occurrence of $Q_1$ and $Q_2$ is independently S, O or —$NR^5$;

each occurrence of $Y_1, Y_2, Y_3, Y_4, Y_5, Y_6, Y_7, Y_8,$ and $Y_9$ is independently —$CR^{10}$ or N, provided no more than two occurrences of $Y_6, Y_7, Y_8,$ and $Y_9$ are N;

or wherein two adjacent occurrences of $X_4$ and $X_5$, $X_6$ and $X_7$, $Y_1$ and $Q_1$, $Y_3$ and $Q_1$, or $Y_1$ and $Y_5$ taken together with the atom to which they are bound, form an optionally substituted fused group selected from 5-6-membered aryl, and 5-6-membered heteroaryl having 1-5 heteroatoms independently selected from nitrogen, oxygen, and sulfur;

wherein $R^{10}$ is —$R^{10b}$, —$V_1$—$R^{10c}$, -$T_1$-$R^{10b}$, or —$V_1$-$T_1$-$R^{10b}$ wherein:

$V_1$ is —$NR^{11}$—, —$NR^{11}$—C(O)—, —$NR^{11}$—C(S)—, —$NR^{11}$—C($NR^{11}$)—, —$NR^{11}$C(O)$OR^{10a}$—, —$NR^{11}$C(O)$NR^{11}$—, —$NR^{11}$C(O)$SR^{10a}$—, —$NR^{11}$C(S)$OR^{10a}$—, —$NR^{11}$C(S)$NR^{11}$—, —$NR^{11}$C(S)$SR^{10a}$—, —$NR^{11}$C($NR^{11}$)$OR^{10a}$—, —$NR^{11}$C($NR^{11}$)$NR^{11}$—, —$NR^{11}$S(O)$_2$—, —$NR^{11}$S(O)$_2$$NR^{11}$—, —C(O)—, —CO$_2$—, —C(O)$NR^{11}$—, —C(O)$NR^{11}$O—, —SO$_2$—, or —SO$_2$$NR^{11}$—;

each occurrence of $R^{10a}$ is independently hydrogen or an optionally substituted group selected from $C_{1-6}$ aliphatic, 3-10-membered cycloaliphatic, 4-10-membered heterocyclyl having 1-5 heteroatoms independently selected from nitrogen, oxygen, and sulfur, 6-10-membered aryl, and 5-10-membered heteroaryl having 1-5 heteroatoms independently selected from nitrogen, oxygen, and sulfur;

$T_1$ is an optionally substituted $C_1$-$C_6$ alkylene chain wherein the alkylene chain optionally is interrupted by —N($R^{11}$)—, —O—, —S—, —S(O)—, —S(O)$_2$—, —C(O)—, —C(O)O—, —C(O)N($R^{11}$)—, —S(O)$_2$N($R^{11}$)—, —OC(O)N($R^{11}$)—, —N($R^{11}$)C(O)—, —N($R^{11}$)SO$_2$—, —N($R^{11a}$)C(O)O—, —$NR^{10a}$C(O)N($R^{10a}$)—, —N($R^{10a}$)S(O)$_2$N($R^{10a}$)—, —OC(O)—, or —C(O)N($R^{11}$)—O— or wherein $T_1$ forms part of an optionally substituted 3-7 membered cycloaliphatic or heterocyclyl ring;

each occurrence of $R^{10b}$ is independently hydrogen, halogen, —CN, —NO$_2$, —N($R^{11}$)$_2$, —$OR^{10a}$, —$SR^{10a}$, —S(O)$_2$$R^{10a}$, —C(O)$R^{10a}$, —C(O)$OR^{10a}$, —C(O)N($R^{11}$)$_2$, —S(O)$_2$N($R^{11}$)$_2$, —OC(O)N($R^{11}$)$_2$, —N($R^{11}$)C(O)$R^{10a}$, —N($R^{11}$)SO$_2$$R^{10a}$, —N($R^{11}$)C(O)$OR^{10a}$, —N($R^{11}$)C(O)N($R^{11}$)$_2$, or —N($R^{11}$)SO$_2$N($R^{11}$)$_2$, or an optionally substituted group selected from $C_{1-6}$ aliphatic, 3-10-membered cycloaliphatic, 4-10-membered heterocyclyl having 1-5 heteroatoms independently selected from nitrogen, oxygen, and sulfur, 6-10-membered aryl, and 5-10-membered heteroaryl having 1-5 heteroatoms independently selected from nitrogen, oxygen, and sulfur;

each occurrence of $R^{10c}$ is independently hydrogen or an optionally substituted group selected from $C_{1-6}$ aliphatic, 3-10-membered cycloaliphatic, 4-10-membered heterocyclyl having 1-5 heteroatoms independently selected from nitrogen, oxygen, and sulfur, 6-10-membered aryl, and 5-10-membered heteroaryl having 1-5 heteroatoms independently selected from nitrogen, oxygen, and sulfur, or $R^{10a}$ and $R^{10c}$ taken together with a nitrogen atom to which they are bound form an optionally substituted 4-7-membered heterocyclyl ring having 0-1 additional heteroatoms independently selected from nitrogen, oxygen, and sulfur;

each occurrence of $R^{11}$ is independently hydrogen, —C(O)$R^{11a}$, —CO$_2$$R^{11a}$, —C(O)N($R^{11a}$)$_2$, —C(O)N($R^{11a}$)—$OR^{11a}$, SO$_2$$R^{11a}$, —SO$_2$N($R^{11a}$)$_2$, or an optionally substituted group selected from $C_{1-6}$ aliphatic, 3-10-membered cycloaliphatic, 4-10-membered heterocyclyl having 1-5 heteroatoms independently selected from nitrogen, oxygen, and sulfur, 6-10-membered aryl, and 5-10-membered heteroaryl having 1-5 heteroatoms independently selected from nitrogen, oxygen, and sulfur;

wherein each occurrence of $R^{11a}$ is independently hydrogen or an optionally substituted group selected from $C_{1-6}$ aliphatic, 3-10-membered cycloaliphatic, 4-10-membered heterocyclyl having 1-5 heteroatoms independently selected from nitrogen, oxygen, and sulfur, 6-10-membered aryl, and 5-10-membered heteroaryl having 1-5 heteroatoms independently selected from nitrogen, oxygen, and sulfur;

each occurrence of $R^5$ is independently hydrogen, —C(O)$R^{5a}$, —CO$_2$$R^{5a}$, —C(O)N($R^{5b}$)$_2$, —SO$_2$$R^{5a}$, —SO$_2$N($R^{5b}$)$_2$, or an optionally substituted group selected from $C_{1-6}$ aliphatic, 3-10-membered cycloaliphatic, 4-10-membered heterocyclyl having 1-5 heteroatoms independently selected from nitrogen, oxygen, and sulfur, 6-10-membered aryl, and 5-10-membered heteroaryl having 1-5 heteratoms independently selected from nitrogen, oxygen, and sulfur;

wherein each occurrence of $R^{5a}$ is independently hydrogen or an optionally substituted group selected from $C_{1-6}$ aliphatic, 3-10-membered cycloaliphatic, 4-10-membered heterocyclyl having 1-5 heteroatoms independently selected from nitrogen, oxygen, and sulfur, 6-10-membered aryl, and 5-10-membered heteroaryl having 1-5 heteroatoms independently selected from nitrogen, oxygen, and sulfur;

wherein each occurrence of $R^{5b}$ is independently hydrogen or an optionally substituted group selected from $C_{1-6}$ aliphatic, 3-10-membered cycloaliphatic, 4-10-membered heterocyclyl having 1-5 heteroatoms independently selected from nitrogen, oxygen, and sulfur, 6-10-membered aryl, and 5-10-membered heteroaryl having 1-5 heteratoms independently selected from nitrogen, oxygen, and sulfur; or two occurrences of $R^{5b}$ taken together with the nitrogen atom to which they are bound, form an optionally substituted group selected from 3-6-membered heterocyclyl having 1-5 heteroatoms independently selected from nitrogen, oxygen, and sulfur, and 5-10-membered heteroaryl having 1-5 heteroatoms independently selected from nitrogen, oxygen, and sulfur.

3. The compound of claim 1 or 2, wherein $R^1$ is CY, and CY is

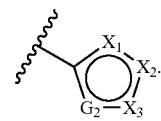

4. The compound of claim 1 or 2, wherein $X_1$ is N, $G_2$ is —N($R^3$)—, and $X_2$ and $X_3$ are CH.

5. The compound of claim 1 or 2, wherein $X_1$ and $X_2$ are N, $G_2$ is —N($R^3$)—, and $X_3$ is CH.

6. The compound of claim 1 or 2, wherein $X_3$ is N, $G_2$ is —N($R^3$)—, and $X_1$ and $X_2$ are CH.

7. The compound of claim 1 or 2, wherein $X_1$ is N, $X_2$ is CH, $X_3$ is —N($R^3$)— and $G_2$ is =N—.

8. The compound of claim 1 or 2, wherein HY is selected from:

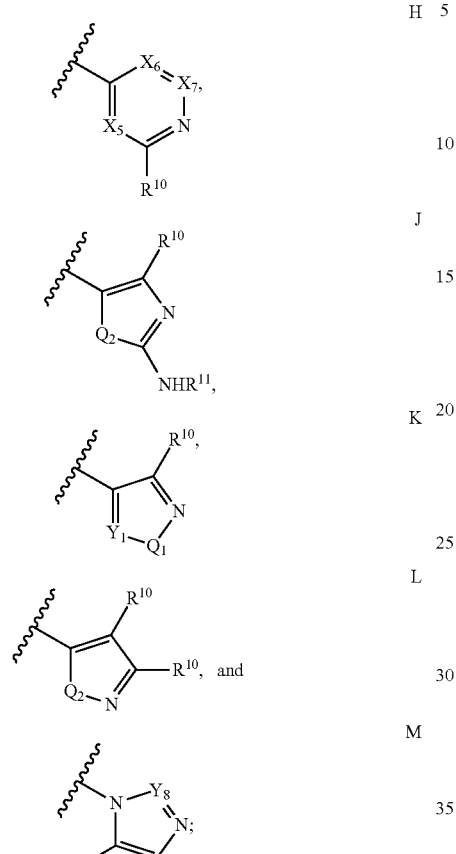

wherein each occurrence of $X_5$, $X_6$, and $X_7$ is independently —$CR^{10}$ or N, provided no more than two occurrences of $X_5$, $X_6$, and $X_7$ are N;

each occurrence of $Q_1$ and $Q_2$ is independently S, O or —$NR^5$;

each occurrence of $Y_1$ and $Y_7$ is independently —$CR^{10}$ or N;

or wherein two adjacent occurrences of $X_6$ and $X_7$, or $Y_1$ and $Q_1$, taken together with the atom to which they are bound, form an optionally substituted fused group selected from 5-6-membered aryl and 5-6-membered heteroaryl having 1-5 heteroatoms independently selected from nitrogen, oxygen, and sulfur.

9. The compound of claim 1 or 2, wherein HY is selected from:

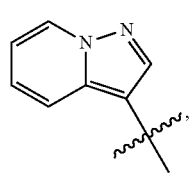  i

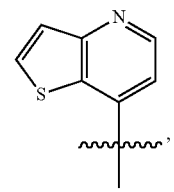  ii

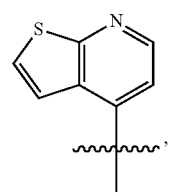  iii

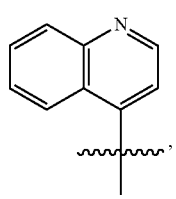  iv

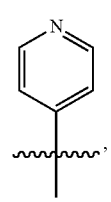  v

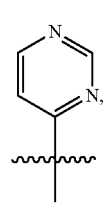  vi

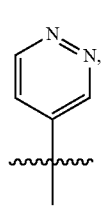  vii

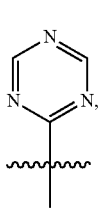  viii

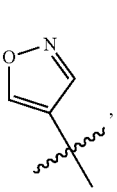  ix

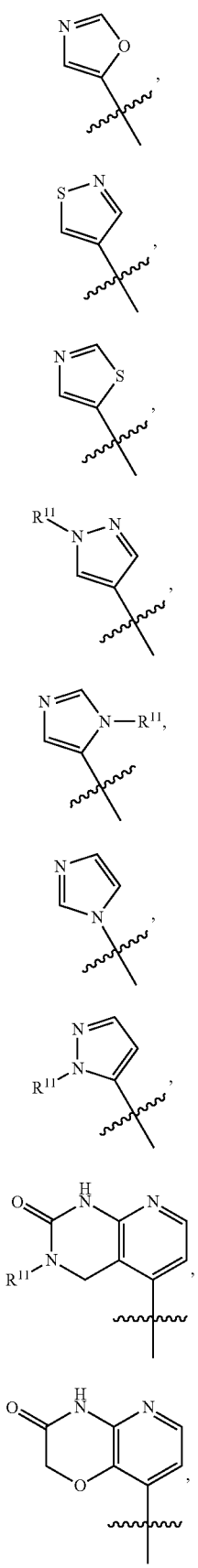
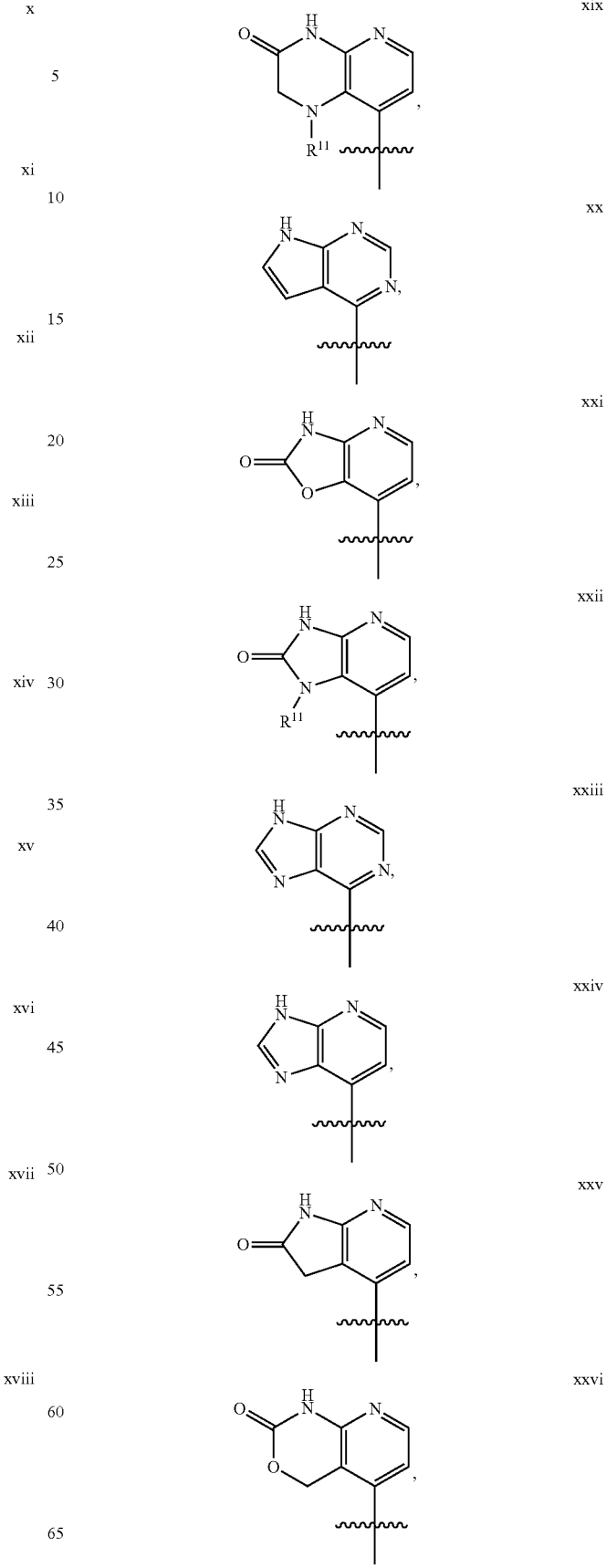

401
-continued
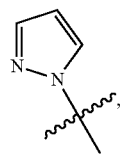
xxvii
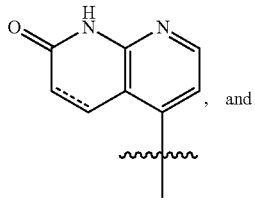, and
xxviii
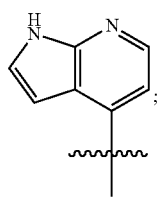;
xxix
wherein each HY group is optionally additionally substituted with one or more occurrences of R$^{10}$, and ----- in xviii represents a single bond or a double bond.
10. The compound of claim 1 or 2, wherein HY is selected from:
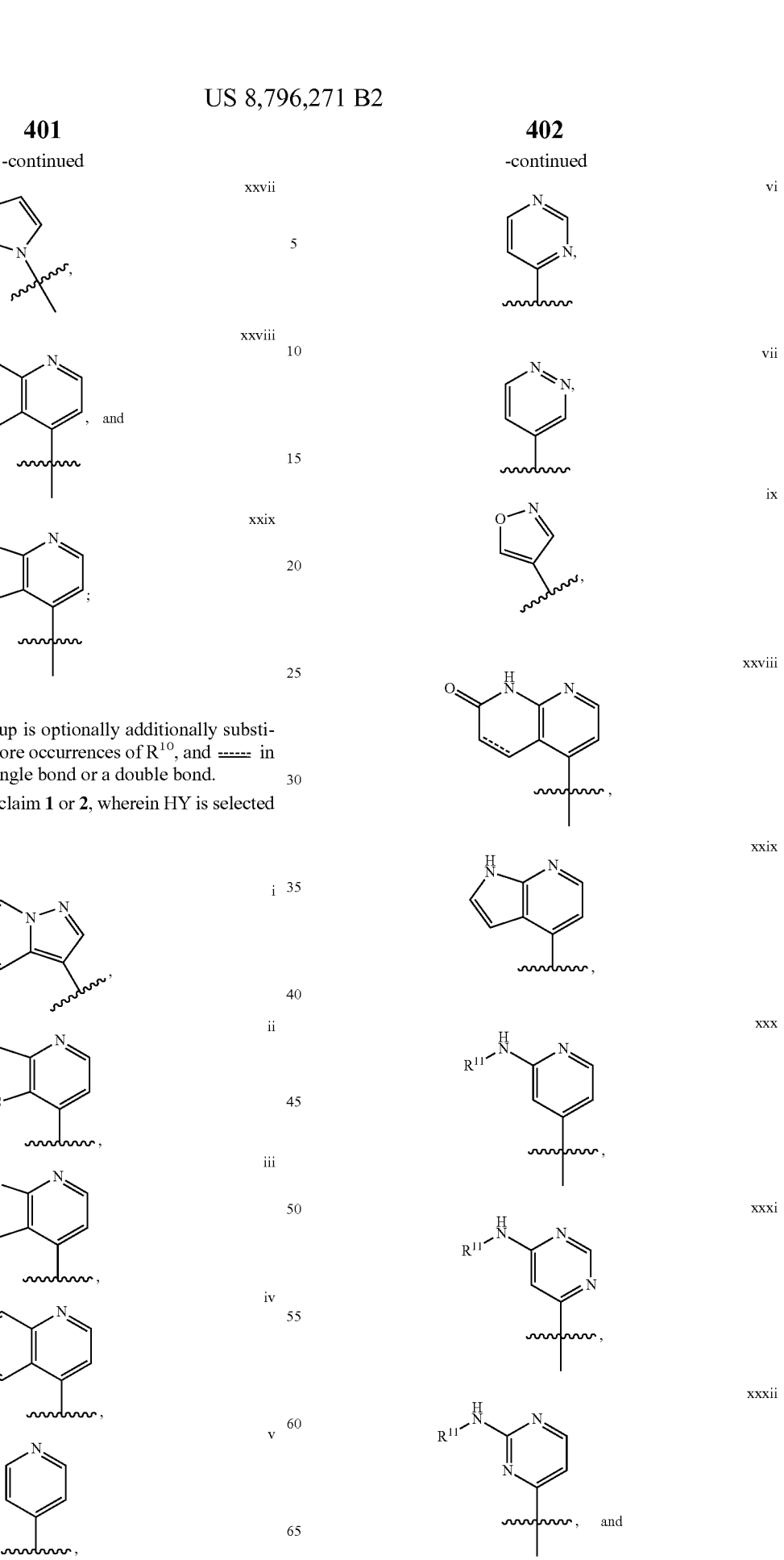

-continued xxxiii

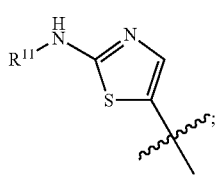

wherein each HY group is optionally additionally substituted with one or more occurrences of $R^{10}$, and ----- in xviii represents a single bond or a double bond.

11. The compound of claim 1 or 2, wherein $G_1$ is CH.

12. The compound of claim 1 or 2, wherein one occurrence of $R^7$ is hydrogen and the other occurrence of $R^7$ is hydrogen, optionally substituted $C_{1-6}$ aliphatic, —$N(R^{7b})_2$, —$OR^{7a}$, —$SR^{7a}$, halo, or —CN; and wherein each occurrence of $R^{7a}$ is independently hydrogen or optionally substituted $C_{1-6}$ aliphatic; and each occurrence of $R^{7b}$ is independently hydrogen, optionally substituted $C_{1-6}$ aliphatic, —$C(O)R^{7a}$, or —$S(O)_2R^{7a}$; or wherein two occurrences of $R^{7b}$, taken together with the nitrogen atom to which they are bound, form an optionally substituted 3-6-membered heterocyclic ring.

13. The compound of claim 12, wherein W is —C(H)(N($R^{7b}$)_2)—, —$CH_2$— or —C(H)($OR^{7a}$)—, wherein each occurrence of $R^{7a}$ is independently hydrogen or optionally substituted $C_{1-6}$ aliphatic; and each occurrence of $R^{7b}$ is independently hydrogen or optionally substituted $C_{1-6}$ aliphatic.

14. The compound of claim 1 or 2, wherein Ring A is 6-10-membered aryl or 5-10-membered heteroaryl having 1-5 heteroatoms independently selected from nitrogen, oxygen, and sulfur; and n is 0 to 3.

15. The compound of claim 14, wherein ring A is a group selected from:

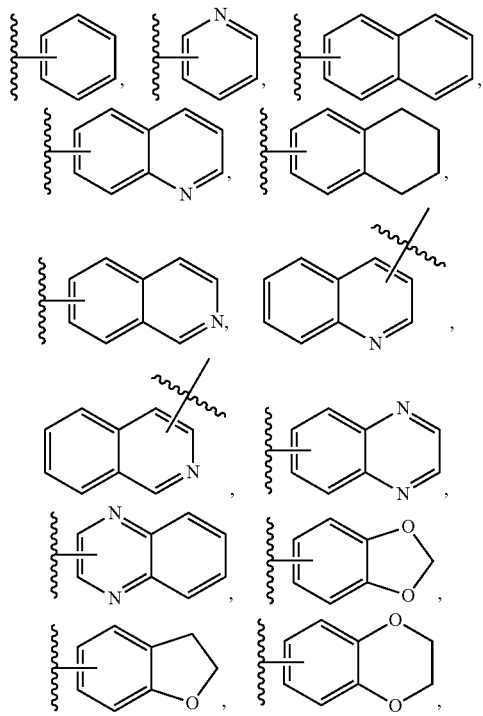

-continued

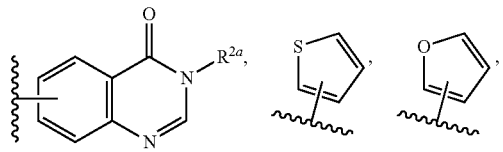

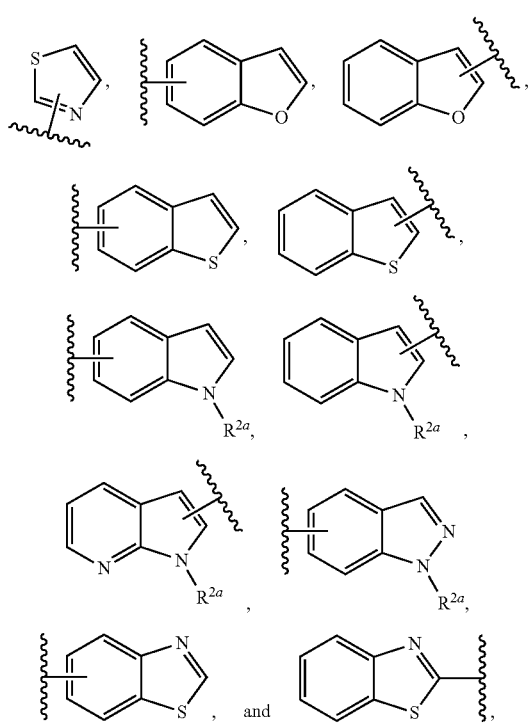

wherein ring A is optionally further substituted by n occurrences of $R^2$, and wherein $R^{2a}$ is hydrogen or an optionally substituted group selected from $C_{1-6}$ aliphatic, 3-10-membered cycloaliphatic, 4-10-membered heterocyclyl having 1-5 heteroatoms independently selected from nitrogen, oxygen, and sulfur, 6-10-membered aryl, and 5-10-membered heteroaryl having 1-5 heteroatoms independently selected from nitrogen, oxygen, and sulfur.

16. The compound of claim 14, wherein ring A is a group selected from:

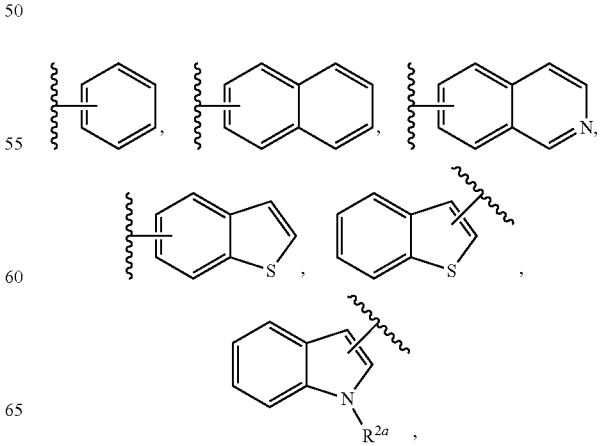

-continued

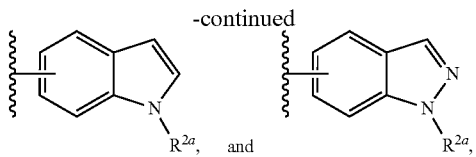

wherein ring A is optionally further substituted by n occurrences of $R^2$, and wherein $R^{2a}$ is hydrogen or an optionally substituted group selected from $C_{1-6}$ aliphatic, 3-10-membered cycloaliphatic, 4-10-membered heterocyclyl having 1-5 heteroatoms independently selected from nitrogen, oxygen, and sulfur, 6-10-membered aryl, and 5-10-membered heteroaryl having 1-5 heteroatoms independently selected from nitrogen, oxygen, and sulfur.

17. The compound of claim 14, wherein:
ring A is a naphthyl group; each occurrence of $R^2$ is independently halogen, $C_{1-3}$ alkyl, —CN, $C_{1-3}$ haloalkyl, —$OC_{1-3}$ alkyl, —$OC_{1-3}$ haloalkyl, —NHC(O)$C_{1-3}$ alkyl, —NHC(O)NHC$_{1-3}$ alkyl, —NHS(O)$_2$C$_{1-3}$ alkyl, or —C(O)H; and n is 0 to 3.

18. The compound of claim 14, wherein:
ring A is a phenyl group; each occurrence of $R^2$ is independently halogen, $C_{1-3}$ alkyl, —CN, $C_{1-3}$ haloalkyl, —$OC_{1-3}$ alkyl, —$OC_{1-3}$ haloalkyl, —NHC(O)$C_{1-3}$ alkyl, —NHC(O)NHC$_{1-3}$ alkyl, —NHS(O)$_2$C$_{1-3}$ alkyl, or —C(O)H; and n is 0 to 3.

19. The compound of claim 17, wherein ring A is a naphthyl group, $R^2$ is halogen and n is 1 to 2.

20. The compound of claim 17, wherein ring A is a naphthyl group and n is 0.

21. The compound of claim 18, wherein Ring A is a phenyl group, $R^2$ is halogen and n is 1 to 2.

22. A compound having the following formula II:

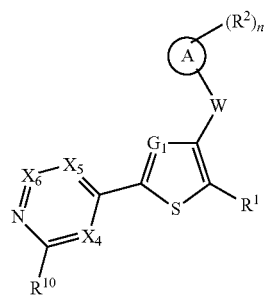

or a pharmaceutically acceptable salt thereof, wherein:
$X_4$, $X_5$ and $X_6$ are each independently —$CR^{10}$ or N, provided no more than two occurrences of $X_4$, $X_5$ and $X_6$ are N;
wherein $R^{10}$ is —$R^{10b}$, —$V_1$—$R^{10c}$, -$T_1$-$R^{10b}$, or —$V_1$-$T_1$-$R^{10b}$ wherein:
$V_1$ is —N$R^{11}$—, —N$R^{11}$—C(O)—, —N$R^{11}$—C(S)—, —N$R^{11}$—C(N$R^{11}$)—, —N$R^{11}$C(O)OR$^{10a}$—, —N$R^{11}$C(O)NR$^{11}$—, —N$R^{11}$C(O)SR$^{10a}$—, —N$R^{11}$C(S)OR$^{10a}$—, —N$R^{11}$C(S)NR$^{11}$—, —N$R^{11}$C(S)SR$^{10a}$—, —N$R^{11}$C(NR$^{11}$)OR$^{10a}$—, —N$R^{11}$C(NR$^{11}$)NR$^{11}$—, —N$R^{11}$S(O)$_2$—, —N$R^{11}$S(O)$_2$NR$^{11}$—, —C(O)—, —CO$_2$—, —C(O)NR$^{11}$—, —C(O)NR$^{11}$O—, —SO$_2$—, or —SO$_2$NR$^{11}$—;
each occurrence of $R^{10a}$ is independently hydrogen or an optionally substituted group selected from $C_{1-6}$ aliphatic, 3-10-membered cycloaliphatic, 4-10-membered heterocyclyl having 1-5 heteroatoms independently selected from nitrogen, oxygen, and sulfur, 6-10-membered aryl, and 5-10-membered heteroaryl having 1-5 heteroatoms independently selected from nitrogen, oxygen, and sulfur;

$T_1$ is an optionally substituted $C_1$-$C_6$ alkylene chain wherein the alkylene chain optionally is interrupted by —N(R$^{11}$)—, —O—, —S—, —S(O)—, —S(O)$_2$—, —C(O)—, C(O)O—, —C(O)N(R$^{11}$)—, —S(O)$_2$N(R$^{11}$)—, —OC(O)N(R$^{11}$)—, —N(R$^{11}$)C(O)—, —N(R$^{11}$)SO$_2$—, —N(R$^{11a}$)C(O)O—, —NR$^{10a}$C(O)N(R$^{10a}$)—, —N(R$^{10a}$)S(O)$_2$N(R$^{10a}$)—, —OC(O)—, or —C(O)N(R$^{11}$)—O— or wherein $T_1$ forms part of an optionally substituted 3-7 membered cycloaliphatic or heterocyclyl ring;
each occurrence of $R^{10b}$ is independently hydrogen, halogen, —CN, —NO$_2$, —N(R$^{11}$)$_2$, —OR$^{10a}$, —SR$^{10a}$, —S(O)$_2$R$^{10a}$, —C(O)R$^{10a}$, —C(O)OR$^{10a}$, —C(O)N(R$^{11}$)$_2$, —S(O)$_2$N(R$^{11}$)$_2$, —OC(O)N(R$^{11}$)$_2$, —N(R$^{11}$)C(O)R$^{10a}$, —N(R$^{11}$)SO$_2$R$^{10a}$, —N(R$^{11}$)C(O)OR$^{10a}$, —N(R$^{11}$)C(O)N(R$^{11}$)$_2$, —N(R$^{11}$)SO$_2$N(R$^{11}$)$_2$, or an optionally substituted group selected from $C_{1-6}$ aliphatic, 3-10-membered cycloaliphatic, 4-10-membered heterocyclyl having 1-5 heteroatoms independently selected from nitrogen, oxygen, and sulfur, 6-10-membered aryl, and 5-10-membered heteroaryl having 1-5 heteroatoms independently selected from nitrogen, oxygen, and sulfur;
each occurrence of $R^{10c}$ is independently hydrogen or an optionally substituted group selected from $C_{1-6}$ aliphatic, 3-10-membered cycloaliphatic, 4-10-membered heterocyclyl having 1-5 heteroatoms independently selected from nitrogen, oxygen, and sulfur, 6-10-membered aryl, and 5-10-membered heteroaryl having 1-5 heteroatoms independently selected from nitrogen, oxygen, and sulfur, or
$R^{10a}$ and $R^{10c}$, taken together with a nitrogen atom to which they are bound, form an optionally substituted 4-7-membered heterocyclyl ring having 0-1 additional heteroatoms independently selected from nitrogen, oxygen, and sulfur;
each occurrence of $R^{11}$ is independently hydrogen, —C(O)R$^{11a}$, —CO$_2$R$^{11a}$, —C(O)N(R$^{11a}$)$_2$, —C(O)N(R$^{11a}$)—OR$^{11a}$, SO$_2$R$^{11a}$, —SO$_2$N(R$^{11a}$)$_2$, or an optionally substituted group selected from $C_{1-6}$ aliphatic, 3-10-membered cycloaliphatic, 4-10-membered heterocyclyl having 1-5 heteroatoms independently selected from nitrogen, oxygen, and sulfur, 6-10-membered aryl, and 5-10-membered heteroaryl having 1-5 heteroatoms independently selected from nitrogen, oxygen, and sulfur;
wherein each occurrence of $R^{11a}$ is independently hydrogen or an optionally substituted group selected from $C_{1-6}$ aliphatic, 3-10-membered cycloaliphatic, 4-10-membered heterocyclyl having 1-5 heteroatoms independently selected from nitrogen, oxygen, and sulfur, 6-10-membered aryl, or 5-10-membered heteroaryl having 1-5 heteroatoms independently selected from nitrogen, oxygen, and sulfur;
each occurrence of $R^5$ is independently hydrogen, —C(O)R$^{5a}$, —CO$_2$R$^{5a}$, —C(O)N(R$^{5b}$)$_2$, —SO$_2$R$^{5a}$, —SO$_2$N(R$^{5b}$)$_2$, or an optionally substituted group selected from $C_{1-6}$ aliphatic, 3-10-membered cycloaliphatic, 4-10-membered heterocyclyl having 1-5 heteroatoms independently selected from nitrogen, oxygen, and sulfur, 6-10-membered aryl, and 5-10-membered heteroaryl having 1-5 heteratoms independently selected from nitrogen, oxygen, and sulfur;
wherein each occurrence of $R^{5a}$ is independently hydrogen or an optionally substituted group selected from $C_{1-6}$ aliphatic, 3-10-membered cycloaliphatic, 4-10-membered heterocyclyl having 1-5 heteroatoms independently selected from nitrogen, oxygen, and sulfur, 6-10-membered aryl, and 5-10-membered heteroaryl having 1-5 heteratoms independently selected from nitrogen, oxygen, and sulfur;
wherein each occurrence of $R^{5b}$ is independently hydrogen or an optionally substituted group selected from $C_{1-6}$ aliphatic, 3-10-membered cycloaliphatic, 4-10-membered heterocyclyl having 1-5 heteroatoms independently selected from nitrogen, oxygen, and sulfur, 6-10-membered aryl, or 5-10-membered heteroaryl having 1-5 heteratoms independently selected from nitrogen, oxygen, and sulfur; or two occurrences of $R^{5b}$ taken together with the nitrogen atom to which they are bound, form an optionally substituted group selected from 3-6-membered heterocyclyl having 1-5 heteroatoms independently selected from nitrogen, oxygen, and sulfur, and 5-10-membered heteroaryl having 1-5 heteratoms independently selected from nitrogen, oxygen, and sulfur;
or two adjacent groups selected from $R^{10}$, $X_4$, $X_5$, and $X_6$, taken together, form an optionally substituted group selected from 3-10-membered cycloaliphatic, 4-10-membered heterocyclyl having 1-5 heteroatoms independently selected from nitrogen, oxygen, and sulfur, 6-10-membered aryl, and 5-10-membered heteroaryl having 1-5 heteroatoms independently selected from nitrogen, oxygen, and sulfur;
$R^1$ is CY, —C(O)N($R^3$)$_2$, —C(O)O$R^3$, —C(O)(NH)OH, —C(=NH)NHOH, —C(O)N$R^3$N($R^3$)$_2$, —C(=N—NH$_2$)NH$_2$, or —C(=N)N($R^3$)$_2$, wherein:
CY is

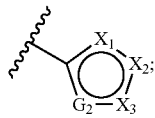

wherein:
$G_2$ is —N=, =N—, or —N($R^{3'}$)—, wherein:
each occurrence of $R^3$ and $R^{3'}$ is independently hydrogen or an optionally substituted $C_{1-6}$ aliphatic, wherein:
$X_1$, $X_2$, and $X_3$, are each independently N, N$R^{3'}$, O, S, or C$R^4$, provided that only one of $X_1$, $X_2$, or $X_3$ may be O, S, or N$R^{3'}$;
each occurrence of $R^4$ is independently hydrogen, —CN, halogen, —$Z_3$—$R^6$, or an optionally substituted group selected from $C_{1-6}$ aliphatic, or 3-10-membered cycloaliphatic, wherein:
$Z_3$ is selected from an optionally substituted $C_{1-3}$ alkylene chain, —O—, —N($R^{4a}$)—, —S—, —S(O)—, —S(O)$_2$—, —C(O)—, —CO$_2$—, —C(O)N$R^{4a}$—, —N($R^{4a}$)C(O)—, —N($R^{4a}$)CO$_2$—, —S(O)$_2$N$R^{4a}$—, —N($R^{4a}$)S(O)$_2$—, —OC(O)N($R^{4a}$)—, —N($R^{4a}$)C(O)N$R^{4a}$—, —N($R^{4a}$)S(O)$_2$N($R^{4a}$)—, and —OC(O)—;
$R^{4a}$ is hydrogen or an optionally substituted $C_{1-4}$ aliphatic, and
$R^6$ is hydrogen or an optionally substituted group selected from $C_{1-6}$ aliphatic, 3-10-membered cycloaliphatic, 4-10-membered heterocyclyl having 1-5 heteroatoms independently selected from nitrogen, oxygen, and sulfur, 6-10-membered aryl, and 5-10-membered heteroaryl having 1-5 heteroatoms independently selected from nitrogen, oxygen, and sulfur;
or wherein two adjacent occurrences of $R^{3'}$ or $R^4$, taken together with the atom to which they are bound, form an optionally substituted fused group selected from 5-6-membered aryl, and 5-6-membered heteroaryl having 1-5 heteroatoms independently selected from nitrogen, oxygen, and sulfur;
Ring A is a group selected from 3-10-membered cycloaliphatic, 4-10-membered heterocyclyl having 1-5 heteroatoms independently selected from nitrogen, oxygen, and sulfur, 6-10-membered aryl, and 5-10-membered heteroaryl having 1-5 heteroatoms independently selected from nitrogen, oxygen, and sulfur;
each occurrence of $R^2$ is independently —$R^{12a}$, -$T_2$-$R^{12d}$, or —$V_2$-$T_2$-$R^{12d}$, and:
each occurrence of $R^{12a}$ is independently halogen, —CN, —NO$_2$, —N($R^{12b}$)$_2$, —O$R^{12b}$, —S$R^{12c}$, —S(O)$_2R^{12c}$, —C(O)$R^{12b}$, —C(O)O$R^{12b}$, —C(O)N($R^{12b}$)$_2$, —S(O)$_2$N($R^{12b}$)$_2$, —OC(O)N($R^{12b}$)$_2$, —N($R^{12e}$)C(O)$R^{12b}$, —N($R^{12e}$)SO$_2R^{12c}$, —N($R^{12e}$)C(O)O$R^{12b}$, —N($R^{12e}$)C(O)N($R^{12b}$)$_2$, or —N($R^{12a}$)SO$_2$N($R^{12b}$)$_2$, or two occurrences of $R^{12b}$, taken together with a nitrogen atom to which they are bound, form an optionally substituted 4-7-membered heterocyclyl ring having 0-1 additional heteroatoms selected from nitrogen, oxygen, and sulfur;
each occurrence of $R^{12b}$ is independently hydrogen or an optionally substituted group selected from $C_1$-$C_6$ aliphatic, 3-10-membered cycloaliphatic, 4-10-membered heterocyclyl having 1-5 heteroatoms independently selected from nitrogen, oxygen, and sulfur, 6-10-membered aryl, and 5-10-membered heteroaryl having 1-5 heteroatoms independently selected from nitrogen, oxygen, and sulfur;
each occurrence of $R^{12c}$ is independently an optionally substituted group selected from $C_1$-$C_6$ aliphatic, 3-10-membered cycloaliphatic, 4-10-membered heterocyclyl having 1-5 heteroatoms independently selected from nitrogen, oxygen, and sulfur, 6-10-membered aryl, and 5-10-membered heteroaryl having 1-5 heteroatoms independently selected from nitrogen, oxygen, and sulfur;
each occurrence of $R^{12d}$ is independently hydrogen or an optionally substituted from 3-10-membered cycloaliphatic, 4-10-membered heterocyclyl having 1-5 heteroatoms independently selected from nitrogen, oxygen, and sulfur, 6-10-membered aryl, or 5-10-membered heteroaryl having 1-5 heteroatoms independently selected from nitrogen, oxygen, and sulfur;
each occurrence of $R^{12e}$ is independently hydrogen or an optionally substituted $C_{1-6}$ aliphatic group;
each occurrence of $V_2$ is independently —N($R^{12e}$)—, —O—, —S—, —S(O)—, —S(O)$_2$—, —C(O)—, —C(O)O—, —C(O)N($R^{12e}$)—, —S(O)$_2$N($R^{12e}$)—, —OC(O)N($R^{12e}$)—, —N($R^{12e}$)C(O)—, —N($R^{12e}$)SO$_2$—, —N($R^{12e}$)C(O)O—, —N($R^{12e}$)C(O)N($R^{12e}$)—, —N($R^{12e}$)SO$_2$N($R^{12e}$)—, —OC(O)—, or —C(O)N($R^{12e}$)—O—; and
$T_2$ is an optionally substituted $C_1$-$C_6$ alkylene chain wherein the alkylene chain optionally is interrupted by —N($R^{13}$)—, —O—, —S—, —S(O)—, —S(O)$_2$—, —C(O)—, —C(O)O—, —C(O)N($R^{13}$)—, —S(O)$_2$N (R¹³)—, —OC(O)N(R¹³)—, —N(R¹³)C(O)—, —N(R¹³)SO₂—, —N(R¹³)C(O)O—, —N(R¹³)C(O)N(R¹³)—, —N(R¹³)S(O)₂N(R¹³)—, —OC(O)—, or —C(O)N(R¹³)—O— or wherein T₂ or a portion thereof optionally forms part of an optionally substituted 3-7 membered cycloaliphatic or heterocyclyl ring, wherein R¹³ is hydrogen or an optionally substituted C₁₋₄ aliphatic group;

n is 0 to 4;

W is —C(R⁷)₂—, wherein:
  each occurrence of R⁷ is independently hydrogen, or an optionally substituted group selected from C₁₋₆ aliphatic, 6-10-membered aryl, 5-10-membered heteroaryl having 1-5 heteroatoms independently selected from nitrogen, oxygen, and sulfur, —N(R⁷ᵇ)₂, —OR⁷ᵃ, —SR⁷ᵃ, halo, or —CN;
  each occurrence of R⁷ᵃ is independently hydrogen or optionally substituted C₁₋₆ aliphatic or optionally substituted C₃₋₆ cycloaliphatic;
  each occurrence of R⁷ᵇ is independently hydrogen, optionally substituted C₁₋₆ aliphatic, optionally substituted C₃₋₆ cycloaliphatic, —C(O)R⁷ᵃ, —C(O)OR⁷ᵃ, S(O)R⁷ᵃ, or —S(O)₂R⁷ᵃ; or
  wherein any two occurrences of R⁷, R⁷ᵃ, or R⁷ᵇ taken together with the atom to which they are bound, form an optionally substituted group selected from a 3-6-membered cycloaliphatic ring, 6-10-membered aryl, 3-6-membered heterocyclyl having 1-5 heteroatoms independently selected from nitrogen, oxygen, and sulfur, and 5-10-membered heteroaryl having 1-5 heteroatoms independently selected from nitrogen, oxygen, and sulfur;
  or wherein any two occurrences of R⁷ᵃ and R², or R⁷ᵇ and R² taken together with the nitrogen atom to which they are bound, form an optionally substituted group selected from 3-6-membered heterocyclyl having 1-5 heteroatoms independently selected from nitrogen, oxygen, and sulfur, and 5-10-membered heteroaryl having 1-5 heteroatoms independently selected from nitrogen, oxygen, and sulfur; and G₁ is —CR⁸, wherein R⁸ is H, —CN, halogen, —Z₂—R⁹, C₁₋₆ aliphatic, or 3-10-membered cycloaliphatic, wherein:
  Z₂ is selected from an optionally substituted C₁₋₃ alkylene chain, —O—, —N(R⁸ᵃ)—, —S—, —S(O)—, S(O)₂—, —C(O)—, —CO₂—, —C(O)NR⁸ᵃ—, —N(R⁸ᵃ)C(O)—, —N(R⁸ᵃ)CO₂—, —S(O)₂NR⁸ᵃ—, —N(R⁸ᵃ)S(O)₂—, —OC(O)N(R⁸ᵃ)—, —N(R⁸ᵃ)C(O)NR⁸ᵃ—, —N(R⁸ᵃ)S(O)₂N(R⁸ᵃ)—, and —OC(O)—;
  R⁸ᵃ is hydrogen or an optionally substituted C₁₋₄ aliphatic, and
  R⁹ is hydrogen or an optionally substituted group selected from C₁₋₆ aliphatic, 3-10-membered cycloaliphatic, 4-10-membered heterocyclyl having 1-5 heteroatoms independently selected from nitrogen, oxygen, and sulfur, 6-10-membered aryl, and 5-10-membered heteroaryl having 1-5 heteroatoms independently selected from nitrogen, oxygen, and sulfur.

23. The compound of claim 22, wherein one of X⁴, X⁵, or X⁶ is N.

24. The compound of claim 22, wherein all of X⁴, X⁵, and X⁶ are CR¹⁰.

25. The compound of claim 22, wherein each occurrence of R¹⁰ is independently selected from —CN, —OR¹⁰ᵃ, —N(R¹¹)₂ halogen, C₁₋₄ alkyl, —N(R¹¹)COR¹⁰ᵃ, or wherein two occurrences of R¹⁰, taken together with the atoms to which they are bound form an optionally substituted group selected from a fused 5- or 6-membered cycloaliphatic, 4-10-membered heterocyclyl, 6-10-membered aryl and 5-10-membered heteroaryl ring, wherein the heterocyclyl and heteroaryl rings have 1-3 heteroatoms independently selected from nitrogen, oxygen, and sulfur.

26. The compound of claim 22, wherein R¹ is CY, and CY is

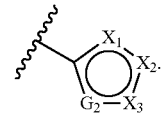

27. The compound of claim 26, wherein X₁ is N, G₂ is —N(R³)—, and X₂ and X₃ are CH.

28. The compound of claim 26, wherein X₁ and X₂ are N, G₂ is —N(R³)—, and X₃ is CH.

29. The compound of claim 26, wherein X₃ is N, G₂ is —N(R³)—, and X₁ and X₂ are CH.

30. The compound of claim 26, wherein X₁ is N, X₂ is CH, X₃ is —N(R³)— and G₂ is =N—.

31. The compound of claim 22, wherein Ring A is an optionally substituted 6-10-membered aryl or 5-10-membered heteroaryl having 1-5 heteroatoms independently selected from nitrogen, oxygen, and sulfur; and n is 0 to 3.

32. The compound of claim 31, wherein ring A is a group selected from:

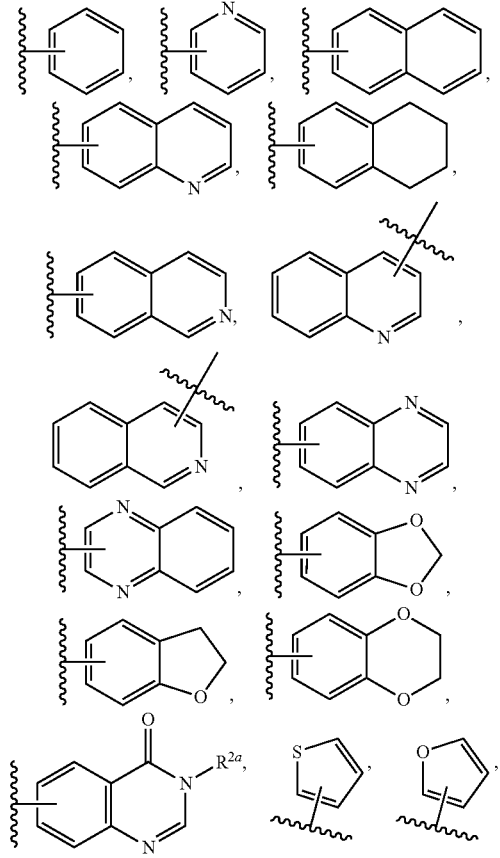

411
-continued

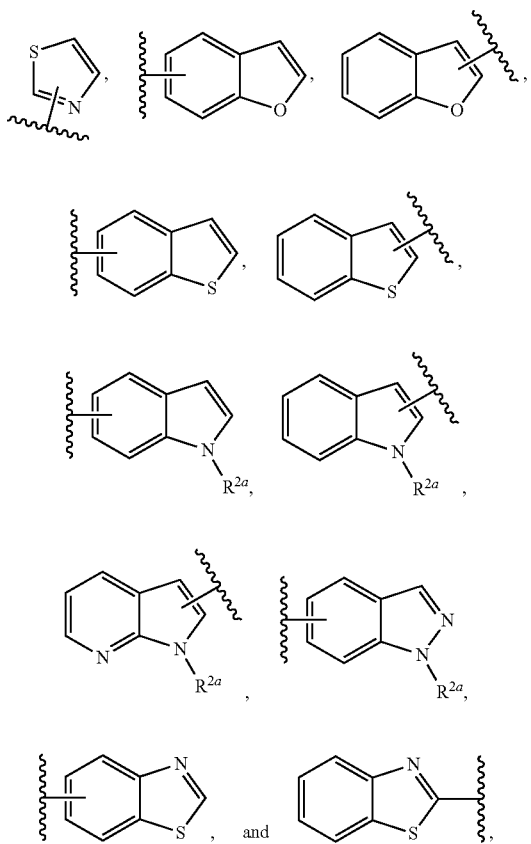

wherein ring A is optionally further substituted by n occurrences of $R^2$, and wherein $R^{2a}$ is hydrogen or an optionally substituted group selected from $C_{1-6}$ aliphatic, 3-10-membered cycloaliphatic, 4-10-membered heterocyclyl having 1-5 heteroatoms independently selected from nitrogen, oxygen, and sulfur, 6-10-membered aryl, and 5-10-membered heteroaryl having 1-5 heteroatoms independently selected from nitrogen, oxygen, and sulfur.

33. The compound of claim 31, wherein ring A is a group selected from:

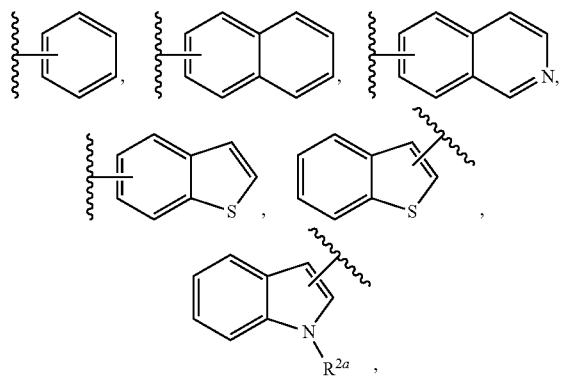

412
-continued

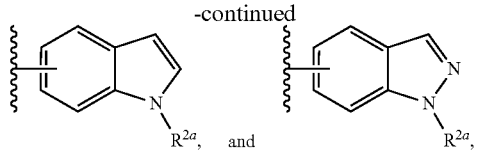

wherein ring A is optionally further substituted by n occurrences of $R^2$, and wherein $R^{2a}$ is hydrogen or an optionally substituted group selected from $C_{1-6}$ aliphatic, 3-10-membered cycloaliphatic, 4-10-membered heterocyclyl having 1-5 heteroatoms independently selected from nitrogen, oxygen, and sulfur, 6-10-membered aryl, and 5-10-membered heteroaryl having 1-5 heteroatoms independently selected from nitrogen, oxygen, and sulfur.

34. The compound of claim 31, wherein:
ring A is a naphthyl group; each occurrence of $R^2$ is independently halogen, $C_{1-3}$ alkyl, —CN, $C_{1-3}$ haloalkyl, —$OC_{1-3}$ alkyl, —$OC_{1-3}$ haloalkyl, —NHC(O)$C_{1-3}$ alkyl, —NHC(O)NHC$_{1-3}$ alkyl, —NHS(O)$_2$C$_{1-3}$alkyl, or —C(O)H; and n is 0 to 3.

35. The compound of claim 31, wherein Ring A is a phenyl group optionally substituted with 1-3 independent occurrences of halogen, $C_{1-3}$ alkyl, —CN, $C_{1-3}$ haloalkyl, —$OC_{1-3}$ alkyl, —$OC_{1-3}$ haloalkyl, —NHC(O)$C_{1-3}$ alkyl, —NHC(O)NHC$_{1-3}$ alkyl, NHS(O)$_2$C$_{1-3}$ alkyl, or —C(O)H; and n is 0 to 3.

36. The compound of claim 34, wherein ring A is a naphthyl group, $R^2$ is halogen and n is 1 to 2.

37. The compound of claim 34, wherein ring A is a naphthyl group and n is 0.

38. The compound of claim 35, wherein Ring A is a phenyl group, $R^2$ is halogen and n is 1 to 2.

39. The compound of claim 22, wherein one occurrence of $R^7$ is hydrogen and the other occurrence of $R^7$ is hydrogen, optionally substituted $C_{1-4}$ aliphatic, —N($R^{7b}$)$_2$, —$OR^{7a}$, —$SR^{7a}$, halo, or —CN; and
wherein each occurrence of $R^{7a}$ is independently hydrogen or optionally substituted $C_{1-6}$ aliphatic;
each occurrence of $R^{7b}$ is independently hydrogen, optionally substituted $C_{1-6}$ aliphatic, —C(O)$R^{7a}$, or —S(O)$_2R^{7a}$; or
wherein any two occurrences of $R^7$, $R^{7a}$, or $R^{7b}$ taken together with the atom to which they are bound, form an optionally substituted group selected from a 3-6-membered cycloaliphatic ring, 6-10-membered aryl, 3-6-membered heterocyclyl having 1-5 heteroatoms independently selected from nitrogen, oxygen, and sulfur, and 5-10-membered heteroaryl having 1-5 heteroatoms independently selected from nitrogen, oxygen, and sulfur; or
any two occurrences of $R^{7a}$ and $R^2$, or $R^{7b}$ and $R^2$ taken together with the nitrogen atom to which they are bound, form an optionally substituted group selected from 3-6-membered heterocyclyl having 1-5 heteroatoms independently selected from nitrogen, oxygen, and sulfur, and 5-10-membered heteroaryl having 1-5 heteroatoms independently selected from nitrogen, oxygen, and sulfur.

40. The compound of claim 39, wherein W is —C(H)(N($R^{7b}$)$_2$)—, —CH$_2$— or —C(H)(OR$^{7a}$)—, wherein each occurrence of $R^{7a}$ is independently hydrogen or optionally substituted $C_{1-6}$ aliphatic; and each occurrence of $R^{7b}$ is independently hydrogen or optionally substituted $C_{1-6}$ aliphatic.

41. A composition comprising a compound of any one of claims 1, 2, or 22, or a pharmaceutically acceptable salt thereof, and a pharmaceutically acceptable carrier.
42. A compound selected from the group consisting of:
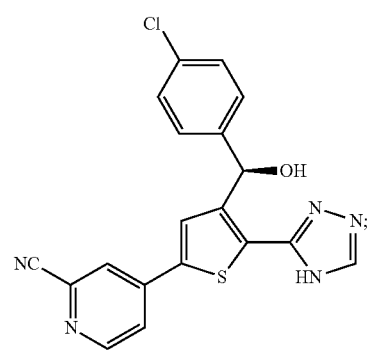
3
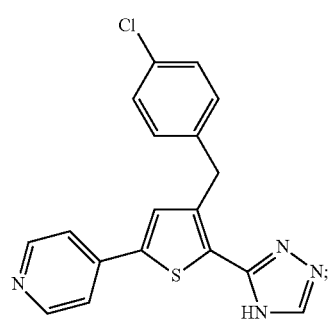
5
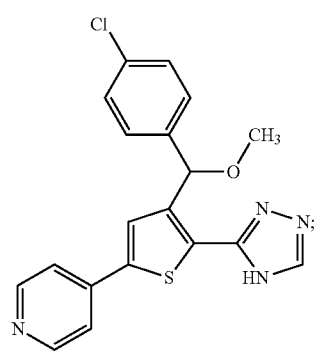
6
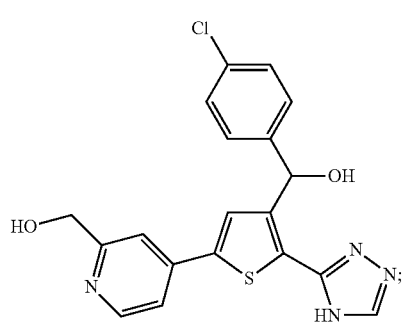
8
-continued
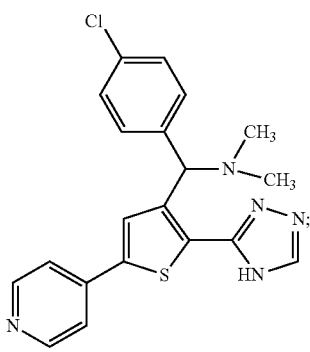
9
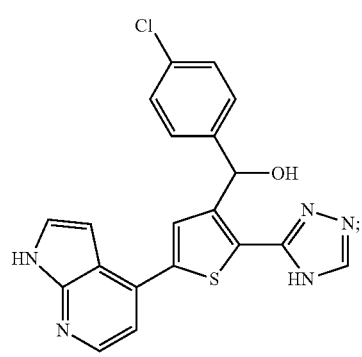
10
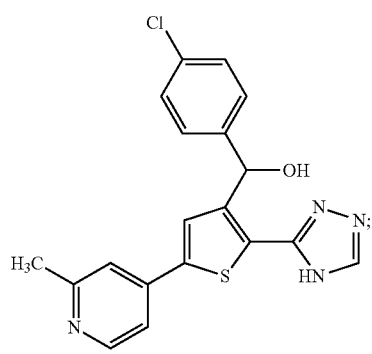
11
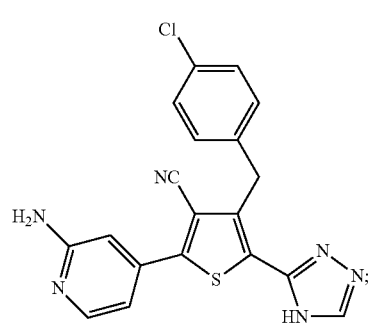
12

-continued

13

16

17

21

23

25

26

28
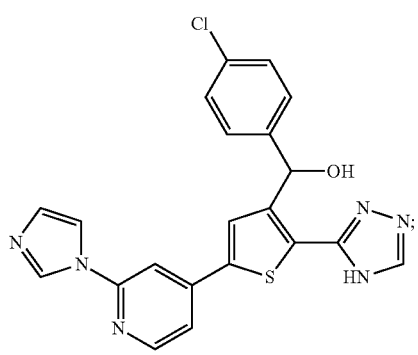
30
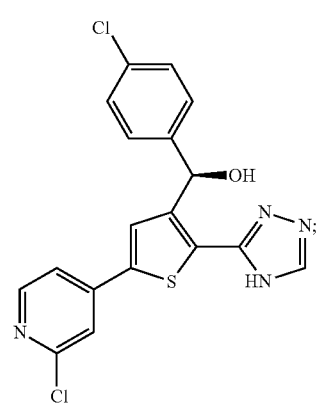
33
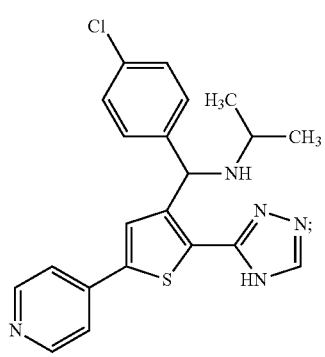
34
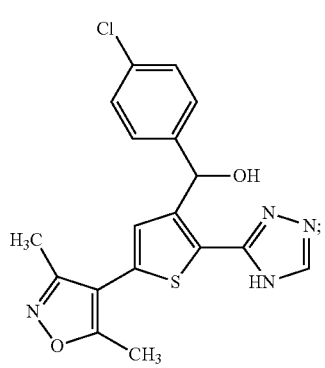
36
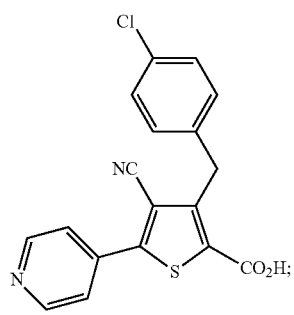
40
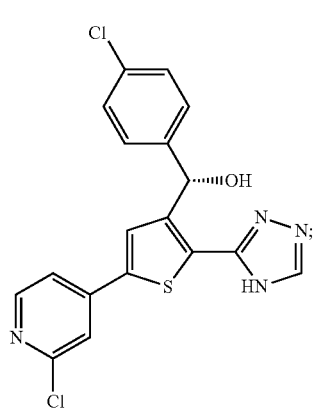
41
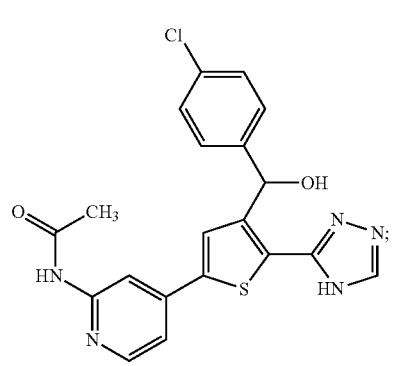
42
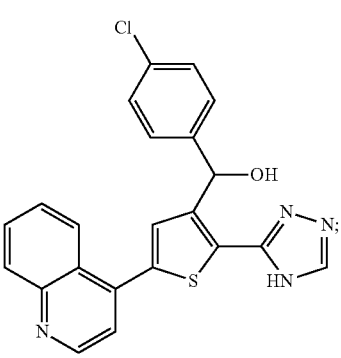

-continued
43
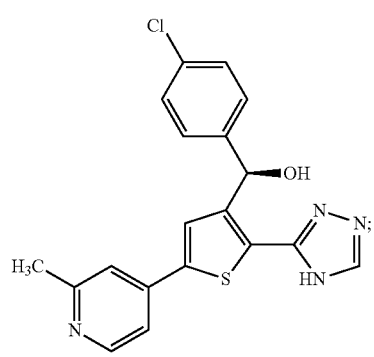
44
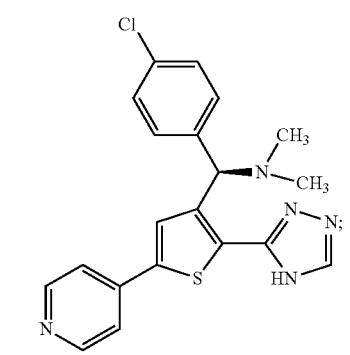
45
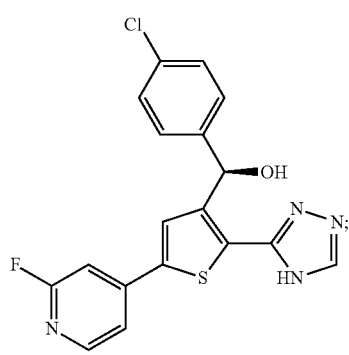
48
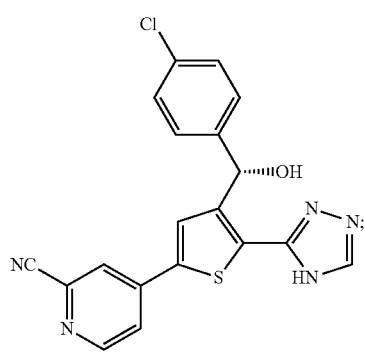
-continued
49
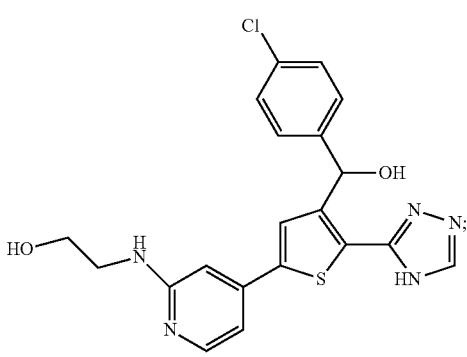
51
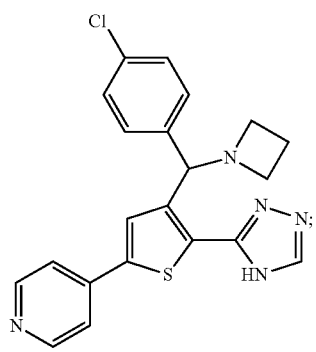
52
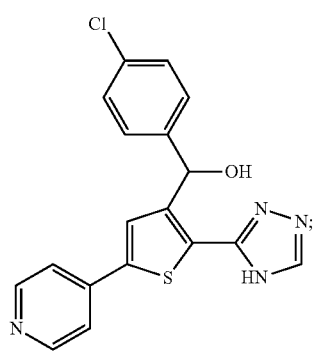
55
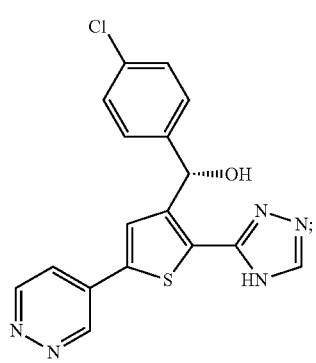

57
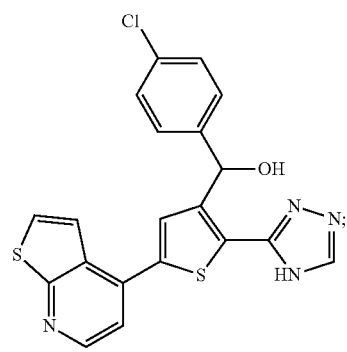
59
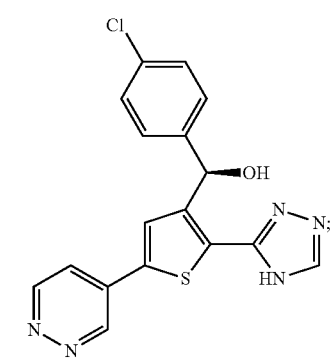
62
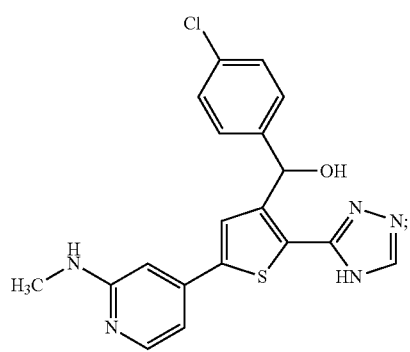
64
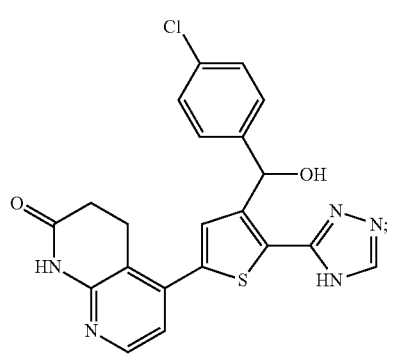
65
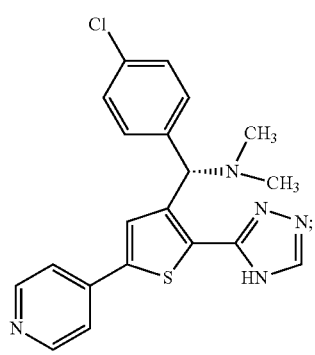
68
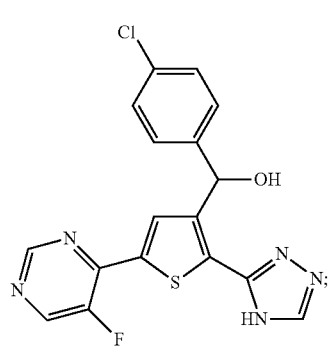
69
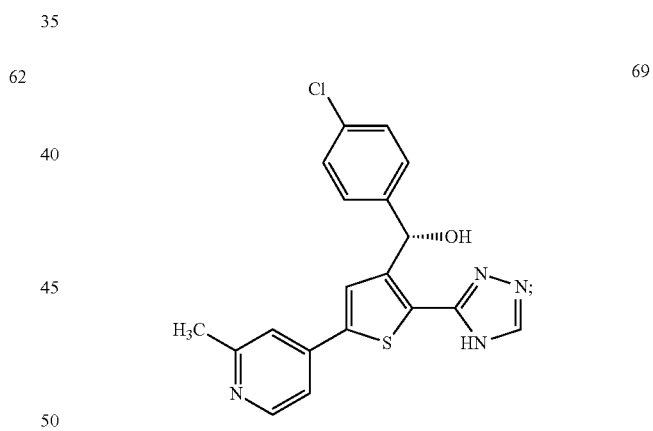
71
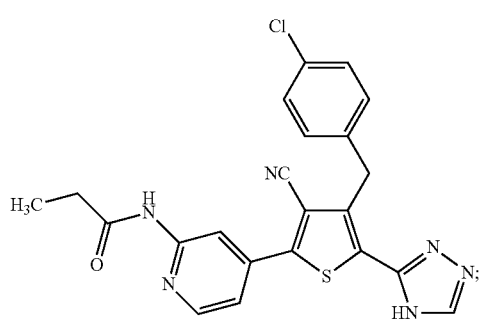

74
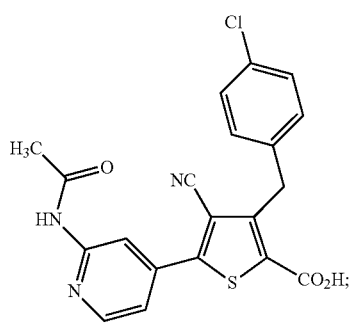
75
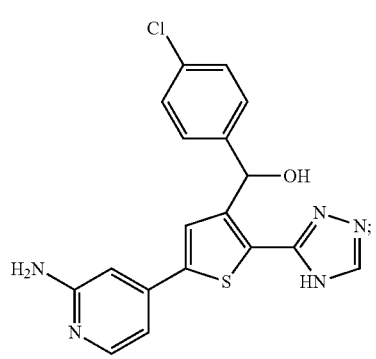
77
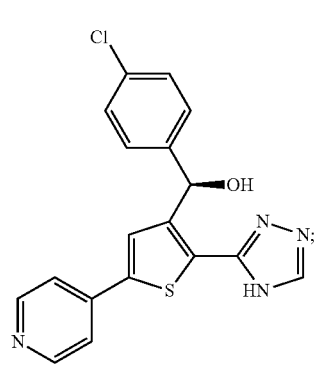
79
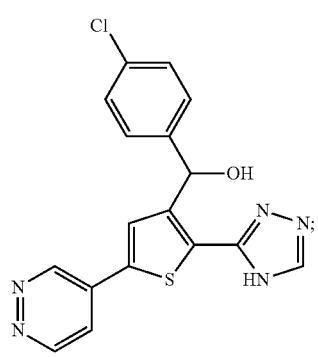
81
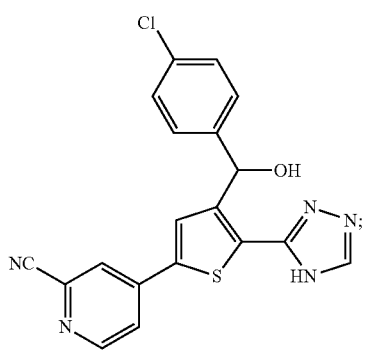
84
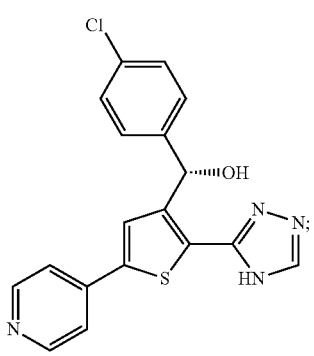
85
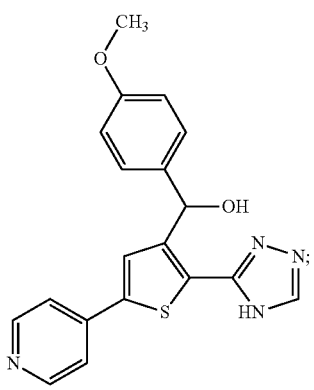
86
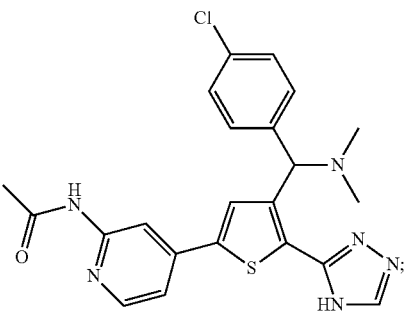

425
-continued
88
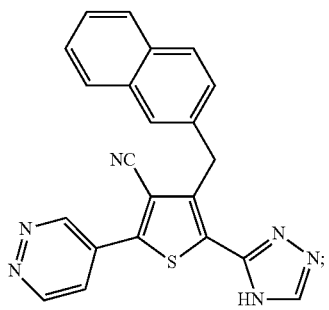
89
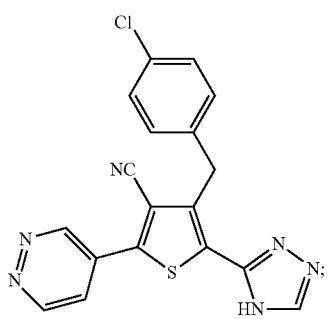
90
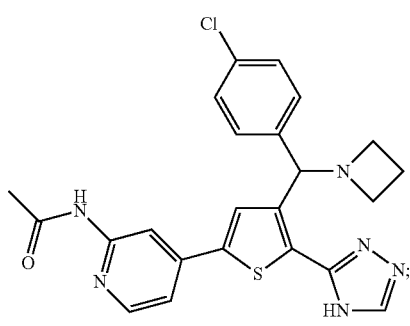
129
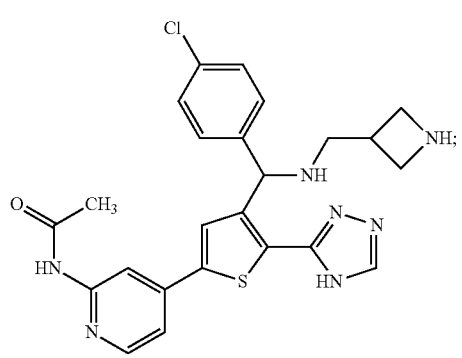
426
-continued
130
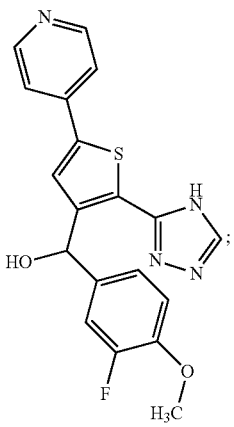
132
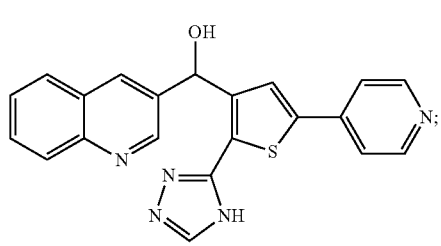
133
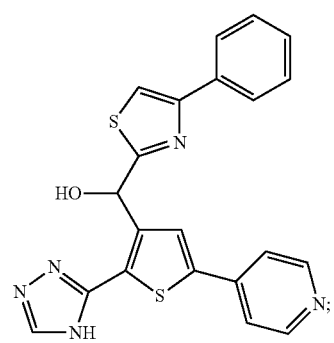
134
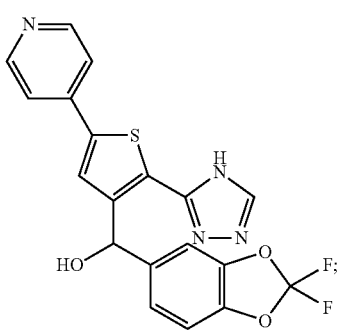

-continued
135
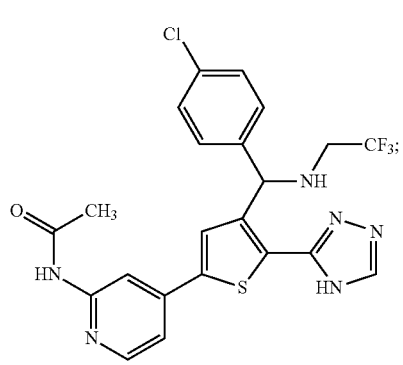
136
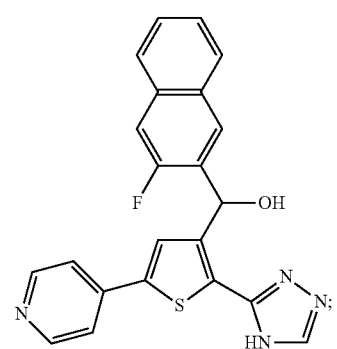
138
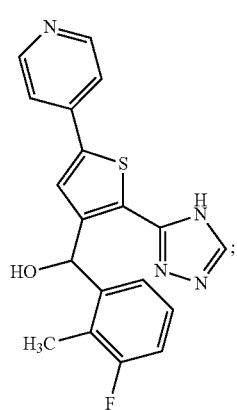
139
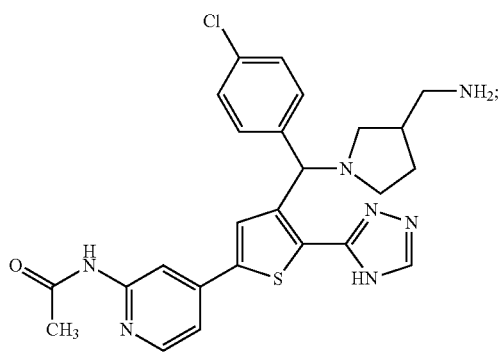
-continued
141
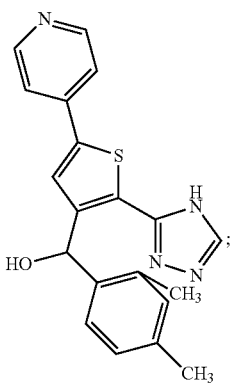
142
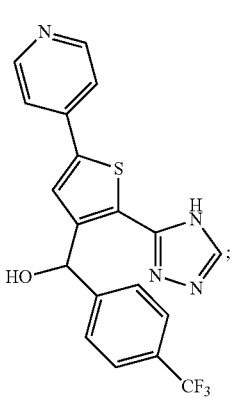
143
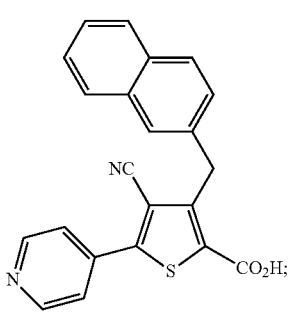
144
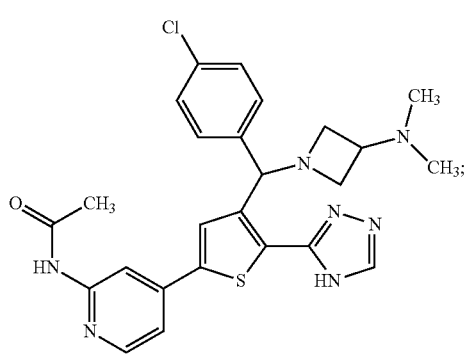

145 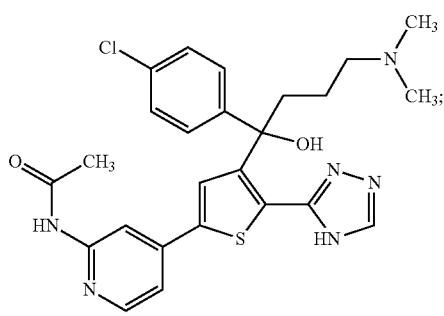
146 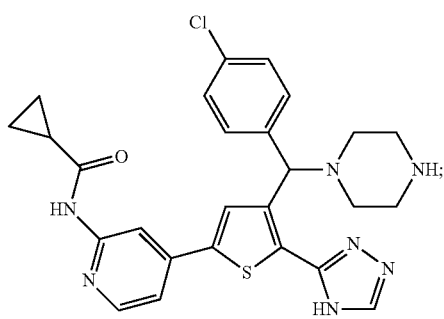
147 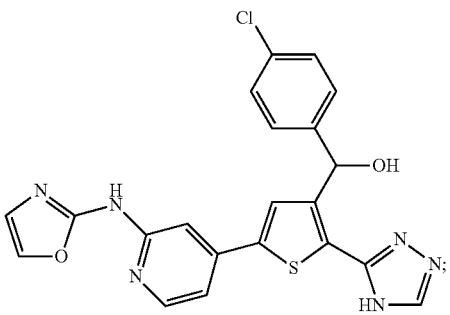
148 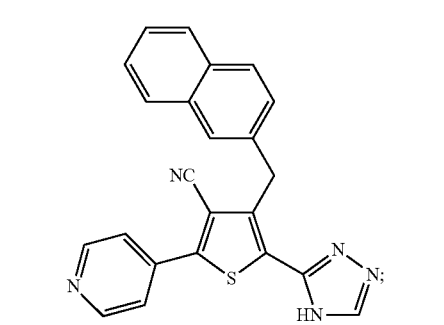
149 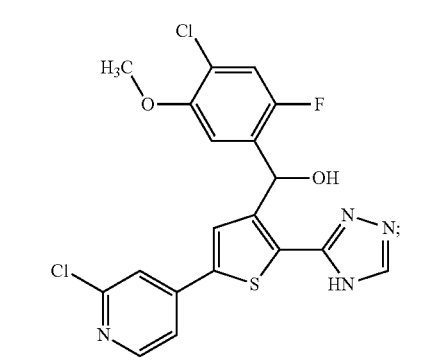
151 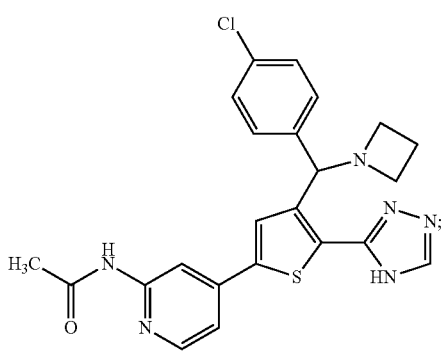
152 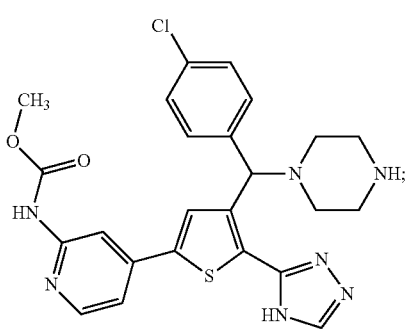
153 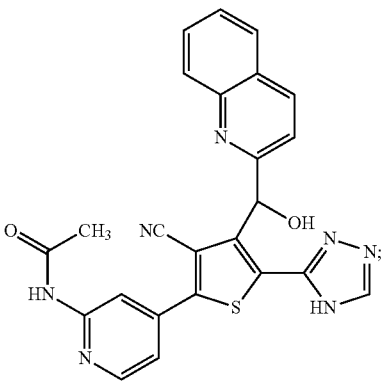
154 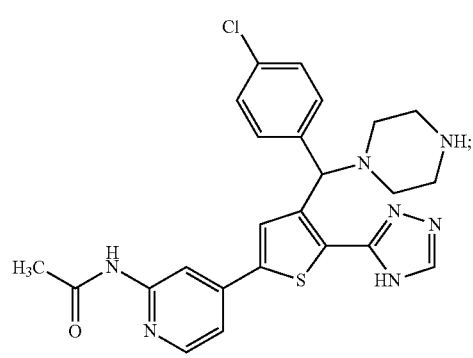

155 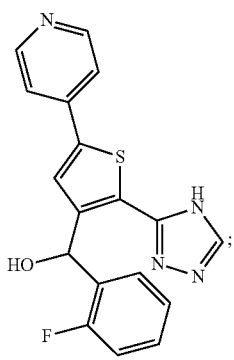
157 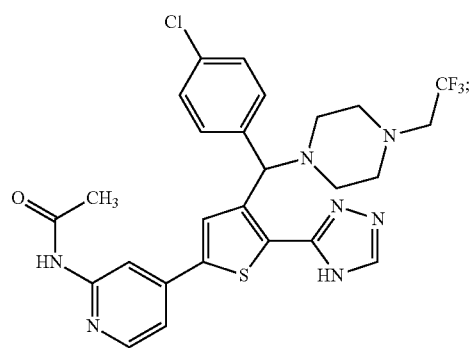
158 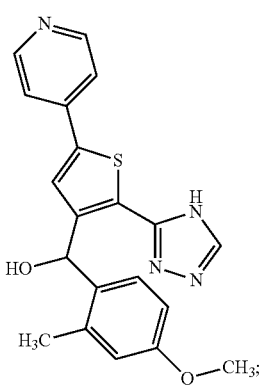
159 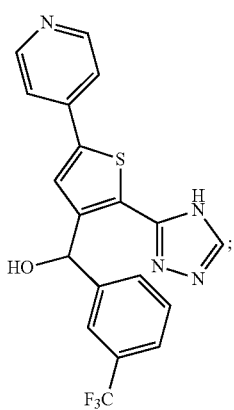
160 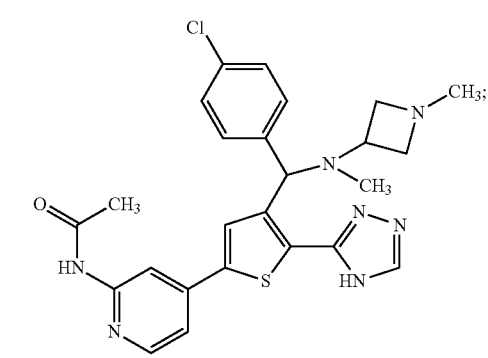
161 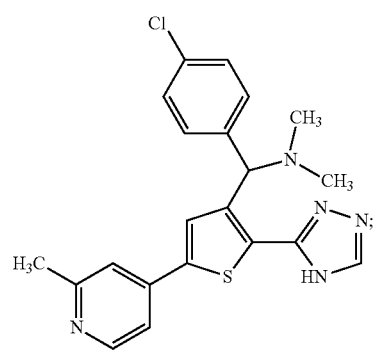
162 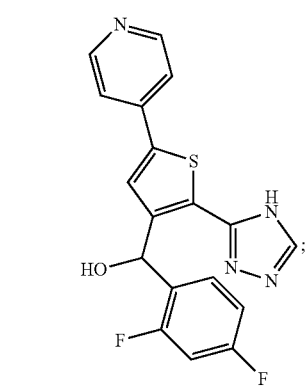
163 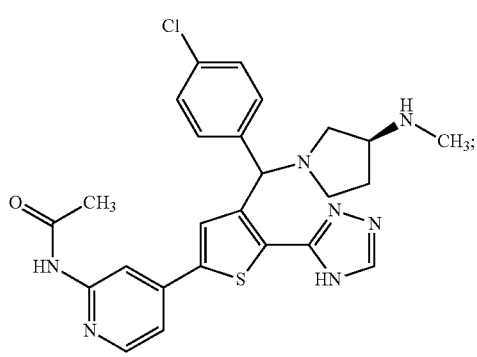

164 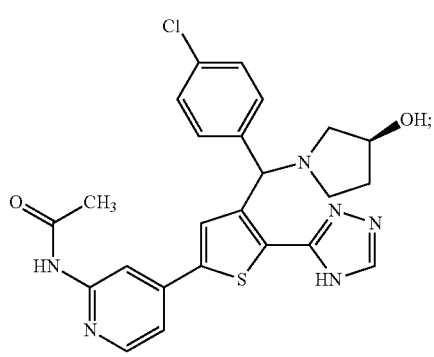
165 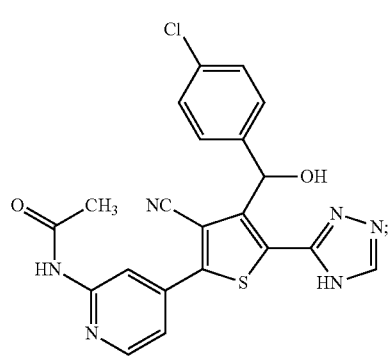
167 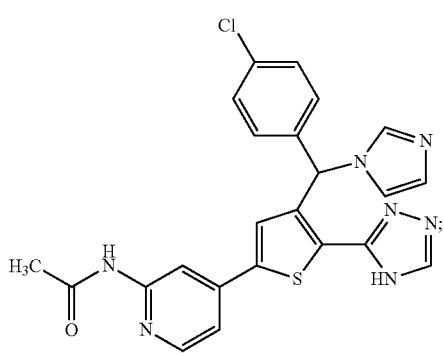
168 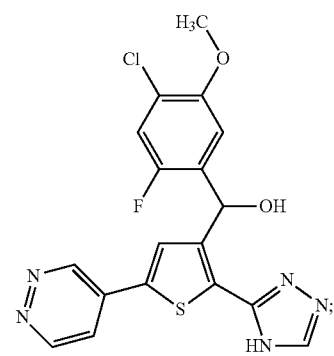
169 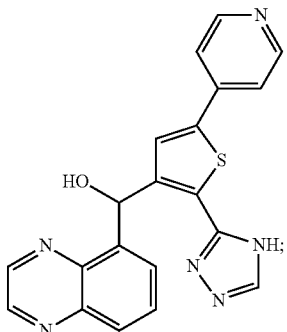
170 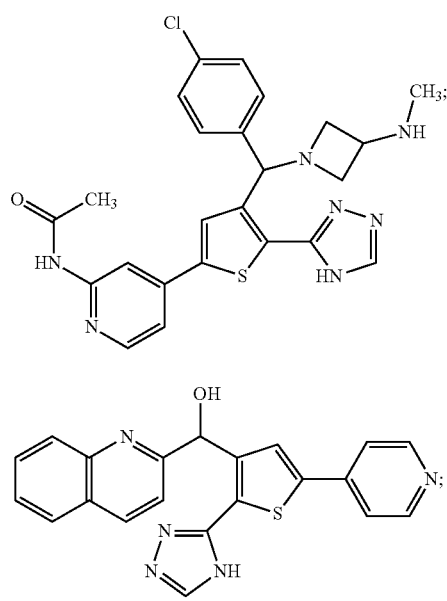
171 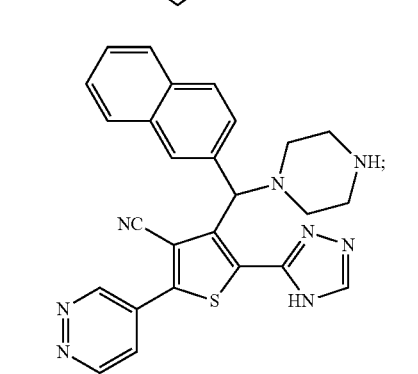
172 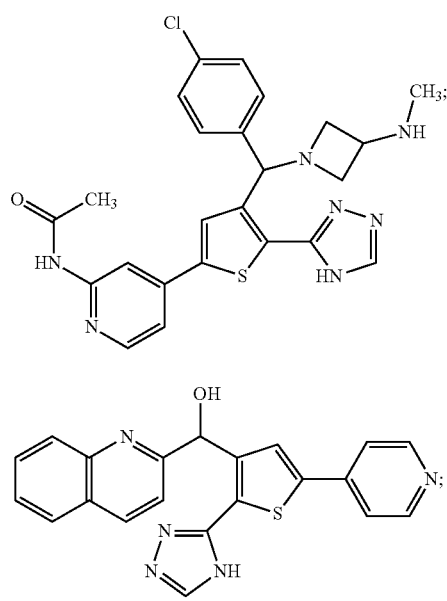
173 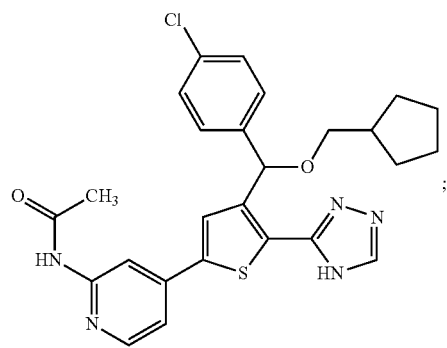

435
-continued
173
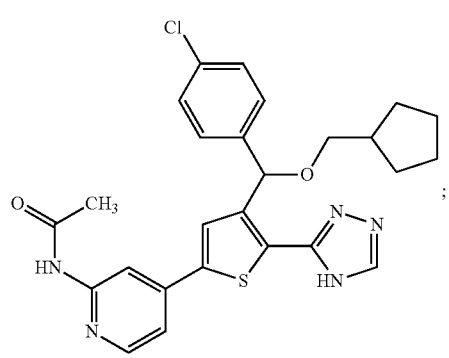
174
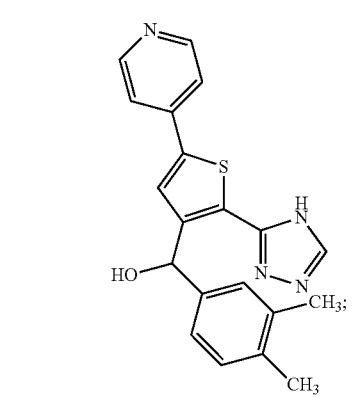
175
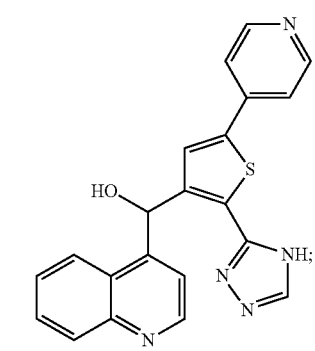
176
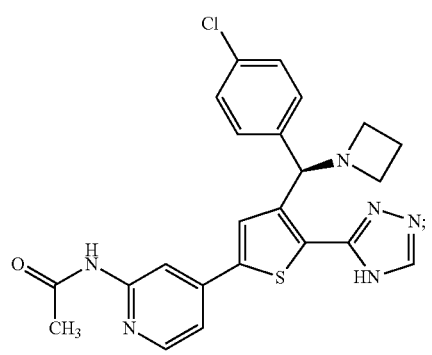
436
-continued
179
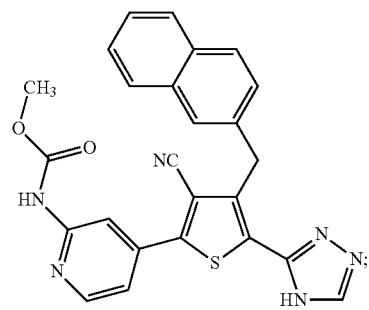
180
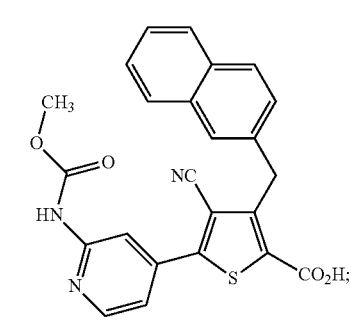
181
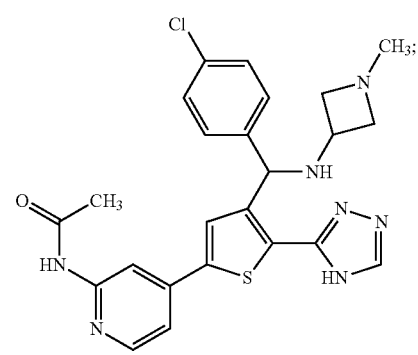
182
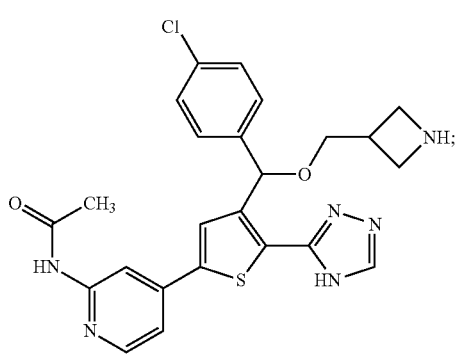

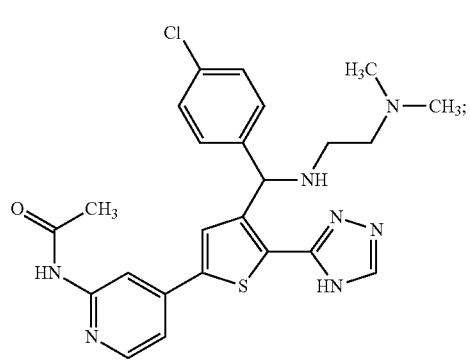
184
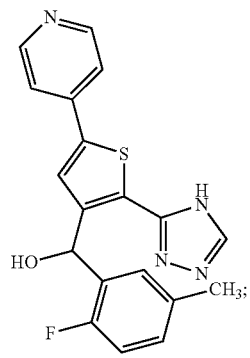
188
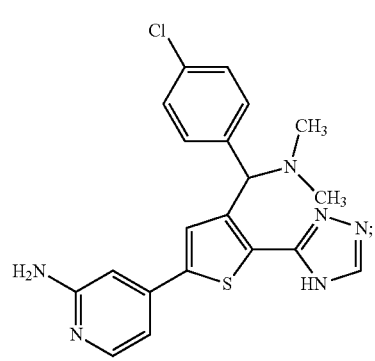
185
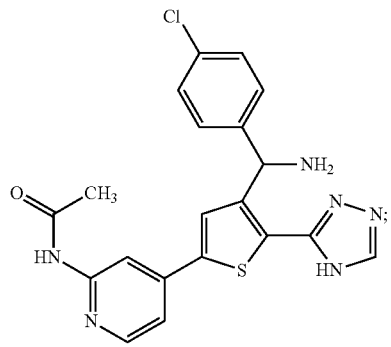
189
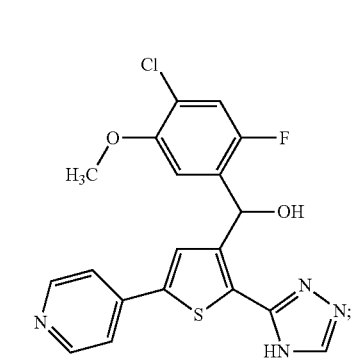
186
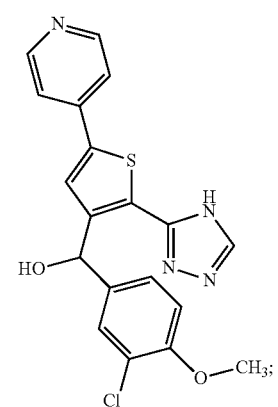
191
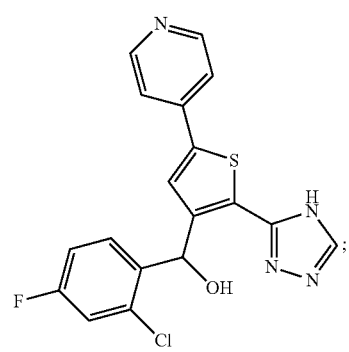
187
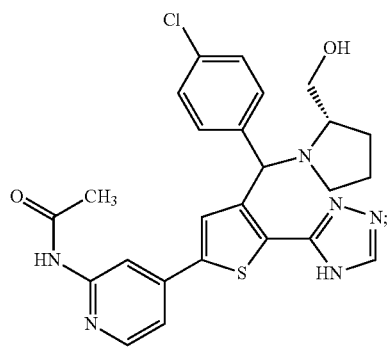
192

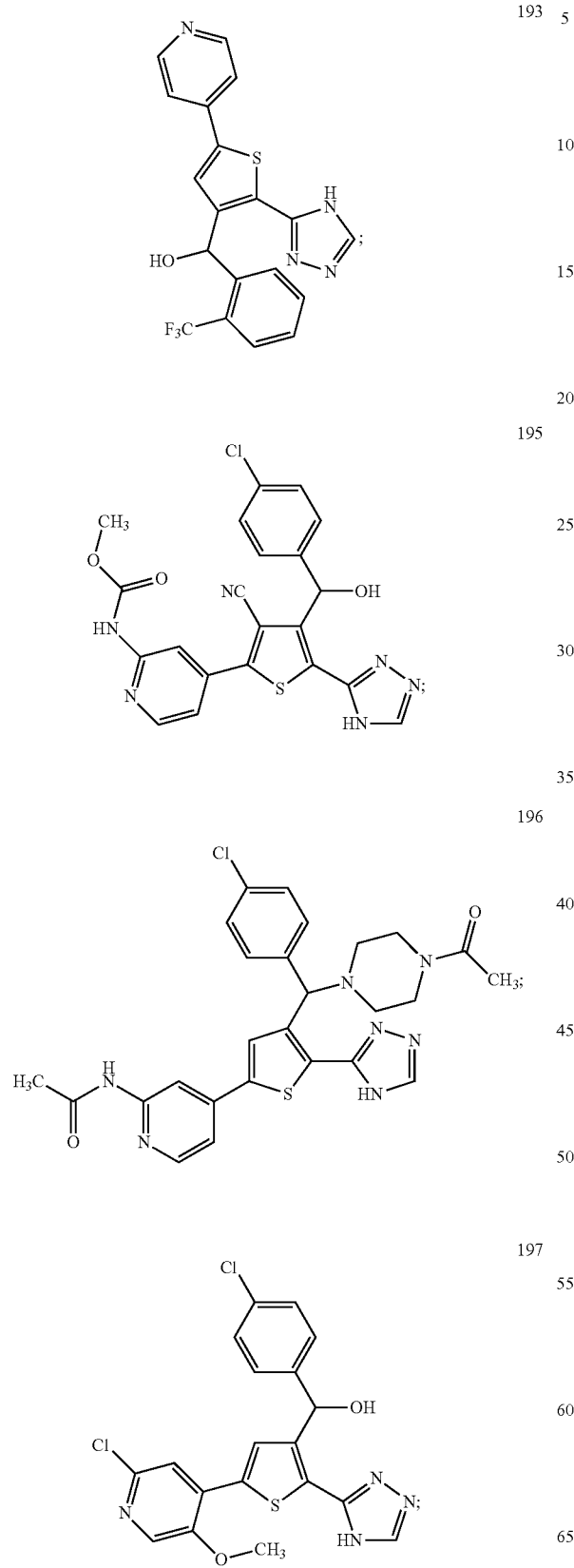

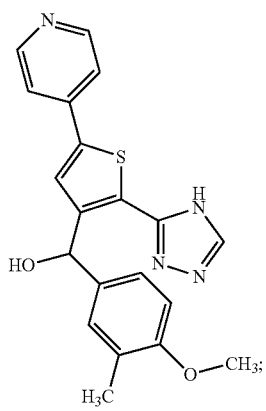
202
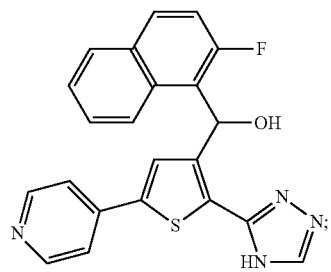
203
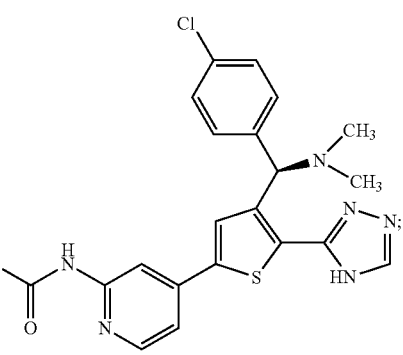
204
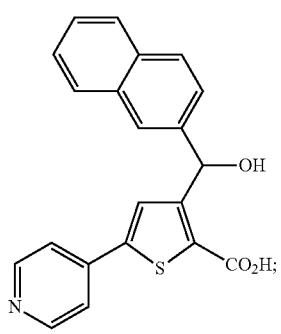
205
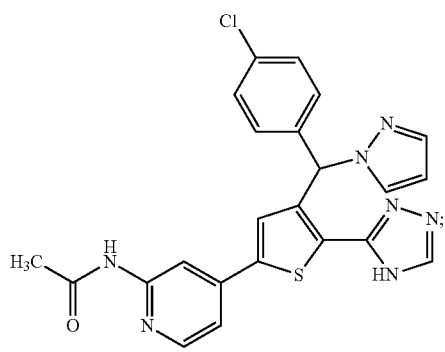
206
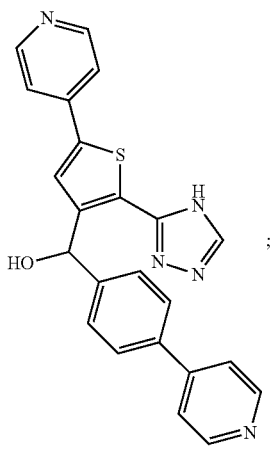
207
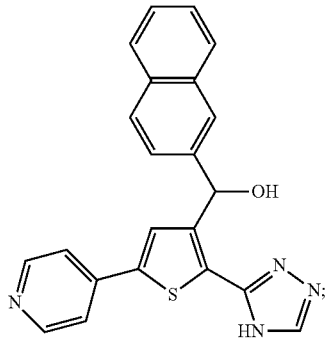
208
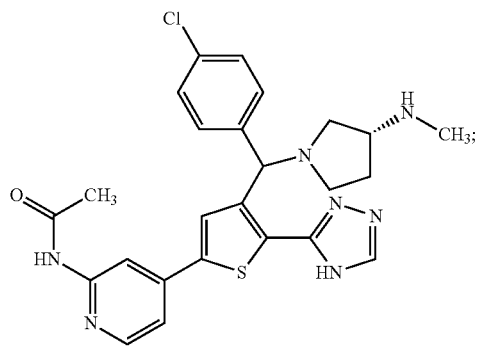
209

210 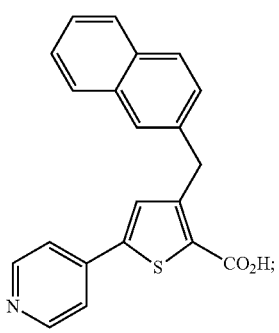
211 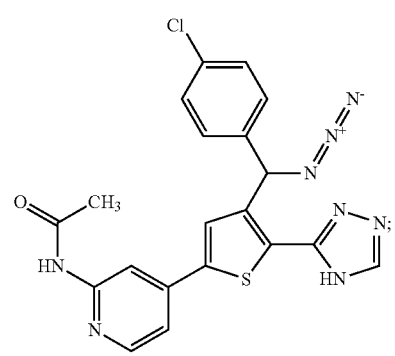
212 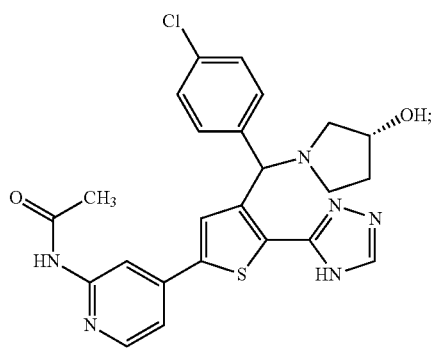
214 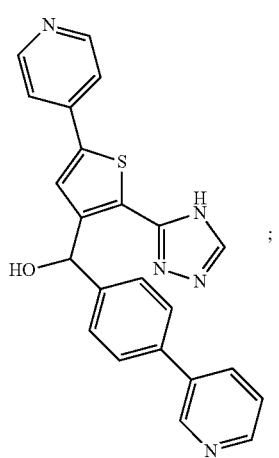
215 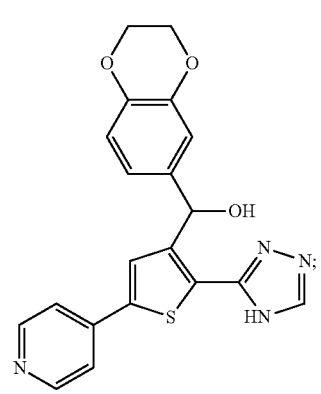
216 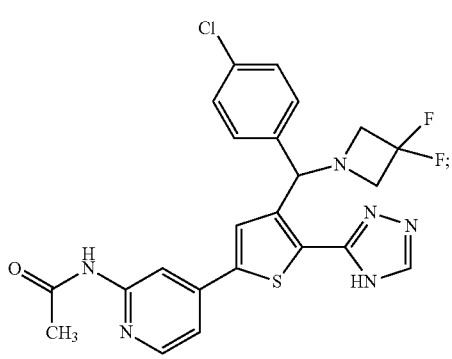
217 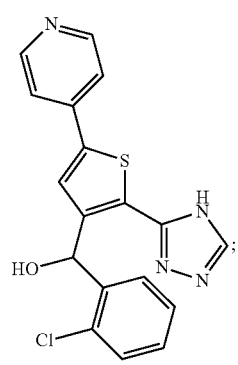
218 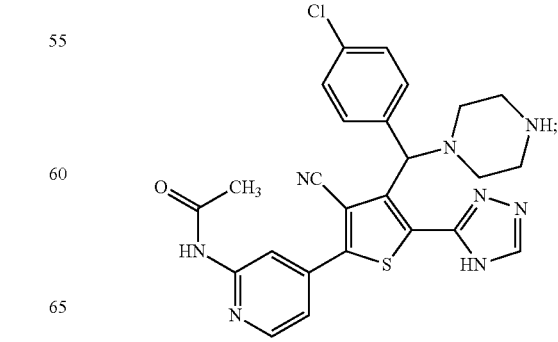

445
-continued
219
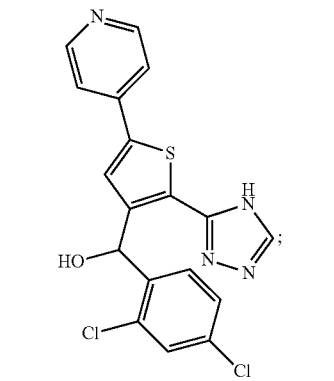
220
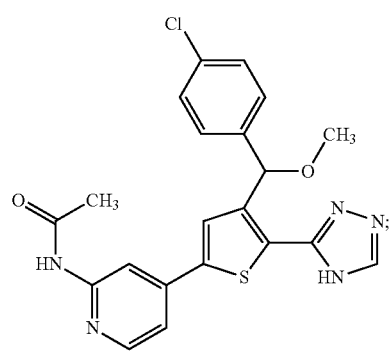
221
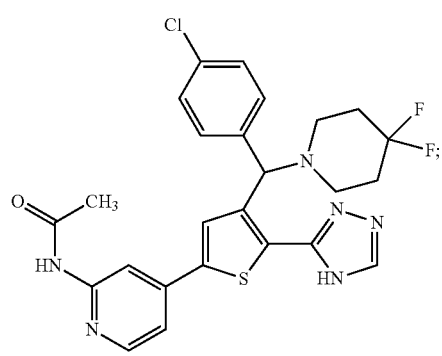
222
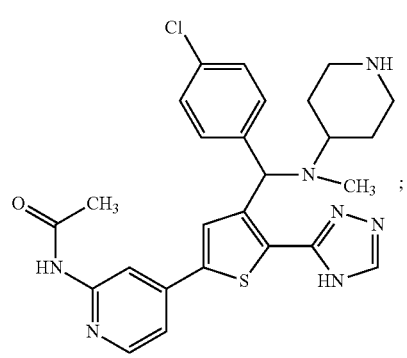
446
-continued
223
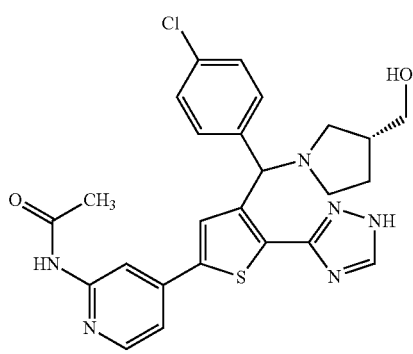
224
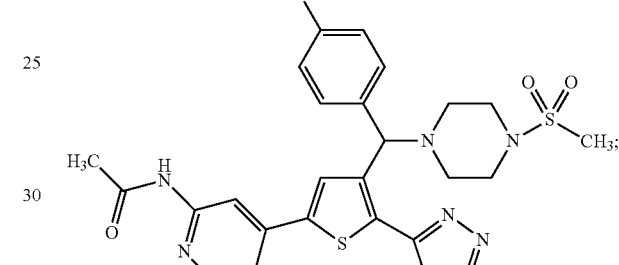
225
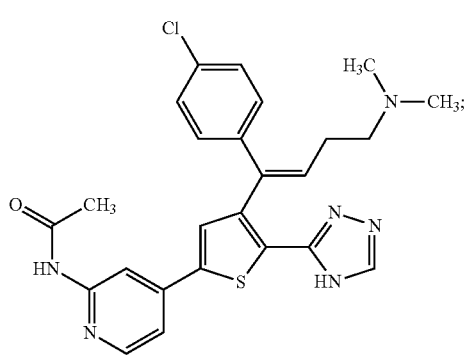
226
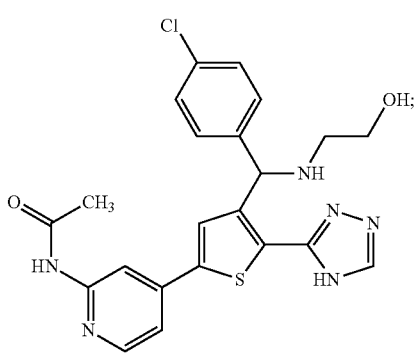

227 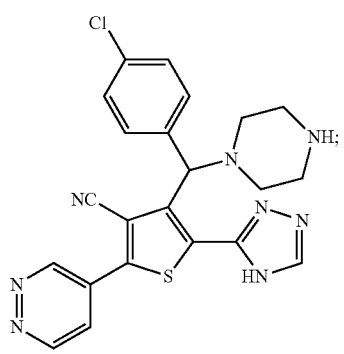
228 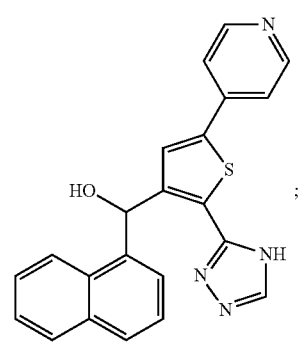
230 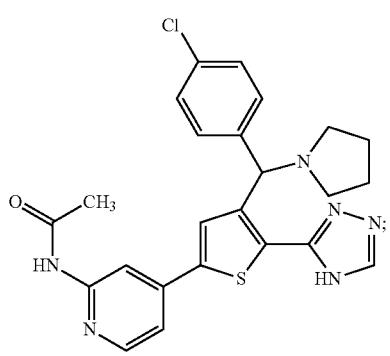
231 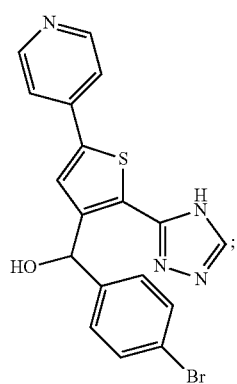
232 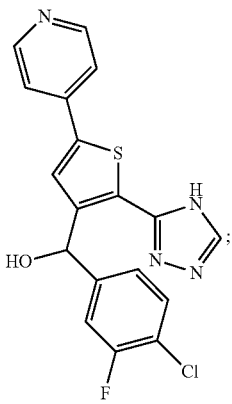
233 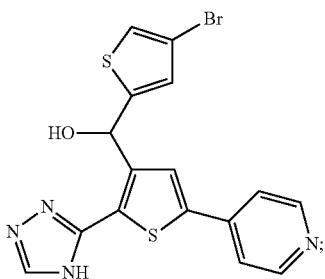
234 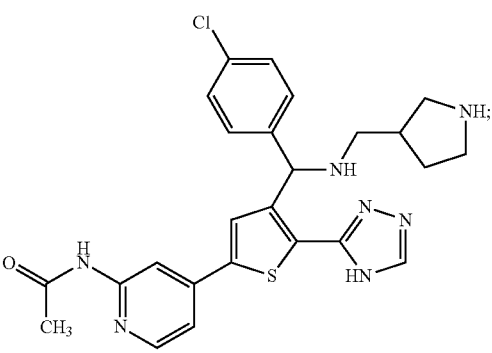
235 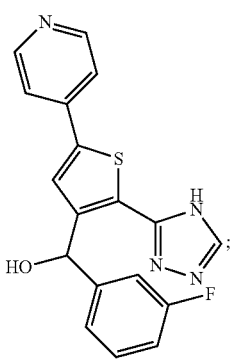

236
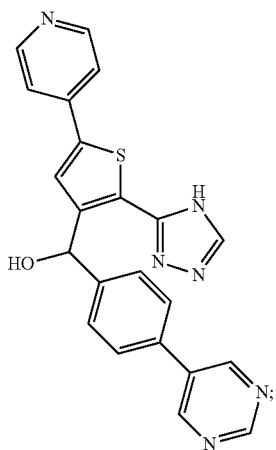
241
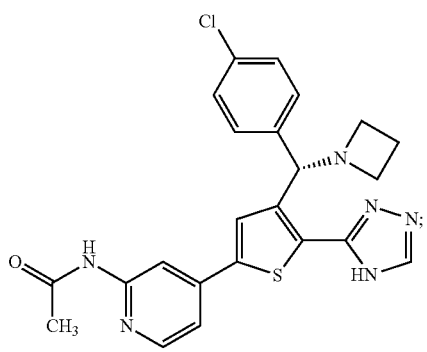
237
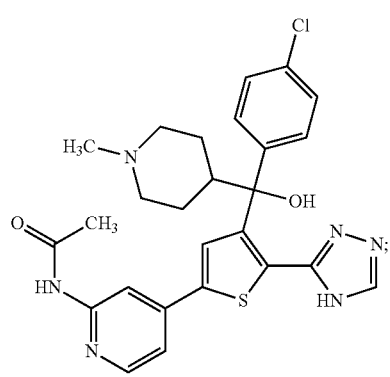
242
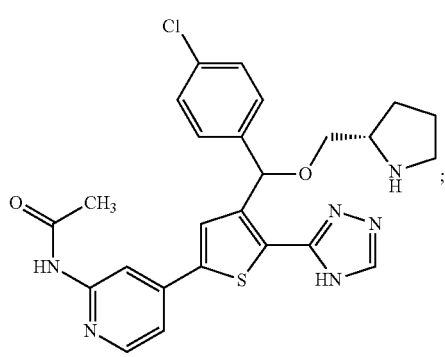
239
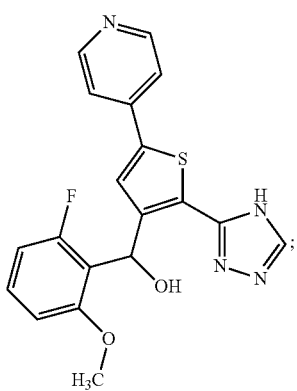
243
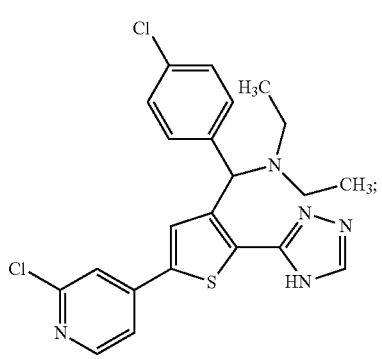
240
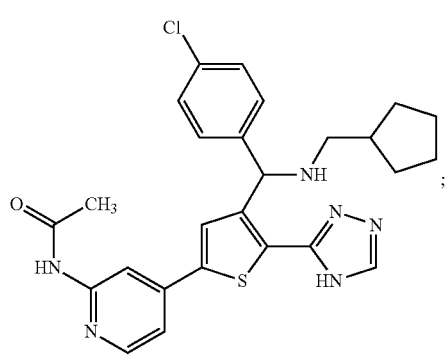
244
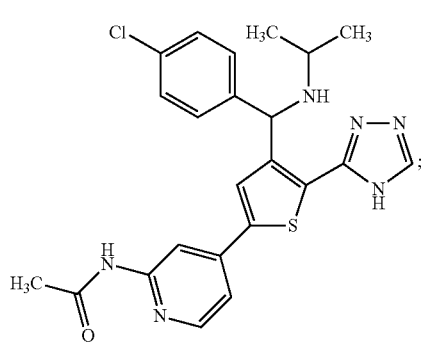

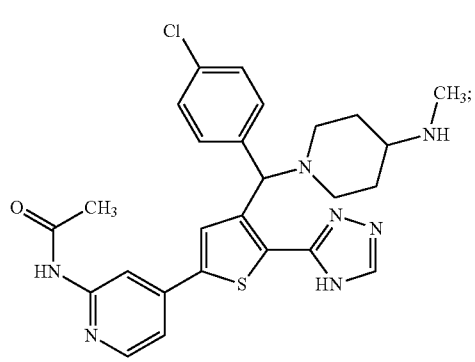
245
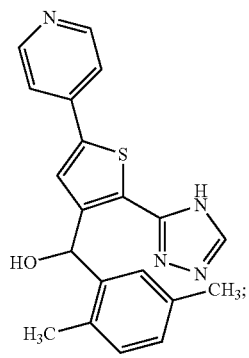
249
246
250
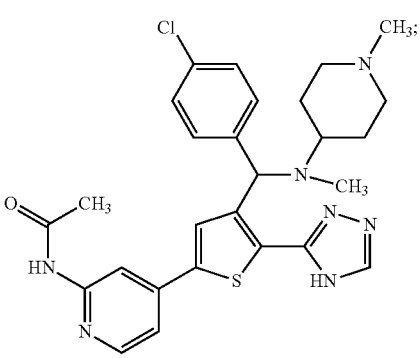
247
251
248
252
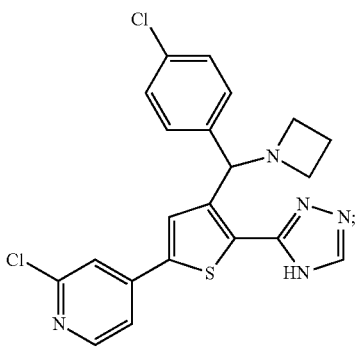
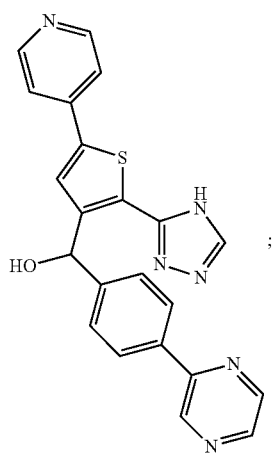

253 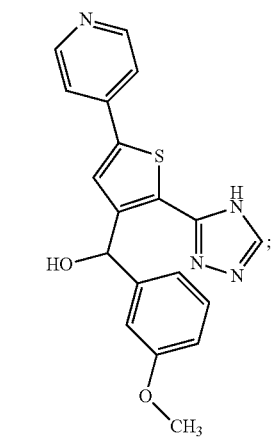
254 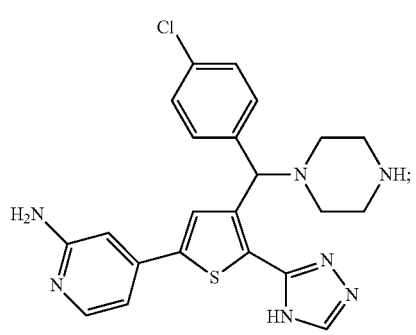
256 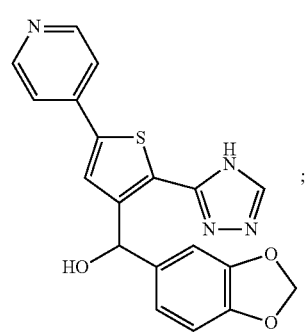
257 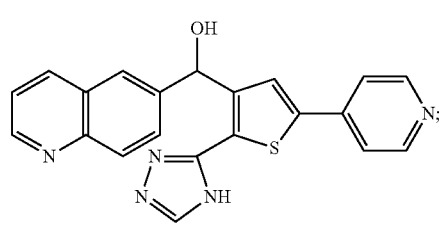
258 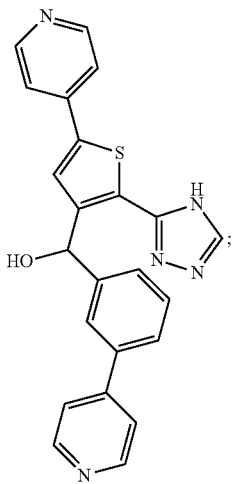
259 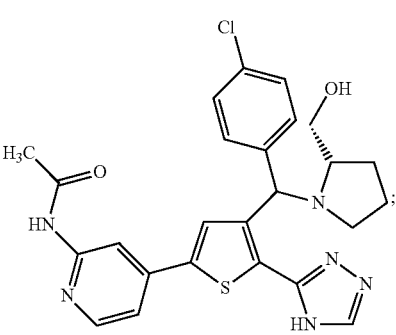
260 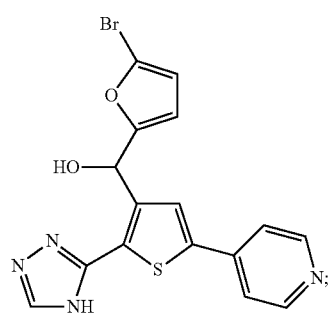
261 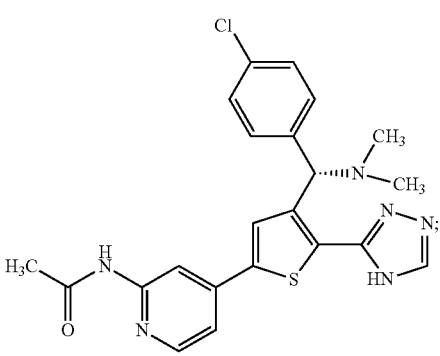

455
-continued
263
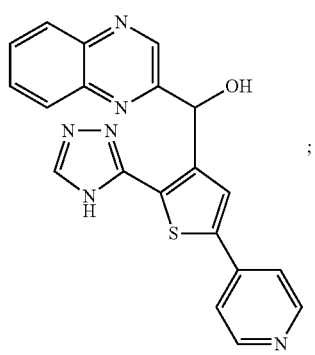
264
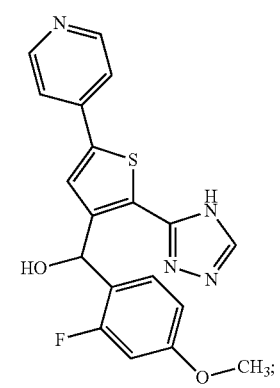
265
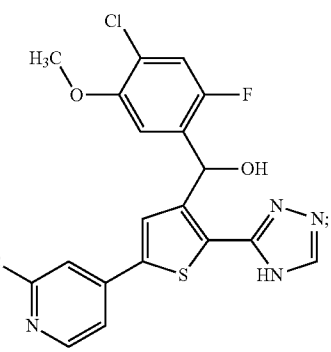
266
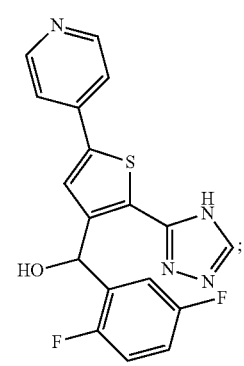
456
-continued
267
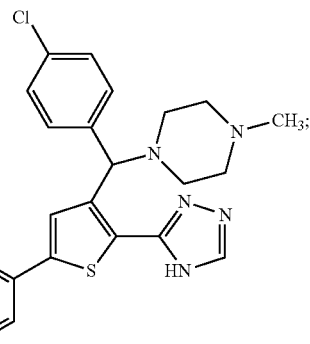
268
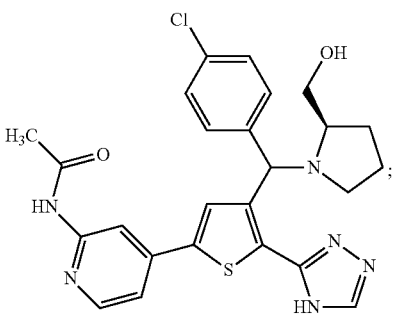
269
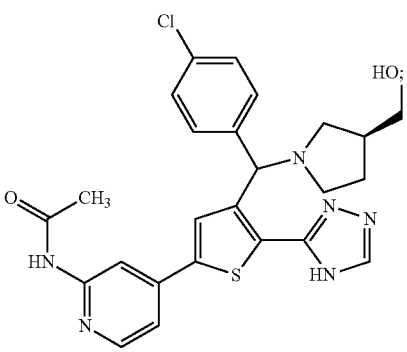
270
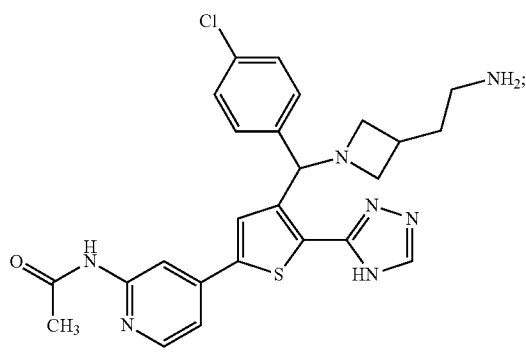

271 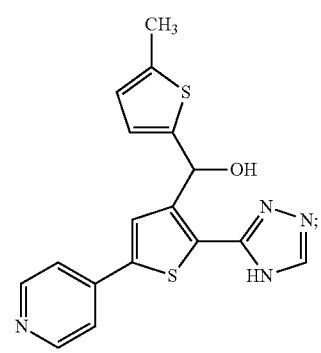
272 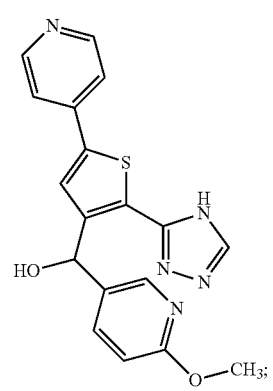
273 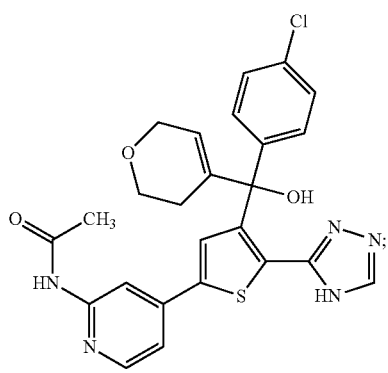
274 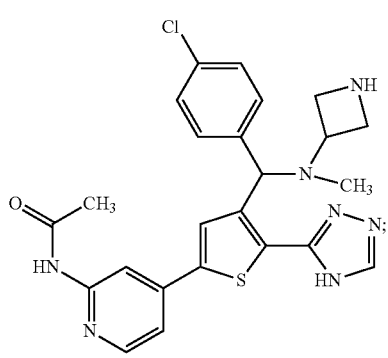
275 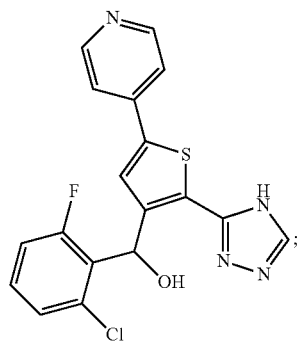
276 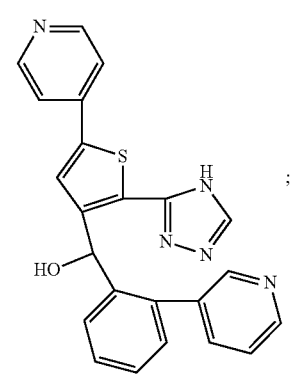
277 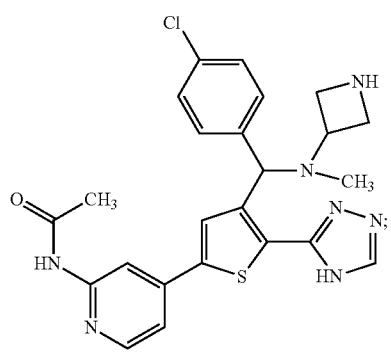
278 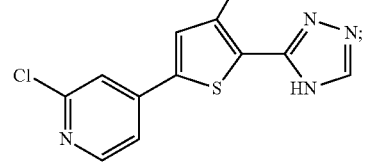

or a pharmaceutically acceptable salt thereof.

43. The compound of claim 1, wherein said compound is a compound of formula IA-a:

IA-a or a pharmaceutically acceptable salt thereof.

44. The compound of claim 1, wherein said compound is a compound of formula IB-a:

IB-a or a pharmaceutically acceptable salt thereof.

45. The compound of claim 2, wherein said compound is a compound of formula IA:

IA or a pharmaceutically acceptable salt thereof.

46. The compound of claim 2, wherein said compound is a compound of formula IB:

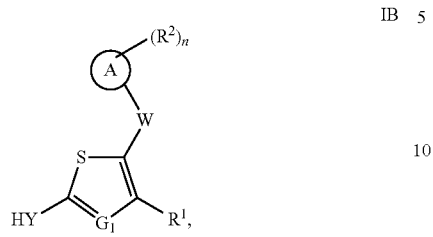

IB or a pharmaceutically acceptable salt thereof.

47. A composition comprising a compound of claim 42, or a pharmaceutically acceptable salt thereof, and a pharmaceutically acceptable carrier.

48. A composition comprising a compound of any one of claims 43-46, or a pharmaceutically acceptable salt thereof, and a pharmaceutically acceptable carrier.

* * * * *